US008956851B2

(12) United States Patent
Argyros et al.

(10) Patent No.: US 8,956,851 B2
(45) Date of Patent: Feb. 17, 2015

(54) METHODS FOR THE IMPROVEMENT OF PRODUCT YIELD AND PRODUCTION IN A MICROORGANISM THROUGH THE ADDITION OF ALTERNATE ELECTRON ACCEPTORS

(75) Inventors: Aaron Argyros, White River Junction, VT (US); William Ryan Sillers, Lebanon, NH (US); Trisha Barrett, Bradford, VT (US); Nicky Caiazza, Lebanon, NH (US); Arthur J. Shaw, IV, Grantham, NH (US)

(73) Assignee: Lallemand Hungary Liquidity Management, LLC, Budapest (HU)

( * ) Notice: Subject to any disclaimer, the term of this patent is extended or adjusted under 35 U.S.C. 154(b) by 0 days.

(21) Appl. No.: 14/110,075

(22) PCT Filed: Apr. 5, 2012

(86) PCT No.: PCT/US2012/032443
§ 371 (c)(1),
(2), (4) Date: Mar. 21, 2014

(87) PCT Pub. No.: WO2012/138942
PCT Pub. Date: Oct. 11, 2012

(65) Prior Publication Data
US 2014/0186930 A1 Jul. 3, 2014

Related U.S. Application Data

(60) Provisional application No. 61/472,085, filed on Apr. 5, 2011.

(51) Int. Cl.
*C12N 9/88* (2006.01)
*C12N 15/52* (2006.01)
*C12N 15/74* (2006.01)
*C12N 15/81* (2006.01)
*C12N 9/04* (2006.01)
*C12N 9/02* (2006.01)
*C12P 7/10* (2006.01)
*C12P 7/40* (2006.01)

(52) U.S. Cl.
CPC .............. *C12N 15/81* (2013.01); *C12N 9/0006* (2013.01); *C12N 9/0008* (2013.01); *C12P 7/10* (2013.01); *C12P 7/40* (2013.01); *Y02E 50/16* (2013.01); *Y02E 50/17* (2013.01)
USPC ................ 435/254.21; 435/254.2; 435/254.3; 435/161; 536/23.2; 560/204

(58) Field of Classification Search
CPC ........ C12N 9/88; C12N 9/0008; C12N 15/52; C12N 15/74; C12N 9/001; C12N 9/1029; C12N 9/00; C12N 9/0036; C12N 15/81; C12N 15/63; C12P 7/06; Y02E 50/17; Y02E 50/10; Y02E 50/16; Y02E 50/343
See application file for complete search history.

(56) References Cited

U.S. PATENT DOCUMENTS

| 5,422,267 A | 6/1995 | Yocum et al. |
|---|---|---|
| 7,226,776 B2 | 6/2007 | Ingram et al. |
| 7,846,712 B2 | 12/2010 | Zhang et al. |
| 2005/0106734 A1 | 5/2005 | Richard et al. |
| 2006/0257983 A1 | 11/2006 | Bro et al. |
| 2010/0009418 A1 | 1/2010 | San et al. |
| 2010/0062505 A1 | 3/2010 | Gunawardena et al. |
| 2011/0189744 A1 | 8/2011 | McBride et al. |
| 2011/0312054 A1 | 12/2011 | Brevnova et al. |
| 2012/0003701 A1 | 1/2012 | Brevnova et al. |

FOREIGN PATENT DOCUMENTS

| EP | 2 277 989 A1 | 1/2011 |
|---|---|---|
| WO | WO 03/089626 A1 | 10/2003 |
| WO | WO 2006/009434 A1 | 1/2006 |

(Continued)

OTHER PUBLICATIONS

Ansell, R., et al., "The two isoenzymes for yeast NAD⁺-dependent glycerol 3-phosphate dehydrogenase encoded by *GPD1* and *GPD2* have distinct roles in osmoadaption and redox regulation," *EMBO J.* 16 (9):2179-87, Nature Publishing Group, England (1997).
Bro, C., et al., "In silico aided metabolic engineering of *Saccharomyces cerevisiae* for improved bioethanol production," *Metabol. Eng.* 8:102-11, Elsevier Inc., United States (2006).
Czakó, M. and Márton, L., "The Herpes Simplex Virus Thymidine Kinase Gene as a Conditional Negative-Selection Marker Gene in *Arabidopsis thaliana*," *Plant Physiol.* 104:1067-71, American Society of Plant Physiologists, United States (1994).
Desai, S.G., et al., "Cloning of L-lactate dehydrogenase and elimination of lactic acid production via gene knockout in *Thermoanaerobacterium saccharolyticum* JW/SL-YS485," *Appl. Microbiol. Biotechnol.* 65:600-05, Springer-Verlag, Germany (2004).
Gardiner, D.M. and Howlett, B.J., "Negative selection using thymidine kinase increases the efficiency of recovery of transformants with targeted genes in the filamentous fungus *Leptosphaeria maculans*," *Curr. Genet.* 45:249-55, Springer-Verlag, Germany (2004).

(Continued)

*Primary Examiner* — Kagnew H Gebreyesus
(74) *Attorney, Agent, or Firm* — Nutter McClennen & Fish LLP

(57) ABSTRACT

The present invention provides for novel metabolic pathways to reduce or eliminate glycerol production and increase product formation. More specifically, the invention provides for a recombinant microorganism comprising a deletion of one or more native enzymes that function to produce glycerol and/or regulate glycerol synthesis and one or more native and/or heterologous enzymes that function in one or more engineered metabolic pathways to convert a carbohydrate source, such as lignocellulose, to a product, such as ethanol, wherein the one or more native and/or heterologous enzymes is activated, upregulated, or downregulated. The invention also provides for a recombinant microorganism comprising one or more heterologous enzymes that function to regulate glycerol synthesis and one or more native and/or heterologous enzymes that function in one or more engineered metabolic pathways to convert a carbohydrate source to ethanol, wherein said one or more native and/or heterologous enzymes is activated, upregulated or downregulated.

18 Claims, 63 Drawing Sheets

(56) References Cited

FOREIGN PATENT DOCUMENTS

| | | |
|---|---|---|
| WO | WO 2007/026957 A2 | 3/2007 |
| WO | WO 2009/138877 A2 | 11/2009 |
| WO | WO 2010/019882 A1 | 2/2010 |
| WO | WO 2010/056805 A2 | 5/2010 |
| WO | WO 2010/060056 A2 | 5/2010 |
| WO | WO 2010/075529 A2 | 7/2010 |
| WO | WO 2011/140386 A2 | 11/2011 |
| WO | WO 2011/153516 A2 | 12/2011 |
| WO | WO 2012/019175 A2 | 2/2012 |
| WO | WO 2012/067510 A1 | 5/2012 |

OTHER PUBLICATIONS

Goldstein, A.L. and McCusker, J.H., "Three New Dominant Drug Resistance Cassettes for Gene Disruption in *Saccharomyces cerevisiae*," *Yeast* 15:1541-53, John Wiley & Sons, Ltd., England (1999).

Güldener, U., et al., "A new efficient gene disruption cassette for repeated use in budding yeast," *Nucleic Acids Research* 24 (13):2519-24, Oxford University Press, England (1996).

Guo, Z.P., et al., "Improving ethanol productivity by modification of glycolytic redox factor generation in glycerol-3-phosphate dehydrogenase mutants of an industrial ethanol yeast," *J. Ind. Microbiol. Biotechnol.* 38:935-43, Springer, Germany (2011).

Guo, Z-P., et al., "Minimization of glycerol synthesis in industrial ethanol yeast without influencing its fermentation performance," *Metabol. Eng.* 13(1):49-59, Elsevier, Inc., United States (2010).

Ito-Harashima, S. and McCusker, J.H., "Positive and negative selection LYS5MX gene replacement cassettes for use in *Saccharomyces cervisiae*," *Yeast* 21:53-61, John Wiley & Sons, Ltd., England (2004).

Jain, V.K., et al., "Effect of alternative $NAD^+$-regenerating pathways on the formation of primary and secondary aroma compounds in a *Saccharomyces cerevisiae* glycerol-defective mutant," *Appl. Microbiol. Biotechnol.* 93:131-41, Springer-Verlag, Germany (2012).

Jeppsson, M., et al., "Reduced Oxidative Pentose Phosphate Pathway Flux in Recombinant Xylose-Utilizing *Saccharomyces cerevisiae* Strains Improves the Ethanol Yield from Xylose," *Appl. Environ. Microbiol.* 68(4):1604-09, American Society for Microbiology, United States (2002).

Karhumaa, K., et al., "Comparision of xylose reductase-xylitol dehydrogenase and the xylose isomerase pathways for xylose fermentation by recombinant *Saccharomyces cerevisiae*," *Microbial Cell Factories* 6(5):1-10, BioMed Central, England (2007).

Karlgren., S., et al., "Conditional Osmotic Stress in Yeast: A System to Study Transport through Aquaglyceroporins and Osmostress Signaling," *J. Biol. Chem.* 280(8):7186-93, The American Society for Biochemistry and Molecular Biology, Inc., United States (2005).

Khang, C.H., et al., "A dual selection based, targeted gene replacement tool for *Magnoporthe grisea* and *Fusarium oxysporum*," *Fungal Genetics and Biology* 42:483-92, Elsevier Inc., United States (2005).

Kuyper, M., et al., "Evolutionary engineering of mixed-sugar utilization by a xylose-fermenting *Saccharomyces cerevisiae* strain," *FEMS Yeast Res.* 5:925-34, Elsevier Science B.V., Netherlands (2005).

Kuyper, M., et al., "Metabolic engineering of a xylose-isomerase-expressing *Saccharomyces cerevisiae* strain for rapid anaerobic xylose fermentation," *FEMS Yeast Res.* 5:399-409, Elsevier Science B.V., Netherlands (2005).

Kuyper, M., et al., "Minimal metabolic engineering of *Saccharomyces cerevisiae* for efficient anaerobic xylose fermentation: a proof of principle," *FEMS Yeast Res.* 4:655-64, Elsevier Science B.V., Netherlands (2004).

Leal, T.F. and SÁ-Nogueira, "Purification, characterization and functional analysis of an endo-arabinanase (AbnA) from *Bacillus subtilis*," *FEBS Microbiol Let.* 241:41-48, Elsevier, B.V., Netherlands (2004).

Lidén, G., et al., "A Glycerol-3-Phosphate Dehydrogenase-Deficient Mutant of *Saccharomyces cerevisiae* Expressing the Heterologous XYL1 Gene," *Appl. Environ. Microbiol.* 62(10):3894-96, American Society for Microbiology, United States (1996).

Lynd, L.R., et al., "Microbial Cellulose Utilization: Fundamentals and Biotechnology," *Microbiol. Mol. Biol. Rev.* 66(3):506-77, American Society for Microbiology, United States (2002).

McLaughlin, S.B., et al., "High-Value Renewable Energy from Prairie Grasses," *Environ. Sci. Technol.* 36 (10):2122-29, American Chemical Society, United States (2002).

Medina, V.G., et al., "Elimination of Glycerol Production in Anaerobic Cultures of a *Saccharomyces cerevisiae* Stain Engineered to Use Acetic Acid as an Electron Acceptor," *Appl. Env. Microbiol.* 76 :190-95, American Society for Microbiology, United States (2010).

Mollapour, M. and Piper, P.W., "Hog1 Mitogen-Activated Protein Kinase Phosphorylation Targets the Yeast Fps1 Aquaglyceroporin for Endocytosis, Thereby Rendering Cells Resistant to Acetic Acid," *Mol. Cell. Biol.* 27 (18):6446-56, American Society for Microbiology, United States (2007).

Mota, L.J., et al., "Control of the Arabinose Regulation in *Bacillus subtilis* by AraR In Vivo: Crucial Roles of Operators, Cooperativity, and DNA Looping," *J. Bacteriol.* 183 (14):4190-4201, American Society for Microbiology, United States (2001).

Mota, L.J., et al., "Mode of action of AraR, the key regulator of L-arabinose metabolism in *Bacillus subtilis*," *Mol. Microbiol.* 33 (3):476-89, Blackwell Science Ltd., England (1999).

Nakamura, Y., et al., "Codon usage tabulated from international DNA sequence databases: status for the year 2000," *Nucleic Acids Res.* 28(1):292, Oxford University Press, England (2000).

Nevoigt, E., "Progress in Metabolic Engineering of *Saccharomyces cerevisiae*," *Microbiol. Mol. Biol. Rev.* 72 (3):379-412, American Society for Microbiology, United States (2008).

Páhlman, A-K., et al., "The Yeast Glycerol 3-Phosphatases Gpp1p and Gpp2p are Required for Glycerol Biosynthesis and Differentially Involved in the Cellular Responses to Osmotic, Anaerobic, and Oxidative Stress," *J. Biol. Chem.* 276 (5):3555-63, American Society for Biochemistry and Molecular Biology, United States (2001).

Remize, F., et al., "Glycerol Export and Glycerol-3-phosphate Dehydrogenase, but not Glycerol Phosphatase, are Rate Limiting for Glycerol Production in *Saccharomyces cerevisiae*," *Metab. Eng.* 3 :301-12, Academic Press, United States (2001).

Sá-Nogueira, I., et al., "The *Bacillus subtilis* L-arabinose (*ara*) operon: nucleotide sequence, genetic organization and expression," *Microbiology* 143 :957-69, Society for General Microbiology, Great Britain (1997).

Schleif, R., "Regulation of the L-arabinose operon of *Escherichia coli*," *Trends in Genet.* 16 (12):559-65, Elsevier Science, Ltd., England (2000).

Somogyi, M., "Notes on Sugar Determination," *J. Biol.Chem.* 195:19-23, American Society for Biochemistry and Molecular Biology, United States (1952).

Stairs, C.W., et al., "Eukaryotic pyruvate formate lyase and its activating enzyme were acquired laterally from a firmicute," *Mol. Biol. Evol.*, Advanced Access published Feb. 3, 2011, 42 pages, Oxford University Press, England (Feb. 2011).

Szybalski, W., "Use of the *HPRT* Gene and the HAT Selection Technique in DNA-Mediated Transformation of Mammalian Cells: First Steps Toward Developing Hybridoma Techniques and Gene Therapy," *BioEssays* 14 (7):495-500, The Company of Biologists Limited, England (1992).

Tamás, M.J., et al., "Fps1p controls the accumulation and release of the compatible solute glycerol in yeast osmoregulation," *Mol. Microbiol.* 31 (4):1087-1104, Blackwell Science Ltd, England (1999).

Vallee, B.L. and Hoch, F.L., "Zinc, A Component of Yeast Alcohol Dehydrogenase," *PNAS* 41 (6):327-38, National Academy of Sciences, United States (1955).

Wach, A., et al., "New Heterologous Modules for Classical or PCR-based Gene Disruptions in *Saccharomyces cerevisiae*," *Yeast* 10 :1793-1808, John Wiley & Sons Ltd, England (1994).

Waks, Z. and Silver, P. A., "Engineering a Synthetic Dual-Organism System for Hydrogen Production," *Appl. Env. Microbiol.* 75 (7):1867-75, American Society for Microbiology, United States (2009).

(56) References Cited

OTHER PUBLICATIONS

Watanabe, S., et al., "Cloning, Expression, and Characterization of Bacterial L-Arabinose 1-Dehydrogenase Involved in an Alternative Pathway of L-Arabinose Metabolism," *J. Biol. Chem. 281* (5):2612-23, American Society for Biochemistry and Molecular Biology, United States (2006).

Yu, K.O., et al., "Improvement of Ethanol Yield from Glycerol via Conversion of Pyruvate to Ethanol in Metabolically Engineered *Saccharomyces cerevisiae*," *Appl. Biochem. Biotechnol. 166* :856-65, Springer Science+Business Media, LLC, United States (2012).

Yu, K.O., et al., "Reduction of glycerol production to improve ethanol yield in an engineered *Saccharomyces cerevisiae* using glycerol as a substrate," *J. Biotechnol. 150* :209-14, Elsevier B.V., Netherlands (2010).

"Backtranseq" accessed at emboss.bioinformatics.nl/cgi/bin/emboss/backtranseq on Mar. 28, 2013, 1 page.

"Backtranslation tool citations" accessed at www.entelechon.com/2008/10/backtranslation-tool/ on Mar. 21, 2014, 2 pages.

"Codon Usage Database" accessed at http://www.kazusa.or.jp/codon/ on Apr. 23, 2013, 1 page.

Cavanaugh, M., "GenBank Release 128.0 Available," published Feb. 21, 2002, accessed at http://www.bio.net/bionet/mm/genbankb/2002-February/000110.html on Nov. 25, 2013, 3 pages.

National Microbial Pathogen Data Resource, SEED Subsystem: L-Arabinose_utilization, accessed at http://www.nmpdr.org/FIG/subsys.cgi?user=&ssa_name=L-Arabinose_utilization&request=show_ssa, accessed on Jun. 11, 2013, 7 pages.

Phibro Animal Health Corporation, "Performance Products: Ethanol Red ® (*Saccharomyces cerevisiae* )," accessed at http://www.pahc.com/Phibro/Performance-Products/Catalog/23/Ethanol-Red.html on Dec. 11, 2013, 1 page.

Locus tag No. JDMI_2085, NCBI Database, accessed at http://www.ncbi.nlm.nih.gov/gene/8188856 on Dec. 11, 2013, 2 pages.

Locus tag No. JDMI_2087, NCBI Database, accessed at http://www.ncbi.nlm.nih.gov/gene/?term=JDMI_2087 on May 1, 2013, 3 pages.

Locus tag No. JDM1_2660, NCBI Database, accessed at http://www.ncbi.nlm.nih.gov/gene/?term=JDM1_2660 on Dec. 11, 2013, 2 pages.

Locus tag No. JDM1_2695, NCBI Database, accessed at http://www.ncbi.nlm.nih.gov/gene/?term=JDM1_2695 on May 1, 2013, 3 pages.

Locus tag No. lp_2596, NCBI Database, accessed at http://www.ncbi.nlm.nih.gov/gene/?term=lp_2596 on Dec. 11, 2013, 2 pages.

Locus tag No. lp_2598, NCBI Database, accessed at http://www.ncbi.nlm.nih.gov/gene/?term=lp_2598 on May 1, 2013, 3 pages.

Locus tag No. lp_3313, NCBI Database, accessed at http://www.ncbi.nlm.nih.gov/gene/?term=lp_3313 on May 1, 2013, 3 pages.

Locus tag No. lp_3314, NCBI Database, accessed at http://www.ncbi.nlm.nih.gov/gene/?term=IP_3314 on Dec. 11, 2013, 2 pages.

Hartzog, P.E., et al., "Cytosine deaminase MX cassettes as positive/negative markers in *Saccharomyces cerevisiae*," *Yeast 22* :789-98, Wiley InterScience, England (2005).

Van Walsum, G.P., and Lynd, L.R., "Allocation of ATP to Synthesis of Cells and Hydrolytic Enzymes in Cellulolytic Fermentative Microorganisms: Bioenergetics, Kinetics, and Bioprocessing," *Biotechnol. Bioeng. 58* (2-3):316-20, John Wiley & Sons, England (1998).

Valadi, H., et al., "Improved ethanol production by glycerol-3-phosphate dehydrogenase mutants of *Saccharomyces cerevisiae*," *Appl. Microbiol. Biotechnol. 50* :434-39, Springer-Verlag, Germany (1998).

Michnick, S. et al., "Modulation of Glycerol and Ethanol Yields During Alcoholic Fermentation in *Saccharomyces cerevisiae* Strains Overexpressed or Disrupted for *GPD1* Encoding Glcyerol 3-Phosphate Dehydrogenase," *Yeast 13* :783-93, John Wiley & Sons, England (1997).

International Search Report for International Application No. PCT/US2012/032443, European Patent Office, Rijswijk, Netherlands, mailed on Jul. 2, 2012, 6 pages.

International Preliminary Report on Patentablility, including the Written Opinion of the International Searching Authority, for International Application No. PCT/US2012/032443, The International Bureau of WIPO, Geneva, Switzerland, issued on Oct. 8, 2013, 8 pages.

GPD1 clean deletion
5626 bp gpd2 clean deletion
5930 bp

Figure 12 (cont'd)

```
                    (387) 387               400        410        420        430        440        450        460        470        483
B. adolescentis pflB (315) IDNIIVMKLRIVRFLRTKDY  KFSGDPYW TWSDAGHGDD  TMVTKTSFRL INTLTLEHIG GPEPNTI  KRF A SIDTSAIQ
C. reinhardtii pflB  (379) IDHFVMKLRI RQERT YY LF GDPTW TCVLGCT AGC AM TKTSERL      TIXNL PAPEPN TVL N NLPAPTKF CAKVS DTSSIQ
Piromyces pflB       (355) IDNIIKLRFARHIRTPEYN IF GDPTN VMSLGGMGSDGRTI VTKTSFRV N      TIXNL PAPEPNI VL N KALPKN KF A KYS DTSSIQ
C. cellulolyticum pflB (293) DHFVMKLRV RFLRTPEYEK IF GDPTNITES GEMGLDCEP  VTKNSFRM H      TLENLIGHAPEPN TV WSVLL   ERKYCSY SI NTSSIQ
E. coli pflB         (305) YDHLVMKIPR VRFLRTPEYD  IFSGDPIWATESIGE  LDGRTE VTKNSFRI N      TIY MGPSPEPNW TWS KL PLNFKKF AKYSIDTSSIQ
L. casei pflB        (302) LIDHLVMKLRMVRFLRTEEYNSL SFSGDPIWAILSLAC NDGRHHVTK AFR IK      TLDNMCAAP  T IW  LPGF A TLVSI SI Q
Consensus            (387) LIDHLVMKLRIVRFLRTPEYNALFSGDPTWAT SLGGMG DGRTLVTKTSFRLLN      TLYNLGPAPEPNITV WSEKLPEGFKKFCAKVSIDTSSIQ (485) 485        490        500        510        520        530        540        550        560        570        581
B. adolescentis pflB (413) ESDK  RSHWG -DDAI IACCVSPMRVGKQMQEFF ARVNSAKAI LYAINGGRDEMIGMQVIDKGVIL   F EADGTID  KA  EKEEWLS  TYV
C. reinhardtii pflB  (475) ESDN MSKLFG -SDY IACCVSAMRVGK MQFFGARA  TPKI LLY LNGGRDE  DQVGPK      FA  S PT-APID  YNA  F GHEWLA  YA
Piromyces pflB       (451) ESDA MSAR  -DDYGIACCVSAMRIGK MQFFGARC AKI MIYV NHGKDE  KQVGPD      FA  K   PI     WET        KAFDAVT
C. cellulolyticum pflB (389) ESDP RYYC -DYGIACCVSPMRIG  MQFFGARC MAKA IAKTMIYAINGGRDEK G QVGPI     YA      MQA  T               MFS HE PW K  
E. coli pflB         (401) ENDE  RPD  N   IACCVSPMIV   NOFF GARA IAKTMI YAINGGVDEKLKMQVGPK      SEP IK                
L. casei pflB        (398) ENDD  NEWGT YYGIACCVSAQP  AC  A FGARAIAKTM LYAINGG  DEIQEAQVGPE       PT S          DYK  TF        MDW LA TYV
Consensus            (485) ESDDLMR     FG DDYGIACCVSAMRIGKQMQFFGARANLAK  LLYAINGGRDEMSGMQVGPK   FAPIKS    G  LDYDEVM  KFDKAMDW LAKLYV (581) 581        590        600        610        620        630        640        650        660        677
B. adolescentis pflB (508) VMALNI IHYMHDKYAYES  MALHD  FV YR   CC MGIS  AP IS ACKY AKVY TYNK AKTTPGHENEYVEGADDIIVC TE   EPLYGND
C. reinhardtii pflB  (567) ANMNI IHYMHDKYDYER QMALIDI I VRLLAFG SGI SY DSLSAIKYA V   IDE         CMTD KIEG-S PE GND
Piromyces pflB       (541) VNMNI IHCHDQYCYESLQMAI HD  RRLMAFGV GLS  AD SFSAIKAV  RDAKT             GIIVDFXIP     FF GND
C. cellulolyticum pflB (479) NLNI IHYMHDK AYERLQMAI HDKY LRTMACG GI SVYAD SL SAIKAVKV  RN                GLAVD  E    NF K G
E. coli pflB         (492) TFLNI IHYMHDKYS  ASIMAI HDRDV IRPMACG GLSV AD SL SAIKY AKVKP IRDED                GLAIDE  EG  EPQ GN
L. casei pflB        (489) VMALNI IHYMHDKYYE  A QMALKDC  NFT ATGISL GLSHAVDSI SAIKY HVKAIPDEN                GVAVDFVA NL PP
Consensus            (581) VNTLNI IHYMHDKYAYEAL QMALHDTDV RTMACGIAGLSVVADSLSAIKYAKVKPIRDED          GLAVDFKIEG  DFFHFGNH (678) 678        690        700        710        720        730        740        750        760        774
B. adolescentis pflB (604) DDRADDIAKWVVSTVMG VKRLPVYRDAVPTQSI LTITSNVEYGKATGA FPSGH KKGT PFXAPGANPENGMDSHGM  PSMFSVGK D NDA DGISLT
C. reinhardtii pflB  (646) DDRDEIAEW  VSTESSKLAKQHTYRNSVPTIES  LTITSNVV GKKTC P  GRK  GEPFAPGANP  HGRDAHGALASINSVAK  PYTMC DGISNT
Piromyces pflB       (621) DDRVDFFAH  TDKI NKLRKTPTYRGATHTESI LTITSNVV GKKTC  T DGKKAG  PFAPCNPMHGR FSGAVASLSSVAK NVDSC NDGISNT
C. cellulolyticum pflB (558) DDRVDNIAVM VKSTMEKLEKO RYRHSVPTIL SI LTITSNVV  GKKTC    T PGRK AGE PF G PGANPMHGRDLNGALAVIKS   KLP QFAQDGISYT
E. coli pflB         (571) DPRVE AVE  ERFMK  QKLHTYRDAI PTQSY LTITSNVV  G  KTG T  PGR AGA PFGANPMHGRDQKGAVASLTSVAKIPFA AKEGISYT
L. casei pflB        (569) DDRADA  A  VKTFYNKMNTFHLYRGAK STS  LTITSNVV G NT TPNGC K  GEPT  PGANPA  GAEKNGALASIMS- AKIPHY TALDGISNT
Consensus            (678) DDRVDDIAKWLV TEM KL K HTYR AVPTLSILTITSNVVYGKKTGSTPDGRKKGEPFAPGANPMHGRD GALASL SVAKLPY YALDGISNT
                                                                                                          *                       *
```

AdhE: alcohol dehydrogenase activity

METHODS FOR THE IMPROVEMENT OF PRODUCT YIELD AND PRODUCTION IN A MICROORGANISM THROUGH THE ADDITION OF ALTERNATE ELECTRON ACCEPTORS

CROSS-REFERENCE TO RELATED APPLICATIONS

This application is the National Stage of International Application Number PCT/US2012/032443, filed Apr. 5, 2012, which claims the benefit of U.S. Provisional Application No. 61/472,085, filed Apr. 5, 2011, which are incorporated by reference herein in their entireties.

REFERENCE TO A SEQUENCE LISTING SUBMITTED ELECTRONICALLY VIA EFS-WEB

The content of the electronically submitted sequence listing (Name: 2608_0550001_SEQIDListing.ascii.txt; Size: 437,882 bytes; and Date of Creation: Oct. 4, 2013) is herein incorporated by reference in its entirety.

BACKGROUND OF THE INVENTION

The conversion of biomass, such as corn, sugarcane or other energy crops, as well as simple sugars, to ethanol is routinely completed through the use of yeast fermentation. However, during yeast metabolism a major byproduct of fermentation is glycerol. Glycerol is formed during anaerobic growth as a way for the yeast to balance its redox state and regenerate $NAD^+$ used as a cofactor during glycolysis. It has been shown that the function of glycerol is likely not as a metabolite itself but rather as an electron sink capturing electrons allowing further growth-linked metabolism to continue. As glycerol is a byproduct with low value, it can be an undesirable by-product of fermentation. It would be beneficial to reduce or eliminate this by-product and further direct more carbon towards desired end-products, such as ethanol.

Several strategies are available in the art for the conversion of glycerol to higher value products though biochemical or other means, but relatively little has been demonstrated for the removal or reduction of glycerol and improvement of overall sugar yield to ethanol or other desired end-products of metabolism. Through engineering of alternate pathways, potentially with the simultaneous reduction or deletion of the glycerol pathway, alternate or replacement electron acceptors for the regeneration of $NAD^+$ can be used during yeast metabolism. Such alternate or replacement electron acceptors could be molecules such as formate or hydrogen.

The elimination of glycerol synthesis genes has been demonstrated but removal of this pathway completely blocked anaerobic growth of the yeast, preventing useful application during an industrial process. Ansell, R., et al., *EMBO J.* 16:2179-87 (1997); Pahlman, A-K., et al., *J. Biol. Chem.* 276:3555-63 (2001); Guo, Z P., et al., *Metab. Eng.* 13:49-59 (2011). Other methods to bypass glycerol formation require the co-utilization of additional carbon sources, such as xylose or acetate, to serve as electron acceptors. Lidén, G., et al., *Appl. Env. Microbiol.* 62:3894-96 (1996); Medina, V. G., et al., *Appl. Env. Microbiol.* 76:190-195 (2010). By incorporating a formate pathway as an alternate electron acceptor, glycerol formation can be bypassed and ethanol yield can be increased. The engineering of a pyruvate formate lyase from *E. coli*, which is capable of converting pyruvate to formate, has been done to increase formate production. Waks, Z., and Silver, P. A., *Appl. Env. Microbiol.* 75:1867-1875 (2009). Formate engineering in Waks and Silver was done, however, to provide a source of formate in *S. cerevisiae* for the production of hydrogen by a secondary microorganism, *E. coli*. Waks and Silver did not combine formate production with the removal of glycerol formation, and the use of formate as an alternate electron acceptor for the reduction of glycerol was not proposed or evaluated. Thus, despite prior efforts to bypass and/or eliminate glycerol production, there exists a need for the engineering of alternate or replacement electron acceptors in a cell to direct more carbon towards desired end-products, such as ethanol.

The importance of engineering alternate or replacement electron acceptors is exemplified in the process of corn mash fermentation. About 16 billion gallons of corn-based ethanol are produced annually, so even small increases in ethanol yield, such as 5-10%, can translate into an extra billion or so gallons of ethanol over current yields. Ethanol production from corn mash typically results in glycerol yields ranging from 10-12 g/L. See Yang, R. D., et al., "Pilot plant studies of ethanol production from whole ground corn, corn flour, and starch," *Fuel Alcohol U.S.A.*, Feb. 13-16, 1982 (reported glycerol levels to be as high as 7.2% w/w of initial sugar consumed in normal corn mash fermentations or approximately 1.4 g/100 mL using 20% sugar). By reducing or eliminating the glycerol yield in the production of ethanol from corn and re-engineering metabolic processes, increased ethanol yields can be achieved. Additional benefits may be gained in the production of ethanol from corn. Corn mash is a nutrient rich medium, in some cases containing lipid and protein content that can be >3% of the total fermentation volume. As a result of the energy contained in these components, even higher ethanol yields may be achieved than what is predicted using, for example, pure sugar. The additional increases can come from the metabolism of lipids or amino acids in the corn mash medium. The recombinant cells and methods of the invention enable increasing ethanol yields from biomass fermentation by reducing or eliminating glycerol.

BRIEF SUMMARY OF THE INVENTION

The invention is generally directed to the reduction or removal of glycerol production in a host cell and to the engineering of an alternate electron acceptor for the regeneration of $NAD^+$.

One aspect of the invention relates to a recombinant microorganism comprising: a deletion of one or more native enzymes that function to produce glycerol and/or regulate glycerol synthesis; and one or more native and/or heterologous enzymes that function in one or more engineered metabolic pathways to convert a carbohydrate source to ethanol, wherein said one or more native and/or heterologous enzymes is activated, upregulated or downregulated. In some embodiments, the recombinant microorganism produces less glycerol than a control recombinant microorganism without deletion of said one or more native enzymes that function to produce glycerol and/or regulate glycerol synthesis. In some embodiments, the carbohydrate source is biomass. In some embodiments, the biomass comprises a lignocellulosic material selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, agave, and combinations thereof. In some embodiments, the biomass is corn mash or corn starch.

In particular aspects, the one or more native enzymes that function to produce glycerol are encoded by a gpd1 polynucleotide, a gpd2 polynucleotide, or both a gpd1 polynucleotide and a gpd2 polynucleotide. In certain embodiments, the recombinant microorganism further comprises a native and/or heterologous gpd1 polynucleotide operably linked to a native gpd2 promoter polynucleotide. In other aspects, the one or more native enzymes that function to produce glycerol are encoded by a gpp1 polynucleotide, a gpp2 polynucleotide, or both a gpp1 polynucleotide and a gpp2 polynucleotide.

In particular aspects, the one or more native enzymes that function to regulate glycerol synthesis are encoded by an fps1 polynucleotide.

In further aspects, the engineered metabolic pathways comprise conversion of pyruvate to acetyl-CoA and formate. In certain embodiments, pyruvate is converted to acetyl-CoA and formate by a pyruvate formate lyase (PFL). In some embodiments, the PFL is of prokaryotic or eukaryotic origin. In some embodiments, PFL is from one or more of a *Bifidobacteria*, an *Escherichia*, a *Thermoanaerobacter*, a *Clostridia*, a *Streptococcus*, a *Lactobacillus*, a *Chlamydomonas*, a *Piromyces*, a *Neocallimastix*, or a *Bacillus* species. In some embodiments, PFL is from one or more of a *Bacillus licheniformis*, a *Streptococcus thermophilus*, a *Lactobacillus plantarum*, a *Lactobacillus casei*, a *Bifidobacterium adolescentis*, a *Clostridium cellulolyticum*, a *Escherichia coli*, a *Chlamydomonas reinhardtii* PflA, a *Piromyces* sp. E2, or a *Neocallimastix frontalis*. In one embodiment, PFL is from a *Bifidobacterium adolescentis*.

In additional aspects, the engineered metabolic pathways comprise conversion of acetyl-CoA to ethanol. In certain embodiments, acetyl-CoA is converted to acetaldehyde by an acetaldehyde dehydrogenase and acetaldehyde is converted to ethanol by an alcohol dehydrogenase. In certain embodiments, acetyl-CoA is converted to ethanol by a bifunctional acetaldehyde/alcohol dehydrogenase. In some embodiments, the acetaldehyde dehydrogenase, alcohol dehydrogenase, or bifuntional acetaldehyde/alcohol dehydrogenase is of prokaryotic or eukaryotic origin. In one embodiment, acetaldehyde dehydrogenase is from *C. phytofermentans*. In some embodiments, bifunctional acetaldehyde/alcohol dehydrogenase is from an *Escherichia*, a *Clostridia*, a *Chlamydomonas*, a *Piromyces*, or a *Bifidobacteria* species. In some embodiments, bifunctional acetaldehyde/alcohol dehydrogenase is from *Escherichia coli*, *Clostridium phytofermentans*, *Chlamydomonas reinhardtii*, *Piromyces* sp. E2, or *Bifidobacterium adolescentis*. In one embodiment, bifunctional acetaldehyde/alcohol dehydrogenase is from a *Bifidobacterium adolescentis* or *Piromyces* sp. E2.

In further aspects, the recombinant microorganism comprises a deletion of one or more native enzymes encoded by an fdh1 polynucleotide, an fdh2 polynucleotide, or both an fdh1 polynucleotide and an fdh2 polynucleotide.

In certain embodiments, the carbohydrate source for the recombinant microorganism is lignocellulose. In certain embodiments, the recombinant microorganism produces ethanol. In certain embodiments, the recombinant microorganism produces formate.

In certain embodiments, the recombinant microorganism is selected from the group consisting of *Saccharomyces cerevisiae*, *Kluyveromyces lactis*, *Kluyveromyces marxianus*, *Pichia pastoris*, *Yarrowia lipolytica*, *Hansenula polymorphs*, *Phaffia rhodozyma*, *Candida utliis*, *Arxula adeninivorans*, *Pichia stipitis*, *Debaryomyces hansenii*, *Debaryomyces polymorphus*, *Schizosaccharomyces pombe*, *Candida albicans*, and *Schwanniomyces occidentalis*. In one embodiment, the recombinant microorganism is *Saccharomyces cerevisiae*.

In certain embodiments, the recombinant microorganism comprises one or more native enzymes that function to produce glycerol encoded by both a gpd1 polynucleotide and a gpd2 polynucleotide, an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to produce glycerol encoded by both a gpp1 polynucleotide and a gpp2 polynucleotide, an engineered metabolic pathway that comprises conversion of pyruvate to acetyl-CoA and formate by a pyruvate formate lyase. In further embodiments, one engineered metabolic pathway of the recombinant microorganism converts acetyl-CoA to ethanol by a bifunctional acetaldehyde/alcohol dehydrogenase and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to regulate glycerol synthesis encoded by an fps1 polynucleotide, an engineered metabolic pathway that comprises conversion of pyruvate to acetyl-CoA and formate by a pyruvate formate lyase. In further embodiments, one engineered metabolic pathway of the recombinant microorganism converts acetyl-CoA to ethanol by a bifunctional acetaldehyde/alcohol dehydrogenase and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to regulate glycerol synthesis encoded by an fps1 polynucleotide and one or more native enzymes that function to produce glycerol encoded by both a gpd1 polynucleotide and a gpd2 polynucleotide, and an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to regulate glycerol synthesis encoded by an fps1 polynucleotide, an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to produce glycerol encoded by both a gpd1 polynucleotide and a gpd2 polynucleotide, an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, and the recombinant microorganism further comprises a native and/or heterologous gpd1 polynucleotide operably linked to a native gpd2 promoter polynucleotide.

In certain embodiments, the recombinant microorganism comprises one or more native enzymes that function to produce glycerol encoded by both a gpd1 polynucleotide and a gpd2 polynucleotide, and an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide and a deletion of one or more native enzymes encoded by both an fdh1 polynucleotide and an fdh2 polynucleotide.

In certain embodiments, the recombinant microorganism comprises one or more native enzymes that function to produce glycerol encoded by both a gpd1 polynucleotide and a gpd2 polynucleotide and one or more native enzymes that function to regulate glycerol synthesis encoded by an fps1 polynucleotide, and an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide.

In certain embodiments, the recombinant microorganism comprises one or more native enzymes that function to produce glycerol encoded by both a gpd1 polynucleotide and a gpd2 polynucleotide and one or more native enzymes that function to regulate glycerol synthesis encoded by an fps1 polynucleotide, and an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide and a deletion of one or more native enzymes encoded by both an fdh1 polynucleotide and an fdh2 polynucleotide.

In some embodiments, the deletion of one or more native enzymes that function to produce glycerol and/or regulate glycerol synthesis in the recombinant microorganism reduces glycerol formation by: more than about 10% of the glycerol produced by a recombinant microorganism without a deletion of one or more native enzymes that function to produce glycerol and/or regulate glycerol synthesis; more than about 20% of the glycerol produced by a recombinant microorganism without a deletion of one or more native enzymes that function to produce glycerol and/or regulate glycerol synthesis; more than about 30% of the glycerol produced by a recombinant microorganism without a deletion of one or more native enzymes that function to produce glycerol and/or regulate glycerol synthesis; more than about 40% of the glycerol produced by a recombinant microorganism without a deletion of one or more native enzymes that function to produce glycerol and/or regulate glycerol synthesis; more than about 50% of the glycerol produced by a recombinant microorganism without a deletion of one or more native enzymes that function to produce glycerol and/or regulate glycerol synthesis; more than about 60% of the glycerol produced by a recombinant microorganism without a deletion of one or more native enzymes that function to produce glycerol and/or regulate glycerol synthesis; more than about 70% of the glycerol produced by a recombinant microorganism without a deletion of one or more native enzymes that function to produce glycerol and/or regulate glycerol synthesis; more than about 80% of the glycerol produced by a recombinant microorganism without a deletion of one or more native enzymes that function to produce glycerol and/or regulate glycerol synthesis; more than about 90% of the glycerol produced by a recombinant microorganism without a deletion of one or more native enzymes that function to produce glycerol and/or regulate glycerol synthesis; more than about 95% of the glycerol produced by a recombinant microorganism without a deletion of one or more native enzymes that function to produce glycerol and/or regulate glycerol synthesis; or more than about 99% of the glycerol produced by a recombinant microorganism without a deletion of one or more native enzymes that function to produce glycerol and/or regulate glycerol synthesis.

In some embodiments, the recombinant microorganism produces an amount of formate selected from: at least about 0.012 g/L in 24 hours; at least about 0.022 g/L in 48 hours; or at least about 2.5 g/L in 142 hours.

In some embodiments, the recombinant microorganism produces a formate yield selected from: at least about 0.05-fold more formate than is produced by a recombinant microorganism without activation, upregulation, or downregulation of one or more native and/or heterologous enzymes; at least about 0.1-fold more formate than is produced by a recombinant microorganism without activation, upregulation, or downregulation of one or more native and/or heterologous enzymes; at least about 0.5-fold more formate than is produced by a recombinant microorganism without activation, upregulation, or downregulation of one or more native and/or heterologous enzymes; at least about 1.0-fold more formate than is produced by a recombinant microorganism without activation, upregulation, or downregulation of one or more native and/or heterologous enzymes; at least about 5.0-fold more formate than is produced by a recombinant microorganism without activation, upregulation, or downregulation of one or more native and/or heterologous enzymes; at least about 10.0-fold more formate than is produced by a recombinant microorganism without activation, upregulation, or downregulation of one or more native and/or heterologous enzymes; at least about 20.0-fold more formate than is produced by a recombinant microorganism without activation, upregulation, or downregulation of one or more native and/or heterologous enzymes; at least about 30.0-fold more formate than is produced by a recombinant microorganism without activation, upregulation, or downregulation of one or more native and/or heterologous enzymes; at least about 40.0-fold more formate than is produced by a recombinant microorganism without activation, upregulation, or downregulation of one or more native and/or heterologous enzymes; at least about 50.0-fold more formate than is produced by a recombinant microorganism without activation, upregulation, or downregulation of one or more native and/or heterologous enzymes; at least about 75.0-fold more formate than is produced by a recombinant microorganism without activation, upregulation, or downregulation of one or more native and/or heterologous enzymes; or at least about 100-fold more formate than is produced by a recombinant microorganism without activation, upregulation, or downregulation of one or more native and/or heterologous enzymes.

In some embodiments, the recombinant microorganism produces an ethanol yield selected from: at least about 1% more ethanol than is produced by a recombinant microorganism without activation, upregulation, or downregulation of one or more native and/or heterologous enzymes; at least about 2% more ethanol than is produced by a recombinant microorganism without activation, upregulation, or downregulation of one or more native and/or heterologous enzymes; at least about 3% more ethanol than is produced by a recombinant microorganism without activation, upregulation, or downregulation of one or more native and/or heterologous enzymes; at least about 4% more ethanol than is produced by a recombinant microorganism without activation, upregulation, or downregulation of one or more native and/or heterologous enzymes; at least about 5% more ethanol than is produced by a recombinant microorganism without activation, upregulation, or downregulation of one or more native and/or heterologous enzymes; at least about 10% more ethanol than is produced by a recombinant microorganism without activation, upregulation, or downregulation of one or more native and/or heterologous enzymes; at least about 20% more ethanol than is produced by a recombinant microorganism without activation, upregulation, or downregulation of one or more native and/or heterologous enzymes; at least about 30% more ethanol than is produced by a recombinant microorganism without activation, upregulation, or downregulation of one or more native and/or heterologous enzymes; at least about 40% more ethanol than is produced by a recombinant microorganism without activation, upregulation, or downregulation of one or more native and/or heterologous enzymes; at least about 50% more ethanol than is produced by a recombinant microorganism without activation, upregulation, or downregulation of one or more native and/or heterologous enzymes; at least about 60% more ethanol than is produced by a recombinant microorganism without activation, upregulation, or downregulation of one or more native and/or heterologous enzymes; at least about 70% more ethanol than is produced by a recombinant microorganism without activation, upregulation, or downregulation of one or more native and/or heterologous enzymes; at least about 80% more ethanol than is produced by a recombinant microorganism without activation, upregulation, or downregulation of one or more native and/or heterologous enzymes; at least about 90% more ethanol than is produced by a recombinant microorganism without activation, upregulation, or downregulation of one or more native and/or heterologous enzymes; at least about 95% more ethanol than is produced by a recombinant microorganism without activation, upregulation, or downregulation of one or more native and/or heterologous enzymes; or at least about 99% more ethanol than is produced by a recombinant microorganism without activation, upregulation, or downregulation of one or more native and/or heterologous enzymes.

In some embodiments, the conversion of the carbohydrate source to ethanol by the recombinant microorganism, or the enzymes engineered therein, is under anaerobic conditions.

In some embodiments, the recombinant microorganism has an acetate uptake (g/L) under anaerobic conditions selected from: at least about 1% more acetate uptake than that taken up by a recombinant microorganism without activation, upregulation, or downregulation of one or more native and/or heterologous enzymes; at least about 10% more acetate uptake than that taken up by a recombinant microorganism without activation, upregulation, or downregulation of one or more native and/or heterologous enzymes; at least about 20% more acetate uptake than that taken up by a recombinant microorganism without activation, upregulation, or downregulation of one or more native and/or heterologous enzymes; at least about 30% more acetate uptake than that taken up by a recombinant microorganism without activation, upregulation, or downregulation of one or more native and/or heterologous enzymes; at least about 40% more acetate uptake than that taken up by a recombinant microorganism without activation, upregulation, or downregulation of one or more native and/or heterologous enzymes; at least about 50% more acetate uptake than that taken up by a recombinant microorganism without activation, upregulation, or downregulation of one or more native and/or heterologous enzymes; at least about 60% more acetate uptake than that taken up by a recombinant microorganism without activation, upregulation, or downregulation of one or more native and/or heterologous enzymes; at least about 70% more acetate uptake than that taken up by a recombinant microorganism without activation, upregulation, or downregulation of one or more native and/or heterologous enzymes; at least about 80% more acetate uptake than that taken up by a recombinant microorganism without activation, upregulation, or downregulation of one or more native and/or heterologous enzymes; and at least about 90% more acetate uptake than that taken up by a recombinant microorganism without activation, upregulation, or downregulation of one or more native and/or heterologous enzymes.

In some embodiments, the recombinant microorganism produces more ethanol at a slower glucose utilization rate compared to a recombinant microorganism without deletion of one or more native enzymes that function to produce glycerol and/or regulate glycerol synthesis, wherein the glucose utilization rate is selected from: at least about 1% less glucose used per hour than that used by a recombinant microorganism without activation, upregulation, or downregulation of one or more native and/or heterologous enzymes; at least about 5% less glucose used per hour than that used by a recombinant microorganism without activation, upregulation, or downregulation of one or more native and/or heterologous enzymes; at least about 10% less glucose used per hour than that used by a recombinant microorganism without activation, upregulation, or downregulation of one or more native and/or heterologous enzymes; at least about 20% less glucose used per hour than that used by a recombinant microorganism without activation, upregulation, or downregulation of one or more native and/or heterologous enzymes; at least about 30% less glucose used per hour than that used by a recombinant microorganism without activation, upregulation, or downregulation of one or more native and/or heterologous enzymes; at least about 40% less glucose used per hour than that used by a recombinant microorganism without activation, upregulation, or downregulation of one or more native and/or heterologous enzymes; at least about 50% less glucose used per hour than that used by a recombinant microorganism without activation, upregulation, or downregulation of one or more native and/or heterologous enzymes; at least about 60% less glucose used per hour than that used by a recombinant microorganism without activation, upregulation, or downregulation of one or more native and/or heterologous enzymes; at least about 70% less glucose used per hour than that used by a recombinant microorganism without activation, upregulation, or downregulation of one or more native and/or heterologous enzymes; at least about 80% less glucose used per hour than that used by a recombinant microorganism without activation, upregulation, or downregulation of one or more native and/or heterologous enzymes; and at least about 90% less glucose used per hour than that used by a recombinant microorganism without activation, upregulation, or downregulation of one or more native and/or heterologous enzymes.

Another aspect of the invention relates to a recombinant microorganism comprising: one or more heterologous enzymes that function to regulate glycerol synthesis, wherein said one or more heterologous enzymes is activated, upregulated or downregulated; and one or more native and/or heterologous enzymes that function in one or more engineered metabolic pathways to convert a carbohydrate source to ethanol, wherein said one or more native and/or heterologous enzymes is activated, upregulated or downregulated. In certain embodiments, the one or more heterologous enzymes that function to regulate glycerol synthesis are encoded by an fps1 polynucleotide. In one embodiment, the fps1 polynucleotide is from *Escherichia coli*.

In some embodiments, one of the engineered metabolic pathways of the above recombinant microorganism comprises conversion of pyruvate to acetyl-CoA and formate. In certain embodiments, pyruvate is converted to acetyl-CoA and formate by a pyruvate formate lyase (PFL). In some embodiments, PFL is of prokaryotic or eukaryotic origin. In some embodiments, PFL is from one or more of a *Bifidobacteria*, an *Escherichia*, a *Thermoanaerobacter*, a *Clostridia*, a *Streptococcus*, a *Lactobacillus*, a *Chlamydomonas*, a *Piromyces*, a *Neocallimastix*, or a *Bacillus* species. In some embodiments, the PFL is from one or more of a *Bacillus licheniformis*, a *Streptococcus thermophilus*, a *Lactobacillus plantarum*, a *Lactobacillus casei*, a *Bifidobacterium adolescentis*, a *Clostridium cellulolyticum*, a *Escherichia coli*, a *Chlamydomonas reinhardtii* PflA, a *Piromyces* sp. E2, or a *Neocallimastix frontalis*. In one embodiment, PFL is from a *Bifidobacterium adolescentis*.

In some embodiments, one of said engineered metabolic pathways of the above recombinant microorganism comprises conversion of acetyl-CoA to ethanol. In some embodiments, acetyl-CoA is converted to acetaldehyde by an acetaldehyde dehydrogenase and acetaldehyde is converted to ethanol by an alcohol dehydrogenase. In other embodiments, acetyl-CoA is converted to ethanol by a bifunctional acetaldehyde/alcohol dehydrogenase. In some embodiments, the acetaldehyde dehydrogenase, alcohol dehydrogenase, or bifuntional acetaldehyde/alcohol dehydrogenase is of prokaryotic or eukaryotic origin. In one embodiment, acetaldehyde dehydrogenase is from *C. phytofermentans*. In certain embodiments, the bifunctional acetaldehyde/alcohol dehydrogenase is from an *Escherichia*, a *Clostridia*, a *Chlamydomonas*, a *Piromyces*, or a *Bifidobacteria* species. In some embodiments, the bifunctional acetaldehyde/alcohol dehydrogenase is from *Escherichia coli, Clostridium phytofermentans, Chlamydomonas reinhardtii, Piromyces* sp. E2, or *Bifidobacterium adolescentis*. In one embodiment, the bifunctional acetaldehyde/alcohol dehydrogenase is from a *Bifidobacterium adolescentis* or *Piromyces* sp. E2.

In further aspects, the recombinant microorganism comprises a deletion of one or more native enzymes encoded by an fdh1 polynucleotide, an fdh2 polynucleotide, or both an fdh1 polynucleotide and an fdh2 polynucleotide.

In some embodiments, the recombinant microorganism produces ethanol. In other embodiments, the recombinant microorganism produces formate. In some embodiments, the recombinant microorganism is selected from the group consisting of *Saccharomyces cerevisiae, Kluyveromyces lactis, Kluyveromyces marxianus, Pichia pastoris, Yarrowia lipolytica, Hansenula polymorphs, Phaffia rhodozyma, Candida utliis, Arxula adeninivorans, Pichia stipitis, Debaryomyces hansenii, Debaryomyces polymorphus, Schizosaccharomyces pombe, Candida albicans*, and *Schwanniomyces occidentalis*. In one embodiment, the recombinant microorganism is *Saccharomyces cerevisiae*.

In some embodiments, the recombinant microorganisms of the invention further comprise one or more native and/or heterologous enzymes that function in one or more engineered metabolic pathways to convert xylose to xylulose-5-phosphate and/or arabinose to xylulose-5-phosphate, wherein the one or more native and/or heterologous enzymes are activated, upregulated or downregulated.

In some embodiments, the recombinant microorganisms of the invention further comprise one or more native and/or heterologous enzymes which encodes a saccharolytic enzyme, including amylases, cellulases, hemicellulases, cellulolytic and amylolytic accessory enzymes, inulinases, levanases, and pentose sugar utilizing enzymes. In one aspect, the saccharolytic enzyme is an amylase, where the amylase is selected from *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum* or *Arabidopsis thaliana*. In another aspect, the saccharolytic enzyme is an amylase from *S. fibuligera* glucoamylase (glu-0111-00).

Another aspect of the invention relates to a method for decreasing cellular glycerol comprising contacting biomass with a recombinant microorganism of the invention. A further aspect of the invention relates to a method for increasing cytosolic formate comprising contacting biomass with a recombinant microorganism of the invention. Another aspect of the invention relates to a process for converting biomass to ethanol comprising contacting biomass with a recombinant microorganism of the invention. In some embodiments, the biomass comprises lignocellulosic biomass. In some embodiments, the lignocellulosic biomass is selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, agave, and combinations thereof. In some embodiments, the biomass is corn mash or corn starch.

In another aspect, the present invention also describes industrial yeast strains that express enzymes for the production of fuel ethanol from corn starch.

BRIEF DESCRIPTION OF THE DRAWINGS/FIGURES

DETAILED DESCRIPTION OF THE INVENTION

Definitions

Figure 1:
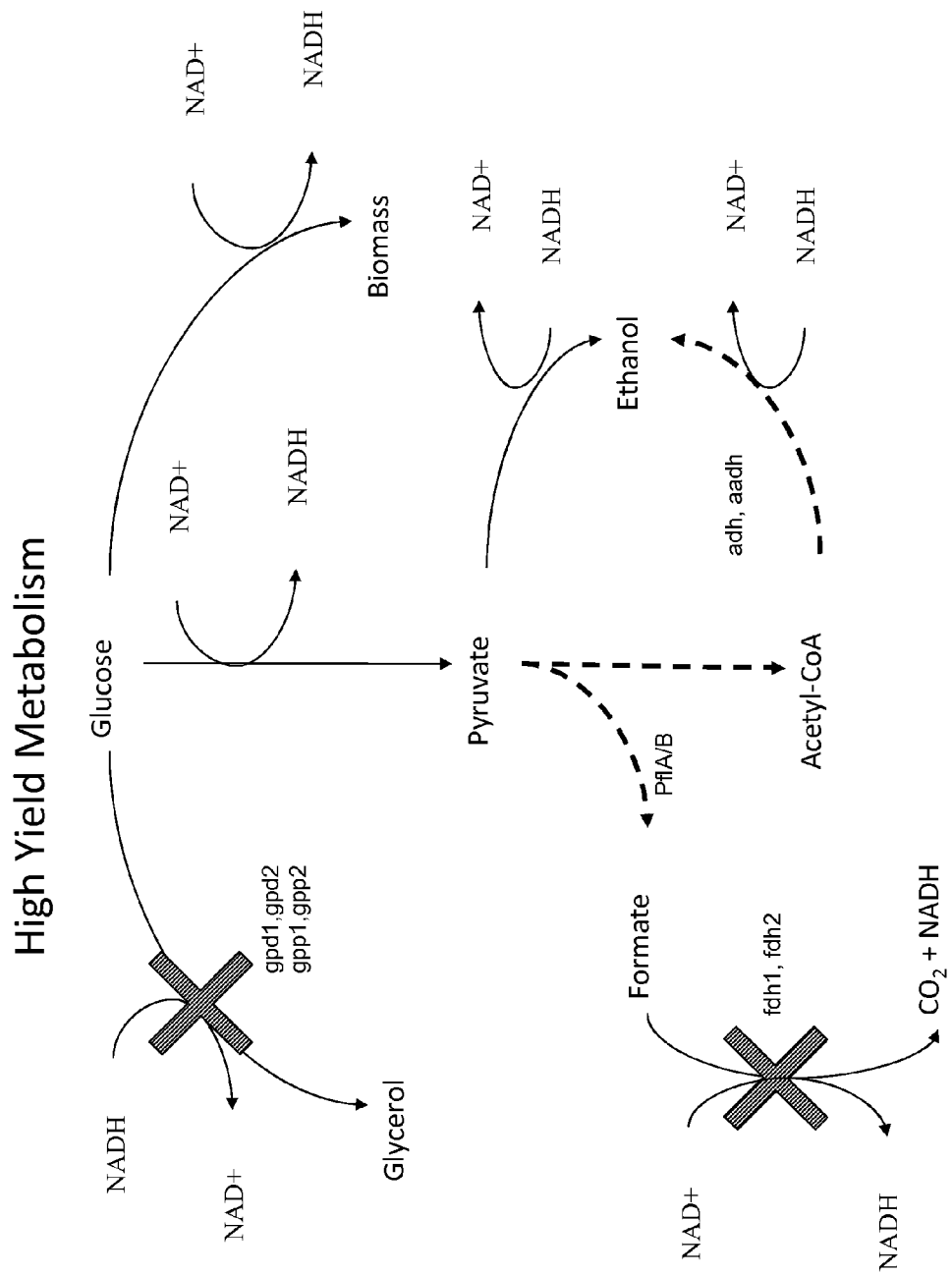
FIG. 1 shows a schematic of high yield metabolism.
Figure 2:
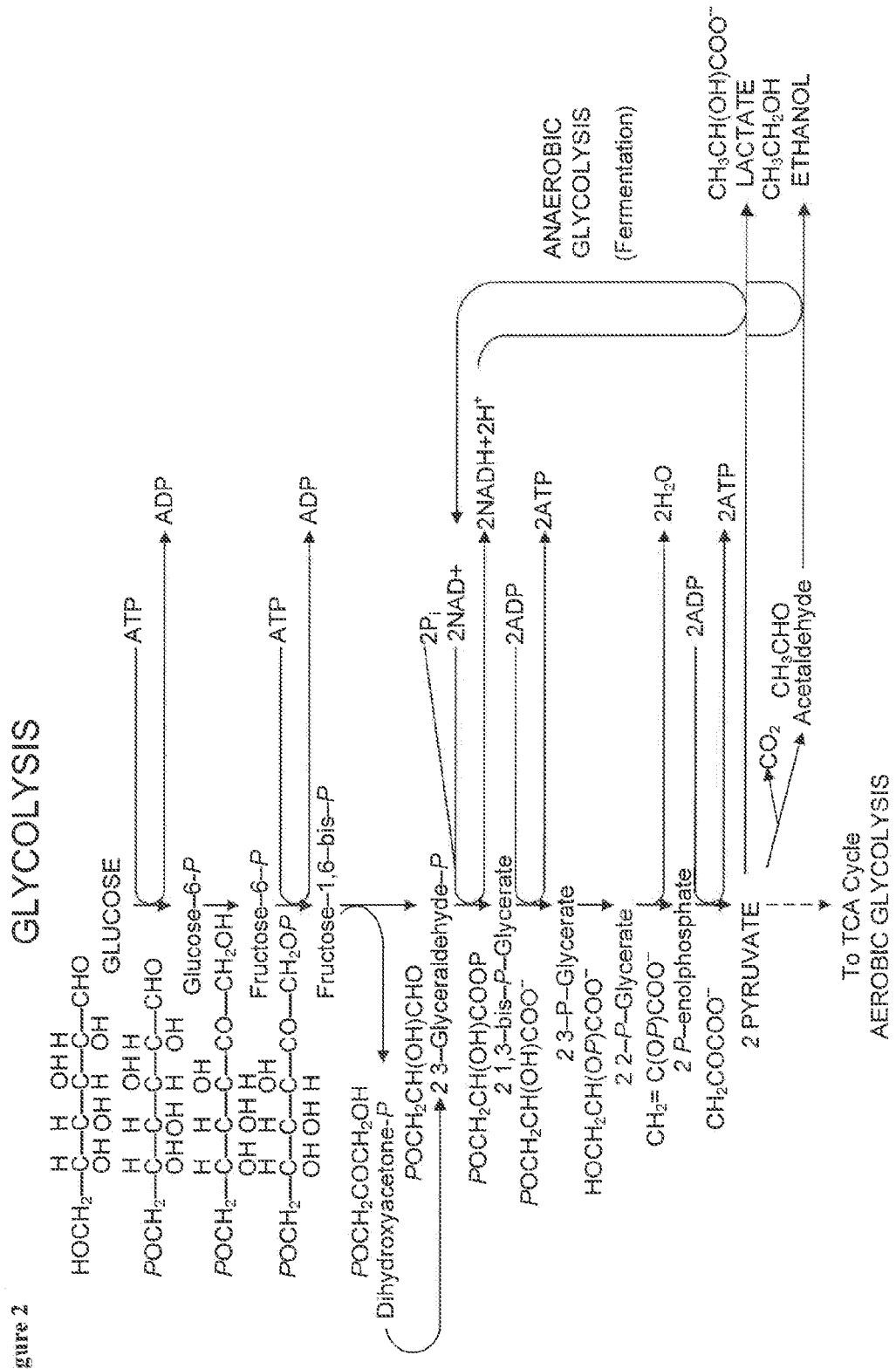
FIG. 2 depicts the glycolysis pathway.
Figure 3:
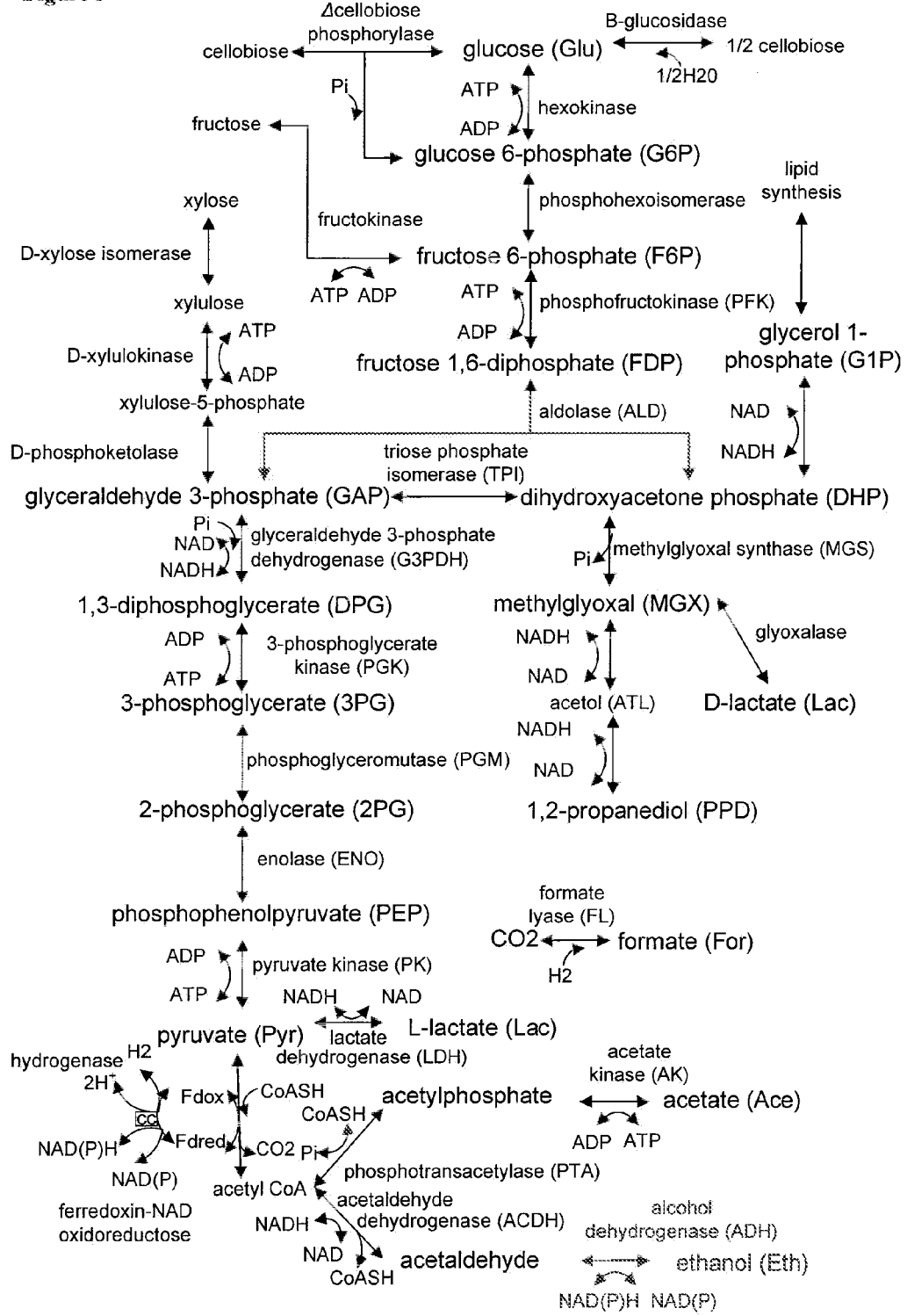
FIG. 3 shows a schematic of the glycolysis/fermentation pathway.
Figure 4:
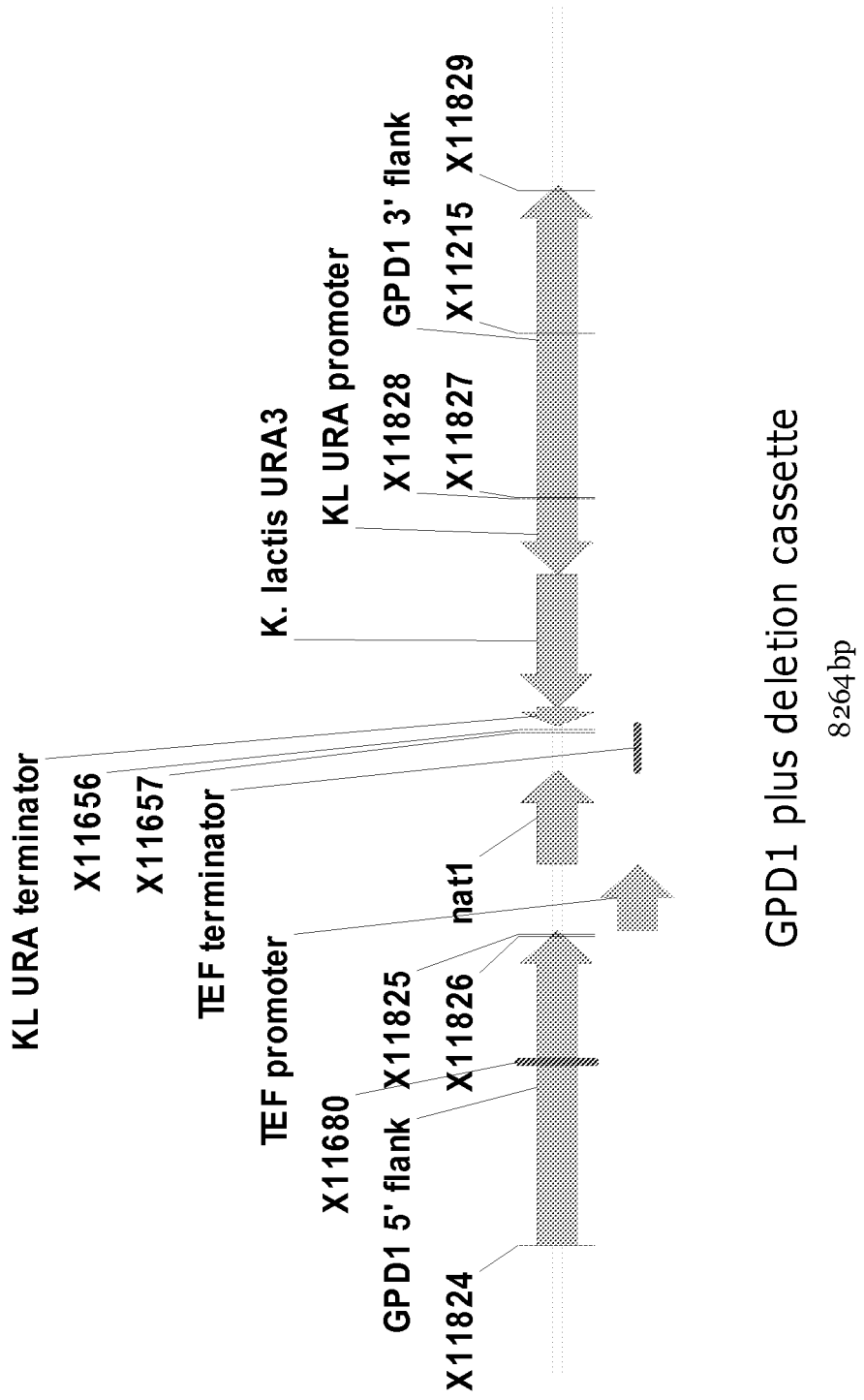
FIG. 4 shows a map depicting location of primers used to make marked deletion of GPD1.
Figure 5:
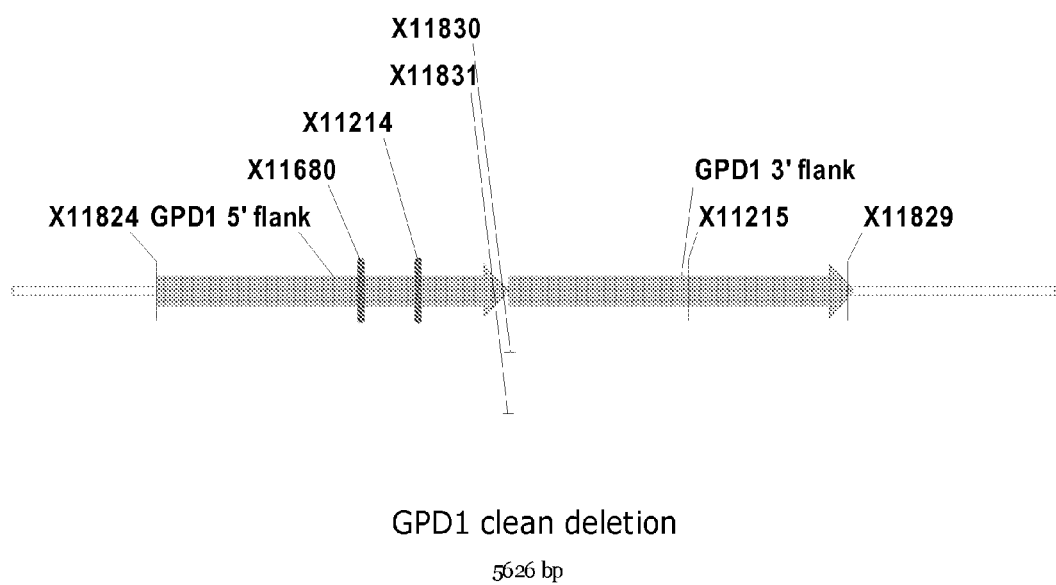
FIG. 5 shows a map depicting location of primers used to remove marker from GPD1 locus.
Figure 6:
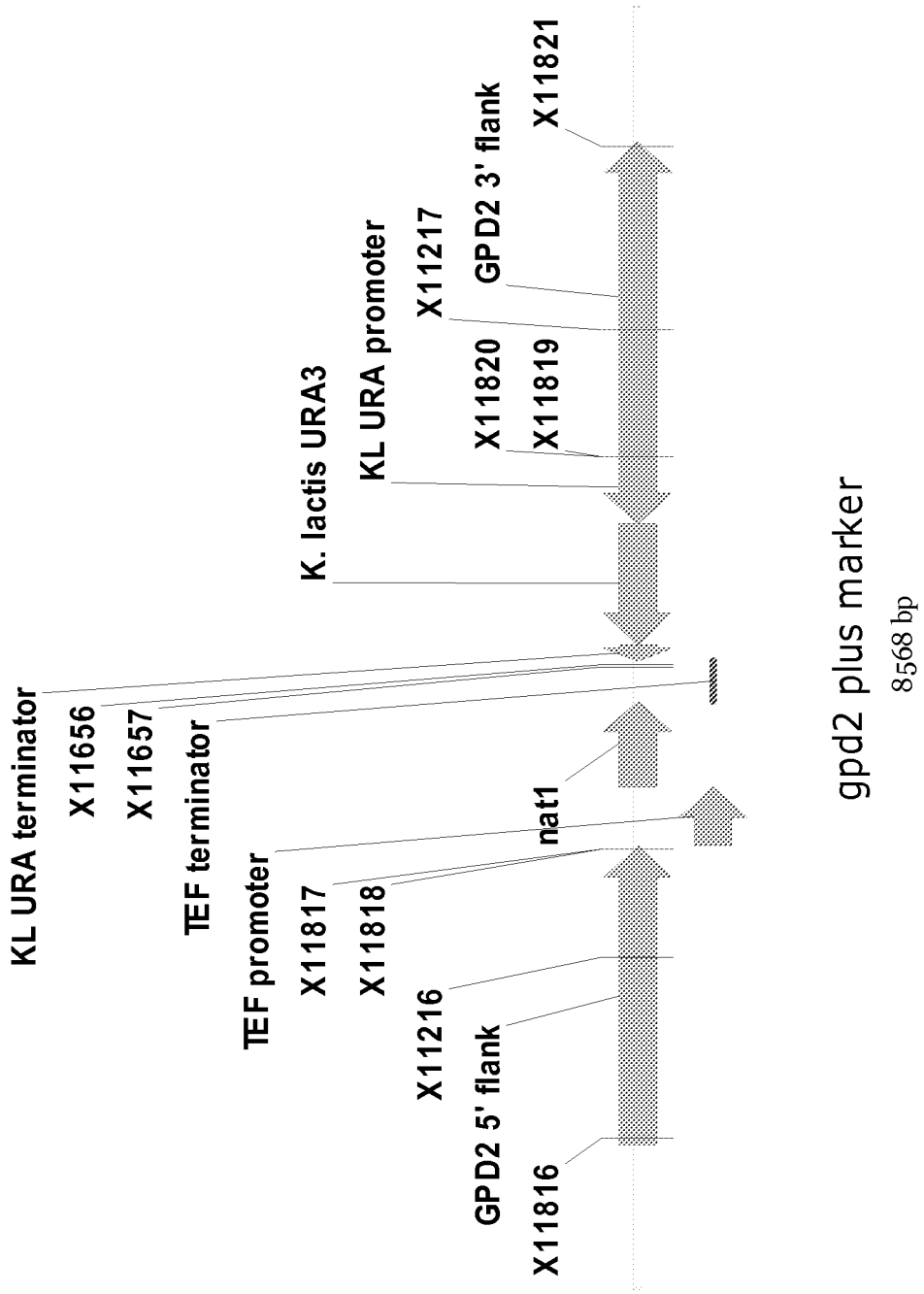
FIG. 6 shows a map depicting location of primers used to make marked deletion of GPD2.
Figure 7:
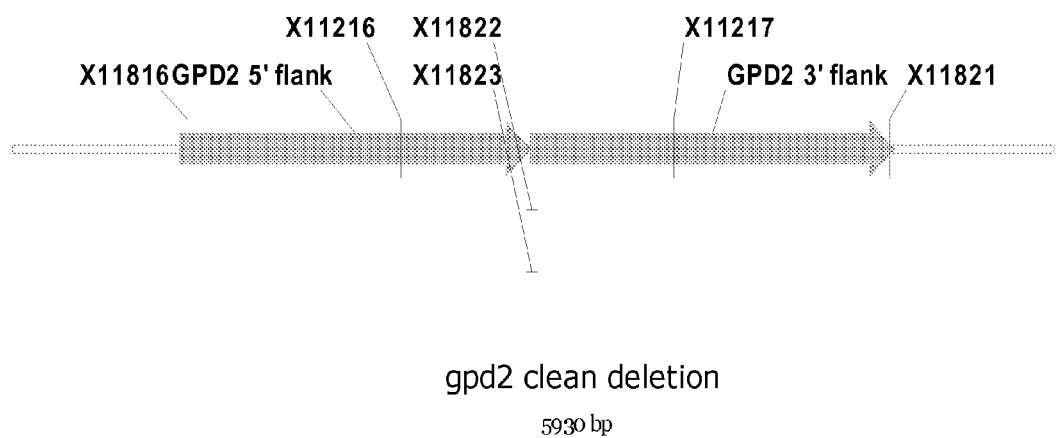
FIG. 7 shows a map depicting location of primers used to remove marker from GPD2 locus.
Figure 8:
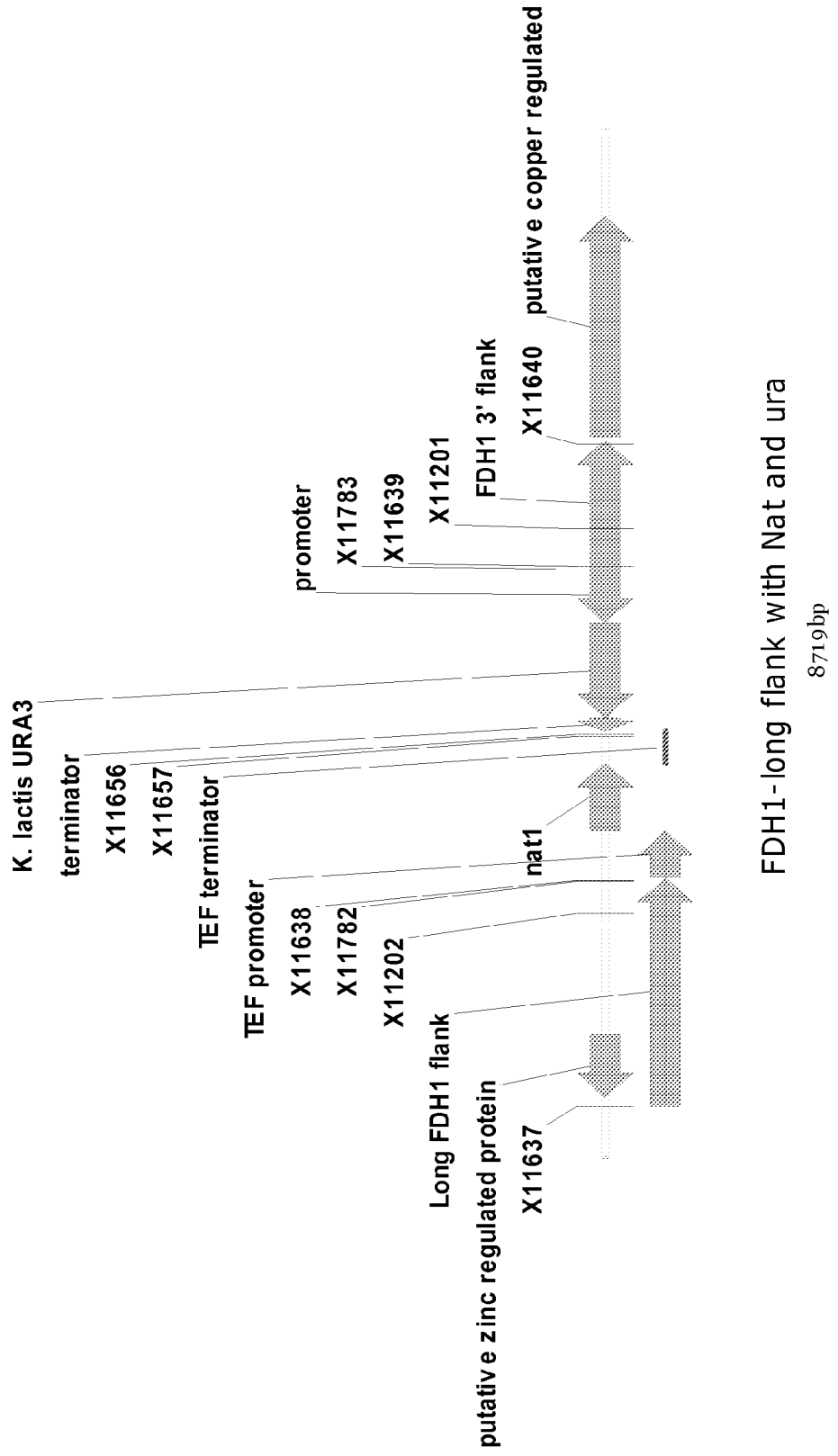
FIG. 8 shows a map depicting location of primers used to make marked deletion of FDH1.
Figure 9:
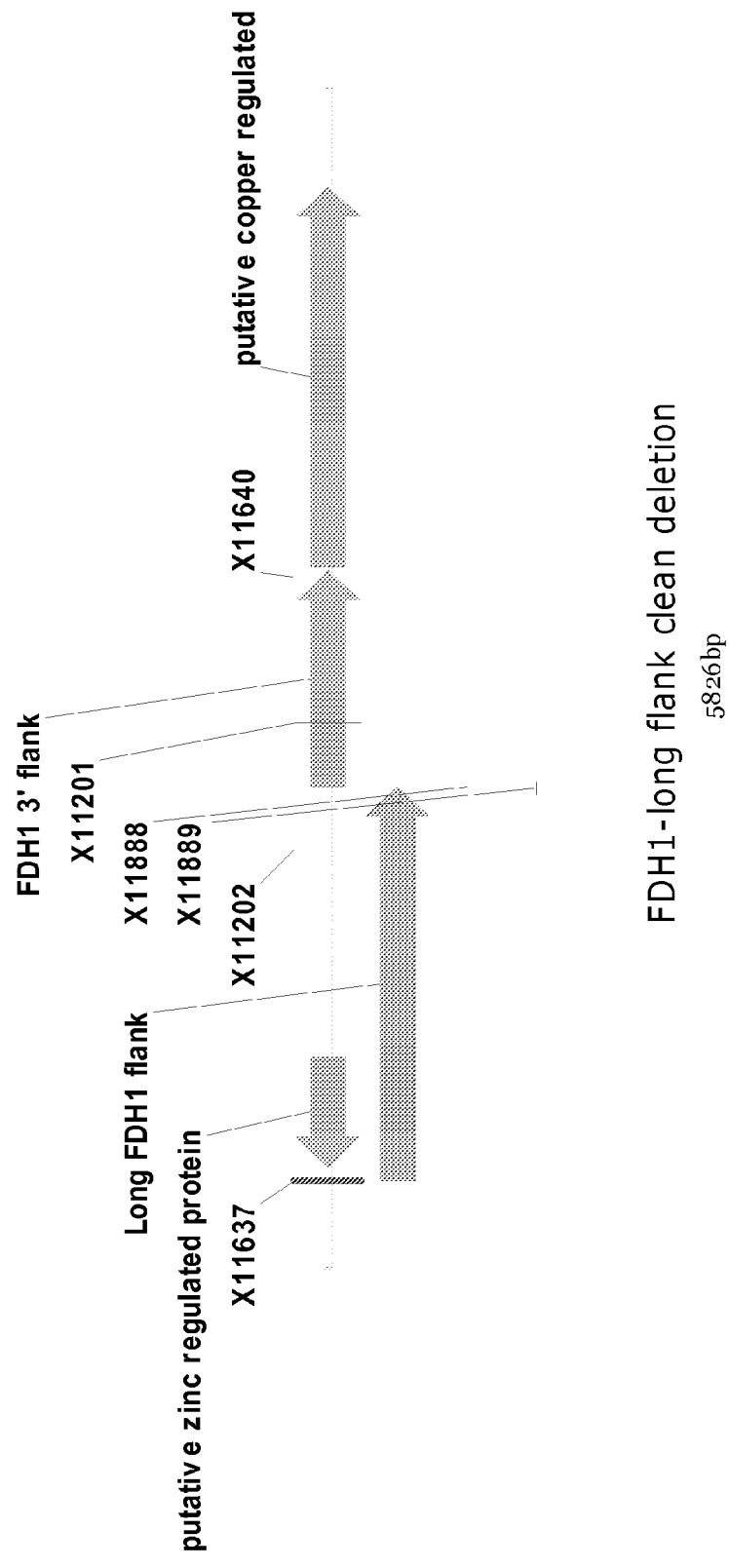
FIG. 9 shows a map depicting location of primers used to remove marker from FDH1 locus.
Figure 10:
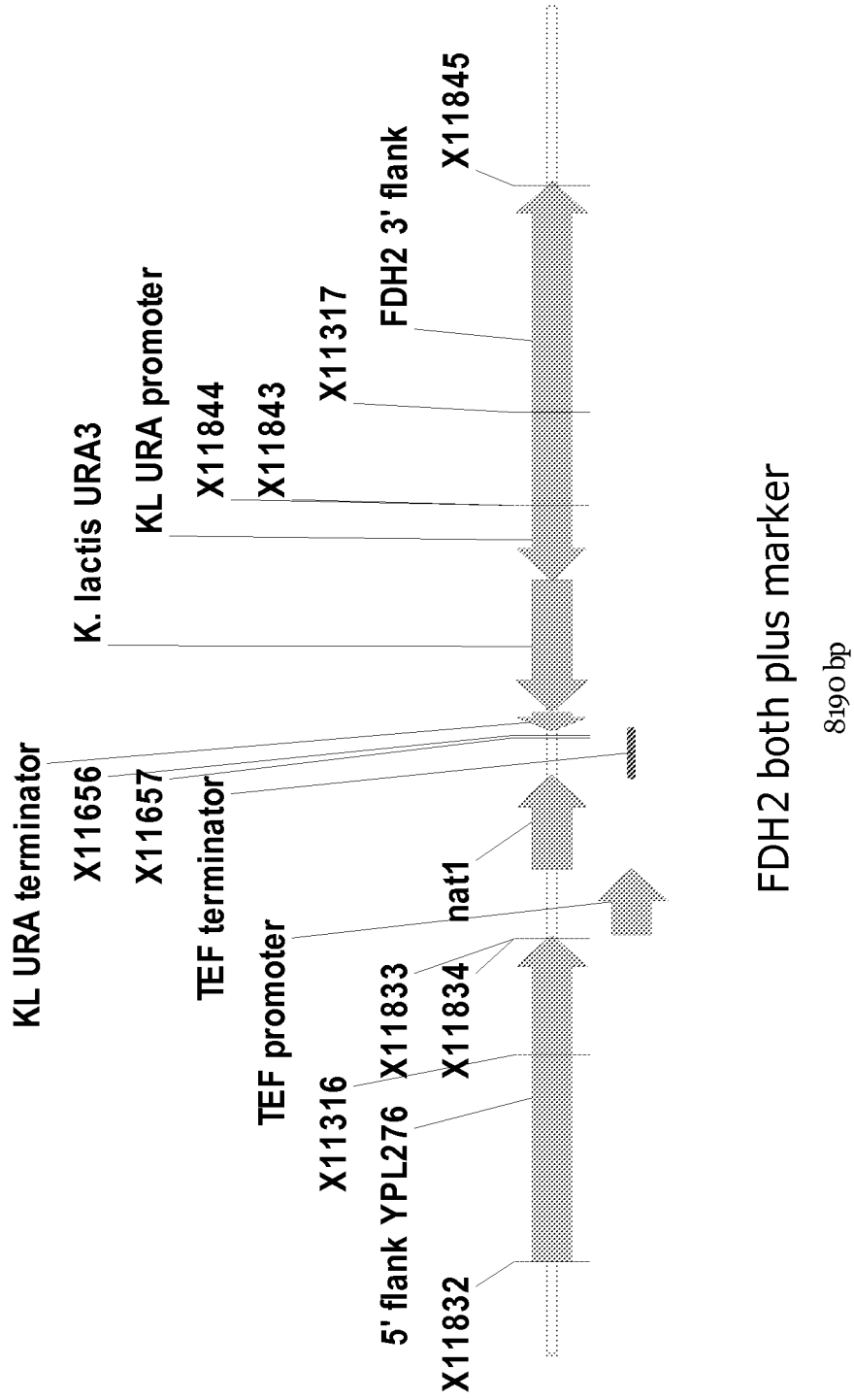
FIG. 10 shows a map depicting location of primers used to make marked deletion of FDH2.
Figure 11:
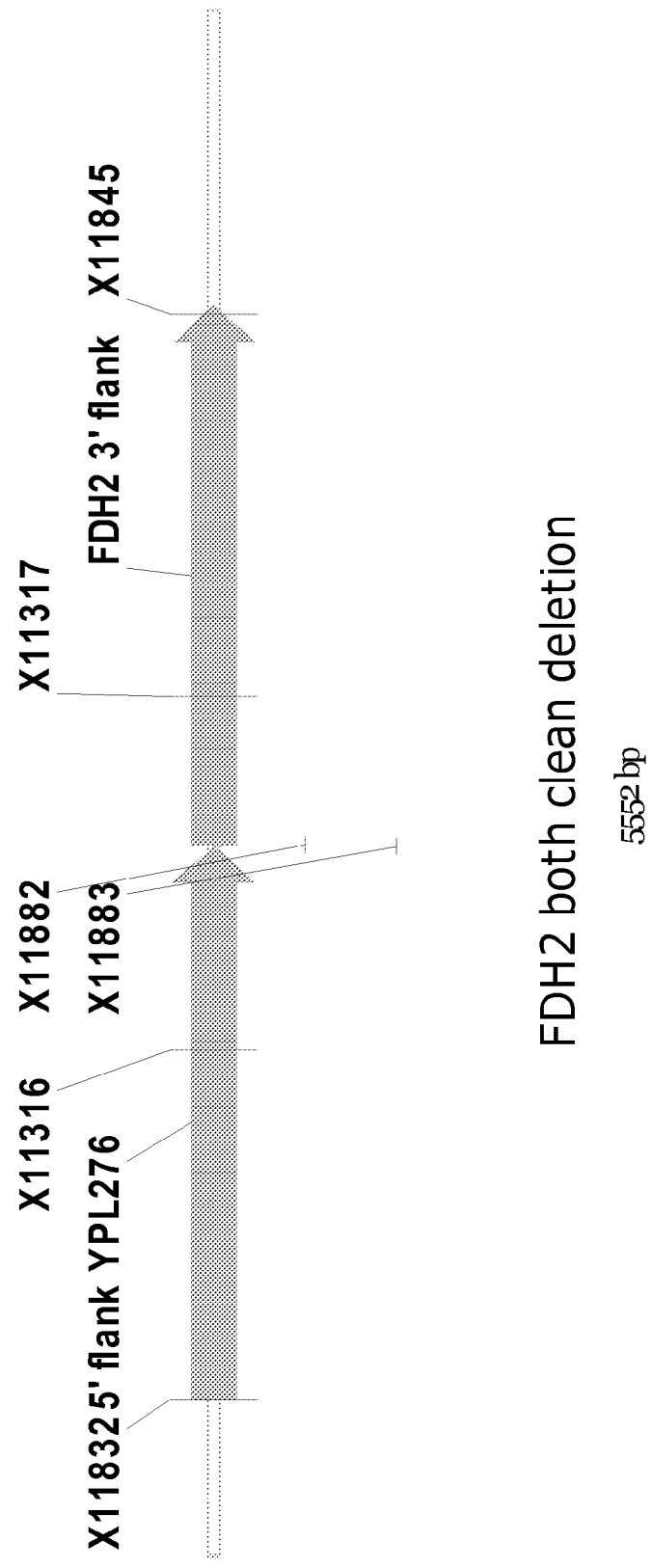
FIG. 11 shows a map depicting location of primers used to remove marker from FDH2 locus.

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes.

The term "heterologous polynucleotide" is intended to include a polynucleotide that encodes one or more polypeptides or portions or fragments of polypeptides. A heterologous polynucleotide may be derived from any source, e.g., eukaryotes, prokaryotes, viruses, or synthetic polynucleotide fragments.

The terms "promoter" or "surrogate promoter" is intended to include a polynucleotide that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. In certain embodiments, the gene or polynucleotide is involved in at least one step in the bioconversion of biomass to, e.g., ethanol. Accordingly, the term is intended to include any gene encoding a polypeptide, such as the enzymes acetate kinase (ACK), phosphotransacetylase (PTA), lactate dehydrogenase (LDH), pyruvate formate lyase (PFL), aldehyde dehydrogenase (ADH) and/or alcohol dehydrogenase (ADH), acetyl-CoA transferase (ACS), acetaldehyde dehydrogenase (ACDH), acetaldehyde/alcohol dehydrogenase (AADH), glycerol-3-phosphate dehydrogenase (GPD), glycerol 3-phosphatase (GPP), acetyl-CoA synthetase, thiolase, CoA transferase, acetoacetate decarboxylase, alcohol acetyltransferase enzymes in the D-xylose pathway, such as xylose isomerase and xylulokinase, enzymes in the L-arabinose pathway, such as L-arabinose isomerase and L-ribulose-5-phosphate 4-epimerase. The term gene is also intended to cover all copies of a particular gene, e.g., all of the DNA sequences in a cell encoding a particular gene product.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more genes is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product, e.g., a polypeptide, of an expressed gene.

The term "increased expression" is intended to include an alteration in gene expression at least at the level of increased mRNA production and, preferably, at the level of polypeptide expression. The term "increased production" is intended to include an increase in the amount of a polypeptide expressed, in the level of the enzymatic activity of the polypeptide, or a combination thereof, as compared to the native production of, or the enzymatic activity, of the polypeptide.

The terms "activity," "activities," "enzymatic activity," and "enzymatic activities" are used interchangeably and are intended to include any functional activity normally attributed to a selected polypeptide when produced under favorable conditions. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "xylanolytic activity" is intended to include the ability to hydrolyze glycosidic linkages in oligopentoses and polypentoses.

The term "arabinolytic activity" is intended to include the ability to hydrolyze glycosidic linkages in oligopentoses and polypentoses.

The term "cellulolytic activity" is intended to include the ability to hydrolyze glycosidic linkages in oligohexoses and polyhexoses. Cellulolytic activity may also include the ability to depolymerize or debranch cellulose and hemicellulose.

As used herein, the term "lactate dehydrogenase" or "LDH" is intended to include the enzymes capable of converting pyruvate into lactate. It is understood that LDH can also catalyze the oxidation of hydroxybutyrate. LDH includes those enzymes that correspond to Enzyme Commission Number 1.1.1.27.

As used herein the term "alcohol dehydrogenase" or "ADH" is intended to include the enzymes capable of converting acetaldehyde into an alcohol, such as ethanol. ADH also includes the enzymes capable of converting acetone to isopropanol. ADH includes those enzymes that correspond to Enzyme Commission Number 1.1.1.1.

As used herein, the term "phosphotransacetylase" or "PTA" is intended to include the enzymes capable of converting acetyl-phosphate into acetyl-CoA. PTA includes those enzymes that correspond to Enzyme Commission Number 2.3.1.8.

As used herein, the term "acetate kinase" or "ACK" is intended to include the enzymes capable of converting acetate into acetyl-phosphate. ACK includes those enzymes that correspond to Enzyme Commission Number 2.7.2.1.

As used herein, the term "pyruvate formate lyase" or "PFL" is intended to include the enzymes capable of converting pyruvate into acetyl-CoA and formate. PFL includes those enzymes that correspond to Enzyme Commission Number 2.3.1.54.

As used herein, the term "formate dehydrogenase" or "FDH" is intended to include the enzymes capable of converting formate and $NAD^+$ to NADH and $CO_2$. FDH includes those enzymes that correspond to Enzyme Commission Number 1.2.1.2.

As used herein, the term "acetaldehyde dehydrogenase" or "ACDH" is intended to include the enzymes capable of converting acetyl-CoA to acetaldehyde. ACDH includes those enzymes that correspond to Enzyme Commission Number 1.2.1.3.

As used herein, the term "acetaldehyde/alcohol dehydrogenase" is intended to include the enzymes capable of converting acetyl-CoA to ethanol. Acetaldehyde/alcohol dehydrogenase includes those enzymes that correspond to Enzyme Commission Numbers 1.2.1.10 and 1.1.1.1.

As used herein, the term "glycerol-3-phosphate dehydrogenase" or "GPD" is intended to include the enzymes capable of converting dihydroxyacetone phosphate to glycerol-3-phosphate. GPD includes those enzymes that correspond to Enzyme Commission Number 1.1.1.8.

As used herein, the term "glycerol 3-phosphatase" or "GPP" is intended to include the enzymes capable of converting glycerol 3-phosphate to glycerol. GPP includes those enzymes that correspond to Enzyme Commission Number 3.1.3.21.

As used herein, the term "acetyl-CoA synthetase" or "ACS" is intended to include the enzymes capable of converting acetate to acetyl-CoA. Acetyl-CoA synthetase includes those enzymes that correspond to Enzyme Commission Number 6.2.1.1.

As used herein, the term "thiolase" is intended to include the enzymes capable of converting acetyl-CoA to acetoacetyl-CoA. Thiolase includes those enzymes that correspond to Enzyme Commission Number 2.3.1.9.

As used herein, the term "CoA transferase" is intended to include the enzymes capable of converting acetate and acetoacetyl-CoA to acetoacetate and acetyl-CoA. CoA transferase includes those enzymes that correspond to Enzyme Commission Number 2.8.3.8.

As used herein, the term "acetoacetate decarboxylase" is intended to include the enzymes capable of converting acetoacetate to acetone and carbon dioxide. Acetoacetate decarboxylase includes those enzymes that correspond to Enzyme Commission Number 4.1.1.4.

As used herein, the term "alcohol acetyltransferase" is intended to include the enzymes capable of converting acetyl-CoA and ethanol to ethyl acetate. Alcohol acetyltransferase includes those enzymes that correspond to Enzyme Commission Number 2.3.1.84.

The term "pyruvate decarboxylase activity" is intended to include the ability of a polypeptide to enzymatically convert pyruvate into acetaldehyde and carbon dioxide (e.g., "pyruvate decarboxylase" or "PDC"). Typically, the activity of a selected polypeptide encompasses the total enzymatic activity associated with the produced polypeptide, comprising, e.g., the superior substrate affinity of the enzyme, thermostability, stability at different pHs, or a combination of these attributes. PDC includes those enzymes that correspond to Enzyme Commission Number 4.1.1.1.

The term "ethanologenic" is intended to include the ability of a microorganism to produce ethanol from a carbohydrate as a fermentation product. The term is intended to include, but is not limited to, naturally occurring ethanologenic organisms, ethanologenic organisms with naturally occurring or induced mutations, and ethanologenic organisms which have been genetically modified.

The terms "fermenting" and "fermentation" are intended to include the enzymatic process (e.g., cellular or acellular, e.g., a lysate or purified polypeptide mixture) by which ethanol is produced from a carbohydrate, in particular, as a product of fermentation.

The term "secreted" is intended to include the movement of polypeptides to the periplasmic space or extracellular milieu. The term "increased secretion" is intended to include situations in which a given polypeptide is secreted at an increased level (i.e., in excess of the naturally-occurring amount of secretion). In certain embodiments, the term "increased secretion" refers to an increase in secretion of a given polypeptide that is at least about 10% or at least about 100%, 200%, 300%, 400%, 500%, 600%, 700%, 800%, 900%, 1000%, or more, as compared to the naturally-occurring level of secretion.

The term "secretory polypeptide" is intended to include any polypeptide(s), alone or in combination with other polypeptides, that facilitate the transport of another polypeptide from the intracellular space of a cell to the extracellular milieu. In certain embodiments, the secretory polypeptide(s) encompass all the necessary secretory polypeptides sufficient to impart secretory activity to a Gram-negative or Gram-positive host cell or to a yeast host cell. Typically, secretory proteins are encoded in a single region or locus that may be isolated from one host cell and transferred to another host cell using genetic engineering. In certain embodiments, the secretory polypeptide(s) are derived from any bacterial cell having secretory activity or any yeast cell having secretory activity. In certain embodiments, the secretory polypeptide(s) are derived from a host cell having Type II secretory activity. In certain embodiments, the host cell is a thermophilic bacterial cell. In certain embodiments, the host cell is a yeast cell.

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from or based on a sequence associated with the indicated polynucleotide source.

The term "recombinant microorganism" or "recombinant host cell" is intended to include progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

By "thermophilic" is meant an organism that thrives at a temperature of about 45° C. or higher.

By "mesophilic" is meant an organism that thrives at a temperature of about 20-45° C.

The term "organic acid" is art-recognized. "Organic acid," as used herein, also includes certain organic solvents such as ethanol. The term "lactic acid" refers to the organic acid 2-hydroxypropionic acid in either the free acid or salt form. The salt form of lactic acid is referred to as "lactate" regardless of the neutralizing agent, i.e., calcium carbonate or ammonium hydroxide. The term "acetic acid" refers to the organic acid methanecarboxylic acid, also known as ethanoic acid, in either free acid or salt form. The salt form of acetic acid is referred to as "acetate."

Certain embodiments of the present invention provide for the "insertion," (e.g., the addition, integration, incorporation, or introduction) of certain genes or particular polynucleotide sequences within thermophilic or mesophilic microorganisms, which insertion of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

Certain embodiments of the present invention provide for the "inactivation" or "deletion" of certain genes or particular polynucleotide sequences within thermophilic or mesophilic microorganisms, which "inactivation" or "deletion" of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

The term "consolidated bioprocessing" or "CBP" refers to biomass processing schemes involving enzymatic or microbial hydrolysis that commonly involve four biologically mediated transformations: (1) the production of saccharolytic enzymes (amylases, cellulases, and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called CBP, which is distinguished from other less highly integrated configurations in that it does not involve a dedicated process step for cellulase and/or hemicellulase production.

The term "CBP organism" is intended to include microorganisms of the invention, e.g., microorganisms that have properties suitable for CBP.

In one aspect of the invention, the genes or particular polynucleotide sequences are inserted to activate the activity for which they encode, such as the expression of an enzyme. In certain embodiments, genes encoding enzymes in the metabolic production of ethanol, e.g., enzymes that metabolize pentose and/or hexose sugars, may be added to a mesophilic or thermophilic organism. In certain embodiments of the invention, the enzyme may confer the ability to metabolize a pentose sugar and be involved, for example, in the D-xylose pathway and/or L-arabinose pathway.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the terms "deletion," "partial deletion," "substantial deletion," or "complete deletion." In certain embodiments, strains of thermophilic or mesophilic microorganisms of interest may be engineered by site directed homologous recombination to knockout the production of organic acids. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Similarly, the enzymes of the invention as described herein can be endogenous to the native strain of the microorganism, and can thus be understood to be referred to as "native" or "endogenous."

The term "upregulated" means increased in activity, e.g., increase in enzymatic activity of the enzyme as compared to activity in a native host organism.

The term "downregulated" means decreased in activity, e.g., decrease in enzymatic activity of the enzyme as compared to activity in a native host organism.

The term "activated" means expressed or metabolically functional.

The term "adapted for growing" means selection of an organism for growth under conditions in which the organism does not otherwise grow or in which the organism grows slowly or minimally. Thus, an organism that is said to be adapted for growing under the selected condition, grows better than an organism that has not been adapted for growing under the selected conditions. Growth can be measured by any methods known in the art, including, but not limited to, measurement of optical density or specific growth rate.

The term "carbohydrate source" is intended to include any source of carbohydrate including, but not limited to, biomass or carbohydrates, such as a sugar or a sugar alcohol. "Carbohydrates" include, but are not limited to, monosaccharides (e.g., glucose, fructose, galactose, xylose, arabinose, or ribose), sugar derivatives (e.g., sorbitol, glycerol, galacturonic acid, rhamnose, xylitol), disaccharides (e.g., sucrose, cellobiose, maltose, or lactose), oligosaccharides (e.g., xylooligomers, cellodextrins, or maltodextrins), and polysaccharides (e.g., xylan, cellulose, starch, mannan, alginate, or pectin).

As used herein, an "amylolytic enzyme" can be any enzyme involved in amylase digestion, metabolism and/or hydrolysis. The term "amylase" refers to an enzyme that breaks starch down into sugar. Amylase is present in human saliva, where it begins the chemical process of digestion. Foods that contain much starch but little sugar, such as rice and potato, taste slightly sweet as they are chewed because amylase turns some of their starch into sugar in the mouth. The pancreas also makes amylase ($\alpha$-amylase) to hydrolyse dietary starch into disaccharides and trisaccharides which are converted by other enzymes to glucose to supply the body with energy. Plants and some bacteria also produce amylase. All amylases are glycoside hydrolases and act on $\alpha$-1,4-glycosidic bonds. Some amylases, such as $\gamma$-amylase (glucoamylase), also act on $\alpha$-1,6-glycosidic bonds. Amylase enzymes include $\alpha$-amylase (EC 3.2.1.1), $\beta$-amylase (EC 3.2.1.2), and $\gamma$-amylase (EC 3.2.1.3). The $\alpha$-amylases are calcium metalloenzymes, unable to function in the absence of calcium. By acting at random locations along the starch chain, $\alpha$-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase. In animals, it is a major digestive enzyme and its optimum pH is about 6.7-7.0. Another form of amylase, β-amylase is also synthesized by bacteria, fungi, and plants. Working from the non-reducing end, β-amylase catalyzes the hydrolysis of the second α-1,4 glycosidic bond, cleaving off two glucose units (maltose) at a time. Many microbes produce amylase to degrade extracellular starches. In addition to cleaving the last α(1-4)glycosidic linkages at the nonreducing end of amylose and amylopectin, yielding glucose, γ-amylase will cleave α(1-6) glycosidic linkages. Another amylolytic enzyme is alpha-glucosidase that acts on maltose and other short malto-oligosaccharides produced by alpha-, beta-, and gamma-amylases, converting them to glucose. Another amylolytic enzyme is pullulanase. Pullulanase is a specific kind of glucanase, an amylolytic exoenzyme, that degrades pullulan. Pullulan is regarded as a chain of maltotriose units linked by alpha-1,6-glycosidic bonds. Pullulanase (EC 3.2.1.41) is also known as pullulan-6-glucanohydrolase (Debranching enzyme). Another amylolytic enzyme, isopullulanase, hydrolyses pullulan to isopanose (6-alpha-maltosylglucose). Isopullulanase (EC 3.2.1.57) is also known as pullulan 4-glucanohydrolase. An "amylase" can be any enzyme involved in amylase digestion, metabolism and/or hydrolysis, including α-amylase, β-amylase, glucoamylase, pullulanase, isopullulanase, and alpha-glucosidase.

As used herein, a "saccharolytic enzyme" can be any enzyme involved in carbohydrate digestion, metabolism and/or hydrolysis, including amylases, cellulases, hemicellulases, cellulolytic and amylolytic accessory enzymes, inulinases, levanases, and pentose sugar utilizing enzymes.

Biomass

Biomass can include any type of biomass known in the art or described herein. For example, biomass can include, but is not limited to, starch, sugar, and lignocellulosic materials. Starch materials can include, but are not limited to, mashes such as corn, wheat, rye, barley, rice, or milo. Sugar materials can include, but are not limited to, sugar beets, artichoke tubers, sweet sorghum, or cane. The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants, and sugar-processing residues. The terms "hemicellulosics," "hemicellulosic portions," and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan, inter alia), pectins (e.g., homogalacturonans, rhamnogalacturonan I and II, and xylogalacturonan), and proteoglycans (e.g., arabinogalactan-protein, extensin, and proline-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Paper sludge is also a viable feedstock for lactate or acetate production. Paper sludge is solid residue arising from pulping and paper-making, and is typically removed from process wastewater in a primary clarifier. At a disposal cost of $30/wet ton, the cost of sludge disposal equates to $5/ton of paper that is produced for sale. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

Glycerol Reduction

Anaerobic growth conditions require the production of endogenouse electron acceptors, such as the coenzyme nicotinamide adenine dinucleotide ($NAD^+$). In cellular redox reactions, the $NAD^+$/NADH couple plays a vital role as a reservoir and carrier of reducing equivalents. Ansell, R., et al., *EMBO J.* 16:2179-87 (1997). Cellular glycerol production, which generates an $NAD^+$, serves as a redox valve to remove excess reducing power during anaerobic fermentation in yeast. Glycerol production is, however, an energetically wasteful process that expends ATP and results in the loss of a reduced three-carbon compound. Ansell, R., et al., *EMBO J.* 16:2179-87 (1997). To generate glycerol from a starting glucose molecule, glycerol 3-phosphate dehydrogenase (GPD) reduces dihydroxyacetone phosphate to glycerol 3-phosphate and glycerol 3-phosphatase (GPP) dephosphorylates glycerol 3-phosphate to glycerol. Despite being energetically wasteful, glycerol production is a necessary metabolic process for anaerobic growth as deleting GPD activity completely inhibits growth under anaeroblic conditions. See Ansell, R., et al., *EMBO J.* 16:2179-87 (1997).

GPD is encoded by two isogenes, gpd1 and gpd2. GPD1 encodes the major isoform in anaerobically growing cells, while GPD2 is required for glycerol production in the absence of oxygen, which stimulates its expression. Pahlman, A-K., et al., *J. Biol. Chem.* 276:3555-63 (2001). The first step in the conversion of dihydroxyacetone phosphate to glycerol by GPD is rate controlling. Guo, Z. P., et al., *Metab. Eng.* 13:49-59 (2011). GPP is also encoded by two isogenes, gpp1 and gpp2. The deletion of GPP genes arrests growth when shifted to anaerobic conditions, demonstrating that GPP is important for cellular tolerance to osmotic and anaerobic stress. See Pahlman, A-K., et al., *J. Biol. Chem.* 276:3555-63 (2001).

Because glycerol is a major by-product of anaerobic production of ethanol, many efforts have been made to delete cellular production of glycerol. However, because of the reducing equivalents produced by glycerol synthesis, deletion of the glycerol synthesis pathway cannot be done without compensating for this valuable metabolic function. Attempts to delete glycerol production and engineer alternate electron acceptors have been made. Lidén, G., et al., *Appl. Env. Microbiol.* 62:3894-96 (1996); Medina, V. G., et al., *Appl. Env. Microbiol.* 76:190-195 (2010). Lidén and Medina both deleted the gpd1 and gpd2 genes and attempted to bypass glycerol formation using additional carbon sources. Lidén engineered a xylose reductase from *Pichia stipitis* into an *S. cerevisiae* gpd1/2 deletion strain. The xylose reductase activity facilitated the anaerobic growth of the glycerol-deleted strain in the presence of xylose. See Lidén, G., et al., *Appl. Env. Microbiol.* 62:3894-96 (1996). Medina engineered an acetylaldehyde dehydrogenase, mhpF, from *E. coli* into an *S. cerevisiae* gpd1/2 deletion strain to convert acetyl-CoA to acetaldehyde. The acetylaldehyde dehydrogenase activity facilitated the anaerobic growth of the glycerol-deletion strain in the presence of acetic acid but not in the presence of glucose as the sole source of carbon. Medina, V. G., et al., *Appl. Env. Microbiol.* 76:190-195 (2010); see also EP 2277989. Medina noted several issues with the mhpF-containing strain that needed to be addressed before implementing industrially, including significantly reduced growth and product formation rates than yeast comprising GPD1 and GPD2.

Additional attempts to redirect flux from glycerol to ethanol have included the engineering of a non-phosphorylating NADP+-dependent glyceraldehydes-3-phosphate dehydrogenase (GAPN) into yeast, either with or without the simultaneous knockout of GPD1. Bro, C., et al., *Metab. Eng.* 8:102-111 (2006); U.S. Patent Appl. Pub. No. US2006/0257983; Guo, Z. P., et al., *Metab. Eng.* 13:49-59 (2011). However, other cellular mechanisms exist to control the production and accumulation of glycerol, including glycerol exporters such as FPS1, that do not require the engineering of alternate NADP+/NADPH coupling or deletion of glycerol synthesis genes. Tamas, M. J., et al., *Mol. Microbiol.* 31:1087-1004 (1999).

FPS1 is a channel protein located in the plasma membrane that controls the accumulation and release of glycerol in yeast osmoregulation. Null mutants of this strain accumulate large amounts of intracellular glycerol, grow much slower than wild-type, and consume the sugar substrate at a slower rate. Tamas, M. J., et al., *Mol. Microbiol.* 31:1087-1004 (1999). Despite slower growth under anaerobic conditions, an fps1Δ strain can serve as an alternative to eliminating $NAD^+$-dependant glycerol activity. An fps1Δ strain has reduced glycerol formation yet has a completely functional $NAD^+$-dependant glycerol synthesis pathway. Alternatively, rather than deleting endogenous FPS1, constitutively active mutants of FPS1 or homologs from other organisms can be used to regulate glycerol synthesis while keep the $NAD^+$-dependant glycerol activity intact. In embodiments of the invention that modulate FPS1, the recombinant host cells can still synthesize and retain glycerol and achieve improved robustness relative to strains that are unable to make glycerol.

An example FPS1 sequence from *S. cerevisiae* is shown below.

*S. cerevisiae* FPS1 (nucleotide; coding sequence underlined; SEQ ID NO: 1):

```
ttgacggcagttctcatagcatctcaaagcaatagcagtgcaaaagtacataaccgtaggaaggtacgcggtaggtat ttgagttcgttggtggttatcctccgcaaggcgcttcggcggttatttgttgatagtcgaagaacaccaaaaaaaatgctgttattgct ttctccgtaaacaataaaacccggtagcgggataacgcggctgatgcttttatttaggaaggaatacttacattatcatgagaacatt gtcaagggcattctgatacgggccttccatcgcaagaaaaaggcagcaacggactgagggacggagagagttacggcataag aagtagtaggagagcagagtgtcataaagttatattattctcgtcctaaagtcaattagttctgttgcgcttgacaatatatgtcgtgta ataccgtcccttagcagaagaaagaaagacggatccatatatgttaaaatgcttcagagatgtttctttaatgtgccgtccaacaaa ggtatcttctgtagcttcctctattttcgatcagatctcatagtgagaaggcgcaattcagtagttaaaagcggggaacagtgtgaat ccggagacggcaagattgcccggcccttttttgcggaaaagataaaacaagatatattgcacttttccaccaagaaaaacaggaa gtggattaaaaaatcaacaaagtataacgcctattgtcccaataagcgtcggttgttcttctttattattttaccaagtacgctcgaggg tacattctaatgcattaaaagacatgagtaatcctcaaaaagctctaaacgactttctgtccagtgaatctgttcatacacatgatagtt ctaggaaacaatctaataagcagtcatccgacgaaggacgctcttcatcacaaccttcacatcatcactctggtggtactaacaac aataataacaataataataataataacagtaacaacaacaacaacggcaacgatgggggaaatgatgacgactatgattatg aaatgcaagattatagaccttctccgcaaagtgcgcggcctactcccacgtatgttccacaatattctgtagaaagtgggactgcttt cccgattcaagaggttattcctagcgcatacattaacacacaagatataaaccataaagataacggtccgccgagtgcaagcagt aatagagcattcaggcctagagggcagaccacagtgtcggccaacgtgcttaacattgaagattttttacaaaaatgcagacgatg cgcataccatcccggagtcacatttatcgagaaggagaagtaggtcgagggctacgagtaatgctgggcacagtgccaataca ggcgccacgaatggcaggactactggtgcccaaactaatatggaaagcaatgaatcaccacgtaacgtcccattatggtgaag ccaaagacattataccagaaccctcaaacacctacagtcttgccctccacataccatccaattaataaatggtcttccgtcaaaaac acttatttgaaggaattttttagccgagtttatgggaacaatggttatgattattttcggtagtgctgttgtttgtcaggtcaatgttgctgg gaaaatacagcaggacaatttcaacgtggctttggataaccttaacgttaccgggtcttctgcagaaacgatagacgctatgaaga gtttaacatccttggtttcatccgttgcgggcggtacctttgatgatgtggcattgggctgggctgctgccgtggtgatgggctatttc tgcgctggtggtagtgccatctcaggtgctcatttgaatccgtctattacattagccaatttggtgtatagaggttttccctgaagaa
```

-continued agttccttattactttgctggacaattgatcggtgccttcacaggcgctttgatcttgtttatttggtacaaaagggtgttacaagaggc atatagcgattggtggatgaatgaaagtgttgcgggaatgttttgcgttttttccaaagccttatctaagttcaggacggcaattttttttc cgaattttatgtggagctatgttacaagcaggaacatttgcgctgaccgatccttatacgtgtttgtcctctgatgttttcccattgatg atgtttattttgattttcattatcaatgcttccatggcttatcagacaggtacagcaatgaatttggctcgtgatctgggcccacgtcttg cactatatgcagttggatttgatcataaaatgctttgggtgcatcatcatcatttcttttgggttcccatggtaggcccatttattggtgc gttaatggggggttggtttacgatgtctgtatttatcagggtcatgaatctccagtcaactggtctttaccagtttataaggaaatgat tatgagagcctggtttagaaggcctggttggaagaagagaaatagagcaagaagaacatcggacctgagtgacttctcatacaat aacgatgatgatgaggaatttggagaaagaatggctcttcaaaagacaaagaccaagtcatctatttcagacaacgaaaatgaag caggagaaaagaaagtgcaatttaaatctgttcagcgcggcaaaagaacgtttggtggtataccaacaattcttgaagaagaaga ttccattgaaactgcttcgctaggtgcgacgacgactgattctattgggttatccgacacatcatcagaagattcgcattatggtaat gctaagaaggtaacatgagaaaacagacaagaaaaagaaacaaataatatagactgatagaaaaaatactgcttactaccgcc ggtataatatatatatatatatatatttacatagatgattgcatagtgttttaaaaagctttcctaggttaagctatgaatcttcataaccta accaactaaatatgaaaatactgacccatcgtcttaagtaagttgacatgaactcagcctggtcacctactatacatgatgtatcgca tggatggaaagaataccaaacgctaccttccaggttaatgatagtatccaaacctagttggaatttgccttgaacatcaagcagcg attcgatatcagttgggagcatcaatttggtcattggaataccatctatgcttttctcctcccatattcgcaaaagtagtaagggctcgtta tatacttttgaatatgtaagatataattctatatgatttagtaatttattttctatacgctcagtattttctgcagttgtcgagtaggtatta aacgcaaagaagtccatcctttcatcattcaaatggacatcttggcaaagggcccagttatggaaaatctgggagtcatacaac gattgcagttggctatgccactcctggtaaggaatcatcaagtctgataattctgttttttagccctttttttttttttttcatggtgttctct tctcattgcttttcaattttaagttcgttacctttcatatagagtttcttaacagaaatttcacaacgaaaatataattaactacaggca S. cerevisiae FPS1 (amino acid; SEQ ID NO:2):
Pyruvate Formate Lyase (PFL)

The conversion of the pyruvate to acetyl-CoA and formate is performed by pyruvate formate lyase (PFL). In E. coli, PFL is the primary enzyme responsible for the production of formate. PFL is a dimer of PflB that requires the activating enzyme PflAE, which is encoded by pflA, radical S-adenosylmethionine, and a single electron donor. See Waks, Z., and Silver, P. A., *Appl. Env. Microbiol.* 75:1867-1875 (2009). Waks and Silver engineered strains of S. cerevisiae to secrete formate by the addition of PFL and AdhE from E. coli and deletion of endogenous formate dehydrogenases and to produce hydrogen in a two-step process using E. coli. Waks and Silver, however, did not combine formate production with the removal of glycerol formation, and the use of formate as an alternate electron acceptor for the reduction of glycerol was not proposed or evaluated.

PFL enzymes for use in the recombinant host cells of the invention can come from a bacterial or eukaryotic source. Examples of bacterial PFL include, but are not limited to, *Bacillus licheniformis* DSM13, *Bacillus licheniformis* ATCC14580, *Streptococcus thermophilus* CNRZ1066, *Streptococcus thermophilus* LMG18311, *Streptococcus thermophilus* LMD-9, *Lactobacillus plantarum* WCFS1 (Gene Accession No. 1p_2598), *Lactobacillus plantarum* WCFS1 (Gene Accession No. 1p_3313), *Lactobacillus plantarum* JDM1 (Gene Accession No. JDM1_2695), *Lactobacillus plantarum* JDM1 (Gene Accession No. JDM1_2087), *Lactobacillus casei* b123, *Lactobacillus casei* ATCC 334, *Bifidobacterium adolescentis*, *Bifidobacterium longum* NCC2705, *Bifidobacterium longum* DJO10A, *Bifidobacterium animalis* DSM 10140, *Clostridium cellulolyticum*, or *Escherichia coli*. Additional PFL enzymes may be from the PFL1 family, the RNR pfl superfamily, or the PFL2 superfamily.

pflA sequences from bacteria include:
Bacillus licheniformis DSM13 (nucleotide; SEQ ID NO:3):
Bacillus licheniformis DSM13 (amino acid; SEQ ID NO:4):
Bacillus licheniformis ATCC14580 (nucleotide; SEQ ID NO:5):
Bacillus licheniformis ATCC14580 (amino acid; SEQ ID NO:6):
Streptococcus thermophilus CNRZ1066 (nucleotide; SEQ ID NO:7):
Streptococcus thermophilus CNRZ1066 (amino acid; SEQ ID NO:8):
Streptococcus thermophilus LMG18311 (nucleotide; SEQ ID NO:9):
Streptococcus thermophilus LMG18311 (amino acid; SEQ ID NO:10):
Streptococcus thermophilus LMD-9 (nucleotide; SEQ ID NO:11):
Streptococcus thermophilus LMD-9 (amino acid; SEQ ID NO:12):
Lactobacillus plantarum WCFS1 (Gene Accession No: 1p_2596) (nucleotide; SEQ ID NO:13):
Lactobacillus plantarum WCFS1 (Gene Accession No: 1p_2596) (amino acid; SEQ ID NO:14):
Lactobacillus plantarum WCFS1 (Gene Accession No: 1p_3314) (nucleotide; SEQ ID NO:15):
Lactobacillus plantarum WCFS1 (Gene Accession No: 1p_3314) (amino acid; SEQ ID NO:16):
Lactobacillus plantarum JDM1 (Gene Accession No: JDM1_2660) (nucleotide; SEQ ID NO:17):
Lactobacillus plantarum JDM1 (Gene Accession No: JDM1_2660) (amino acid; SEQ ID NO:18):

*Lactobacillus plantarum* JDM1 (Gene Accession No: JDM1_2085) (nucleotide; SEQ ID NO:19):
*Lactobacillus plantarum* JDM1 (Gene Accession No: JDM1_2085) (amino acid; SEQ ID NO:20):
*Lactobacillus casei* b123 (nucleotide; SEQ ID NO:21):
*Lactobacillus casei* b123 (amino acid; SEQ ID NO:22):
*Lactobacillus casei* ATCC 334 (nucleotide; SEQ ID NO:23):
*Lactobacillus casei* ATCC 334 (amino acid; SEQ ID NO:24):
*Bifidobacterium adolescentis* (nucleotide; SEQ ID NO:25):
*Bifidobacterium adolescentis* (amino acid; SEQ ID NO:26):
*Bifidobacterium longum* NCC2705 (nucleotide; SEQ ID NO:27):
*Bifidobacterium longum* NCC2705 (amino acid; SEQ ID NO:28):
*Bifidobacterium longum* DJO10A (nucleotide; SEQ ID NO:29):
*Bifidobacterium longum* DJO10A (amino acid; SEQ ID NO:30):
*Bifidobacterium animalis* DSM 10140 (nucleotide; SEQ ID NO:31):
*Bifidobacterium animalis* DSM 10140 (amino acid; SEQ ID NO:32):
*Clostridium cellulolyticum* (nucleotide; SEQ ID NO:33):
*Clostridium cellulolyticum* (amino acid; SEQ ID NO:34):
*Escherichia coli* (nucleotide; SEQ ID NO:35):
*Escherichia coli* (amino acid; SEQ ID NO:36):
pflB sequences from bacteria include:
*Bacillus licheniformis* DSM13 (nucleotide; SEQ ID NO:37):
*Bacillus licheniformis* DSM13 (amino acid; SEQ ID NO:38):
*Bacillus licheniformis* ATCC14580 (nucleotide; SEQ ID NO:39):
*Bacillus licheniformis* ATCC14580 (amino acid; SEQ ID NO:40):
*Streptococcus thermophilus* CNRZ1066 (nucleotide; SEQ ID NO:41):
*Streptococcus thermophilus* CNRZ1066 (amino acid; SEQ ID NO:42):
*Streptococcus thermophilus* LMG18311 (nucleotide; SEQ ID NO:43):
*Streptococcus thermophilus* LMG18311 (amino acid; SEQ ID NO:44):
*Streptococcus thermophilus* LMD-9 (nucleotide; SEQ ID NO:45):
*Streptococcus thermophilus* LMD-9 (amino acid; SEQ ID NO:46):
*Lactobacillus plantarum* WCFS1 (Gene Accession No. 1p_2598) (nucleotide; SEQ ID NO:47):
*Lactobacillus plantarum* WCFS1 (Gene Accession No. 1p_2598) (amino acid; SEQ ID NO:48):
*Lactobacillus plantarum* WCFS1 (Gene Accession No: 1p_3313) (nucleotide; SEQ ID NO:49):
*Lactobacillus plantarum* WCFS1 (Gene Accession No: 1p_3313) (amino acid; SEQ ID NO:50):
*Lactobacillus plantarum* JDM1 (Gene Accession No: JDM1_2695) (nucleotide; SEQ ID NO:51):
*Lactobacillus plantarum* JDM1 (Gene Accession No: JDM1_2695) (amino acid; SEQ ID NO:52):
*Lactobacillus plantarum* JDM1 (Gene Accession No: JDM1_2087) (nucleotide; SEQ ID NO:53):
*Lactobacillus plantarum* JDM1 (Gene Accession No: JDM1_2087) (amino acid; SEQ ID NO:54):
*Lactobacillus casei* b123 (nucleotide; SEQ ID NO:55):
*Lactobacillus casei* b123 (amino acid; SEQ ID NO:56):
*Lactobacillus casei* ATCC 334 (nucleotide; SEQ ID NO:57):
*Lactobacillus casei* ATCC 334 (amino acid; SEQ ID NO:58):
*Bifidobacterium adolescentis* (nucleotide; SEQ ID NO:59):
*Bifidobacterium adolescentis* (amino acid; SEQ ID NO:60):
*Bifidobacterium longum* NCC2705 (nucleotide; SEQ ID NO:61):
*Bifidobacterium longum* NCC2705 (amino acid; SEQ ID NO:62):
*Bifidobacterium longum* DJO10A (nucleotide; SEQ ID NO:63):
*Bifidobacterium longum* DJO10A (amino acid; SEQ ID NO:64):
*Bifidobacterium animalis* DSM 10140 (nucleotide; SEQ ID NO:65):
*Bifidobacterium animalis* DSM 10140 (amino acid; SEQ ID NO:66):
*Clostridium cellulolyticum* (nucleotide; SEQ ID NO:67):
*Clostridium cellulolyticum* (amino acid; SEQ ID NO:68):
*Escherichia coli* (nucleotide; SEQ ID NO:69):
*Escherichia coli* (amino acid; SEQ ID NO:70):

Examples of eukaryotic PFL include, but are not limited to, *Chlamydomonas reinhardtii* PflA1, *Piromyces* sp. E2, or *Neocallimastix frontalis*, *Acetabularia acetabulum*, *Haematococcus pluvialis*, *Volvox carteri*, *Ostreococcus tauri*, *Ostreococcus lucimarinus*, *Micromonas pusilla*, *Micromonas* sp., *Porphyra haitanensis*, and *Cyanophora paradoxa*), an opisthokont (*Amoebidium parasiticum*), an amoebozoan (*Mastigamoeba balamuthi*), a stramenopile (*Thalassiosira pseudonana* (2)) and a haptophyte (*Prymnesium parvum*), *M. pusilla*, *Micromonas* sp. *O. tauri* and *O. lucimarinus*) an amoebozoan (*M. balamuthi*), and a stramenopile (*T. pseudonana*). See Stairs, C. W., et al., "Eukaryotic pyruvate formate lyase and its activating enzyme were acquired laterally from a firmicute," Mol. Biol. and Evol., published on-line on Feb. 3, 2011, at http://mbe.oxfordjournals.org/.

pflA sequences from eukaryotes include:
*Chlamydomonas reinhardtii* PflA1 (nucleotide; SEQ ID NO:71):
*Chlamydomonas reinhardtii* PflA1 (amino acid; SEQ ID NO:72):
*Neocallimastix frontalis* (nucleotide; SEQ ID NO:73):
*Neocallimastix frontalis* (amino acid; SEQ ID NO:74):
pfl1 sequences from eukaryotes include:
*Chlamydomonas reinhardtii* PflA (nucleotide; SEQ ID NO:75):
*Chlamydomonas reinhardtii* PflA (amino acid; SEQ ID NO:76):
*Piromyces* sp. E2 (nucleotide; SEQ ID NO:77):
*Piromyces* sp. E2 (amino acid; SEQ ID NO:78):
*Neocallimastix frontalis* (nucleotide—partial CDS, missing start; SEQ ID NO:79):
*Neocallimastix frontalis* (amino acid—partial CDS, missing start; SEQ ID NO:80):

Acetaldehyde/Alcohol Dehydrogenases

Engineering of acetaldehyde dehydrogenases, alcohol dehydrogenases, and/or bifunctional acetylaldehyde/alcohol dehydrogenases into a cell can increase the production of ethanol. However, because the production of ethanol is redox neutral, an acetaldehyde/alcohol dehydrogenase activity cannot serve as an alternative for the redox balancing that the production of glycerol provides to a cell in anaerobic metabolism. When Medina attempted to express an acetylaldehyde dehydrogenase, mhpF, from *E. coli* in an *S. cerevisiae* gpd1/2 deletion strain, the strain did not grow under anaerobic conditions in the presence of glucose as the sole source of carbon. Medina, V. G., et al., *Appl. Env. Microbiol.* 76:190-195 (2010); see also EP 2277989. Rather, the anaerobic growth of the glycerol-deletion strain required the presence of acetic acid. However, an acetylaldehyde dehydrogenase has not been expressed in combination with PFL or with the recombinant host cells of the invention. Additionally, replacing the endogenous acetylaldehyde dehydrogenase activity with either an improved acetaldehyde dehydrogenase or using a bifunctional acetaldehyde/alcohol dehydrogenase (AADH) can positively affect the in vivo kinetics of the reaction providing for improved growth of the host strain.

AADH enzymes for use in the recombinant host cells of the invention can come from a bacterial or eukaryotic source. Examples of bacterial AADH include, but are not limited to, *Clostridium phytofermentans, Escherichia coli, Bacillus coagulans, Bacillus lentus, Bacillus licheniformis, Bacillus pumilus, Bacillus subtilis, Bacteroides amylophilus, Bacteroides capillosus, Bacteroides ruminocola, Bacteroides suis, Bifidobacterium adolescentis, Bifidobacterium animalis, Bifidobacterium bifidum, Bifidobacterium infantis, Bifidobacterium longum, Bifidobacterium thermophilum, Lactobacillus acidophilus, Lactobacillus brevis, Lactobacillus buchneri* (cattle only), *Lactobacillus bulgaricus, Lactobacillus casei, Lactobacillus cellobiosus, Lactobacillus curvatus, Lactobacillus delbruekii, Lactobacillus farciminis* (swine only), *Lactobacillus fermentum, Lactobacillus helveticus, Lactobacillus lactis, Lactobacillus plantarum, Lactobacillus reuterii, Leuconostoc mesenteroides, Pediococcus acidilactici, Pediococcus pentosaceus, Propionibacterium acidpropionici* (cattle only), *Propionibacterium freudenreichii, Propionibacterium shermanii, Enterococcus cremoris, Enterococcus diacetylactis, Enterococcus faecium, Enterococcus intermedius, Enterococcus lactis,* or *Enterococcus thermophilus*

AdhE bacterial sequences include:
*Clostridium phytofermentans* (nucleotide; SEQ ID NO:81):
*Clostridium phytofermentans* (amino acid; SEQ ID NO:82):
*Escherichia coli* (nucleotide; SEQ ID NO:83):
*Escherichia coli* (amino acid; SEQ ID NO:84):
*Bifidobacterium adolescentis* (amino acid; SEQ ID NO:100):
*Bacillus coagulans* (amino acid; SEQ ID NO:101):
*Bacillus licheniformis* (amino acid; SEQ ID NO: 102):
*Enterococcus faecium* TX1330 (amino acid; SEQ ID NO:103):

Examples of eukaryotic AdhE include, but are not limited to, *Chlamydomonas reinhardtii* AdhE, *Piromyces* sp. E2, or *Neocallimastix frontalis*.

AdhE sequences from eukaryotes include:
*Chlamydomonas reinhardtii* AdhE (nucleotide; SEQ ID NO:85):
*Chlamydomonas reinhardtii* AdhE (amino acid; SEQ ID NO:86):
*Piromyces* sp. E2 (nucleotide; SEQ ID NO:87):
*Piromyces* sp. E2 (amino acid; SEQ ID NO:88):

Consolidated Bioprocessing

Consolidated bioprocessing (CBP) is a processing strategy for cellulosic biomass that involves consolidating into a single process step four biologically-mediated events: enzyme production, hydrolysis, hexose fermentation, and pentose fermentation. Implementing this strategy requires development of microorganisms that both utilize cellulose, hemicellulosics, and other biomass components while also producing a product of interest at sufficiently high yield and concentrations. The feasibility of CBP is supported by kinetic and bioenergetic analysis. See van Walsum and Lynd (1998) *Biotech. Bioeng.* 58:316.

CBP offers the potential for lower cost and higher efficiency than processes featuring dedicated saccharolytic enzyme production. The benefits result in part from avoided capital costs, substrate and other raw materials, and utilities associated with saccharolytic enzyme production. In addition, several factors support the realization of higher rates of hydrolysis, and hence reduced reactor volume and capital investment using CBP, including enzyme-microbe synergy and the use of thermophilic organisms and/or complexed saccharolytic systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring saccharolytic microorganisms to improve product-related properties, such as yield and titer; and engineering non-saccharolytic organisms that exhibit high product yields and titers to express a heterologous saccharolytic enzyme system enabling starch, cellulose, and, hemicellulose utilization.

Starch and Cellulose Degradation

The degradation of starch into component sugar units proceeds via amylolytic enzymes. Amylase is an example of an amylolytic enzyme that is present in human saliva, where it begins the chemical process of digestion. The pancreas also makes amylase (alpha amylase) to hydrolyze dietary starch into disaccharides and trisaccharides which are converted by other enzymes to glucose to supply the body with energy. Plants and some bacteria also produce amylases. Amylases are glycoside hydrolases and act on α-1,4-glycosidic bonds.

Several amylolytic enzymes are implicated in starch hydrolysis. Alpha-amylases (EC 3.2.1.1) (alternate names: 1,4-α-D-glucan glucanohydrolase; glycogenase) are calcium metalloenzymes, i.e., completely unable to function in the absence of calcium. By acting at random locations along the starch chain, alpha-amylase breaks down long-chain carbohydrates, ultimately yielding maltotriose and maltose from amylose, or maltose, glucose and "limit dextrin" from amylopectin. Because it can act anywhere on the substrate, alpha-amylase tends to be faster-acting than beta-amylase. Another form of amylase, beta-amylase (EC 3.2.1.2) (alternate names: 1,4-α-D-glucan maltohydrolase; glycogenase; saccharogen amylase) catalyzes the hydrolysis of the second α-1,4 glycosidic bond, cleaving off two glucose units (maltose) at a time. The third amylase is gamma-amylase (EC 3.2.1.3) (alternate names: Glucan 1,4-α-glucosidase; amyloglucosidase; Exo-1, 4-α-glucosidase; glucoamylase; lysosomal α-glucosidase; 1,4-α-D-glucan glucohydrolase). In addition to cleaving the last α(1-4)glycosidic linkages at the nonreducing end of amylose and amylopectin, yielding glucose, gamma-amylase will cleave α(1-6) glycosidic linkages.

A fourth enzyme, alpha-glucosidase, acts on maltose and other short malto-oligosaccharides produced by alpha-, beta-, and gamma-amylases, converting them to glucose.

Three major types of enzymatic activities degrade native cellulose. The first type is endoglucanases (1,4-f3-D-glucan 4-glucanohydrolases; EC 3.2.1.4). Endoglucanases cut at random in the cellulose polysaccharide chain of amorphous cellulose, generating oligosaccharides of varying lengths and consequently new chain ends. The second type are exoglucanases, including cellodextrinases (1,4-β-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. The third type are β-glucosidases (β-glucoside glucohydrolases; EC 3.2.1.21). β-Glucosidases hydrolyze soluble cellodextrins and cellobiose to glucose units.

Even though yeast strains expressing enzymes for the production of fuel ethanol from whole grain or starch have been previously disclosed, the application has not been commercialized in the grain-based fuel ethanol industry, due to the relatively poor ability of the resulting strains to produce/tolerate high levels of ethanol. For example, U.S. Pat. No. 7,226,776 discloses that a polysaccharase enzyme expressing ethanologen can make ethanol directly from carbohydrate polymers, but the maximal ethanol titer demonstrated is 3.9 g/l. U.S. Pat. No. 5,422,267 discloses the use of a glucoamylase in yeast for production of alcoholic beverages; however, no commercially relevant titers of ethanol are disclosed.

Heterologous Saccharolytic Enzymes

According to one aspect of the present invention, the expression of heterologous saccharolytic enzymes the recombinant microorganisms of the invention can be used advantageously to produce products such as ethanol from biomass sources. For example, cellulases from a variety of sources can be heterologously expressed to successfully increase efficiency of ethanol production. The saccharolytic enzymes can be from fungi, yeast, bacteria, plant, protozoan or termite sources. In some embodiments, the saccharolytic enzyme is from *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum* or *Arabidopsis thaliana.*

In some embodiments, the cellulase for expression in the recombinant microorganisms of the invention is any cellulase disclosed in Table 4 or Table 7 in copending International Appl. No. PCT/US2011/039192, incorporated by reference herein, or any cellulase suitable for expression in an appropriate host cell. In other embodiments, the amylase for expression in the recombinant microorganisms of the invention is any amylase such as alpha-amylases, beta-amylases, glucoamylases, alpha-glucosidases, pullulanase, or isopullulanase paralogues or orthologues, any amylase disclosed in Tables 15-19, preferably in Table 19, in copending International Appl. No. PCT/US2011/039192, incorporated by reference herein, or any amylase suitable for expression in an appropriate host cell. In some embodiments of the invention, multiple saccharolytic enzymes from a single organism are co-expressed in the same recombinant microorganism. In some embodiments of the invention, multiple saccharolytic enzymes from different organisms are co-expressed in the same recombinant microorganism. In particular, saccharolytic enzymes from two, three, four, five, six, seven, eight, nine or more organisms can be co-expressed in the same recombinant microorganism. Similarly, the invention can encompass co-cultures of yeast strains, wherein the yeast strains express different saccharolytic enzymes. Co-cultures can include yeast strains expressing heterologous saccharolytic enzymes from the same organisms or from different organisms. Co-cultures can include yeast strains expressing saccharolytic enzymes from two, three, four, five, six, seven, eight, nine or more organisms.

Lignocellulases for expression in the recombinant microorganisms of the present invention include both endoglucanases and exoglucanases. Other lignocellulases for expression in the recombinant microorganisms of the invention include accesory enzymes which can act on the lignocellulosic material. The lignocellulases can be, for example, endoglucanases, glucosidases, cellobiohydrolases, xylanases, glucanases, xylosidases, xylan esterases, arabinofuranosidases, galactosidases, cellobiose phosphorylases, cellodextrin phosphorylases, mannanases, mannosidases, xyloglucanases, endoxylanases, glucuronidases, acetylxylanesterases, arabinofuranohydrolases, swollenins, glucuronyl esterases, expansins, pectinases, and feruoyl esterases. In some embodiments, the lignocellulases of the invention can be any suitable enzyme for digesting the desired lignocellulosic material.

In certain embodiments of the invention, the lignocellulase can be an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase paralogue or orthologue. In particular embodiments, the lignocellulase is derived from any species named in Tables 4 and 7, in copending International Appl. No. PCT/US2011/039192, incorporated by reference herein.

Xylose Metabolism

Xylose is a five-carbon monosaccharide that can be metabolized into useful products by a variety of organisms. There are two main pathways of xylose metabolism, each unique in the characteristic enzymes they utilize. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR, encoded by the XYL1 gene, is responsible for the reduction of xylose to xylitol and is aided by cofactors NADH or NADPH. Xylitol is then oxidized to xylulose by XDH, which is expressed through the XYL2 gene, and accomplished exclusively with the cofactor $NAD^+$. Because of the varying cofactors needed in this pathway and the degree to which they are available for usage, an imbalance can result in an overproduction of xylitol byproduct and an inefficient production of desirable ethanol. Varying expression of the XR and XDH enzyme levels have been tested in the laboratory in the attempt to optimize the efficiency of the xylose metabolism pathway.

The other pathway for xylose metabolism is called the "Xylose Isomerase" (XI) pathway. Enzyme XI is responsible for direct conversion of xylose into xylulose, and does not proceed via a xylitol intermediate. Both pathways create xylulose, although the enzymes utilized are different. After production of xylulose both the XR-XDH and XI pathways proceed through the enzyme xylulokinase (XK), encoded on gene XKS1, to further modify xylulose into xylulose-5-phosphate where it then enters the pentose phosphate pathway for further catabolism.

Studies on flux through the pentose phosphate pathway during xylose metabolism have revealed that limiting the speed of this step may be beneficial to the efficiency of fermentation to ethanol. Modifications to this flux that may improve ethanol production include a) lowering phosphoglucose isomerase activity, b) deleting the GND1 gene, and c) deleting the ZWF1 gene (Jeppsson et al., *Appl. Environ. Microbiol.* 68:1604-09 (2002)). Since the pentose phosphate pathway produces additional NADPH during metabolism, limiting this step will help to correct the already evident imbalance between NAD(P)H and NAD$^+$ cofactors and reduce xylitol byproduct. Another experiment comparing the two xylose metabolizing pathways revealed that the XI pathway was best able to metabolize xylose to produce the greatest ethanol yield, while the XR-XDH pathway reached a much faster rate of ethanol production (Karhumaa et al., *Microb Cell Fact.* 2007 Feb. 5; 6:5). See also International Publication No. WO2006/009434, incorporated herein by reference in its entirety.

In some embodiments, the recombinant microorganisms of the invention have the ability to metabolize xylose using one or more of the above enzymes.

Arabinose Metabolism

Arabinose is a five-carbon monosaccharide that can be metabolized into useful products by a variety of organisms. L-Arabinose residues are found widely distributed among many heteropolysaccharides of different plant tissues, such as arabinans, arabinogalactans, xylans and arabinoxylans. *Bacillus* species in the soil participate in the early stages of plant material decomposition, and *B. subtilis* secretes three enzymes, an endo-arabanase and two arabinosidases, capable of releasing arabinosyl oligomers and L-arabinose from plant cell.

Three pathways for L-arabinose metabolism in microorganisms have been described. Many bacteria, including *Escherichia coli*, use arabinose isomerase (AraA; E.C. 5.3.1.4), ribulokinase (AraB; E.C. 2.7.1.16), and ribulose phosphate epimerase (AraD; E.C. 5.1.3.4) to sequentially convert L-arabinose to D-xylulose-5-phosphate through L-ribulose and L-ribulose 5-phosphate. See, e.g., Sa-Nogueira I, et al., *Microbiology* 143:957-69 (1997). The D-xylulose-5-phosphate then enters the pentose phosphate pathway for further catabolism. In the second pathway, L-arabinose is converted to L-2-keto-3-deoxyarabonate (L-KDA) by the consecutive action of enzymes arabinose dehydrogenase (ADH), arabinolactone (AL), and arabinonate dehydratase (AraC). See, e.g., Watanabe, S, et al., *J. Biol. Chem.* 281: 2612-2623 (2006). L-KDA can be further metabolized in two alternative pathways: 1) L-KDA conversion to 2-ketoglutarate via 2-ketoglutaric semialdehyde (KGSA) by L-KDA dehydratase and KGSA dehydrogenase or 2) L-KDA conversion to pyruvate and glycolaldehyde by L-KDA aldolase. In the third, fungal pathway, L-arabinose is converted to D-xylulose-5-phosphate through L-arabinitol, L-xylulose, and xylitol, by enzymes such as NAD(P)H-dependent aldose reductase (AR), L-arabinitol 4-dehydrogenase (ALDH), L-xylulose reductase (LXR), xylitol dehydrogenase (XylD), and xylulokinase (XylB). These, and additional proteins involved in arabinose metabolism and regulation may be found at http://www.nmpdr.org/FIG/wiki/rest.cgi/NmpdrPlugin/SeedViewer?page=Subsystems;su bsystem=L-Arabinose_utilization, visited Mar. 21, 2011, which is incorporated by reference herein in its entirety.

AraC protein regulates expression of its own synthesis and the other genes of the Ara system. See Schleif, R., *Trends Genet.* 16(12):559-65 (2000). In the *E. coli*, the AraC protein positively and negatively regulates expression of the proteins required for the uptake and catabolism of the sugar L-arabinose. Homologs of AraC, such as regulatory proteins RhaR and RhaS of the rhamnose operon, have been identified that contain regions homologous to the DNA-binding domain of AraC (Leal, T. F. and de Sa-Nogueira, I., *FEMS Microbiol Lett.* 241(1):41-48 (2004)). Such arabinose regulatory proteins are referred to as the AraC/XylS family. See also, Mota, L. J., et al., *Mol. Microbiol.* 33(3):476-89 (1999); Mota, L. J., et al., *J Bacteriol.* 183(14):4190-201 (2001).

In *E. coli*, the transport of L-arabinose across the *E. coli* cytoplasmic membrane requires the expression of either the high-affinity transport operon, araFGH, a binding protein-dependent system on the low-affinity transport operon, araE, a proton symporter. Additional arabinose transporters include those identified from *K. marxianus* and *P. guilliermondii*, disclosed in U.S. Pat. No. 7,846,712, which is incorporated by reference herein.

In some embodiments, the recombinant microorganisms of the invention have the ability to metabolize arabinose using one or more of the above enzymes.

Microorganisms

The present invention includes multiple strategies for the development of microorganisms with the combination of substrate-utilization and product-formation properties required for CBP. The "native cellulolytic strategy" involves engineering naturally occurring cellulolytic microorganisms to improve product-related properties, such as yield and titer. The "recombinant cellulolytic strategy" involves engineering natively non-cellulolytic organisms that exhibit high product yields and titers to express a heterologous cellulase system that enables cellulose utilization or hemicellulose utilization or both.

Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. For example, under aerobic conditions pyruvate may be oxidized to acetyl coenzyme A (acetyl-CoA), which then enters the tricarboxylic acid cycle (TCA), which in turn generates synthetic precursors, $CO_2$, and reduced cofactors. The cofactors are then oxidized by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidized in reactions involving the reduction of organic substrates to products, such as lactate and ethanol. In addition, ATP is regenerated from the production of organic acids, such as acetate, in a process known as substrate level phosphorylation. Therefore, the fermentation products of glycolysis and pyruvate metabolism include a variety of organic acids, alcohols and $CO_2$.

Most facultative anaerobes metabolize pyruvate aerobically via pyruvate dehydrogenase (PDH) and the tricarboxylic acid cycle (TCA). Under anaerobic conditions, the main energy pathway for the metabolism of pyruvate is via pyruvate-formate-lyase (PFL) pathway to give formate and acetyl-CoA. Acetyl-CoA is then converted to acetate, via phosphotransacetylase (PTA) and acetate kinase (ACK) with the co-production of ATP, or reduced to ethanol via acetaldehyde dehydrogenase (ACDH) and alcohol dehydrogenase (ADH). In order to maintain a balance of reducing equivalents, excess NADH produced from glycolysis is re-oxidized to NAD$^+$ by lactate dehydrogenase (LDH) during the reduction of pyruvate to lactate. NADH can also be re-oxidized by ACDH and ADH during the reduction of acetyl-CoA to ethanol, but this is a minor reaction in cells with a functional LDH.

Host Cells

Host cells useful in the present invention include any prokaryotic or eukaryotic cells; for example, microorganisms selected from bacterial, algal, and yeast cells. Among host cells thus suitable for the present invention are microorganisms, for example, of the genera *Aeromonas, Aspergillus, Bacillus, Escherichia, Kluyveromyces, Pichia, Rhodococcus, Saccharomyces* and *Streptomyces*.

In some embodiments, the host cells are microorganisms. In one embodiment the microorganism is a yeast. According to the present invention the yeast host cell can be, for example, from the genera *Saccharomyces, Kluyveromyces, Candida, Pichia, Schizosaccharomyces, Hansenula, Kloeckera, Schwanniomyces,* and *Yarrowia*. Yeast species as host cells may include, for example, *S. cerevisiae, S. bulderi, S. barnetti, S. exiguus, S. uvarum, S. diastaticus, K. lactis, K. marxianus,* or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In another embodiment, the yeast is a thermotolerant *Saccharomyces cerevisiae*. The selection of an appropriate host is deemed to be within the scope of those skilled in the art from the teachings herein.

In some embodiments, the host cell is an oleaginous cell. The oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. According to the present invention, the oleaginous host cell can be an oleaginous microalgae host cell. For example, the oleaginous microalgae host cell can be from the genera *Thraustochytrium* or *Schizochytrium*. Biodiesel could then be produced from the triglyceride produced by the oleaginous organisms using conventional lipid transesterification processes. In some particular embodiments, the oleaginous host cells can be induced to secrete synthesized lipids. Embodiments using oleaginous host cells are advantageous because they can produce biodiesel from lignocellulosic feedstocks which, relative to oilseed substrates, are cheaper, can be grown more densely, show lower life cycle carbon dioxide emissions, and can be cultivated on marginal lands.

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

Thermotolerant host cells can include, for example, *Issatchenkia orientalis, Pichia mississippiensis, Pichia mexicana, Pichia farinosa, Clavispora opuntiae, Clavispora lusitaniae, Candida mexicana, Hansenula polymorpha* and *Kluyveromyces* host cells. In some embodiments, the thermotolerant cell is an *S. cerevisiae* strain, or other yeast strain, that has been adapted to grow in high temperatures, for example, by selection for growth at high temperatures in a cytostat.

In some particular embodiments, the host cell is a *Kluyveromyces* host cell. For example, the *Kluyveromyces* host cell can be a *K. lactis, K. marxianus, K. blattae, K. phaffii, K. yarrowii, K. aestuarii, K. dobzhanskii, K. wickerhamii K. thermotolerans,* or *K. waltii* host cell. In one embodiment, the host cell is a *K. lactis,* or *K. marxianus* host cell. In another embodiment, the host cell is a *K. marxianus* host cell.

In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments of the present invention, the thermotolerant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the host cell has the ability to metabolize xylose. Detailed information regarding the development of the xylose-utilizing technology can be found in the following publications: Kuyper M et al. *FEMS Yeast Res.* 4: 655-64 (2004), Kuyper M et al. *FEMS Yeast Res.* 5:399-409 (2005), and Kuyper M et al. *FEMS Yeast Res.* 5:925-34 (2005), which are herein incorporated by reference in their entirety. For example, xylose-utilization can be accomplished in *S. cerevisiae* by heterologously expressing the xylose isomerase gene, XylA, e.g., from the anaerobic fungus *Piromyces* sp. E2, overexpressing five *S. cerevisiae* enzymes involved in the conversion of xylulose to glycolytic intermediates (xylulokinase, ribulose 5-phosphate isomerase, ribulose 5-phosphate epimerase, transketolase and transaldolase) and deleting the GRE3 gene encoding aldose reductase to minimise xylitol production.

In some embodiments, the host cell has the ability to metabolize arabinose. For example, arabinose-utilization can be accomplished by heterologously expressing, e.g., one or more of arabinose isomerase, ribulokinase, or ribulose phosphate epimerase.

The host cells can contain antibiotic markers or can contain no antibiotic markers.

In certain embodiments, the host cell is a microorganism that is a species of the genera *Thermoanaerobacterium, Thermoanaerobacter, Clostridium, Geobacillus, Saccharococcus, Paenibacillus, Bacillus, Caldicellulosiruptor, Anaerocellum,* or *Anoxybacillus*. In certain embodiments, the host cell is a bacterium selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharo-*

*lyticus, Caldicellulosiruptor kristjanssonii, Caldicellulosiruptor owensensis, Caldicellulosiruptor lactoaceticus,* and *Anaerocellum thermophilum.* In certain embodiments, the host cell is *Clostridium thermocellum, Clostridium cellulolyticum,* or *Thermoanaerobacterium saccharolyticum.*

Codon Optimized Polynucleotides

The polynucleotides encoding heterologous cellulases can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |

TABLE 1-continued

The Standard Genetic Code

| | T | C | A | G |
|---|---|---|---|---|
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at http://www.kazusa.or.jp/codon/ (visited Feb. 28, 2011), and these tables can be adapted in a number of ways. See Nakamura, Y., et al. "Codon usage tabulated from the international DNA sequence databases: status for the year 2000," *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |

TABLE 2-continued

Codon Usage Table for *Saccharomyces cerevisiae* Genes

| Amino Acid | Codon | Number | Frequency per hundred |
|---|---|---|---|
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTl Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at www.entelechon.com/2008/10/backtranslation-tool/ (visited Feb. 28, 2011) and the "backtranseq" function available at emboss.bioinformatics.nl/cgi-bin/emboss/backtranseq (visited Feb. 28, 2011). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

Transposons

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extrachromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker(s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce more ethanol, or less lactic acid and/or more acetate.

Native Cellulolytic Strategy

Naturally occurring cellulolytic microorganisms are starting points for CBP organism development via the native strategy. Anaerobes and facultative anaerobes are of particular interest. The primary objective is to engineer the metabolization of biomass to solvents, including but not limited to, acetone, isopropanol, ethyl acetate, or ethanol. Metabolic engineering of mixed-acid fermentations in relation to, for example, ethanol production, has been successful in the case of mesophilic, non-cellulolytic, enteric bacteria. Recent developments in suitable gene-transfer techniques allow for this type of work to be undertaken with cellulolytic bacteria.

Recombinant Cellulolytic Strategy

Non-cellulolytic microorganisms with desired product-formation properties are starting points for CBP organism development by the recombinant cellulolytic strategy. The primary objective of such developments is to engineer a heterologous cellulase system that enables growth and fermentation on pretreated lignocellulose. The heterologous production of cellulases has been pursued primarily with bacterial hosts producing ethanol at high yield (engineered strains of *E. coli*, *Klebsiella oxytoca*, and *Zymomonas mobilis*) and the yeast *Saccharomyces cerevisiae*. Cellulase expression in strains of *K. oxytoca* resulted in increased hydrolysis yields—but not growth without added cellulase—for microcrystalline cellulose, and anaerobic growth on amorphous cellulose. Although dozens of saccharolytic enzymes have been functionally expressed in *S. cerevisiae*, anaerobic growth on cellulose as the result of such expression has not been definitively demonstrated.

Aspects of the present invention relate to the use of thermophilic or mesophilic microorganisms as hosts for modification via the native cellulolytic strategy. Their potential in process applications in biotechnology stems from their ability to grow at relatively high temperatures with attendant high metabolic rates, production of physically and chemically stable enzymes, and elevated yields of end products. Major groups of thermophilic bacteria include eubacteria and archaebacteria. Thermophilic eubacteria include: phototropic bacteria, such as cyanobacteria, purple bacteria, and green bacteria; Gram-positive bacteria, such as *Bacillus*, *Clostridium*, Lactic acid bacteria, and *Actinomyces*; and other eubacteria, such as *Thiobacillus*, Spirochete, *Desulfotomaculum*, Gram-negative aerobes, Gram-negative anaerobes, and *Thermotoga*. Within archaebacteria are considered Methanogens, extreme thermophiles (an art-recognized term), and *Thermoplasma*. In certain embodiments, the present invention relates to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus*, *Thermoproteus* (rod-shaped), *Thermofilum* (rod-shaped), *Pyrodictium*, *Acidianus*, *Sulfolobus*, *Pyrobaculum*, *Pyrococcus*, *Thermodiscus*, *Staphylothermus*, *Desulfurococ-* cus, *Archaeoglobus*, and *Methanopyrus*. Some examples of thermophilic or mesophilic (including bacteria, procaryotic microorganism, and fungi), which may be suitable for the present invention include, but are not limited to: *Clostridium thermosulfurogenes*, *Clostridium cellulolyticum*, *Clostridium thermocellum*, *Clostridium the rmohydrosulfuricum*, *Clostridium thermoaceticum*, *Clostridium thermosaccharolyticum*, *Clostridium tartarivorum*, *Clostridium thermocellulaseum*, *Clostridium phytofermentans*, *Clostridium straminosolvens*, *Thermoanaerobacterium thermosaccarolyticum*, *Thermoanaerobacterium saccharolyticum*, *Thermobacteroides acetoethylicus*, *Thermoanaerobium brockii*, *Methanobacterium thermoautotrophicum*, *Anaerocellum thermophilium*, *Pyrodictium occultum*, *Thermoproteus neutrophilus*, *Thermofilum librum*, *Thermothrix thioparus*, *Desulfovibrio thermophilus*, *Thermoplasma acidophilum*, *Hydrogenomonas thermophilus*, *Thermomicrobium roseum*, *Thermus flavas*, *Thermus ruber*, *Pyrococcus furiosus*, *Thermus aquaticus*, *Thermus thermophilus*, *Chloroflexus aurantiacus*, *Thermococcus litoralis*, *Pyrodictium abyssi*, *Bacillus stearothermophilus*, *Cyanidium caldarium*, *Mastigocladus laminosus*, *Chlamydothrix calidissima*, *Chlamydothrix penicillata*, *Thiothrix carnea*, *Phormidium tenuissimum*, *Phormidium geysericola*, *Phormidium subterraneum*, *Phormidium bijahensi*, *Oscillatoria filiformis*, *Synechococcus lividus*, *Chloroflexus aurantiacus*, *Pyrodictium brockii*, *Thiobacillus thiooxidans*, *Sulfolobus acidocaldarius*, *Thiobacillus thermophilica*, *Bacillus stearothermophilus*, *Cercosulcifer hamathensis*, *Vahlkampfia reichi*, *Cyclidium citrullus*, *Dactylaria gallopava*, *Synechococcus lividus*, *Synechococcus elongatus*, *Synechococcus minervae*, *Synechocystis aquatilus*, *Aphanocapsa thermalis*, *Oscillatoria terebriformis*, *Oscillatoria amphibia*, *Oscillatoria germinate*, *Oscillatoria okenii*, *Phormidium laminosum*, *Phormidium parparasiens*, *Symploca thermalis*, *Bacillus acidocaldarias*, *Bacillus coagulans*, *Bacillus thermocatenalatus*, *Bacillus licheniformis*, *Bacillus pamilas*, *Bacillus macerans*, *Bacillus circulans*, *Bacillus laterosporus*, *Bacillus brevis*, *Bacillus subtilis*, *Bacillus sphaericus*, *Desulfotomaculum nigrificans*, *Streptococcus thermophilus*, *Lactobacillus thermophilus*, *Lactobacillus bulgaricus*, *Bifidobacterium thermophilum*, *Streptomyces fragmentosporus*, *Streptomyces thermonitrificans*, *Streptomyces thermovulgaris*, *Pseudonocardia thermophila*, *Thermoactinomyces vulgaris*, *Thermoactinomyces sacchari*, *Thermoactinomyces candidas*, *Thermomonospora curvata*, *Thermomonospora viridis*, *Thermomonospora citrina*, *Microbispora thermodiastatica*, *Microbispora aerata*, *Microbispora bispora*, *Actinobifida dichotomica*, *Actinobifida chromogens*, *Micropolyspora caesia*, *Micropolyspora faeni*, *Micropolyspora cectivugida*, *Micropolyspora cabrobrunea*, *Micropolyspora thermovirida*, *Micropolyspora viridinigra*, *Methanobacterium thermoautothropicum*, *Caldicellulosiruptor acetigenus*, *Caldicellulosiruptor saccharolyticus*, *Caldicellulosiruptor kristjanssonii*, *Caldicellulosiruptor owensensis*, *Caldicellulosiruptor lactoaceticus*, variants thereof, and/or progeny thereof.

In particular embodiments, the present invention relates to thermophilic bacteria selected from the group consisting of *Clostridium cellulolyticum*, *Clostridium thermocellum*, and *Thermoanaerobacterium saccharolyticum*.

In certain embodiments, the present invention relates to thermophilic bacteria selected from the group consisting of *Fervidobacterium gondwanense*, *Clostridium thermolacticum*, *Moorella* sp., and *Rhodothermus marinus*.

In certain embodiments, the present invention relates to thermophilic bacteria of the genera *Thermoanaerobacterium* or *Thermoanaerobacter*, including, but not limited to, species selected from the group consisting of: *Thermoanaerobacterium thermosulfurigenes*, *Thermoanaerobacterium aotearoense*, *Thermoanaerobacterium polysaccharolyticum*, *Thermoanaerobacterium zeae*, *Thermoanaerobacterium xylanolyticum*, *Thermoanaerobacterium saccharolyticum*, *Thermoanaerobium brockii*, *Thermoanaerobacterium thermosaccharolyticum*, *Thermoanaerobacter thermohydrosulfuricus*, *Thermoanaerobacter ethanolicus*, *Thermoanaerobacter brockii*, variants thereof, and progeny thereof.

In certain embodiments, the present invention relates to microorganisms of the genera *Geobacillus*, *Saccharococcus*, *Paenibacillus*, *Bacillus*, and *Anoxybacillus*, including, but not limited to, species selected from the group consisting of: *Geobacillus thermoglucosidasius*, *Geobacillus stearothermophilus*, *Saccharococcus caldoxylosilyticus*, *Saccharoccus thermophilus*, *Paenibacillus campinasensis*, *Bacillus flavothermus*, *Anoxybacillus kamchatkensis*, *Anoxybacillus gonensis*, variants thereof, and progeny thereof.

In certain embodiments, the present invention relates to mesophilic bacteria selected from the group consisting of *Saccharophagus degradans*; *Flavobacterium johnsoniae*; *Fibrobacter succinogenes*; *Clostridium hungatei*; *Clostridium phytofermentans*; *Clostridium cellulolyticum*; *Clostridium aldrichii*; *Clostridium termitididis*; *Acetivibrio cellulolyticus*; *Acetivibrio ethanolgignens*; *Acetivibrio multivorans*; *Bacteroides cellulosolvens*; and *Alkalibacter saccharofomentans*, variants thereof and progeny thereof.

Organism Development Via the Native Cellulolytic Strategy

One approach to organism development for CBP begins with organisms that naturally utilize cellulose, hemicellulose and/or other biomass components, which are then genetically engineered to enhance product yield and tolerance. For example, *Clostridium thermocellum* is a thermophilic bacterium that has among the highest rates of cellulose utilization reported. Other organisms of interest are xylose-utilizing thermophiles such as *Thermoanaerobacterium saccharolyticum* and *Thermoanaerobacterium thermosaccharolyticum*. Organic acid production may be responsible for the low concentrations of produced ethanol generally associated with these organisms. Thus, one objective is to eliminate production of acetic and lactic acid in these organisms via metabolic engineering. Substantial efforts have been devoted to developing gene transfer systems for the above-described target organisms and multiple *C. thermocellum* isolates from nature have been characterized. See McLaughlin et al. (2002) *Environ. Sci. Technol.* 36:2122. Metabolic engineering of thermophilic, saccharolytic bacteria is an active area of interest, and knockout of lactate dehydrogenase in *T. saccharolyticum* has recently been reported. See Desai et al. (2004) *Appl. Microbiol. Biotechnol.* 65:600. Knockout of acetate kinase and phosphotransacetylase in this organism is also possible.

Organism Development Via the Recombinant Cellulolytic Strategy

An alternative approach to organism development for CBP involves conferring the ability to grow on lignocellulosic materials to microorganisms that naturally have high product yield and tolerance via expression of a heterologous cellulasic system and perhaps other features. For example, *Saccharomyces cerevisiae* has been engineered to express over two dozen different saccharolytic enzymes. See Lynd et al. (2002) *Microbiol. Mol. Biol. Rev.* 66:506.

Whereas cellulosic hydrolysis has been approached in the literature primarily in the context of an enzymatically-oriented intellectual paradigm, the CBP processing strategy requires that cellulosic hydrolysis be viewed in terms of a microbial paradigm. This microbial paradigm naturally leads to an emphasis on different fundamental issues, organisms, cellulasic systems, and applied milestones compared to those of the enzymatic paradigm. In this context, *C. thermocellum* has been a model organism because of its high growth rate on cellulose together with its potential utility for CBP.

In certain embodiments, organisms useful in the present invention may be applicable to the process known as simultaneous saccharification and fermentation (SSF), which is intended to include the use of said microorganisms and/or one or more recombinant hosts (or extracts thereof, including purified or unpurified extracts) for the contemporaneous degradation or depolymerization of a complex sugar (i.e., cellulosic biomass) and bioconversion of that sugar residue into ethanol by fermentation.

Ethanol Production

According to the present invention, a recombinant microorganism can be used to produce ethanol from biomass, which is referred to herein as lignocellulosic material, lignocellulosic substrate, or cellulosic biomass. Methods of producing ethanol can be accomplished, for example, by contacting the biomass with a recombinant microorganism as described herein, and as described in commonly owned U.S. Patent Application Publication No. 2011/0189744 A1, U.S. Patent Application Publication No. 2011/0312054 A1, U.S. Patent Application Publication No. 2012/0003701, International Appl. No. PCT/US2009/065571, International Appl. No. PCT/US2009/069443, International Appl. No. PCT/US2009/064128, International Appl. No. PCT/IB2009/005881, and PCT/US2009/065571, the contents of each are incorporated by reference herein.

Numerous cellulosic substrates can be used in accordance with the present invention. Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

In some embodiments, the invention is directed to a method for hydrolyzing a cellulosic substrate, for example a cellulosic substrate as described above, by contacting the cellulosic substrate with a recombinant microorganism of the invention. In some embodiments, the invention is directed to a method for hydrolyzing a cellulosic substrate, for example a cellulosic substrate as described above, by contacting the cellulosic substrate with a co-culture comprising yeast cells expressing heterologous cellulases.

In some embodiments, the invention is directed to a method for fermenting cellulose. Such methods can be accomplished, for example, by culturing a host cell or co-culture in a medium that contains insoluble cellulose to allow saccharification and fermentation of the cellulose.

The production of ethanol can, according to the present invention, be performed at temperatures of at least about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C. In some embodiments of the present invention, the thermotolerant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, methods of producing ethanol can comprise contacting a cellulosic substrate with a recombinant microorganism or co-culture of the invention and additionally contacting the cellulosic substrate with externally produced cellulase enzymes. Exemplary externally produced cellulase enzymes are commercially available and are known to those of skill in the art.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter.

In some embodiments, the host cells of the present invention can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter more than a control strain (e.g., a wild-type strain) and grown under the same conditions. In some embodiments, the ethanol can be produced in the absence of any externally added cellulases.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein. The U.S. Department of Energy (DOE) provides a method for calculating theoretical ethanol yield. Accordingly, if the weight percentages are known of C6 sugars (i.e., glucan, galactan, mannan), the theoretical yield of ethanol in gallons per dry ton of total C6 polymers can be determined by applying a conversion factor as follows:

> (1.11 pounds of C6 sugar/pound of polymeric sugar)×(0.51 pounds of ethanol/pound of sugar)×(2000 pounds of ethanol/ton of C6 polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

And if the weight percentages are known of C5 sugars (i.e., xylan, arabinan), the theoretical yield of ethanol in gallons per dry ton of total C5 polymers can be determined by applying a conversion factor as follows:

> (1.136 pounds of C5 sugar/pound of C5 polymeric sugar)×(0.51 pounds of ethanol/pound of sugar)×(2000 pounds of ethanol/ton of C5 polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

It follows that by adding the theoretical yield of ethanol in gallons per dry ton of the total C6 polymers to the theoretical yield of ethanol in gallons per dry ton of the total C5 polymers gives the total theoretical yield of ethanol in gallons per dry ton of feedstock.

Applying this analysis, the DOE provides the following examples of theoretical yield of ethanol in gallons per dry ton of feedstock: corn grain, 124.4; corn stover, 113.0; rice straw, 109.9; cotton gin trash, 56.8; forest thinnings, 81.5; harwood sawdust, 100.8; bagasse, 111.5; and mixed paper, 116.2. It is important to note that these are theoretical yields. The DOE warns that depending on the nature of the feedstock and the process employed, actual yield could be anywhere from 60% to 90% of theoretical, and further states that "achieving high yield may be costly, however, so lower yield processes may often be more cost effective." (Ibid.)

EXEMPLIFICATION

The invention now being generally described, it will be more readily understood by reference to the following examples, which are included merely for purposes of illustration of certain aspects and embodiments of the present invention, and are not intended to limit the invention.

Example 1

Improving Ethanol Yield Through Engineering of Alternate Electron Acceptors

The present Example describes pathways to reduce or eliminate glycerol by engineering alternate electron acceptors in a yeast cell. Glycerol is an undesired by-product of sugar metabolism during anaerobic growth in yeast. The amount of glycerol produced during anaeroblic growth on glucose has been empirically determined by Medina, V G, et al., *Appl. Env. Microbiol.* 76:190-95 (2010):

> 56 mmol glucose→1 g biomass+88 mmol ethanol+95 mmol CO$_2$+11 mmol glycerol+1.7 mmol acetate Assuming glycerol production is primarily for the regeneration of NAD$^+$ for the continuation of glycolysis, a half reaction for glycerol production is (Medina, V G, et al., *Appl. Env. Microbiol.* 76:190-95 (2010)):

> 0.5 glucose+NADH+H$^+$+ATP→glycerol+NAD$^+$ ADP+P$_i$

The following pathways describe engineering an alternate electron acceptor for glycerol in the above half reaction, engineering an increase in ethanol yield during anaerobic growth on glucose by using improved enzyme activities for converting glucose to ethanol, and/or deleting endogenous glycerol-producing or glycerol-regulating genes.

1.1 Engineering of a Formate Pathway in Yeast

Production of formate from glucose can provide similar reducing equivalents as glycerol, as shown in the following half reaction:

> 0.5 glucose+NADH+H$^+$+ADP+P$_i$→formate+NAD$^+$+ATP+ethanol

In addition to balancing the redox constraints of the cell, this pathway provides increased ATP yield and results in an overall anaerobic growth equation of:

> 56 mmol glucose→1 g biomass+99 mmol ethanol+95 mmol CO$_2$+11 mmol formate+1.7 mmol acetate Engineering in a formate pathway as an alternate electron acceptor to glycerol results in an increase of 12.5% in the theoretical yield of ethanol. Enzymes than can be targeted to engineer such an increase include pyruvate formate lyase (PFL) and formate dehydrogenase (FDH). See FIG. 1.

1.1.1 Expression of PFL

The conversion of pyruvate to acetyl-CoA and formate is performed by PFL.

Thus, to produce formate in yeast, a PFL can be expressed. PFLs are common in bacteria from a variety of sources. Vigorous hydrogen producing bacteria, such as from a *clostridium*, *thermoanaerobacterium*, or other anaerobic bacteria will likely result in an increased productivity. Examples of PFL include, but are not limited, *Bacillus licheniformis*, *Streptococcus thermophilus*, *Lactobacillus plantarum*, *Lactobacillus casei*, *Bifidobacterium adolescentis*, *Clostridium cellulolyticum*, *Escherichia coli*, *Chlamydomonas reinhardtii* PflA, *Piromyces* sp. E2, or *Neocallimastix frontalis*. See Example 4 and Table 1 below.

1.1.2 Deletion of FDH

To prevent yeast from converting formate to CO$_2$ and NADH, endogeneous FDH genes can be deleted or downregulated. Deleting or downregulating fdh1, fdh2, or both genes can enhance the redox balance and ethanol yield of the recombinant microorganisms of the invention.

1.2 Improving Conversion of Acetyl-CoA to Ethanol

To improve the conversion of acetyl-CoA to ethanol, endogenous yeast genes can be replaced or complimented with either an improved acetaldehyde dehydrogenase (e.g., from *C. phytofermentans* or other source) to convert acetyl-CoA to acetaldehyde, or a bifunctional acetaldehyde/alcohol dehydrogenase (AADH) to convert acetyl-CoA to acetaldehyde and acetaldehyde to ethanol. By engineering in one or more such enzymes, the in vivo kinetics of the conversion of acetyl-CoA to ethanol can be increased, providing for improved growth of the host strain. The bi-functional alcohol/aldehyde dehydrogenase can come from a variety of microbial sources, including but not limited to *E. coli*, *C. acetobutylicum*, *T saccharolyticum*, *C. thermocellum*, *C. phytofermentans*, *Piromyces* SP E2, or *Bifidobacterium adolescentis*.

1.3 Deletion or Downregulation of Glycerol Pathway

Deleting or altering expression of glycerol formation genes will reduce or block endogenous production of glycerol and may enhance acetate uptake. Deletion of gpd1, gpd2, or both genes and/or deletion of gpp1, gpp2, or both genes may be used to eliminate glycerol formation and enhance ethanol yield. However, the complete elimination of glycerol may not be practical for an industrial process. See Guo, Z P., et al., *Metab. Eng.* 13:49-59 (2011). Thus, rather than the complete removal of any one, all, or some combination of these glycerol formation genes, one or more of these genes can be altered or downregulated to reduce glycerol formation and enhance ethanol yield.

Example 2

Deletion or Downregulation of Glycerol-Regulating Gene FPS 1 to Improve Ethanol Yield Instead of, or in addition to, downregulating glycerol production through deletion or alteration of glycerol-forming genes, glycerol production can be downregulated by deletion or alteration of a glycerol-regulating gene. FPS1 is an aquaglyceroporin responsible for efflux of glycerol. An fps1Δ strain has reduced glycerol formation yet has a completely functional $NAD^+$-dependant glycerol synthesis pathway. In addition to deletion of FPS1, constitutively active mutants of FPS1 or homologs from other organisms can be expressed to alter glycerol production. Because such FPS1 deletion or alteration strains can still synthesize and retain glycerol, improved robustness may be observed relative to strains that are unable to make glycerol.

Null mutants of an fps1Δ strain grow much slower anaerobically than wild-type due to intracellular glycerol accumulation. Tamás, M. J., et al., *Molecular Microbiol.* 31(4):1087-1104 (1999). However, preliminary data indicates that expression of a *B. adolescentis* bifunctional AADH in conjunction with *B. adolescentis* PFL in an fps1Δ strain can enable anaerobic growth of fps1Δ strain (see Example 7 and FIGS. 22 and 24). Additionally, significantly improved osmotic tolerance was also observed when FPS1 was deleted in glycerol mutant strains containing ADH and PFL alone. Increased resistance to osmotic stress was determined by observation of improved growth of the fps1Δ mutant on several different high osmolarity media including 1M sodium chloride, 1M sorbitol, and 1M xylitol. The fps1Δ mutant was created by marker recycle resulting in a deletion of a large region of the FPS1 coding sequence (sequence of native and deletion below).

Sequence of FPS1 locus (coding sequence is underlined; SEQ ID NO:104):

```
aacgcggctgatgcttttatttaggaaggaatacttacattatcatgagaacattgtcaagggcattctgatacgggcctt ccatcgcaagaaaaaggcagcaacggactgagggacggagagagttacggcataagaagtagtaggagagcagagtgtcat aaagttatattattctcgtcctaaagtcaattagttctgttgcgcttgacaatatatgtcgtgtaataccgtcccttagcagaagaaaga aagacggatccatatatgttaaaatgcttcagagatgtttctttaatgtgccgtccaacaaaggtatcttctgtagcttcctctattttcg atcagatctcatagtgagaaggcgcaattcagtagttaaaagcggggaacagtgtgaatccggagacggcaagattgcccggc ccttttgcggaaaagataaaacaagatatattgcacttttccaccaagaaaaacaggaagtggattaaaaaatcaacaaagtata acgcctattgtcccaataagcgtcggttgttcttctttattattttaccaagtacgctcgagggtacattctaatgcattaaaagacatg agtaatcctcaaaaagctctaaacgactttctgtccagtgaatctgttcatacacatgatagttctaggaaacaatctaataagcagtc atccgacgaaggacgctcttcatcacaaccttcacatcatcactctggtggtactaacaacaataataacaataataataataat aacagtaacaacaacaacggcaacgatgggggaaatgatgacgactatgattatgaaatgcaagattatagaccttctccgc aaagtgcgcggcctactcccacgtatgttccacaatattctgtagaaagtgggactgctttcccgattcaagaggttattcctagcg catacattaacacacaagatataaaccataaagataacggtccgccgagtgcaagcagtaatagagcattcaggcctagaggc agaccacagtgtcggccaacgtgcttaacattgaagattttacaaaaatgcagacgatgcgcataccatcccggagtcacatttat cgagaaggagaagtaggtcgagggctacgagtaatgctgggcacagtgccaatacaggcgccacgaatggcaggactactg gtgcccaaactaatatggaaagcaatgaatcaccacgtaacgtccccattatggtgaagccaaagacattataccagaaccctca aacacctacagtcttgccctccacataccatccaattaataaatggtcttccgtcaaaaacacttatttgaaggaattttttagccgagtt tatgggaacaatggttatgattattttcggtagtgctgttgtttgtcaggtcaatgttgctgggaaaatacagcaggacaatttcaacg tggctttggataaccttaacgttaccgggtcttctgcagaaacgatagacgctatgaagagtttaacatccttggtttcatccgttgcg ggcggtacctttgatgatgtggcattgggctgggctgctgccgtggtgatgggctatttctgcgctggtggtagtgccatctcaggt gctcatttgaatccgtctattacattagccaattggtgtatagaggttttcccctgaagaaagttccttattactttgctggacaattgat cggtgccttcacaggcgctttgatcttgtttatttggtacaaaagggtgttacaagaggcatatagcgattggtggatgaatgaaagt gttgcgggaatgttttgcgtttttccaaagccttatctaagttcaggacggcaattttttttccgaatttttatgtggagctatgttacaagc aggaacatttgcgctgaccgatccttatacgtgtttgtcctctgatgttttcccattgatgatgtttattttgattttcattatcaatgcttcc atggcttatcagacaggtacagcaatgaatttggctcgtgatctgggcccacgtcttgcactatatgcagttggatttgatcataaaa tgctttgggtgcatcatcatcatttcttttgggttcccatggtaggcccatttattggtgcgttaatgggggggttggtttacgatgtctg tatttatcagggtcatgaatctccagtcaactggtcttttaccagtttataaggaaatgattatgagagcctggtttagaaggcctggtt ggaagaagagaaatagagcaagaagaacatcggacctgagtgacttctcatacaataacgatgatgatgaggaatttggagaaa
```

-continued

```
gaatggctcttcaaaagacaaagaccaagtcatctatttcagacaacgaaaatgaagcaggagaaaagaaagtgcaatttaaatc tgttcagcgcggcaaaagaacgtttggtggtataccaacaattcttgaagaagaagattccattgaaactgcttcgctaggtgcga cgacgactgattctattgggttatccgacacatcatcagaagattcgcattatggtaatgctaagaaggtaacatgagaaaacaga
``` caagaaaaagaaacaaataatatagactgatagaaaaaaatactgcttactaccgccggtataatatatatatatatatatttacat agatgattgcatagtgttttaaaaagctttcctaggttaagctatgaatcttcataacctaaccaactaaatatgaaaatactgacccat cgtcttaagtaagttgacatgaactcagcctggtcacctactatacatgatgtatcgcatggatggaaagaataccaaacgctacct tccaggttaatgatagtatccaaacctagttggaatttgccttgaacatcaagcagcgattcgatatcagttgggagcatcaatttgg tcattggaataccatctatgcttttctcctcccatattcgcaaaagtagtaagggctcgttatatacttttgaatatgtaagatataattct atatgatttagtaatttattttctatacgctcagtattttctgcagttgtcgagtaggtattaaacgcaaaagaagtccatccttttcatca ttcaaatggacatcttggcaaagggcccagttatggaaaatctgggagtcatacaacgattgcagttggctatgccactcctggta aggaatcatcaagtctgataattctgtttttagcccttttttttttttttcatg

20

Sequence of fps1Δ mutation (part of the fps1 coding sequence was not deleted (underlined) and the region that was deleted is represented by a Δ; SEQ ID NO:105):

aacgcggctgatgcttttatttaggaaggaatacttacattatcatgagaacattgtcaagggcattctgatacgggcctt ccatcgcaagaaaaaggcagcaacggactgagggacggagagagttacggcataagaagtagtaggagagcagagtgtcat aaagttatattattctcgtcctaaagtcaattagttctgttgcgcttgacaatatatgtcgtgtaataccgtcccttagcagaagaaaga aagacggatccatatatgttaaaatgcttcagagatgtttctttaatgtgccgtccaacaaaggtatcttctgtagcttcctctatttttcg atcagatctcatagtgagaaggcgcaattcagtagttaaaagcggggaacagtgtgaatccggagacggcaagattgcccggc ccttttgcggaaaagataaaacaagatatattgcacttttttccaccaagaaaaacaggaagtggattaaaaaatcaacaaagtata acgcctattgtcccaataagcgtcggttgttcttctttattattttaccaagtacgctcgagggtacattctaatgcattaaaagacΔg attcgcattatggtaatgctaagaaggtaacatgagaaaacagacaagaaaaagaaacaaataatatagactgatagaaaaaaat actgcttactaccgccggtataatatatatatatatatatttacatagatgattgcatagtgttttaaaaagctttcctaggttaagctat gaatcttcataacctaaccaactaaatatgaaaatactgacccatcgtcttaagtaagttgacatgaactcagcctggtcaccta tacatgatgtatcgcatggatggaaagaataccaaacgctacctccaggttaatgatagtatccaaacctagttggaatttgccttg aacatcaagcagcgattcgatatcagttgggagcatcaatttggtcattggaataccatctatgcttttctcctcccatattcgcaaaa gtagtaagggctcgttatatacttttgaatatgtaagatataattctatatgatttagtaatttattttctatacgctcagtattttctgcagt tgtcgagtaggtattaaacgcaaaagaagtccatccttttcatcattcaaatggacatcttggcaaagggcccagttatggaaaatct gggagtcatacaacgattgcagttggctatgccactcctggtaaggaatcatcaagtctgataattctgtttttagccctttttttttttt ttcatg

Example 3

Generating Yeast Strains with a Deleted or Downregulated Glycerol-Production Pathway To create yeast strains with altered glycerol production, endogenous glycerol-producing or regulating genes can either be deleted or downregulated, by generating the following genetic backgrounds:

|  | Haploid Strains | Diploid Strains |
|---|---|---|
| Glycerol Elimination | gpd1Δ gpd2Δ fdh1Δ fdh2Δ fdh1Δ fdh2Δ fps1Δ | gpd1Δ/gpd1Δ gpd2Δ/gpd2Δ fdh1Δ/fdh1Δ fdh2Δ/fdh2Δ |
| Background | gpd1Δ gpd2Δ fdh1Δ fdh2Δ fps1Δ | fdh1Δ/fdh1Δ fdh2Δ/fdh2Δ fps1Δ/fps1Δ |
|  | gpd1Δ gpd2Δ fps1Δ | gpd1Δ/gpd1Δ gpd2Δ/gpd2Δ |
|  | gpd1Δ gpd2Δ | fdh1Δ/fdh1Δ fdh2Δ/fdh2Δ fps1Δ/fps1Δ |
|  |  | gpd1Δ/gpd1Δ gpd2Δ/gpd2Δ fps1Δ/fps1Δ |
|  |  | gpd1Δ/gpd1Δ gpd2Δ/gpd2Δ |
| Glycerol Reduction Background | gpd1Δ gpd2Δ::GPD1 fdh1Δ fdh2Δ | gpd1Δ/gpd1Δ gpd2Δ/gpd2Δ::GPD1/GPD1 fdh1Δ/fdh1Δ fdh2Δ/fdh2Δ |
|  | gpd1Δ gpd2Δ::GPD1 | gpd1Δ/gpd1Δ |
|  | gpd1Δ gpd2Δ::GPD1 fdh1Δ fdh2Δ fps1Δ | gpd2Δ/gpd2Δ::GPD1/GPD1 |
|  | gpd1Δ gpd2Δ::GPD1 fps1Δ | gpd1Δ/gpd1Δ |

-continued

| Haploid Strains | Diploid Strains |
|---|---|
| gpd1Δ: GPD2 gpd2Δ GPD1::GPD2 gpd2Δ fdh1Δfdh2Δ | gpd2Δ/gpd2Δ::GPD1/GPD1 fdh1Δ/fdh1Δ fdh2Δ/fdh2Δ fps1Δ/fps1Δ gpd1Δ/gpd1Δ gpd2Δ/gpd2Δ::GPD1/GPD1 fps1Δ/fps1Δ gpd1Δ/gpd1Δ::GPD2/GPD2 gpd2Δ/gpd2Δ gpd1Δ/gpd1Δ::GPD2/GPD2 gpd2Δ/gpd2Δ fdh1Δ/fdh1Δ fdh2Δ/fdh2Δ |

Strains in the glycerol elimination background were created by deleting one or more of the following genes: gpd1, gpd2, fdh1, fdh2, and/or fps1. Strains in the glycerol reduction background have been created by by deleting one or more of the following genes: gpd1, gpd2, fdh1, fdh2, and/or fps1, and by expressing GPD 1 under the control of the gpd2 promoter (designated gpd2Δ:: GPD1). These strains in which GPD1 is expressed from the gpd2 promoter make a smaller amount of glycerol relative to a wild-type strain.

3.1 Generation of Glycerol-Elimination Strain gpd1Δ gpd2Δ fdh1Δ fdh2Δ

To produce glycerol-elimination strain gpd1Δ gpd2Δ fdh1Δ fdh2Δ, the following methods were used. All genetic modications were generated using positive selections to insert genetic elements and negative selections to remove genetic elements. See FIGS. 4-11. The genetic elements were amplified by PCR and transformed into host strains, followed by selection and screening for the desired modification. The sequence of native gpd1, gpd2, fdh1, fdh2 from *S. cerevisiae*, and resulting loci following deletion, are listed below.

Sequence of GPD1 locus (coding sequence is underlined; SEQ ID NO:89):

```
tacaaacgcaacacgaaagaacaaaaaaagaagaaaacagaaggccaagacagggtcaatgagactgttgtcctc ctactgtccctatgtctctggccgatcacgcgccattgtccctcagaaacaaatcaaacacccacaccccgggcacccaaagtcc ccacccacaccaccaatacgtaaacggggcgcccctgcaggccctcctgcgcgcggcctcccgccttgcttctctccccttcc ttttcttttccagttttccctattttgtccctttttccgcacaacaagtatcagaatgggttcatcaaatctatccaacctaattcgcacgt agactggcttggtattggcagtttcgtagttatatatatactaccatgagtgaaactgttacgttaccttaaattctttctcccctttaattttc ttttatcttactctcctacataagacatcaagaaacaattgtatattgtacacccccccctccacaaacacaaatattgataatataaa gatgtctgctgctgctgatagattaaacttaacttccggccacttgaatgctggtagaaagagaagttcctcttctgtttctttgaagg ctgccgaaaagcctttcaaggttactgtgattggatctggtaactggggtactactattgccaaggtggttgccgaaaattgtaagg gatacccagaagttttcgctccaatagtacaaatgtgggtgttcgaagaagagatcaatggtgaaaaattgactgaaatcataaata ctagacatcaaaacgtgaaatacttgcctggcatcactctacccgacaatttggttgctaatccagacttgattgattcagtcaagga tgtcgacatcatcgttttcaacattccacatcaattttttgccccgtatctgtagccaattgaaaggtcatgttgattcacacgtcagagc tatctcctgtctaaagggttttgaagttggtgctaaaggtgtccaattgctatcctcttacatcactgaggaactaggtattcaatgtgg tgctctatctggtgctaacattgccaccgaagtcgctcaagaacactggtctgaaacaacagttgcttaccacattccaaaggattt cagaggcgagggcaaggacgtcgaccataaggttctaaaggccttgttccacagaccttacttccacgttagtgtcatcgaagat gttgctggtatctccatctgtggtgctttgaagaacgttgttgccttaggttgtggtttcgtcgaaggtctaggctggggtaacaacg cttctgctgccatccaaagagtcggtttgggtgagatcatcagattcggtcaaatgttttttcccagaatctagagaagaaacatacta ccaagagtctgctggtgttgctgatttgatcaccacctgcgctggtggtagaaacgtcaaggttgctaggctaatggctacttctgg taaggacgcctgggaatgtgaaaaggagttgttgaatggccaatccgctcaaggtttaattacctgcaaagaagttcacgaatggt tggaaacatgtggctctgtcgaagacttcccattatttgaagccgtataccaaatcgtttacaacaactacccaatgaagaacctgc cggacatgattgaagaattagatctacatgaagattagatttattggagaaagataacatatcatactttcccccactttttcgaggctct tctatatcatattcataaattagcattatgtcatttctcataactactttatcacgttagaaattacttattattattaaattaatacaaaatt tagtaaccaaataaatataaataaatatgtatatttaaattttaaaaaaaaatcctatagagcaaaaggattttccattataatattagct gtacacctcttccgcattttttgagggtggttacaacaccactcattcagaggctgtcggcacagttgcttctagcatctggcgtccg tatgtatgggtgtatttttaaataataaacaaagtgccacaccttcaccaattatgtctttaagaaatggacaagttccaaagagcttgc ccaaggctcgacaaggatgtactttggaatatctatattcaagtacgtggcgcgcatatgtttgagtgtgcacacaataaaggtt
```

Sequence of gpd1Δ mutation (part of the gpd1 coding sequence was not deleted (underlined) and the region that was deleted is represented by a Δ; SEQ ID NO:90):

tacaaacgcaacacgaaagaacaaaaaaagaagaaaacagaaggccaagacagggtcaatgagactgttgtcctc ctactgtccctatgtctctggccgatcacgcgccattgtccctcagaaacaaatcaaacacccacacccccgggcacccaaagtcc ccacccacaccaccaatacgtaaacggggcgcccctgcaggccctcctgcgcgcggcctcccgccttgcttctctcccttcc ttttcttttccagttttccctattttgtcccttttccgcacaacaagtatcagaatgggttcatcaaatctatccaacctaattcgcacgt agactggcttggtattggcagtttcgtagttatatatatactaccatgagtgaaactgttacgttaccttaaattctttctcccttaattttc ttttatcttactctcctacataagacatcaagaaacaattgtatattgtacacccccccctccacaaacacaaatattgataatataaa gatgtctgctgctgctgatagΔtctacatgaagattagatttattggagaaagataacatatcatactttcccccactttttcgaggctc ttctatatcatattcataaattagcattatgtcatttctcataactactttatcacgttagaaattacttattattattaaattaatacaaaat ttagtaaccaaataaatataaataaatatgtatatttaaattttaaaaaaaaaatcctatagagcaaaaggattttccattataatattagc tgtacacctcttccgcattttttgagggtggttacaacaccactcattcagaggctgtcggcacagttgcttctagcatctggcgtcc gtatgtatgggtgtattttaaataataaacaaagtgccacaccttcaccaattatgtctttaagaaatggacaagttccaaagagcttg cccaaggctcgacaaggatgtactttggaatatctatattcaagtacgtggcgcgcatatgtttgagtgtgcacacaataaaggtt Sequence of GPD2 locus (coding sequence is underlined; SEQ ID NO:91):

atagccatcatgcaagcgtgtatcttctaagattcagtcatcatcattaccgagtttgttttccttcacatgatgaagaaggtttgagtat gctcgaaacaataagacgacgatggctctgccattgttatattacgcttttgcggcgaggtgccgatgggttgctgaggggaagagtgtt tagcttacggacctattgccattgttattccgattaatctattgttcagcagctcttctctaccctgtcattctagtatttttttttttttttt ttggttttactttttttttcttcttgccttttttttcttgttacttttttctagttttttttccttccactaagcttttccttgatttatccttgggttcttc tttctactccttttagatttttttttatatattaattttttaagtttatgtattttggtagattcaattctctttcccttccttttccttcgct cccctccttatcaatgcttgctgtcagaagattaacaagatacacattccttaagcgaacgcatccggtgttatatactcgtcgtgca tataaaattttgccttcaagatctactttcctaagaagatcattattacaaacacaactgcactcaaagatgactgctcatactaatatc aaacagcacaaacactgtcatgaggaccatcctatcagaagatcggactctgccgtgtcaattgtacatttgaaacgtgcgcccttt caaggttacagtgattggttctggtaactgggggaccaccatcgccaaagtcattgcggaaaacacagaattgcattcccatatctt cgagccagaggtgagaatgtgggtttttgatgaaaagatcggcgacgaaaatctgacggatatcataaatacaagacaccagaa cgttaaatatctacccaatattgacctgccccataatctagtggccgatcctgatcttttacactccatcaagggtgctgacatccttgt tttcaacatccctcatcaatttttaccaaacatagtcaaacaattgcaaggccacgtggcccctcatgtaagggccatctcgtgtcta aaagggttcgagttgggctccaagggtgtgcaattgctatcctcctatgttactgatgagttaggaatccaatgtggcgcactatct ggtgcaaacttggcaccggaagtggccaaggagcattggtccgaaaccaccgtggcttaccaactaccaaaggattatcaaggt gatggcaaggatgtagatcataagatttgaaattgctgttccacagaccttacttccacgtcaatgtcatcgatgatgttgctggtat atccattgccggtgccttgaagaacgtcgtggcacttgcatgtggttcgtagaaggtatgggatggggtaacaatgcctccgcag ccattcaaaggctgggtttaggtgaaattatcaagttcggtagaatgttttcccagaatccaaagtcgagacctactatcaagaatc cgctggtgttgcagatctgatcaccacctgctcaggcggtagaaacgtcaaggttgccacatacatggccaagaccggtaagtc agccttggaagcagaaaaggaattgcttaacggtcaatccgcccaagggataatcacatgcagagaagttcacgagtggctaca aacatgtgagttgacccaagaattcccattattcgaggcagtctaccagatagtctacaacaacgtccgcatggaagacctaccg gagatgattgaagagctagacatcgatgacgaatagacactctccccccccctcccctctgatctttcctgttgcctcttttcccc caaccaatttatcattatacacaagttctacaactactactagtaacattactacagttattataattttctattctcttttcttaagaatct atcattaacgttaatttctatatatacataactaccattatacacgctattcgttacatatcacatcaccgttaatgaaagatacgaca ccctgtacactaacacaattaaataatcgccataaccttttctgttatctatagcccttaaagctgtttcttcgagctttttcactgcagta attctccacatgggcccagccactgagataagagcgctatgttagtcactactgacggctctccagtcatttatgtgattttttagtga ctcatgtcgcatttggcccgttttttccgctgtcgcaacctatttccattaacggtgccgtatggaagagtcatttaaaggcaggaga gagagattactcatcttcattggatcagattgatgactgcgtacggcagat Sequence of gpd2Δ mutation (the entire coding sequence was deleted, which is represented by a Δ; SEQ ID NO:92):

atagccatcatgcaagcgtgtatcttctaagattcagtcatcatcattac cgagtttgttttccttcacatgatgaagaaggtttgagtatgctcgaaac aataagacgacgatggctctgccattgttatattacgcttttgcggcga ggtgccgatgggttgctgagggaagagtgtttagcttacggacctattg ccattgttattccgattaatctattgttcagcagctcttctctaccctgt cattctagtattttttttttttttttttggttttacttttttttcttctt gccttttttttcttgttactttttttctagttttttttccttccactaagc ttttttccttgatttatccttgggttcttctttctactccttttagattttt tttttatatattaattttttaagtttatgtattttggtagattcaattc tctttccctttccttttccttcgctccccttccttatcΔctctga tctttcctgttgcctctttttccccccaaccaatttatcattatacacaag -continued ttctacaactactactagtaacattactacagttattataattttctatt ctcttttcttaagaatctatcattaacgttaatttctatatatacata actaccattatacacgctattatcgtttacatatcacatcaccgtt aatgaaagatacgacaccctgtacactaacacaattaaata atcgccataaccttttctgttatctatagcccttaaagctgtttcttc gagcttttcactgcagtaattctccacatgggcccagccactg agataagagcgctatgttagtcactactgacggctctccagtc atttatgtgattttttagtgactcatgtcgcatttggcccgttttttcc gctgtcgcaacctatttccattaacggtgccgtatggaagag tcatttaaaggcaggagagagagattactcatcttcattgga tcagattgatgactgcgtacggcagat Sequence of FDH1 locus (coding sequence is underlined; SEQ ID NO:93):

tattttctatagatatttacactccgcaagtgcaaaaaaaagcattatcgctaacgatcaagaggaactgagaccttatt agttgtctttgttggcgtaacataaatttcttaggaaaagagaaaattatctcgaaggcaaaaataaaccaagcctcgagtttaatgg ttttctaaaaaacacttttaaaaacagatcgccataaaaggagaagctccgtaggagaccgttttcgaaacctatgtagaaataaag ggaaagctccaacggtttggataaatctttagaagcatagagtttatacaacattcagtacgaaatgtactctcgaaacgttctcttt cacggtgcttagtagcagaaaaagtgtcggaaattacctattttgtcaccactcgaggataggcttgaaagagagttttaaccccca acttttctatttttgcacttgtttggctatggtttaaaacattctgtttggaccaacagcccaagcggcttatccctttctttttttcccttata atcgggaatttccttactaggaaggcaccgatactagaactccgaatgaaaagacatgccagtaataaaactattttgatgttatg cggaatatactattcttggattattcactgttaactaaaagttggagaaatcactctgcactgtcaatcattgaaaaaagaacatata aaagggcacaaaattgagtctcttttttaatgagttcttgctgaggaaagtttagttaatatatcatttacgtaaaatatgcatattcttgtatt gtgcttttttttattcattttaagcaggaacaatttacaagtattgcaacgctaatcaaatcaaaataacagctgaaaattaat<u>atgtcgaa</u>

<u>gggaaaggttttgctggttcttttacgaaggtggtaagcatgctgaagagcaggaaaagttattggggtgtattgaaaatgaacttg</u>

<u>gtatcagaaatttcattgaagaacagggatacgagttggttactaccattgacaaggaccctgagccaacctcaacggtagacag</u>

<u>ggagttgaaagacgctgaaattgtcattactacgcccttttccccgcctacatctcgagaaacaggattgcagaagctcctaacct</u>

<u>gaagctctgtgtaaccgctggcgtcggttcagaccatgtcgatttagaagctgcaaatgaacggaaaatcacggtcaccgaagtt</u>

<u>actggttctaacgtcgtttctgtcgcagagcacgttatggccacaattttggttttgataagaaactataatggtggtcatcaacaagc</u>

<u>aattaatggtgagtgggatattgccggcgtggctaaaaatgagtatgatctggaagacaaaataatttcaacggtaggtgccggta</u>

<u>gaattggatatagggttctggaaagattggtcgcatttaatccgaagaagttactgtactacgactaccaggaactacctgcggaa</u>

<u>gcaatcaatagattgaacgaggccagcaagcttttcaatggcagaggtgatattgttcagagagtagagaaattggaggatatgg</u>

<u>ttgctcagtcagatgttgttaccatcaactgtccattgcacaaggactcaaggggtttattcaataaaaagcttatttcccacatgaaa</u>

<u>gatggtgcatacttggtgaataccgctagaggtgctatttgtgtcgcagaagatgttgccgaggcagtcaagtctggtaaattggct</u>

<u>ggctatggtggtgatgtctgggataagcaaccagcaccaaaagaccatccctggaggactatggacaataaggaccacgtggg</u>

<u>aaacgcaatgactgttcatatcagtgghccacatctctggatgctcaaaagaggtacgctcagggagtaaagaacatcctaaatagtt</u> acttttccaaaaagtttgattaccgtccacaggatattattgtgcagaatggttcttatgccaccagagcttatggacagaagaaata agagtgattatgagtatttgtgagcagaagttttccggtctccttttgttcttgttttggcgtattctccactattcgtccatagcacattta taccttagctaaatattttgtaaagcaaaattttcgttatctcttaaaaaatagaagagcggtttattaatatcaaataattgaaactgctg atatggtagctatatacaaaatctgctgtcaaaatttggcagtaaacgatcttcacggtagcggttcaaataaagaggaaaagtcttt ctcccttactgtttttctggaatttggctcgtcgttaataacagaactaaagatacagtaaaaggagagatcgcaatcaacttcattaa ttgtaacagtagcataatcacaactgatcatctacactataaacagttttatttctaattatgggcgcctggccggctcaaacattgtg cttttaagactccaaaagtatctgctgcagaaaagagccatataatgttaagtgttcagggataggttatcgcttactacttcaaacgt ttcgaaggaaagccagggaagcctatatctgattccctgtttcataatccaatgcagccactagcttataattatttgaactatttgtcg aacatcacagtaataaaatccccagaaagttccacttgctgcatattggcacctgttgattcactctccatcactttttgttagccgcc cagcctagaaagtctttaaatacatctgaaatttttttttttttaacagtgcacccgtgcatcatacctcatgcaaggtaccttttttttctca aaggtattgtcttccattgaagtggcactatggcatgatgaaccctgagcatttctgaattcaacagaaccaaattgtccagaaataa atctgtccgacatgaattatgaaactttttttcaattaagtgaagagaattttgcagcgtcttaccattattttgacccattggtcgcatgt ttgcgctttgacttcgagaaccatgttaaagcttacttgtacgacaaccaatgaagtatattacggcagttttttttggactgggtcaaa aaaagtgttgcataatcaaatcaggaacacattaaaatgttgtaaaatttgtcttagtatcacctgagtggttattcattacgtacta Sequence of fdh1Δ mutation (the entire coding sequence was deleted, which is represented by a Δ; SEQ ID NO:94):

tatttttctatagatatttacactccgcaagtgcaaaaaaaagcattatcgctaacgatcaagaggaactgagaccttatt agttgtctttgttggcgtaacataaatttcttaggaaaagagaaaattatctcgaaggcaaaaataaaccaagcctcgagtttaatgg ttttctaaaaaacactttaaaaacagatcgccataaaaggagaagctccgtaggagaccgttttcgaaacctatgtagaaataaag ggaaagctccaacggtttggataaatctttagaagcatagagtttatacaacattcagtacgaaatgtactctcgaaacgttctctttt cacggtgcttagtagcagaaaaagtgtcggaaattacctattttgtcaccactcgaggataggcttgaaagagagttttaaccccca acttttctatttttgcacttgtttggctatggtttaaaacattctgtttggaccaacagcccaagcggcttatccctttctttttttcccttata atcgggaatttccttactaggaaggcaccgatactagaactccgaatgaaaaagacatgccagtaataaaactattttgatgttatg cggaatatactattcttggattattcactgttaactaaaagttggagaaatcactctgcactgtcaΔtggcagtaaacgatcttcacg gtagcggttcaaataaagaggaaaagtctttctcccttactgtttttctggaatttggctcgtcgttaataacagaactaaagatacag taaaaggagagatcgcaatcaacttcattaattgtaacagtagcataatcacaactgatcatctacactataaacagttttatttctaa ttatgggcgcctggccggctcaaacattgtgcttttaagactccaaaagtatctgctgcagaaaagagccatataatgttaagtgttc agggataggttatcgcttactacttcaaacgtttcgaaggaaagccagggaagcctatatctgattccctgtttcataatccaatgca gccactagcttataattatttgaactatttgtcgaacatcacagtaataaaatccccagaaagttccacttgctgcatattggcacctgt tgattcactctccatcactttttgttagccgcccagcctagaaagtctttaaatacatctgaatttttttttttttaacagtgcacccgtg catcatacctcatgcaaggtaccttttttttctcaaaggtattgtcttccattgaagtggcactatggcatgatgaaccctgagcatttct gaattcaacagaaccaaattgtccagaaataaatctgtccgacatgaattatgaaactttttttcaattaagtgaagagaattttgcag cgtcttaccattattttgacccattggtcgcatgtttgcgctttgacttcgagaaccatgttaaagcttacttgtacgacaaccaatgaa gtatattacggcagttttttttggactgggtcaaaaaaagtgttgcataatcaaatcaggaacacattaaaatgttgtaaaatttgtctta gtatcacctgagtggttattcattacgtacta Sequence of FDH2 locus (coding sequence is underlined; SEQ ID NO:95):

tgtcgagacaatgtcattgcaagttatataaacattgtaatacatcacctcgatgaaagagaaactggaatgatagatct cttttttctcaaaatttcgttaatatgtaataataaggttcctgatgtaatttgttttttgtacaaattattttagattctggaggttcaaataaaa tatatattacagccaacgattagggggggacaagacttgattacacattttttcgttggtaacttgactcttttatgaaaagaaaacattaa gttgaaggtgcacgcttgaggcgctccttttttcatggtgcttagcagcagatgaaagtgtcagaagttacctattttgtcaccatttga gaataagcttgaaagaaagttgtaaccccaacttttctatcttgcacttgtttggaccaacagccaaacggcttatcccttttcttttcc cttataatcgggaatttccttactaggaaggcaccgatactataactccgaatgaaaaagacatgccagtaataaaaataattgatgt tatgcggaatatactattcttggattattcactgttaactaaaagttggagaaatcactctgcactgtcaatcattgaaaaaagaacat ataaaagggcacaaaatcgagtctttttttaatgagttcttgctgaggaaaatttagttaatatatcatttacataaaacatgcatattatt gtgttgtactttctttattcattttaagcaggaataattacaagtattgcaacgctaatcaaatcgaataacagctgaaaattaat<u>atgt</u>

<u>cgaagggaaaggttttgctggttctttatgaaggtggtaagcatgctgaagagcaggaaaagttattgggtgtattgaaaatgaa</u>

<u>cttggtatcagaaatttcattgaagaacagggatacgagttggttactaccattgacaaggaccctgagccaacctcaacggtaga</u>

<u>cagggagttgaaagacgctgaaattgtcattactacgcccttttccccgcctacatctcgagaaacaggattgcagaagctccta</u>

<u>acctgaagctctgtgtaaccgctggcgtcggttcagaccatgtcgatttagaagctgcaaatgaacggaaaatcacggtcaccga</u>

<u>agttactggttctaacgtcgtttctgtcgcagagcacgttatggccacaattttggttttgataagaaactataatggtggtcatcaata</u>

<u>agcaattaatggtgagtgggatattgccggcgtggctaaaaaatgagtatgatctggaagacaaaataatttcaacggtaggtgcc</u>

<u>ggtagaattggatataggggttctggaaagattggtcgcatttaatccgaagaagttactgtactacgactaccaggaactacctgcg</u>

<u>gaagcaatcaatagattgaacgaggccagcaagcttttcaatggcagaggtgatattgttcagagagtagagaaattggaggata</u>

<u>tggttgctcagtcagatgttgttaccatcaactgtccattgcacaaggactcaagggggtttattcaataaaaagcttatttcccacatg</u>

<u>aaagatggtgcatacttggtgaataccgctagaggtgctatttgtgtcgcagaagatgttgccgaggcagtcaagtctggtaaatt</u>

<u>ggctggctatggtggtgatgtctgggataagcaaccagcaccaaaagaccatccctggaggactatggacaataaggaccacg</u>

<u>tgggaaacgcaatgactgttcatatcagtggcacatctctgcatgctcaaaagagggtacgctcagggagtaaagaacatcctaaa</u>

<u>tagttacttttccaaaaagtttgattaccgtccacaggatattattgtgcagaatggttcttatgccaccagagcttatggacagaaga</u>

<u>aa</u>taagagtgattatgagtatttgtgagcagaagttttccggtctccttttgttcttgttttggcgtattctccactattcgtccatagcac atttataccttagctaaatattttgtaaagcaaaattttcgttatctcttaaaaaatagaagagcggtttattaatatcaaataattgaaact gctgatatggtagctatatacaaaatctgctgtcaaaatttggcagtaaacgatcttcacggtagcggttcaaataaagaggaaaag tccttctcccttactgtttttctggaatttggctcgtcgttaataacagaactaaagatacagtaaaaggagagatcgcaatcaacttc attaattgtaacagtagcataatcacaactggttatctgcgttatagacaattcttactcacaatgatgggcgcttagttggctgtaaac gtcgcttttttaaaactccgaaaagttaccgctacagaaaaaaaccataaatgtatgctagttgcgcagagaggtttagggtccaaa atttactaccctgtcgctcactacagcgactgtcccgaattaagcccgaagagacgcagaactgttgtatgaacctcatgaaacca ctgatcttgaagatttagaccttcagaatcgttttcaattagaagtatacaagaagtctttgtacaataatgtcaagacagagctctga attatagttcagccttgttattttttttt Sequence of fdh2Δ mutation (the entire coding sequence was deleted, which is represented by a Δ; SEQ ID NO:96):

tgtcgagacaatgtcattgcaagttatataaacattgtaatacatcacctcgatgaaagagaaactggaatgatagatct cttttttctcaaaatttcgttaatatgtaataataaggttcctgatgtaatttgttttttgtacaaattattttagattctggaggttcaaataaaa tatatattacagccaacgattagggggggacaagacttgattacacattttttcgttggtaacttgactcttttatgaaaagaaaacattaa gttgaaggtgcacgcttgaggcgctccttttttcatggtgcttagcagcagatgaaagtgtcagaagttacctattttgtcaccatttga gaataagcttgaaagaaagttgtaaccccaacttttctatcttgcacttgtttggaccaacagccaaacggcttatcccttttcttttcc

```
cttataatcgggaatttccttactaggaaggcaccgatactataactccgaatgaaaaagacatgccagtaataaaaataattgatgt tatgcggaatatactattcttggattattcactgttaactaaaagttggagaaatcactctgcactgtcaatcattgaaaaaaagaacat ataaaagggcacaaaatcgagtcttttttaatgagttcttgctgaggaaaatttagttaatatatcatttacataaaacatgcatattatt gtgttgtactttctttattcattttaagcaggaataattacaagtattgcaacgctaatcaaatcgaaataacagctgaaaattaatΔta agagtgattatgagtatttgtgagcagaagttttccggtctccttttgttcttgttttggcgtattctccactattcgtccatagcacattta taccttagctaaatattttgtaaagcaaaattttcgttatctcttaaaaaatagaagagcggtttattaatatcaaataattgaaactgctg atatggtagctatatacaaaatctgctgtcaaaatttggcagtaaacgatcttcacggtagcggttcaaataaagaggaaaagtcctt ctcccttactgtttttctggaatttggctcgtcgttaataacagaactaaagatacagtaaaaggagagatcgcaatcaacttcattaa ttgtaacagtagcataatcacaactggttatctgcgttatagacaattcttactcacaatgatgggcgcttagttggctgtaaacgtcg cttttttaaaactccgaaaagttaccgctacagaaaaaaaccataaatgtatgctagttgcgcagagaggtttagggtccaaaattta ctaccctgtcgctcactacagcgactgtcccgaattaagcccgaagagacgcagaactgttgtatgaacctcatgaaaccactga tcttgaagatttagaccttcagaatcgttttcaattagaagtatacaagaagtctttgtacaataatgtcaagacagagctctgaattat agttcagccttgttattttttttt
```

3.2 Generation of Glycerol-Reduced Strain Comprising gpd2Δ::GPD1

Glycerol-reduction strain gpd2Δ::GPD1, was constructed as described above. The sequence of gpd1Δ/gpd1Δ gpd2Δ/gpd2Δ::GPD1/GPD1 is provided below.

Sequence of GPD1 at GPD2 locus (inserted GPD1 is underlined; SEQ ID NO:97):

```
agtaactgtgacgatatcaactctttttttattatgtaataagcaaacaagcacgaatggggaaagcctatgtgcaatcaccaaggtc gtccctttttcccatttgctaatttagaatttaaagaaaccaaaagaatgaagaaagaaaacaaatactagccctaaccctgacttc gtttctatgataataccctgctttaatgaacggtatgccctagggtatatctcactctgtacgttacaaactccggttattttatcggaac atccgagcacccgcgccttcctcaacccaggcaccgcccccaggtaaccgtgcgcgatgagctaatcctgagccatcacccac cccacccgttgatgacagcaattcgggagggcgaaaaataaaaactggagcaaggaattaccatcaccgtcaccatcaccatca tatcgccttagcctctagccatagccatcatgcaagcgtgtatcttctaagattcagtcatcatcattaccgagtttgttttccttcacat gatgaagaaggtttgagtatgctcgaaacaataagacgacgatggctctgccattgttatattacgcttttgcggcgaggtgccgat gggttgctgaggggaagagtgtttagcttacggacctattgccattgttattccgattaatctattgttcagcagctcttctctaccctg tcattctagtattttttttttttttttttggttttacttttttttcttcttgccttttttttcttgttactttttttctagtttttttttcc ttccactaagcttttttccttgatttatccttgggttcttctttctactcctttagatttttttttttatatattaatttttaagtttatgt attttggtagattcaattctctttcccttttcttttccttcgctccccttccttatcaatgtctgctgctgctgatagattaaacttaac ttccggccacttgaatgctggtagaaagagaagttcctcttctgtttctttgaaggctgccgaaaagcctttcaaggttactgtgattgg atctggtaactgggtactactattgccaaggtggttgccgaaaattgtaagggatacccagaagttttcgctccaatagtacaaatgt gggtgttcgaagaagagatcaatggtgaaaaattgactgaaatcataaatactagacatcaaaacgtgaaatacttgcctggcatcactc tacccgacaatttggttgctaatccagacttgattgattcagtcaaggatgtcgacatcatcgttttcaacattccacatcaattttttgc cccgtatctgtagccaattgaaaggtcatgttgattcacacgtcagagctatctcctgtctaaaggqtttgaagttggtgctaaaggtg tccaattgctatcctcttacatcactgaggaactaggtattcaatgtggtgctctatctggtgctaacattgccaccgaagtcgctcaag aacactggtctgaaacaacagttgcttaccacattccaaaggatttcagaggcgagggcaaggacgtcgaccataaggttctaaaggcct tgttccacagaccttacttccacgttagtgtcatcgaagatgttgctggtatctccatctgtggtgctttgaagaacgttgttgccttag gttgtggtttcgtcgaaggtctaggctggggtaacaacgcttctgctgccatccaaagagtcggtttgggtgagatcatcagattcggtc aaatgtttttcccagaatctagagaagaaacatactaccaagagtctgctggtgttgctgatttgatcaccacctgcgctggtggtagaa acgtcaaggttgctaggctaatggctacttctggtaaggacgcctgggaatgtgaaaaggagttgttgaatggccaatccgctcaaggtt taattacctgcaaagaagttcacgaatggttggaaacatgtggctctgtcgaagacttcccattatttgaagccgtataccaaatcgttt acaacaactacccaatgaagaacctgccggacatgattgaagaattagatctacatgaagattagacactctccccccccctcccctctg
```

-continued

```
atctttcctgttgcctcttttccccccaaccaatttatcattatacacaagttctacaactactactagtaacattactacagttattataatt ttctattctcttttttctttaagaatctatcattaacgttaatttctatatatacataactaccattatacacgctattatcgtttacatatc acatcaccgttaatgaaagatacgacaccctgtacactaacacaattaaataatcgccataaccttttctgttatctatagcccttaaagctg tttcttcgagctttttcactgcagtaattctccacatgggcccagccactgagataagagcgctatgttagtcactactgacggctctc cagtcatttatgtgattttttagtgactcatgtcgcatttggcccgttttttccgctgtcgcaacctatttccattaacggtgccgtatgg aagagtcatttaaaggcaggagagagagattactcatcttcattggatcagattgatgactgcgtacggcagatagtgtaatctga gcagttgcgagacccagactggcactgtctcaatagtatattaatgggcatacattcgtactcccttgttcttgcccacagttctctct ctctttacttcttgtatcttgtctccccattgtgcagcgataaggaacattgttctaatatacacggatacaaaagaaatacacat
```

Example 4

Cloning and Characterization of PFL and AADH Enzymes

Figure 22:
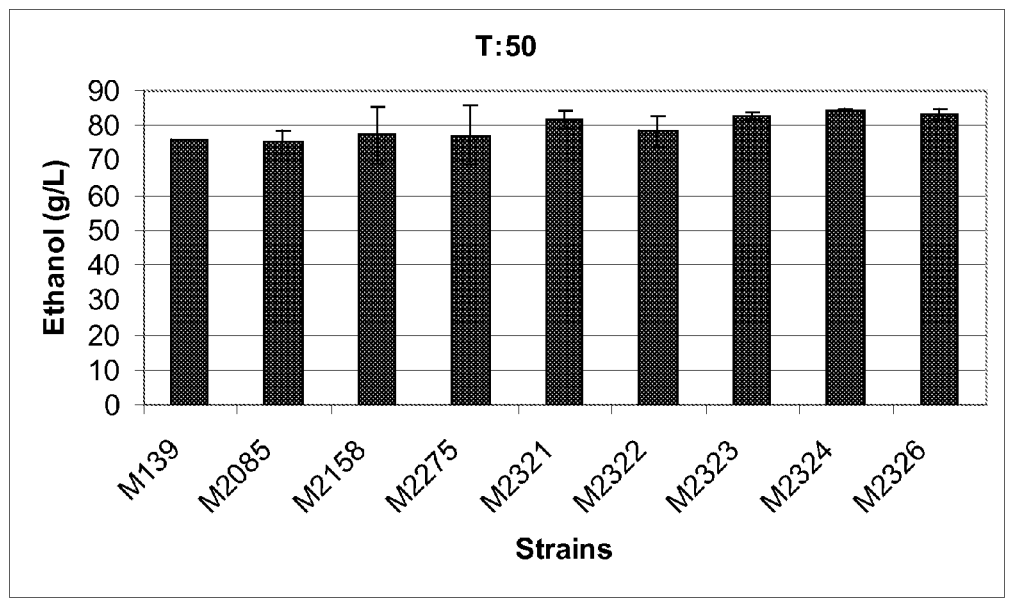
FIG. 22 shows a graph of ethanol production (g/L) of strains of the invention after 50 hours of fermentation.

To identify PFL enzymes for use in the strains of the invention, several PFL enzymes were identified for cloning and functional analysis. See Table 1. Functionality was determined by plasmid based expression of each PFL in the fcyΔ:: ADHE gpd1Δ::ADHE gpd2Δfdh1Δfdh2Δ (M2158) background. FIG. 22 shows fermentation performance in 20% corn mash. A PFL was determined to be functional based on the presence or absence of a yield increase over M2085. The *C. cellulolyticum* PFL was determined to be non-functional based on data shown in FIG. 13. The strain listed as M1992+pMU2481 is M2085 plus a plasmid expressing the *C. cellulolyticum* PFL. This strain does not appear to make formate.

TABLE 1

Analysis of PFL Enzymes

| Organism | Functional | SEQ ID NOs: |
|---|---|---|
| *Bacillus licheniformis* ATCC_14580 | nd | 6 and 40 |
| *Streptococcus thermophilus* LMD_9 | nd | 12 and 46 |
| *Lactobacillus plantarum* WCFS1 (lp_3314 and lp_3313) | nd | 16 and 50 |
| *Lactobacillus casei* ATCC_334 | yes | 24 and 58 |
| *Bifidobacterium adolescentis* | yes | 26 and 60 |
| *Clostridium cellulolyticum* | no | 34 and 68 |
| *Escherichia coli* | yes | 36 and 70 |
| *Chlamydomonas reinhardtii* PflA | yes | 72 and 76 |
| *Piromyces* sp. E2 | yes | 78 |
| *Neocallimastix frontalis* | yes | 74 and 80 |

Figure 12:
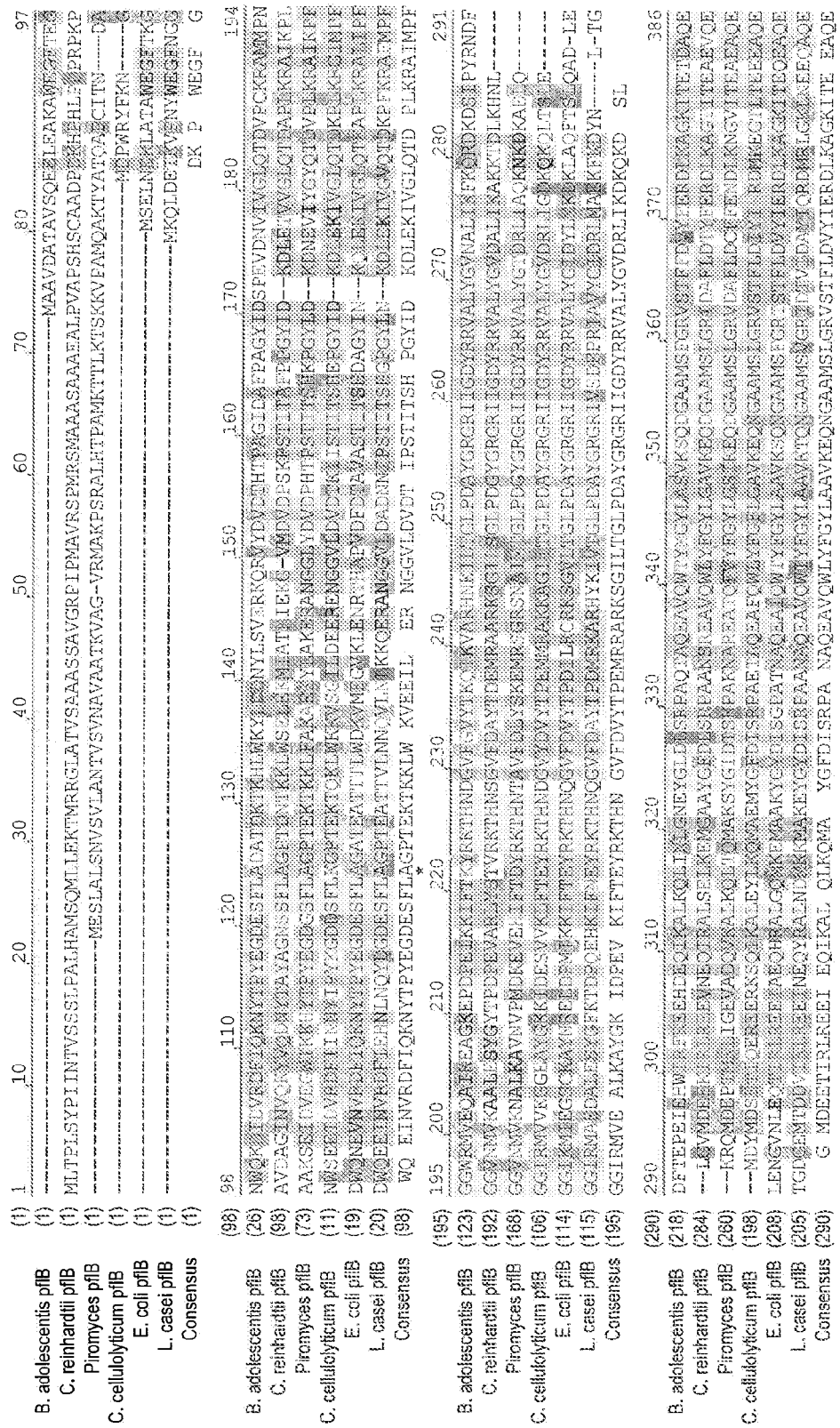
FIG. 12 shows an alignment of PFL enzymes from various organisms.
Figure 12:
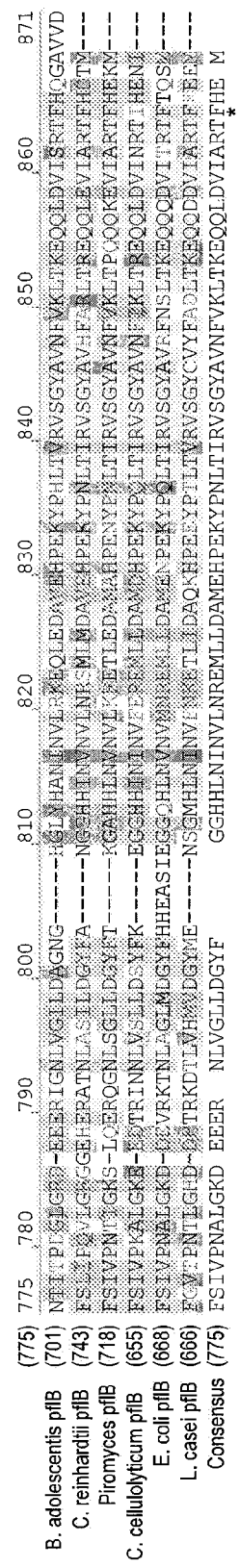

As shown in Example 7, eight of nine PFL enzymes that were tested can enable the glycerol elimination and glycerol reduction technologies described herein. An alignment of six of these PFL enzymes is shown in FIG. 12. Four of the residues are absent in *C. cellulolyticum* yet conserved among the other PFL enzymes (indicated with asterisks in FIG. 12). There is an insertion of 18 amino acids at position 640 of the *B. adolescentis* PFL, which is not present in the other PFL enzymes. The eukaryotic PFLs (*Piromyces* and *Chlamydomonas*) have an N-terminal extension which has been reported to be involved in mitochondrial targeting. Deletion of this sequence may improve the performance of these enzymes in *S. cerevisiae*. These differences may provide insights into identifying additional PFL enzymes for use in the strains of the invention.

To identify AADH enzymes for use in the strains of the invention, several AADH enzymes were identified for cloning and functional analysis. See Table 2. Functionality was determined though analysis of the data listed in Table 3 below and shown in FIG. 20. An AADH enzyme was determined to be functional if a strain containing the genotype gpd1Δgpd2Δ plus a given AADH, had a faster anaerobic growth rate than strain gpd1Δgpd2Δ (FIG. 20) and there was evidence for acetate consumption (Table 3).

TABLE 2

Analysis of AADH Enzymes

| Organism | Functional | SEQ ID NO: |
|---|---|---|
| *Escherichia coli* | yes | 84 |
| *Clostridium phytofermentans* | yes | 82 |
| *Chlamydomonas reinhardtii* | yes | 86 |
| *Piromyces* sp. E2 | yes | 88 |
| *Bifidobacterium adolescentis* | yes | 100 |

Figure 20:
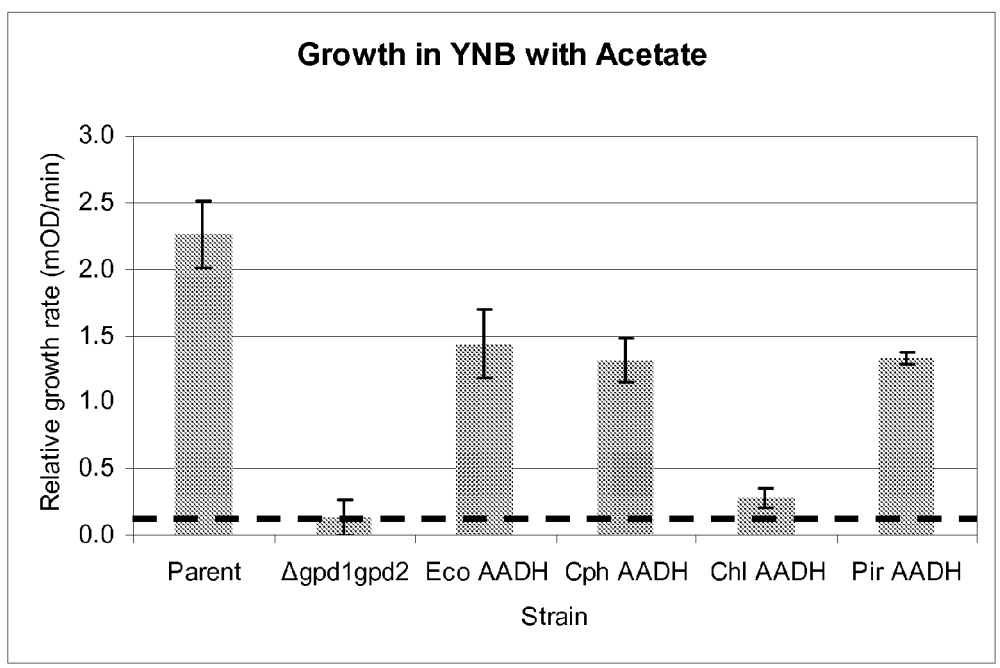
FIG. 20 shows a graph of the relative growth rate (mOD/min) of strains of the invention.

When glycerol deletion strains are grown anaerobically, they are not capable of growth or fermentation and cannot consume sugar during glycolysis. However, if these glycerol deletion strains are complemented with an AADH, the strains are able to grow with the supplementation of acetate in the media. FIG. 20 shows the growth rates of the parental strain, the glycerol deletion strain, and four glycerol deletion strains expressing AADHs from *Escherichia coli* (Eco), *Clostridium phytofermentans* (Cph), *Chlamydomonas reinhardtii* (Chl), and *Piromyces* sp. E2 (Pir). As shown in FIG. 20, all four genes can restore growth levels above the glycerol deletion strain (as noted by the dotted line) indicating a functional AADH.

The product yields and conversion of acetate by the strains above, as well as additional strains, are shown in Table 3. The glycerol deletion strain was unable to consume sugar or produce ethanol. The parent strain produced glycerol and ethanol but was unable to convert the acetate in the media, initially present at ~2 g/L, giving an ethanol yield of 0.41 g/g glucose, consistent with anaerobic ethanol yields. The glycerol deletion strains complemented with AADHs, however, were able to consume glucose and produce ethanol without producing glycerol, or the glycerol production was significantly decreased compared to the parent strain (Chl AADH). See Table 3. In these glycerol deletion mutants, the acetate levels were also reduced, resulting in higher ethanol yields (calculated as grams ethanol produced per gram consumed glucose) than was achieved by the parent strain.

TABLE 3

Product Yields and Acetate Conversion of Glycerol Deletion Strains Expressing AADH

| Strain | Glycerol[a] | Acetate Uptake[a] | Ethanol[a] | Ethanol Yield[b] | Growth rate (hr$^{-1}$) |
|---|---|---|---|---|---|
| Parent M139 | 1.37 | 0.14 | 10.41 | 0.42 | 0.27 |
| Δgpd1Δgpd2 M2032 | 0.00 | 0.00 | 0.00 | 0.00 | 0.01 |
| Eco AADH M1991 | 0.00 | 0.62 | 11.39 | 0.46 | 0.17 |
| Cph AADH M1991 | 0.00 | 0.66 | 11.21 | 0.45 | 0.18 |
| Chl AADH M1991 | 0.00 | 0.32 | 9.04 | 0.47 | 0.04 |
| Pir AADH M1991 | 0.00 | 0.68 | 11.17 | 0.45 | 0.17 |
| Bad AADH M1991 | 0.00 | 0.67 | 10.95 | 0.44 | 0.18 |
| Eco mhpF M1991 | 0.00 | 0.03 | 0.50 | 0.02 | 0.06 |
| Cph ADH (1428) M1991 | 0.00 | 0.60 | 11.29 | 0.45 | 0.19 |
| Cph ADH (2642) M1991 | 0.00 | 0.74 | 11.22 | 0.45 | 0.20 |
| Tsac AADH M1991 | 0.00 | 0.59 | 11.89 | 0.48 | 0.16 |

[a] grams per liter
[b] gram ethanol produced per gram sugar consumed

Example 5

Expression of PFL and AADH and Detection of Formate

To examine the expression of formate in a yeast strain of the invention, *E. coli* PFL was cloned and expressed in an FDH deletion strain. Strain M1992+pMU2483 has deletions of FDH1 and FDH2 and a plasmid expressing the *E. coli* PflA and PflB. This strain was constructed by transforming strain M1992 (fdh1Δfdh2Δ) with plasmids expressing either *C. cellulolyticum* PFL (pMU2481) or *E. coli* PFL (pMU2483).

Figure 13:
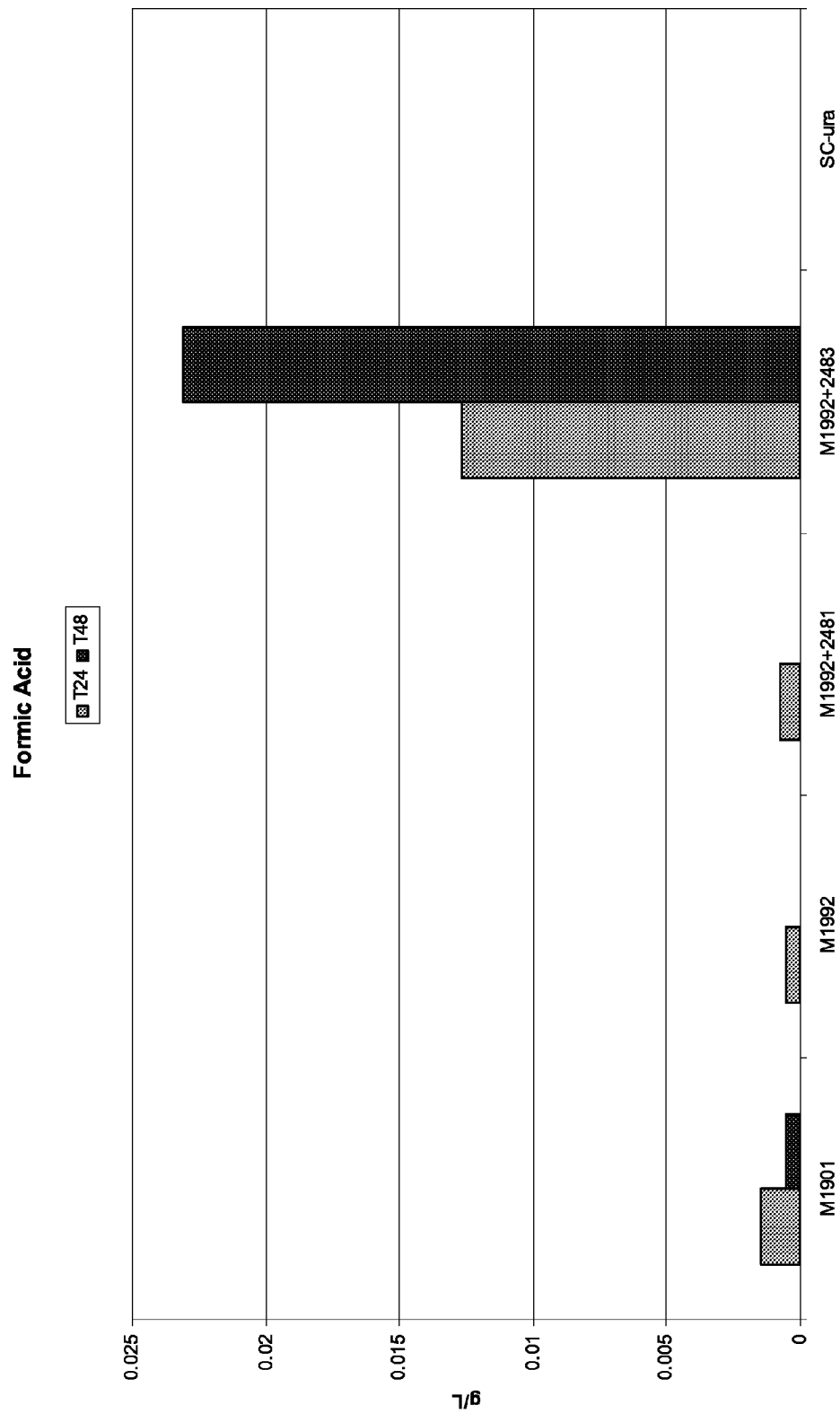
FIG. 13 shows a graph of formate production over 48 hours.

The strains were grown in YNB medium buffered with HEPES at pH 6.5, and formate was measured using a formate detection kit from Megazymes (Cat. No. K-FORM), according to manufacturer's specifications. As shown in FIG. 13, approximately 0.0125 g/L and 0.023 g/L formate was measured after 24 hours and 48 hours of growth, respectively. Similar results have been achieved by overexpressing an *E. coli* PFL in *S. cerevisiae*. Waks and Silver, *Appl. Env. Microbiol.* 75:1867-75 (2009).

Figure 26:
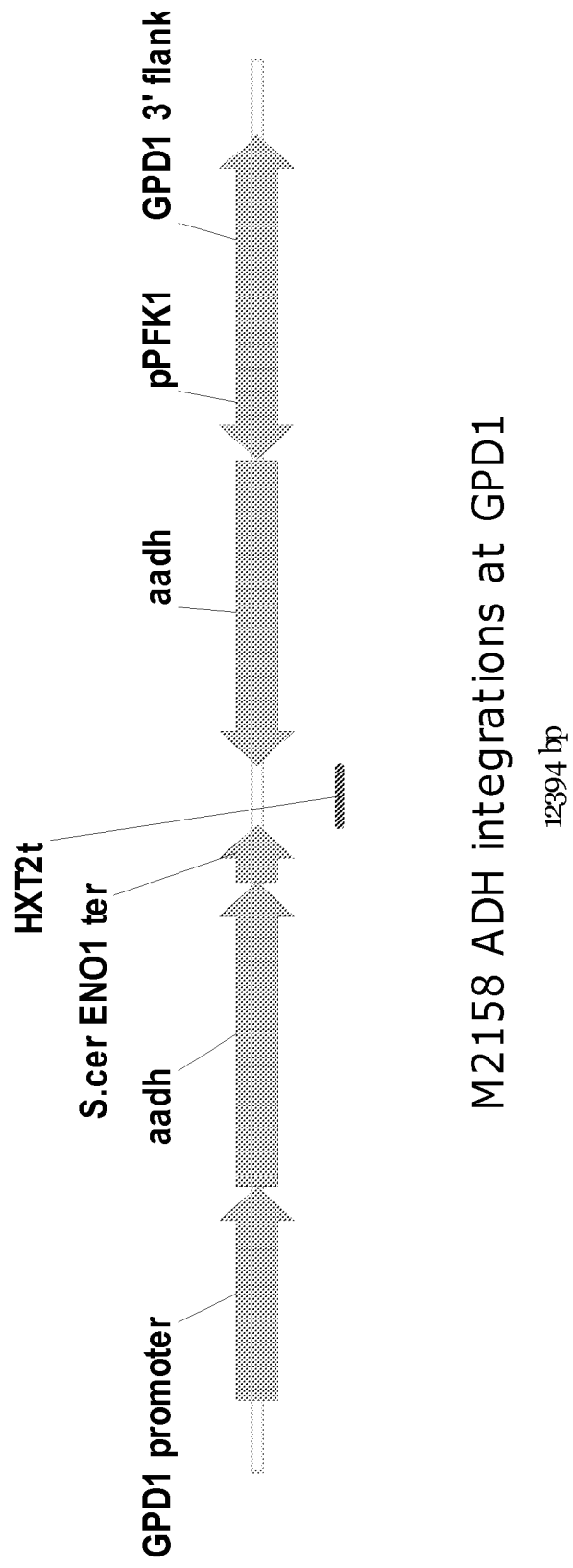
FIG. 26 shows a diagram depicting integration of *E. coli* AADHs at the GPD1 locus.
Figure 27:
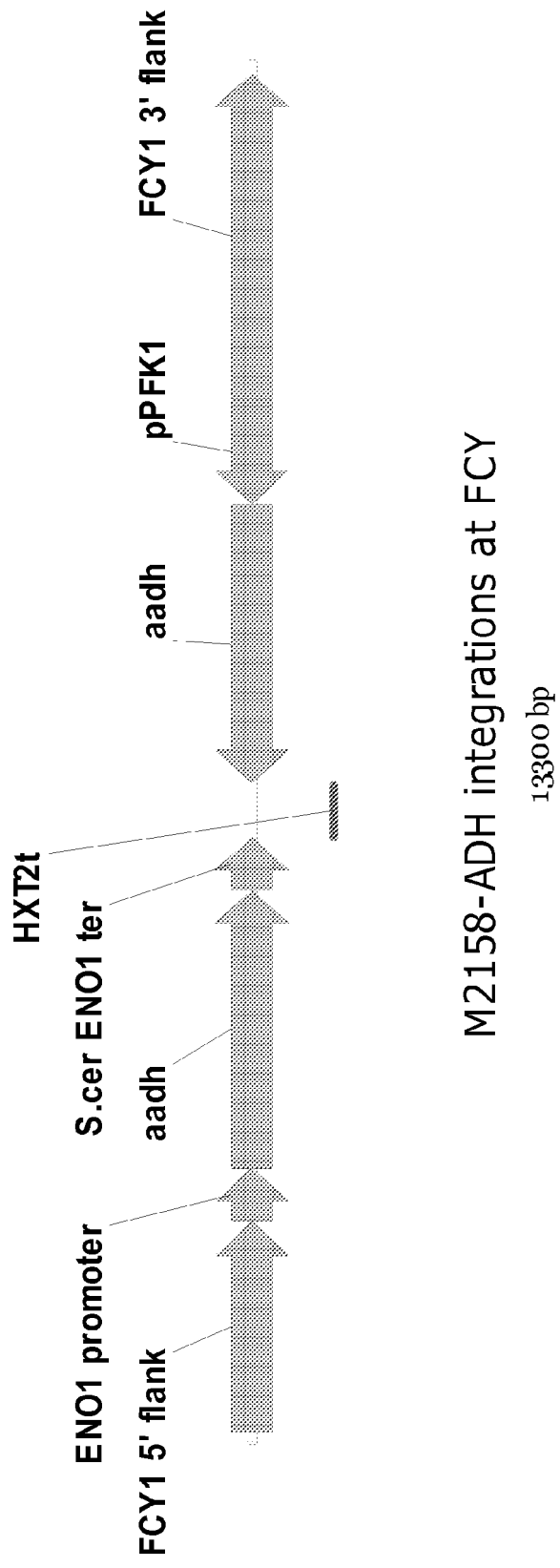
FIG. 27 shows a diagram depicting integration of *E. coli* AADHs at the FCY1 locus

PFL was also co-expressed in a strain expressing AADH. See FIG. 14. M2085 is a background strain with the genotype gpd1Δgpd2Δfdh1Δfdh2Δ and M2032 has the genotype gpd1Δgpd2Δ. Both of these strains are unable to grow anaerobically even in the presence of acetate. M2158 was created by integrating multiple copies of *E. coli* AADHs at the GPD1 and FCY1 locus in the M2085 background. The integration schemes are shown in FIGS. 26 and 27 and the corresponding nucleotide sequences for M2158 are listed below. One copy of AADH is driven by the native GPD1 promoter. See FIG. 26. The second copy is oriented in the reverse direction and is driven by the phosphofructokinase promoter. See FIG. 26. For AADH integration in FCY1, one copy is driven by the ENOL promoter and a second copy is driven by the PFK1 promoter. See FIG. 27. M2182 was created by transforming a vector expressing the *B. adolescentis* PFLs into the M2158 background.

Sequence of M2158 AADH integrations at the GPD1 locus (nucleotide; SEQ ID NO:98):

```
tagattcttttcgaatttgtggtgaagataggaaagttggtacagttctccatcaattttccatattttgctaaaaactcccttg
catgtctctttgcattcatttctcctgtatacgggttcaacacatcaatcgaattttgcaaagttgtctccatttctagaagactttcatcg
ggaataaaaaattcatatccattattcaaaaacgataatgatccctcgtacttacctgtgtaattggatattttataccatacttcaaaaa
tatccttggcctcacttctggtaggatacctttcgccatgtctgccaatcatttgaacttgcgttaatctacaaccttcaggaatatcagt
gggtataccgtagttagcgggaaaggagaaatatggcgcagaccctccaagaaagggaaacagactcttctgagagccaatta
gttcaatatccgcaaaacttctgagtgggatggagagtgccttagataatagaacacctaaacaaatggcaaaaataacgggcttc
accattgttcctgtatggtgtattagaacatagctgaaaatacttctgcctcaaaaaagtgttaaaaaaagaggcattatatagagg
taaagcctacaggcgcaagataacacatcaccgctctccccctctcatgaaaagtcatcgctaaagaggaacactgaaggttcc
cgtaggttgtctttggcacaaggtagtacatggtaaaaactcaggatggaataattcaaattcaccaatttcaacgtcccttgtttaaa
aagaaaagaattttctctttaaggtagcactaatgcattatcgatgatgtaaccattcacacaggttatttagcttttgatccttgaacc
attaattaacccagaaatagaaattacccaagtggggctctccaacacaatgagaggaaaggtgacttttaaggggccagacc
ctgttaaaaacctttgatggctatgtaataatagtaaattaagtgcaaacatgtaagaaagattctcggtaacgaccatacaaatattg
ggcgtgtggcgtagtcggtagcgcgctcccttagcatgggagaggtctccggttcgattccggactcgtccaaattatttttactttt
ccgcggtgccgagatgcagacgtggccaactgtgtctgccgtcgcaaaatgatttgaattttgcgtcgcgcacgtttctcacgtac
ataataagtattttcatacagttctagcaagacgaggtggtcaaaatagaagcgtcctatgtttacagtacaagacagtccatactg
aaatgacaacgtacttgacttttcagtattttcttttctcacagtctggttattttttgaaagcgcacgaaatatatgtaggcaagcatttt
ctgagtctgctgacctctaaaattaatgctattgtgcaccttagtaacccaaggcaggacagttaccttgcgtggtgttactatggcc
ggaagcccgaaagagttatcgttactccgattatttttgtacagctgatgggaccttgccgtcttcattttttttttttcacctatagagc
```

-continued cgggcagagctgcccggcttaactaagggccggaaaaaaaacggaaaaaagaaagccaagcgtgtagacgtagtataacagt
atatctgacacgcacgtgatgaccacgtaatcgcatcgcccctcacctctcacctctcaccgctgactcagcttcactaaaagga
aaatatatactctttcccaggcaaggtgacagcggtcccgtctcctccacaaaggcctctcctggggtttgagcaagtctaagttt
acgtagcataaaaattctcggattgcgtcaaataataaaaaaagtaaccccacttctacttctacatcggaaaaacattccattcaca
tatcgtctttggcctatcttgttttgtcctcggtagatcaggtcagtacaaacgcaacacgaaagaacaaaaaaagaagaaaacag
aaggccaagacagggtcaatgagactgttgtcctcctactgtccctatgtctctggccgatcacgcgccattgtccctcagaaaca
aatcaaacacccacaccccgggcacccaaagtccccacccacaccaccaatacgtaaacggggcgcccctgcaggccctc
ctgcgcgcggcctcccgccttgcttctctccccttcctttttcttttccagttttcctattttgtcccttttccgcacaacaagtatcaga
atgggttcatcaaatctatccaacctaattcgcacgtagactggcttggtattggcagtttcgtagttatatatatactaccatgagtga
aactgttacgttaccttaaattctttctcccttttaattttcttttatcttactctcctacataagacatcaagaaacaattgtatattgtacacc
ccccccctccacaaacacaaatattgataatataaagatggctgttactaatgtcgctgaacttaacgcactcgtagagcgtgtaaa
aaaagcccagcgtgaatatgccagtttcactcaagagcaagtagacaaaatcttccgcgccgccgctctggctgctgcagatgct
cgaatcccactcgcgaaaatggccgttgccgaatccggcatgggtatcgtcgaagataaagtgatcaaaaaccactttgcttctg
aatatatctacaacgcctataaagatgaaaaaacctgtggtgttctgtctgaagacgacacttttggtaccatcactatcgctgaacc
aatcggtattatttgcggtatcgttccgaccactaacccgacttcaactgctatcttcaaatcgctgatcagtctgaagacccgtaac
gccattatcttctccccgcacccgcgtgcaaaagatgccaccaacaaagcggctgatatcgttctgcaggctgctatcgctgccg
gtgctccgaaagatctgatcggctggatcgatcaaccttctgttgaactgtctaacgcactgatgcaccacccagacatcaacctg
atcctcgcgactggtggtccgggcatggttaaagccgcatacagctccggtaaaccagctatcggtgtaggcgcgggcaacact
ccagttgttatcgatgaaactgctgatatcaaacgtgcagttgcatctgtactgatgtccaaaaccttcgacaacgcgtaatctgtg
cttctgaacagtctgttgttgttgttgactctgtttatgacgctgtacgtgaacgttttgcaacccacggcggctatctgttgcagggta
aagagctgaaagctgttcaggatgttatcctgaaaaacggtgcgctgaacgcggctatcgttggtcagccagcctataaaattgct
gaactggcaggcttctctgtaccagaaaacaccaagattctgatcggtgaagtgaccgttgttgatgaaagcgaaccgttcgcac
atgaaaaactgtccccgactctggcaatgtaccgcgctaaagatttcgaagacgcggtagaaaaagcagagaaactggttgctat
gggcggtatcggtcatacctcttgcctgtacactgaccaggataaccaaccggctcgcgtttcttacttcggtcagaaaatgaaaa
cggcgcgtatcctgattaacaccccagcgtctcagggtggtatcggtgacctgtataacttcaaactcgcacctttccctgactctgg
gttgtggttcttggggtggtaactccatctctgaaaacgttggtccgaaacacctgatcaacaagaaaaccgttgctaagcgagct
gaaaacatgttgtggcacaaacttccgaaatctatctacttccgccgtggctccctgccaatcgcgctggatgaagtgattactgat
ggccacaaacgtgcgctcatcgtgactgaccgcttcctgttcaacaatggttatgctgatcagatcacttccgtactgaaagcagc
aggcgttgaaactgaagtcttcttcgaagtagaagcggacccgaccctgagcatcgttcgtaaaggtgcagaactggcaaactc
cttcaaaccagacgtgattatcgcgctgggtggtggttccccgatggacgccgcgaagatcatgtgggttatgtacgaacatccg
gaaactcacttcgaagagctggcgctgcgctttatggatatccgtaaacgtatctacaagttcccgaaaatgggcgtgaaagcga
aaatgatcgctgtcaccaccacttctggtacaggttctgaagtcactccgtttgcggttgtaactgacgacgctactggtcagaaat
atccgctggcagactatgcgctgactccggatatggcgattgtcgacgccaacctggttatggacatgccgaagtccctgtgtgct
ttcggtggtctggacgcagtaactcacgccatggaagcttatgtttctgtactggcatctgagttctctgatggtcaggctctgcagg
cactgaaactgctgaaagaatatctgccagcgtcctaccacgaagggtctaaaaatccggtagcgcgtgaacgtgttcacagtgc
agcgactatcgcgggtatcgcgtttgcgaacgccttcctgggtgtatgtcactcaatggcgcacaaactgggttcccagttccatat
tccgcacggtctggcaaacgccctgctgatttgtaacgttattcgctacaatgcgaacgacaacccgaccaagcagactgcattc
agccagtatgaccgtccgcaggctcgccgtcgttatgctgaaattgccgaccacttgggtctgagcgcaccgggcgaccgtact
gctgctaagatcgagaaactgctggcatggctggaaacgctgaaagctgaactgggtattccgaaatctatccgtgaagctggc
gttcaggaagcagacttcctggcgaacgtggataaactgtctgaagatgcattcgatgaccagtgcaccggcgctaacccgcgtt
acccgctgatctccgagctgaaacagattctgctggataccta ctacggtcgtgattatgtagaaggtgaaactgcagcgaagaa -continued agaagctgctccggctaaagctgagaaaaaagcgaaaaaatccgcttaagtcgagagcttttgattaagccttctagtccaaaaaacacg tttttttgtcatttatttcattttcttagaatagtttagtttattcattttatagtcacgaatgttttatgattctatatagggttgcaaacaag cattttcatttatgttaaaacaatttcaggtttaccttttattctgcttgtggtgacgcgtgtatccgcccgctcttttggtcaccca tgtatttaattgcataaataattcttaaaagtggagctagtctatttctatttacatacctctcatttctctcattcctcctaatgtgtcaatgat catattcttaactggaccgatcttattcgtcagattcaaaccaaaagttcttagggctaccacaggaggaaaattagtgtgatataatt taaataatttatccgccattcctaatagaacgttgttcgacggatatctttctgcccaaaagggttctaagctcaatgaagagccaatg tctaaacctcgttacattgaaaatacagtaaatggttccaccattattatgttggtcttgtttagtatggccgatcggcgtgtgttttgttt gcaccttttatatagtagaagaatatttgtcttaattcttattagtactgcaacctaaccactaattatcaacaattattggattatataaag gaggtaaattgccggattaaaatcaaatatcattcatcaacaagtattcatattgtcggcatattttacatgcggtgtaagtatttggat cgtattcttatagtgtcaatacctcgaagcagcgtttcaagtaccagacgtatgtaggaacttttttaacgtcgagtccgtaagatttga tcagtattaaaaaaatctagataaatgagtggtacaaataaaaacatcattaaaaatcgttaaataaaaaagtatgaagatcatctatt aaagtattagtagccattagccttaaaaaaatcagtgctagtttaagtataatctcgggcgcgccggccgaggcggttaagcggat tttttcgcttttttctcagctttagccggagcagcttctttcttcgctgcagtttcaccttctacataatcacgaccgtagtaggtatccag cagaatctgtttcagctcggagatcagcgggtaacgcgggttagcgccggtgcactggtcatcgaatgcatcttcagacagtttat ccacgttcgccaggaagtctgcttcctgaacgccagcttcacggatagatttcggaatacccagttcagctttcagcgtttccagcc atgccagcagtttctcgatcttagcagcagtacggtcgcccggtgcgctcagacccaagtggtcggcaatttcagcataacgacg gcgagcctgcggacggtcatactggctgaatgcagtctgcttggtcgggttgtcgttcgcattgtagcgaataacgttacaaatca gcagggcgtttgccagaccgtgcggaatatggaactgggaacccagtttgtgcgccattgagtgacatacacccaggaaggcg ttcgcaaacgcgatacccgcgatagtcgctgcactgtgaacacgttcacgcgctaccggattttttagacccttcgtggtaggacgc tggcagatattctttcagcagtttcagtgcctgcagagcctgaccatcagagaactcagatgccagtacagaaacataagcttcca tggcgtgagttactgcgtccagaccaccgaaagcacacagggacttcggcatgtccataaccaggttggcgtcgacaatcgcca tatccggagtcagcgcatagtctgccagcggatatttctgaccagtagcgtcgtcagttacaaccgcaaacggagtgacttcaga acctgtaccagaagtggtggtgacagcgatcattttcgctttcacgcccattttcgggaacttgtagatacgtttacggatatccata aagcgcagcgccagctcttcgaagtgagtttccggatgttcgtacataacccacatgatcttcgcggcgtccatcggggaaccac cacccagcgcgataatcacgtctggtttgaaggagtttgccagttctgcacctttacgaacgatgctcagggtcgggtccgcttcta cttcgaagaagacttcagtttcaacgcctgctgctttcagtacggaagtgatctgatcagcataaccattgttgaacaggaagcggt cagtcacgatgagcgcacgtttgtggccatcagtaatcacttcatccagcgcgattggcagggagccacggcggaagtagatag atttcggaagtttgtgccacaacatgttttcagctcgcttagcaacggttttcttgttgatcaggtgtttcggaccaacgttttcagagat ggagttaccaccccaagaaccacaacccagagtcagggaaggtgcgagtttgaagttatacaggtcaccgataccaccctgag acgctggggtgttaatcaggatacgcgccgttttcattttctgaccgaagtaagaaacgcgagccggttggttatcctggtcagtgt acaggcaagaggtatgaccgataccgcccatagcaaccagtttctctgcttttttctaccgcgtcttcgaaatctttagcgcggtacat tgccagagtcggggacagttttcatgtgcgaacggttcgctttcatcaacaacggtcacttcaccgatcagaatcttggtgttttctg gtacagagaagcctgccagttcagcaattttataggctggctgaccaacgatagccgcgttcagcgcaccgttttttcaggataaca tcctgaacagctttcagctctttaccctgcaacagatagccgccgtgggttgcaaaacgttcacgtacagcgtcataaacagagtc aacaacaacaacagactgttcagaagcacagattacgccgttgtcgaaggttttggacatcagtacagatgcaactgcacgtttga tatcagcagtttcatcgataacaactggagtgttgcccgcgcctacaccgatagctggtttaccggagctgtatgcggctttaacca tgcccggaccaccagtcgcgaggatcaggttgatgtctgggtggtgcatcagtgcgttagacagttcaacagaaggttgatcgat ccagccgatcagatcttcggagcaccggcagcgatagcagcctgcagaacgatatcagccgctttgttggtggcatcttttgca cgcgggtgcggggagaagtaatggcgttacgggtcttcagactgatcagcgatttgaagatagcagttgaagtcgggttagtg gtcggaacgataccgcaaataataccgattggttcagcgatagtgatggtaccaaaagtgtcgtcttcagacagaacaccacagg -continued

```
tttttcatctttataggcgttgtagatatattcagaagcaaagtggttttgatcactttatcttcgacgatacccatgccggattcggca acggccattttcgcgagtgggattcgagcatctgcagcagccagagcggcggcgcggaagattttgtctacttgctcttgagtga aactggcatattcacgctgggcttttttttacacgctctacgagtgcgttaagttcagcgacattagtaacagccataattcttaattaac tttgatatgattttgtttcagatttttatataaaagctttcccaaatagtgctaaagtgaacttagattttttggtacctgtttcgaaattaaa aatagaaaaatttctctccctatattgttattcttacttcaaatttgtttatcgtttatttactaggcgagacttgagtagacgacaatccaa atagaattaacagatttattggtagaaagcaataatattctttagatggttgagaataaagaagtaaaaaaaccagtaaagagaaa aagaaaaggaagaaaattaaagaaaaaggatgattacacaagaagataataaaaaaactcctttattaagagcggaagaatttaa taatgaagatgggaataagcaaaacaaaacaaagaagggaaaaaaaataaaaaatcgtatttatttatttaaaaaatcatgttgat gacgacaatggaaaaaaaaaaccgatttcactttctcatccttatattttttcaaaggttgatgcaagtcgatctcaaatcggataacg ctgccaactgggaaattccgcaattccgcaagaaaaaaaaaatgtgaaaacgtgattgcattttttacaggtcctaaaggatttag cccacatatcaagagggtggcagtaattgcactgattaagcattcgtcagcattaggcgaatgtgtgcatgaatattgccagtgtgc tcgatattagagagtacattgaagaatattgtaccggattatgtacaataacttgttaatgagatattaatttttcttttttactagccgcta tcccatgcacgatgctaaatttcaagaagaaactgagatttaaaaaattagtggaagctgataaaacggactataatggtgtatgga ttgaggaatctcgacatgttttccatcgttttcaacgatgactgtaacccgtagattgaaccaggcatgccaaagttagttagatcag ggtaaaaattatagatgaggtatttattggagaaagataacatatcatactttcccccactttttcgaggctcttctatatcatattcata aattagcattatgtcatttctcataactactttatcacgttagaaattacttattattattaaattaatacaaaatttagtaaccaaataaata taaataaatatgtatatttaaattttaaaaaaaaaatcctatagagcaaaggattttccattataatattagctgtacacctcttccgcat tttttgagggtggttacaacaccactcattcagaggctgtcggcacagttgcttctagcatctggcgtccgtatgtatgggtgtatttt aaataataaacaaagtgccacaccttcaccaattatgtctttaagaaatggacaagttccaaagagcttgcccaaggctcgacaag gatgtactttggaatatctatattcaagtacgtggcgcgcatatgtttgagtgtgcacacaataaaggttttagatattttgcggcgtc ctaagaaaataaggggtttcttaaaaaataacaatagcaaacaaagttccttacgatgatttcagatgtgaatagcatggtcatgatg agtatatacgtttttataaataattaaaagttttcctcttgtctgttttttttgttggctcgtggttgttctcgaaaaaggagagttttcattttc gaaataggtgattatcatcatgttgttatcacccacgacgaagataatacggagctcaccgttttcttttttttttccctttggctgaaatt tcccaccagaacaaacgtgacaaaattatctttgaatccaaagtagcttatatatatacgtagaagtgtttcgagacacacatccaaa tacgaggttgttcaatttaaacccaagaatacataaaaaaaatatagatatattaacttagtaaacaatgactgcaagcacaccatcc aatgtcatgacattgttcttgttaaggcatggacaaagtgaattgaatcacgagaatatattctgtggttggattgacgctaagctaac cgaaaaaggtaaagaacaagctcgtcattctgccgagctaatcgaacaatattgtaaagctaataatttgagattaccccagattgg ttacacctcacgtttaattaggacccaacagaccatagaaacgatgtgtgaagaatttaagttaaagccacaactgcaggttgttta cgactttaataaaatcaaacttggagacgaatttggcagtgatgacaaggataatatgaaaatcccgattcttcaaacttggaggct aaatgaacgtcattacggttcctggcagggccagaggaaaccgaatgttttaaaagaatatggtaaggataaatatatgttcattag gagagattacgagggtaagccaccacctgtagatcttgaccgtgagatgattcaacaagaaaatgagaagggctcttctactggg tacgaattcaaggagccaaacagacaaataaaatgaattggaatgcagcaatcatgacattgtattaccggattccgaatctctt cgtgaagtggtttatagattgaatccttttctacaaaatgtcatattaaaattagccaatcaatatgatgaatcttcatgcctgattgtgg gccatggaagttcagtgagatcgctactgaaaattctggagggtatatcagatgatgacatcaagaatgttgatattccaaatggta tccccttagtcgttgaattagataagaataatggtcttaagtttatcagaaaattctacctagatcctgaatctgctaagatcaatgctg agaaagtccgtaatgagggtttcataaaaaatccttaaggggggtaagtatataatataattgtgtattttccgaagtataatgaaaac caatagaaaacttattataagtccaatgaggtactttaaaaatgtgatatttataagaacattcctgaatgcagatatatgatatatattgtaaa tatatatagatgtgtatatgtatttccattttgtgtgaggttttcttcttttatctcctatataatttgtaaccttaattaacccatgacat aaccaatattagcctttgcaaattttgtaacttcttgacgttgttctaacgacaaatcttcatgcttcgattttatatgccttgttaaagcat ccagtctcgaaaacgtcttctgatagccctcagatccaagaattttatacactccgagcaacggaagacaatcttcctttagcgtg aatggtattttggtgtctcgttaaatcataggaccttgaaaattgggcaccacacggttcatttgtaatgagattcattatctgacacgt
```

-continued aaatatttcgttattaccgtcagaagatgacgtatgggccgatggtgatgcagtcgaaggtttcgaattcgaatttgtagatgaatgt gaagataagtgcttc Sequence of M2158 AADH integrations at the GPD1 locus (nucleotide; SEQ ID NO:99):

cagaattggtgatattcttcattatccctcgacatctttacttttgatcagctttgtgtatagcgggatatccgattggaact tggcttcagcaacaaacttgccaaagtggattctcctactcaagctttgcaaacattctatatctctagtggcaacagaaccgaagttattc ttatcatcaccatctcttttcgaaattaatggtataatcttttcaatataaactttttttattttatcattgtaattaacttctggggcataa ggcgccaaaatttgtgggtagttaatgctcggtaagaatgatttctgaatcttgtcaggaaagaagggagtttcatcaggtgattcg aatcttctgatgcgagaatgcgcaatttcaagatttgaaagagcccaatccaagaaagatcctttaaaattcggaatttctaaacctg gatggtttgcctcataaactgaaggacatgtggcgaaatgcgacctctcaataaatttgaagatgatcgaatcctccattctaactaatt catctctaatattttgtagatttaaaacagtttctggttttgtgaaatccatatcttataccaattttatgcaggatgctgagtgctatttgt tagcaaaacggaatcgatgtttcaacttttcaatactttttttcttcttttcttcgaacttcgaagattatagagatccattgaaaatttacg ataaaggaaatgcaacacgaagtttgaaaaaaagttgatattgaaaaaaaaaaaaaagagaaccaaaaaaaaattaaaaaacg tgaaaacgatggttaacaacttttttcgaatttggtatacgtggaaaaacgaatgtatagatgcattttttaaagaatatatataaaattt agtaattgtattccgcgagcggcgcaataggtgatttcatttagctgctttcagtttgcgtatcatttcttcattgatcttggcttctctatc taaatcctctttcgacttgtaaagtccccaagttctaaaccataagaaccgcctcaatctggaaaatttgtcagtatcaagaccataat tcgtgtatgactgaatcaaatgtaatccactttcgtcatgagtaaattcggccttgctcagagactcctggattttggctaacaacgca gtcccttcgatgcatatagctaggccacaaattatgccaataacggtccatgggttgatgttttcttgaattcttcgtttttcatgctattt gcgtcttcccaagtcccagcgttccagtattcatactgcgcgttagagtggtagccataagagccggcatattggtaattttcagtat taacgttagaacgtggtgaatacgatgtggtccagccttgcctcgttgtgtcatatacgatcttttctttgggtcacaaagaatatcat atgcttgagagatgactttaaatctatgtagttttttcgcttgatgttagcagcagcggtgatttactatcactgttggtaaccttttctgag ctaaatatttgaatgttatcggaatggtcagggtggtacaattttacataacgatgatatttttttttttaacgacttcttgtccagtttagga tttccagatccggcctttggaatgccaaaaatatcataggggagttggatctgccaactcaggccattgttcatcccttatcgtaagttt tctattgccatttttatcgttcgctgtagcatacttagctataaaagtgatttgtggggacacttttctacacatgataagtgccacttg aataaaaatgggtatacgaacttatggtgtagcataacaaatatattgcaagtagtgacctatggtgtgtagatatacgtacagttag ttacgagcctaaagacacaacgtgtttgttaattatactgtcgctgtaatatcttctcttccattatcaccggtcattccttgcaggggc ggtagtacccggagaccctgaactttctttttttttttgcgaaattaaaaagttcattttcaattcgacaatgagatctacaagccattgt tttatgttgatgagagccagcttaaagagttaaaaatttcatagctactagtcttctaggcgggttatctactgatccgagcttccacta ggatagcacccaaacacctgcatatttggacgacctttacttacaccaccaaaaaccactttcgcctctcccgccctgataacgtc cactaattgagcgattacctgagcggtcctcttttgtttgcagcatgagacttgcatactgcaaatcgtaagtagcaacgtctcaagg tcaaaactgtatggaaaccttgtcacctcacttaattctagctagcctaccctgcaagtcaagaggtctccgtgattcctagccacct caaggtatgcctctccccggaaactgtggcctttctggcacacatgatctccacgatttcaacatataaatagcttttgataatggcaata ttaatcaaatttattttacttctttcttgtaacatctctcttgtaatcccttattccttctagctattttcataaaaaaccaagcaactgct tatcaacacacaaacactaaatcaaaatggctgttactaatgtcgctgaacttaacgcactcgtagagcgtgtaaaaaaagcccag cgtgaatatgccagtttcactcaagagcaagtagacaaaatcttccgcgccgccgctctggctgctgcagatgctcgaatcccact cgcgaaaatggccgttgccgaatccggcatgggtatcgtcgaagataaagtgatcaaaaaccactttgcttctgaatatatctaca acgcctataaagatgaaaaaacctgtggtgttctgtctgaagacgacacttttggtaccatcactatcgctgaaccaatcggtattat ttgcggtatcgttccgaccactaacccgacttcaactgctatcttcaaatcgctgatcagtctgaagacccgtaacgccattatcttct ccccgcacccgcgtgcaaaagatgccaccaacaaagcggctgatatcgttctgcaggctgctatcgctgccggtgctccgaaa

```
gatctgatcggctggatcgatcaaccttctgttgaactgtctaacgcactgatgcaccacccagacatcaacctgatcctcgcgact
ggtggtccgggcatggttaaagccgcatacagctccggtaaaccagctatcggtgtaggcgcgggcaacactccagttgttatc
gatgaaactgctgatatcaaacgtgcagttgcatctgtactgatgtccaaaaccttcgacaacggcgtaatctgtgcttctgaacag
tctgttgttgttgttgactctgtttatgacgctgtacgtgaacgttttgcaaccacggcggctatctgttgcagggtaaagagctgaa
agctgttcaggatgttatcctgaaaaacggtgcgctgaacgcggctatcgttggtcagccagcctataaaattgctgaactggcag
gcttctctgtaccagaaaacaccaagattctgatcggtgaagtgaccgttgttgatgaaagcgaaccgttcgcacatgaaaaactg
tccccgactctggcaatgtaccgcgctaaagatttcgaagacgcggtagaaaaagcagagaaactggttgctatgggcggtatc
ggtcatacctcttgcctgtacactgaccaggataaccaaccggctcgcgtttcttacttcggtcagaaaatgaaaacgcgcgtat
cctgattaacaccccagcgtctcagggtggtatcggtgacctgtataacttcaaactcgcaccttccctgactctgggttgtggttct
tggggtggtaactccatctctgaaaacgttggtccgaaacacctgatcaacaagaaaaccgttgctaagcgagctgaaaacatgt
tgtggcacaaacttccgaaatctatctacttccgccgtggctccctgccaatcgcgctggatgaagtgattactgatggccacaaa
cgtgcgctcatcgtgactgaccgcttcctgttcaacaatggttatgctgatcagatcacttccgtactgaaagcagcaggcgttgaa
actgaagtcttcttcgaagtagaagcggacccgaccctgagcatcgttcgtaaaggtgcagaactggcaaactccttcaaaccag
acgtgattatcgcgctgggtggtggttccccgatggacgccgcgaagatcatgtgggttatgtacgaacatccggaaactcactt
cgaagagctggcgctgcgctttatggatatccgtaaacgtatctacaagttcccgaaaatgggcgtgaaagcgaaaatgatcgct
gtcaccaccacttctggtacaggttctgaagtcactccgtttgcggttgtaactgacgacgctactggtcagaaatatccgctggca
gactatgcgctgactccggatatggcgattgtcgacgccaacctggttatggacatgccgaagtccctgtgtgctttcggtggtct
ggacgcagtaactcacgccatggaagcttatgtttctgtactggcatctgagttctctgatggtcaggctctgcaggcactgaaact
gctgaaagaatatctgccagcgtcctaccacgaagggctctaaaaatccggtagcgcgtgaacgtgttcacagtgcagcgactat
cgcgggtatcgcgtttgcgaacgccttcctgggtgtatgtcactcaatggcgcacaaactgggttcccagttccatattccgcacg
gtctggcaaacgccctgctgatttgtaacgttattcgctacaatgcgaacgacaacccgaccaagcagactgcattcagccagtat
gaccgtccgcaggctcgccgtcgttatgctgaaattgccgaccacttgggtctgagcgcaccgggcgaccgtactgctgctaag
atcgagaaactgctggcatggctggaaacgctgaaagctgaactgggtattccgaaatctatccgtgaagctggcgttcaggaa
gcagacttcctggcgaacgtggataaactgtctgaagatgcattcgatgaccagtgcaccggcgctaacccgcgttacccgctg
atctccgagctgaaacagattctgctggataacctactacggtcgtgattatgtgaaaggtgaaactgcagcgaagaaagaagctg
ctccggctaaagctgagaaaaaagcgaaaaaatccgcttaagtcgagagcttttgattaagccttctagtccaaaaaacacgttttttttgt
catttatttcattttcttagaatagtttagtttattcattttatagtcacgaatgttttatgattctatatagggttgcaaacaagcattttt
cattttatgttaaaacaatttcaggtttacctttttattctgcttgtggtgacgcgtgtatccgcccgctcttttggtcacccatgtatttaat
tgcataaataattcttaaaagtggagctagtctatttctatttacatacctctcatttctcatttcctcctaatgtgtcaatgatcatattct
taactggaccgatcttattcgtcagattcaaaccaaaagttcttagggctaccacaggaggaaaattagtgtgatataatttaaataattt
atccgccattcctaatagaacgttgttcgacggatatctttctgcccaaaagggttctaagctcaatgaagagccaatgtctaaacct
cgttacattgaaaatacagtaaatggttccaccattattatgttggtcttgtttagtatggccgatcggcgtgtgttttgtttgcaccttta
tatagtagaagaatatttgtcttaattcttattagtactgcaacctaaccactaattatcaacaattattggattatataaaggaggtaaat
tgccggattaaaatcaaatatcattcatcaacaagtattcatattgtcggcatatttttacatgcggtgtaagtatttggatcgtattctta
tagtgtcaatacctcgaagcagcgtttcaagtaccagacgtatgtaggaacttttttaacgtcgagtccgtaagatttgatcagtattaa
aaaaatctagataaatgagtggtacaaataaaaacatcattaaaaatcgttaaataaaaagtatgaagatcatctattaaagtatta
gtagccattagccttaaaaaaatcagtgctagtttaagtataatctcgggcgcgccggccgaggcggttaagcggatttttttcgcttt
tttctcagctttagccggagcagcttcttcttcgctgcagtttcaccttctacataatcacgaccgtagtaggtatccagcagaatctg
tttcagctcggagatcagcgggtaacgcgggttagcgccggtgcactggtcatcgaatgcatcttcagacagtttatccacgttcg
ccaggaagtctgcttcctgaacgccagcttcacggatagatttcggaatacccagttcagctttcagcgtttccagccatgccagc
agtttctcgatcttagcagcagtacggtcgcccggtgcgctcagacccaagtggtcggcaatttcagcataacgacggcgagcct
```

-continued gcggacggtcatactggctgaatgcagtctgcttggtcgggttgtcgttcgcattgtagcgaataacgttacaaatcagcagggcg tttgccagaccgtgcggaatatggaactgggaacccagtttgtgcgccattgagtgacatacacccaggaaggcgttcgcaaac gcgatacccgcgatagtcgctgcactgtgaacacgttcacgcgctaccggattttagacccttcgtggtaggacgctggcagat attctttcagcagtttcagtgcctgcagagcctgaccatcagagaactcagatgccagtacagaaacataagcttccatggcgtga gttactgcgtccagaccaccgaaagcacacagggacttcggcatgtccataaccaggttggcgtcgacaatcgccatatccgga gtcagcgcatagtctgccagcggatatttctgaccagtagcgtcgtcagttacaaccgcaaacggagtgacttcagaacctgtac cagaagtggtggtgacagcgatcattttcgctttcacgcccattttcgggaacttgtagatacgtttacggatatccataaagcgca gcgccagctcttcgaagtgagtttccggatgttcgtacataacccacatgatcttcgcggcgtccatcgggaaccaccacccag cgcgataatcacgtctggtttgaaggagtttgccagttctgcacctttacgaacgatgctcagggtcgggtccgcttctacttcgaa gaagacttcagtttcaacgcctgctgctttcagtacggaagtgatctgatcagcataaccattgttgaacaggaagcggtcagtca cgatgagcgcacgtttgtggccatcagtaatcacttcatccagcgcgattggcagggagccacggcggaagtagatagatttcg gaagtttgtgccacaacatgttttcagctcgcttagcaacggttttcttgttgatcaggtgtttcggaccaacgttttcagagatggagt taccaccccaagaaccacaacccagagtcagggaaggtgcgagtttgaagttatacaggtcaccgataccaccctgagacgct ggggtgttaatcaggatacgcgccgttttcattttctgaccgaagtaagaaacgcgagccggttggttatcctggtcagtgtacag gcaagaggtatgaccgataccgcccatagcaaccagtttctctgcttttctaccgcgtcttcgaaatctttagcgcggtacattgcc agagtcgggacagttttcatgtgcgaacggttcgctttcatcaacaacggtcacttcaccgatcagaatcttggtgttttctggtac agagaagcctgccagttcagcaattttataggctggctgaccaacgatagccgcgttcagcgcaccgttttcaggataacatcct gaacagctttcagctctttaccctgcaacagatagccgccgtgggttgcaaaacgttcacgtacagcgtcataaacagagtcaac aacaacaacagactgttcagaagcacagattacgccgttgtcgaaggttttggacatcagtacagatgcaactgcacgtttgatat cagcagtttcatcgataacaactggagtgttgcccgcgcctacaccgatagctggtttaccggagctgtatgcggctttaaccatg cccggaccaccagtcgcgaggatcaggttgatgtctgggtggtgcatcagtgcgttagacagttcaacagaaggttgatcgatcc agccgatcagatctttcggagcaccggcagcgatagcagcctgcagaacgatatcagccgctttgttggtggcatctttttgcacg cgggtgcggggagaagataatggcgttacgggtcttcagactgatcagcgatttgaagatagcagttgaagtcgggttagtggtc ggaacgataccgcaaataataccgattggttcagcgatagtgatggtaccaaaagtgtcgtcttcagacagaacaccacaggtttt ttcatctttataggcgttgtagatatattcagaagcaaagtggttttttgatcactttatcttcgacgatacccatgccggattcggcaac ggccattttcgcgagtgggattcgagcatctgcagcagccagagcggcggcgcggaagattttgtctacttgctcttgagtgaaa ctggcatattcacgctgggcttttttttacacgctctacgagtgcgttaagttcagcgacattagtaacagccataattcttaattaactttga tatgattttgtttcagatttttttatataaaagctttcccaaatagtgctaaagtgaacttagattttttggtacctgtttcgaaattaaaaa tagaaaaatttctctccctatattgttattcttacttcaaatttgtttatcgtttatttactaggcgagacttgagtagacgacaatccaaat agaattaacagattttattggtagaaagcaataatattctttagatggttgagaataaagaagtaaaaaaaccagtaaagagaaaaa gaaaggaagaaattaaagaaaaggatgattacacaagaagataataaaaaaactcctttattaagagcggaagaatttaata atgaagatgggaataagcaaaacaaaaacaaagaagggaaaaaaaataaaaaatcgtatttatttatttaaaaaatcatgttgatga cgacaatggaaaaaaaaaccgatttcactttctcatccttatattttcaaaggttgatgcaagtcgatctcaaatcggataacgctg ccaactgggaaattccgcaattccgcaagaaaaaaaaaatgtgaaaacgtgattgcattttttacaggtcctaaaggatttagccc acatatcaagagggtggcagtaattgcactgattaagcattcgtcagcattaggcgaatgtgtgcatgaatattgccagtgtgctcg atattagagagtacattgaagaatattgtaccggattatgtacaataactttgttaatgagatattaattttctttttttactagccgctatcc catgcacgatgctaaatttcaagaagaaactgagatttaaaaaattagtggaagctgataaaacggactataatggtgtatggattg aggaatctcgacatgttttttccatcgttttcaacgatgactgtaacccgtagattgaaccaggcatgccaaagttagttagatcaggg taaaaattatagatgaggtttaattaaacaagcacgcagcacgctgtatttacgtatttaattttatatatttgtgcatacactactaggg aagacttgaaaaaaacctaggaaatgaaaaaacgacacaggaagtcccgtatttactattttttccttccttttgatggggcagggc -continued

```
ggaaatagaggataggataagcctactgcttagctgtttccgtctctacttcggtagttgtctcaattgtcgtttcagtattaccttttaga
gccgctagacgatggttgagctatttgttgagggaaaactaagttcatgtaacacacgcataacccgattaaactcatgaatagctt
gattgcaggaggctggtccattggagatggtgccttattttccttataggcaacgatgatgtcttcgtcggtgttcaggtagtagtgta
cactctgaatcagggagaaccaggcaatgaacttgttcctcaagaaaatagcggccataggcatggattggttaaccacaccag
atatgcttggtgtggcagaatatagtccttttggtggcgcaattttcttgtacctgtggtagaaagggagcggttgaactgttagtata
tattggcaatatcagcaaatttgaaagaaaattgtcggtgaaaaacatacgaaacacaaaggtcgggccttgcaacgttattcaaa
gtcattgtttagttgaggaggtagcagcggagtatatgtattccttttttttgcctatggatgttgtaccatgcccattctgctcaagcttt
tgttaaaattattttttcagtattttttcttccatgttgcgcgttacgagaacagaagcgacagataaccgcaatcatacaactagcgcta
ctgcggggtgtaaaaagcacaagaactaagccaagatcacaacagttatcgataaaatagcagtgtttgcatggccattgagaag
gacaacattggcgtgcgcgccaatgttgtctcaccatgtagctccaaacgagttgtaagagacggaccgctcacgcttccgaag
cggtcagaaaacgcttcccagtatgcagttgacctacattcaacctgcaaatattgctttgcttcaagaaatgattacacagacgtct
attttcttctacataatgcacgaaacttgggcatttagtcatgtagccgcctagcgagcctgggtgccgtcctatctcctttgttcgtgc
aaagagacaggaacacacactgcgttctcttgcggccggtctggcggactcaggggtgcggcgtttgcttaaccggagggaat
aataaaatcggggtgacgcaagtatgaagtcatgtgtgcttagcaattacgtagagggattagaaataatagtgtgcggttatcgg
aaccggctcttgttccgtttagagcaacccaggtgcaggcgtactttaaagtattttctttctttttttttcctgctacttacgctaggag
ctgccgcagctgcaaagccgacgtcggagaggcaggtgatcttcggctcggccgacaaatcccctggatatcattggcctgtcg
aggtatcggccgcgtgaactaccgggaattactatgcaaaacaattggaaatctggtaggaaaaccttgttctagaacttggcg
attgctgacaaagaagaaaagggcctattgttgctgcctcttttgttgttcttcctcgtattgtcttgccggtgttctttgtgtcttttgtgt
gtaggttcttactattatagtgctctttgctattatattttcttcgttttcactttgcgtaatgtaacggtcttaaacaaagttttttttttt
tcgctcttgcattttccttttctgctctatcttatttgctaattgtagtttcagaagttttacttaaatatagcactattttccagttttaat
gtttcttctcattgctttcttttataattttcgcatataattatacatttacggtgtcttaactctccctcttcaccccctcattattccagaa
aatactaatacttcttcacacaaaagaacgcagttagacaatcaacaatgaatcctaaatcctctacacctaagattccaagacccaagaacg
catttattctgttcagacagcactaccacaggatcttaatagacgaatggaccgctcaaggtgtggaaataccccataattcaaacatttct
aaaattattggtacgaagtggaagggcttacaaccggaagataaggcacactgggaaaatctagcggagaaggagaaactaga
acatgaaaggaagtatcctgaatacaaatacaagccggtaagaaagtctaagaagaagcaactacttttgaaggaaatcgagca
acagcagcagcaacaacagaaagaacagcagcagcagaaacagtcacaaccgcaattacaacagccctttaacaacaatata
gttcttatgaaaagagcacattctctttcaccatcttcctcggtgtcaagctcgaacagctatcagttccaattgaacaatgatcttaag
aggttgcctattccttctgttaatacttctaactatatggtctccagatctttaagtggactacctttgacgcatgataagacggcaaga
gacctaccacagctgtcatctcaactaaattctattccatattactcagctccacacgacccttcaacgagacatcattacctcaacg
tcgctcaagctcaaccaagggctaactcgacccctcaattgccctttatttcatccattatcaacaacagcagtcaaacaccggtaa
ctacaactaccacatccacaacaactgcgacatcttctcctgggaaattctcctcttctccgaactcctctgtactggagaacaaca
gattaaacagtatcaacaattcaaatcaatatttacctcccccctctattaccttctctgcaagattttcaactggatcagtaccagcagc
taaagcagatgggaccaacttatattgtcaaaccactgtctcacaccaggaacaatctattgtccacaactacccctacgcatcatc
acattcctcatataccaaaccaaaacattcctctacatcaaattataaactcaagcaacactgaggtcaccgctaaaactagcctag
tttctccgaaatgatttttttttccatttcttctttccgttatattatattatactatattcccttttaactaaaaatttatgcatttggct
cctgtttaataaaagtttaaatc
```

Figure 14:
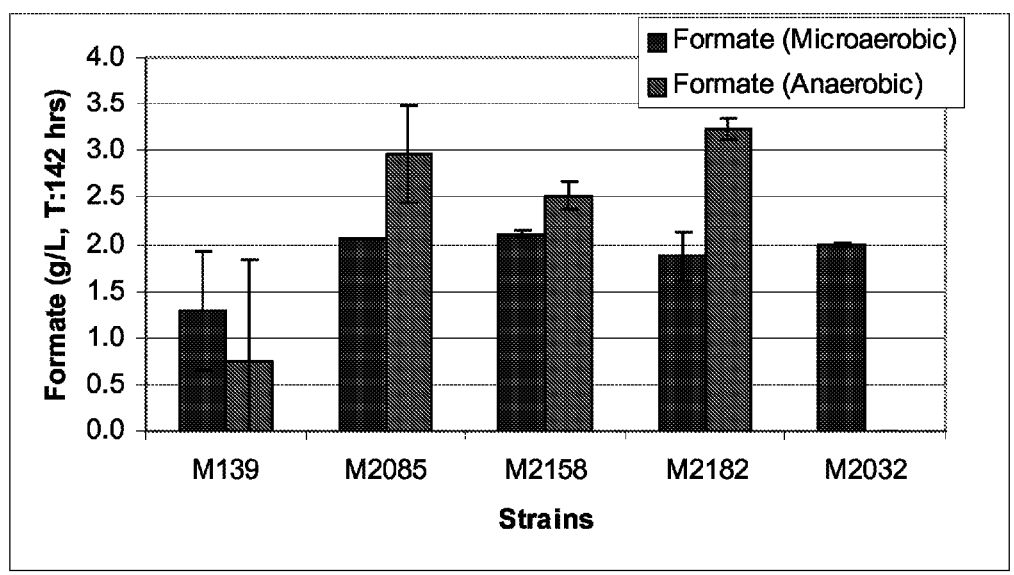
FIG. 14 shows a graph of formate production at the end of 142 hours in microaerobic and anaerobic conditions.

These strains were grown in YPD containing 50 g/L glucose under anaerobic and microaerobic conditions, and formate was measured over 142 hours. As shown in FIG. 14, at the end of 142 hours, strains containing the heterologous PFL and AADH made more formate than the wildtype strain M139.

Example 6

Expression of PFL and AADH and Detection of Ethanol

The purpose of this Example is to determine whether formate production can confer anaerobic growth on fdh, gpd, and/or fps deletion strains. Yeast strains containing an fdh1Δfdh2Δgpd1Δgpd2Δ genetic background (M2025) were transformed with vectors expressing PflA/B cassettes from *C. cellulolyticum* (TB274) and *E. coli* (TB275). Each of these strains also contained a second construct expressing the *E. coli* AdhE. YPD medium was prepared and added to hungate tubes, oxygen was purged with nitrogen, and the tubes were autoclaved for 20 minutes. A pre-culture of TB274 and TB275 was prepared overnight in YPD medium containing antibiotics which select for maintenance of both plasmids. A pre-culture of M1901, the parent strain of M2025, and M2025 itself were prepared in YPD and included as positive and negative controls, respectively. A strain referred to as TB267 was created which contains only the bifunctional ADH plasmid. This strain was prepared in YPD plus antibiotic to select for the plasmid. This strain controls for the potential effect of ADH or other electron acceptors that may be present in YPD medium.

Figure 15:
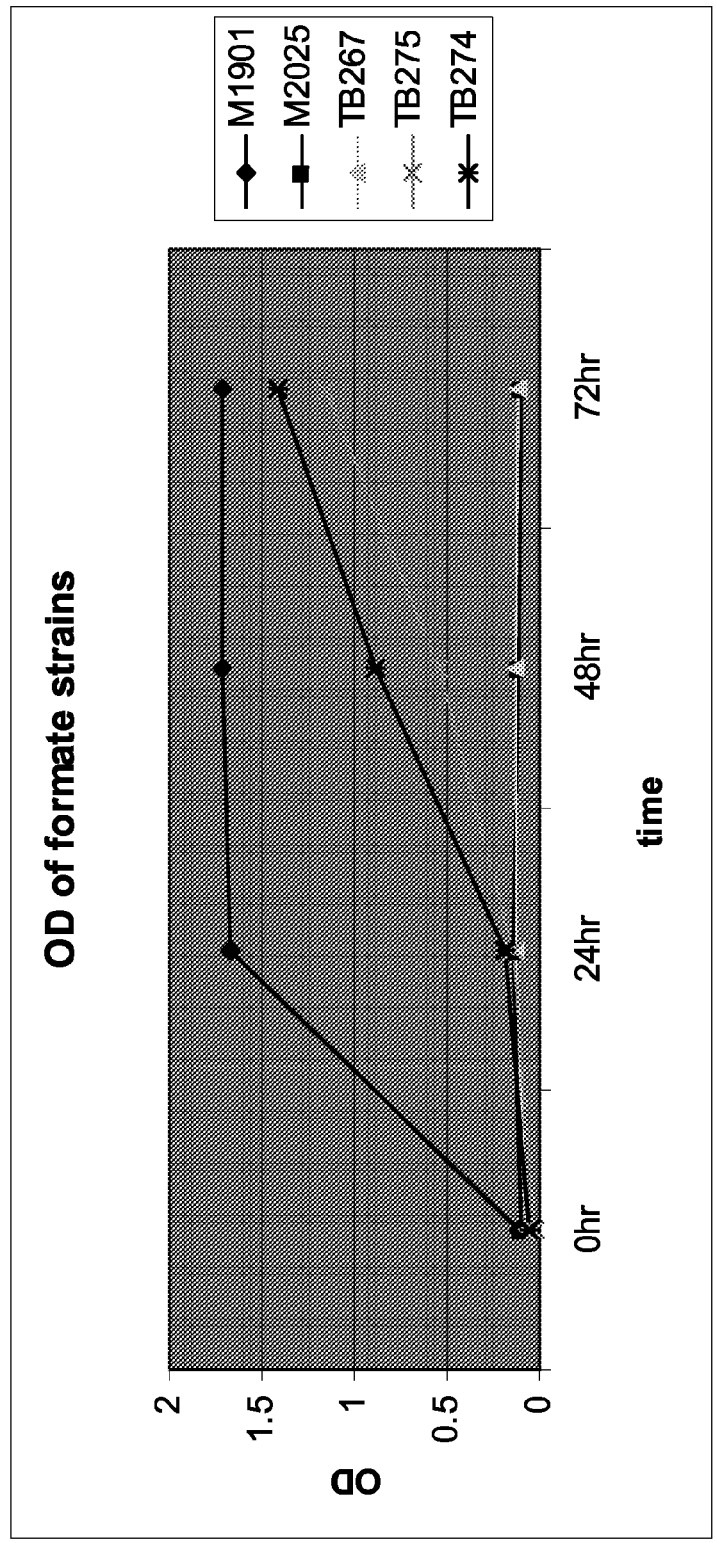
FIG. 15 shows a graph of the growth of strains of the invention over 72 hours as measured by OD.

All strains were inoculated to final OD's of about 0.05 or below. The OD of each culture was measured at 0, 24, 48, and 72 hours (FIG. 15), and samples were prepared and submitted for HPLC determination of metabolite levels. As expected, the M1901 strain grew fairly quickly, consuming all the sugar substrate by 24 hours. The M2025 and TB267 strains, which are unable to make glycerol, did not show a significant increase in OD during this experiment. The TB274 and TB275 strains, which express both PFL and ADH, were able to grow after a 24 hour lag time. See FIG. 15. These data indicate that the introduced metabolic pathway in TB274 and TB275 does not block cellular growth.

Figure 16:
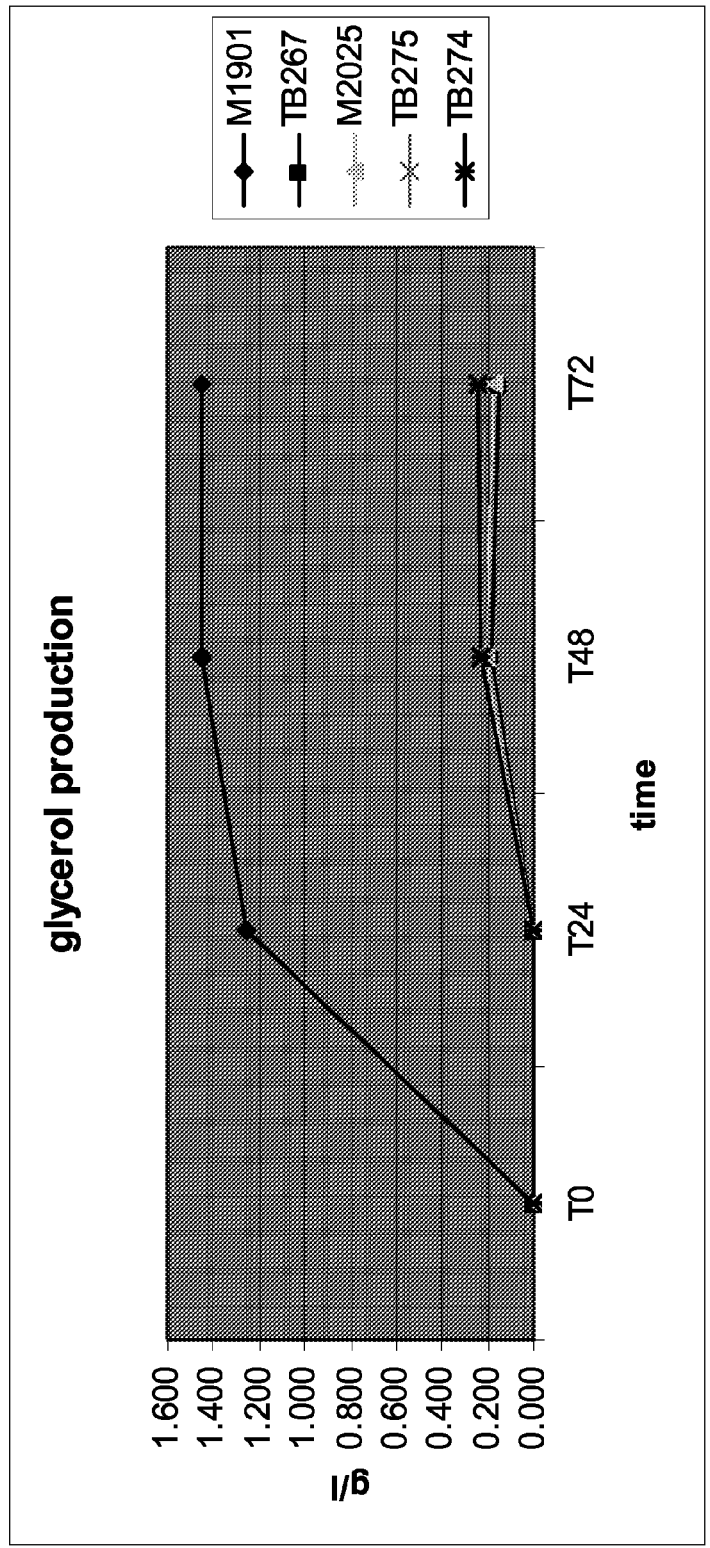
FIG. 16 shows a graph of glycerol production (g/L) of strains of the invention over 72 hours.

The production of glycerol in these strains is shown in FIG. 16. The anaerobic growth of M1901 was accompanied by glycerol production as expected. A trace amount of glycerol was observed in the PflA/B containing strains TB274 and TB275, but this was at or below the level of the negative controls which did not grow. See FIG. 16. These data, in conjunction with the OD data, indicate that the expression of PflA/B and AdhE allowed for anaerobic growth of M2025 without associated glycerol production.

Figure 17:
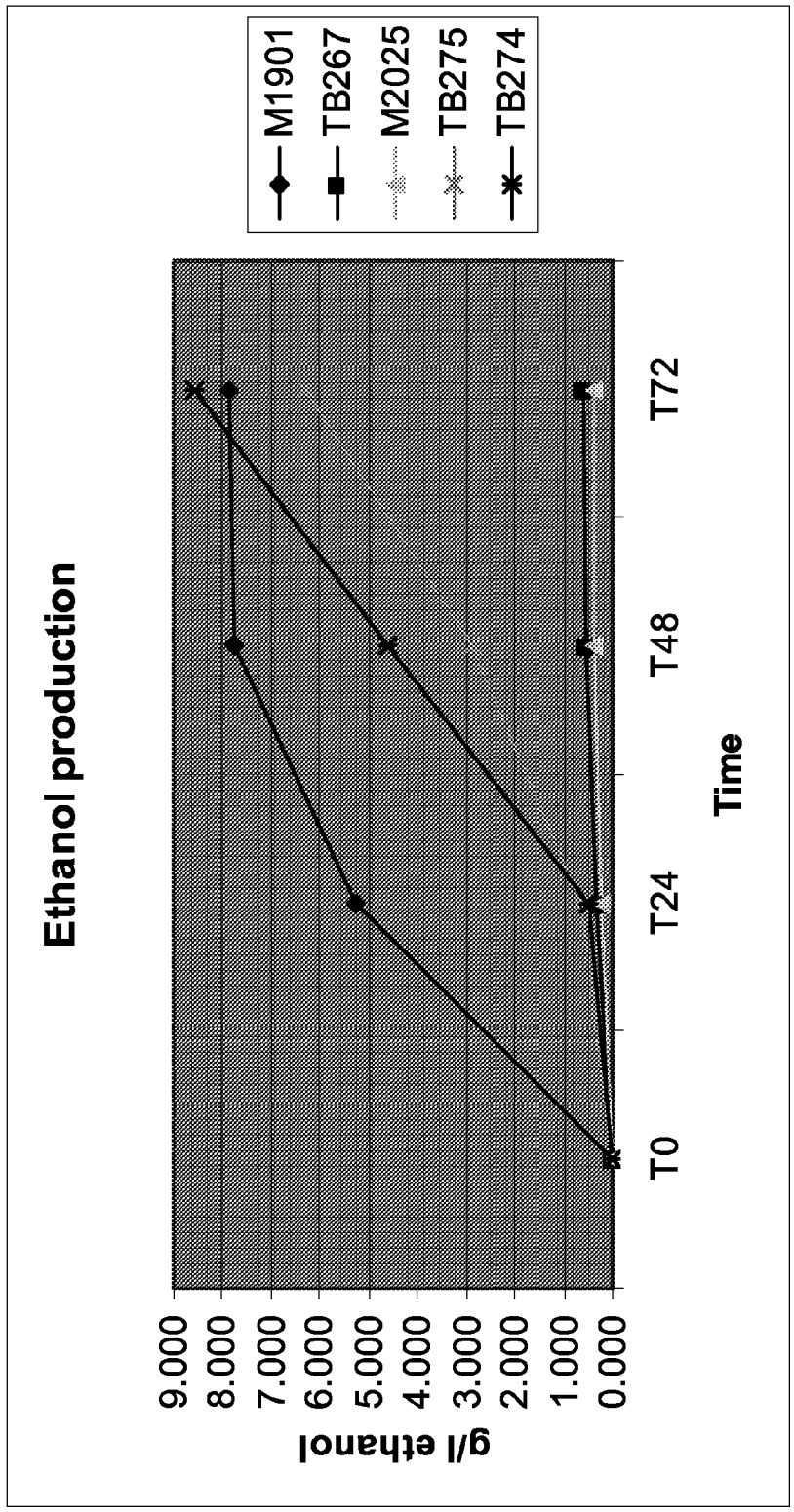
FIG. 17 shows a graph of ethanol production (g/L) of strains of the invention over 72 hours.
Figure 18:
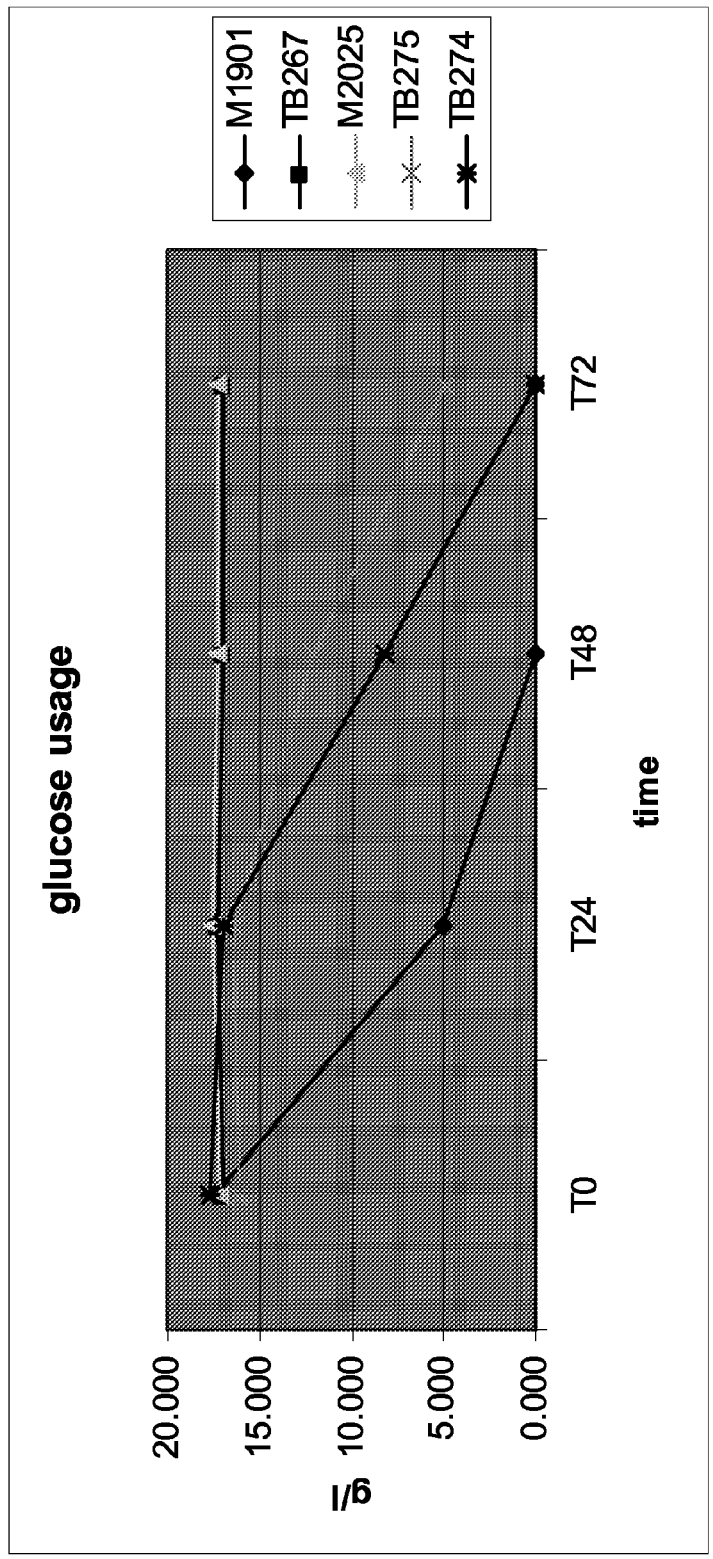
FIG. 18 shows a graph of glucose utilization (g/L) of strains of the invention over 72 hours.

The production of ethanol and glucose concentration are shown in FIGS. 17 and 18, respectively. Both M1901 and TB274 consumed all the sugar, but about 5 g/L glucose remained in the TB275 fermentation. See FIG. 18. TB274 had an 11% increase in ethanol yield in comparison to M1901. See FIG. 17. The increase in yield was higher than expected and likely came partially at the expense of biomass, although this was not determined.

Strains containing PFL and AADH were compared to other strains engineered to express AADH. A description of these strains appears in Table 4.

TABLE 4

Genetic Backgrounds for PFL Expression

| Strain Name | Genetic Background |
|---|---|
| M139 | wt control |
| M2085 | gdp1Δ gpd2Δ fdh1Δ fdh2Δ |
| M2158 | gdp1Δ gpd2Δ fdh1Δ fdh2Δ + AADH |
| M2182 | gdp1Δ gpd2Δ fdh1Δ fdh2Δ + AADH and PFL |

Figure 19:
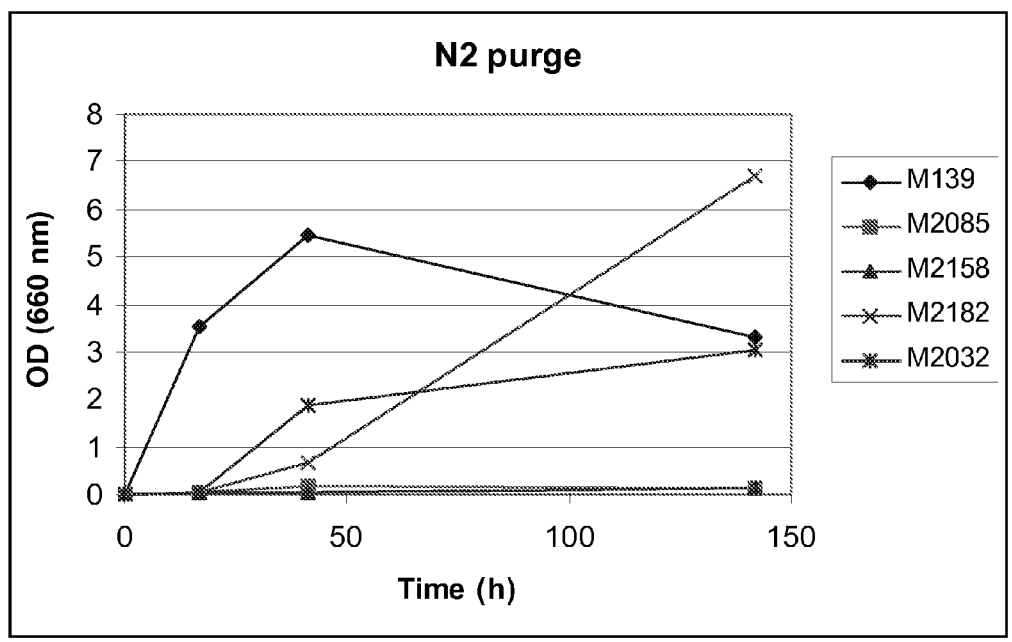
FIG. 19 shows a graph of the growth of a strain of the invention over 142 hours as measured by OD.

These five strains were tested in nitrogen purged bottles. As shown in FIG. 19, strain M2182 which has both PFL and AADH expression cassettes in a gdp1Δ gpd2Δ fdh1Δ fdh2Δ background, had a faster growth rate and reached a higher OD than M2158, which contains only the bifunctional ADH activity and did not appear to grow at all. See FIG. 19. These data show that a strain expressing both PFL and AADH activities grows better than the other engineered functionalities. Similar improvements over these other engineered functionalities are also observed in corn mash fermentations (see Example 7 below).

Example 7

Production of Ethanol from Corn Mash

The purpose of this experiment was to determine whether PFLs cloned from the organisms listed below in Table 5 could provide for increased ethanol yield when used in fermentation of 20% corn mash. A total of nine PFLs have been tested for function in yeast. Of these, only the *C. cellulolyticum* PFL had no positive effect on growth of glycerol synthesis mutants in corn mash fermentations. Additionally, no formate was observed in formate assays when using a strain containing *C. cellulolyticum* PFL. This strain was not tested for performance on corn mash fermentation.

Eight PFLs were tested for functionality in strain M2158 which has the *E. coli* AADH integrated on the chromosome of a gpd1Δ gpd2Δ fdh1Δ fdh2Δ background (M2085) or M2275, which is identical to M2158 except that it also has the gpd2Δ::GPD1 glycerol reduction mutation. Two separate corn mash fermentation experiments were performed using 20% solids in a baffled shake flask using the strains listed in Table 5. Performance of the strains was evaluated by HPLC analysis of metabolites.

TABLE 5

Genetic Backgrounds for Corn Mash Fermentations

| Strain Name | Genetic Background |
|---|---|
| M139 | wt control |
| M2085 | gpd1Δ gpd2Δ fdh1Δ fdh2Δ |
| M2158 | integrated AADH |
| M2180 | M2158 + *B. lichenformis* PFL |
| M2181 | M2158 + *L. planatarum* PFL |
| M2182 | M2158 + *B. adolescentis* PFL |
| M2183 | M2158 + *S. thermophilus* PFL |
| M2184 | M2158 + *E. coli* PFL |
| M2321 | M2158 + *L. casei* PFL |
| M2322 | M2158 + *C. reinhardtii* PFL |
| M2323 | M2158 + *Piromyces* PFL |
| M2324 | M2158 + *E. coli* PFL |
| M2275 | M2158 + gpdΔ::GPD1 |
| M2326 | M2275 + *B. adolescentis* PFL |

Figure 21:
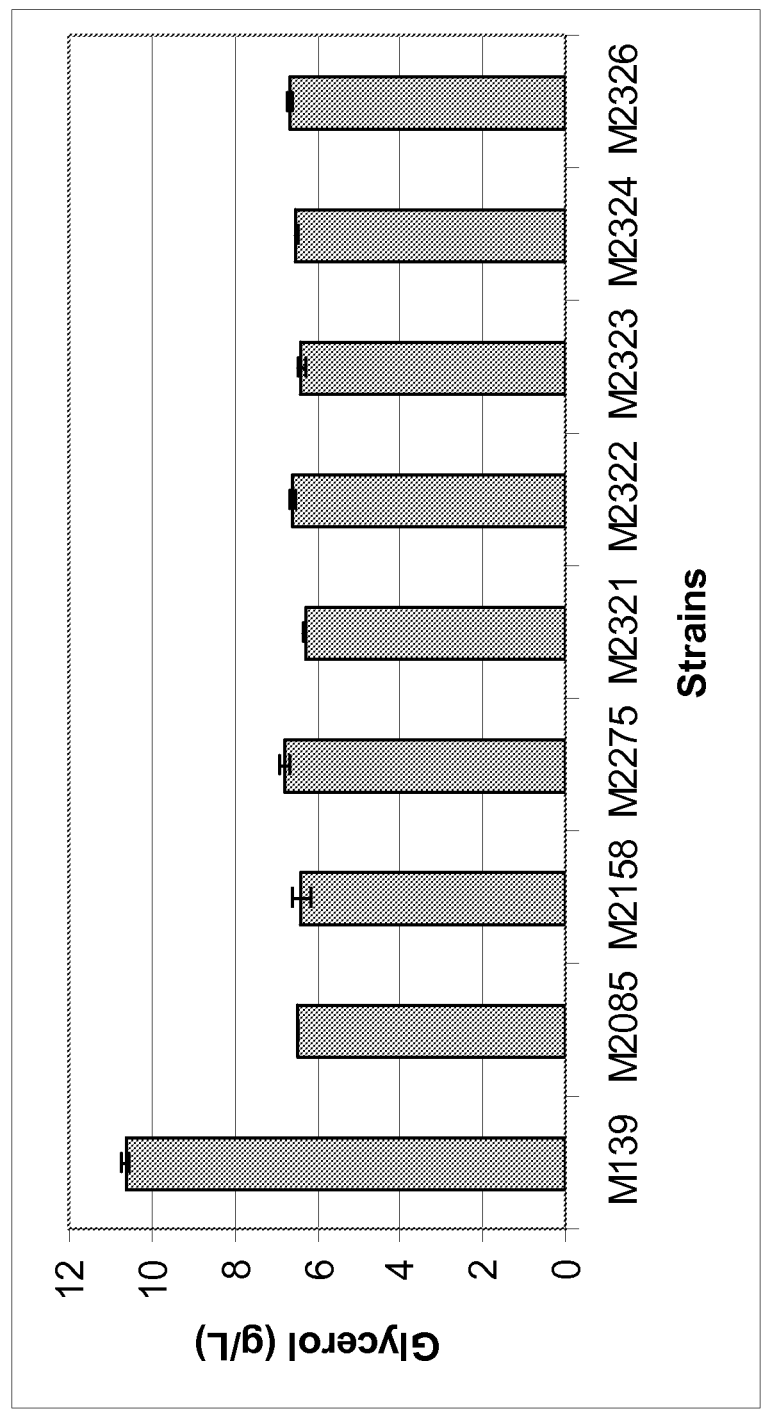
FIG. 21 shows a graph of ethanol production (g/L) of strains of the invention after 50 hours of fermentation.
Figure 23:
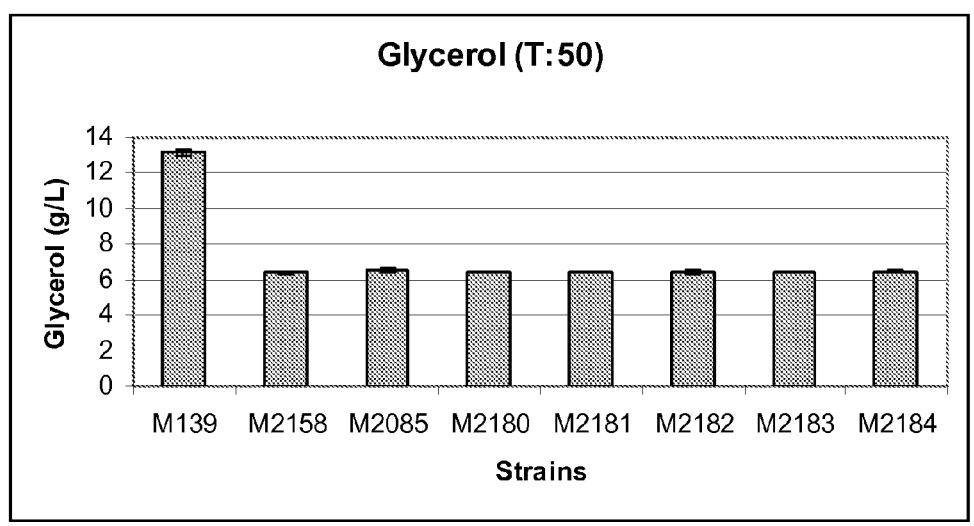
FIG. 23 shows a graph of glycerol production (g/L) of strains of the invention after 50 hours of fermentation.
Figure 24:
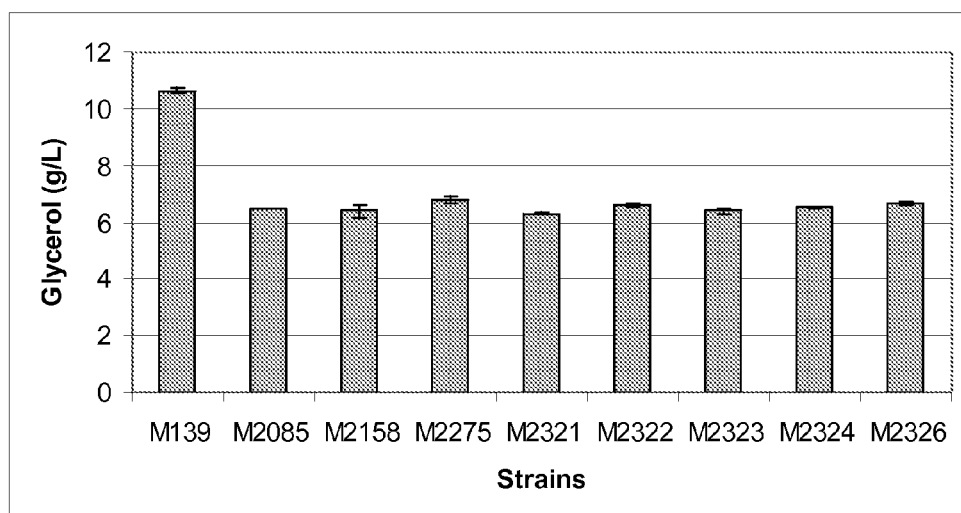
FIG. 24 shows a graph of glycerol production (g/L) of strains of the invention after 50 hours of fermentation.
Figure 25:
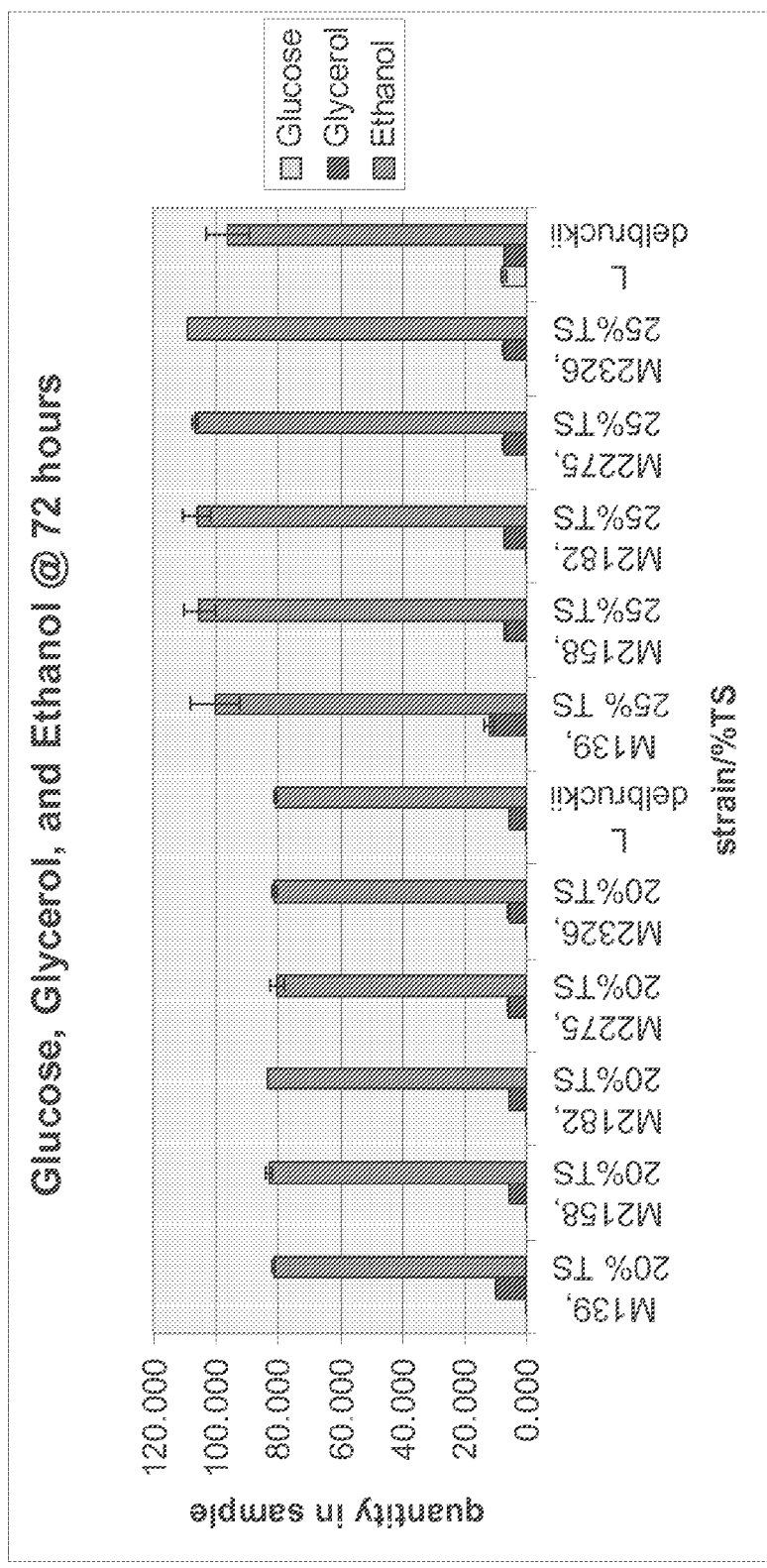
FIG. 25 shows a graph of glucose utilization (g/L), glycerol production (g/L), and ethanol production (g/L) after 72 hours of fermentation.

As shown in FIGS. 21 and 22, the addition of PFL improves the ethanol yield of strains containing only AADH. FIGS. 23 and 24 show that these strains do not make glycerol as expected. The approximately 4 g/L glycerol observed is already in the industrial mash substrate used for this experiment. FIG. 25 demonstrates a 9% increase in ethanol yield with strain M2326, which is a glycerol reduction strain.

Example 8

The following example demonstrates the creation of the *Saccharomyces cerevisiae* strain M3625. The genotype of strain M3625 is: Δgpd2:: *B. adolescentis* pflA/pflB/adhE Δfdh1 Δfdh2::*B. adolescentis* pflA/pflB/adhE fcy1Δ::*S.* fibuligera glucoamylase (glu-0111-CO). Strain M2390 is referred to as Ethanol Red (new) from LaSaffre (pahc.com/Phibro/Performance-Products/Catalog/23/Ethanol-Red.html).

The genetic modification techniques utilized to develop Saccharomyces cerevisiae strain M3625 relied upon directed integration to insert the genes for Bifidobacterium adolescentis pflA, pflB, AdhE and S. fibuligera glu-0111-CO at specific and known sites within the yeast chromosome. The directed integration approach creates transgenic strains with integration events that are stable and easy to characterize. Chromosomal integration, by its very nature, reduces the probability of any mobilization of the heterologous DNA and enhances strain stability relative to other approaches.

The MX cassettes are the most commonly used engineering tool when an insertion or deletion of a genetic element is desired at a given chromosomal loci (Wach A, et al., Yeast 10(13):1793-1808 (1994)). A recyclable MX cassette contains one or more markers which enable both dominant and negative selection (Goldstein, A. L. and McCusker, J. H., Yeast 15:1541-1553 (1999); Ito-Harashima, S. and McCusker, J. H., Yeast 21:53-61 (2004)). The dominant marker enables selection for the modification and the counter selectable marker enables subsequent removal of the marker system via Cre-Lox mediated recombination (Güldener, Ulrich, et al., Nucleic Acids Research (1996) 24(13) 2519-2524) or recombination between duplicated homologous regions flanking the cassette. Since the markers are removed, they can be reused during subsequent engineering steps and ensures no undesirable foreign genetic material remains in the strain.

To create stable homozygous integrations in M3625, two new HSV-thymidine kinase (TDK) based MX cassettes were developed. Expression of thymidine kinase in S. cerevisiae results in sensitivity to the compound fluoro-deoxyuracil (FUDR). The cellular toxicity of FUDR is dependent on the presence of two enzymes involved in pyrimidine metabolism: thymidine kinase (Tdk) and thymidilate synthetase (ThyA). Tdk converts FUDR to fluoro-dUMP (F-dUMP) which is a covalent inhibitor of ThyA and the basis for counter selection in a variety of eukaryotic organisms (Czako, M., and L. Marton, (1994) Plant Physiol 104:1067-1071; Gardiner, D. M., and B. J. Howlett, (2004) Curr Genet 45:249-255; Khang, C. H., et al., (2005) Fungal Genet Biol 42:483-492; Szybalski, W. (1992) Bioessays 14:495-500).

Figure 28:
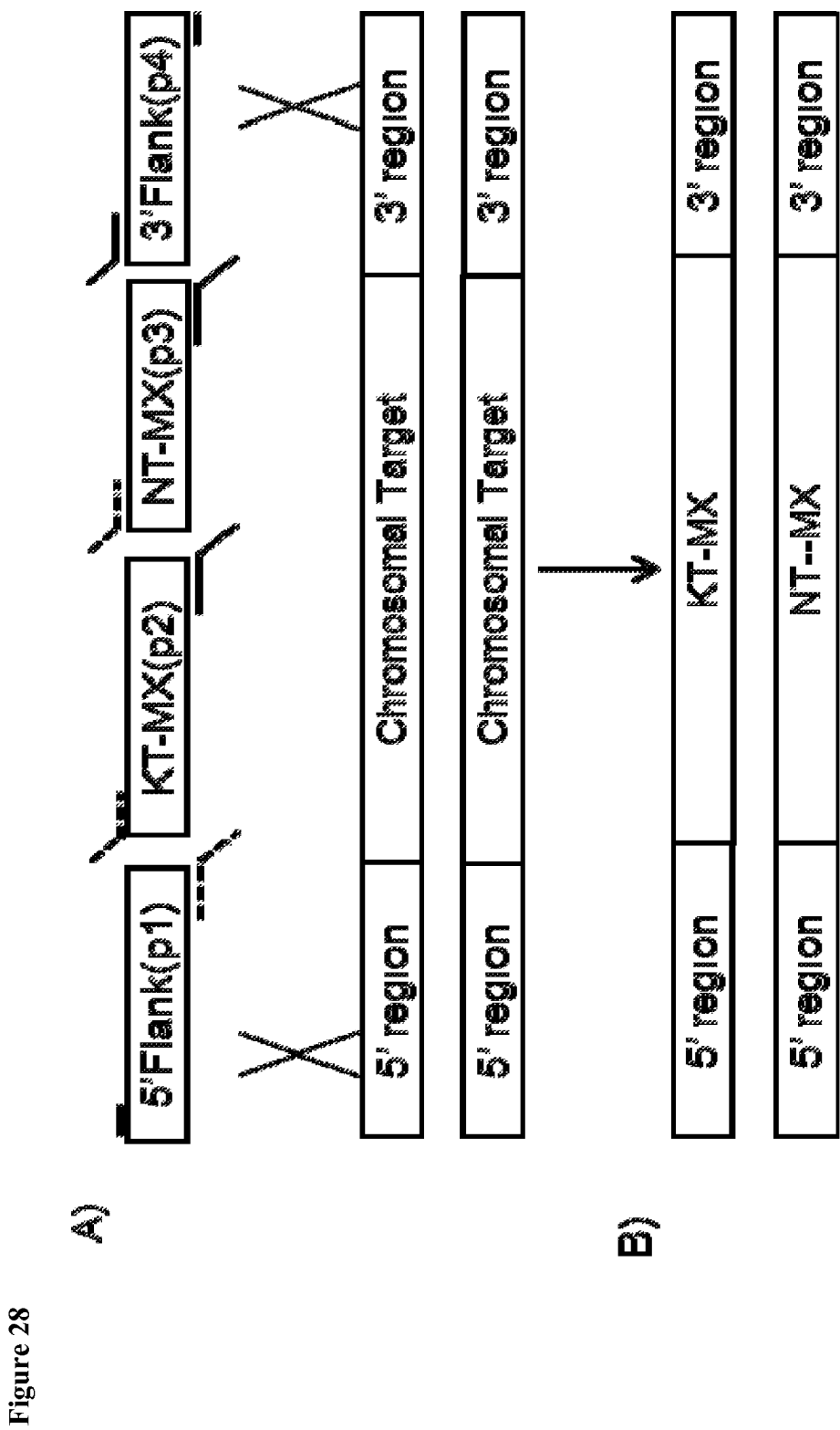
FIG. 28 shows a schematic diagram of a strategy for PCR construction and integration of KT-MX and NT-MX integration cassettes into both chromosomes of a target loci.

The HSV-TDK expression cassette was independently fused to two commonly used dominant selectable markers which confer resistance to the drugs G418 (Kan) or nourseothricin (Nat) (Goldstein, A. L. and McCusker, J. H., Yeast 15:1541-1553 (1999)). Transformation of both double expression cassettes, referred to as KT-MX and NT-MX, enables positive selection for integration into both chromosomes as illustrated in FIG. 28A. The transformed deletion assembly contains four PCR products, a 5'flank(p1) which is homologous upstream of the target site, KT-MX cassette(p2), NT-MX cassette(p3), and a 3' flank(p4) homologous downstream of the target site. Each component is amplified individually using primers which create homologous overlapping extensions of each PCR product. See Tables 7 and 8. The bent dashed lines in FIG. 28A represent homology between the KT/NT-MX cassettes and the 5' flank and the bent solid lines represent homology with the 3' flank. For each round of engineering, PCR amplicons of upstream and downstream regions flanking the target site are designed to contain homologous tails for both the KT-MX and NT-MX cassettes. Both the flanks and the markers are transformed followed by selection on YPD medium containing both G418 and Nat. See FIG. 28B. FIG. 28B shows a schematic of the chromosome after replacement of the target site with KT-MX and NT-MX.

Figure 29:
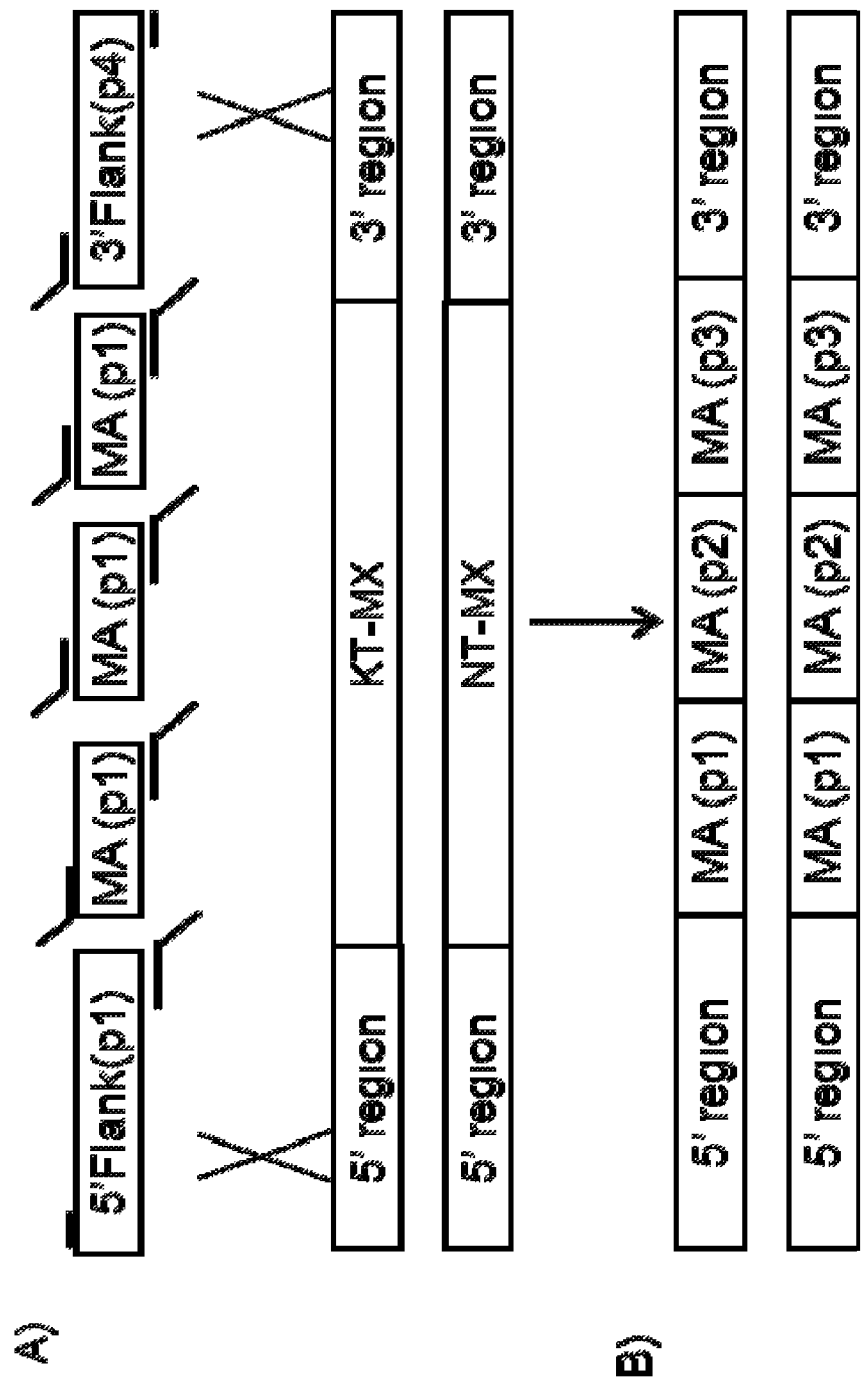
FIG. 29 shows a schematic diagram of strategy used to replace integrated KT-MX and NT-MX selection cassettes with a Mascoma Assembly on both chromosomes of a target loci.

After each engineering step taken in the construction of M3625, all markers are subsequently deleted and/or replaced with a desired expression cassette (Mascoma Assembly) resulting in a strain free of antibiotic markers (FIG. 29). FIG. 29 demonstrates that the transformed Mascoma Assembly contains a quantity of PCR products which is dependent on the desired engineering event (pX), a 5'flank(p1) which homologous upstream of the target site and a 3' flank (p4) homologous downstream of the target site. Each component is amplified individually using primers which create homologous overlapping extensions. The overlapping bent lines in FIG. 29 represent homology at the end of those PCR products. FIG. 29B shows a schematic of a chromosome following selection on FUDR and replacement of genetic markers with the Mascoma assembly. Confirmation of marker removal was evaluated by southern blot, PCR and dilution plating onto selective medium as described below.

Four loci were modified during the construction of M3625. The integration procedure strategy described above was used at the FDH1, GPD1 and GPD2 loci using the Mascoma Assemblies listed in Table 6. Detailed molecular maps depicting the components of each Mascoma Assembly are provided in FIGS. 30-37.

TABLE 6

Genetic modifications contained in M3625.

| Target Locus | Locus Modification | Cassette ID | Cassette Description |
|---|---|---|---|
| FDH1 | Clean Deletion | MA0370 | Clean Deletion of FDH1 |
| FDH2 | Replaced with expression cassette | MA0280 | 2 copies of pflA/B and 4 copies of adhE |
| GPD2 | Replaced with expression cassette | MA0289 | 2 copies of pflA/B and 4 copies of adhE |
| FCY1 | Replaced with expression cassette | MA0317 | Four copies of Glucoamylase |

TABLE 7

Primers used for the creation of strain M3625.

| Target Locus | PCR Product 1; Primer Pair | PCR Product 2; Primer Pair | PCR Product 3; Primer Pair |
|---|---|---|---|
| GPD1 | GPD1 5' Flank; X11824/X15546 | pAGTEF-kan/nat-pHXT2-TDK; X15380/X15382 | GPD1 3' Flank; X15547/X11829 |
| GPD2 | GPD2 5' Flank; X11816/X15548 | pAGTEF-kan/nat-pHXT2-TDK; X15380/X15382 | GPD2 3' flank; X15549/X11821 |
| FDH2 | FDH2 5' Flank; X16096/X15554 | pAGTEF-kan/nat-pHXT2-TDK; X15380/X15382 | FDH2 3' flank; X15555/X11845 |
| FDH1 | FHD1 5' Flank; X15559/X15550 | pAGTEF-kan/nat-pHXT2-TDK; X15380/X15382 | FDH1 3' flank; X15552/X15553 |

TABLE 8

Sequences of Primers used for creation of strain M3625

| Primer | Sequence | SEQ ID NO |
|---|---|---|
| X11824 | aagcctacaggcgcaagataacacatcac | 110 |
| X15546 | ggacgaggcaagctaaacagatctctagacctactttatattatcaatatttgtgtttg | 111 |
| X15380 | taggtctagagatctgtttagcttgc | 112 |
| X15382 | gagactacatgatagtccaaaga | 113 |
| X15547 | ccgtttcttttctttggactatcatgtagtctcatttattggagaaagataacatatca | 114 |
| X11829 | ctcagcattgatcttagcagattcaggatctaggt | 115 |
| X11816 | gcagtcatcaggatcgtaggagataagca | 116 |
| X15548 | ggacgaggcaagctaaacagatctctagacctatgataaggaaggggagcgaaggaaaa | 117 |
| X15549 | ccgtttcttttctttggactatcatgtagtctcctctgatctttcctgttgcctctttt | 118 |
| X11821 | tcacaagagtgtgcagaaataggaggtgga | 119 |
| X16096 | catggtgcttagcagcagatgaaagtgtca | 120 |
| X15554 | ggacgaggcaagctaaacagatctctagacctaattaattttcagctgttatttcgatt | 121 |
| X15555 | ccgtttcttttctttggactatcatgtagtctcgagtgattatgagtatttgtgagcag | 122 |
| X11845 | ttacttgtgaaactgtctccgctatgtcag | 123 |
| X15559 | ggaaggcaccgatactagaactccg | 124 |
| X15550 | gggacgaggcaagctaaacagatctctagacctaattaattttcagctgttattttgat | 125 |
| X15552 | ccgtttcttttctttggactatcatgtagtctcgagtgattatgagtatttgtgagcag | 126 |
| X15553 | accagcgtctggtggacaaacggccttcaac | 127 |

Genotyping and Sequencing of MA0370

Figure 30:
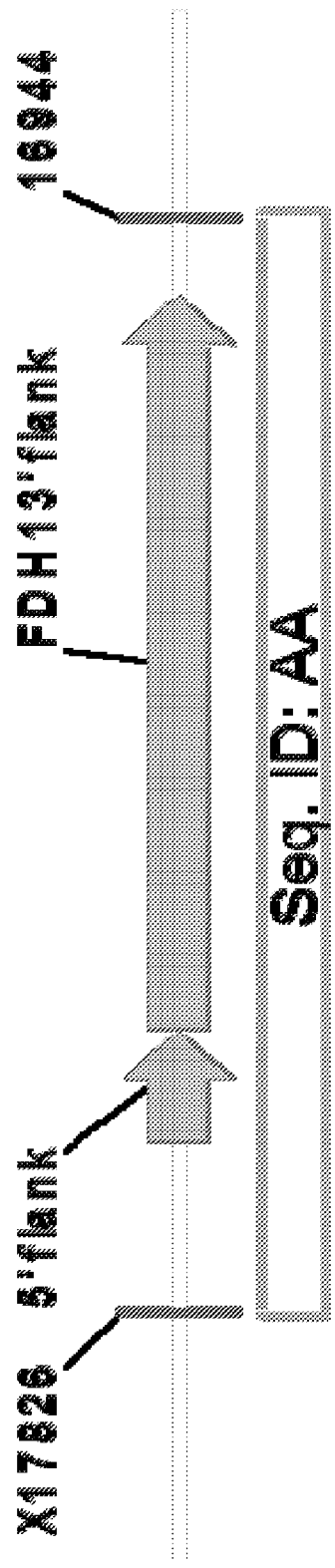
FIG. 30 shows a molecular map and genotyping of MA0370 integrated at the FDH1 site of M3625.
Figure 31:
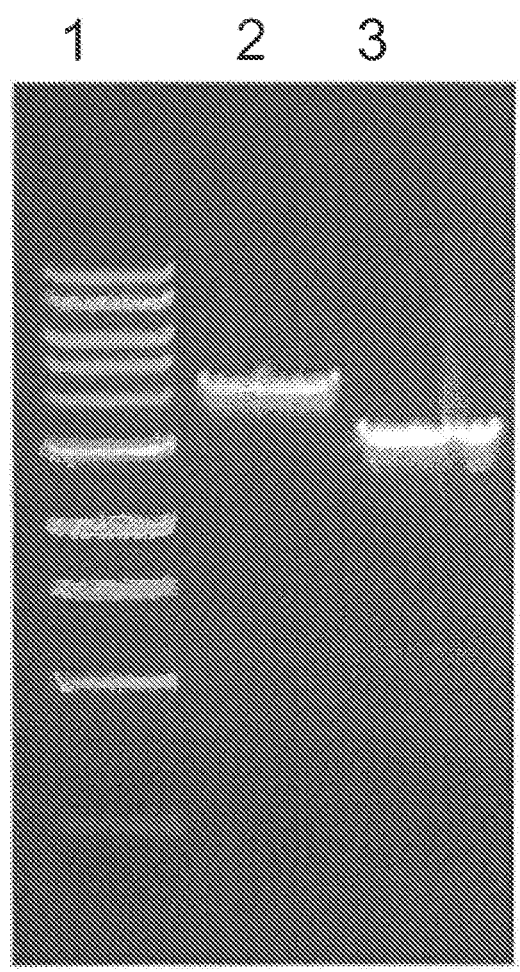
FIG. 31 shows an image of an agarose gel containing PCR products used to genotype and sequence the MA0370 site.

To confirm that FDH1 was deleted after insertion of MA370, PCR products were amplified from M2390 and M3625 genomic DNA using primers X17826 and X16944. The expected results are listed in Table 10 and the sequences of the primers used are listed in Table 11. A molecular map depicting the MA0370 integration site is shown in FIG. 30. The molecular map depicts the location of flanks used to remove the KT-MX and NT-MX markers and the position of primers used for genotyping. See FIG. 30 (5' flank, *S. cerevisiae* FDH1 upstream flanking region; 3' flank—*S. cerevisiae* FDH1 downstream flanking region. Region AA—amplified and sequenced chromosomal DNA region). Primer pair X15556/X15871 was used for the FDH1 5' Flank and primer pair X15870/X15553 was used for the FHD1 3' Flank to create the assembly shown in FIG. 30. Sequences for the primers for assembly used are found in Table 9. An agarose gel image showing PCR products used to determine genotype is shown in FIG. 31 (lane 1: 1 KB ladder; lane 2: M2390 (X17826/X16944); lane 3: M3625 (X17826/X16944)) (see Table 11).

TABLE 9

Primers used to create the MA0370 integration site.

| Primer | Sequence | SEQ ID NO |
|---|---|---|
| X15556 | ccactcgaggataggcttgaaaga | 128 |
| X15870 | ctaatcaaatcaaaataacagctgaaaattaatgagtgattatgagtatttgtgagcag | 129 |
| X15871 | aaaacttctgctcacaaatactcataatcactcattaattctcagctgttattttgatt | 130 |
| X15553 | accagcgtctggtggacaaacggccttcaac | 127 |

In order to determine the exact DNA sequence of the M3625 MA0370 site, region AA was amplified from genomic DNA of M3625 strain in 5 independent PCR reactions. All PCR products were purified and sequenced by the Sanger method at the Dartmouth College Sequencing facility.

TABLE 10

Primers and summary of results of MA0370 genotyping.

| Lane | Template DNA | Primers | Expected size(bp) | Correct Size Observed |
|---|---|---|---|---|
| 1 | 1KB ladder | N/A | N/A | N/A |
| 2 | M2390 | X17826/X16944 | 4386 bp | yes |
| 3 | M3625 | X17826/X16944 | 3237 | yes |

TABLE 11

Sequence of primers used for MA0370 genotyping.

| Primer | Sequence | SEQ ID NO |
|---|---|---|
| X17826 | tcgctaacgatcaagaggaactg | 152 |
| X16944 | tacacgtgcatttggacctatc | 153 |

Genotyping and Sequencing of MA0280

Figure 32:
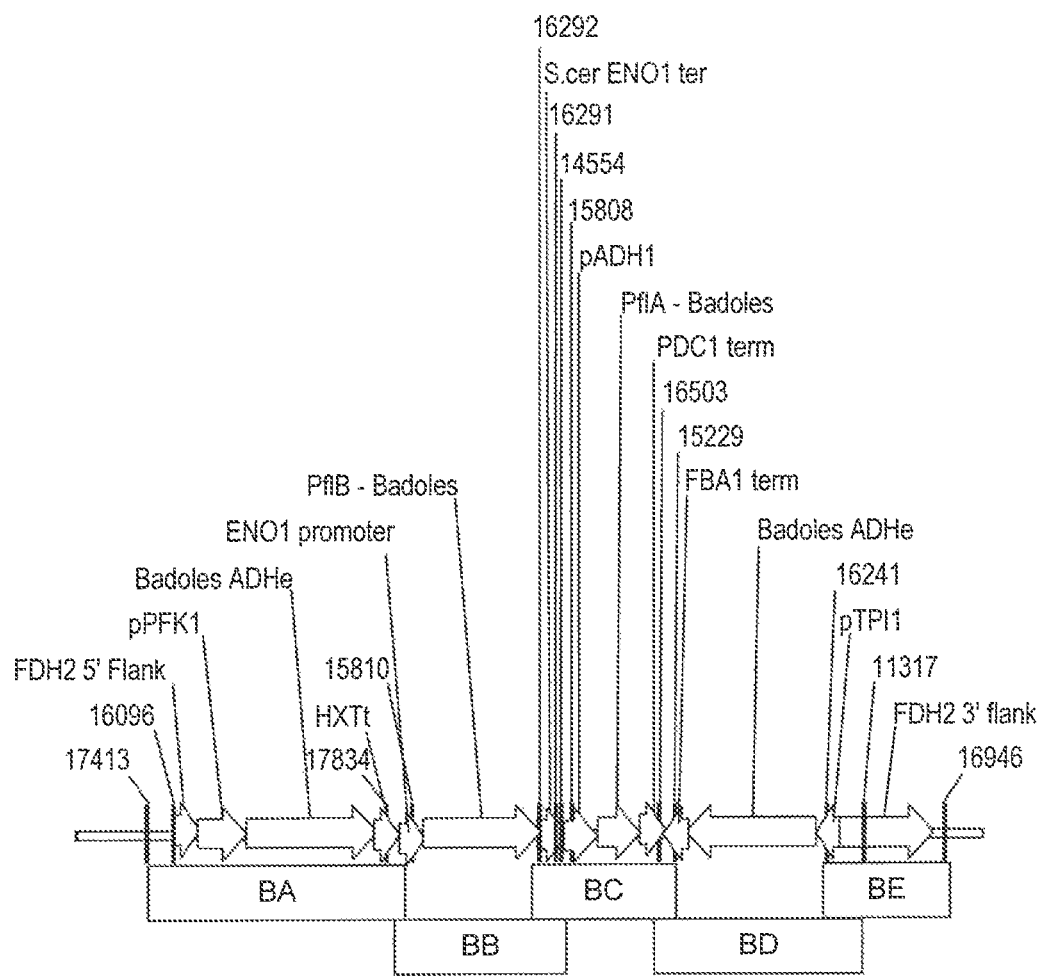
FIG. 32 shows a molecular map and genotyping of MA0280 integrated at the FDH2 site of M3625.
Figure 33:
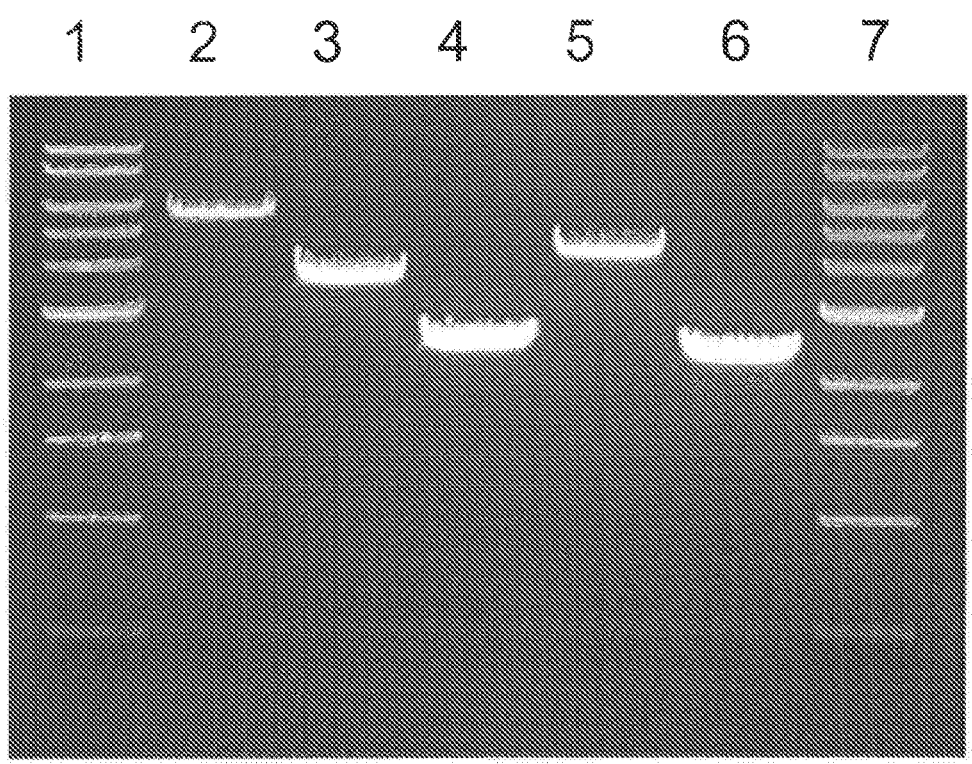
FIG. 33 shows an image of an agarose gel containing PCR products used to genotype and sequence the MA0280 site.

To confirm that MA280 was inserted at the FDH2 site, PCR products were amplified from M3625 genomic DNA. The primers and expected genotyping results are listed in Table 13. Sequences of the primers used for genotyping and sequencing MA0280 are listed in Table 14. A molecular map depicting the MA0280 integration site is shown in FIG. 32. The molecular map depicts the location of flanks used to replace the KT-MX and NT-MX markers and insert the MA0280 expression cassette. The position of primers used for genotyping for genotyping are indicated on the map. See FIG. 32 (Feature description on map of MA0280 site of the M3625 strain; FDH2 5' flank—*S. cerevisiae* FDH2 upstream flanking region; PFK1p—*S. cerevisiae* PFK1 gene promoter; ADHE—*Bifidobacterium adolescentis* ADHE coding gene; HXT2t—*S. cerevisiae* HXT2 gene terminator; ENO1p—*S. cerevisiae* ENO1 gene promoter; PFLB—*Bifidobacterium adolescentis* PFLB coding gene; ENO1t—*S. cerevisiae* ENOL gene terminator; ADH1p—*S. cerevisiae* ADH1 gene promoter; PFLA—*Bifidobacterium adolescentis* PFLA coding gene; PDC1t—*S. cerevisiae* PDC1 gene terminator; FBA1t—*S. cerevisiae* FBA1 gene terminator; TPI1p—*S. cerevisiae* TPI1 gene promoter; FDH2 3' flank—*S. cerevisiae* FDH2 downstream flanking region. Regions BA-BE, amplified and sequenced chromosomal DNA regions). Primer pair X16096/X17243 was used for the FDH2 5' Flank, primer pair X16738/X16620 was used for pPFK1-ADH-HXT2, primer pair X16621/X13208 was used for pENO1-PFL-ENO1t, primer pair X13209/X17242 was used for pADH1-PFL-PDC1t, primer pair X17241/X16744 was used for pTPI-ADH-FBA1trc, and primer pair X17244/X11845 was used for the FDH2 5' Flank to create the assembly shown in FIG. 32. Sequences for the primers used to create the assembly shown in FIG. 32 are found in Table 12. An agarose gel image showing PCR products used to genotype and sequence the MA0280 site is shown in FIG. 33 (lane 1: 1 KB ladder; lane 2: M3625 (17413/15810); lane 3: M3625 (17834/14554); lane 4: M3625 (16291/15229); lane 5: M3625 (16503/11317); lane 6: (16241/16946) lane 7: 1 KB ladder) (see Table 14).

TABLE 12

Primers used to create the MA0280 integration site.

| Primer | Sequence | SEQ ID NO |
|---|---|---|
| X16096 | catggtgcttagcagcagatgaaagtgtca | 120 |
| X17243 | tagttagatcagggtaaaaattatagatgaggtattaatt ttcagctgttatttcgatt | 131 |
| X16738 | ctaatcaaatcgaaataacagctgaaaattaatacctcat ctataattttacctgat | 132 |
| X16620 | tcggatcagtagataacccgcctagaagactaggttac attgaaaatacagtaaatggt | 133 |
| X16621 | tggtggaaccatttactgtattttcaatgtaacctagtc ttctaggcgggttatctact | 134 |
| X13208 | ccgaaatattccacggtttagaaaaaaatcggaggttt agacattggctcttcattgag | 135 |
| X13209 | aagctcaatgaagagccaatgtctaaacctccgattttt tctaaaccgtggaatattt | 136 |
| X17242 | acatcatcttttaacttgaatttattctctagctttcaa tcattggagcaatcatttta | 137 |
| X17241 | gtccatgtaaaatgattgctccaatgattgaaagctagag aataaattcaagttaaaag | 138 |
| X16744 | aaaaacttctgctcacaaatactcataatcactcctac ttattcccttcgagattatatc | 139 |
| X17244 | gttcctagatataatctcgaagggaataagtaggagtg attatgagtatttgtgagcag | 140 |
| X11845 | ttacttgtgaaactgtctccgctatgtcag | 141 |

In order to determine exact DNA sequence of the M3625 MA0280 site, regions BA-BE were amplified from genomic DNA of M3625 strain in 5 independent PCR reactions. All PCR products were purified and sequenced by the Sanger method at the Dartmouth College Sequencing facility.

TABLE 13

Primers and summary of results of MA0280 genotyping.

| Lane | Template DNA | Primers | Expected size(bp) | Correct Size Observed |
|---|---|---|---|---|
| 1 | 1 KB ladder | N/A | N/A | N/A |
| 2 | M3625 | 17413/15810 | 5567 | Yes |
| 3 | M3625 | 17834/14554 | 3686 | Yes |
| 4 | M3625 | 16291/15229 | 2569 | Yes |
| 5 | M3625 | 16503/11317 | 4352 | yes |
| 6 | M3625 | 16241/16946 | 2478 | yes |
| 7 | 1KB ladder | N/A | N/A | N/A |

TABLE 14

Sequence of primers used for genotyping MA0280.

| Primer | Sequence | SEQ ID NO |
|---|---|---|
| 17413 | ggattcttcgagagctaaga | 154 |
| 15810 | gacttgcagggtaggctagctagaatt | 155 |
| 17834 | gctgcttcgaggtattgaca | 156 |
| 14554 | ggctcttcattgagcttagaaccc | 157 |

TABLE 14-continued

Sequence of primers used for genotyping MA0280.

| Primer | Sequence | SEQ ID NO |
|---|---|---|
| 16291 | aactggaccgatcttattcgt | 158 |
| 15229 | agtccactgcggagtcatttcaaag | 159 |
| 16503 | ctgccagcgaattcgactctgcaat | 160 |
| 11317 | cagtcgctgtagtgagcgacagggtagtaa | 161 |
| 16241 | ctttgcattagcatgcgta | 162 |
| 16946 | taggtcgagaccagaatgcatgt | 163 |

Genotyping and Sequencing of MA0289

Figure 34:
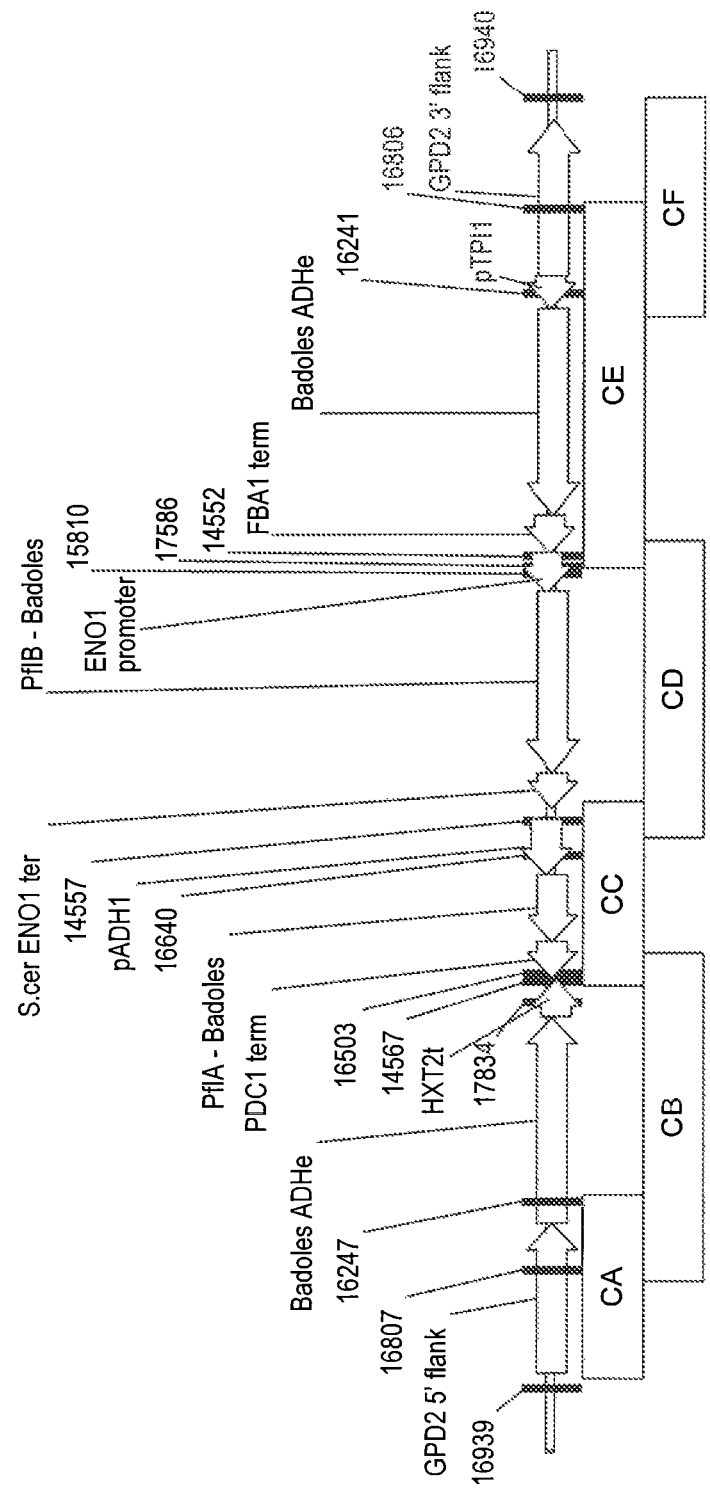
FIG. 34 shows a molecular map and genotyping of MA0289 integrated at the GPD2 site of M3625.
Figure 35:
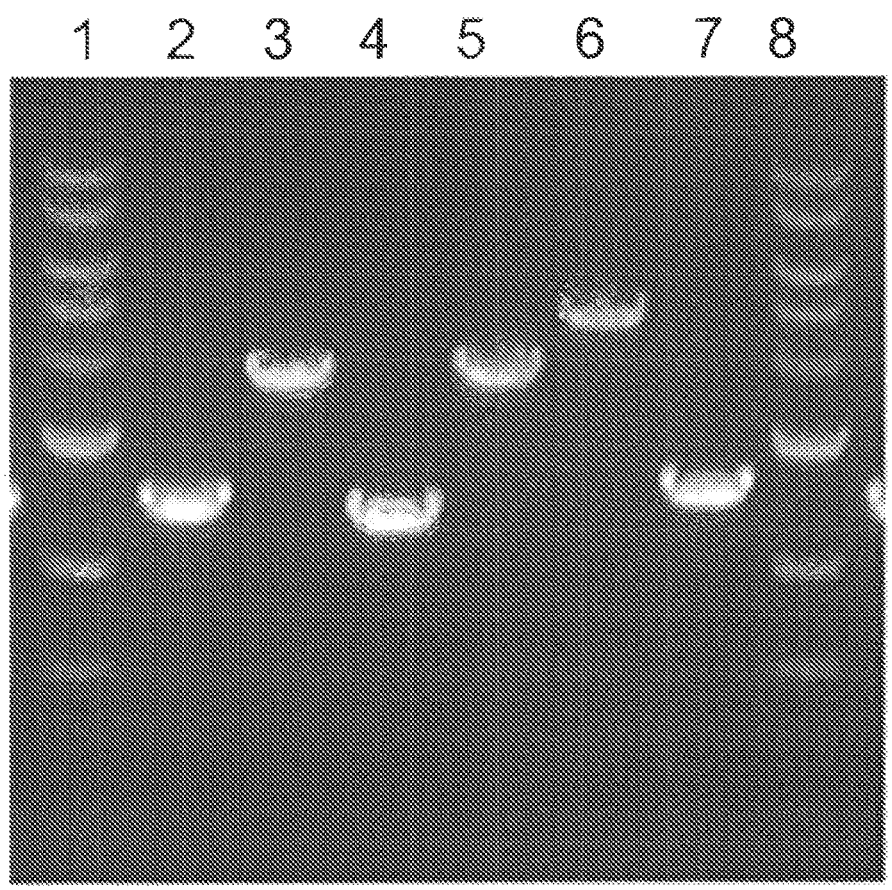
FIG. 35 shows an image of an agarose gel containing PCR products used to genotype and sequence the MA0370 site.

To confirm that MA0289 was inserted at the GPD2 site, PCR products were amplified from M3625 genomic DNA. The primers and expected genotyping results are listed in Table 16. Sequences for the primers used for genotyping MA0289 are listed in Table 17. A molecular map depicting the MA0289 integration site is shown in FIG. 34. The molecular map depicts the location of flanks used to replace the KT-MX and NT-MX markers and insert the MA0280 expression cassette. The position of primers used for genotyping are indicated on the map. See FIG. 34 (Feature description on map of MA0280 site of the M3625 strain; GPD2 5' flank—S. cerevisiae GPD2 upstream flanking region; ADHE—Bifidobacterium adolescentis ADHE coding gene; HXT2t—S. cerevisiae HXT2 gene terminator; PDC1t—S. cerevisiae PDC1 gene terminator; PFLA—Bifidobacterium adolescentis PFLA coding gene; ADH1p—S. cerevisiae ADH1 gene promoter; ENO1t—S. cerevisiae ENOL gene terminator; PFLB—Bifidobacterium adolescentis PFLB coding gene; ENO1p—S. cerevisiae ENOL gene promoter; FBA1t—S. cerevisiae FBA1 gene terminator; TPI1p—S. cerevisiae TPI1 gene promoter; GPD2 3' flank—S. cerevisiae GPD2 downstream flanking region; Regions CA-CF—amplified and sequenced chromosomal DNA regions). Primer pair X15473/X17460 was used for the GPD2 5' Flank, primer pair X17459/X17289 was used for ADH-HXT2, primer pair X17290/X13209 was used for pADH1-PFL-PDC1trc, primer pair X13208/X15735 was used for pENO1-PFL-ENO1trc, primer pair X15736/X17457 was used for pTPI-ADH-FBA1trc, and primer pair X17458/X15476 was used for the GPD2 3' Flank to create the assembly shown in FIG. 34. Sequences for the primers used to create the assembly shown in FIG. 34 are found in Table 15. An agarose gel image showing PCR products used to genotype and sequence the MA0280 site is shown in FIG. 35 (lane 1: 1 KB ladder; lane 2: M3625 (17413/15810); lane 3: M3625 (17834/14554); lane 4: M3625 (16291/15229); lane 5: M3625 (16503/11317); lane 6: (16241/16946); lane 7: 1 KB ladder).

TABLE 15

Primers used to create the MA0289 integration site.

| Primer | Sequence | SEQ ID NO |
|---|---|---|
| X15473 | agtcatcaggatcgtaggagataagc | 142 |
| X17460 | agaagataatatttttatataattatattaatcctaatctcatgtagatctaattctt | 143 |
| X17459 | cctttccttttccttcgctccccttccttatcaatggcagacgcaaagaagaaggaaga | 144 |
| X17289 | gtccatgtaaaatgattgctccaatgattgaaagttacattgaaaatacagtaaatggt | 145 |
| X17290 | tggtggaaccatttactgtattttcaatgtaactttcaatcattggagcaatcatttta | 146 |
| X13208 | ccgaaatattccacggtttagaaaaaaatcggaggtttagacattggctcttcattgag | 135 |
| X13209 | aagctcaatgaagagccaatgtctaaacctccgattttttctaaaccgtggaatattt | 136 |
| X15735 | catcttttaacttgaatttattctctagcctagtcttctaggcgggttatctactgat | 147 |
| X15736 | agataacccgcctagaagactaggctagagaataaattcaagttaaaagatgatgttga | 148 |
| X17457 | tgggggaaaaagaggcaacaggaaagatcagagctacttattcccttcgagattatatc | 149 |
| X17458 | gttcctagatataatctcgaagggaataagtagctctgatcttcctgttgcctctttt | 150 |
| X15476 | gtagatctgcccagaatgatgacgtt | 151 |

In order to determine exact DNA sequence of the M3625 MA0289 site, regions CA-CF were amplified from genomic DNA of M3625 strain in 5 independent PCR reactions. All PCR products were purified and sequenced by the Sanger method at the Dartmouth College Sequencing facility.

TABLE 16

Primers and summary of results of MA0289 genotyping.

| Lane | Template DNA | Primers | Expected size(bp) | Correct Size Observed |
|---|---|---|---|---|
| 1 | 1 KB ladder | N/A | N/A | N/A |
| 2 | M3625 | 16939/16940 | 2477 | Yes |
| 3 | M3625 | 16807/14567 | 3831 | Yes |
| 4 | M3625 | 17834/14557 | 2478 | Yes |
| 5 | M3625 | 16640/14552 | 3978 | yes |
| 6 | M3625 | 17586/16806 | 4789 | yes |
| 7 | 1KB ladder | N/A | N/A | N/A |

TABLE 17

Sequence of primers used for genotyping MA0289.

| Primer | Sequence | SEQ ID NO |
|---|---|---|
| 16939 | atgctgatgcatgtccacaaag | 164 |
| 16940 | ccttatcagtcaattgaggaaag | 165 |
| 16807 | gcgatgagctaatcctgagccat | 166 |
| 14567 | tggttccaccattattatgttggt | 167 |
| 17834 | gctgcttcgaggtattgaca | 168 |
| 14557 | ctaaaccgtggaatatttcggatat | 169 |

TABLE 17-continued

Sequence of primers used for genotyping MA0289.

| Primer | Sequence | SEQ ID NO |
|---|---|---|
| 16640 | cctcatcagctctggaacaacga | 170 |
| 14552 | gatccgagcttccactaggatagc | 171 |
| 17586 | gcagtatgcaagtctcatgctg | 172 |
| 16806 | gaacttgcaggcaccgatcttca | 173 |

Genotyping and Sequencing of MA0317

Figure 36:
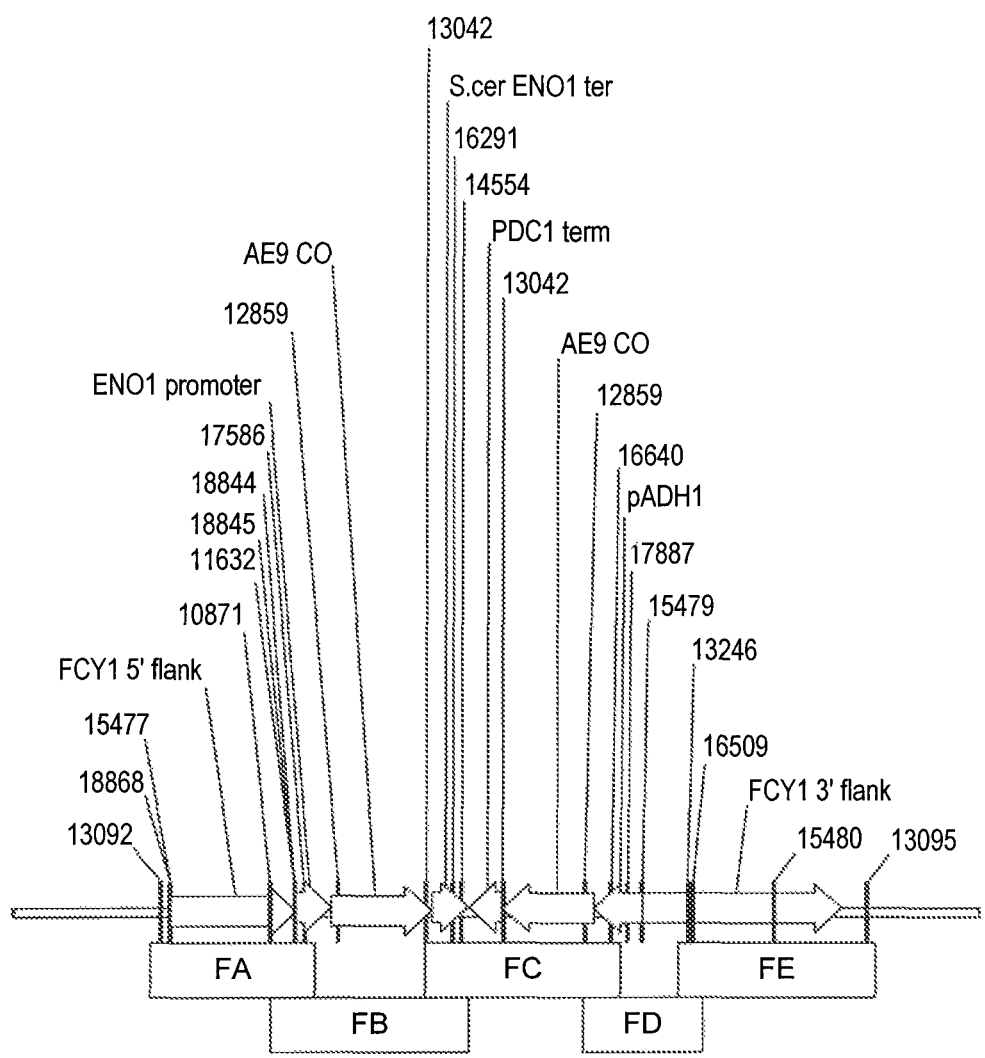
FIG. 36 shows a molecular map and genotyping of MA0317 integrated at the FCY1 site of M3625.
Figure 37:
FIG. 37 shows an image of an agarose gel containing PCR products used to genotype and sequence the MA0317 site.

To confirm that MA0317 was inserted at the FCY1 site, PCR products were amplified from M3625 genomic DNA. The primers and expected genotyping results are listed in Table 19. Sequences for the primers used to genotype MA0317 are listed in Table 20. A molecular map depicting the MA0317 integration site is shown in FIG. 36. The molecular map depicts the location of flanks used to replace the FCY1 gene with MA0317 and the position or primers used for genotyping. See FIG. 36 (Feature description on the map of MA0371 site of M3625; FCY1 5' flank—*S. cerevisiae* FCY1 upstream flanking region; ENO1p—*S. cerevisiae* ENOL gene promoter; AE9 —*S. fibuligera* glu 0111 coding gene; ENO1t—*S. cerevisiae* ENOL gene terminator; PDC1t—*S. cerevisiae* PDC1 terminator; ADH1p—*S. cerevisiae* ADH1 gene promoter; FCY1 3' flank—*S. cerevisiae* FCY1 downstream flanking region; Regions FA-FE, amplified and sequenced chromosomal DNA regions). Primer pair X18868/X18844 was used for the FCY 5' Flank, primer pair X18845/X15464 was used for pENO-AE9-ENO1t, primer pair X15465/X11750 was used for pADH1-AE9-PDC1t, and primer pair X15479/X18869 was used for the FCY 3' Flank to create the assembly shown in FIG. 36. Sequences for the primers used to create the assembly shown in FIG. 36 are found in Table 18. An agarose gel image showing PCR products used to determine genotype is shown in FIG. 37 (lane 1: 1 KB ladder; lane 2: M3625 (13092/17586); lane 3: M3625 (10871/14554); lane 4: M3625 (16291/17887); lane 5: M3625 (16640/16509); lane 6: M3625 (13246/13095); lane 7: 1 KB ladder).

TABLE 18

Primers used to create the MA0317 integration site.

| Primer | Sequence | SEQ ID NO |
|---|---|---|
| X18868 | gccaaagtggattctcctactcaagctttgc | 184 |
| X18844 | tcggatcagtagataacccgcctagaagactagtagctat gaaattttaactctttaa | 185 |
| X18845 | agccagcttaaagagttaaaaatttcatagctactagtctt ctaggcgggttatctact | 186 |
| X15464 | gtccatgtaaaatgattgctccaatgattgaaagaggttta gacattggctcttcattg | 187 |
| X15465 | ctaagctcaatgaagagccaatgtctaaacctctttcaatc attggagcaatcatttta | 188 |
| X11750 | ataaaattaaatacgtaaatacagcgtgctgcgtgctcg attttttctaaaccgtgga | 189 |
| X15479 | agcacgcagcacgctgtatttacgta | 190 |
| X18869 | agatcctgtggtagtgctgtctgaacagaa | 191 |

In order to determine exact DNA sequence of the M3625 MA0317 site, regions FA-FE were amplified from genomic DNA of M3625 strain in 5 independent PCR reactions. All PCR products were purified and sequenced by the Sanger method at the Dartmouth College Sequencing facility.

TABLE 19

Primers and summary of results of MA0317 genotyping.

| Lane | Template DNA | Primers | Expected size(bp) | Correct Size Observed |
|---|---|---|---|---|
| 1 | 1 KB ladder | N/A | N/A | N/A |
| 2 | M3625 | 13092/17586 | 2368 | yes |
| 3 | M3625 | 10871/14554 | 2966 | yes |
| 4 | M3625 | 16291/17887 | 2778 | yes |
| 5 | M3625 | 16640/16509 | 1334 | yes |
| 6 | M3625 | 13246/13095 | 2863 | yes |
| 7 | 1KB ladder | N/A | N/A | N/A |

TABLE 20

Sequence of primers used for genotyping MA0317.

| Primer | Sequence | SEQ ID NO |
|---|---|---|
| 13092 | ccacaccatagacttcagccttcttag | 174 |
| 17586 | gcagtatgcaagtctcatgctg | 175 |
| 10871 | cgttcgctgtagcatacttagctat | 176 |
| 14554 | ggctcttcattgagcttagaaccc | 177 |
| 16291 | aactggaccgatcttattcgt | 178 |
| 17887 | actgcctcattgatggtggta | 179 |
| 16640 | cctcatcagctctggaacaacga | 180 |
| 16509 | gtatgattgcggttatctgtcgc | 181 |
| 13246 | cctatggatgttgtaccatgcc | 182 |
| 13095 | ccaatatcttgcagtccatcctcgtcgc | 183 |

Figure 38:
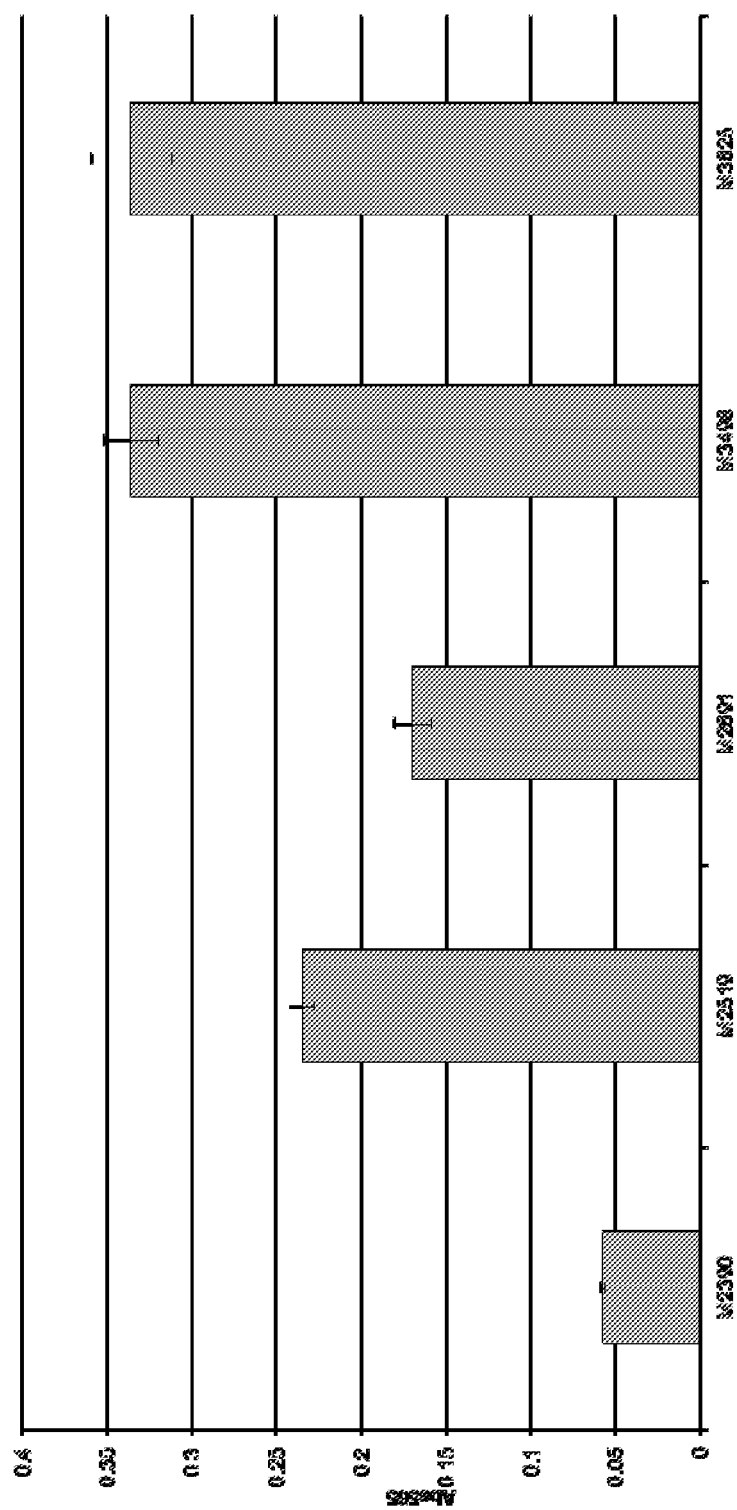
FIG. 38 shows a graph depicting the results of a starch assay performed with strains M2390, M2519, M2691, M3498, and M3625.

FIG. 38 shows the results of starch assay demonstrating starch degrading activity in M3625. The assay was performed as described in copending International Appl. No. PCT/US2011/039192, incorporated by reference herein in its entirey.

Western Blot Protein Detection:

Anti-PflA, Anti-PflB, Anti-GA (AE9) and Anti-AdhE Antibodies:

In an effort to detect the presence of and help characterize a number of enzymes engineered into the yeast strain, polyclonal antibodies were produced in rabbits at Lampire Biological Products, Pipersville, Pa., against synthesized peptides with sequence similarity to the engineered proteins. Table 11 depicts the peptides that were used as immunogens for the rabbits:

TABLE 21

Immunogens used for antibody production

| Protein | Immunogen | SEQ ID NO |
|---|---|---|
| Sf GA (AE9) | intact purified protein DNKNRYKINGNYKAGC NSGKKHIVESPQLSSRGGC CDHIDDNGQLTEEINRYTG | 106 |
| Ba pflA | CQNPDTWKMRDGKPVYYE GLTSSEENVENVAKIC | 107 |
| Ba pflB | WEGFTEGNWQKDIDVRDC KQRDKDSIPYRNDFTECPEC CNTITPDGLGRDEEEERIGN | 108 |
| Ba AdhE | DAKKKEEPTKPTPEEKLC CKNLGVNPGKTPEEGVEN CGSYGGNSVSGVNQAVN | 109 |

For all of the synthesized peptides a terminal Cys was added for conjugation. Both the peptides and the purified GA protein were conjugated to KLH prior to injection into the rabbit. A 50 day protocol was used for antibody production with ELISA monitoring of the various bleeds against the immunogen. After testing these polyclonal antibodies in a Western blot against the lysate from the engineered yeast strains, serum from the positive rabbits was purified using a Protein G column. The purified antibodies were dialyzed into PBS, concentration was determined by absorbance at 280 nm and the antibodies were used for further evaluation of the strains. Upon evaluation by SDS-PAGE, the antibodies appeared to be >90% pure.

Antibodies raised against the synthesized peptides were used in Western blot detection of each engineered protein in cell extracts and culture supernatants as described below.

Strain Growth Conditions:

Cells were plated from freezer stock on YPD (20 g/L peptone, 10 g/L yeast extract, 20 g/L glucose) agar for 48 hours and used to inoculate 25 mL YPD (20 g/L peptone, 10 g/L yeast extract, 20 g/L glucose) in a 50 mL culture tube. Cells were grown aerobically for 8 hours at 35° C. with shaking at 250 rpm, then lmL was removed to inoculate a sealed, CO2 purged serum bottle containing 50 mL YPD (20 g/L peptone, 10 g/L yeast extract, 20 g/L glucose) with 7 mg/L ergosterol, 289 mg/L ethanol and 544 mg/L Tween 80. These cultures were then grown anaerobically overnight (~16 h) at 35° C. with shaking at 250 rpm. Cells were harvested by centrifugation and washed with 25 mL deionized water. The resulting wet cell pellets were used for Western blot detection of PflA, PflB and AdhE.

Aerobic cultures used to inoculate the serum bottles were returned to the shaking incubator for an additional 40 hours. At the end of incubation, cells were pelleted by centrifugation and the supernatant was recovered and concentrated ~10× using a 10 kDa molecular weight cut-off (MWCO) filter membrane. The resulting concentrates were used for Western blot detection of extracellular AE9 glucoamylase.

Cell Lysis and Sample Preparation:

For Western blots of PflB and AdhE, cells were homogenized by mechanical disruption with 0.5 mm diameter beads and agitation at 4800 rpm in a bead beater. 100 μL of wet cells were added to homogenization buffer containing 1 mM phenylmethanesulfonylfluoride (PMSF), 2 mM dithiothreitol (DTT) and 1% dimethyl sulfoxide (DMSO) in 100 mM sodium phosphate buffer pH 7.4. Cells were agitated for 6 cycles of 10 seconds each, cooling on ice between cycles. Cell debris was pelleted by centrifugation and supernatant was recovered. 15 μL of the resulting supernatant was added to 15 μL 2× concentrated SDS-PAGE sample buffer with 50 mM DTT and loaded onto a 4-20% Tris-*Glycine* SDS-PAGE gel.

For Western blot detection of PflA, cells were lysed by adding 40 μL wet cells to 40 μL 2× concentrated SDS-PAGE sample buffer with 50 mM DTT. The mixture was then incubated at room temperature for 30 minutes, followed by heating at 100° C. for 2 minutes. Cells were pelleted by centrifugation and 30 μL of the supernatant was loaded onto a 4-20% Tris-*Glycine* SDS-PAGE gel.

For AE9 analysis, 154, of concentrated aerobic culture supernatant was added to 15 μL, 2× concentrated SDS-PAGE sample buffer with 50 mM DTT and loaded onto a 4-20% Tris-*Glycine* SDS-PAGE gel.

Following gel electrophoresis, proteins were transferred to a polyvinylidine fluoride (PVDF) membrane and blocked overnight with Tris buffered saline (TBS; 10 mM Tris, 150 mM sodium chloride pH 7.5) containing 2% weight by volume (w/v) bovine serum albumin (BSA). The blocking solution was then removed, and primary peptide antibodies were diluted to approximately 2 μg/mL in Tris buffered saline with Tween 20 (TBST; TBS with 0.1% v/v Tween 20) and added to each membrane. After a 1 hour incubation, the primary antibody was discarded and the membrane was washed for 3 periods of 5 minutes each in 10 mM Tris, 500 mM sodium chloride, 0.1% Tween 20 pH 7.5 (THST). The secondary antibody, goat anti-rabbit with horseradish peroxidase label, was diluted 1:7500 in TBST, added to the blot and incubated for 1 hour. The secondary antibody was then discarded and the blot was again washed with THST for 3 periods of 5 minutes each. The wash solution was then discarded, enhanced chemiluminescence (ECL) substrate was added, and the blot was read by a series of composite exposures using a gel imaging camera.

Figure 39:
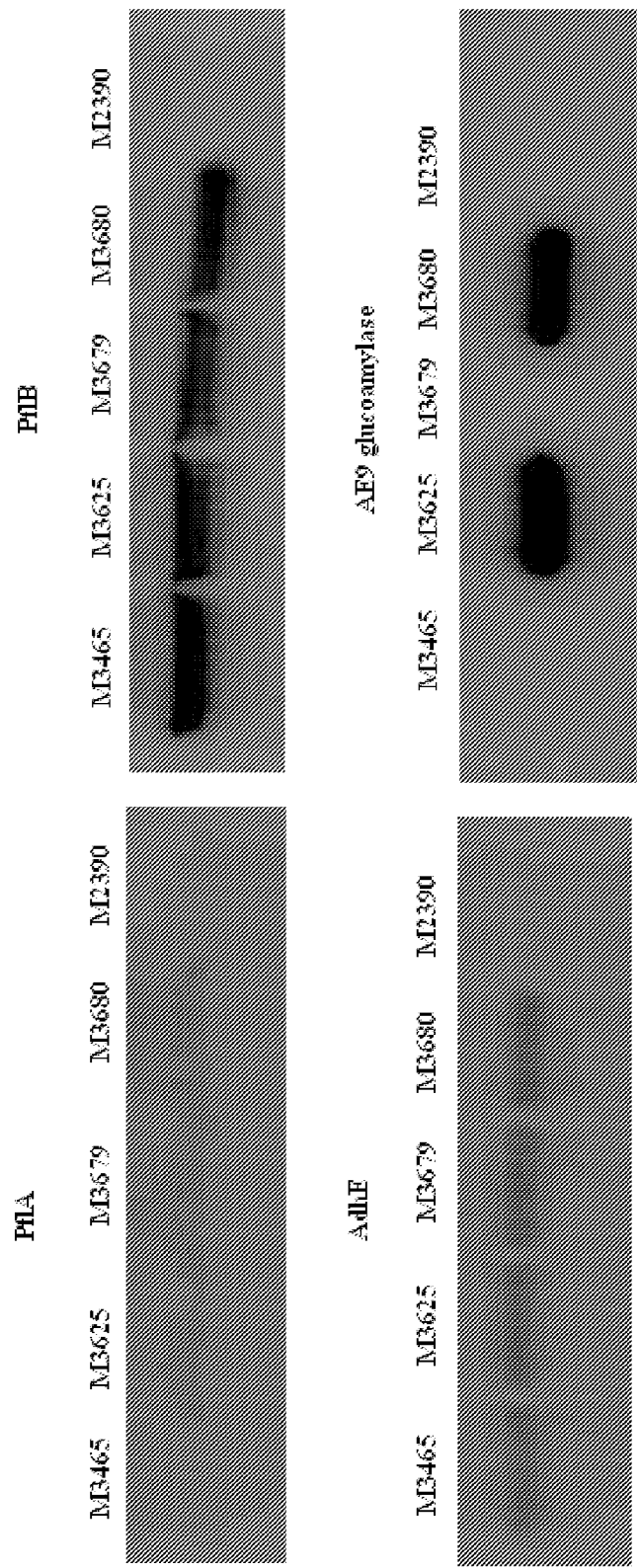
FIG. 39 shows an anti-peptide Western blot analysis of cell extracts (PflA, PflB, AdhE) and aerobic culture supernatants (AE9).

As shown in FIG. 39, for anti-PflA, PflB and AdhE primary antibodies, bands of approximately the correct molecular weight were detected in each experimental strain, whereas no band was detected in the background control strain (M2390). For anti-AE9, bands were detected in strains engineered to express the protein (M3625 and M3680) but were absent in other strains. See FIG. 39. There appeared to be two distinct bands for PflB, which may indicate oxygenic cleavage of the protein due to aerobic cell lysis conditions.

Pyruvate Formate Lyase Activity Assay:

Pyruvate formate lyase (PflB) is activated in the absence of oxygen by Pfl activase (PflA) and catalyzes the reaction of pyruvate and CoA to formate and acetyl-CoA. The activity of PflB was measured in cell extracts by measuring formate production when extracts were added to a reaction mixture containing pyruvate, CoA and DTT.

Strain Growth Conditions:

Cells were plated from freezer stock on YPD (20 g/L peptone, 10 g/L yeast extract, 20 g/L dextrose) agar for 48 hours and used to inoculate 25 mL YPD (20 g/L peptone, 10 g/L yeast extract, 20 g/L dextrose) in a 50 mL culture tube. Cells were grown aerobically for 8 hours at 35° C. with shaking at 250 rpm, then lmL was removed to inoculate a sealed, CO2 purged serum bottle containing 50 mL YPD (20 g/L peptone, 10 g/L yeast extract, 20 g/L dextrose) with 7 mg/L ergosterol, 289 mg/L ethanol and 544 mg/L Tween 80. These cultures were then grown anaerobically overnight (~16 h) at 35° C. with shaking at 250 rpm. Cells were harvested by centrifugation and washed with 25 mL deionized water in an anaerobic chamber.

Cell Lysis and Sample Preparation:

Cells were homogenized in an anaerobic chamber by mechanical disruption with 0.5 mm diameter beads and agitation at 4800 rpm in a bead beater. 100 μL of wet cells were added to homogenization buffer containing 1 mM PMSF, 2 mM DTT and 1% DMSO in 100 mM sodium phosphate buffer pH 7.4. Cells were agitated for 6 cycles of 10 seconds each, cooling on ice between cycles. Cell debris was pelleted by centrifugation at 14,100×g for 10 minutes and supernatant was recovered and clarified by filtration through a 0.22 μm filter membrane. The resulting extract was used directly in the activity assay.

Pfl Activity Assay:

A 2× concentrated assay substrate mixture consisted of 20 mM sodium pyruvate, 0.11 mM CoA and 20 mM DTT. Reagents were weighed out, brought into an anaerobic chamber and added to 10 mL of 100 mM sodium phosphate buffer pH 7.4 which had been thoroughly degassed. 100 μL of cell extract was added to 100 μL of the concentrated assay mixture and incubated at ambient temperature (~29° C.) for 30 minutes. Samples were then removed from the anaerobic chamber and heated in a heating block at 100° C. for 90 seconds followed by cooling on ice to precipitate protein. Precipitate was removed by centrifugation at 15,000×g for 10 minutes. The resulting supernatant was analyzed for formate concentration using the formic acid assay kit available from Megazyme International Ireland, Bray, Co. Wicklow, Ireland.

Remaining cell extracts were diluted 1:8 in 100 mM sodium phosphate buffer pH 7.4 and assayed for total protein content using the BCA total protein determination method. Formate concentrations of the Pfl assay samples were normalized to the total protein concentration of the sample.

Figure 40:
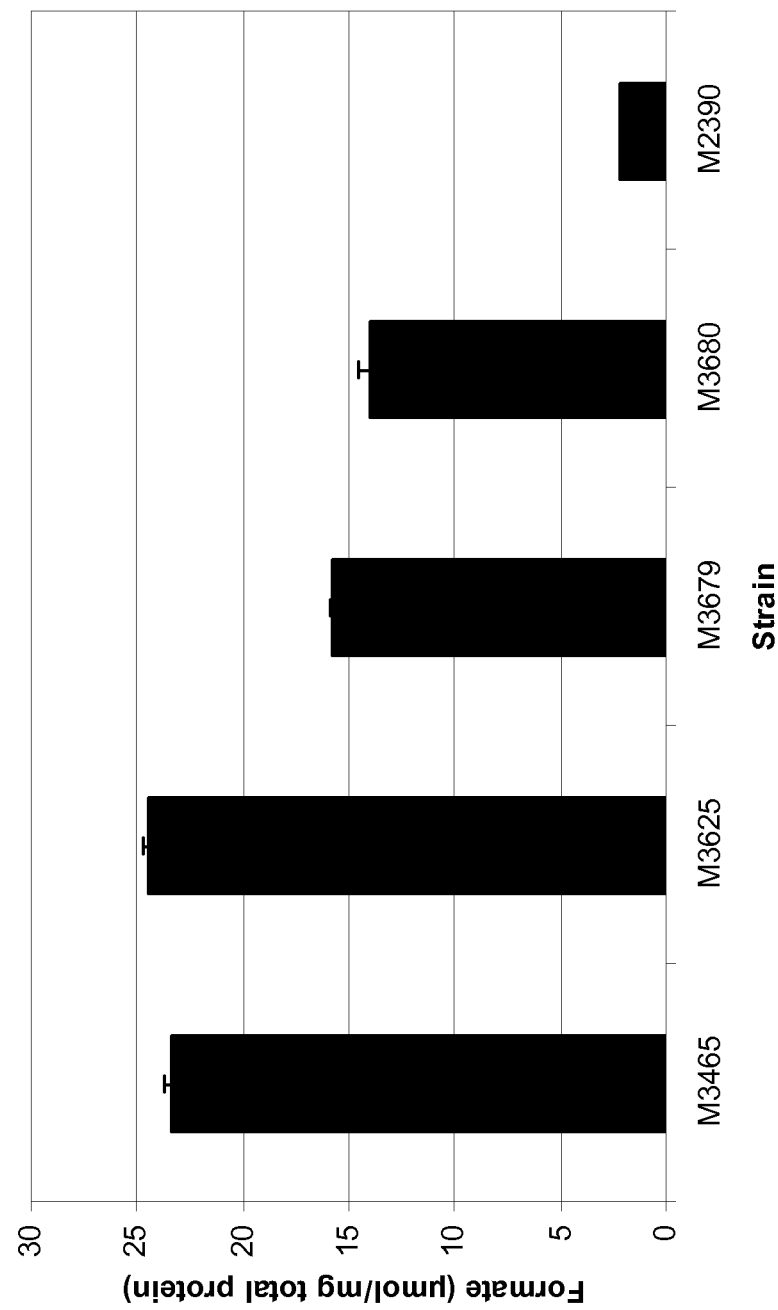
FIG. 40 shows a graph depicting the results of a formate lyase assay performed with engineered strains M3465, M3625, M3679, M3680, and M2390.

As shown in FIG. 40, experimental strains with engineered Pfl activity (M3465, M3625, M3679, and M3680) showed significantly higher amounts of formate present after incubation with the reaction mixture than the background control strain (M2390).

Alcohol Dehydrogenase E (AdhE) Enzymatic Activity Assays

AdhE is an intracellular bi-functional enzyme catalyzing the formation of ethanol from acetyl-CoA by way of acetaldehyde as an intermediate. This is accomplished by an acetaldehyde dehydrogenase activity and an alcohol dehydrogenase activity working in series. *Saccharomyces cerevisiae* strains have native alcohol dehydrogenase (Adh) activity; the intent of these activity assays is to show that Adh activity is retained by the engineered strains, and an additional acetaldehyde dehydrogenase activity (from AdhE) is present.

Figure 49:
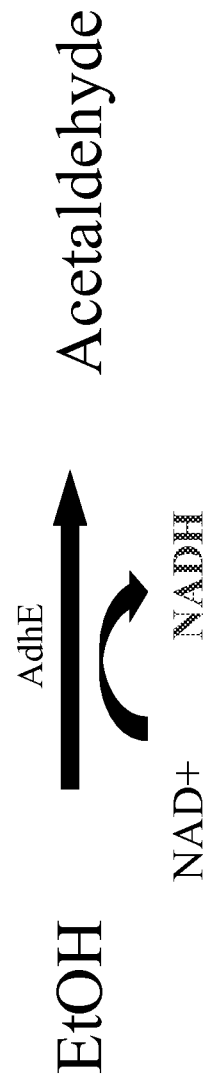
FIG. 49 shows the reverse reaction catalyzed by *Bifidobacterium adolecentis* bifunctional alcohol dehydrogenase (AdhE) in which ethanol is converted to acetaldehyde.

Alcohol Dehydrogenase Activity:

As mentioned above, *Bifidobacterium adolecentis* bifunctional alcohol dehydrogenase (AdhE) has 2 primary functions. One function is the conversion of acetaldehyde to ethanol. This reversible reaction utilizes NADH as a cofactor. In order to evaluate the presence of this enzyme and ensure that it has the desired activity, an assay was developed to evaluate the reverse reaction in which ethanol is converted to acetaldehyde. See FIG. 49. The rate of the reaction is monitored by NADH absorbance at 340 nm.

Strain Growth Conditions:

Strains were patched from freezer stock onto a YPD (20 g/L peptone, 10 g/L yeast extract, 20 g/L dextrose) agar plate and incubated overnight at 35° C. From that plate, 50 mL shake tubes with 25 mL YPD (20 g/L peptone, 10 g/L yeast extract, 20 g/L dextrose) were inoculated and incubated at 35° C., 250 rpm overnight. The cultures were centrifuged at 5000 rpm×5 min at 4 C, washed with deionized (DI) water and centrifuged at 5000 rpm×5 min at 4 C, washed a second time with DI water and centrifuged at 5000 rpm×5 min at 4 C, and then put on ice.

Cell Lysis and Sample Preparation:

100 μL of wet cell pellet was pipetted into a Zymo Research BashingBead 0.5 mm Tubes along with 500 μL 100 mM Na2PO4, 2.5 mM MgCl2, 0.5 mM CaCl2 pH 7.4 buffer and 6 μL 100 mM phenylmethylsulfonyl fluoride (PMSF). The cells were lysed by mechanical disruption using a MP FastPrep-24 set to run at 4.0 m/s for 10 seconds three times with cooling on ice for 10 seconds between each run. This was repeated three times with chilling on ice for one minute in between each run. Each tube was then centrifuged for 10 minutes at 15,000 rpm using an Eppendorf centrifuge 5424. The supernatant was removed and transferred to 2 mL tubes. 1 μL of New England Biolabs DNAse I was added to each tube. The tubes were inverted and placed into an incubator set at 37° C. for 30 min. The tubes were removed from the incubator and the samples were transferred to 0.22 μm filter centrifuge tubes which were centrifuged for 2 min at 10,000 rpm. 50 μL of sample was pulled and diluted with 450 μL 100 mM $Na_2PO_4$ pH 7.4 in separate sample tubes and then placed on ice.

Alcohol Dehydrogenase Activity Assay:

The assay used to determine alcohol dehydrogenase activity of AdhE was adapted from the method of Vallee, B. L. and Hoch, F. L., *Proc Natl Acad Sci USA* (1955) 41(6): 327-338. 100 μL 0.1M Na4P2O7 pH 9.6 buffer, 32 μL 2M ethanol, and 1.664, 0.025M $NAD^+$ were added to each well in a 96 well plate. Once the lysate was added to the reaction mixture, the total volume of reaction was equivalent to 153.66 μL resulting in final concentrations of 65 mM $Na_4P_2O_7$ pH 9.6 buffer, 416.5 mM ethanol, and 0.27 mM $NAD^+$. To begin the reaction, 20 μL of 1:10 diluted lysate was pipetted into each well and the absorbance at 340 nm was observed and recorded over 1.7 min using Spectramax M2 and Softmax software. Each sample was done in duplicate to ensure reproducibility. Thermo Scientific's BCA Protein Assay Kit was used to measure total protein concentration from the lysate generated. This data was used to normalize the data generated from the actual reaction during analysis.

TABLE 22

Data for alcohol dehydrogenase activity assay

| | Average activity (μmol NADH/min/mg) | Standard Deviation | % CV | % Change | p-value |
|---|---|---|---|---|---|
| M2390 | 599 | 15.6 | 2.6 | | |
| M3465 | 659 | 16.2 | 2.5 | 10 | 0.1942 |
| M3625 | 999.5 | 132 | 13.2 | 66.9 | 0.0108 |
| M3679 | 755 | 82 | 10.9 | 26 | 0.0603 |
| M3680 | 698 | 29.7 | 4.3 | 16.5 | 0.0996 |

Alcohol dehydrogenase activities of engineered strains. p-value was based on a one-tailed T-test.

Figure 41:
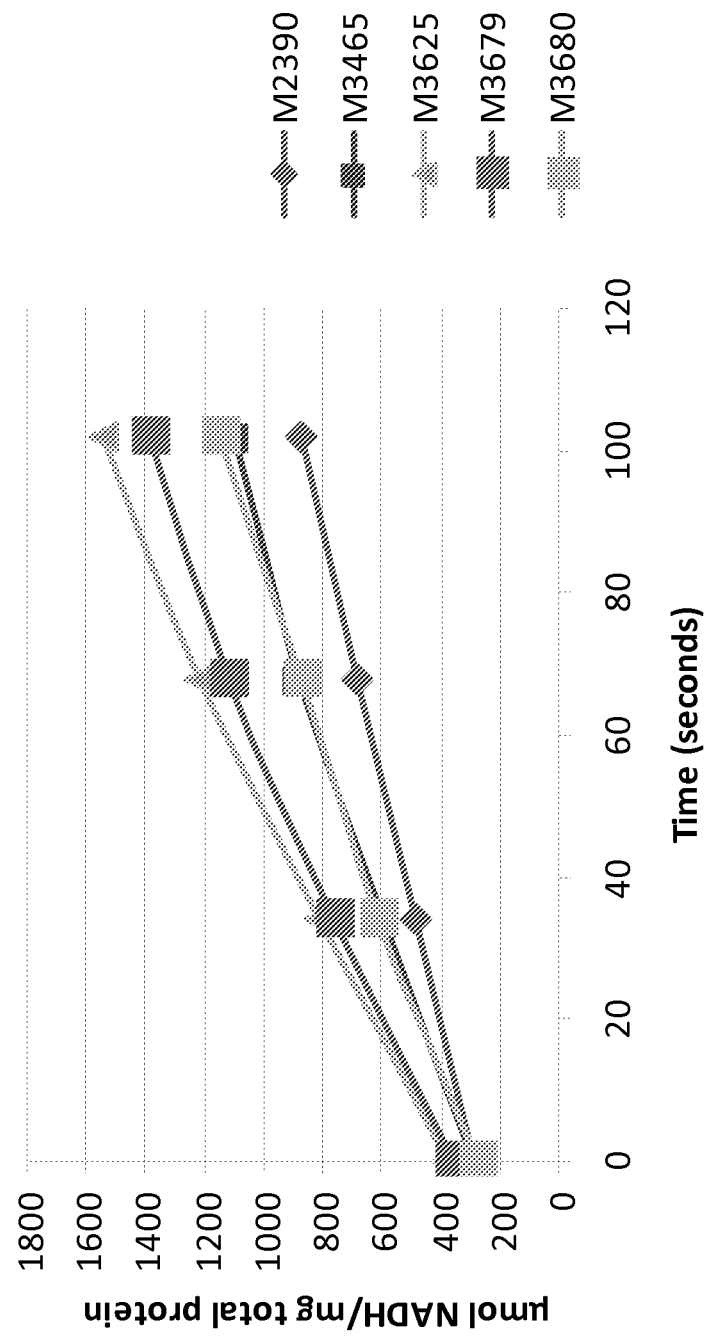
FIG. 41 shows a graph depicting the results of an alcohol dehydrogenase assay performed with engineered strains M3465, M3625, M3679, and M3680.

The background strain, M2390, performed as expected in this assay. Although it did not have AdhE engineered into its genome, it still expressed wild-type alcohol dehydrogenase and thus was active in the alcohol dehydrogenase assay. Other strains with AdhE engineered into their genomes should have expressed the bi-functional enzyme and should have been more active given the total protein concentration was equal in each sample used in the assay. With a p-value of <0.05, M3625 demonstrated a statistically significant higher activity than the background strain. However, the other strains have a p-value>0.05 indicating that they are within error of the background strain even though there was an increase in activity as shown by the % change over the background activity. See Table 22. After normalizing the protein concentrations, a graphical representation of the data shows that each strain was more active than the background strain M2390 during a 1.7 minute reaction period. FIG. 41 shows the activity of each strain plotted in μmol NADH/mg total protein vs. time during a 1.7 minute reaction.

Based on these results, the assay showed alcohol dehydrogenase activity in all strains. However, M2390 is less active and slower at converting $NAD^+$ to NADH than the other strains indicating that the engineered AdhE is present in each strain and it appears to be functioning properly.

Figure 50:
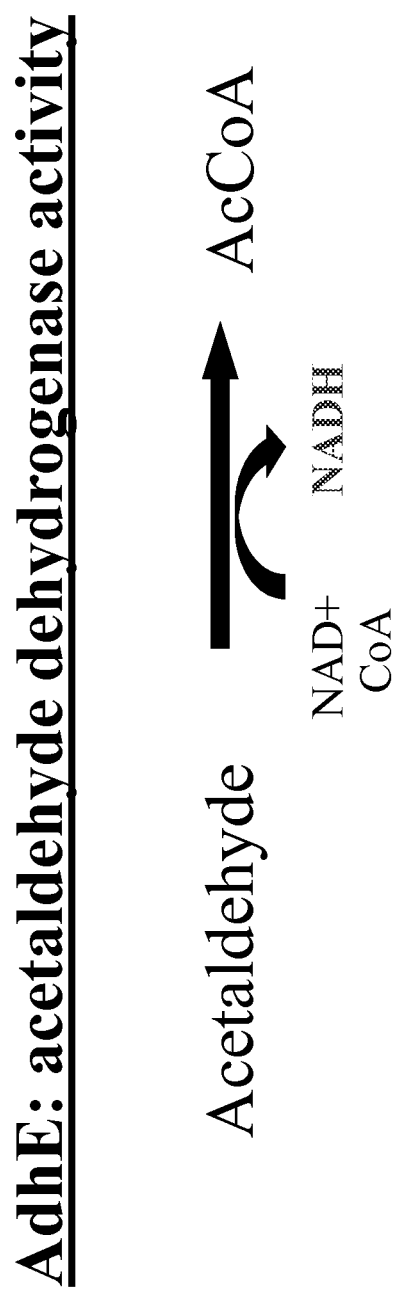
FIG. 50 shows a diagram of the reaction for the conversion of acetaldehyde to acetyl CoA by AdhE.

Acetaldehyde Dehydrogenase Activity:

The second activity of AdhE is the reversible reaction converting acetaldehyde to acetyl coenzyme A. This activity is not native to *Saccharomyces cerevisiae* strains, and should only be present in the engineered strains. In order to evaluate the presence of this enzyme and ensure that it has the desired activity, an assay was developed to measure the conversion of acetaldehyde to acetyl CoA by AdhE. The rate of the reaction is monitored by NADH absorbance at 340 nm. A diagram of the reaction is provided in FIG. 50.

Strain Growth Conditions:

Strains were patched from a freezer stock onto a YPD (20 g/L peptone, 10 g/L yeast extract, 20 g/L dextrose) agar plate and incubated overnight at 35° C. From that plate, 50 mL shake tubes with 25 mL YPD (20 g/L peptone, 10 g/L yeast extract, 20 g/L dextrose) were inoculated and incubated at 35° C., 250 rpm overnight. The cultures were centrifuged at 5000 rpm×5 min at 4° C., washed with DI water and centrifuged at 5000 rpm×5 min at 4 C, washed a second time with DI water and centrifuged at 5000 rpm×5 min at 4° C., and then put on ice.

Cell Lysis and Sample Preparation:

100 μL of wet cell pellet was pipetted into a Zymo Research BashingBead 0.5 mm Tubes along with 500 μL 100 mM $Na_2PO_4$, 2.5 mM $MgCl_2$, 0.5 mM $CaCl_2$ pH 7.4 buffer and 64, 100 mM phenylmethylsulfonyl fluoride (PMSF). The cells were lysed by mechanical disruption using a MP FastPrep-24 set to run at 4.0 m/s for 10 seconds three times with cooling on ice for 10 seconds between each run. This was repeated three times with chilling on ice for one minute in between each run. Each tube was then centrifuged for 10 minutes at 15,000 rpm using an Eppendorf centrifuge 5424. The supernatant was removed and transferred to 2 mL tubes. 1 μL of New England Biolabs DNAse I was added to each tube. The tubes were inverted and placed into an incubator set at 37° C. for 30 min. The tubes were removed from the incubator and the samples were transferred to 0.22 μm filter centrifuge tubes which were centrifuged for 2 min at 10,000 rpm using the Eppendorf centrifuge 5424. 50 μL of sample was pulled and diluted with 450 μL 100 mM $Na_2PO_4$ pH 7.4 in separate sample tubes and then were placed on ice.

Acetaldehyde Dehydrogenase Activity Assay:

800 μL 50 mM $Na_4P_2O_7$ pH 9.6, 50 μL 0.025M NAD+, 50 μL 1M acetaldehyde, and 50 μL 1:10 diluted lysate were added to a Plastibrand micro UV-cuvette. The cuvette was placed into a Shimadzu UV-1700 set to read absorbance at 340 nm. 50 μL of 2 mM CoA were pipetted into the cuvette which was then mixed by gently pipetting the contents of the cuvette and the absorbance was monitored for 5 minutes. The resulting final concentrations of each reagent were 40 mM $Na_4P_2O_7$ pH 9.6, 1.25 mM $NAD^+$, 50 mM acetaldehyde, and 0.1 mM CoA. Each sample was done in duplicate to ensure reproducibility. Thermo Scientific's BCA Protein Assay Kit was used to measure total protein concentration from the lysate generated. This data was used to normalize the data generated from the actual reaction during analysis.

Data for alcohol dehydrogenase (acetaldehyde dehydrogenase activity) assay is shown in Table 23. Note the lysate used in this assay was the same lysate used in the alcohol dehydrogenase assay detailed in the previous section.

TABLE 23

Acetaldehyde Dehydrogenase Activity

| | Average activity (μmol NADH/min/mg) | Standard Deviation | % CV | p-value |
|---|---|---|---|---|
| M2390 | 0 | 0 | 0.0 | |
| M3465 | 163 | 24 | 14.7 | 0.0054 |
| M3625 | 115 | 7.07 | 6.2 | 0.0009 |
| M3679 | 106 | 9.97 | 9.4 | 0.0022 |
| M3680 | 177 | 7.07 | 4.0 | 0.0004 |

Acetaldehyde dehydrogenase activity. p-value was based on a one-tailed T-test.

The background strain, M2390, performed as expected in this assay. The wild-type strain should have no acetaldehyde dehydrogenase activity, as demonstrated by this assay. The other strains with AdhE engineered into their genomes should have expressed the protein and had acetaldehyde dehydrogenase activity. This activity was observed in all of the engineered strains (M3465, M3625, M3679, and M3680) with minimal error and a p-value of <0.05.

Formate Dehydrogenase Activity

In strains M3465, M3625, M3679, and M3680 formate dehydrogenase was knocked out of the genome in the hopes to balance redox with the various engineering steps that were undertaken. The background strain, M2390, should have the gene intact. To ensure that the native *Saccharomyces cerevisiae* formate dehydrogenase gene was removed, an enzymatic assay was developed. Formate dehydrogenase catalyzes the conversion of formate to carbon dioxide at the expense of $NAD^+$.

Formate+$NAD^+$→CO2+NADH     FDH

Enzymatic activity can be monitored by measuring NADH formation at 340 nm.

Strain Growth Conditions:

M2390, M3465, M3625, M3679, and M3680 were patched from a freezer stock onto a YPD (20 g/L peptone, 10 g/L yeast extract, 20 g/L dextrose) agar plate and incubated overnight at 35° C. From that plate, 50 mL shake tubes with 25 mL YPD+24 mM Sodium Formate were inoculated and incubated at 35° C., 250 rpm overnight (20 g/L peptone, 10 g/L yeast extract, 20 g/L dextrose). The cultures were centrifuged at 5000 rpm×5 min at 4° C., washed with DI water and centrifuged at 5000 rpm×5 min at 4° C., washed a second time with DI water and centrifuged at 5000 rpm×5 min at 4 C, and then put on ice.

Cell Lysis and Sample Preparation:

100 μL of wet cell pellet was pipetted into a Zymo Research BashingBead 0.5 mm Tubes along with 500 μL 100 mM $Na_2PO_4$, 2.5 mM $MgCl_2$, 0.5 mM $CaCl_2$ pH 7.4 buffer and 64, 100 mM phenylmethylsulfonyl fluoride (PMSF). The cells were lysed by mechanical disruption using a MP FastPrep-24 set to run at 4.0 m/s for 10 seconds three times with cooling on ice for 10 seconds between each run. This was repeated three times with chilling on ice for one minute in between each run. Each tube was then centrifuged for 10 minutes at 15,000 rpm using an Eppendorf centrifuge 5424. The supernatant was removed and transferred to 2 mL tubes. 1 μL of New England Biolabs DNAse I was added to each tube. The tubes were inverted and placed into an incubator set at 37° C. for 30 min. The tubes were removed from the incubator and the samples were transferred to 0.22 μm filter centrifuge tubes which were centrifuged for 2 min at 10,000 rpm using the Eppendorf centrifuge 5424.

Formate Dehydrogenase Activity Assay:

800 μL 62.5 mM $K_2PO_4$ pH 7.0, 50 μL 40 mM NAD+, and 50 uL 1M Sodium Formate were added to a Plastibrand micro UV-cuvette. The cuvette was placed into a Shimadzu UV-1700 set to read absorbance at 340 nm and blanked. 100 μL of undiluted lysate sample were pipetted into the cuvette which was then mixed by gently pipetting the contents of the cuvette and the absorbance was monitored for 2.5 minutes. The resulting final concentrations of each reagent were 50 mM Potassium Phosphate, 2 mM NAD+, and 0.05M Sodium Formate. Each sample was done in duplicate to ensure reproducibility.

TABLE 24

Fdh activity of engineered strains

| | Average μmol NADH/min | Standard Deviation | % CV |
|---|---|---|---|
| M3631 | 0.03 | 0.00269 | 0.865 |
| M2390 | 0.008 | 0 | 0 |
| M3465 | 0 | 0 | 0 |
| M3625 | 0 | 0 | 0 |
| M3679 | 0 | 0 | 0 |
| M3680 | 0 | 0 | 0 |

As shown in Table 24, the FDH knockout strains (M3465, M3625, M3679, and M3680) did not exhibit any formate dehydrogenase activity. The background strain, M2390, had minimal activity. The positive control strain, M3631, which overexpresses FDH was active and produced a significant amount of NADH that was observed and recorded.

AE9 Glucoamylase Activity Assay:

*Saccharomycopsis fibuligera* GLUT glucoamylase (AE9) produces glucose from starch.

Extracellular AE9 glucoamylase activity on raw corn starch was assayed to determine the presence of glucoamylase activity in aerobic culture supernatants of engineered strains. Cells were grown aerobically, removed by centrifugation, and the resulting supernatant was assayed for activity and compared to supernatant from strain M2390, which does not contain AE9.

Cell Growth Conditions:

Cells were plated on YPD (20 g/L peptone, 10 g/L yeast extract, 20 g/L dextrose) agar for 48 hours and used to inoculate 25 mL YPD (20 g/L peptone, 10 g/L yeast extract, 20 g/L glucose) in a 50 mL culture tube. Cells were grown aerobically for 48 hours at 35° C. with shaking at 250 rpm. After 48 hours, cells were removed via centrifugation and the supernatant was recovered.

Sample Preparation:

The recovered aerobic culture supernatant was clarified by filtration through a 0.22 μm filter membrane and concentrated ~10× using a 10 kDa molecular weight cut-off filter. The retained concentrate was then analyzed for AE9 concentration via a phenyl reverse phase (phenyl-RP) HPLC method developed in-house using purified AE9 as a standard. Samples were diluted to an AE9 concentration of 50 m/mL and used directly in the activity assay.

Glucoamylase Activity Assay:

A 2.2% (weight by volume) corn starch solution was made up in 50 mM sodium acetate buffer pH 5.0. In a 96-well assay plate, 50 μL of supernatant (adjusted to 50 m/mL AE9 concentration) was added to 450 μL 2.2% starch. The plate was incubated at room temperature without shaking, and 50 μL of sample was taken at 1, 2, 5, 10, 30, 120 and 210 minutes. Wells were mixed by pipette aspiration after initial enzyme addition, as well as at each sampling thereafter. Samples were analyzed via 3,5-dinitrosalicylic acid (DNS) method to determine reducing sugars.

Figure 42:
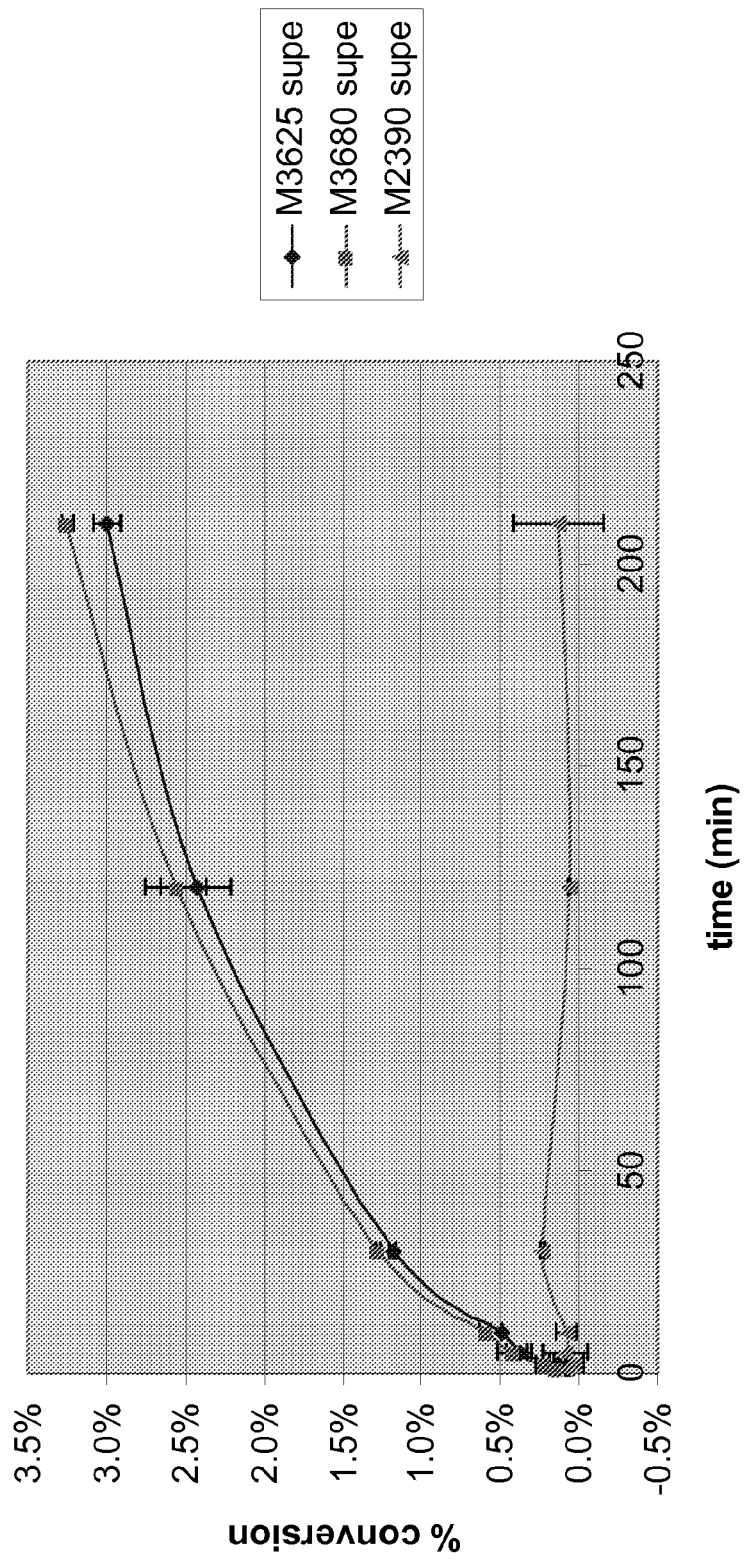
FIG. 42 shows a graph depicting the results of a glucoamylase activity assay performed with engineered strains M3625 and M3680 using 50 µg/mL AE9 on corn starch at room temperature (~25° C.).

As shown in FIG. 42, the aerobic culture supernatants of M3625 and M3680 showed similar activity on raw corn starch, as measured by DNS analysis (Somogyi, M., Notes on Sugar Determination, JBC (200)45 (1952)). Amylolytic activity of M2390 supernatant was negligible in this assay.

The above data show that pflA, pflB and AdhE are present in strain M3625 and have the proper activity. Fdh activity, seen in the background strain as well as in the positive control when fdh was overexpressed, was not present in the engineered strains indicating that this gene was knocked out successfully.

Example 9

Figure 43A:
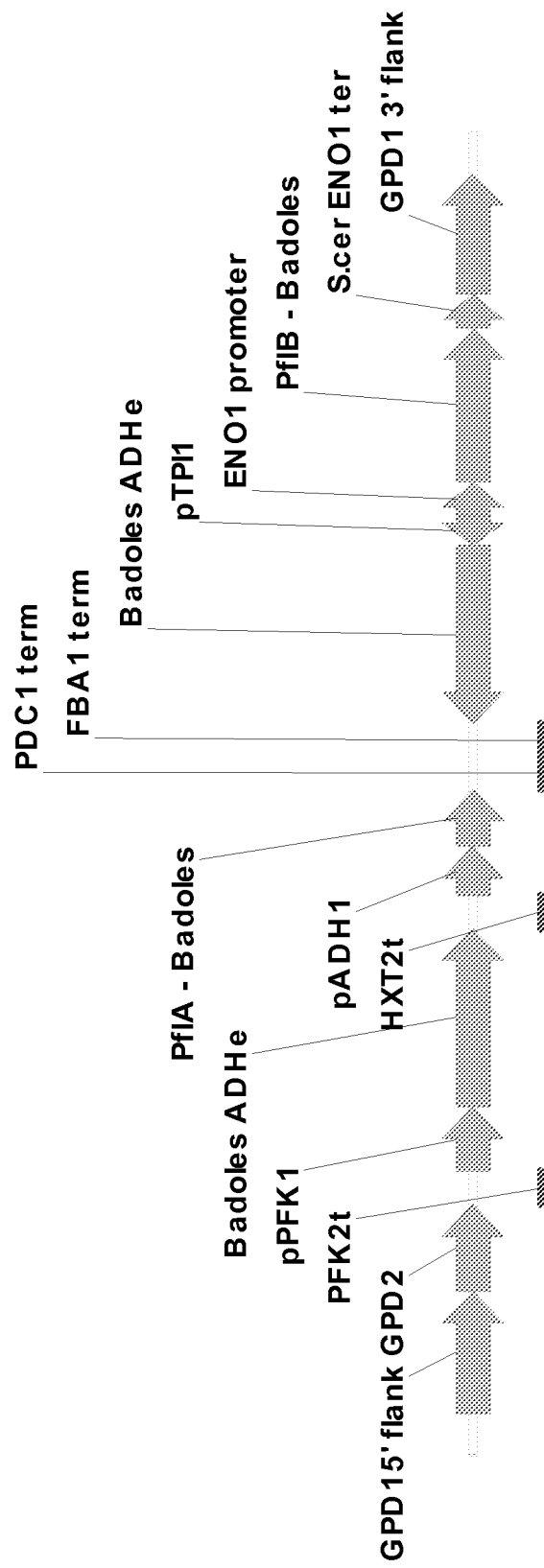
FIG. 43A is a schematic showing insertion of promoters and terminators used to express, GPD2, and *B. adolescentis* pflA, pflB and adhE at the GPD1 locus in M3624 and M3515.
Figure 43B:
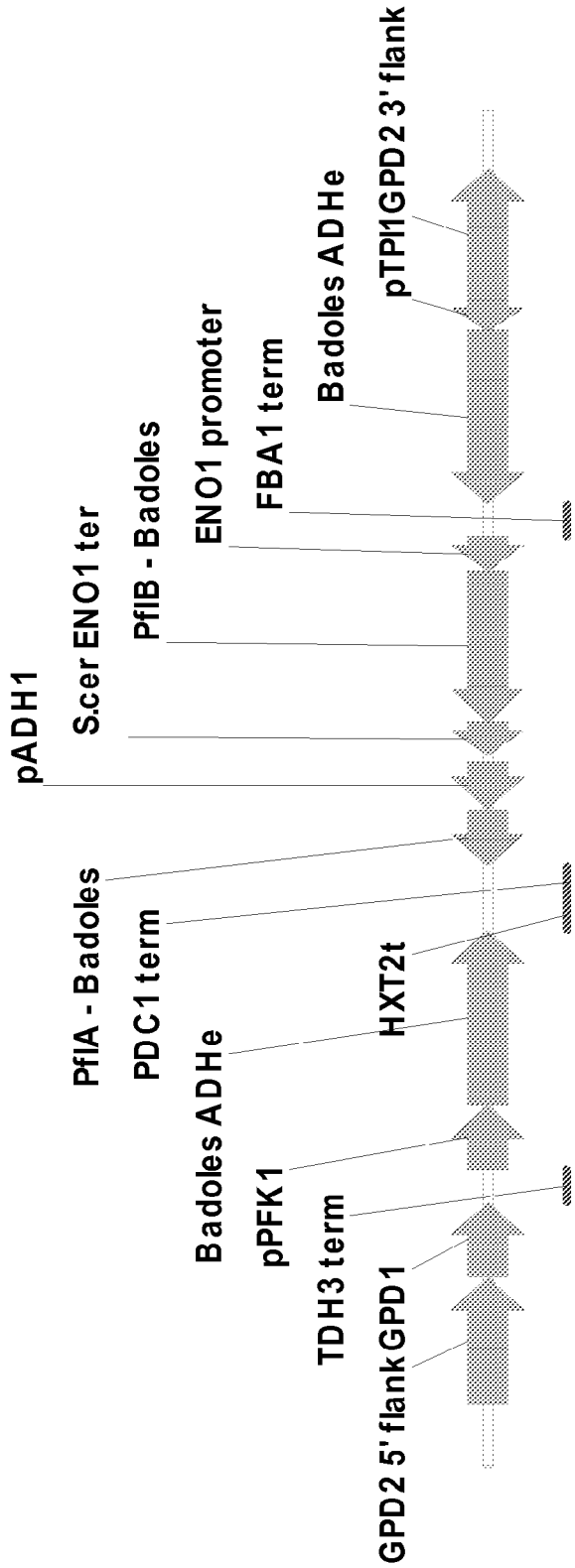
FIG. 43B is a schematic showing insertion of promoters and terminators used to express GPD1 and *B. adolescentis* pflA, pflB and adhE at the GPD2 locus in M3624 and M3515.
Figure 43C:
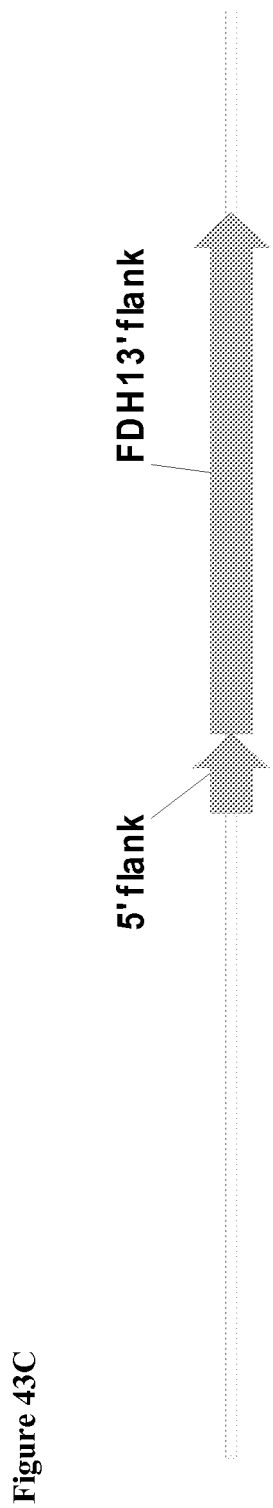
FIG. 43C is a schematic showing deletion of the FDH1 gene in M3624 and M3515.
Figure 43D:
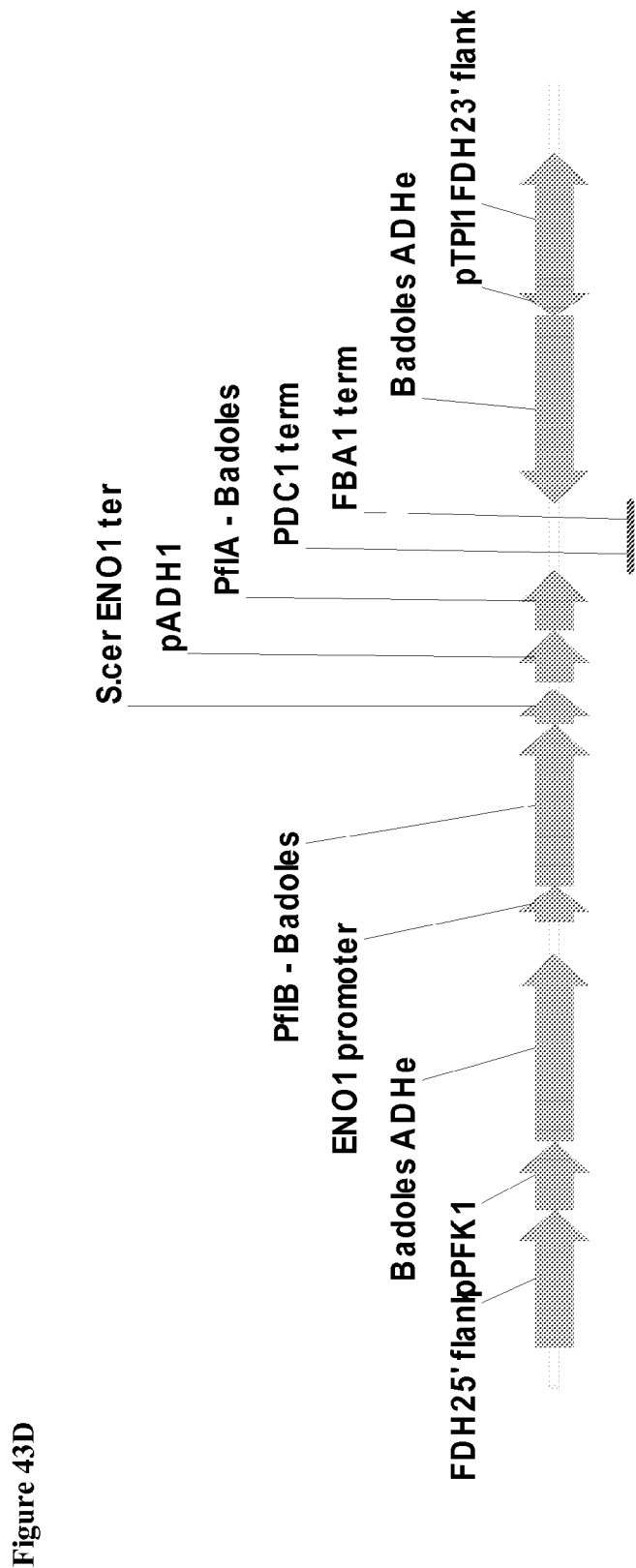
FIG. 43D is a schematic showing insertions of promoters and terminators used to express *B. adolescentis* pflA, pflB and adhE at the FDH2 locus in M3624 and M3515.

The following example demonstrates the ethanol yield of the *Saccharomyces cerevisiae* strain M3624. The genotype of strain M3624 is: Δgpd1::GPD2-*B. adolescentis* pflA/pFlB/adhEΔgpd2::GPD 1-*B. adolescentis* pflA/pflB/adhE Δfdh1 Δfdh2::*B. adolescentis* pflA/pflB/adhE. Strain M3624 was created according to the same methods employed above in Example 8. Detailed molecular maps for strain M3624 are shown in FIGS. 43A-D. FIG. 43A shows insertion at the GPD1 locus; GPD2 expressed from the GPD1 promoter; PFK2t-PFK2 terminator; HXT2t-HXT2 terminator; pADH1-ADH1 promoter; PDC1 term-PDC1 terminator; FBA1 term-FBA1 terminator; pTPI1-TPI1 promoter; Scer ENOL ter-ENOL terminator. FIG. 43B shows insertion at the GPD2 locus; GPD1 expressed from the GPD2 promoter; TDH3 term-TDH3 terminator; pPFK1-PFK1 promoter; HXT2t-HXT2 terminator; PDC1 term-PDC1 terminator; pADH1-ADH1 promoter; S. cer ENOL ter-ENOL terminator; FBA1 term-FBA1 terminator; pTPI1-TPI1 promoter. FIG. 43C shows deletion of the FDH1 gene; flanking regions to create deletion of FDH1. FIG. 43D shows insertion at the FDH2 locus; pPFK1-PFK1 promoter, S. cer ENOL ter-ENOL terminator; pADH1-ADh1 promoter; FBA1 term-FBA1 terminator; PDC1 term-PDC1 terminator; pTPI-TPI1 promoter.

Figure 44:
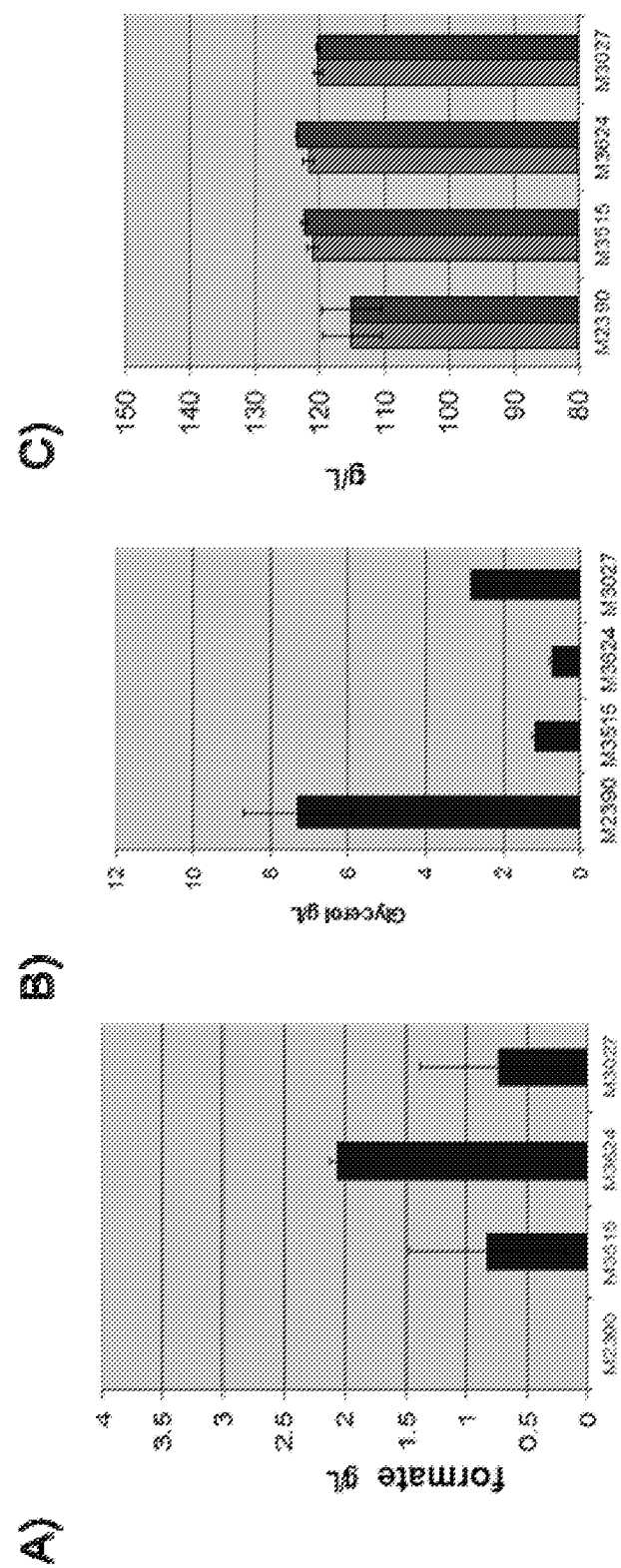
FIG. 44A shows HPLC analysis of formate produced by glycerol reduction strains during fermentation of 28% solids corn mash.
FIG. 44B shows HPLC analysis of glycerol produced by glycerol reduction strains during fermentation of 28% solids corn mash.
FIG. 44C shows HPLC analysis of ethanol produced by glycerol reduction strains during fermentation of 28% solids corn mash.

The data shown in FIG. 44 demonstrates that a 3.4% ethanol yield increase is obtained through reduction of glycerol and production of formate. M2390 is the control strain, M3515 and M3624 are engineered with the genotype Δgpd1:: GPD2-*B. adolescenits* pflA/pflB/adhE Δgpd2::GPD1-*B. adolescentis* pflA/PFlB/adhE fdh1Δfdh2Δ::*B. adolescentis* pflA/pflB/adhE. M3027 is engineered with the genotype Δgpd1 Δgpd2::GPD1-*B. adolescentis* pflA/PFlB/adhE fdh1Δfdh2Δ::*B. adolescentis* pflA/pflB/adhE. Panel A shows measurement of formate concentration, panel B shows measurement of glycerol concentration, and panel C shows measurement of ethanol concentration.

Both M3515 and M3624 have been engineered at 4 separate loci. The GPD1 gene is expressed from the GPD2 promoter and the GPD2 gene is expressed from the GPD1 promoter, the FDH1 and FDH2 genes have been deleted. Additionally, the *B. adolescentis* pflA, pflB and adhE genes are expressed as shown in FIGS. 43A, B, and D.

Example 10

Figure 45A:
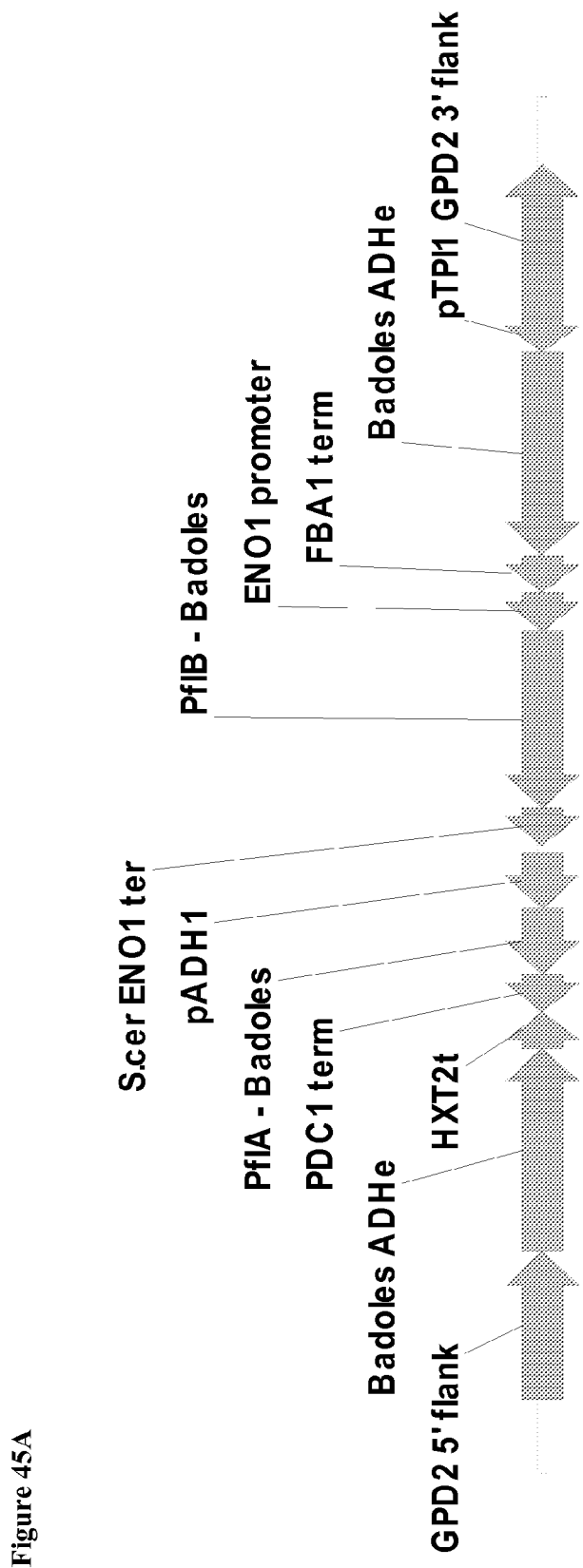
FIG. 45A is a schematic showing insertion of promoters and terminators used to express *B. adolescentis* pflA, pflB and adhE at the GPD2 locus in M3465.
Figure 45B:
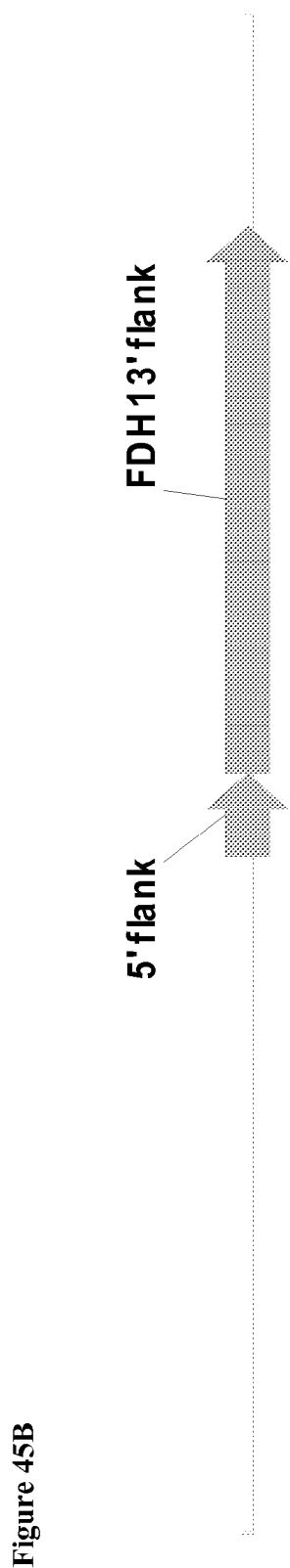
FIG. 45B is a schematic showing deletion of the FDH1 gene in M3465.
Figure 45C:
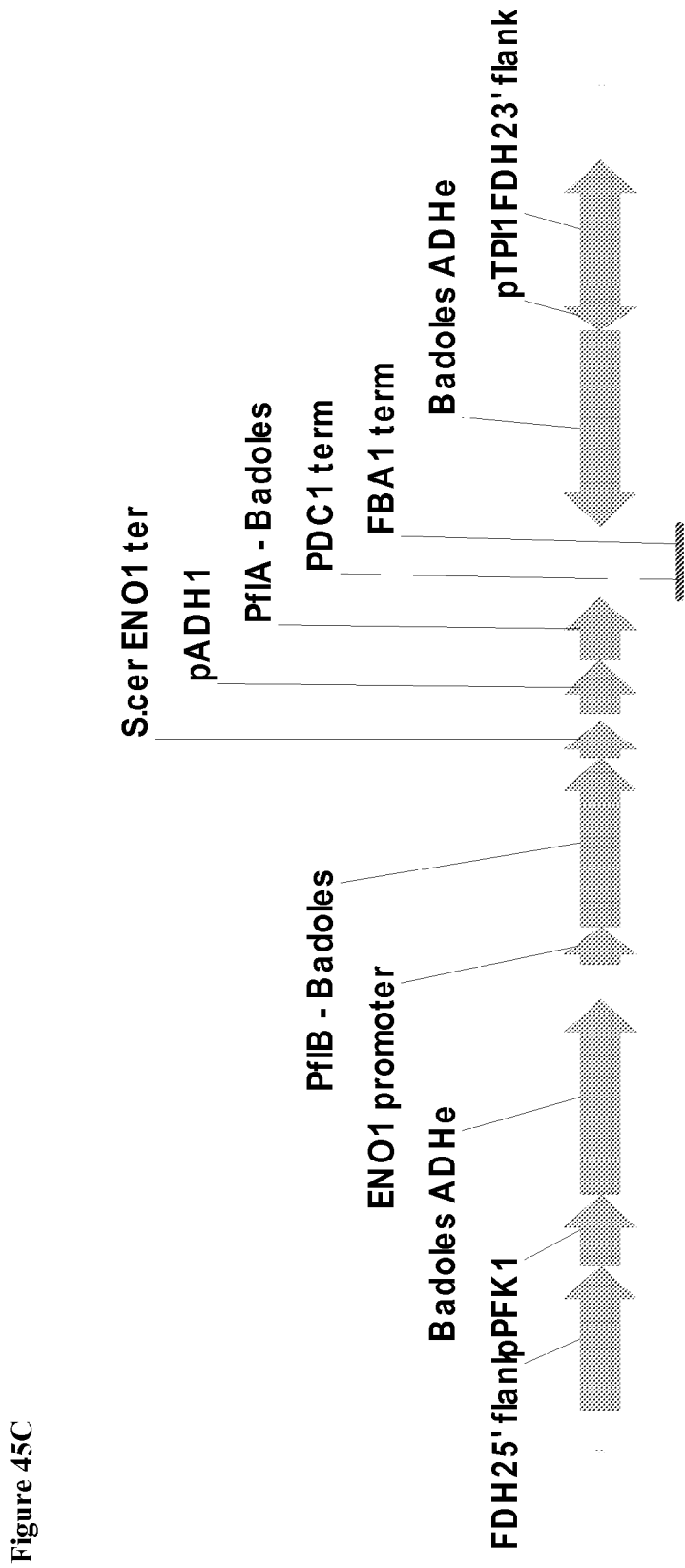
FIG. 45C is a schematic showing insertion of promoters and terminators used to express *B. adolescentis* pflA, pflB and adhE at the FDH2 locus in M3465.
Figure 46A:
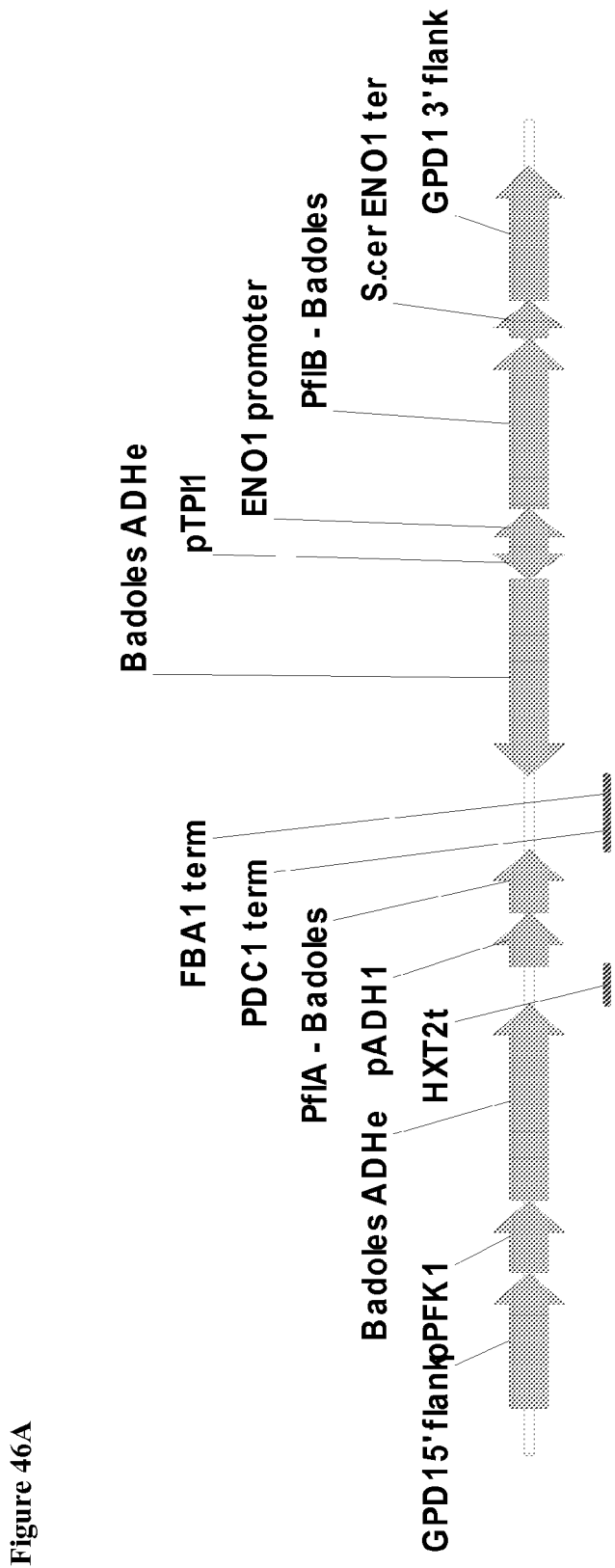
FIG. 46A is a schematic showing insertion of promoters and terminators used to express *B. adolescentis* pflA, pflB and adhE at the GPD1 locus in M3469.
Figure 46B:
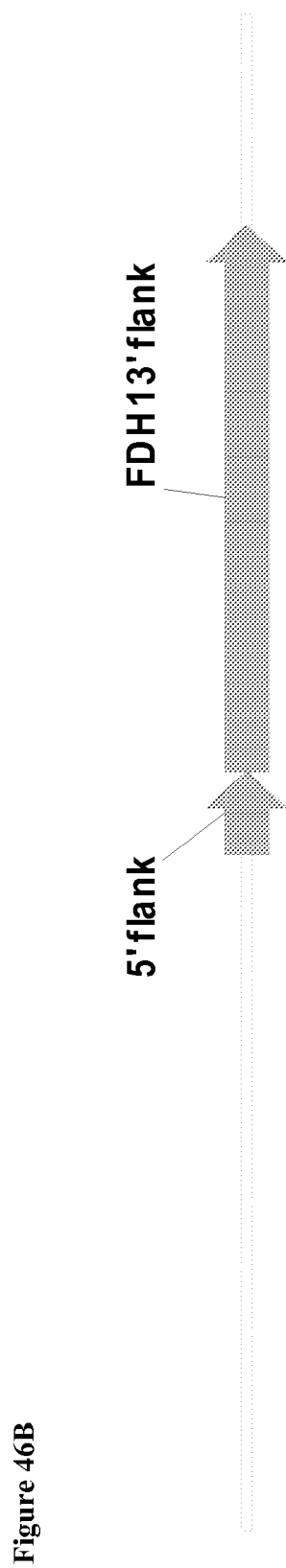
FIG. 46B is a schematic showing deletion of the FDH1 gene in M3469.
Figure 46C:
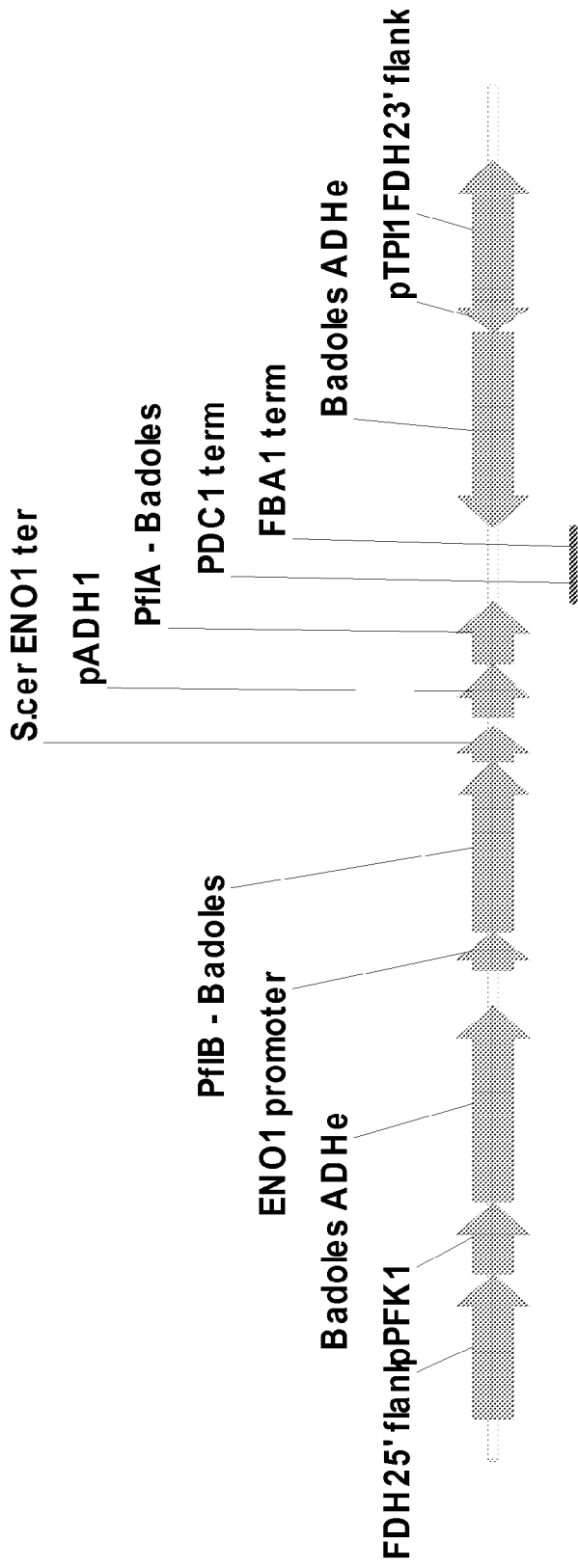
FIG. 46C is a schematic showing insertion of promoters and terminators used to express *B. adolescentis* pflA, pflB and adhE at the FDH2 locus in M3469.

The following example demonstrates the ethanol yield of the *Saccharomyces cerevisiae* strains M3465 and M3469. The genotype of strain M3465 is: Δgpd2:: *B. adolescentis* pflA/pflB/adhE Δfdh1Δ fdh2:: *B. adolescentis* pflA/pflB/adhE. The genotype of strain M3469 is: Δgpd1:: *B. adoles-* centis pflA/pflB/adhE fdh1 Δ fdh2Δ:: *B. adolescentis* pflA/pflB/adhE. Strains M3465 and M3469 were created according to the same methods employed above in Example 8. Detailed molecular maps of strains M3465 and M3469 are shown in FIGS. 45 A-C and 46 A-C, respectively. FIG. 45A shows insertion at the GPD2 locus; pPFK1-PFK1 promoter; HXT2t-HXT2 terminator; PDC1 term-PDC1 terminator; pADH1-ADH1 promoter; S. cer ENOL ter-ENOL terminator; FBA1 term-FBA1 terminator; pTPI1-TPI1 promoter. FIG. 45B shows deletion of the FDH1 gene; flanking regions to create deletion of FDH1. FIG. 45C shows insertion at the FDH2 locus; pPFK1-PFK1 promoter; S. cer ENOL ter-ENOL terminator; pADH1-ADh1 promoter; FBA1 term-FBA1 terminator; PDC1 term-PDC1 terminator; pTPI-TPI1 promoter. FIG. 46A shows insertion at the GPD1 locus; pPFK1-PFK1 promoter; HXT2t-HXT2 terminator; PDC1 term-PDC1 terminator; pADH1-ADH1 promoter; S. cer ENO1 ter-ENO1 terminator; FBA1 term-FBA1 terminator; pTPI 1-TPI1 promoter. FIG. 46B shows deletion of the FDH1 gene; flanking regions to create deletion of FDH1. FIG. 46C shows insertion at the FDH2 locus; pPFK1-PFK1 promoter, S. cer ENOL ter-ENO1 terminator; pADH1-ADh1 promoter; FBA1 term-FBA1 terminator; PDC1 term-PDC1 terminator; pTPI-TPI1 promoter.

Figure 47:
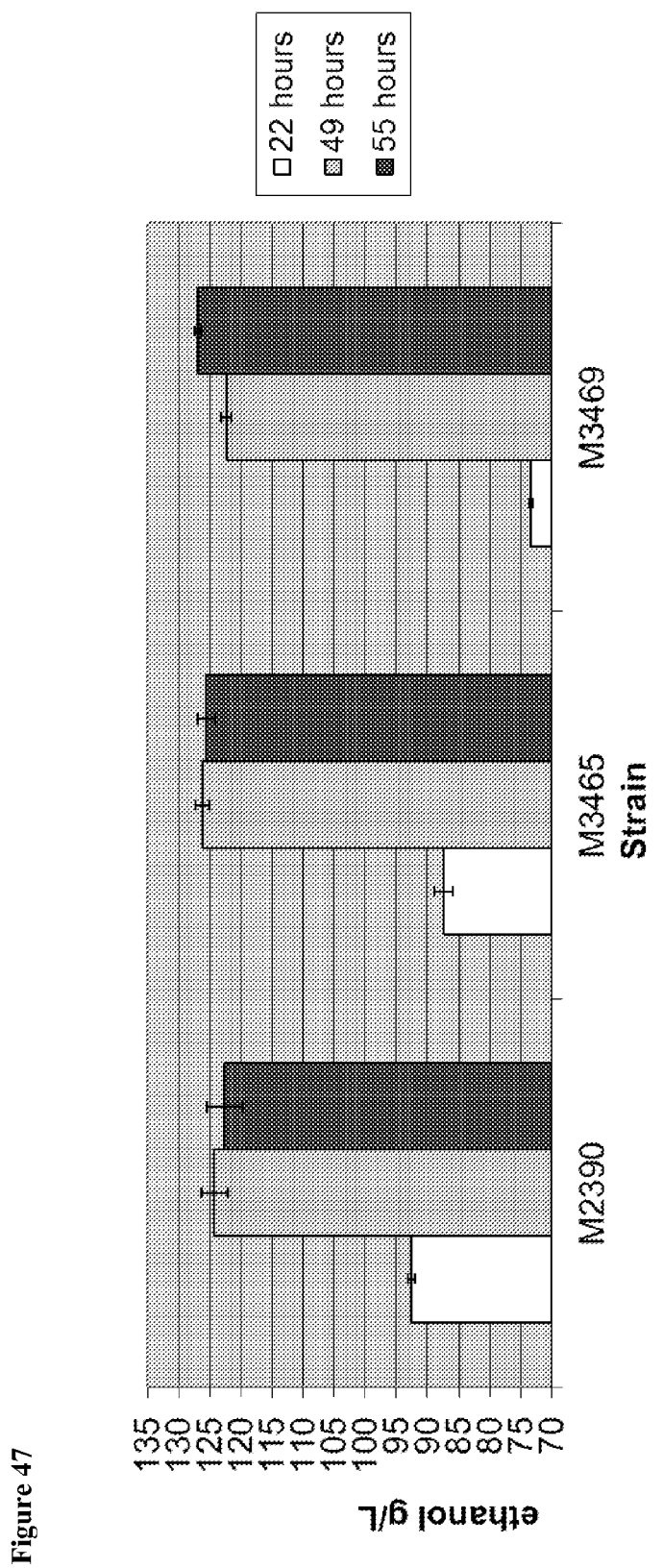
FIG. 47 shows HPLC analysis of ethanol titers produced by glycerol reduction strains during fermentation of 30% solids corn mash.
Figure 48:
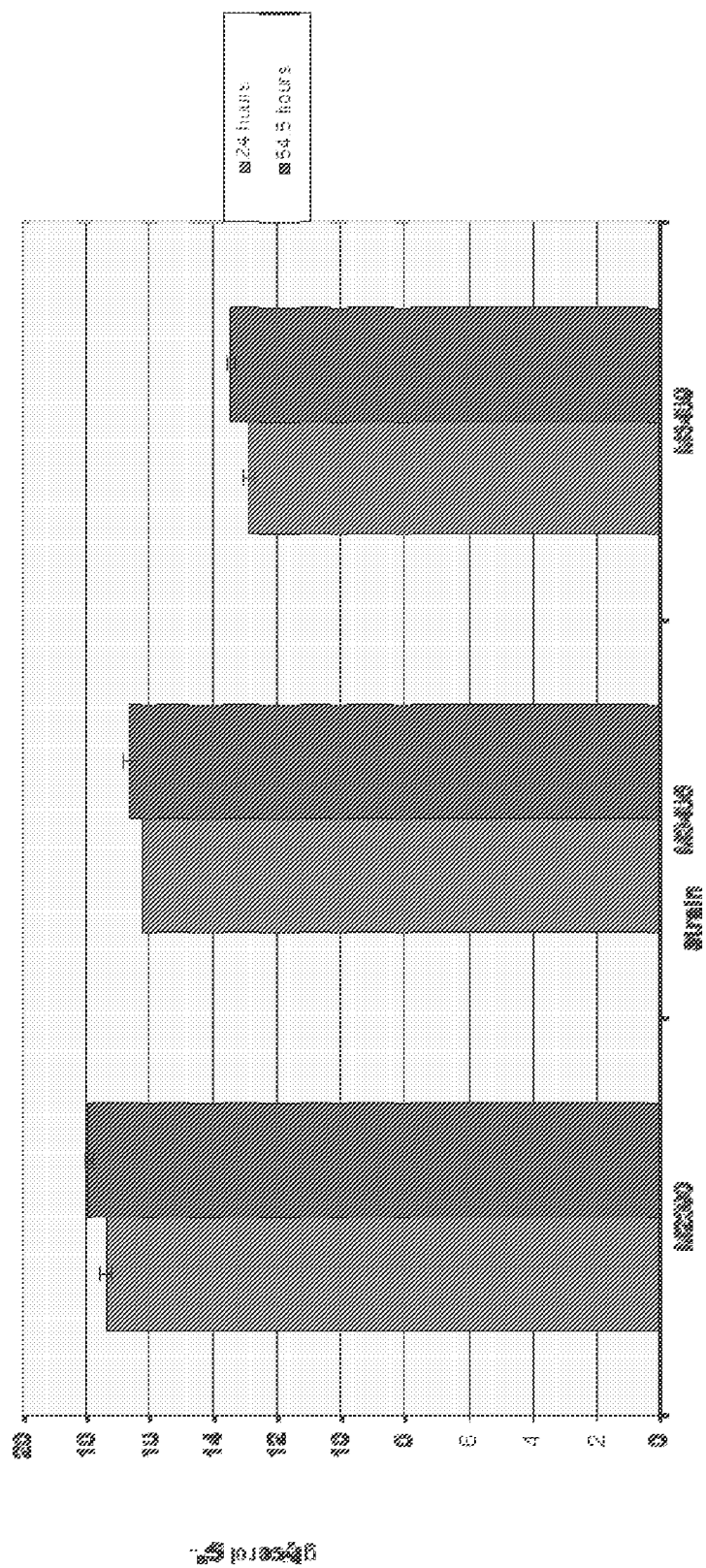
FIG. 48 shows HPLC analysis of glycerol titers produced by glycerol reduction strains during fermentation of 30% solids corn mash.

This example demonstrates that the ethanol yield increase is dependent on the level of glycerol reduction. Fermentation of 30% solids corn mash by M3465, which contains a deletion of the GPD2, FDH1 and FDH2 genes and expression of *B. adolescentis* pflA, pflB and adhE genes from the GPD2 and FDH2 loci, results in a 1.5% increase in ethanol titer. As shown in FIG. 47, fermentation of 30% solids corn mash by M3469, which contains a deletion of the GPD1, FDH1 and FDH2 genes and expression of *B. adolescentis* pflA, pflB and adhE genes from the GPD1 and FDH2 loci, results in a 2.5% increase in ethanol titer. M2390 is the control parent strain. As shown in FIG. 48, fermentation of corn mash by M3465 and M3469 results in ~15% lower glycerol and 30% lower glycerol levels respectively. M2390, represented in FIGS. 47 and 48, is the control strain.

Example 11

Figure 53:
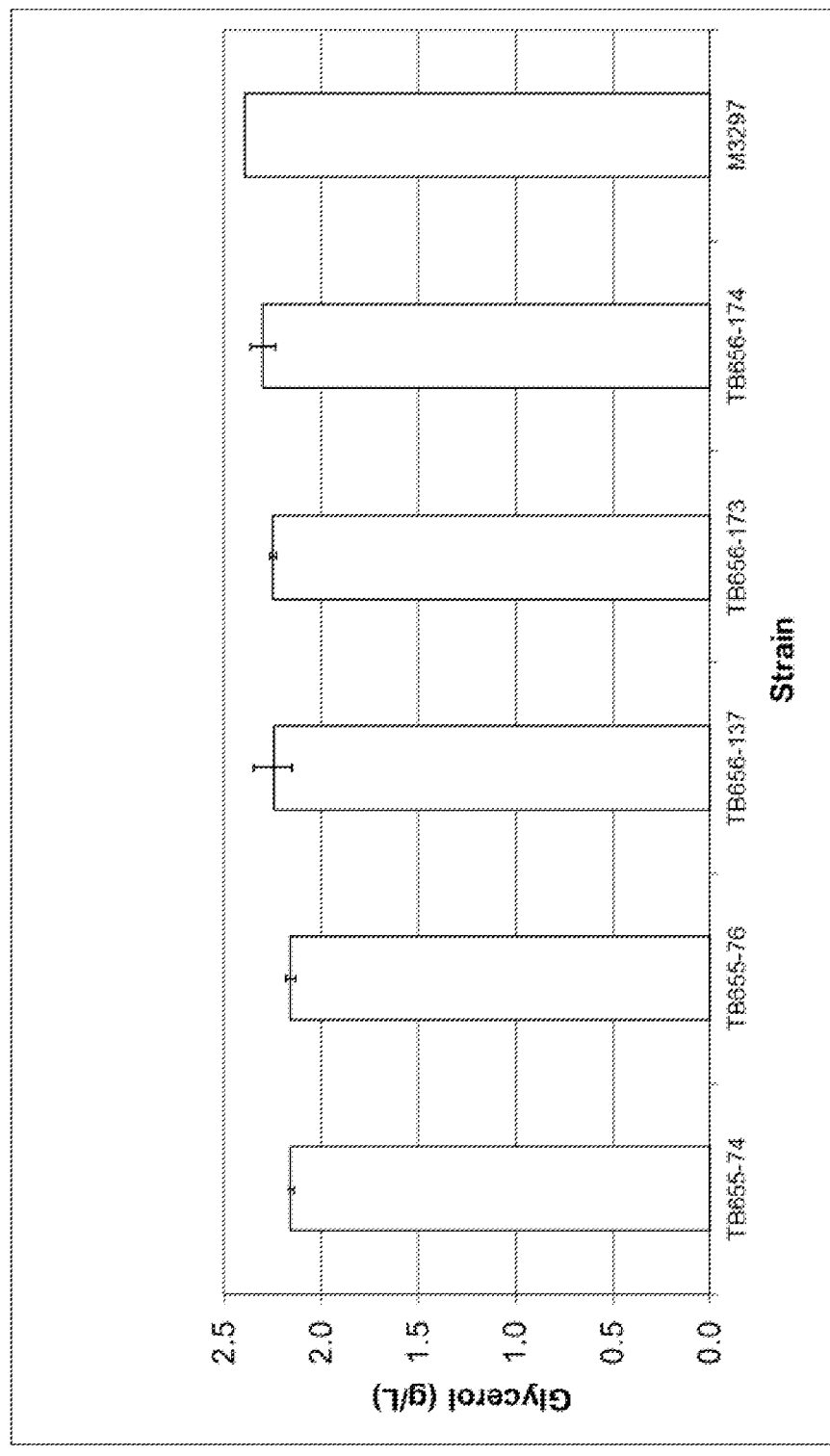
FIG. 53 is a graph depicting decreased glycerol formation in strains TB655 and TB656 compared to strain M3297.
Figure 54:
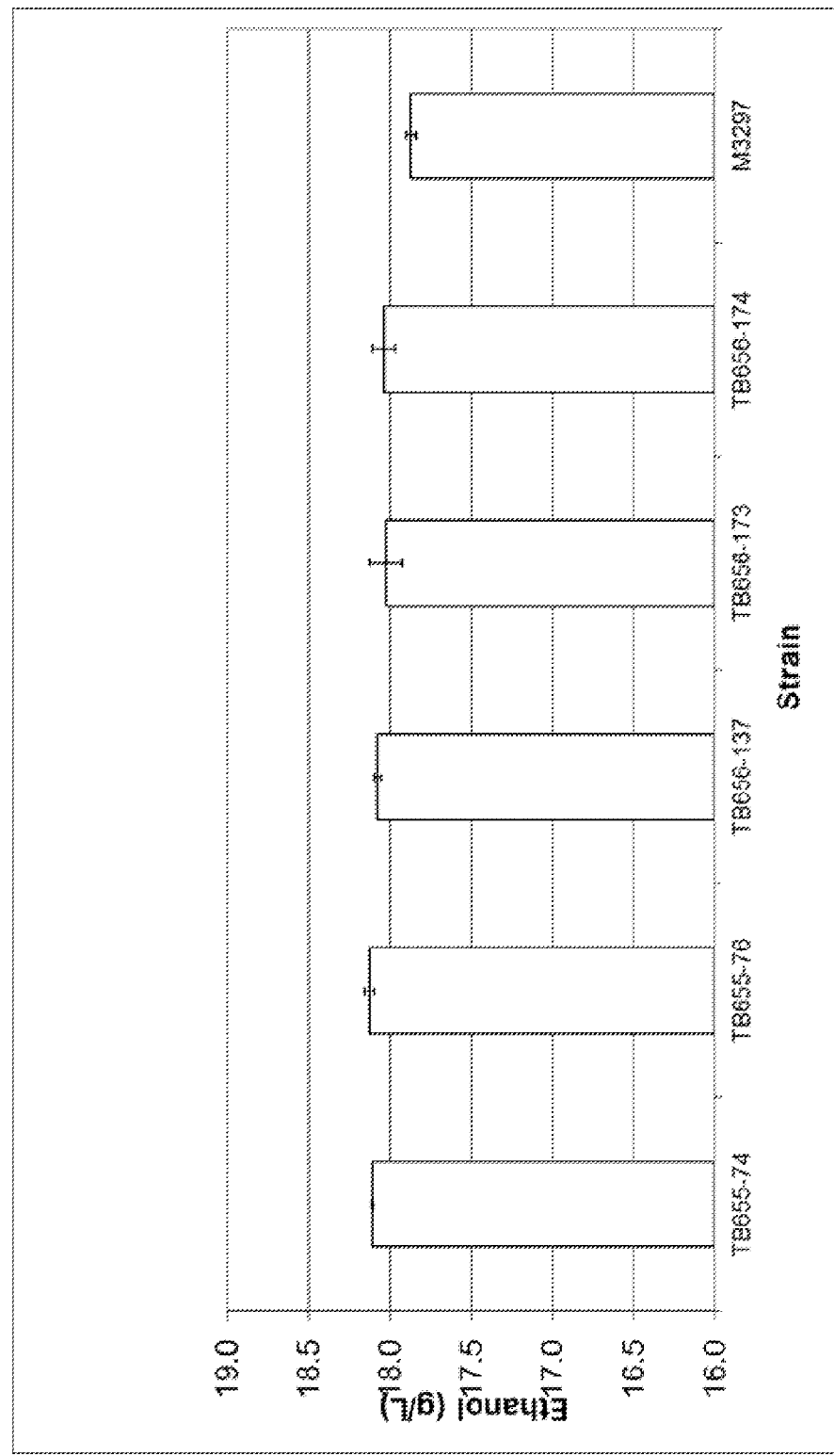
FIG. 54 is a graph depicting increased ethanol yield in strains TB655 and TB656 compared to strain M3297.
Figure 55:
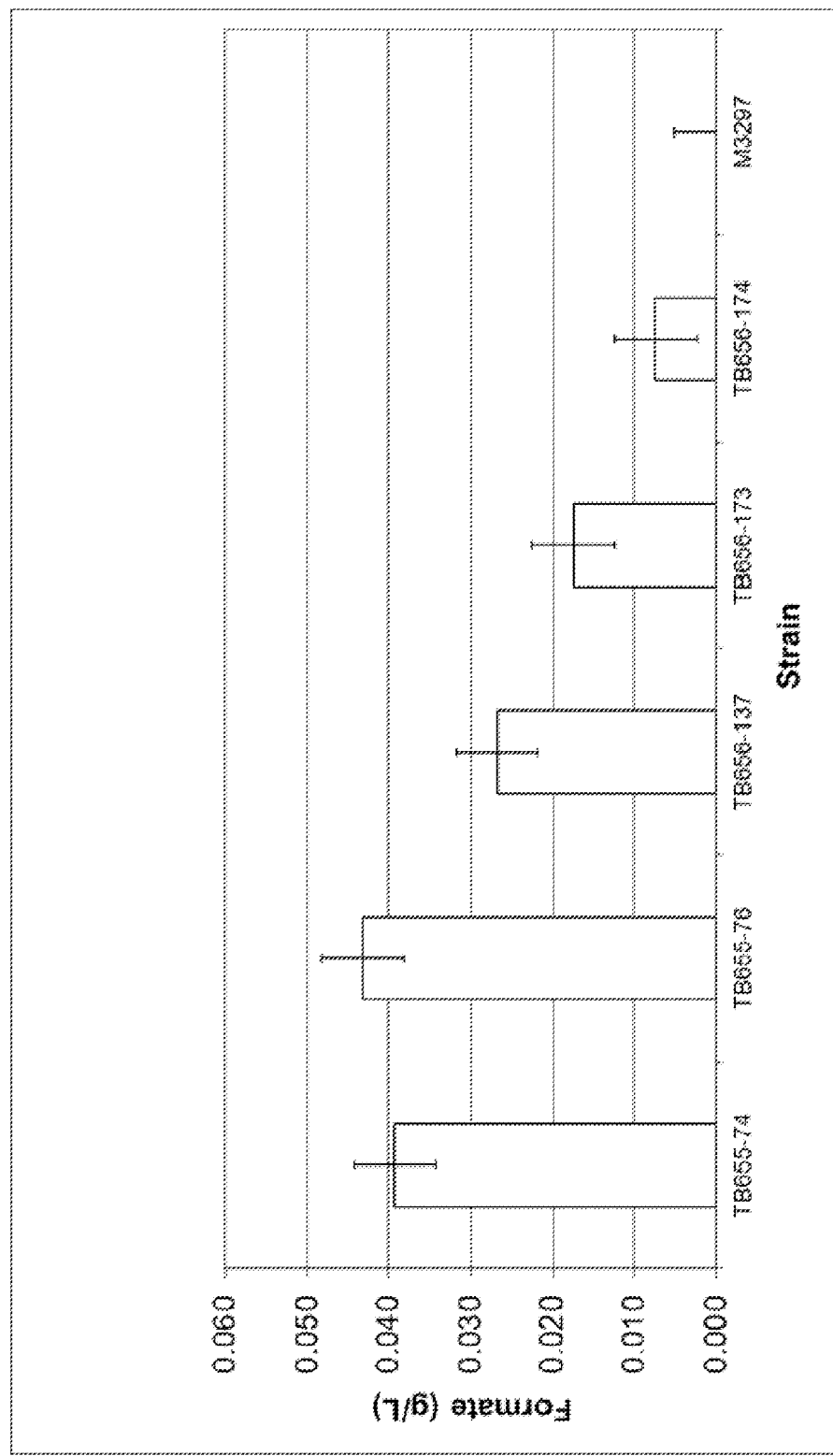
FIG. 55 is a graph depicting formate production in strains TB655, TB656, and M3297.

An alternative way to reduce glycerol formation is through deletion of the glycerol-3-phosphate phosphatase (GPP) genes. *Saccharomyces* contains two copies of these genes, GPP1 and GPP2. The data below demonstrates that expression of *B. adolescentis* pflA, pflB and adhE in backgrounds containing deletions of FDH1, FDH2 and either GPP1 or GPP2 results in decreased glycerol formation (FIG. 53; strain comparison, min buff medium, glucose 40 g/L, anaerobic fermentations, 35° C.—72 hr.) and increased ethanol yield (FIG. 54; strain comparison, min buff medium, glucose 40 g/L, anaerobic fermentations, 35° C.—72 hr.). Production of formate was also observed. See FIG. 55 (strain comparison, min buff medium, glucose 40 g/L, anaerobic fermentations, 35° C.—72 hr.).

Figure 51:
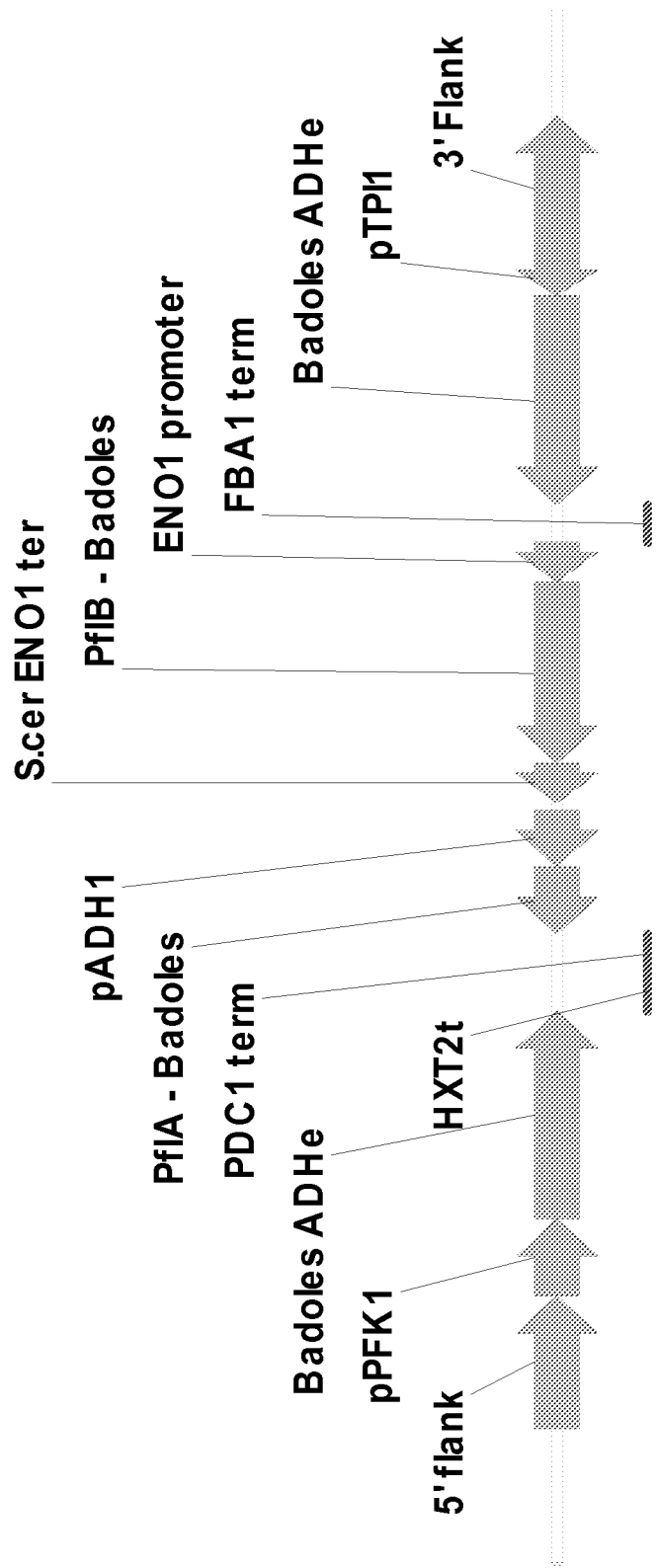
FIG. 51 is a schematic showing insertion of promoters and terminators used to express *B. adolescentis* pflA, pflB and adhE at the GPP1 locus in TB655.
Figure 52:
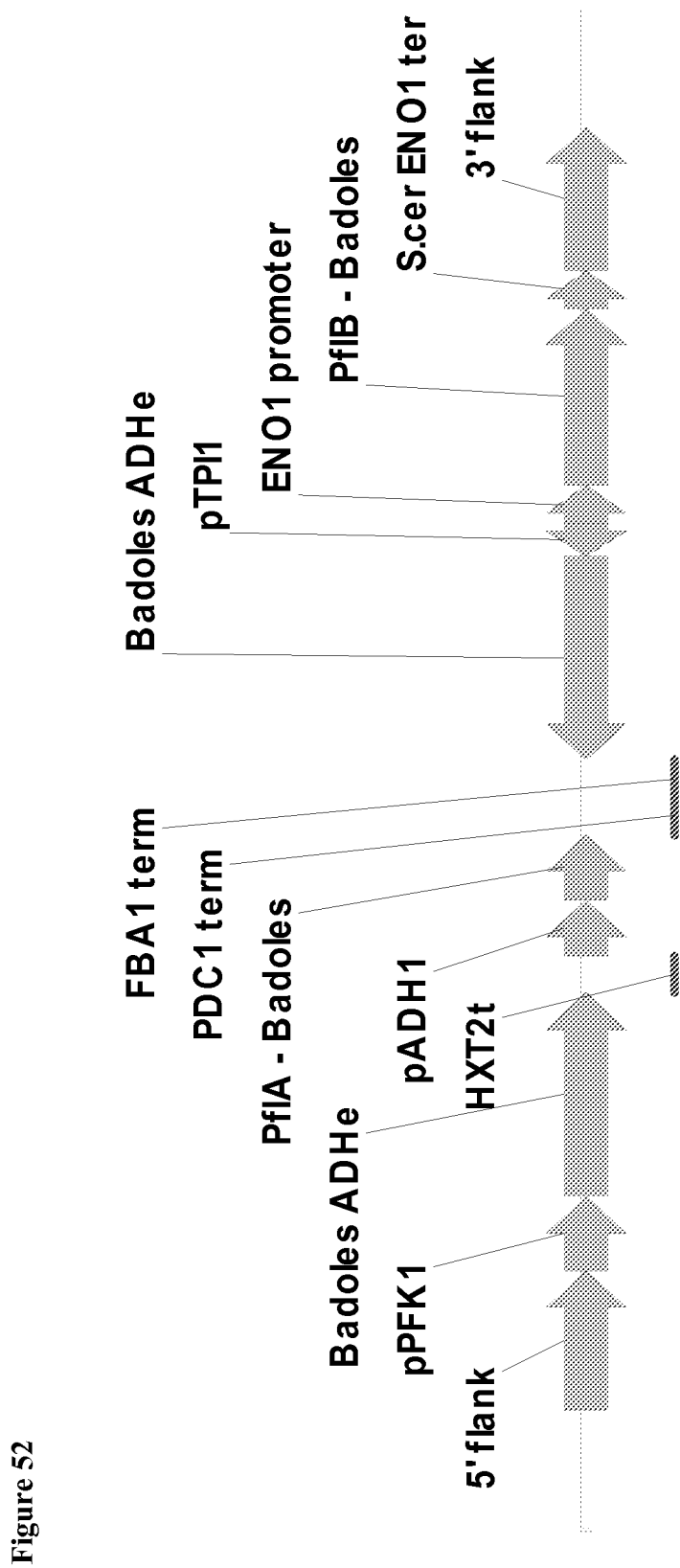
FIG. 52 is a schematic showing insertion of promoters and terminators used to express *B. adolescentis* pflA, pflB and adhE at the GPP2 locus in TB656.

The strains engineered to measure the glycerol formation, ethanol yield, and formate production were the *Saccharomyces cerevisiae* strains M3297, TB655, and TB656. Strains M3297, TB655, and TB656 were created according to the same methods employed above in Example 8. The genotype of strain M3297 is: Δfdh1Δfdh2::pflA/pflB/adhE. This strain contains only deletion in the FDH genes plus expression of pflA, pflB and AdhE. The genotype of strain TB655 is: Δfdh1Δfdh2::pflA/pflB/adhEΔgpp1::pflA/pflB/adhE. This strain contains deletion in the FDH genes, expression of pflA, pflB and AdhE, and deletion of GPP1. See FIG. 51. The genotype of strain TB656 is: Δfdh1Δfdh2::pflA/pflB/adhEΔgpp2::pflA/pflB/adhE. This strain contains deletion in the FDH genes, expression of pflA, pflB and AdhE and deletion of GPP1. See FIG. 52.

The amount of ethanol, glycerol, and formate produced by strains TB655 and TB656 was measured using the methods described above. Compared to the control strain M3297, strains TB655 and TB656 demonstrated statistically significant changes in the amount of ethanol, glycerol, and formate produced. Relative to strain M3297, strain TB655 (gpp1 mutant) demonstrated a 1.3% increase in ethanol titer, 10% reduction in glycerol, and 100% more formate produced, whereas strain TB656 (gpp2 mutant) demonstrated a 0.95% increase in ethanol titer, 6.1% reduction in glycerol formation, and 100% more formate produced. These results demonstrate the novel combination of GPP mutation with a metabolic engineering solution to balance redox during anaerobic growth.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant microorganism comprising:
   (a) a deletion of one or more native enzymes that function to produce glycerol and/or regulate glycerol synthesis, wherein said one or more enzymes is encoded by a glycerol-3-phosphate dehydrogenase (gpd1), glycerol-3-phosphate dehydrogenase (gpd2) glycerol 3-phosphatase 1', glycerol 3-phosphatase 2 or fps1 polynucleotide; and
   (b) one or more native and/or heterologous enzymes that function in one or more engineered metabolic pathways to convert a carbohydrate source to ethanol, wherein one of said metabolic pathways comprises conversion of pyruvate to acetyl-CoA and formate by a pyruvate formate lyase, wherein one of said metabolic pathways comprises conversion of acetyl-CoA to ethanol by an acetaldehyde dehydrogenase, alcohol dehydrogenase, or a bifunctional acetaldehyde/alcohol dehydrogenase, and wherein said one or more native and/or heterologous enzymes is activated, upregulated or downregulated.

2. The recombinant microorganism of claim 1, wherein said one or more native enzymes that function to produce glycerol is encoded by both a gpd1 polynucleotide and a gpd2 polynucleotide, and wherein one of said engineered metabolic pathways comprises conversion of acetyl-CoA to ethanol by a bifunctional acetaldehyde/alcohol dehydrogenase, and further comprising a deletion of one or more native enzymes encoded by both an fdh1 polynucleotide and an fdh2 polynucleotide.

3. The recombinant microorganism of claim 1, wherein said one or more native enzymes that function to produce glycerol is encoded by both a gpp1 polynucleotide and a gpp2 polynucleotide, and wherein one of said engineered metabolic pathways comprises conversion of acetyl-CoA to ethanol by a bifunctional acetaldehyde/alcohol dehydrogenase, and further comprising a deletion of one or more native enzymes encoded by both an fdh1 polynucleotide and an fdh2 polynucleotide.

4. The recombinant microorganism of claim 1, wherein said one or more native enzymes that function to regulate glycerol synthesis is encoded by an fps1 polynucleotide, and wherein one of said engineered metabolic pathways comprises conversion of acetyl-CoA to ethanol by a bifunctional acetaldehyde/alcohol dehydrogenase, and further comprising a deletion of one or more native enzymes encoded by both an fdh1 polynucleotide and an fdh2 polynucleotide.

5. The recombinant microorganism of claim 1, wherein said one or more native enzymes that function to regulate glycerol synthesis is encoded by an fps1 polynucleotide and said one or more native enzymes that function to produce glycerol is encoded by both a gpd1 polynucleotide and a gpd2 polynucleotide, wherein one of said engineered metabolic pathways comprises conversion of acetyl-CoA to ethanol by a bifunctional acetaldehyde/alcohol dehydrogenase, and further comprising a deletion of one or more native enzymes encoded by both an fdh1 polynucleotide and an fdh2 polynucleotide.

6. The recombinant microorganism of claim 1, wherein said one or more native enzymes that function to produce glycerol is encoded by both a gpd1 polynucleotide and a gpd2 polynucleotide and wherein one of said engineered metabolic pathways comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide.

7. The recombinant microorganism of claim 6, further comprising a deletion of one or more native enzymes encoded by both an fdh1 polynucleotide and an fdh2 polynucleotide.

8. The recombinant microorganism of claim 1, wherein said one or more native enzymes that function to produce glycerol is encoded by both a gpd1 polynucleotide and a gpd2 polynucleotide and said one or more native enzymes that function to regulate glycerol synthesis is encoded by an fps1 polynucleotide, and wherein one of said engineered metabolic pathways comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide.

9. The recombinant microorganism of claim 8, further comprising a deletion of one or more native enzymes encoded by both an fdh1 polynucleotide and an fdh2 polynucleotide.

10. The recombinant microorganism of claim 2, wherein one of said engineered metabolic pathways comprises conversion of a carbohydrate source to one or more sugar units by a saccharolytic enzyme.

11. The recombinant microorganism of claim 3, wherein one of said engineered metabolic pathways comprises conversion of a carbohydrate source to one or more sugar units by a saccharolytic enzyme.

12. The recombinant microorganism of claim 4, wherein one of said engineered metabolic pathways comprises conversion of a carbohydrate source to one or more sugar units by a saccharolytic enzyme.

13. The recombinant microorganism of claim 5, wherein one of said engineered metabolic pathways comprises conversion of a carbohydrate source to one or more sugar units by a saccharolytic enzyme.

14. The recombinant microorganism of claim 6, wherein one of said engineered metabolic pathways comprises conversion of a carbohydrate source to one or more sugar units by a saccharolytic enzyme.

15. The recombinant microorganism of claim 7, wherein one of said engineered metabolic pathways comprises conversion of a carbohydrate source to one or more sugar units by a saccharolytic enzyme.

16. The recombinant microorganism of claim 8, wherein one of said engineered metabolic pathways comprises conversion of a carbohydrate source to one or more sugar units by a saccharolytic enzyme.

17. The recombinant microorganism of claim 9, wherein one of said engineered metabolic pathways comprises conversion of a carbohydrate source to one or more sugar units by a saccharolytic enzyme.

18. The recombinant microorganism of claim 1, wherein said one or more native enzymes that function to produce glycerol is encoded by a gpd2 polynucleotide, and wherein one of said engineered metabolic pathways comprises conversion of acetyl-CoA to ethanol by a bifunctional acetaldehyde/alcohol dehydrogenase and one of said engineered metabolic pathways comprises conversion of a carbohydrate source to one or more sugar units by a saccharolytic enzyme, and further comprising a deletion of one or more native enzymes encoded by both an fdh1 polynucleotide and an fdh2 polynucleotide.

* * * * *

SEQUENCE LISTING

```
<160> NUMBER OF SEQ ID NOS: 191

<210> SEQ ID NO 1
<211> LENGTH: 3599
<212> TYPE: DNA
<213> ORGANISM: Saccharomyces cerevisiae
<220> FEATURE:
<221> NAME/KEY: misc_feature
<223> OTHER INFORMATION: FPS1
<220> FEATURE:
<221> NAME/KEY: misc_feature
<222> LOCATION: (801)..(2810)
<223> OTHER INFORMATION: coding sequence

<400> SEQUENCE: 1
```

-continued

```
ttgacggcag ttctcatagc atctcaaagc aatagcagtg caaaagtaca taaccgtagg      60
aaggtacgcg gtaggtattt gagttcgttg gtggttatcc tccgcaaggc gcttcggcgg     120
ttatttgttg atagtcgaag aacaccaaaa aaaatgctgt tattgctttc tccgtaaaca     180
ataaaacccg gtagcgggat aacgcggctg atgcttttat ttaggaagga atacttacat     240
tatcatgaga acattgtcaa gggcattctg atacgggcct tccatcgcaa gaaaaaggca     300
gcaacggact gagggacgga gagagttacg gcataagaag tagtaggaga gcagagtgtc     360
ataaagttat attattctcg tcctaaagtc aattagttct gttgcgcttg acaatatatg     420
tcgtgtaata ccgtccctta gcagaagaaa gaaagacgga tccatatatg ttaaaatgct     480
tcagagatgt ttcttttaatg tgccgtccaa caaaggtatc ttctgtagct tcctctattt     540
tcgatcagat ctcatagtga gaaggcgcaa ttcagtagtt aaaagcgggg aacagtgtga     600
atccggagac ggcaagattg cccggccctt tttgcggaaa agataaaaca agatatattg     660 cacttttttcc accaagaaaa acaggaagtg gattaaaaaa tcaacaaagt ataacgccta     720
ttgtcccaat aagcgtcggt tgttcttctt tattatttta ccaagtacgc tcgagggtac     780
attctaatgc attaaaagac atgagtaatc ctcaaaaagc tctaaacgac tttctgtcca     840
gtgaatctgt tcatacacat gatagttcta ggaaacaatc taataagcag tcatccgacg     900
aaggacgctc ttcatcacaa ccttcacatc atcactctgg tggtactaac aacaataata     960
acaataataa taataataat aacagtaaca acaacaacaa cggcaacgat gggggaaatg    1020
atgacgacta tgattatgaa atgcaagatt atagaccttc tccgcaaagt gcgcggccta    1080
ctcccacgta tgttccacaa tattctgtag aaagtgggac tgctttcccg attcaagagg    1140
ttattcctag cgcatacatt aacacacaag atataaacca taaagataac ggtccgccga    1200
gtgcaagcag taatagagca ttcaggccta gagggcagac cacagtgtcg gccaacgtgc    1260
ttaacattga agatttttac aaaaatgcag acgatgcgca taccatcccg gagtcacatt    1320
tatcgagaag gagaagtagg tcgagggcta cgagtaatgc tgggcacagt gccaatacag    1380
gcgccacgaa tggcaggact actggtgccc aaactaatat ggaaagcaat gaatcaccac    1440
gtaacgtccc cattatggtg aagccaaaga cattatacca gaaccctcaa acacctacag    1500
tcttgccctc cacataccat ccaattaata aatggtcttc cgtcaaaaac acttatttga    1560
aggaattttt agccgagttt atgggaacaa tggttatgat tatttttcggt agtgctgttg    1620 tttgtcaggt caatgttgct gggaaaatac agcaggacaa tttcaacgtg gctttggata    1680
accttaacgt taccgggtct tctgcagaaa cgatagacgc tatgaagagt ttaacatcct    1740
tggtttcatc cgttgcgggc ggtacctttg atgatgtggc attgggctgg gctgctgccg    1800
tggtgatggg ctatttctgc gctggtggta gtgccatctc aggtgctcat ttgaatccgt    1860
ctattacatt agccaatttg gtgtatagag gttttcccct gaagaaagtt ccttattact    1920
ttgctggaca attgatcggt gccttcacag gcgctttgat cttgtttatt tggtacaaaa    1980
gggtgttaca agaggcatat agcgattggt ggatgaatga aagtgttgcg ggaatgtttt    2040 gcgttttttcc aaagccttat ctaagttcag gacggcaatt ttttttccgaa ttttttatgtg    2100 gagctatgtt acaagcagga acatttgcgc tgaccgatcc ttatacgtgt ttgtcctctg    2160 atgtttttccc attgatgatg tttatttttga ttttcattat caatgcttcc atggcttatc    2220
agacaggtac agcaatgaat ttggctcgtg atctgggccc acgtcttgca ctatatgcag    2280
ttggatttga tcataaaatg ctttgggtgc atcatcatca tttctttttgg gttcccatgg    2340 taggcccatt tattggtgcg ttaatggggg ggttggttta cgatgtctgt atttatcagg    2400
```

-continued

```
gtcatgaatc tccagtcaac tggtctttac cagtttataa ggaaatgatt atgagagcct    2460
ggtttagaag gcctggttgg aagaagagaa atagagcaag aagaacatcg gacctgagtg    2520
acttctcata caataacgat gatgatgagg aatttggaga agaatggct cttcaaaaga     2580 caaagaccaa gtcatctatt tcagacaacg aaaatgaagc aggagaaaag aaagtgcaat    2640
ttaaatctgt tcagcgcggc aaaagaacgt ttggtggtat accaacaatt cttgaagaag    2700
aagattccat tgaaactgct tcgctaggtg cgacgacgac tgattctatt gggttatccg    2760
acacatcatc agaagattcg cattatggta atgctaagaa ggtaacatga aaaacagac     2820 aagaaaaaga aacaaataat atagactgat agaaaaaaat actgcttact accgccggta    2880
taatatatat atatatatat atttacatag atgattgcat agtgttttaa aaagctttcc    2940
taggttaagc tatgaatctt cataacctaa ccaactaaat atgaaaatac tgacccatcg    3000
tcttaagtaa gttgacatga actcagcctg gtcacctact atacatgatg tatcgcatgg    3060
atggaaagaa taccaaacgc taccttccag gttaatgata gtatccaaac ctagttggaa    3120
tttgccttga acatcaagca gcgattcgat atcagttggg agcatcaatt tggtcattgg    3180
aataccatct atgcttttct cctcccatat tcgcaaaagt agtaagggct cgttatatac    3240
ttttgaatat gtaagatata attctatatg atttagtaat ttattttcta tacgctcagt    3300 attttctgc agttgtcgag taggtattaa acgcaaaaga agtccatcct tttcatcatt     3360
caaatggaca tcttggcaaa gggcccagtt atggaaaatc tgggagtcat acaacgattg    3420
cagttggcta tgccactcct ggtaaggaat catcaagtct gataattctg ttttttagcc    3480
cttttttttt tttttcatg gtgttctctt ctcattgctt ttcaattta agttcgttac      3540 ctttcatata gagtttctta acagaaattt cacaacgaaa atataattaa ctacaggca     3599
```

```
<210> SEQ ID NO 2
<211> LENGTH: 669
<212> TYPE: PRT
<213> ORGANISM: Saccharomyces cerevisiae
<220> FEATURE:
<221> NAME/KEY: MISC_FEATURE
<223> OTHER INFORMATION: FPS1

<400> SEQUENCE: 2
```

```
Met Ser Asn Pro Gln Lys Ala Leu Asn Asp Phe Leu Ser Ser Glu Ser
1               5                   10                  15

Val His Thr His Asp Ser Ser Arg Lys Gln Ser Asn Lys Gln Ser Ser
            20                  25                  30

Asp Glu Gly Arg Ser Ser Ser Gln Pro Ser His His His Ser Gly Gly
        35                  40                  45

Thr Asn Asn Asn Asn Asn Asn Asn Asn Asn Asn Ser Asn Asn
    50                  55                  60

Asn Asn Asn Gly Asn Asp Gly Gly Asn Asp Asp Tyr Asp Tyr Glu
65                  70                  75                  80

Met Gln Asp Tyr Arg Pro Ser Pro Gln Ser Ala Arg Pro Thr Pro Thr
                85                  90                  95

Tyr Val Pro Gln Tyr Ser Val Glu Ser Gly Thr Ala Phe Pro Ile Gln
            100                 105                 110

Glu Val Ile Pro Ser Ala Tyr Ile Asn Thr Gln Asp Ile Asn His Lys
        115                 120                 125

Asp Asn Gly Pro Pro Ser Ala Ser Ser Asn Arg Ala Phe Arg Pro Arg
    130                 135                 140
```

-continued

```
Gly Gln Thr Thr Val Ser Ala Asn Val Leu Asn Ile Glu Asp Phe Tyr
145                 150                 155                 160

Lys Asn Ala Asp Asp Ala His Thr Ile Pro Glu Ser His Leu Ser Arg
                165                 170                 175

Arg Arg Ser Arg Ser Arg Ala Thr Ser Asn Ala Gly His Ser Ala Asn
            180                 185                 190

Thr Gly Ala Thr Asn Gly Arg Thr Gly Ala Gln Thr Asn Met Glu
        195                 200                 205

Ser Asn Glu Ser Pro Arg Asn Val Pro Ile Met Val Lys Pro Lys Thr
    210                 215                 220

Leu Tyr Gln Asn Pro Gln Thr Pro Thr Val Leu Pro Ser Thr Tyr His
225                 230                 235                 240

Pro Ile Asn Lys Trp Ser Ser Val Lys Asn Thr Tyr Leu Lys Glu Phe
                245                 250                 255

Leu Ala Glu Phe Met Gly Thr Met Val Met Ile Ile Phe Gly Ser Ala
                260                 265                 270

Val Val Cys Gln Val Asn Val Ala Gly Lys Ile Gln Gln Asp Asn Phe
        275                 280                 285

Asn Val Ala Leu Asp Asn Leu Asn Val Thr Gly Ser Ser Ala Glu Thr
    290                 295                 300

Ile Asp Ala Met Lys Ser Leu Thr Ser Leu Val Ser Ser Val Ala Gly
305                 310                 315                 320

Gly Thr Phe Asp Asp Val Ala Leu Gly Trp Ala Ala Val Val Met
                325                 330                 335

Gly Tyr Phe Cys Ala Gly Gly Ser Ala Ile Ser Gly Ala His Leu Asn
                340                 345                 350

Pro Ser Ile Thr Leu Ala Asn Leu Val Tyr Arg Gly Phe Pro Leu Lys
                355                 360                 365

Lys Val Pro Tyr Tyr Phe Ala Gly Gln Leu Ile Gly Ala Phe Thr Gly
        370                 375                 380

Ala Leu Ile Leu Phe Ile Trp Tyr Lys Arg Val Leu Gln Glu Ala Tyr
385                 390                 395                 400

Ser Asp Trp Trp Met Asn Glu Ser Val Ala Gly Met Phe Cys Val Phe
                405                 410                 415

Pro Lys Pro Tyr Leu Ser Ser Gly Arg Gln Phe Phe Ser Glu Phe Leu
            420                 425                 430

Cys Gly Ala Met Leu Gln Ala Gly Thr Phe Ala Leu Thr Asp Pro Tyr
        435                 440                 445

Thr Cys Leu Ser Ser Asp Val Phe Pro Leu Met Met Phe Ile Leu Ile
    450                 455                 460

Phe Ile Ile Asn Ala Ser Met Ala Tyr Gln Thr Gly Thr Ala Met Asn
465                 470                 475                 480

Leu Ala Arg Asp Leu Gly Pro Arg Leu Ala Leu Tyr Ala Val Gly Phe
                485                 490                 495

Asp His Lys Met Leu Trp Val His His His Phe Phe Trp Val Pro
            500                 505                 510

Met Val Gly Pro Phe Ile Gly Ala Leu Met Gly Gly Leu Val Tyr Asp
        515                 520                 525

Val Cys Ile Tyr Gln Gly His Glu Ser Pro Val Asn Trp Ser Leu Pro
    530                 535                 540

Val Tyr Lys Glu Met Ile Met Arg Ala Trp Phe Arg Arg Pro Gly Trp
545                 550                 555                 560

Lys Lys Arg Asn Arg Ala Arg Arg Thr Ser Asp Leu Ser Asp Phe Ser
```

```
                      565                 570                 575
Tyr Asn Asn Asp Asp Glu Glu Phe Gly Glu Arg Met Ala Leu Gln
                580                 585                 590

Lys Thr Lys Thr Lys Ser Ser Ile Ser Asp Asn Glu Asn Glu Ala Gly
            595                 600                 605

Glu Lys Lys Val Gln Phe Lys Ser Val Gln Arg Gly Lys Arg Thr Phe
        610                 615                 620

Gly Gly Ile Pro Thr Ile Leu Glu Glu Glu Asp Ser Ile Glu Thr Ala
625                 630                 635                 640

Ser Leu Gly Ala Thr Thr Thr Asp Ser Ile Gly Leu Ser Asp Thr Ser
                645                 650                 655

Ser Glu Asp Ser His Tyr Gly Asn Ala Lys Lys Val Thr
                660                 665

<210> SEQ ID NO 3
<211> LENGTH: 759
<212> TYPE: DNA
<213> ORGANISM: Bacillus licheniformis
<220> FEATURE:
<221> NAME/KEY: misc_feature
<223> OTHER INFORMATION: DSM13

<400> SEQUENCE: 3
atggatggaa atattcattc gatcgaaaca ttcggcaccg ttgacggtcc aggcatcagg      60
tatgtcgtct tcacacaagg ctgcctgatg cgctgtcaat tttgccataa tgctgatact     120
tgggaaatcg gaaccggaaa acaaatgacg gtttccgaaa tcgttcagga tgtccagcat     180
tatctcccgt ttattcaatc atcgggcgga ggcatcaccg tgagcggagg cgagccgctt     240
ttacaactgc cgttttaat cgagctgttc aaagcatgca aaagcctcgg cattcacacg      300
gcactcgatt cgtccggcgg atgctattcg gctgcgccgg catttcaaga gcagatcaaa     360
gaactgatcc agtatacaga ccttgttttg cttgacctca gcatcacaa cagaaaaaaa     420 catatcaacc tgacaggaat gccgaatgac acatttttag aatttgcccg gtttctcgct     480
gaacatcaag ttcccgtctg gatccgccac gtactggttc cggggatctc cgatatcgat     540
gccgatttaa cggccctcgg cacgtttatc ggcacgcttg cgaacgttca gaaggtggag     600
gttcttcctt atcacaagct cggcgtctac aaatgggaag cgcttggcct ggattatccg     660 ttaaagggg ttgaaccgcc aagtgccgac agggccgaaa atgcgtacag actgctcacc     720
gcacacttgc aaggcggatc cttgctgcaa gagacataa                            759

<210> SEQ ID NO 4
<211> LENGTH: 252
<212> TYPE: PRT
<213> ORGANISM: Bacillus licheniformis
<220> FEATURE:
<221> NAME/KEY: MISC_FEATURE
<223> OTHER INFORMATION: DSM13

<400> SEQUENCE: 4

Met Asp Gly Asn Ile His Ser Ile Glu Thr Phe Gly Thr Val Asp Gly
1               5                   10                  15

Pro Gly Ile Arg Tyr Val Val Phe Thr Gln Gly Cys Leu Met Arg Cys
            20                  25                  30

Gln Phe Cys His Asn Ala Asp Thr Trp Glu Ile Gly Thr Gly Lys Gln
        35                  40                  45

Met Thr Val Ser Glu Ile Val Gln Asp Val Gln His Tyr Leu Pro Phe
    50                  55                  60
```

```
Ile Gln Ser Ser Gly Gly Ile Thr Val Ser Gly Glu Pro Leu
65                  70                  75                  80

Leu Gln Leu Pro Phe Leu Ile Glu Leu Phe Lys Ala Cys Lys Ser Leu
                85                  90                  95

Gly Ile His Thr Ala Leu Asp Ser Ser Gly Cys Tyr Ser Ala Ala
            100                 105                 110

Pro Ala Phe Gln Glu Gln Ile Lys Glu Leu Ile Gln Tyr Thr Asp Leu
            115                 120                 125

Val Leu Leu Asp Leu Lys His His Asn Arg Lys Lys His Ile Asn Leu
130                 135                 140

Thr Gly Met Pro Asn Asp His Ile Leu Glu Phe Ala Arg Phe Leu Ala
145                 150                 155                 160

Glu His Gln Val Pro Val Trp Ile Arg His Val Leu Val Pro Gly Ile
                165                 170                 175

Ser Asp Ile Asp Ala Asp Leu Thr Ala Leu Gly Thr Phe Ile Gly Thr
            180                 185                 190

Leu Ala Asn Val Gln Lys Val Glu Val Leu Pro Tyr His Lys Leu Gly
            195                 200                 205

Val Tyr Lys Trp Glu Ala Leu Gly Leu Asp Tyr Pro Leu Lys Gly Val
210                 215                 220

Glu Pro Pro Ser Ala Asp Arg Ala Glu Asn Ala Tyr Arg Leu Leu Thr
225                 230                 235                 240

Ala His Leu Gln Gly Gly Ser Leu Leu Gln Glu Thr
            245                 250

<210> SEQ ID NO 5
<211> LENGTH: 759
<212> TYPE: DNA
<213> ORGANISM: Bacillus licheniformis
<220> FEATURE:
<221> NAME/KEY: misc_feature
<223> OTHER INFORMATION: ATCC14580

<400> SEQUENCE: 5
atggatggaa atattcattc gatcgaaaca ttcggcaccg ttgacggtcc aggcatcagg      60
tatgtcgtct tcacacaagg ctgcctgatg cgctgtcaat tttgccataa tgctgatact     120
tgggaaatcg gaaccggaaa acaaatgacg gtttccgaaa tcgttcagga tgtccagcat     180
tatctcccgt ttattcaatc atcgggcgga ggcatcaccg tgagcggagg cgagccgctt     240
ttacaactgc cgttttttaat cgagctgttc aaagcatgca aaagcctcgg cattcacacg     300
gcactcgatt cgtccggcgg atgctattcg gctgcgccgg catttcaaga gcagatcaaa     360
gaactgatcc agtatacaga ccttgttttg cttgacctca agcatcacaa cagaaaaaaa     420
catatcaacc tgacaggaat gccgaatgac cacattttag aatttgcccg gtttctcgct     480
gaacatcaag ttcccgtctg gatccgccac gtactggttc cggggatctc cgatatcgat     540
gccgatttaa cggccctcgg cacgtttatc ggcacgcttg cgaacgttca gaaggtggag     600
gttcttcctt atcacaagct cggcgtctac aaatgggaag cgcttggcct ggattatccg     660
ttaaaagggg ttgaaccgcc aagtgccgac agggccgaaa atgcgtacag actgctcacc     720
gcacacttgc aaggcggatc cttgctgcaa gagacataa                            759

<210> SEQ ID NO 6
<211> LENGTH: 252
<212> TYPE: PRT
<213> ORGANISM: Bacillus licheniformis
```

-continued

```
<220> FEATURE:
<221> NAME/KEY: MISC_FEATURE
<223> OTHER INFORMATION: ATCC14580

<400> SEQUENCE: 6
```

Met Asp Gly Asn Ile His Ser Ile Glu Thr Phe Gly Thr Val Asp Gly
1               5                   10                  15

Pro Gly Ile Arg Tyr Val Val Phe Thr Gln Gly Cys Leu Met Arg Cys
            20                  25                  30

Gln Phe Cys His Asn Ala Asp Thr Trp Glu Ile Gly Thr Gly Lys Gln
        35                  40                  45

Met Thr Val Ser Glu Ile Val Gln Asp Val Gln His Tyr Leu Pro Phe
50                  55                  60

Ile Gln Ser Ser Gly Gly Ile Thr Val Ser Gly Gly Glu Pro Leu
65                  70                  75                  80

Leu Gln Leu Pro Phe Leu Ile Glu Leu Phe Lys Ala Cys Lys Ser Leu
                85                  90                  95

Gly Ile His Thr Ala Leu Asp Ser Ser Gly Gly Cys Tyr Ser Ala Ala
            100                 105                 110

Pro Ala Phe Gln Glu Gln Ile Lys Glu Leu Ile Gln Tyr Thr Asp Leu
        115                 120                 125

Val Leu Leu Asp Leu Lys His His Asn Arg Lys Lys His Ile Asn Leu
130                 135                 140

Thr Gly Met Pro Asn Asp His Ile Leu Glu Phe Ala Arg Phe Leu Ala
145                 150                 155                 160

Glu His Gln Val Pro Val Trp Ile Arg His Val Leu Val Pro Gly Ile
                165                 170                 175

Ser Asp Ile Asp Ala Asp Leu Thr Ala Leu Gly Thr Phe Ile Gly Thr
            180                 185                 190

Leu Ala Asn Val Gln Lys Val Glu Val Leu Pro Tyr His Lys Leu Gly
        195                 200                 205

Val Tyr Lys Trp Glu Ala Leu Gly Leu Asp Tyr Pro Leu Lys Gly Val
210                 215                 220

Glu Pro Pro Ser Ala Asp Arg Ala Glu Asn Ala Tyr Arg Leu Leu Thr
225                 230                 235                 240

Ala His Leu Gln Gly Gly Ser Leu Leu Gln Glu Thr
                245                 250

```
<210> SEQ ID NO 7
<211> LENGTH: 801
<212> TYPE: DNA
<213> ORGANISM: Streptococcus thermophilus
<220> FEATURE:
<221> NAME/KEY: misc_feature
<223> OTHER INFORMATION: CNRZ1066

<400> SEQUENCE: 7
atggcagaaa ttgattacag tcaggtgact ggacttgttc attcaaccga aagtttcgga      60
tccgtagatg gtcctggtat ccgttttatt gtgtttatgc aaggctgtaa gctgcgttgc     120
caatattgtc ataacccaga tacttgggcc atgaagtcaa ataaggctgt tgaacgtaca     180
gttgaagatg tcttagaaga ggctcttcgc ttccgtcatt tctggggtga gcatggtgga     240
atcactgtat caggtggtga agccatgctt cagattgatt ttgtcactgc cctctttaca     300
gaggctaaga agttagggat tcactgtacg cttgatacgt gtggcttgtc ttatcgtaat     360
actccagagt atcatgaagt tgtcgacaaa cttttggctg taactgactt ggttctactg     420
```

-continued

```
gatatcaaag agattgaccc cgaacaacac aagtttgtga cccgtcaacc taataagaat    480
atcttggaat ttgctcaata tctgtctgat aaacaagttc cggtctggat tcgtcatgtc    540
ttggtacctg gtttgacaga ttttgacgaa cacttggtta agctcggcga gtttgtaaag    600
accttgaaaa atgtcgataa atttgaaatt cttccatatc atacgatggg ggaattcaag    660
tggcgtgaac ttggcatccc ttatccattg gaaggtgtca aaccaccaac tgcagatcgt    720
gttaaaaatg ctaaggctct tatgcatacg gaaacttatc aagagtataa gaatcgtatc    780
ggggttaaaa ccttggatta a                                              801
```

<210> SEQ ID NO 8
<211> LENGTH: 266
<212> TYPE: PRT
<213> ORGANISM: Streptococcus thermophilus
<220> FEATURE:
<221> NAME/KEY: MISC_FEATURE
<223> OTHER INFORMATION: CNRZ1066

<400> SEQUENCE: 8

Met Ala Glu Ile Asp Tyr Ser Gln Val Thr Gly Leu Val His Ser Thr
1               5                   10                  15

Glu Ser Phe Gly Ser Val Asp Gly Pro Gly Ile Arg Phe Ile Val Phe
            20                  25                  30

Met Gln Gly Cys Lys Leu Arg Cys Gln Tyr Cys His Asn Pro Asp Thr
        35                  40                  45

Trp Ala Met Lys Ser Asn Lys Ala Val Glu Arg Thr Val Glu Asp Val
    50                  55                  60

Leu Glu Glu Ala Leu Arg Phe Arg His Phe Trp Gly Glu His Gly Gly
65                  70                  75                  80

Ile Thr Val Ser Gly Gly Glu Ala Met Leu Gln Ile Asp Phe Val Thr
                85                  90                  95

Ala Leu Phe Thr Glu Ala Lys Lys Leu Gly Ile His Cys Thr Leu Asp
            100                 105                 110

Thr Cys Gly Leu Ser Tyr Arg Asn Thr Pro Glu Tyr His Glu Val Val
        115                 120                 125

Asp Lys Leu Leu Ala Val Thr Asp Leu Val Leu Leu Asp Ile Lys Glu
130                 135                 140

Ile Asp Pro Glu Gln His Lys Phe Val Thr Arg Gln Pro Asn Lys Asn
145                 150                 155                 160

Ile Leu Glu Phe Ala Gln Tyr Leu Ser Asp Lys Gln Val Pro Val Trp
                165                 170                 175

Ile Arg His Val Leu Val Pro Gly Leu Thr Asp Phe Asp Glu His Leu
            180                 185                 190

Val Lys Leu Gly Glu Phe Val Lys Thr Leu Lys Asn Val Asp Lys Phe
        195                 200                 205

Glu Ile Leu Pro Tyr His Thr Met Gly Glu Phe Lys Trp Arg Glu Leu
    210                 215                 220

Gly Ile Pro Tyr Pro Leu Glu Gly Val Lys Pro Thr Ala Asp Arg
225                 230                 235                 240

Val Lys Asn Ala Lys Ala Leu Met His Thr Glu Thr Tyr Gln Glu Tyr
                245                 250                 255

Lys Asn Arg Ile Gly Val Lys Thr Leu Asp
            260                 265

<210> SEQ ID NO 9
<211> LENGTH: 801

<212> TYPE: DNA
<213> ORGANISM: Streptococcus thermophilus
<220> FEATURE:
<221> NAME/KEY: misc_feature
<223> OTHER INFORMATION: LMG18311

<400> SEQUENCE: 9

```
atggcagaaa ttgattacag tcaggtgact ggacttgttc attcaaccga aagtttcgga      60
tccgtagatg gtcctggtat ccgttttatt gtgtttatgc aaggctgtaa gctgcgttgc     120
caatattgtc ataacccaga tacttgggcc atgaagtcaa ataaggctgt tgaacgtaca     180
gttgaagatg tcttagaaga ggctcttcgc ttccgtcatt tctggggtga gcatggtgga     240
atcactgtat caggtggtga agccatgctt cagattgatt ttgtcactgc cctctttaca     300
gaggctaaga agttagggat tcactgtacg cttgatacgt gtggcttgtc ttatcgtaat     360
actccagagt atcatgaagt tgtcgacaaa cttttggctg taactgactt ggttctactg     420
gatatcaaag agattgaccc cgaacaacac aagtttgtga cccgtcaacc taataagaat     480
atcttggaat ttgctcaata tctgtctgat aaacaagttc cggtctggat tcgtcatgtc     540
ttggtacctg gtttgacaga ttttgacgaa cacttggtta agctcggcga gtttgtaaag     600
accttgaaaa atgtcgataa atttgaaatt cttccatatc atacgatggg ggaattcaag     660
tggcgtgaac ttggcatccc ttatccattg gaaggtgtca aaccaccaac tgcagatcgt     720
gttaaaaatg ctaaggctct tatgcatacg gaaacttatc aagagtataa gaatcgtatc     780
ggggttaaaa ccttggatta a                                                801
```

<210> SEQ ID NO 10
<211> LENGTH: 266
<212> TYPE: PRT
<213> ORGANISM: Streptococcus thermophilus
<220> FEATURE:
<221> NAME/KEY: MISC_FEATURE
<223> OTHER INFORMATION: LMG18311

<400> SEQUENCE: 10

```
Met Ala Glu Ile Asp Tyr Ser Gln Val Thr Gly Leu Val His Ser Thr
1               5                   10                  15

Glu Ser Phe Gly Ser Val Asp Gly Pro Gly Ile Arg Phe Ile Val Phe
                20                  25                  30

Met Gln Gly Cys Lys Leu Arg Cys Gln Tyr Cys His Asn Pro Asp Thr
            35                  40                  45

Trp Ala Met Lys Ser Asn Lys Ala Val Glu Arg Thr Val Glu Asp Val
        50                  55                  60

Leu Glu Glu Ala Leu Arg Phe Arg His Phe Trp Gly Glu His Gly Gly
65                  70                  75                  80

Ile Thr Val Ser Gly Gly Glu Ala Met Leu Gln Ile Asp Phe Val Thr
                85                  90                  95

Ala Leu Phe Thr Glu Ala Lys Lys Leu Gly Ile His Cys Thr Leu Asp
            100                 105                 110

Thr Cys Gly Leu Ser Tyr Arg Asn Thr Pro Glu Tyr His Glu Val Val
        115                 120                 125

Asp Lys Leu Leu Ala Val Thr Asp Leu Val Leu Leu Asp Ile Lys Glu
    130                 135                 140

Ile Asp Pro Glu Gln His Lys Phe Val Thr Arg Gln Pro Asn Lys Asn
145                 150                 155                 160

Ile Leu Glu Phe Ala Gln Tyr Leu Ser Asp Lys Gln Val Pro Val Trp
                165                 170                 175
```

Ile Arg His Val Leu Val Pro Gly Leu Thr Asp Phe Asp Glu His Leu
            180                 185                 190

Val Lys Leu Gly Glu Phe Val Lys Thr Leu Lys Asn Val Asp Lys Phe
        195                 200                 205

Glu Ile Leu Pro Tyr His Thr Met Gly Glu Phe Lys Trp Arg Glu Leu
    210                 215                 220

Gly Ile Pro Tyr Pro Leu Glu Gly Val Lys Pro Pro Thr Ala Asp Arg
225                 230                 235                 240

Val Lys Asn Ala Lys Ala Leu Met His Thr Glu Thr Tyr Gln Glu Tyr
            245                 250                 255

Lys Asn Arg Ile Gly Val Lys Thr Leu Asp
            260                 265

<210> SEQ ID NO 11
<211> LENGTH: 801
<212> TYPE: DNA
<213> ORGANISM: Streptococcus thermophilus
<220> FEATURE:
<221> NAME/KEY: misc_feature
<223> OTHER INFORMATION: LMD-9

<400> SEQUENCE: 11

| | | | | | |
|---|---|---|---|---|---|
| atggcagaaa | ttgattacag | tcaggtgact | ggacttgttc | attcaaccga | aagtttcgga | 60 |
| tccgtagatg | gtcctggtat | ccgttttatt | gtgtttatgc | aaggctgtaa | gctgcgttgc | 120 |
| caatattgtc | ataacccaga | tacttgggcc | atgaagtcaa | ataaggctgt | gaacgtaca | 180 |
| gttgaagatg | tcttagaaga | ggctcttcgc | ttccgtcatt | tctggggtga | gcatggtgga | 240 |
| atcactgtat | caggtggtga | agccatgctt | cagattgatt | ttgtcactgc | cctctttaca | 300 |
| gaggctaaga | agttagggat | tcactgtacg | cttgatacgt | gtggcttgtc | ttatcgtaat | 360 |
| actccagagt | atcatgaagt | tgtcgacaaa | cttttggctg | taactgactt | ggttctactg | 420 |
| gatatcaaag | agattgaccc | cgaacaacac | aagtttgtga | cccgtcaacc | taataagaat | 480 |
| atcttggaat | tgctcaata | tctgtctgat | aaacaagttc | cggtctggat | tcgtcatgtc | 540 |
| ttggtacctg | gtttgacaga | ttttgacgaa | cacttggtta | agctcggcga | gtttgtaaag | 600 |
| accttgaaaa | atgtcgataa | atttgaaatt | cttccatatc | atacgatggg | ggaattcaag | 660 |
| tggcgtgaac | ttggcatccc | ttatccattg | gaaggtgtca | aaccaccaac | tgcagatcgt | 720 |
| gttaaaaatg | ctaaggctct | tatgcatacg | gaaacttatc | aagagtataa | gaatcgtatc | 780 |
| ggggttaaaa | ccttggatta | a | | | | 801 |

<210> SEQ ID NO 12
<211> LENGTH: 266
<212> TYPE: PRT
<213> ORGANISM: Streptococcus thermophilus
<220> FEATURE:
<221> NAME/KEY: MISC_FEATURE
<223> OTHER INFORMATION: LMD-9

<400> SEQUENCE: 12

Met Ala Glu Ile Asp Tyr Ser Gln Val Thr Gly Leu Val His Ser Thr
1               5                   10                  15

Glu Ser Phe Gly Ser Val Asp Gly Pro Gly Ile Arg Phe Ile Val Phe
            20                  25                  30

Met Gln Gly Cys Lys Leu Arg Cys Gln Tyr Cys His Asn Pro Asp Thr
        35                  40                  45

Trp Ala Met Lys Ser Asn Lys Ala Val Glu Arg Thr Val Glu Asp Val

```
            50                  55                  60
Leu Glu Glu Ala Leu Arg Phe Arg His Phe Trp Gly Glu His Gly Gly
65                  70                  75                  80

Ile Thr Val Ser Gly Gly Glu Ala Met Leu Gln Ile Asp Phe Val Thr
                85                  90                  95

Ala Leu Phe Thr Glu Ala Lys Lys Leu Gly Ile His Cys Thr Leu Asp
            100                 105                 110

Thr Cys Gly Leu Ser Tyr Arg Asn Thr Pro Glu Tyr His Glu Val Val
        115                 120                 125

Asp Lys Leu Leu Ala Val Thr Asp Leu Val Leu Leu Asp Ile Lys Glu
130                 135                 140

Ile Asp Pro Glu Gln His Lys Phe Val Thr Arg Gln Pro Asn Lys Asn
145                 150                 155                 160

Ile Leu Glu Phe Ala Gln Tyr Leu Ser Asp Lys Gln Val Pro Val Trp
                165                 170                 175

Ile Arg His Val Leu Val Pro Gly Leu Thr Asp Phe Asp Glu His Leu
            180                 185                 190

Val Lys Leu Gly Glu Phe Val Lys Thr Leu Lys Asn Val Asp Lys Phe
        195                 200                 205

Glu Ile Leu Pro Tyr His Thr Met Gly Glu Phe Lys Trp Arg Glu Leu
210                 215                 220

Gly Ile Pro Tyr Pro Leu Glu Gly Val Lys Pro Pro Thr Ala Asp Arg
225                 230                 235                 240

Val Lys Asn Ala Lys Ala Leu Met His Thr Glu Thr Tyr Gln Glu Tyr
                245                 250                 255

Lys Asn Arg Ile Gly Val Lys Thr Leu Asp
            260                 265

<210> SEQ ID NO 13
<211> LENGTH: 804
<212> TYPE: DNA
<213> ORGANISM: Lactobacillus plantarum
<220> FEATURE:
<221> NAME/KEY: misc_feature
<223> OTHER INFORMATION: WCFS1

<400> SEQUENCE: 13
atgccaacga tcacaactaa gacgcccgta aaaggactaa tatttaacat tcaaaaattt      60
agtatcaatg atggaccagg tattcgaaca gtagttttct ttaaagggtg cccgttacgc     120
tgcaagtggt gttctaatcc agaatcacaa tcaggtgagc aagaatcaat gtatgatgaa     180
cagaccgcca agcaaaccat cgtcggtgat tatatgacgg ttgatgatat tatgaaagtt     240
attctacaag ataaagactt ctatgaagag tctggcggtg gggtaacctt ctctggtggt     300
gaagttcttt ttcaagcttc ctttgcgatt gagcttgcta aggcagttaa agcagctggc     360
attaatttag cctgtgagac aactggttac gcacggccta aggttttaa tgaattcatg     420 tcttatatgg acttcatgta ttatgactgt aaacaatggg acccagccca acatcgaatc     480
ggaacgggtg ccgataacgg ggtaatttta cgtaacttag caactgcagt gcaagctcat     540
caaaagatga tggttcggat tccggttatt ccaggtttta attatacatt gaatgacgcg     600
gatcattttg acaactatt taatcagatt ggcgtaaccg aagttgaatt attgccattt     660
caccagtttg ggttgaaaaa gtatcaagat ttgggccgaa atatgcgct agttaatgtt     720 aaacagttac aagcgatga cttaattgat tatgctgaac atattcgtgc acatggtgtt     780
aaagtacggg tgaatgggtg gtaa                                             804
```

<210> SEQ ID NO 14
<211> LENGTH: 267
<212> TYPE: PRT
<213> ORGANISM: Lactobacillus plantarum
<220> FEATURE:
<221> NAME/KEY: MISC_FEATURE
<223> OTHER INFORMATION: WCFS1

<400> SEQUENCE: 14

Met Pro Thr Ile Thr Thr Lys Thr Pro Val Lys Gly Leu Ile Phe Asn
1               5                   10                  15

Ile Gln Lys Phe Ser Ile Asn Asp Gly Pro Gly Ile Arg Thr Val Val
            20                  25                  30

Phe Phe Lys Gly Cys Pro Leu Arg Cys Lys Trp Cys Ser Asn Pro Glu
        35                  40                  45

Ser Gln Ser Gly Glu Gln Glu Ser Met Tyr Asp Glu Gln Thr Ala Lys
    50                  55                  60

Gln Thr Ile Val Gly Asp Tyr Met Thr Val Asp Ile Met Lys Val
65                  70                  75                  80

Ile Leu Gln Asp Lys Asp Phe Tyr Glu Glu Ser Gly Gly Val Thr
                85                  90                  95

Phe Ser Gly Gly Glu Val Leu Phe Gln Ala Ser Phe Ala Ile Glu Leu
            100                 105                 110

Ala Lys Ala Val Lys Ala Ala Gly Ile Asn Leu Ala Cys Glu Thr Thr
        115                 120                 125

Gly Tyr Ala Arg Pro Lys Val Phe Asn Glu Phe Met Ser Tyr Met Asp
    130                 135                 140

Phe Met Tyr Tyr Asp Cys Lys Gln Trp Asp Pro Ala Gln His Arg Ile
145                 150                 155                 160

Gly Thr Gly Ala Asp Asn Gly Val Ile Leu Arg Asn Leu Ala Thr Ala
                165                 170                 175

Val Gln Ala His Gln Lys Met Met Val Arg Ile Pro Val Ile Pro Gly
            180                 185                 190

Phe Asn Tyr Thr Leu Asn Asp Ala Asp His Phe Gly Gln Leu Phe Asn
        195                 200                 205

Gln Ile Gly Val Thr Glu Val Glu Leu Leu Pro Phe His Gln Phe Gly
    210                 215                 220

Leu Lys Lys Tyr Gln Asp Leu Gly Arg Lys Tyr Ala Leu Val Asn Val
225                 230                 235                 240

Lys Gln Leu Gln Ala Asp Asp Leu Ile Asp Tyr Ala Glu His Ile Arg
                245                 250                 255

Ala His Gly Val Lys Val Arg Val Asn Gly Trp
            260                 265

<210> SEQ ID NO 15
<211> LENGTH: 822
<212> TYPE: DNA
<213> ORGANISM: Lactobacillus plantarum
<220> FEATURE:
<221> NAME/KEY: misc_feature
<223> OTHER INFORMATION: WCFS1

<400> SEQUENCE: 15
atggaaaaca aacaagtttc aacaacgcaa gcggcggcaa aggagccttt gataggctac      60
gttcactcca tcgaaacgtt tggctccgtt gacggaccag gtatccgtta cgtggcattc     120
cttcaaggat gccacatgcg ttgccaatac tgtcacaacc ctgatacttg gaaactcaac     180

```
gttggcgatc aaatgacggc cgacgagatt ctcgaagacg cggctaaata ccgggctttc     240
tggggcaaga cgggtggcat cacagtcagt ggtggtgaat cactggtaca aatcgacttc     300
atcttagact tattcgaaaa agccaaggcg atgaatatca gtacttgtct ggatacctct     360
ggacagcctt ttacccgaga caacctttc tttgacaagt cgaacgtct aatgaaggtc       420 acggacattt cgttggtcga cattaagcac atcgattctg ccaaacacaa gcagttgacc     480
cagtatggga acgaaaatat cttggatatg attcagtaca tggcccaaca ccacgatgat    540
atgtggattc gtcacgtcct ggttccccaa cggactgatt acgatgaaga cttgaagaaa     600
ctcggcgatt acattgctaa aattccaaac gacgtcgttc aaaaagtcga agtattgccg     660
taccatactt tgggcgttaa aaaatatcat gaaatgaaga tcaagtaccg gcttgaagga     720
atcgagtctc aacccaaga tcgggtggca aatgccgaaa agctactgca cactgctgat      780
tacaacgggt acaagacatg gatgccattg ccaaaacttt aa                        822
```

```
<210> SEQ ID NO 16
<211> LENGTH: 273
<212> TYPE: PRT
<213> ORGANISM: Lactobacillus plantarum
<220> FEATURE:
<221> NAME/KEY: MISC_FEATURE
<223> OTHER INFORMATION: WCFS1

<400> SEQUENCE: 16
```

Met Glu Asn Lys Gln Val Ser Thr Thr Gln Ala Ala Lys Glu Pro
1               5                   10                  15

Leu Ile Gly Tyr Val His Ser Ile Glu Thr Phe Gly Ser Val Asp Gly
            20                  25                  30

Pro Gly Ile Arg Tyr Val Ala Phe Leu Gln Gly Cys His Met Arg Cys
        35                  40                  45

Gln Tyr Cys His Asn Pro Asp Thr Trp Lys Leu Asn Val Gly Asp Gln
    50                  55                  60

Met Thr Ala Asp Glu Ile Leu Glu Asp Ala Ala Lys Tyr Arg Ala Phe
65                  70                  75                  80

Trp Gly Lys Thr Gly Gly Ile Thr Val Ser Gly Gly Glu Ser Leu Val
                85                  90                  95

Gln Ile Asp Phe Ile Leu Asp Leu Phe Glu Lys Ala Lys Ala Met Asn
            100                 105                 110

Ile Ser Thr Cys Leu Asp Thr Ser Gly Gln Pro Phe Thr Arg Glu Gln
        115                 120                 125

Pro Phe Phe Asp Lys Phe Glu Arg Leu Met Lys Val Thr Asp Ile Ser
    130                 135                 140

Leu Val Asp Ile Lys His Ile Asp Ser Ala Lys His Lys Gln Leu Thr
145                 150                 155                 160

Gln Tyr Gly Asn Glu Asn Ile Leu Asp Met Ile Gln Tyr Met Ala Gln
                165                 170                 175

His His Asp Asp Met Trp Ile Arg His Val Leu Val Pro Gln Arg Thr
            180                 185                 190

Asp Tyr Asp Glu Asp Leu Lys Lys Leu Gly Asp Tyr Ile Ala Lys Ile
        195                 200                 205

Pro Asn Asp Val Val Gln Lys Val Glu Val Leu Pro Tyr His Thr Leu
    210                 215                 220

Gly Val Lys Lys Tyr His Glu Met Lys Ile Lys Tyr Arg Leu Glu Gly
225                 230                 235                 240

Ile Glu Ser Pro Thr Gln Asp Arg Val Ala Asn Ala Glu Lys Leu Leu
                245                 250                 255

His Thr Ala Asp Tyr Asn Gly Tyr Lys Thr Trp Met Pro Leu Pro Lys
        260                 265                 270

Leu

<210> SEQ ID NO 17
<211> LENGTH: 822
<212> TYPE: DNA
<213> ORGANISM: Lactobacillus plantarum
<220> FEATURE:
<221> NAME/KEY: misc_feature
<223> OTHER INFORMATION: JDM1

<400> SEQUENCE: 17

| | | | | | |
|---|---|---|---|---|---|
| atggaaaaca | aacaagtttc | aacaacgcaa | gcggcggcaa | aagagccttt | gataggctac | 60 |
| gttcactcca | tcgaaacgtt | tggctccgtt | gacggaccag | gtatccgtta | cgtggcattc | 120 |
| cttcaaggat | gccacatgcg | ttgccaatac | tgtcacaacc | ctgatacttg | gaaactcaac | 180 |
| gttggcgatc | aaatgacggc | cgacgagatt | ctcgaagacg | cggctaaata | ccgggctttc | 240 |
| tgggcaaga | cgggtggcat | cacagtcagt | ggtggtgaat | cactggtaca | aatcgacttc | 300 |
| atcttagact | tattcgaaaa | agccaaggcg | atgaatatca | gtacttgtct | ggatacctct | 360 |
| ggacagcctt | ttacccgaga | caaccttttc | tttgacaagt | cgaacgtct | aatgaaggtc | 420 |
| acggacattt | cgttggtcga | cattaagcac | atcgattctg | ccaaacacaa | gcagttgacc | 480 |
| cagtatggga | acgaaaatat | cttggatatg | attcagtaca | tggcccaaca | ccacgatgat | 540 |
| atgtggattc | gtcacgtcct | ggttccccaa | cggactgatt | acgatgaaga | cttgaagaaa | 600 |
| ctcggcgatt | acattgctaa | gattccaaac | gacgtcgttc | aaaaagtcga | agtattgccg | 660 |
| taccatactt | tgggcgttaa | aaaatatcat | gaaatgaaga | tcaagtaccg | gcttgaagga | 720 |
| atcgagtctc | caacccaaga | tcgggtggca | aatgccgaaa | agctactgca | cactgctgat | 780 |
| tacaacgggt | acaagacatg | gatgccattg | ccaaaacttt | aa | | 822 |

<210> SEQ ID NO 18
<211> LENGTH: 273
<212> TYPE: PRT
<213> ORGANISM: Lactobacillus plantarum
<220> FEATURE:
<221> NAME/KEY: MISC_FEATURE
<223> OTHER INFORMATION: JDM1

<400> SEQUENCE: 18

Met Glu Asn Lys Gln Val Ser Thr Thr Gln Ala Ala Ala Lys Glu Pro
1               5                   10                  15

Leu Ile Gly Tyr Val His Ser Ile Glu Thr Phe Gly Ser Val Asp Gly
            20                  25                  30

Pro Gly Ile Arg Tyr Val Ala Phe Leu Gln Gly Cys His Met Arg Cys
        35                  40                  45

Gln Tyr Cys His Asn Pro Asp Thr Trp Lys Leu Asn Val Gly Asp Gln
    50                  55                  60

Met Thr Ala Asp Glu Ile Leu Glu Asp Ala Ala Lys Tyr Arg Ala Phe
65                  70                  75                  80

Trp Gly Lys Thr Gly Gly Ile Thr Val Ser Gly Gly Glu Ser Leu Val
                85                  90                  95

Gln Ile Asp Phe Ile Leu Asp Leu Phe Glu Lys Ala Lys Ala Met Asn
            100                 105                 110

```
Ile Ser Thr Cys Leu Asp Thr Ser Gly Gln Pro Phe Thr Arg Glu Gln
        115                 120                 125
Pro Phe Phe Asp Lys Phe Glu Arg Leu Met Lys Val Thr Asp Ile Ser
    130                 135                 140
Leu Val Asp Ile Lys His Ile Asp Ser Ala Lys His Lys Gln Leu Thr
145                 150                 155                 160
Gln Tyr Gly Asn Glu Asn Ile Leu Asp Met Ile Gln Tyr Met Ala Gln
                165                 170                 175
His His Asp Asp Met Trp Ile Arg His Val Leu Val Pro Gln Arg Thr
            180                 185                 190
Asp Tyr Asp Glu Asp Leu Lys Lys Leu Gly Asp Tyr Ile Ala Lys Ile
        195                 200                 205
Pro Asn Asp Val Val Gln Lys Val Glu Val Leu Pro Tyr His Thr Leu
    210                 215                 220
Gly Val Lys Lys Tyr His Glu Met Lys Ile Lys Tyr Arg Leu Glu Gly
225                 230                 235                 240
Ile Glu Ser Pro Thr Gln Asp Arg Val Ala Asn Ala Glu Lys Leu Leu
                245                 250                 255
His Thr Ala Asp Tyr Asn Gly Tyr Lys Thr Trp Met Pro Leu Pro Lys
            260                 265                 270
Leu

<210> SEQ ID NO 19
<211> LENGTH: 804
<212> TYPE: DNA
<213> ORGANISM: Lactobacillus plantarum
<220> FEATURE:
<221> NAME/KEY: misc_feature
<223> OTHER INFORMATION: JDM1

<400> SEQUENCE: 19
atgccaacga tcacaactaa gacgcccgta aaaggactaa tatttaacat tcaaaatttt      60
agtatcaatg atggaccagg tattcgaaca gtagttttct ttaaagggtg cccgttacgc     120
tgcaagtggt gttctaatcc agaatcacaa tcaggtgagc aagaatcaat gtatgatgaa     180
cagaccgcca agcaaaccat cgtcggtgat tatatgacgg ttgatgatat tatgaaagtt     240
attctacaag ataaagactt ctatgaagag tctggcggtg gggtaaccct ctctggtggt     300
gaagttcttt ttcaagcttc ctttgcgatt gagcttgcta aggcagttaa agcagctggc     360
attaatttag cctgtgagac aactggttac gcacggccta aggtttttaa tgaattcatg     420
tcttatatgg acttcatgta ttatgactgt aaacaatggg acccagccca acatcgaatc     480
ggaacgggtg ccgataacgg ggtaatttta cgtaacttag caactgcagt gcaagctcat     540
caaaagatga tggttcggat tccggttatt ccaggtttta attatacatt gaatgacgcg     600
gatcattttg acaactatt taatcagatt ggcgtaaccg aagttgaatt attgccattt     660
caccagtttg ggttgaaaaa gtatcaagat ttgggccgaa aatatgcgct agttaatgtt     720
aaacagttac aagcggatga cttaattgat tatgctgaac atattcgtgc acatggtgtt     780
aaagtacggg tgaatgggtg gtaa                                            804

<210> SEQ ID NO 20
<211> LENGTH: 267
<212> TYPE: PRT
<213> ORGANISM: Lactobacillus plantarum
<220> FEATURE:
<221> NAME/KEY: MISC_FEATURE
<223> OTHER INFORMATION: JDM1
```

<400> SEQUENCE: 20

```
Met Pro Thr Ile Thr Thr Lys Thr Pro Val Lys Gly Leu Ile Phe Asn
1               5                   10                  15

Ile Gln Lys Phe Ser Ile Asn Asp Gly Pro Gly Ile Arg Thr Val Val
            20                  25                  30

Phe Phe Lys Gly Cys Pro Leu Arg Cys Lys Trp Cys Ser Asn Pro Glu
        35                  40                  45

Ser Gln Ser Gly Glu Gln Glu Ser Met Tyr Asp Gln Thr Ala Lys
    50                  55                  60

Gln Thr Ile Val Gly Asp Tyr Met Thr Val Asp Ile Met Lys Val
65                  70                  75                  80

Ile Leu Gln Asp Lys Asp Phe Tyr Glu Glu Ser Gly Gly Val Thr
                85                  90                  95

Phe Ser Gly Gly Glu Val Leu Phe Gln Ala Ser Phe Ala Ile Glu Leu
            100                 105                 110

Ala Lys Ala Val Lys Ala Ala Gly Ile Asn Leu Ala Cys Glu Thr Thr
            115                 120                 125

Gly Tyr Ala Arg Pro Lys Val Phe Asn Glu Phe Met Ser Tyr Met Asp
130                 135                 140

Phe Met Tyr Tyr Asp Cys Lys Gln Trp Asp Pro Ala Gln His Arg Ile
145                 150                 155                 160

Gly Thr Gly Ala Asp Asn Gly Val Ile Leu Arg Asn Leu Ala Thr Ala
                165                 170                 175

Val Gln Ala His Gln Lys Met Met Val Arg Ile Pro Val Ile Pro Gly
            180                 185                 190

Phe Asn Tyr Thr Leu Asn Asp Ala Asp His Phe Gly Gln Leu Phe Asn
            195                 200                 205

Gln Ile Gly Val Thr Glu Val Glu Leu Leu Pro Phe His Gln Phe Gly
    210                 215                 220

Leu Lys Lys Tyr Gln Asp Leu Gly Arg Lys Tyr Ala Leu Val Asn Val
225                 230                 235                 240

Lys Gln Leu Gln Ala Asp Asp Leu Ile Asp Tyr Ala Glu His Ile Arg
                245                 250                 255

Ala His Gly Val Lys Val Arg Val Asn Gly Trp
            260                 265
```

<210> SEQ ID NO 21
<211> LENGTH: 852
<212> TYPE: DNA
<213> ORGANISM: Lactobacillus casei
<220> FEATURE:
<221> NAME/KEY: misc_feature
<223> OTHER INFORMATION: bl23

<400> SEQUENCE: 21

```
atgaaactca tcgatcagtc acaaagccca ttaaatatct tagaacaagt tggtcaggat      60
catgatggcc cgatcaaagg gtatgttcac tcggtcgaaa gttttggttc ggtcgatggc     120
cctggtattc gcttcgttgt ctttatgcaa gggtgtcgca tgcgttgcca gtattgtcac     180
aaccctgaca cctggaacat tggggttggt gaagaaatga cggccgatca aattttggcg     240
gatgcccagc gctataaagc attctggggt gaccaagggg gtattacctg cagtggcggt     300
gagagtttgg tacaaatcga tttcattctc gaactcttca ccaaggctaa ggcactggga     360
atttcgactt gcctcgatac gtcaggtggc cccttcacgc gtgaccaacc gtggtttggc     420
```

-continued

```
cagtttgaaa agctgatggc tgttactgac atctcattag ttgatattaa acacattgat    480
tcggccgagc ataaaaagct caccggtttt cctaatgaga atattttgga tatggtgcag    540
tatatgtcgg cgcatggtga tgacatgtgg attcgccacg ttctggtccc ggaacgcact    600
gactttgacc cttatctcaa acggttaggg gactatattg cgacattgga caaaaacgtg    660
gtccaaaaag ttgagattct gccgtatcac acgttaggcg ttaaaaagta tcacgagctt    720
ggcattacgt acccgcttga aggcatcgaa ccgccgtctg ccgaacgcgt taagaatgca    780
gagaatctgc tgcacgttaa ggattatacc ggatggcaaa gctggcgtcc gaaaccagtt    840
gcgagcaact ga                                                        852
```

<210> SEQ ID NO 22
<211> LENGTH: 283
<212> TYPE: PRT
<213> ORGANISM: Lactobacillus casei
<220> FEATURE:
<221> NAME/KEY: MISC_FEATURE
<223> OTHER INFORMATION: b123

<400> SEQUENCE: 22

```
Met Lys Leu Ile Asp Gln Ser Gln Ser Pro Leu Asn Ile Leu Glu Gln
1               5                   10                  15

Val Gly Gln Asp His Asp Gly Pro Ile Lys Gly Tyr Val His Ser Val
            20                  25                  30

Glu Ser Phe Gly Ser Val Asp Gly Pro Gly Ile Arg Phe Val Val Phe
        35                  40                  45

Met Gln Gly Cys Arg Met Arg Cys Gln Tyr Cys His Asn Pro Asp Thr
    50                  55                  60

Trp Asn Ile Gly Val Gly Glu Met Thr Ala Asp Gln Ile Leu Ala
65                  70                  75                  80

Asp Ala Gln Arg Tyr Lys Ala Phe Trp Gly Asp Gln Gly Gly Ile Thr
                85                  90                  95

Cys Ser Gly Gly Glu Ser Leu Val Gln Ile Asp Phe Ile Leu Glu Leu
            100                 105                 110

Phe Thr Lys Ala Lys Ala Leu Gly Ile Ser Thr Cys Leu Asp Thr Ser
        115                 120                 125

Gly Gly Pro Phe Thr Arg Asp Gln Pro Trp Phe Gly Gln Phe Glu Lys
    130                 135                 140

Leu Met Ala Val Thr Asp Ile Ser Leu Val Asp Ile Lys His Ile Asp
145                 150                 155                 160

Ser Ala Glu His Lys Lys Leu Thr Gly Phe Pro Asn Glu Asn Ile Leu
                165                 170                 175

Asp Met Val Gln Tyr Met Ser Ala His Gly Asp Asp Met Trp Ile Arg
            180                 185                 190

His Val Leu Val Pro Glu Arg Thr Asp Phe Asp Pro Tyr Leu Lys Arg
        195                 200                 205

Leu Gly Asp Tyr Ile Ala Thr Leu Asp Lys Asn Val Val Gln Lys Val
    210                 215                 220

Glu Ile Leu Pro Tyr His Thr Leu Gly Val Lys Lys Tyr His Glu Leu
225                 230                 235                 240

Gly Ile Thr Tyr Pro Leu Glu Gly Ile Glu Pro Pro Ser Ala Glu Arg
                245                 250                 255

Val Lys Asn Ala Glu Asn Leu Leu His Val Lys Asp Tyr Thr Gly Trp
            260                 265                 270

Gln Ser Trp Arg Pro Lys Pro Val Ala Ser Asn
        275                 280
```

<210> SEQ ID NO 23
<211> LENGTH: 852
<212> TYPE: DNA
<213> ORGANISM: Lactobacillus casei
<220> FEATURE:
<221> NAME/KEY: misc_feature
<223> OTHER INFORMATION: ATCC 334

<400> SEQUENCE: 23

```
atgaaactca tcgatcagtc acaaagccca ttaaatatct tagaacaagt tggtcaggat      60
catgatggcc cgatcaaagg gtatgttcac tcggtcgaaa gttttggttc ggtcgatggc     120
cctggtattc gcttcgttgt ctttatgcaa gggtgtcgca tgcgttgcca gtattgtcac     180
aaccctgaca cctggaacat tggggttggt gaagaaatga cggccgatca aattttggcg     240
gatgcccagc gctataaagc attctggggt gaccaagggg gtattacgtg cagtggcggt     300
gagagtttgg tacaaatcga tttcattctc gaactcttca ccaaggctaa ggcactggga     360
atttcgactt gcctcgatac gtcaggcggc cccttcacgc gtgaccaacc gtggtttggc     420
cagtttgaaa agctgatggc tgttactgac atctcattag ttgatattaa acacatcgat     480
tcggccgagc ataaaaagct caccggtttt cctaatgaaa atattttaga tatggtgcag     540
tatatgtcgg cgcatggtga tgacatgtgg attcgccacg ttctggtccc ggaacgcact     600
gactttgacc cttatctcaa acgattaggg gactatattg cgacattgga caaaaacgtg     660
gtccaaaaag ttgagattct gccgtatcac acgttaggcg ttaaaaagta tcacgagctt     720
ggcattacgt acccgcttga aggcatcgaa ccgccgtctg ccgatcgcgt taagaatgca     780
gagaatctgc tgcacgttaa ggattatacc ggatggcaaa gctggcgtcc gaaaccagtt     840
gcgagcaact ga                                                         852
```

<210> SEQ ID NO 24
<211> LENGTH: 283
<212> TYPE: PRT
<213> ORGANISM: Lactobacillus casei
<220> FEATURE:
<221> NAME/KEY: MISC_FEATURE
<223> OTHER INFORMATION: ATCC 334

<400> SEQUENCE: 24

```
Met Lys Leu Ile Asp Gln Ser Gln Ser Pro Leu Asn Ile Leu Glu Gln
  1               5                  10                  15

Val Gly Gln Asp His Asp Gly Pro Ile Lys Gly Tyr Val His Ser Val
             20                  25                  30

Glu Ser Phe Gly Ser Val Asp Gly Pro Gly Ile Arg Phe Val Val Phe
         35                  40                  45

Met Gln Gly Cys Arg Met Arg Cys Gln Tyr Cys His Asn Pro Asp Thr
     50                  55                  60

Trp Asn Ile Gly Val Gly Glu Glu Met Thr Ala Asp Gln Ile Leu Ala
 65                  70                  75                  80

Asp Ala Gln Arg Tyr Lys Ala Phe Trp Gly Asp Gln Gly Gly Ile Thr
                 85                  90                  95

Cys Ser Gly Gly Glu Ser Leu Val Gln Ile Asp Phe Ile Leu Glu Leu
            100                 105                 110

Phe Thr Lys Ala Lys Ala Leu Gly Ile Ser Thr Cys Leu Asp Thr Ser
        115                 120                 125

Gly Gly Pro Phe Thr Arg Asp Gln Pro Trp Phe Gly Gln Phe Glu Lys
```

```
                130                 135                 140
Leu Met Ala Val Thr Asp Ile Ser Leu Val Asp Ile Lys His Ile Asp
145                 150                 155                 160

Ser Ala Glu His Lys Lys Leu Thr Gly Phe Pro Asn Glu Asn Ile Leu
                165                 170                 175

Asp Met Val Gln Tyr Met Ser Ala His Gly Asp Met Trp Ile Arg
                180                 185                 190

His Val Leu Val Pro Glu Arg Thr Asp Phe Asp Pro Tyr Leu Lys Arg
            195                 200                 205

Leu Gly Asp Tyr Ile Ala Thr Leu Asp Lys Asn Val Val Gln Lys Val
        210                 215                 220

Glu Ile Leu Pro Tyr His Thr Leu Gly Val Lys Lys Tyr His Glu Leu
225                 230                 235                 240

Gly Ile Thr Tyr Pro Leu Glu Gly Ile Glu Pro Pro Ser Ala Asp Arg
                245                 250                 255

Val Lys Asn Ala Glu Asn Leu Leu His Val Lys Asp Tyr Thr Gly Trp
                260                 265                 270

Gln Ser Trp Arg Pro Lys Pro Val Ala Ser Asn
            275                 280
```

<210> SEQ ID NO 25
<211> LENGTH: 879
<212> TYPE: DNA
<213> ORGANISM: Bifidobacterium adolescentis

<400> SEQUENCE: 25

```
atgtctgaac atattttccg ttccacgacc agacacatgc tgagggattc caaggactac      60
gtcaatcaga cgctgatggg aggcctgtcc ggattcgaat cgccaatcgg cttggaccgt     120
ctcgaccgca tcaaggcgtt gaaaagcggc gatatcggtt cgtgcactc gtgggacatc      180
aacacttccg tggatggtcc tggcaccaga atgaccgtgt catgagcgg atgccctctg      240
cgctgccagt actgccagaa tccggatact tggaagatgc gcgacggcaa gcccgtctac     300
tacgaagcca tggtcaagaa aatcgagcgg tatgccgatt tattcaaggc caccggcggc     360
ggcatcactt tctccggcgg cgaatccatg atgcagccgg ctttcgtgtc acgcgtgttc     420
catgccgcca gcagatggg agtgcatacc tgcctcgaca cgtccggatt cctcggggcg      480
agctacaccg atgacatggt ggatgacatc gacctgtgcc tgcttgacgt caaatccggc     540
gatgaggaga cctaccataa ggtgaccggg gcatcctgc agccgaccat cgacttcgga      600
cagcgtctgg ccaaggcagg caagaagatc tgggtgcgtt cgtgctcgt gccgggcctc      660
acatcctccg aagaaaacgt cgagaacgtg gcgaagatct gcgagacctt cggcgacgcg     720
ttggaacata tcgacgtatt gcccttccac cagcttggcc gtccgaagtg cacatgctg      780
aacatcccat acccgttgga ggaccagaaa ggcccgtccg cggcaatgaa caacgtgtg     840
gtcgagcagt ccagtcgca cggcttcacc gtgtactaa                            879
```

<210> SEQ ID NO 26
<211> LENGTH: 292
<212> TYPE: PRT
<213> ORGANISM: Bifidobacterium adolescentis

<400> SEQUENCE: 26

```
Met Ser Glu His Ile Phe Arg Ser Thr Thr Arg His Met Leu Arg Asp
1               5                   10                  15

Ser Lys Asp Tyr Val Asn Gln Thr Leu Met Gly Gly Leu Ser Gly Phe
```

```
        20                  25                  30
Glu Ser Pro Ile Gly Leu Asp Arg Leu Asp Arg Ile Lys Ala Leu Lys
         35                  40                  45

Ser Gly Asp Ile Gly Phe Val His Ser Trp Asp Ile Asn Thr Ser Val
 50                  55                  60

Asp Gly Pro Gly Thr Arg Met Thr Val Phe Met Ser Gly Cys Pro Leu
 65                  70                  75                  80

Arg Cys Gln Tyr Cys Gln Asn Pro Asp Thr Trp Lys Met Arg Asp Gly
                 85                  90                  95

Lys Pro Val Tyr Tyr Glu Ala Met Val Lys Lys Ile Glu Arg Tyr Ala
                100                 105                 110

Asp Leu Phe Lys Ala Thr Gly Gly Ile Thr Phe Ser Gly Gly Glu
            115                 120                 125

Ser Met Met Gln Pro Ala Phe Val Ser Arg Val Phe His Ala Ala Lys
    130                 135                 140

Gln Met Gly Val His Thr Cys Leu Asp Thr Ser Gly Phe Leu Gly Ala
145                 150                 155                 160

Ser Tyr Thr Asp Asp Met Val Asp Ile Asp Leu Cys Leu Leu Asp
                165                 170                 175

Val Lys Ser Gly Asp Glu Thr Tyr His Lys Val Thr Gly Gly Ile
            180                 185                 190

Leu Gln Pro Thr Ile Asp Phe Gly Gln Arg Leu Ala Lys Ala Gly Lys
    195                 200                 205

Lys Ile Trp Val Arg Phe Val Leu Val Pro Gly Leu Thr Ser Ser Glu
210                 215                 220

Glu Asn Val Glu Asn Val Ala Lys Ile Cys Glu Thr Phe Gly Asp Ala
225                 230                 235                 240

Leu Glu His Ile Asp Val Leu Pro Phe His Gln Leu Gly Arg Pro Lys
                245                 250                 255

Trp His Met Leu Asn Ile Pro Tyr Pro Leu Glu Asp Gln Lys Gly Pro
            260                 265                 270

Ser Ala Ala Met Lys Gln Arg Val Val Glu Gln Phe Gln Ser His Gly
    275                 280                 285

Phe Thr Val Tyr
    290

<210> SEQ ID NO 27
<211> LENGTH: 882
<212> TYPE: DNA
<213> ORGANISM: Bifidobacterium longum
<220> FEATURE:
<221> NAME/KEY: misc_feature
<223> OTHER INFORMATION: NCC2705

<400> SEQUENCE: 27
atgcccgcaa cacccacgtt ccgcaccacg accaggcata tgctcaagga atcgaagacc      60
tatgcctcgc agactttgat gggcggcctt tccggctttg aatccccaat cggactcgac     120
cgacgtgacc gcctttccgc cctgaaatcc ggcgatatcg gcttcgtcca ctcttgggac     180
atcaacacct ccgtggacgg accgggcacc cgtatgaccg tgttcatgtc cggctgcccg     240
ctgcgctgcc agtactgcca gaacccggac acttggaaga tgcgcgacgg caagcccgtc     300
taccttgacg ccatgatcaa gaaggtcgat cgttacaagg acctgttcaa ggccacgcat     360
ggcggtatca ccttctccgg cggcgaatcc atgatgcagc ccgccttcgt ctcgcgtgtg     420
ttccatgccg ccaaggagat gggcgtgcac acctgcctcg acacgtccgg cttcctcaac     480
```

-continued

```
acgaattaca ccgacgagat gctcgaggac atcgacctgt gtctgctcga cgtcaaatcc    540
ggcgacgagg agacctatca aaggtcacc ggcggcacct tgcagcccac catcgatttt    600
ggccagcgac tggccaaggc cggcaagaag atctgggtgc gatttgtgct cgtgccgggc    660
ctgaccgact ccgaagagaa cgtcgaaaac gtggcgaaga tctgcgagtc cttcggcgat    720
gccgtcgaac acatcgacgt gctgggattc caccagcttg gccgcccgaa gtggcacgaa    780
ctgcgcatcc cataccccgct ggagaaccag aagggaccca acgccgccac cgcgaacgg    840 gtggccaacc agttcaagga ccacggcttc accgtgtatt aa                        882
```

<210> SEQ ID NO 28
<211> LENGTH: 293
<212> TYPE: PRT
<213> ORGANISM: Bifidobacterium longum
<220> FEATURE:
<221> NAME/KEY: MISC_FEATURE
<223> OTHER INFORMATION: NCC2705

<400> SEQUENCE: 28

```
Met Pro Ala Thr Pro Thr Phe Arg Thr Thr Thr Arg His Met Leu Lys
1               5                   10                  15

Glu Ser Lys Thr Tyr Ala Ser Gln Thr Leu Met Gly Gly Leu Ser Gly
                20                  25                  30

Phe Glu Ser Pro Ile Gly Leu Asp Arg Arg Asp Arg Leu Ser Ala Leu
            35                  40                  45

Lys Ser Gly Asp Ile Gly Phe Val His Ser Trp Asp Ile Asn Thr Ser
    50                  55                  60

Val Asp Gly Pro Gly Thr Arg Met Thr Val Phe Met Ser Gly Cys Pro
65                  70                  75                  80

Leu Arg Cys Gln Tyr Cys Gln Asn Pro Asp Thr Trp Lys Met Arg Asp
                85                  90                  95

Gly Lys Pro Val Tyr Leu Asp Ala Met Ile Lys Lys Val Asp Arg Tyr
            100                 105                 110

Lys Asp Leu Phe Lys Ala Thr His Gly Gly Ile Thr Phe Ser Gly Gly
        115                 120                 125

Glu Ser Met Met Gln Pro Ala Phe Val Ser Arg Val Phe His Ala Ala
    130                 135                 140

Lys Glu Met Gly Val His Thr Cys Leu Asp Thr Ser Gly Phe Leu Asn
145                 150                 155                 160

Thr Asn Tyr Thr Asp Glu Met Leu Glu Asp Ile Asp Leu Cys Leu Leu
                165                 170                 175

Asp Val Lys Ser Gly Asp Glu Glu Thr Tyr His Lys Val Thr Gly Gly
            180                 185                 190

Thr Leu Gln Pro Thr Ile Asp Phe Gly Gln Arg Leu Ala Lys Ala Gly
        195                 200                 205

Lys Lys Ile Trp Val Arg Phe Val Leu Val Pro Gly Leu Thr Asp Ser
    210                 215                 220

Glu Glu Asn Val Glu Asn Val Ala Lys Ile Cys Glu Ser Phe Gly Asp
225                 230                 235                 240

Ala Val Glu His Ile Asp Val Leu Gly Phe His Gln Leu Gly Arg Pro
                245                 250                 255

Lys Trp His Glu Leu Arg Ile Pro Tyr Pro Leu Glu Asn Gln Lys Gly
            260                 265                 270

Pro Asn Ala Ala Thr Arg Glu Arg Val Ala Asn Gln Phe Lys Asp His
        275                 280                 285
```

Gly Phe Thr Val Tyr
    290

<210> SEQ ID NO 29
<211> LENGTH: 882
<212> TYPE: DNA
<213> ORGANISM: Bifidobacterium longum
<220> FEATURE:
<221> NAME/KEY: misc_feature
<223> OTHER INFORMATION: DJO10A

<400> SEQUENCE: 29

```
atgcccgcaa cacccacgtt ccgcaccacg accaggcata tgctcaagga atcgaagacc    60
tatgcctcgc agactttgat gggtggcctt tccggctttg aatccccaat cggactcgac   120
cgacgtgacc gcctttccgc cctgaaatcc ggtgatatcg gcttcgtcca ctcttgggac   180
atcaacacct ccgtggatgg accgggcacc cgcatgaccg tgttcatgtc cggctgcccg   240
ctgcgctgcc agtactgcca gaacccggac acttggaaga tgcgcgacgg caagcccgtc   300
taccttgacg ccatgatcaa gaaggtcgat cgttacaagg acctgttcaa ggccacgcat   360
ggcggtatca ccttctccgg cggcgaatcc atgatgcagc cgccttcgt ctcgcgtgtg   420
ttccatgccg ccaaggagat gggcgtgcac acctgcctcg atacgtccgg cttcctcaac   480
acgaattaca ccgacgagat gctcgaggac atcgacctgt gtctgctcga cgtcaaatcc   540
ggcgacgagg agacctatca aaggtcaccg gcggcacct tgcagcccac catcgatttt   600
ggccagcgac tggccaaggc cggcaagaag atctgggtgc gatttgtgct cgtgccgggc   660
ctgaccgact ccgaagagaa cgtcgaaaac gtggcgaaga tctgcgagtc cttcggtgat   720
gccgtcgaac acatcgacgt gctgggattc caccagcttg ccgcccgaa gtggcacgaa   780
ctgcgtatcc cataccgct ggagaaccag aagggaccca acgccgccac ccgcgaacgg   840
gtgaccaacc agttcaagga ccacggcttc accgtgtatt aa                      882
```

<210> SEQ ID NO 30
<211> LENGTH: 293
<212> TYPE: PRT
<213> ORGANISM: Bifidobacterium longum
<220> FEATURE:
<221> NAME/KEY: MISC_FEATURE
<223> OTHER INFORMATION: DJO10A

<400> SEQUENCE: 30

Met Pro Ala Thr Pro Thr Phe Arg Thr Thr Arg His Met Leu Lys
1               5                   10                  15

Glu Ser Lys Thr Tyr Ala Ser Gln Thr Leu Met Gly Gly Leu Ser Gly
            20                  25                  30

Phe Glu Ser Pro Ile Gly Leu Asp Arg Arg Asp Arg Leu Ser Ala Leu
        35                  40                  45

Lys Ser Gly Asp Ile Gly Phe Val His Ser Trp Asp Ile Asn Thr Ser
    50                  55                  60

Val Asp Gly Pro Gly Thr Arg Met Thr Val Phe Met Ser Gly Cys Pro
65                  70                  75                  80

Leu Arg Cys Gln Tyr Cys Gln Asn Pro Asp Thr Trp Lys Met Arg Asp
                85                  90                  95

Gly Lys Pro Val Tyr Leu Asp Ala Met Ile Lys Lys Val Asp Arg Tyr
            100                 105                 110

Lys Asp Leu Phe Lys Ala Thr His Gly Gly Ile Thr Phe Ser Gly Gly
        115                 120                 125

Glu Ser Met Met Gln Pro Ala Phe Val Ser Arg Val Phe His Ala Ala
    130                 135                 140

Lys Glu Met Gly Val His Thr Cys Leu Asp Thr Ser Gly Phe Leu Asn
145                 150                 155                 160

Thr Asn Tyr Thr Asp Glu Met Leu Glu Asp Ile Asp Leu Cys Leu Leu
                165                 170                 175

Asp Val Lys Ser Gly Asp Glu Thr Tyr His Lys Val Thr Gly Gly
            180                 185                 190

Thr Leu Gln Pro Thr Ile Asp Phe Gly Gln Arg Leu Ala Lys Ala Gly
        195                 200                 205

Lys Lys Ile Trp Val Arg Phe Val Leu Val Pro Gly Leu Thr Asp Ser
    210                 215                 220

Glu Glu Asn Val Glu Asn Val Ala Lys Ile Cys Glu Ser Phe Gly Asp
225                 230                 235                 240

Ala Val Glu His Ile Asp Val Leu Gly Phe His Gln Leu Gly Arg Pro
                245                 250                 255

Lys Trp His Glu Leu Arg Ile Pro Tyr Pro Leu Glu Asn Gln Lys Gly
            260                 265                 270

Pro Asn Ala Ala Thr Arg Glu Arg Val Thr Asn Gln Phe Lys Asp His
        275                 280                 285

Gly Phe Thr Val Tyr
    290

<210> SEQ ID NO 31
<211> LENGTH: 903
<212> TYPE: DNA
<213> ORGANISM: Bifidobacterium animalis
<220> FEATURE:
<221> NAME/KEY: misc_feature
<223> OTHER INFORMATION: DSM 10140

<400> SEQUENCE: 31
atgtcgaatt cagagtcgaa tcacggtgca tccgcattcc gcaccacgac gcggcacatg      60
ctcaagtcgt cgaaggagta ccagcgcaag acgctcatgg gcggtctgtc aggattcgaa     120
tcgcccatcg gactcgatcg gcgtgaccgc atcaatgcgt tgaaaaccgg cgacataggt     180
tttgtgcatt cctgggacat caatacgtcg gtggacggcc cgggcacccg catgacggta     240
ttcctgagcg gctgcccact cgctgccag tactgccaga accccgacac ctggaagatg     300
cgcgacggca agccggtgta cctcgatgcc atggtggtca agatcgaacg gtacaaggac     360
ctgttcgaag ccacgaaagg cggcatcacc ttctcgggcg cgagtccat gatgcagccg     420 gcattcgtgt cgcgggtgtt ccgggcggcc aaggagatgg gtgtgcacac ctgccttgat     480
acttcgggct tcctcaacgc caactattcg gatgaaatga tcgacgacat cgatctgtgc     540
ctgctcgatg tgaagtccgg agacgaggag acctacaagc gggtaaccgg ggagtgctc     600 cagcccacca tcgatttcgg acagcggttg aacaggaggg caagaagat ctgggtgcgc     660 ttcgtgctgg ttcccgggct cacctcgtcg gaggagaacg tggagaatgt ggcccgcatc     720
tgtgagagct tcggcgacgc ggtggagcat atagacgtgc tgccgttcca ccagctcggg     780
cgtccgaagt ggcatgagct gcgaatccct tacccgttgg aggaccagaa gggaccttcc     840
caggcgttgc gcgaccgcgt gcgccagcag ttcgagagcc acggattcac ggtctacgtc     900
taa                                                                  903

<210> SEQ ID NO 32

-continued

```
<211> LENGTH: 300
<212> TYPE: PRT
<213> ORGANISM: Bifidobacterium animalis
<220> FEATURE:
<221> NAME/KEY: MISC_FEATURE
<223> OTHER INFORMATION: DSM 10140

<400> SEQUENCE: 32

Met Ser Asn Ser Glu Ser Asn His Gly Ala Ser Ala Phe Arg Thr Thr
1               5                   10                  15

Thr Arg His Met Leu Lys Ser Ser Lys Glu Tyr Gln Arg Lys Thr Leu
            20                  25                  30

Met Gly Gly Leu Ser Gly Phe Glu Ser Pro Ile Gly Leu Asp Arg Arg
        35                  40                  45

Asp Arg Ile Asn Ala Leu Lys Thr Gly Asp Ile Gly Phe Val His Ser
    50                  55                  60

Trp Asp Ile Asn Thr Ser Val Asp Gly Pro Gly Thr Arg Met Thr Val
65                  70                  75                  80

Phe Leu Ser Gly Cys Pro Leu Arg Cys Gln Tyr Cys Gln Asn Pro Asp
                85                  90                  95

Thr Trp Lys Met Arg Asp Gly Lys Pro Val Tyr Leu Asp Ala Met Val
            100                 105                 110

Val Lys Ile Glu Arg Tyr Lys Asp Leu Phe Glu Ala Thr Lys Gly Gly
        115                 120                 125

Ile Thr Phe Ser Gly Gly Glu Ser Met Met Gln Pro Ala Phe Val Ser
    130                 135                 140

Arg Val Phe Arg Ala Ala Lys Glu Met Gly Val His Thr Cys Leu Asp
145                 150                 155                 160

Thr Ser Gly Phe Leu Asn Ala Asn Tyr Ser Asp Glu Met Ile Asp Asp
                165                 170                 175

Ile Asp Leu Cys Leu Leu Asp Val Lys Ser Gly Asp Glu Glu Thr Tyr
            180                 185                 190

Lys Arg Val Thr Gly Gly Val Leu Gln Pro Thr Ile Asp Phe Gly Gln
        195                 200                 205

Arg Leu Asn Arg Arg Gly Lys Lys Ile Trp Val Arg Phe Val Leu Val
    210                 215                 220

Pro Gly Leu Thr Ser Ser Glu Glu Asn Val Glu Asn Val Ala Arg Ile
225                 230                 235                 240

Cys Glu Ser Phe Gly Asp Ala Val Glu His Ile Asp Val Leu Pro Phe
                245                 250                 255

His Gln Leu Gly Arg Pro Lys Trp His Glu Leu Arg Ile Pro Tyr Pro
            260                 265                 270

Leu Glu Asp Gln Lys Gly Pro Ser Gln Ala Leu Arg Asp Arg Val Arg
        275                 280                 285

Gln Gln Phe Glu Ser His Gly Phe Thr Val Tyr Val
    290                 295                 300

<210> SEQ ID NO 33
<211> LENGTH: 720
<212> TYPE: DNA
<213> ORGANISM: Clostridium cellulolyticum

<400> SEQUENCE: 33
atggagatta aagggaggat acattcattt gagacatttg ggaccgtgga cggtcccgga      60
attagattta ttgtgtttct gaagggctgc ccgcttcgct gtaagtactg ccacaacaga     120
gatgcatgga gttcagaggg tgcaaaactg tacagtcctc aagaggtgtt gaaggaaatc     180
```

```
cagaaataca ggaattttat agatgcctct catggaggaa taacagtcag cggggagaa      240 cctttaattc agcatgaatt tgtaaaggaa ctatttaaat tatgtcgtga agctgggata      300
cataccgctg tggacacttc cggctacgtc aatgtggaag atgtaaagga cacactagag      360
tatacagacc ttgttcttct tgatttaaag caggcaaatg cacagaagca tttggaattg      420
acaggagtgg agaataagcg tatcaagctg tttacaacct acctgggtga atcggaaaa       480 cctgtttgga taagatatgt gcttataccg ggttatacag atggtgaaga ggatttgctg      540
gcagcataca attatttaaa gggatttaaa aatatagaga aaatagaggt tcttccatat      600
cacataatgg gaaaggcaaa atgggagaag ctgaacgtac aatatcccct ggagggagtt      660
ccttccccta cacaggaaga ggtggacagg gccaaaaaca tcctgactac aggaaaaccg      720
```

<210> SEQ ID NO 34
<211> LENGTH: 240
<212> TYPE: PRT
<213> ORGANISM: Clostridium cellulolyticum

<400> SEQUENCE: 34

```
Met Glu Ile Lys Gly Arg Ile His Ser Phe Glu Thr Phe Gly Thr Val
1               5                   10                  15

Asp Gly Pro Gly Ile Arg Phe Ile Val Phe Leu Lys Gly Cys Pro Leu
            20                  25                  30

Arg Cys Lys Tyr Cys His Asn Arg Asp Ala Trp Ser Ser Glu Gly Ala
        35                  40                  45

Lys Leu Tyr Ser Pro Gln Glu Val Leu Lys Glu Ile Gln Lys Tyr Arg
    50                  55                  60

Asn Phe Ile Asp Ala Ser His Gly Gly Ile Thr Val Ser Gly Gly Glu
65                  70                  75                  80

Pro Leu Ile Gln His Glu Phe Val Lys Glu Leu Phe Lys Leu Cys Arg
                85                  90                  95

Glu Ala Gly Ile His Thr Ala Val Asp Thr Ser Gly Tyr Val Asn Val
            100                 105                 110

Glu Asp Val Lys Asp Thr Leu Glu Tyr Thr Asp Leu Val Leu Leu Asp
        115                 120                 125

Leu Lys Gln Ala Asn Ala Gln Lys His Leu Glu Leu Thr Gly Val Glu
    130                 135                 140

Asn Lys Arg Ile Lys Leu Phe Thr Thr Tyr Leu Gly Glu Ile Gly Lys
145                 150                 155                 160

Pro Val Trp Ile Arg Tyr Val Leu Ile Pro Gly Tyr Thr Asp Gly Glu
                165                 170                 175

Glu Asp Leu Leu Ala Ala Tyr Asn Tyr Leu Lys Gly Phe Lys Asn Ile
            180                 185                 190

Glu Lys Ile Glu Val Leu Pro Tyr His Ile Met Gly Lys Ala Lys Trp
        195                 200                 205

Glu Lys Leu Asn Val Gln Tyr Pro Leu Glu Gly Val Pro Ser Pro Thr
    210                 215                 220

Gln Glu Glu Val Asp Arg Ala Lys Asn Ile Leu Thr Thr Gly Lys Pro
225                 230                 235                 240
```

<210> SEQ ID NO 35
<211> LENGTH: 741
<212> TYPE: DNA
<213> ORGANISM: Escherichia coli

<400> SEQUENCE: 35

```
atgtcagtta ttggtcgcat tcactccttt gaatcctgtg gaaccgtaga cggcccaggt    60
attcgcttta tcaccttttt ccagggctgc ctgatgcgct gcctgtattg tcataaccgc   120
gacacctggg acacgcatgg cggtaaagaa gttaccgttg aagatttgat gaaggaagtg   180
gtgacctatc gccactttat gaacgcttcc ggcggcggcg ttaccgcatc cggcggtgaa   240
gcaatcctgc aagctgagtt tgttcgtgac tggttccgcg cctgcaaaaa agaaggcatt   300
catacctgtc tggacaccaa cggttttgtt cgtcgttacg atccggtgat tgatgaactg   360
ctggaagtaa ccgacctggt aatgctcgat ctcaaacaga tgaacgacga gatccaccaa   420
aatctggttg gagtttccaa ccaccgcacg ctggagttcg ctaaatatct ggcgaacaaa   480
aatgtgaagg tgtggatccg ctacgttgtt gtcccaggct ggtctgacga tgacgattca   540
gcgcatcgcc tcggtgaatt tacccgtgat atgggcaacg ttgagaaaat cgagcttctc   600
ccctaccacg agctgggcaa acacaaatgg gtggcaatgg gtgaagagta caaactcgac   660
ggtgttaaac caccgaagaa agagaccatg gaacgcgtga aaggcattct tgagcagtac   720
ggtcataagg taatgttcta a                                             741
```

<210> SEQ ID NO 36
<211> LENGTH: 246
<212> TYPE: PRT
<213> ORGANISM: Escherichia coli

<400> SEQUENCE: 36

```
Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
                20                  25                  30

Arg Cys Leu Tyr Cys His Asn Arg Asp Thr Trp Asp Thr His Gly Gly
            35                  40                  45

Lys Glu Val Thr Val Glu Asp Leu Met Lys Glu Val Val Thr Tyr Arg
        50                  55                  60

His Phe Met Asn Ala Ser Gly Gly Val Thr Ala Ser Gly Gly Glu
65                  70                  75                  80

Ala Ile Leu Gln Ala Glu Phe Val Arg Asp Trp Phe Arg Ala Cys Lys
                85                  90                  95

Lys Glu Gly Ile His Thr Cys Leu Asp Thr Asn Gly Phe Val Arg Arg
            100                 105                 110

Tyr Asp Pro Val Ile Asp Glu Leu Leu Glu Val Thr Asp Leu Val Met
        115                 120                 125

Leu Asp Leu Lys Gln Met Asn Asp Glu Ile His Gln Asn Leu Val Gly
130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Pro Gly Trp Ser Asp
                165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
        195                 200                 205

Lys Trp Val Ala Met Gly Glu Glu Tyr Lys Leu Asp Gly Val Lys Pro
    210                 215                 220

Pro Lys Lys Glu Thr Met Glu Arg Val Lys Gly Ile Leu Glu Gln Tyr
225                 230                 235                 240
```

Gly His Lys Val Met Phe
            245

<210> SEQ ID NO 37
<211> LENGTH: 2226
<212> TYPE: DNA
<213> ORGANISM: Bacillus licheniformis
<220> FEATURE:
<221> NAME/KEY: misc_feature
<223> OTHER INFORMATION: DSM13

<400> SEQUENCE: 37

```
atggaacaat ggaaaggttt caccacaaac gtttggcaaa aagaagtcaa tgtccgcgat      60
tttattctct cgaactttga gccatatcaa ggtgacgaat cgtttctcga acctccgacg     120
gaagctacat cggcattatg ggatcatgta atggatttga caaaaaaaga gcgtgaaaac     180
ggaggcgtcc ttgatatgga tacagagatc gtctcaacga tcacctcgca cggtcccgga     240
tatttgaaca agacctggaa aaagtcgtc ggcgttcaaa ccgatgagcc gtttaaacgg      300
tcgcttcagc ctttcggcgg catccgaatg gcaaagcagg catgcgaatc ctatggtttt     360
aaactgaatg aagaagtgga aaggatcttt accgattacc gcaaaactca taaccaaggc     420
gtgtttgacg catatacgga cgaaatgaag ctcgcccgaa aagtcggaat cattaccgga     480
ctgcctgatg cttacgggcg cgggcgcatc atcggtgatt accggagagt ggcgctttac     540
ggcgtggatt tcttgatcga tgaaaagaaa aaagatgcgg ccggcacctc tcgggtgatg     600
tctgaagaaa acatccgcct tcgtgaagaa ctgtcagaac aaatccgagc attgaacgaa     660
cttaaagcgc ttgcaaaaag ctatgggttt gacatttcca gcctgcggc gaatgcaaga     720
gaagcatttc aatggctgta ttttgcctat ttggctgcca ttaaagagca aaacggagca     780
gcaatgagcc ttggccgcgt gtccacgttc cttgatattt acatcgaaag agatttgaaa     840
acgggcgtat taacagagcg tgaagcccaa gagcttgtcg accatttcgt catgaagctg     900
cgtttggtca aattcgcgcg cacacctgac tacaatgaac tgttcagcgg cgatccgacg     960
tgggtgacag aatcaatcgg cggaatggcg cacgacggac gcgccctggt gacgaaaaac    1020
tcgttccgtt cctgcatac gcttgacaat ttaggcccgg cgcctgaacc gaatttaacc    1080
gttctttggt ctgtcagact gccgcaaaag tttaaaaact actgtgccaa aatgtcgatt    1140
aaaacaagct cgatccaata cgaaaatgac gatatcatgc gtccagaata cggtgatgac    1200
tacggaatcg cctgctgtgt atcggcaatg gcaatcggca acaaatgca gttcttcgga    1260
gcacgcgcca acttggcgaa agctctttta tatgcgatta acggcggaaa agacgaaaag    1320
cataaaatgc aagtcggtcc ggaaatgccg ccggttgctt ccgacgtgct ggactatgac    1380
gaagtgatgc ataaattcga tcagacgatg gaatggctcg caggcttgta catcaacacg    1440
ctcaatgtca ttcactacat gcatgataaa tattgctatg aaagaattga atggccctg    1500
cacgacacg aaattttgcg gacgatggcc actgggatcg ccggcttgag tgttgtcgcc    1560
gattcattaa gcgctgtcaa atatgccaaa gtcagcgtgg tccgcgatga aaacggcatt    1620
gcggtcgatt ttgaaacaga aggcgacttt cctaagtacg gaaataacga tgaccgcgtc    1680
gacgcgatcg ccgttgacat tgtcaagcgc tttatgaaaa actgcgcaa gcatcagaca    1740
tatcgccagt ccgttcagac catgtcaatt ttaacgatca cgtcaaacgt cgtttacggc    1800
aagaaaaccg gaaatacgcc ggatggacgc gcgcgggag aaccgtttgc tccaggtgcg    1860
aatccgatgc acggccgcga tactaaaggg acgcttgcat cgctgtcttc agtggcaaag    1920
```

```
ctgccttaca gctatgcgct cgacggcatt tccaacacct tttcaatcgt cccgaaagcg     1980
cttggcaaag acgaagagag ccgcgccgcc aatttgtcaa gcatccttga cggatatgcc     2040
gcaaaaacag gacatcactt aaatgtaaac gtatttaaca gagagacact gctcgacgcc     2100
atggaacatc cagaggaata tccgcagtta acgattcgcg tctcaggcta tgcggtcaac     2160
tttattaagc tgacgaaaga acagcagtta gacgtcatca gcagaacctt ccatgaatcg     2220
atgtag                                                                 2226

<210> SEQ ID NO 38
<211> LENGTH: 741
<212> TYPE: PRT
<213> ORGANISM: Bacillus licheniformis
<220> FEATURE:
<221> NAME/KEY: MISC_FEATURE
<223> OTHER INFORMATION: DSM13

<400> SEQUENCE: 38
```

Met Gln Gln Trp Lys Gly Phe Thr Thr Asn Val Trp Gln Lys Glu Val
1               5                   10                  15

Asn Val Arg Asp Phe Ile Leu Ser Asn Phe Glu Pro Tyr Gln Gly Asp
            20                  25                  30

Glu Ser Phe Leu Glu Pro Pro Thr Glu Ala Thr Ser Ala Leu Trp Asp
        35                  40                  45

His Val Met Asp Leu Thr Lys Lys Glu Arg Glu Asn Gly Gly Val Leu
    50                  55                  60

Asp Met Asp Thr Glu Ile Val Ser Thr Ile Thr Ser His Gly Pro Gly
65                  70                  75                  80

Tyr Leu Asn Lys Asp Leu Glu Lys Val Val Gly Val Gln Thr Asp Glu
                85                  90                  95

Pro Phe Lys Arg Ser Leu Gln Pro Phe Gly Gly Ile Arg Met Ala Lys
            100                 105                 110

Gln Ala Cys Glu Ser Tyr Gly Phe Lys Leu Asn Glu Glu Val Glu Arg
        115                 120                 125

Ile Phe Thr Asp Tyr Arg Lys Thr His Asn Gln Gly Val Phe Asp Ala
    130                 135                 140

Tyr Thr Asp Glu Met Lys Leu Ala Arg Lys Val Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Phe Leu Ile Asp Glu Lys Lys Lys Asp
            180                 185                 190

Ala Ala Gly Thr Ser Arg Val Met Ser Glu Glu Asn Ile Arg Leu Arg
        195                 200                 205

Glu Glu Leu Ser Glu Gln Ile Arg Ala Leu Asn Glu Leu Lys Ala Leu
    210                 215                 220

Ala Lys Ser Tyr Gly Phe Asp Ile Ser Lys Pro Ala Ala Asn Ala Arg
225                 230                 235                 240

Glu Ala Phe Gln Trp Leu Tyr Phe Ala Tyr Leu Ala Ala Ile Lys Glu
                245                 250                 255

Gln Asn Gly Ala Ala Met Ser Leu Gly Arg Val Ser Thr Phe Leu Asp
            260                 265                 270

Ile Tyr Ile Glu Arg Asp Leu Lys Thr Gly Val Leu Thr Glu Arg Glu
        275                 280                 285

Ala Gln Glu Leu Val Asp His Phe Val Met Lys Leu Arg Leu Val Lys
    290                 295                 300

-continued

Phe Ala Arg Thr Pro Asp Tyr Asn Glu Leu Phe Ser Gly Asp Pro Thr
305                 310                 315                 320

Trp Val Thr Glu Ser Ile Gly Gly Met Ala His Asp Gly Arg Ala Leu
            325                 330                 335

Val Thr Lys Asn Ser Phe Arg Phe Leu His Thr Leu Asp Asn Leu Gly
        340                 345                 350

Pro Ala Pro Glu Pro Asn Leu Thr Val Leu Trp Ser Val Arg Leu Pro
    355                 360                 365

Gln Lys Phe Lys Asn Tyr Cys Ala Lys Met Ser Ile Lys Thr Ser Ser
370                 375                 380

Ile Gln Tyr Glu Asn Asp Asp Ile Met Arg Pro Glu Tyr Gly Asp Asp
385                 390                 395                 400

Tyr Gly Ile Ala Cys Cys Val Ser Ala Met Ala Ile Gly Lys Gln Met
                405                 410                 415

Gln Phe Phe Gly Ala Arg Ala Asn Leu Ala Lys Ala Leu Leu Tyr Ala
            420                 425                 430

Ile Asn Gly Gly Lys Asp Glu Lys His Lys Met Gln Val Gly Pro Glu
        435                 440                 445

Met Pro Pro Val Ala Ser Asp Val Leu Asp Tyr Asp Glu Val Met His
    450                 455                 460

Lys Phe Asp Gln Thr Met Glu Trp Leu Ala Gly Leu Tyr Ile Asn Thr
465                 470                 475                 480

Leu Asn Val Ile His Tyr Met His Asp Lys Tyr Cys Tyr Glu Arg Ile
                485                 490                 495

Glu Met Ala Leu His Asp Thr Glu Ile Leu Arg Thr Met Ala Thr Gly
            500                 505                 510

Ile Ala Gly Leu Ser Val Val Ala Asp Ser Leu Ser Ala Val Lys Tyr
        515                 520                 525

Ala Lys Val Ser Val Val Arg Asp Glu Asn Gly Ile Ala Val Asp Phe
    530                 535                 540

Glu Thr Glu Gly Asp Phe Pro Lys Tyr Gly Asn Asn Asp Asp Arg Val
545                 550                 555                 560

Asp Ala Ile Ala Val Asp Ile Val Lys Arg Phe Met Lys Lys Leu Arg
                565                 570                 575

Lys His Gln Thr Tyr Arg Gln Ser Val Gln Thr Met Ser Ile Leu Thr
            580                 585                 590

Ile Thr Ser Asn Val Val Tyr Gly Lys Lys Thr Gly Asn Thr Pro Asp
        595                 600                 605

Gly Arg Arg Ala Gly Glu Pro Phe Ala Pro Gly Ala Asn Pro Met His
    610                 615                 620

Gly Arg Asp Thr Lys Gly Thr Leu Ala Ser Leu Ser Ser Val Ala Lys
625                 630                 635                 640

Leu Pro Tyr Ser Tyr Ala Leu Asp Gly Ile Ser Asn Thr Phe Ser Ile
                645                 650                 655

Val Pro Lys Ala Leu Gly Lys Asp Glu Ser Arg Ala Ala Asn Leu
            660                 665                 670

Ser Ser Ile Leu Asp Gly Tyr Ala Ala Lys Thr Gly His His Leu Asn
        675                 680                 685

Val Asn Val Phe Asn Arg Glu Thr Leu Leu Asp Ala Met Glu His Pro
    690                 695                 700

Glu Glu Tyr Pro Gln Leu Thr Ile Arg Val Ser Gly Tyr Ala Val Asn
705                 710                 715                 720

Phe Ile Lys Leu Thr Lys Glu Gln Gln Leu Asp Val Ile Ser Arg Thr
            725                 730                 735

Phe His Glu Ser Met
        740

<210> SEQ ID NO 39
<211> LENGTH: 2226
<212> TYPE: DNA
<213> ORGANISM: Bacillus licheniformis
<220> FEATURE:
<221> NAME/KEY: misc_feature
<223> OTHER INFORMATION: ATCC14580

<400> SEQUENCE: 39

| | | |
|---|---|---|
| atggaacaat ggaaaggttt caccacaaac gtttggcaaa agaagtcaa tgtccgcgat | 60 |
| tttattctct cgaactttga gccatatcaa ggtgacgaat cgtttctcga acctccgacg | 120 |
| gaagctacat cggcattatg ggatcatgta atggatttga caaaaaaga gcgtgaaaac | 180 |
| ggaggcgtcc ttgatatgga tacagagatc gtctcaacga tcacctcgca cggtcccgga | 240 |
| tatttgaaca agacctgga aaaagtcgtc ggcgttcaaa ccgatgagcc gtttaaacgg | 300 |
| tcgcttcagc ctttcggcgg catccgaatg caaagcagg catgcgaatc ctatggtttt | 360 |
| aaactgaatg aagaagtgga aaggatcttt accgattacc gcaaaactca taaccaaggc | 420 |
| gtgtttgacg catatacgga cgaaatgaag ctcgcccgaa aagtcggaat cattaccgga | 480 |
| ctgcctgatg cttacgggcg cggcgcatc atcggtgatt accggagagt ggcgctttac | 540 |
| ggcgtggatt tcttgatcga tgaaaagaaa aaagatgcgg ccggcacctc tcgggtgatg | 600 |
| tctgaagaaa acatccgcct tcgtgaagaa ctgtcagaac aaatccgagc attgaacgaa | 660 |
| cttaaagcgc ttgcaaaaag ctatgggttt gacatttcca gcctgcggc gaatgcaaga | 720 |
| gaagcatttc aatggctgta ttttgcctat ttggctgcca ttaaagagca aaacggagca | 780 |
| gcaatgagcc ttggccgcgt gtccacgttc cttgatattt acatcgaaag agatttgaaa | 840 |
| acgggcgtat taacagagcg tgaagcccaa gagcttgtcg accatttcgt catgaagctg | 900 |
| cgtttggtca aattcgcgcg cacacctgac tacaatgaac tgttcagcgg cgatccgacg | 960 |
| tgggtgacag aatcaatcgg cggaatggcg cacgacggac gcgccctggt gacgaaaaac | 1020 |
| tcgttccgtt tcctgcatac gcttgacaat ttaggcccgg cgcctgaacc gaatttaacc | 1080 |
| gttctttggt ctgtcagact gccgcaaaag tttaaaaact actgtgccaa atgtcgatt | 1140 |
| aaaacaagct cgatccaata cgaaaatgac gatatcatgc gtccagaata cggtgatgac | 1200 |
| tacggaatcg cctgctgtgt atcggcaatg gcaatcggca acaaatgca gttcttcgga | 1260 |
| gcacgcgcca acttggcgaa agctcttttta tatgcgatta acggcggaaa agacgaaaag | 1320 |
| cataaaatgc aagtcggtcc ggaaatgccg ccggttgctt ccgacgtgct ggactatgac | 1380 |
| gaagtgatgc ataaattcga tcagacgatg gaatggctcg caggcttgta catcaacacg | 1440 |
| ctcaatgtca ttcactacat gcatgataaa tattgctatg aaagaattga atgccctg | 1500 |
| cacgacacgg aaattttgcg gacgatggcc actgggatcg ccggcttgag tgttgtcgcc | 1560 |
| gattcattaa gcgctgtcaa atatgccaaa gtcagcgtgg tccgcgatga aaacggcatt | 1620 |
| gcggtcgatt ttgaaacaga aggcgacttt cctaagtacg aaataacga tgaccgcgtc | 1680 |
| gacgcgatcg ccgttgacat tgtcaagcgc tttatgaaaa aactgcgcaa gcatcagaca | 1740 |
| tatcgccagt ccgttcagac catgtcaatt ttaacgatca cgtcaaacgt cgtttacggc | 1800 |
| aagaaaaccg gaaatacgcc ggatggacgc cgcgcgggag aaccgtttgc tccaggtgcg | 1860 |

| | | | |
|---|---|---|---|
| aatccgatgc acggccgcga tactaaaggg acgcttgcat cgctgtcttc agtggcaaag | | | 1920 |
| ctgccttaca gctatgcgct cgacggcatt tccaacacct tttcaatcgt cccgaaagcg | | | 1980 |
| cttggcaaag acgaagagag ccgcgccgcc aatttgtcaa gcatccttga cggatatgcc | | | 2040 |
| gcaaaaacag acatcactt aaatgtaaac gtatttaaca gagagacact gctcgacgcc | | | 2100 |
| atggaacatc cagaggaata tccgcagtta acgattgcg tctcaggcta tgcggtcaac | | | 2160 |
| tttattaagc tgacgaaaga acagcagtta gacgtcatca gcagaacctt ccatgaatcg | | | 2220 |
| atgtag | | | 2226 |

```
<210> SEQ ID NO 40
<211> LENGTH: 741
<212> TYPE: PRT
<213> ORGANISM: Bacillus licheniformis
<220> FEATURE:
<221> NAME/KEY: MISC_FEATURE
<223> OTHER INFORMATION: ATCC14580

<400> SEQUENCE: 40

Met Glu Gln Trp Lys Gly Phe Thr Thr Asn Val Trp Gln Lys Glu Val
1               5                   10                  15

Asn Val Arg Asp Phe Ile Leu Ser Asn Phe Glu Pro Tyr Gln Gly Asp
            20                  25                  30

Glu Ser Phe Leu Glu Pro Pro Thr Glu Ala Thr Ser Ala Leu Trp Asp
        35                  40                  45

His Val Met Asp Leu Thr Lys Lys Glu Arg Glu Asn Gly Gly Val Leu
    50                  55                  60

Asp Met Asp Thr Glu Ile Val Ser Thr Ile Thr Ser His Gly Pro Gly
65                  70                  75                  80

Tyr Leu Asn Lys Asp Leu Glu Lys Val Val Gly Val Gln Thr Asp Glu
                85                  90                  95

Pro Phe Lys Arg Ser Leu Gln Pro Phe Gly Gly Ile Arg Met Ala Lys
            100                 105                 110

Gln Ala Cys Glu Ser Tyr Gly Phe Lys Leu Asn Glu Glu Val Glu Arg
        115                 120                 125

Ile Phe Thr Asp Tyr Arg Lys Thr His Asn Gln Gly Val Phe Asp Ala
    130                 135                 140

Tyr Thr Asp Glu Met Lys Leu Ala Arg Lys Val Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Phe Leu Ile Asp Glu Lys Lys Lys Asp
            180                 185                 190

Ala Ala Gly Thr Ser Arg Val Met Ser Glu Glu Asn Ile Arg Leu Arg
        195                 200                 205

Glu Glu Leu Ser Glu Gln Ile Arg Ala Leu Asn Glu Leu Lys Ala Leu
    210                 215                 220

Ala Lys Ser Tyr Gly Phe Asp Ile Ser Lys Pro Ala Ala Asn Ala Arg
225                 230                 235                 240

Glu Ala Phe Gln Trp Leu Tyr Phe Ala Tyr Leu Ala Ala Ile Lys Glu
                245                 250                 255

Gln Asn Gly Ala Ala Met Ser Leu Gly Arg Val Ser Thr Phe Leu Asp
            260                 265                 270

Ile Tyr Ile Glu Arg Asp Leu Lys Thr Gly Val Leu Thr Glu Arg Glu
        275                 280                 285
```

```
Ala Gln Glu Leu Val Asp His Phe Val Met Lys Leu Arg Leu Val Lys
290                 295                 300

Phe Ala Arg Thr Pro Asp Tyr Asn Glu Leu Phe Ser Gly Asp Pro Thr
305                 310                 315                 320

Trp Val Thr Glu Ser Ile Gly Gly Met Ala His Asp Gly Arg Ala Leu
                325                 330                 335

Val Thr Lys Asn Ser Phe Arg Phe Leu His Thr Leu Asp Asn Leu Gly
            340                 345                 350

Pro Ala Pro Glu Pro Asn Leu Thr Val Leu Trp Ser Val Arg Leu Pro
        355                 360                 365

Gln Lys Phe Lys Asn Tyr Cys Ala Lys Met Ser Ile Lys Thr Ser Ser
370                 375                 380

Ile Gln Tyr Glu Asn Asp Asp Ile Met Arg Pro Glu Tyr Gly Asp Asp
385                 390                 395                 400

Tyr Gly Ile Ala Cys Cys Val Ser Ala Met Ala Ile Gly Lys Gln Met
                405                 410                 415

Gln Phe Phe Gly Ala Arg Ala Asn Leu Ala Lys Ala Leu Leu Tyr Ala
                420                 425                 430

Ile Asn Gly Gly Lys Asp Glu Lys His Lys Met Gln Val Gly Pro Glu
            435                 440                 445

Met Pro Pro Val Ala Ser Asp Val Leu Asp Tyr Asp Glu Val Met His
450                 455                 460

Lys Phe Asp Gln Thr Met Glu Trp Leu Ala Gly Leu Tyr Ile Asn Thr
465                 470                 475                 480

Leu Asn Val Ile His Tyr Met His Asp Lys Tyr Cys Tyr Glu Arg Ile
                485                 490                 495

Glu Met Ala Leu His Asp Thr Glu Ile Leu Arg Thr Met Ala Thr Gly
                500                 505                 510

Ile Ala Gly Leu Ser Val Val Ala Asp Ser Leu Ser Ala Val Lys Tyr
            515                 520                 525

Ala Lys Val Ser Val Val Arg Asp Glu Asn Gly Ile Ala Val Asp Phe
530                 535                 540

Glu Thr Glu Gly Asp Phe Pro Lys Tyr Gly Asn Asn Asp Asp Arg Val
545                 550                 555                 560

Asp Ala Ile Ala Val Asp Ile Val Lys Arg Phe Met Lys Lys Leu Arg
                565                 570                 575

Lys His Gln Thr Tyr Arg Gln Ser Val Gln Thr Met Ser Ile Leu Thr
                580                 585                 590

Ile Thr Ser Asn Val Val Tyr Gly Lys Lys Thr Gly Asn Thr Pro Asp
            595                 600                 605

Gly Arg Arg Ala Gly Glu Pro Phe Ala Pro Gly Ala Asn Pro Met His
610                 615                 620

Gly Arg Asp Thr Lys Gly Thr Leu Ala Ser Leu Ser Ser Val Ala Lys
625                 630                 635                 640

Leu Pro Tyr Ser Tyr Ala Leu Asp Gly Ile Ser Asn Thr Phe Ser Ile
                645                 650                 655

Val Pro Lys Ala Leu Gly Lys Asp Glu Glu Ser Arg Ala Ala Asn Leu
            660                 665                 670

Ser Ser Ile Leu Asp Gly Tyr Ala Lys Thr Gly His His Leu Asn
        675                 680                 685

Val Asn Val Phe Asn Arg Glu Thr Leu Leu Asp Ala Met Glu His Pro
690                 695                 700

Glu Glu Tyr Pro Gln Leu Thr Ile Arg Val Ser Gly Tyr Ala Val Asn
```

Phe Ile Lys Leu Thr Lys Glu Gln Gln Leu Asp Val Ile Ser Arg Thr
705                 710                 715                 720

Phe His Glu Ser Met
        740

<210> SEQ ID NO 41
<211> LENGTH: 2310
<212> TYPE: DNA
<213> ORGANISM: Streptococcus thermophilus
<220> FEATURE:
<221> NAME/KEY: misc_feature
<223> OTHER INFORMATION: CNRZ1066

<400> SEQUENCE: 41

| | | | | |
|---|---|---|---|---|
| atggcaacgg | ttaaaactaa | cacagatgtt | tttgaaaaag | cgtgggaagg | ctttaaagga | 60 |
| actgactgga | agaaaaaagc | aagtgtgtct | cgcttcgtac | aagcaaacta | cacaccatat | 120 |
| gatggtgatg | aaagcttcct | tgcaggacca | actgaacgct | cacttaaaat | caaaaaaatc | 180 |
| attgaagaaa | ctaaagccca | ctacgaagaa | actcgtttcc | caatggatac | tcgtccgaca | 240 |
| tcaatcgcag | atattcctgc | cggctatatt | tcaaaagacg | acgaactaat | ctacggtatt | 300 |
| caaaatgatg | agttattcaa | attgaatttc | atgccaaaag | gcggaattcg | tatggcagaa | 360 |
| acagctctca | aggaacatgg | ctatgaacct | gatccagctg | ttcacgaaat | ttttacaaaa | 420 |
| catgtaacta | cagtaaatga | cggtatcttc | cgtgcttata | catcaaatat | ccgtcgtgca | 480 |
| cgtcacgcac | acactataac | tggacttcca | gatgcttact | ctcgtggacg | tatcatcggt | 540 |
| gtttatgctc | gccttgctct | ttacggtgct | gacttcttga | tgcaagaaaa | agtaaacgac | 600 |
| tggaactcta | tcgaagaaat | caacgaagaa | actattcgtc | ttcgtgaaga | agttaacctt | 660 |
| caataccaag | cacttcaaga | tgttgttcgc | cttggtgacc | tttacggtgt | agatgttcgt | 720 |
| cgtccagcct | tcgatactaa | agaagctatc | caatggacaa | acattgcttt | tatggctgta | 780 |
| tgtcgtgtta | tcaatggtgc | ggctacttca | cttggtcgtg | tgccaatcgt | ccttgacata | 840 |
| tatgcagaac | gtgaccttgc | tcgtggtact | tacactgaat | cagaaatcca | agaattcgtt | 900 |
| gatgattttg | tcttgaaact | tcgtactgta | aaattcgcac | gtacaaaagc | ttacgacgaa | 960 |
| ctttactcag | gtgacccaac | attcatcaca | acttctatgg | ctggtatggg | tgctgacgga | 1020 |
| cgtcaccgtg | ttactaaaat | ggactaccgt | ttccttgaaca | cacttgataa | tattggtaat | 1080 |
| gctccagaac | caaacttgac | agttctttgg | tctgacaaat | tgccttactc | attccgtcgc | 1140 |
| tactgtatgc | acatgagtca | caagcactct | tctattcaat | acgaaggtgt | gactactatg | 1200 |
| gctaaagacg | gatacggtga | aatgagctgt | atctcatgtt | gtgtatcacc | acttgaccca | 1260 |
| gaaaacgaag | aacaacgcca | aacatccaa | tacttcggtg | ctcgtgttaa | cgtacttaaa | 1320 |
| gcccttctta | ctggtttgaa | cggtggttac | gacgatgttc | ataaagacta | caaagtatt | 1380 |
| gacatcgatc | cagtccgtga | tgaagttctt | gactttgaca | ctgttaaagc | taacttcgaa | 1440 |
| aaatctcttg | actggttgac | tgacacttat | gtagatgccc | ttaacatcat | ccactacatg | 1500 |
| actgataagt | acaactacga | agctgttcaa | atggccttct | tgccaactaa | caacgtgct | 1560 |
| aacatgggat | tcggtatctg | tggtttcgca | atactgttg | atacattgtc | agctatcaag | 1620 |
| tacgctacag | ttaaaccaat | ccgtgacgaa | gatggctaca | tctacgacta | cgaaacaatc | 1680 |
| ggtgaatacc | cacgttgggg | tgaagatgac | ccacgttcaa | acgaattggc | agaatggttg | 1740 |
| attgaagctt | cacactactcg | tcttcgtagc | cataaactct | acaaagatgc | agaagctaca | 1800 |

```
gtttcacttc ttacaatcac ttcgaacgtt gcttactcta acaaactgg taactctcca    1860 gttcacaaag gggtatacct caacgaagat ggttcagtga acttgtccaa attggaattc    1920
ttctcaccag gtgctaaccc atctaacaaa gctaaaggtg gatggttgca aaacttgaac    1980
tcacttgcaa gccttgactt cggttatgca gctgacggta tctcacttac tactcaagta    2040
tcacctcgtg cccttggtaa gactcgcgac gaacaagttg ataacctcgt aactatcctt    2100
gacggatact tcgaaaacgg tggacaacac cttaacttga acgttatgga cttgtcagct    2160
gtttacaaaa agatcatgag cggtgaagat gttatcgtac gtatctctgg atactgtgta    2220
aacactaaat acctcactcc agaacaaaaa actgaattga cacaacgtgt cttccacgaa    2280
gttctttcaa cggacgatgc tatgggataa                                    2310
```

<210> SEQ ID NO 42
<211> LENGTH: 769
<212> TYPE: PRT
<213> ORGANISM: Streptococcus thermophilus
<220> FEATURE:
<221> NAME/KEY: MISC_FEATURE
<223> OTHER INFORMATION: CNRZ1066

<400> SEQUENCE: 42

```
Met Ala Thr Val Lys Thr Asn Thr Asp Val Phe Glu Lys Ala Trp Glu
1               5                   10                  15

Gly Phe Lys Gly Thr Asp Trp Lys Glu Lys Ala Ser Val Ser Arg Phe
            20                  25                  30

Val Gln Ala Asn Tyr Thr Pro Tyr Asp Gly Asp Glu Ser Phe Leu Ala
        35                  40                  45

Gly Pro Thr Glu Arg Ser Leu Lys Ile Lys Lys Ile Ile Glu Glu Thr
    50                  55                  60

Lys Ala His Tyr Glu Glu Thr Arg Phe Pro Met Asp Thr Arg Pro Thr
65                  70                  75                  80

Ser Ile Ala Asp Ile Pro Ala Gly Tyr Ile Ser Lys Asp Asp Glu Leu
                85                  90                  95

Ile Tyr Gly Ile Gln Asn Asp Glu Leu Phe Lys Leu Asn Phe Met Pro
            100                 105                 110

Lys Gly Gly Ile Arg Met Ala Glu Thr Ala Leu Lys Glu His Gly Tyr
        115                 120                 125

Glu Pro Asp Pro Ala Val His Glu Ile Phe Thr Lys His Val Thr Thr
    130                 135                 140

Val Asn Asp Gly Ile Phe Arg Ala Tyr Thr Ser Asn Ile Arg Arg Ala
145                 150                 155                 160

Arg His Ala His Thr Ile Thr Gly Leu Pro Asp Ala Tyr Ser Arg Gly
                165                 170                 175

Arg Ile Ile Gly Val Tyr Ala Arg Leu Ala Leu Tyr Gly Ala Asp Phe
            180                 185                 190

Leu Met Gln Glu Lys Val Asn Asp Trp Asn Ser Ile Glu Glu Ile Asn
        195                 200                 205

Glu Glu Thr Ile Arg Leu Arg Glu Glu Val Asn Leu Gln Tyr Gln Ala
    210                 215                 220

Leu Gln Asp Val Val Arg Leu Gly Asp Leu Tyr Gly Val Asp Val Arg
225                 230                 235                 240

Arg Pro Ala Phe Asp Thr Lys Glu Ala Ile Gln Trp Thr Asn Ile Ala
                245                 250                 255

Phe Met Ala Val Cys Arg Val Ile Asn Gly Ala Ala Thr Ser Leu Gly
            260                 265                 270
```

-continued

```
Arg Val Pro Ile Val Leu Asp Ile Tyr Ala Glu Arg Asp Leu Ala Arg
        275                 280                 285

Gly Thr Tyr Thr Glu Ser Glu Ile Gln Glu Phe Val Asp Asp Phe Val
    290                 295                 300

Leu Lys Leu Arg Thr Val Lys Phe Ala Arg Thr Lys Ala Tyr Asp Glu
305                 310                 315                 320

Leu Tyr Ser Gly Asp Pro Thr Phe Ile Thr Thr Ser Met Ala Gly Met
                325                 330                 335

Gly Ala Asp Gly Arg His Arg Val Thr Lys Met Asp Tyr Arg Phe Leu
                340                 345                 350

Asn Thr Leu Asp Asn Ile Gly Asn Ala Pro Glu Pro Asn Leu Thr Val
                355                 360                 365

Leu Trp Ser Asp Lys Leu Pro Tyr Ser Phe Arg Arg Tyr Cys Met His
        370                 375                 380

Met Ser His Lys His Ser Ser Ile Gln Tyr Glu Gly Val Thr Thr Met
385                 390                 395                 400

Ala Lys Asp Gly Tyr Gly Glu Met Ser Cys Ile Ser Cys Cys Val Ser
                405                 410                 415

Pro Leu Asp Pro Glu Asn Glu Glu Gln Arg His Asn Ile Gln Tyr Phe
                420                 425                 430

Gly Ala Arg Val Asn Val Leu Lys Ala Leu Leu Thr Gly Leu Asn Gly
        435                 440                 445

Gly Tyr Asp Asp Val His Lys Asp Tyr Lys Val Phe Asp Ile Asp Pro
    450                 455                 460

Val Arg Asp Glu Val Leu Asp Phe Asp Thr Val Lys Ala Asn Phe Glu
465                 470                 475                 480

Lys Ser Leu Asp Trp Leu Thr Asp Thr Tyr Val Asp Ala Leu Asn Ile
                485                 490                 495

Ile His Tyr Met Thr Asp Lys Tyr Asn Tyr Glu Ala Val Gln Met Ala
                500                 505                 510

Phe Leu Pro Thr Lys Gln Arg Ala Asn Met Gly Phe Gly Ile Cys Gly
        515                 520                 525

Phe Ala Asn Thr Val Asp Thr Leu Ser Ala Ile Lys Tyr Ala Thr Val
    530                 535                 540

Lys Pro Ile Arg Asp Glu Asp Gly Tyr Ile Tyr Asp Tyr Glu Thr Ile
545                 550                 555                 560

Gly Glu Tyr Pro Arg Trp Gly Glu Asp Pro Arg Ser Asn Glu Leu
                565                 570                 575

Ala Glu Trp Leu Ile Glu Ala Tyr Thr Thr Arg Leu Arg Ser His Lys
                580                 585                 590

Leu Tyr Lys Asp Ala Glu Ala Thr Val Ser Leu Leu Thr Ile Thr Ser
        595                 600                 605

Asn Val Ala Tyr Ser Lys Gln Thr Gly Asn Ser Pro Val His Lys Gly
    610                 615                 620

Val Tyr Leu Asn Glu Asp Gly Ser Val Asn Leu Ser Lys Leu Glu Phe
625                 630                 635                 640

Phe Ser Pro Gly Ala Asn Pro Ser Asn Lys Ala Lys Gly Gly Trp Leu
                645                 650                 655

Gln Asn Leu Asn Ser Leu Ala Ser Leu Asp Phe Gly Tyr Ala Ala Asp
                660                 665                 670

Gly Ile Ser Leu Thr Thr Gln Val Ser Pro Arg Ala Leu Gly Lys Thr
        675                 680                 685
```

```
Arg Asp Glu Gln Val Asp Asn Leu Val Thr Ile Leu Asp Gly Tyr Phe
    690                 695                 700

Glu Asn Gly Gly Gln His Leu Asn Leu Asn Val Met Asp Leu Ser Ala
705                 710                 715                 720

Val Tyr Lys Lys Ile Met Ser Gly Glu Asp Val Ile Val Arg Ile Ser
                725                 730                 735

Gly Tyr Cys Val Asn Thr Lys Tyr Leu Thr Pro Glu Gln Lys Thr Glu
            740                 745                 750

Leu Thr Gln Arg Val Phe His Glu Val Leu Ser Thr Asp Asp Ala Met
        755                 760                 765

Gly

<210> SEQ ID NO 43
<211> LENGTH: 2310
<212> TYPE: DNA
<213> ORGANISM: Streptococcus thermophilus
<220> FEATURE:
<221> NAME/KEY: MISC_FEATURE
<223> OTHER INFORMATION: LMG18311

<400> SEQUENCE: 43
atggcaacgg ttaaaactaa cacagatgtt tttgaaaaag cgtgggaagg ctttaaagga      60
actgactgga agaaaaaagc aagtgtgtct cgcttcgtac aagcaaacta cacaccatat    120
gatggtgatg aaagcttcct tgcaggacca actgaacgct cacttaaaat caaaaaaatc    180
attgaagaaa ctaaagctca ctacgaagaa actcgtttcc caatggatac tcgtccgaca    240
tcaatcgcag atattcctgc cggctatatt tcaaagacg acgaactaat ctacggtatt    300
caaaatgatg agttattcaa attgaatttc atgccaaaag gcggaattcg tatggcagaa    360
acagctctca aggaacatgg ctatgaacct gatccagctg ttcacgaaat ttttacaaaa    420
catgtaacta cagtaaatga cggtatcttc cgtgcttata catcaaatat ccgtcgtgca    480
cgtcacgcac acactataac tggacttcca gatgcttact ctcgtggacg tatcatcggt    540
gtttatgctc gccttgctct ttacggtgct gacttcttga tgcaagaaaa agtaaacgac    600
tggaactcta tcgaagaaat caacgaagaa actattcgtc ttcgtgaaga agttaacctt    660
caataccaag cacttcaaga tgttgttcgc cttggtgacc tttacggtgt agatgttcgt    720
cgtccagcct tcgatactaa agaagctatc aatggacaa acattgcttt tatggctgta    780
tgtcgtgtta tcaatggtgc ggctacttca cttggtcgtg tgccaatcgt ccttgacata    840
tatgcagaac gtgaccttgc tcgtggtact tacactgaat cagaaatcca agaattcgtt    900
gatgattttg tcttgaaact tcgtactgta aaattcgcac gtacaaaagc ttacgacgaa    960
ctttactcag gtgacccaac attcatcaca acttctatgg ctggtatggg tgctgacgga   1020
cgtcaccgtg ttactaaaat ggactaccgt ttcttgaaca cacttgataa tattggtaat   1080
gctccagaac caaacttgac agttctttgg tctgacaaat tgccttactc attccgtcgc   1140
tactgtatgc acatgagtca caagcactct tctattcaat acgaaggtgt gactactatg   1200
gctaaagacg gatacggtga atgagctgt atctcatgtt gtgtatcacc acttgaccca   1260
gaaaacgaag aacaacgcca caatccaa tacttcggtg ctcgtgttaa cgtacttaaa   1320
gcccttctta ctggtttgaa cggtggttac gacgatgttc ataaagacta caagtatt   1380 gacatcgatc cagtccgtga tgaagttctt gactttgaca ctgttaaagc taacttcgaa   1440
aaatctcttg actggttgac tgacacttat gtagatgccc ttaacatcat ccactacatg   1500
actgataagt acaactacga agctgttcaa atggccttct tgccaactaa caacgtgct   1560
```

-continued

```
aacatgggat tcggtatctg tggtttcgca aatactgttg atacattgtc agctatcaag   1620
tacgctacag ttaaaccaat ccgtgacgaa gatggctaca tctacgacta cgaaacaatc   1680
ggtgaatacc cacgttgggg tgaagatgac ccacgttcaa acgaattggc agaatggttg   1740
attgaagctt acactactcg tcttcgtagc cataaactct acaaagatgc agaagctaca   1800
gtttcacttc ttacaatcac ttcgaacgtt gcttactcta aacaaactgg taactctcca   1860
gttcacaaag gggtatacct caacgaagat ggttcagtga acttgtctaa attggaattc   1920
ttctcaccag gtgctaaccc atcaacaaaa gctaaggtg gatggttgca aaacttgaac     1980
tcacttgcaa gccttgactt cggttatgca gctgacggta tctcacttac tactcaagta   2040
tcacctcgtg cccttggtaa gactcgcgac gaacaagttg ataacctcgt aactatcctt   2100
gacggatact tcgaaaacgg tggacaacac cttaacttga acgttatgga cttgtcagct   2160
gtttacaaaa agatcatgag cggtgaagat gttatcgtac gtatctctgg atactgtgta   2220
aacactaaat acctcactcc agaacaaaaa actgaattga cacaacgtgt cttccacgaa   2280
gttctttcaa cggacgatgc tatgggataa                                     2310
```

<210> SEQ ID NO 44
<211> LENGTH: 769
<212> TYPE: PRT
<213> ORGANISM: Streptococcus thermophilus
<220> FEATURE:
<221> NAME/KEY: MISC_FEATURE
<223> OTHER INFORMATION: LMG18311

<400> SEQUENCE: 44

```
Met Ala Thr Val Lys Thr Asn Thr Asp Val Phe Glu Lys Ala Trp Glu
  1               5                  10                  15

Gly Phe Lys Gly Thr Asp Trp Lys Glu Lys Ala Ser Val Ser Arg Phe
                 20                  25                  30

Val Gln Ala Asn Tyr Thr Pro Tyr Asp Gly Asp Glu Ser Phe Leu Ala
             35                  40                  45

Gly Pro Thr Glu Arg Ser Leu Lys Ile Lys Lys Ile Glu Glu Thr
         50                  55                  60

Lys Ala His Tyr Glu Glu Thr Arg Phe Pro Met Asp Thr Arg Pro Thr
 65                  70                  75                  80

Ser Ile Ala Asp Ile Pro Ala Gly Tyr Ile Ser Lys Asp Asp Glu Leu
                 85                  90                  95

Ile Tyr Gly Ile Gln Asn Asp Glu Leu Phe Lys Leu Asn Phe Met Pro
            100                 105                 110

Lys Gly Gly Ile Arg Met Ala Glu Thr Ala Leu Lys Glu His Gly Tyr
        115                 120                 125

Glu Pro Asp Pro Ala Val His Glu Ile Phe Thr Lys His Val Thr Thr
    130                 135                 140

Val Asn Asp Gly Ile Phe Arg Ala Tyr Thr Ser Asn Ile Arg Arg Ala
145                 150                 155                 160

Arg His Ala His Thr Ile Thr Gly Leu Pro Asp Ala Tyr Ser Arg Gly
                165                 170                 175

Arg Ile Ile Gly Val Tyr Ala Arg Leu Ala Leu Tyr Gly Ala Asp Phe
            180                 185                 190

Leu Met Gln Glu Lys Val Asn Asp Trp Asn Ser Ile Glu Glu Ile Asn
        195                 200                 205

Glu Glu Thr Ile Arg Leu Arg Glu Glu Val Asn Leu Gln Tyr Gln Ala
    210                 215                 220
```

```
Leu Gln Asp Val Val Arg Leu Gly Asp Leu Tyr Gly Val Asp Val Arg
225                 230                 235                 240

Arg Pro Ala Phe Asp Thr Lys Glu Ala Ile Gln Trp Thr Asn Ile Ala
                245                 250                 255

Phe Met Ala Val Cys Arg Val Ile Asn Gly Ala Ala Thr Ser Leu Gly
            260                 265                 270

Arg Val Pro Ile Val Leu Asp Ile Tyr Ala Glu Arg Asp Leu Ala Arg
        275                 280                 285

Gly Thr Tyr Thr Glu Ser Glu Ile Gln Glu Phe Val Asp Asp Phe Val
    290                 295                 300

Leu Lys Leu Arg Thr Val Lys Phe Ala Arg Thr Lys Ala Tyr Asp Glu
305                 310                 315                 320

Leu Tyr Ser Gly Asp Pro Thr Phe Ile Thr Thr Ser Met Ala Gly Met
                325                 330                 335

Gly Ala Asp Gly Arg His Arg Val Thr Lys Met Asp Tyr Arg Phe Leu
            340                 345                 350

Asn Thr Leu Asp Asn Ile Gly Asn Ala Pro Glu Pro Asn Leu Thr Val
        355                 360                 365

Leu Trp Ser Asp Lys Leu Pro Tyr Ser Phe Arg Arg Tyr Cys Met His
    370                 375                 380

Met Ser His Lys His Ser Ser Ile Gln Tyr Glu Gly Val Thr Thr Met
385                 390                 395                 400

Ala Lys Asp Gly Tyr Gly Glu Met Ser Cys Ile Ser Cys Cys Val Ser
                405                 410                 415

Pro Leu Asp Pro Glu Asn Glu Gln Arg His Asn Ile Gln Tyr Phe
            420                 425                 430

Gly Ala Arg Val Asn Val Leu Lys Ala Leu Leu Thr Gly Leu Asn Gly
        435                 440                 445

Gly Tyr Asp Asp Val His Lys Asp Tyr Lys Val Phe Asp Ile Asp Pro
    450                 455                 460

Val Arg Asp Glu Val Leu Asp Phe Asp Thr Val Lys Ala Asn Phe Glu
465                 470                 475                 480

Lys Ser Leu Asp Trp Leu Thr Asp Thr Tyr Val Asp Ala Leu Asn Ile
                485                 490                 495

Ile His Tyr Met Thr Asp Lys Tyr Asn Tyr Glu Ala Val Gln Met Ala
            500                 505                 510

Phe Leu Pro Thr Lys Gln Arg Ala Asn Met Gly Phe Gly Ile Cys Gly
        515                 520                 525

Phe Ala Asn Thr Val Asp Thr Leu Ser Ala Ile Lys Tyr Ala Thr Val
    530                 535                 540

Lys Pro Ile Arg Asp Glu Asp Gly Tyr Ile Tyr Asp Tyr Glu Thr Ile
545                 550                 555                 560

Gly Glu Tyr Pro Arg Trp Gly Glu Asp Pro Arg Ser Asn Glu Leu
                565                 570                 575

Ala Glu Trp Leu Ile Glu Ala Tyr Thr Thr Arg Leu Arg Ser His Lys
            580                 585                 590

Leu Tyr Lys Asp Ala Glu Ala Thr Val Ser Leu Leu Thr Ile Thr Ser
        595                 600                 605

Asn Val Ala Tyr Ser Lys Gln Thr Gly Asn Ser Pro Val His Lys Gly
    610                 615                 620

Val Tyr Leu Asn Glu Asp Gly Ser Val Asn Leu Ser Lys Leu Glu Phe
625                 630                 635                 640
```

```
Phe Ser Pro Gly Ala Asn Pro Ser Asn Lys Ala Lys Gly Gly Trp Leu
                645                 650                 655

Gln Asn Leu Asn Ser Leu Ala Ser Leu Asp Phe Gly Tyr Ala Ala Asp
        660                 665                 670

Gly Ile Ser Leu Thr Thr Gln Val Ser Pro Arg Ala Leu Gly Lys Thr
            675                 680                 685

Arg Asp Glu Gln Val Asp Asn Leu Val Thr Ile Leu Asp Gly Tyr Phe
690                 695                 700

Glu Asn Gly Gly Gln His Leu Asn Leu Asn Val Met Asp Leu Ser Ala
705                 710                 715                 720

Val Tyr Lys Lys Ile Met Ser Gly Glu Asp Val Ile Val Arg Ile Ser
                725                 730                 735

Gly Tyr Cys Val Asn Thr Lys Tyr Leu Thr Pro Glu Gln Lys Thr Glu
            740                 745                 750

Leu Thr Gln Arg Val Phe His Glu Val Leu Ser Thr Asp Asp Ala Met
        755                 760                 765

Gly
```

<210> SEQ ID NO 45
<211> LENGTH: 2310
<212> TYPE: DNA
<213> ORGANISM: Streptococcus thermophilus
<220> FEATURE:
<221> NAME/KEY: misc_feature
<223> OTHER INFORMATION: LMD-9

<400> SEQUENCE: 45

```
atggcaacgg ttaaaactaa cacagatgtt tttgaaaaag cgtgggaagg ctttaaagga      60
actgactgga agaaaaaagc aagtgtgtct cgcttcgtac aagcaaacta cacaccatat     120
gatggtgatg aaagcttcct tgcaggacca actgaacgct cacttaaaat caaaaaaatc     180
attgaagaaa ctaaagctca ctacgaagaa actcgtttcc caatggatac tcgtccgaca     240
tcaatcgcag atattcctgc cggctatatt tcaaaagacg acgaactaat ctacggtatt     300
caaaatgatg agttattcaa attgaatttc atgccaaaag gcggaattcg tatggcagaa     360
acagctctca aggaacatgg ctatgaacct gatccagctg ttcacgaaat ttttacaaaa     420
catgtaacta cagtaaatga cggtatcttc cgtgcttata catcaaatat ccgtcgtgca     480
cgtcacgcac acactataac tggacttcca gatgcttact ctcgtggacg tatcatcggt     540
gtttatgctc gccttgctct ttacggtgct gacttcttga tgcaagaaaa agtaaacgac     600
tggaactcta tcgaagaaat caacgaagaa actattcgtc ttcgtgaaga gttaaccttt     660
caataccaag cacttcaaga tgttgttcgc cttggtgacc tttacggtgt agatgttcgt     720
cgtccagcct tcgatactaa agaagctatc aatggacaa acattgcttt tatggctgta     780
tgtcgtgtta tcaatggtgc ggctacttca cttggtcgtg tgccaatcgt ccttgacata     840
tatgcagaac gtgaccttgc tcgtggtact tacactgaat cagaaatcca gaattcgtt     900 gatgattttg tcttgaaact tcgtactgta aaattcgcac gtacaaaagc ttacgacgaa     960
ctttactcag gtgacccaac attcatcaca acttctatgg ctggtatggg tgctgacgga    1020
cgtcaccgtg ttactaaaat ggactaccgt ttccttgaaca cacttgataa tattggtaat    1080
gctccagaac caaacttgac agttctttgg tctgacaaat tgccttactc attccgtcgc    1140
tactgtatgc acatgagtca caagcactct tctattcaat acgaaggtgt gactactatg    1200
gctaaagacg gatacggtga aatgagctgt atctcatgtt gtgtatcacc acttgaccca    1260
```

-continued

```
gaaaacgaag aacaacgcca caacatccaa tacttcggtg ctcgtgttaa cgtacttaaa   1320
gcccttctta ctggtttgaa cggtggttac gacgatgttc ataaagacta caaagtattt   1380
gacatcgatc cagtccgtga tgaagttctt gactttgaca ctgttaaagc taacttcgaa   1440
aaatctcttg actggttgac tgacacttat gtagatgccc ttaacatcat ccactacatg   1500
actgataagt acaactacga agctgttcaa atggccttct tgccaactaa caacgtgct    1560 aacatgggat tcggtatctg tggtttcgca aatactgttg atacattgtc agctatcaag   1620
tacgctacag ttaaaccaat ccgtgacgaa gatggctaca tctacgacta cgaaacaatc   1680
ggtgaatacc cacgttgggg tgaagatgac ccacgttcaa acgaattggc agaatggttg   1740
attgaagctt acactactcg tcttcgtagc cataaactct acaaagatgc agaagctaca   1800
gtttcacttc ttacaatcac ttcgaacgtt gcttactcta aacaaactgg taactctcca   1860
gttcacaaag gggtatacct caacgaagat ggttcagtga acttgtctaa attggaattc   1920
ttctcaccag gtgctaaccc atctaacaaa gctaaaggtg atggttgca aaacttgaac    1980 tcacttgcaa gccttgactt cggttatgca gctgacggta tctcgcttac tactcaagta   2040
tcacctcgtg cccttggtaa gactcgcgac gaacaagttg ataacctcgt aactatcctt   2100
gacggatact tcgaaaacgg tggacaacac cttaacttga cgttatgga cttgtcagct    2160 gtttacaaaa agatcatgag cggtgaagat gttatcgtac gtatctctgg atactgtgta   2220
aacactaaat acctcactcc agaacaaaaa actgaattga cacaacgtgt cttccacgaa   2280
gttctttcaa cggacgatgc tatgggataa                                   2310
```

<210> SEQ ID NO 46
<211> LENGTH: 769
<212> TYPE: PRT
<213> ORGANISM: Streptococcus thermophilus
<220> FEATURE:
<221> NAME/KEY: MISC_FEATURE
<223> OTHER INFORMATION: LMD-9

<400> SEQUENCE: 46

```
Met Ala Thr Val Lys Thr Asn Thr Asp Val Phe Glu Lys Ala Trp Glu
1               5                   10                  15

Gly Phe Lys Gly Thr Asp Trp Lys Glu Lys Ala Ser Val Ser Arg Phe
                20                  25                  30

Val Gln Ala Asn Tyr Thr Pro Tyr Asp Gly Asp Glu Ser Phe Leu Ala
            35                  40                  45

Gly Pro Thr Glu Arg Ser Leu Lys Ile Lys Lys Ile Glu Glu Thr
        50                  55                  60

Lys Ala His Tyr Glu Glu Thr Arg Phe Pro Met Asp Thr Arg Pro Thr
65                  70                  75                  80

Ser Ile Ala Asp Ile Pro Ala Gly Tyr Ile Ser Lys Asp Asp Glu Leu
                85                  90                  95

Ile Tyr Gly Ile Gln Asn Asp Glu Leu Phe Lys Leu Asn Phe Met Pro
            100                 105                 110

Lys Gly Gly Ile Arg Met Ala Glu Thr Ala Leu Lys Glu His Gly Tyr
        115                 120                 125

Glu Pro Asp Pro Ala Val His Glu Ile Phe Thr Lys His Val Thr Thr
    130                 135                 140

Val Asn Asp Gly Ile Phe Arg Ala Tyr Thr Ser Asn Ile Arg Arg Ala
145                 150                 155                 160

Arg His Ala His Thr Ile Thr Gly Leu Pro Asp Ala Tyr Ser Arg Gly
                165                 170                 175
```

```
Arg Ile Ile Gly Val Tyr Ala Arg Leu Ala Leu Tyr Gly Ala Asp Phe
            180                 185                 190

Leu Met Gln Glu Lys Val Asn Asp Trp Asn Ser Ile Glu Glu Ile Asn
        195                 200                 205

Glu Glu Thr Ile Arg Leu Arg Glu Val Asn Leu Gln Tyr Gln Ala
    210                 215                 220

Leu Gln Asp Val Val Arg Leu Gly Asp Leu Tyr Gly Val Asp Val Arg
225                 230                 235                 240

Arg Pro Ala Phe Asp Thr Lys Glu Ala Ile Gln Trp Thr Asn Ile Ala
                245                 250                 255

Phe Met Ala Val Cys Arg Val Ile Asn Gly Ala Thr Ser Leu Gly
            260                 265                 270

Arg Val Pro Ile Val Leu Asp Ile Tyr Ala Glu Arg Asp Leu Ala Arg
            275                 280                 285

Gly Thr Tyr Thr Glu Ser Glu Ile Gln Glu Phe Val Asp Asp Phe Val
    290                 295                 300

Leu Lys Leu Arg Thr Val Lys Phe Ala Arg Thr Lys Ala Tyr Asp Glu
305                 310                 315                 320

Leu Tyr Ser Gly Asp Pro Thr Phe Ile Thr Thr Ser Met Ala Gly Met
                325                 330                 335

Gly Ala Asp Gly Arg His Arg Val Thr Lys Met Asp Tyr Arg Phe Leu
            340                 345                 350

Asn Thr Leu Asp Asn Ile Gly Asn Ala Pro Glu Pro Asn Leu Thr Val
        355                 360                 365

Leu Trp Ser Asp Lys Leu Pro Tyr Ser Phe Arg Arg Tyr Cys Met His
    370                 375                 380

Met Ser His Lys His Ser Ser Ile Gln Tyr Glu Gly Val Thr Thr Met
385                 390                 395                 400

Ala Lys Asp Gly Tyr Gly Glu Met Ser Cys Ile Ser Cys Val Ser
                405                 410                 415

Pro Leu Asp Pro Glu Asn Glu Glu Gln Arg His Asn Ile Gln Tyr Phe
            420                 425                 430

Gly Ala Arg Val Asn Val Leu Lys Ala Leu Leu Thr Gly Leu Asn Gly
            435                 440                 445

Gly Tyr Asp Asp Val His Lys Asp Tyr Lys Val Phe Asp Ile Asp Pro
    450                 455                 460

Val Arg Asp Glu Val Leu Asp Phe Asp Thr Val Lys Ala Asn Phe Glu
465                 470                 475                 480

Lys Ser Leu Asp Trp Leu Thr Asp Thr Tyr Val Asp Ala Leu Asn Ile
                485                 490                 495

Ile His Tyr Met Thr Asp Lys Tyr Asn Tyr Glu Ala Val Gln Met Ala
            500                 505                 510

Phe Leu Pro Thr Lys Gln Arg Ala Asn Met Gly Phe Gly Ile Cys Gly
        515                 520                 525

Phe Ala Asn Thr Val Asp Thr Leu Ser Ala Ile Lys Tyr Ala Thr Val
    530                 535                 540

Lys Pro Ile Arg Asp Glu Asp Gly Tyr Ile Tyr Asp Tyr Glu Thr Ile
545                 550                 555                 560

Gly Glu Tyr Pro Arg Trp Gly Glu Asp Pro Arg Ser Asn Glu Leu
                565                 570                 575

Ala Glu Trp Leu Ile Glu Ala Tyr Thr Thr Arg Leu Arg Ser His Lys
            580                 585                 590
```

| | | | | | | | | | | | | |
|---|---|---|---|---|---|---|---|---|---|---|---|---|
| Leu | Tyr | Lys | Asp | Ala | Glu | Ala | Thr | Val | Ser | Leu | Leu | Thr | Ile | Thr | Ser |
| | | 595 | | | | 600 | | | | 605 | | | |

Asn Val Ala Tyr Ser Lys Gln Thr Gly Asn Ser Pro Val His Lys Gly
    610                 615                 620

Val Tyr Leu Asn Glu Asp Gly Ser Val Asn Leu Ser Lys Leu Glu Phe
625                 630                 635                 640

Phe Ser Pro Gly Ala Asn Pro Ser Asn Lys Ala Lys Gly Gly Trp Leu
            645                 650                 655

Gln Asn Leu Asn Ser Leu Ala Ser Leu Asp Phe Gly Tyr Ala Ala Asp
        660                 665                 670

Gly Ile Ser Leu Thr Thr Gln Val Ser Pro Arg Ala Leu Gly Lys Thr
    675                 680                 685

Arg Asp Glu Gln Val Asp Asn Leu Val Thr Ile Leu Asp Gly Tyr Phe
690                 695                 700

Glu Asn Gly Gly Gln His Leu Asn Leu Asn Val Met Asp Leu Ser Ala
705                 710                 715                 720

Val Tyr Lys Lys Ile Met Ser Gly Glu Asp Val Ile Val Arg Ile Ser
                725                 730                 735

Gly Tyr Cys Val Asn Thr Lys Tyr Leu Thr Pro Glu Gln Lys Thr Glu
            740                 745                 750

Leu Thr Gln Arg Val Phe His Glu Val Leu Ser Thr Asp Asp Ala Met
        755                 760                 765

Gly

<210> SEQ ID NO 47
<211> LENGTH: 2445
<212> TYPE: DNA
<213> ORGANISM: Lactobacillus plantarum
<220> FEATURE:
<221> NAME/KEY: misc_feature
<223> OTHER INFORMATION: WCFS1

<400> SEQUENCE: 47

```
atgatcatgt ctgaaacttt aactaaaaca acgacaacta ttaaccactt cggtaaattg      60
acgccaatga tggatcgctt acgcgatagc atcattgatg caaaacctta tgtcgatcca     120
gaacgggcga ttctcacaac cgaaacttat cgacaacacc aagacgaaca agtcgatata     180
ttacgggcta aaatgcttga acacgttctt gataaaatga gtatcttcat tgaagatgat     240
actttaattg ttggtaacca agcacgccaa atcgttggg caccagtatt ccctgagtat     300
tctatgaatt gggtcattga tgaattagat acatttgaga agcgtcctgg tgacgttttc     360
tatattacgg agaaatccaa ggaagaactt cgtgcgattg cgcctttctg gaaacataat     420
acccttggaag accgcggcta cgctagtttt ccagaagcaa gtcgtatttt ttatgattta     480
ggtattattg gagccgatgg taatatcact tctggtgatg gtcacattgc ggtcgactat     540
aaaaacgttg ttaataaggg acttaaatgg tatgaagacc gcattaagac agcacttgct     600
aatcttgacc ttactgattt taaccagcaa aaacaatact atttctataa agcgggccta     660
attgtaattg atgccattca caattttgct aaacgttacg cccaattagc gtccaagcaa     720
gctcaaaaca cgacatccgc aactcgcaaa gcacaacttg aaaaaatcgc ccaaattcta     780
aacaaggttc cttacgaacc tgcaaattca tttatgaag cgattcaagc tgtctggtta     840
gttcatctga ccttacaaat cgaatccaac ggtcattctg tctcatatgg tcgtctagat     900
cagtacctag ctccattcta tgagcacgat ttaaaaactg gtgctattga cgccaacggt     960
gcaaccgaat tactcacaaa cttatgtctt aagacgttaa cgattaataa agtacgctca    1020
```

```
tggcaacata ctgaattttc tgcagggagt cccctctacc aaaacattac gattggtggt   1080
caaacaccag atggtaaaga tgccgttaat ccgacgtcct atctgatttt acgagcaatt   1140
gcgcaagcac atttaccaca acccaactta acggtccgtt atcaccatgg cttaagcgat   1200
aagtttatgc gtgaatgtgt cgaagttatt aaacaaggct taggtatgcc tgcgtttaat   1260
aacgacgaaa ttattattcc gtcgtttatt cgtcgtggcg tcaagaaaga agacgcctat   1320
aattacagtg ccatcggttg tgtcgaaaca gcgatccctg aaaatgggg ctatcgttgc    1380
accgggatga gcttcattaa cttcccacgc gttctcttac tcattatgaa tggtggcatt   1440
gatcctgaat ctggcaaacg gttattaccc gattatggta agttcactga tatgacttct   1500
tttgatcaac ttatgactgc ttgggacaaa gcgctccgtg aaatgacacg acaaagtgtg   1560
attatcgaaa atagttgtga tttggctttg aacaaaaatt atcctgatat tctctgctcc   1620
gttttaaccg acgattgtat cggtcgtggt aagaccatta agaaggtgg cgcggtatac    1680
gactttatca gtggattaca agttggtatt gctaacctag cggactccct agctgcaatc   1740
aagaaacttg tctttgaaga aaagaagttg acaacaaccc aactttggca cgcacttacc   1800
actgattttg cggatgaaga tggtgaaaag attcggcaga tgctcattaa tgatgcccca   1860
aagtatggta acgatgatga ttatgttgat gatttgattg ttgaagctta taaaccatat   1920
attgatgaaa ttgccaagta caaaaacacg cgctacggtc gcggccctat tggtggcttg   1980
cgctacgcag gaacctcttc tatttcggcc aacgttggtc aagggcacag cactttggct   2040
acaccagatg tcggcacgcc tcggacacca ttagccgaag gttgctcacc agaacatgca   2100
atggatactg atggcccaac tgctgtgttc aaatcagttt ccaaattatc cactaaggac   2160
atcactggtg gcgtattact gaaccaaaag atgtcaccac aaattctacg gagtgatgaa   2220
agctgcatga aattggttgc actactacgg accttcttca atcgacttca tggttaccat   2280
gtccaataca acattgtttc acgggatacc ttgattgatg cacagaacca tcctgacaag   2340
caccgtgact tgattgttcg ggttgctgga tattccgcct tcttcgtggg cctatccaaa   2400
gaaacccaag atgatattat cgaacggacg gagcagtctc tataa                  2445
```

<210> SEQ ID NO 48
<211> LENGTH: 814
<212> TYPE: PRT
<213> ORGANISM: Lactobacillus plantarum
<220> FEATURE:
<221> NAME/KEY: MISC_FEATURE
<223> OTHER INFORMATION: WCFS1

<400> SEQUENCE: 48

Met Ile Met Ser Glu Thr Leu Thr Lys Thr Thr Thr Ile Asn His
1               5                   10                  15

Phe Gly Lys Leu Thr Pro Met Met Asp Arg Leu Arg Asp Ser Ile Ile
                20                  25                  30

Asp Ala Lys Pro Tyr Val Asp Pro Glu Arg Ala Ile Leu Thr Thr Glu
            35                  40                  45

Thr Tyr Arg Gln His Gln Asp Glu Gln Val Asp Ile Leu Arg Ala Lys
        50                  55                  60

Met Leu Glu His Val Leu Asp Lys Met Ser Ile Phe Ile Glu Asp Asp
65                  70                  75                  80

Thr Leu Ile Val Gly Asn Gln Ala Arg Gln Asn Arg Trp Ala Pro Val
                85                  90                  95

Phe Pro Glu Tyr Ser Met Asn Trp Val Ile Asp Glu Leu Asp Thr Phe

```
                    100                 105                 110
Glu Lys Arg Pro Gly Asp Val Phe Tyr Ile Thr Glu Lys Ser Lys Glu
            115                 120                 125

Glu Leu Arg Ala Ile Ala Pro Phe Trp Lys His Asn Thr Leu Glu Asp
            130                 135                 140

Arg Gly Tyr Ala Ser Phe Pro Glu Ala Ser Arg Ile Phe Tyr Asp Leu
145                 150                 155                 160

Gly Ile Ile Gly Ala Asp Gly Asn Ile Thr Ser Gly Asp Gly His Ile
            165                 170                 175

Ala Val Asp Tyr Lys Asn Val Val Asn Lys Gly Leu Lys Trp Tyr Glu
            180                 185                 190

Asp Arg Ile Lys Thr Ala Leu Ala Asn Leu Asp Leu Thr Asp Phe Asn
            195                 200                 205

Gln Gln Lys Gln Tyr Tyr Phe Tyr Lys Ala Gly Leu Ile Val Ile Asp
            210                 215                 220

Ala Ile His Asn Phe Ala Lys Arg Tyr Ala Gln Leu Ala Ser Lys Gln
225                 230                 235                 240

Ala Gln Asn Thr Thr Ser Ala Thr Arg Lys Ala Gln Leu Glu Lys Ile
            245                 250                 255

Ala Gln Ile Leu Asn Lys Val Pro Tyr Glu Pro Ala Asn Ser Phe Tyr
            260                 265                 270

Glu Ala Ile Gln Ala Val Trp Leu Val His Leu Thr Leu Gln Ile Glu
            275                 280                 285

Ser Asn Gly His Ser Val Ser Tyr Gly Arg Leu Asp Gln Tyr Leu Ala
            290                 295                 300

Pro Phe Tyr Glu His Asp Leu Lys Thr Gly Ala Ile Asp Ala Asn Gly
305                 310                 315                 320

Ala Thr Glu Leu Leu Thr Asn Leu Cys Leu Lys Thr Leu Thr Ile Asn
            325                 330                 335

Lys Val Arg Ser Trp Gln His Thr Glu Phe Ser Ala Gly Ser Pro Leu
            340                 345                 350

Tyr Gln Asn Ile Thr Ile Gly Gly Gln Thr Pro Asp Gly Lys Asp Ala
            355                 360                 365

Val Asn Pro Thr Ser Tyr Leu Ile Leu Arg Ala Ile Ala Gln Ala His
            370                 375                 380

Leu Pro Gln Pro Asn Leu Thr Val Arg Tyr His His Gly Leu Ser Asp
385                 390                 395                 400

Lys Phe Met Arg Glu Cys Val Glu Val Ile Lys Gln Gly Leu Gly Met
            405                 410                 415

Pro Ala Phe Asn Asn Asp Glu Ile Ile Pro Ser Phe Ile Arg Arg
            420                 425                 430

Gly Val Lys Lys Glu Asp Ala Tyr Asn Tyr Ser Ala Ile Gly Cys Val
            435                 440                 445

Glu Thr Ala Ile Pro Gly Lys Trp Gly Tyr Arg Cys Thr Gly Met Ser
            450                 455                 460

Phe Ile Asn Phe Pro Arg Val Leu Leu Leu Ile Met Asn Gly Gly Ile
465                 470                 475                 480

Asp Pro Glu Ser Gly Lys Arg Leu Leu Pro Asp Tyr Gly Lys Phe Thr
            485                 490                 495

Asp Met Thr Ser Phe Asp Gln Leu Met Thr Ala Trp Asp Lys Ala Leu
            500                 505                 510

Arg Glu Met Thr Arg Gln Ser Val Ile Ile Glu Asn Ser Cys Asp Leu
            515                 520                 525
```

```
Ala Leu Glu Gln Asn Tyr Pro Asp Ile Leu Cys Ser Val Leu Thr Asp
        530                 535                 540

Asp Cys Ile Gly Arg Gly Lys Thr Ile Lys Glu Gly Gly Ala Val Tyr
545                 550                 555                 560

Asp Phe Ile Ser Gly Leu Gln Val Gly Ile Ala Asn Leu Ala Asp Ser
                565                 570                 575

Leu Ala Ala Ile Lys Lys Leu Val Phe Glu Glu Lys Lys Leu Thr Thr
            580                 585                 590

Thr Gln Leu Trp His Ala Leu Thr Thr Asp Phe Ala Asp Glu Asp Gly
        595                 600                 605

Glu Lys Ile Arg Gln Met Leu Ile Asn Asp Ala Pro Lys Tyr Gly Asn
    610                 615                 620

Asp Asp Asp Tyr Val Asp Asp Leu Ile Val Glu Ala Tyr Lys Pro Tyr
625                 630                 635                 640

Ile Asp Glu Ile Ala Lys Tyr Lys Asn Thr Arg Tyr Gly Arg Gly Pro
                645                 650                 655

Ile Gly Gly Leu Arg Tyr Ala Gly Thr Ser Ser Ile Ser Ala Asn Val
            660                 665                 670

Gly Gln Gly His Ser Thr Leu Ala Thr Pro Asp Gly Arg His Ala Arg
        675                 680                 685

Thr Pro Leu Ala Glu Gly Cys Ser Pro Glu His Ala Met Asp Thr Asp
    690                 695                 700

Gly Pro Thr Ala Val Phe Lys Ser Val Ser Lys Leu Ser Thr Lys Asp
705                 710                 715                 720

Ile Thr Gly Gly Val Leu Leu Asn Gln Lys Met Ser Pro Gln Ile Leu
                725                 730                 735

Arg Ser Asp Glu Ser Cys Met Lys Leu Val Ala Leu Leu Arg Thr Phe
            740                 745                 750

Phe Asn Arg Leu His Gly Tyr His Val Gln Tyr Asn Ile Val Ser Arg
        755                 760                 765

Asp Thr Leu Ile Asp Ala Gln Asn His Pro Asp Lys His Arg Asp Leu
    770                 775                 780

Ile Val Arg Val Ala Gly Tyr Ser Ala Phe Phe Val Gly Leu Ser Lys
785                 790                 795                 800

Glu Thr Gln Asp Asp Ile Ile Glu Arg Thr Glu Gln Ser Leu
                805                 810

<210> SEQ ID NO 49
<211> LENGTH: 2259
<212> TYPE: DNA
<213> ORGANISM: Lactobacillus plantarum
<220> FEATURE:
<221> NAME/KEY: misc_feature
<223> OTHER INFORMATION: WCFS1

<400> SEQUENCE: 49
atgattacat cagaaaagac aacaaaacca gcagcttgga aaggtttcaa aggcgggcac      60
tggcaggaag aaatcaacat tcgtgatttt attcaaaata acttcacaca gtacaatggc    120
gacgaaagct tcctggccgg accaacagcc gctactaaga ccttgaatga caaagtctta    180
gaattaaaga acaagaacg tgccgctggt ggtgtgttgg atgctgatac taaagtcgtt    240
gcaacgatta cttcacacgg ccctggttat attcaaaaag atctcgaaaa gattgttggt    300
ctccagactg acaagccttt gaagcgggcc ttcatgccat tggtggtat tcgaatggct    360 gatgacgctt tgaaatcata cggttatacc cctgatgaag aaaacgacaa gattttcact    420
```

```
gaatatcgca agactcataa ccaaggcgtc ttcgatgttt atactcctga catgcggaaa    480
gcacgtcact acaagatcat caccggacta ccagatgcat acgcacgtgg ccgtctcatt    540
cctgatcttc cacgggtcgc tgtttatggg atcgatcgtt taatggaaga caaagctaat    600
gactttgccc acattggtga tggtgaattg actgatgatg ttattcgcct ccgtgaagaa    660
gttcaagatc aataccgtgc tttagcagat atgaagaaga tggctgccag ttatggctac    720
gatattagca agcctgcaac taatgctcaa gaagctattc aatggatgta cttcgcttac    780
ttagctgcta tcaagaccca aaacggcgct gcaatgtccg ttggccggat tgatacaacg    840
atggacatct tcatccaacg tgacttggac aatggtgttc tggacgaaag ccaagctcaa    900
gaattaattg atcaattcgt catgaaacta cggatggttc ggttcatccg tactgaagaa    960
tacaattctc tcttctctgg tgacccaatc tgggcaacct tatcaatgtg tggtttaggc   1020
gtcgacggtc aacaccatgt gactaagact gctttccgga ttttaaagac tttggacaac   1080
atgggcgccg caccgaaacc aaacatcacg attttatggt cagaccgctt accagaagac   1140
ttcaaacgtt acgcaactga agtttcaatc gacagttcaa ccattcagta tgaaaatgat   1200
gacttgatgc gggtacaatg gggtaccgat tattatggca ttgcttgctg tgtttccgca   1260
caaccaattg ctgatggaat ccagtacttc ggtgcccggg caaacttagc caaagcgatt   1320
ctttatgcca tcaatggtgg ccgcgacgaa attgctggag atcaagttgg ccctgcttac   1380
gaaccaatta cttcagaata catcgattac gacgaattca tgaagaaatt agacaagcaa   1440
atggattggt tagctgacac ttacgttaac tcactgaatg caattcatta tatgcatgat   1500
aagtactact atgaagctgc ccaattagct ttgaagaata ctgatcttga tcggacctt    1560
gcaactggga tttctggctt atcacatgcc gcggattcaa tctcagctat caagtatggt   1620
cacgttaaag taattcgtga cgaacgtggt atcgccgttg acttcaaagc cgacaatgac   1680
tacccacgtt atgggaacaa tgacgatcgc gctgatgaca ttgctaaatg gttagtcaaa   1740
gaattataca gcaagatgaa cacgcatcac ctctatcgga atgccaaact ttcaacttct   1800
gttttgacga ttacctccaa cgttgtttat ggtaagaaca ctggtaccac gccaaatggc   1860
cgtcaaaaag gcgaaccatt ctcaccaggt gctaaccctg catacggtgc tgaaaagagt   1920
ggtgcattag cttcacttct ttcaactgcc aaattaccat accgttacgc aactgacggg   1980
atttccaaca cgttcggcgt tacccctaac acgttaggcc atgacctcga atcacggaaa   2040
gacacgttag taaacatgtt agacggttac atgaagaacg atgggatgca cttgaacatc   2100
aacgtcttca ataaagacac tttgattgat gctcagaaac ccctgaaga ataccccaaca   2160
ttaacggttc gggtttctgg ctattgtgtc tacttcgcag atttaaccaa ggaacaacaa   2220
gatgacgtta tttcacggac attcttcgaa tcaatgtaa                          2259
```

<210> SEQ ID NO 50
<211> LENGTH: 752
<212> TYPE: PRT
<213> ORGANISM: Lactobacillus plantarum
<220> FEATURE:
<221> NAME/KEY: MISC_FEATURE
<223> OTHER INFORMATION: WCFS1

<400> SEQUENCE: 50

Met Ile Thr Ser Glu Lys Thr Thr Lys Pro Ala Ala Trp Lys Gly Phe
1               5                   10                  15

Lys Gly Gly His Trp Gln Glu Glu Ile Asn Ile Arg Asp Phe Ile Gln
            20                  25                  30

-continued

Asn Asn Phe Thr Gln Tyr Asn Gly Asp Glu Ser Phe Leu Ala Gly Pro
            35                  40                  45

Thr Ala Ala Thr Lys Thr Leu Asn Asp Lys Val Leu Glu Leu Lys Lys
 50                  55                  60

Gln Glu Arg Ala Ala Gly Gly Val Leu Asp Ala Asp Thr Lys Val Val
 65                  70                  75                  80

Ala Thr Ile Thr Ser His Gly Pro Gly Tyr Ile Gln Lys Asp Leu Glu
                 85                  90                  95

Lys Ile Val Gly Leu Gln Thr Asp Lys Pro Leu Lys Arg Ala Phe Met
                100                 105                 110

Pro Phe Gly Gly Ile Arg Met Ala Asp Asp Ala Leu Lys Ser Tyr Gly
                115                 120                 125

Tyr Thr Pro Asp Glu Glu Asn Asp Lys Ile Phe Thr Glu Tyr Arg Lys
                130                 135                 140

Thr His Asn Gln Gly Val Phe Asp Val Tyr Thr Pro Asp Met Arg Lys
145                 150                 155                 160

Ala Arg His Tyr Lys Ile Ile Thr Gly Leu Pro Asp Ala Tyr Ala Arg
                165                 170                 175

Gly Arg Leu Ile Pro Asp Leu Pro Arg Val Ala Val Tyr Gly Ile Asp
                180                 185                 190

Arg Leu Met Glu Asp Lys Ala Asn Asp Phe Ala His Ile Gly Asp Gly
                195                 200                 205

Glu Leu Thr Asp Asp Val Ile Arg Leu Arg Glu Glu Val Gln Asp Gln
                210                 215                 220

Tyr Arg Ala Leu Ala Asp Met Lys Lys Met Ala Ala Ser Tyr Gly Tyr
225                 230                 235                 240

Asp Ile Ser Lys Pro Ala Thr Asn Ala Gln Glu Ala Ile Gln Trp Met
                245                 250                 255

Tyr Phe Ala Tyr Leu Ala Ala Ile Lys Thr Gln Asn Gly Ala Ala Met
                260                 265                 270

Ser Val Gly Arg Ile Asp Thr Thr Met Asp Ile Phe Ile Gln Arg Asp
                275                 280                 285

Leu Asp Asn Gly Val Leu Asp Glu Ser Gln Ala Gln Glu Leu Ile Asp
                290                 295                 300

Gln Phe Val Met Lys Leu Arg Met Val Arg Phe Ile Arg Thr Glu Glu
305                 310                 315                 320

Tyr Asn Ser Leu Phe Ser Gly Asp Pro Ile Trp Ala Thr Leu Ser Met
                325                 330                 335

Cys Gly Leu Gly Val Asp Gly Gln His Val Thr Lys Thr Ala Phe
                340                 345                 350

Arg Ile Leu Lys Thr Leu Asp Asn Met Gly Ala Ala Pro Glu Pro Asn
                355                 360                 365

Ile Thr Ile Leu Trp Ser Asp Arg Leu Pro Glu Asp Phe Lys Arg Tyr
                370                 375                 380

Ala Thr Glu Val Ser Ile Asp Ser Ser Thr Ile Gln Tyr Glu Asn Asp
385                 390                 395                 400

Asp Leu Met Arg Val Gln Trp Gly Thr Asp Tyr Tyr Gly Ile Ala Cys
                405                 410                 415

Cys Val Ser Ala Gln Pro Ile Ala Asp Gly Ile Gln Tyr Phe Gly Ala
                420                 425                 430

Arg Ala Asn Leu Ala Lys Ala Ile Leu Tyr Ala Ile Asn Gly Gly Arg
                435                 440                 445

```
Asp Glu Ile Ala Gly Asp Gln Val Gly Pro Ala Tyr Glu Pro Ile Thr
        450                 455                 460

Ser Glu Tyr Ile Asp Tyr Asp Glu Phe Met Lys Lys Leu Asp Lys Gln
465                 470                 475                 480

Met Asp Trp Leu Ala Asp Thr Tyr Val Asn Ser Leu Asn Ala Ile His
            485                 490                 495

Tyr Met His Asp Lys Tyr Tyr Glu Ala Ala Gln Leu Ala Leu Lys
        500                 505                 510

Asn Thr Asp Leu Asp Arg Thr Phe Ala Thr Gly Ile Ser Gly Leu Ser
        515                 520                 525

His Ala Ala Asp Ser Ile Ser Ala Ile Lys Tyr Gly His Val Lys Val
        530                 535                 540

Ile Arg Asp Glu Arg Gly Ile Ala Val Asp Phe Lys Ala Asp Asn Asp
545                 550                 555                 560

Tyr Pro Arg Tyr Gly Asn Asn Asp Asp Arg Ala Asp Asp Ile Ala Lys
                565                 570                 575

Trp Leu Val Lys Glu Leu Tyr Ser Lys Met Asn Thr His His Leu Tyr
            580                 585                 590

Arg Asn Ala Lys Leu Ser Thr Ser Val Leu Thr Ile Thr Ser Asn Val
        595                 600                 605

Val Tyr Gly Lys Asn Thr Gly Thr Thr Pro Asn Gly Arg Gln Lys Gly
        610                 615                 620

Glu Pro Phe Ser Pro Gly Ala Asn Pro Ala Tyr Gly Ala Glu Lys Ser
625                 630                 635                 640

Gly Ala Leu Ala Ser Leu Leu Ser Thr Ala Lys Leu Pro Tyr Arg Tyr
                645                 650                 655

Ala Thr Asp Gly Ile Ser Asn Thr Phe Gly Val Thr Pro Asn Thr Leu
            660                 665                 670

Gly His Asp Leu Glu Ser Arg Lys Asp Thr Leu Val Asn Met Leu Asp
        675                 680                 685

Gly Tyr Met Lys Asn Asp Gly Met His Leu Asn Ile Asn Val Phe Asn
        690                 695                 700

Lys Asp Thr Leu Ile Asp Ala Gln Lys His Pro Glu Glu Tyr Pro Thr
705                 710                 715                 720

Leu Thr Val Arg Val Ser Gly Tyr Cys Val Tyr Phe Ala Asp Leu Thr
                725                 730                 735

Lys Glu Gln Gln Asp Asp Val Ile Ser Arg Thr Phe Phe Glu Ser Met
            740                 745                 750

<210> SEQ ID NO 51
<211> LENGTH: 2259
<212> TYPE: DNA
<213> ORGANISM: Lactobacillus plantarum
<220> FEATURE:
<221> NAME/KEY: misc_feature
<223> OTHER INFORMATION: JDM1

<400> SEQUENCE: 51
atgattacat cagaaaagac aacaaaacca gcagcttgga aaggtttcaa aggcgggcac     60
tggcaggaag aaatcaacat tcgtgatttt attcaaaata acttcacaca gtacaatggc    120
gacgaaagct tcctggccgg accaacagcc gctactaaga ccttgaatga caaagtctta    180
gaattaaaga acaagaacg tgccgctggt ggtgtgttgg acgctgatac taaagtcgtt    240
gcaacgatta cttcacacgg ccctggttat attcaaaaag atctcgaaaa gattgttggt    300
ctccagactg acaagccttt gaagcgggcc ttcatgccat tggtggtat tcgaatggct    360
```

```
gatgacgctt tgaaatcata cggttatacc cctgatgaag aaaacgacaa gattttcact    420
gaatatcgca agactcataa ccaaggcgtc ttcgatgttt atactcctga catgcggaaa    480
gcacgtcact acaagatcat caccggacta ccagatgcat acgcacgtgg ccgtctcatt    540
cctgatcttc cacgggtcgc tgtttatggg atcgatcgtt taatggaaga caaagctaat    600
gactttgccc acattggtga tggtgaattg actgatgatg ttattcgcct ccgtgaagaa    660
gttcaagatc aataccgtgc tttagcagat atgaagaaga tggctgccag ttatggctac    720
gatattagca agcctgcaac taatgctcaa gaagctattc aatggatgta cttcgcttac    780
ttagctgcta tcaagaccca aaacggcgct gcaatgtccg ttggccggat tgatacaacg    840
atggacatct tcatccaacg tgacttggac aatggtgttc tggacgaaag ccaagctcaa    900
gaattaattg atcaattcgt catgaaacta cggatggttc ggttcatccg tactgaagaa    960
tacaattctc tcttctctgg tgacccaatc tgggcaacct tatcaatgtg tggtttaggc   1020
gtcgacggtc aacaccatgt gactaagacc gctttccgga ttttaaagac tttggacaac   1080
atgggcgccg caccagaacc aaacatcacg attttatggt cagatcgctt accagaagac   1140
ttcaaacgtt acgcaactga agtttcaatc gacagttcaa ccattcagta tgaaaatgat   1200
gacttgatgc gggtacaatg gggtaccgat tattatggca ttgcttgctg tgtttccgca   1260
caaccaattg ctgatggaat ccagtacttc ggtgcccggg caaacttagc caaagcgatt   1320
cttatgcca tcaatggtgg ccgcgacgaa attgctggag atcaagttgg ccctgcttac   1380
gaaccaatta cttcagaata catcgattac gacgaattca tgaagaaatt agacaagcaa   1440
atggattggt tagctgacac ttacgtgaac tcactgaatg caattcatta tatgcatgat   1500
aagtactact atgaagctgc ccaattagct ttgaagaata ctgatcttga tcggaccttt   1560
gcaactggga tttctggctt atcacatgcc gcggattcaa tctcagctat caagtatggt   1620
cacgttaaag taattcgtga cgaacgtggt atcgccgttg acttcaaagc cgacaatgac   1680
tacccacgtt atgggaacaa tgacgatcgc gctgatgaca ttgctaaatg gttagtcaaa   1740
gaattataca gcaagatgaa cacgcatcac ctctatcgga atgccaaact ttcaacttct   1800
gttttgacga ttacctccaa cgttgtttat ggtaagaaca ctggtaccac accaaatggc   1860
cgtcaaaaag gcgaaccatt ctcaccaggt gctaaccctg catacggtgc tgaaaagagt   1920
ggtgcattag cttcacttct ttcaactgcc aaattaccat accgttacgc aactgacggg   1980
atttccaaca cgttcggcgt taccccctaac acgttaggcc atgacctcga atcacggaaa   2040
gacacgttag taaacatgtt agacggttac atgaagaacg atgggatgca cttgaacatc   2100
aacgtcttca ataaagacac tttgattgat gctcagaaac accctgaaga atacccaaca   2160
ttaacggttc gggtttctgg ctactgtgtc tacttcgcag atttaaccaa ggaacaacaa   2220
gatgacgtta tttcacggac attcttcgaa tcaatgtaa                          2259
```

<210> SEQ ID NO 52
<211> LENGTH: 752
<212> TYPE: PRT
<213> ORGANISM: Lactobacillus plantarum
<220> FEATURE:
<221> NAME/KEY: misc_feature
<223> OTHER INFORMATION: JDM1

<400> SEQUENCE: 52

Met Ile Thr Ser Glu Lys Thr Thr Lys Pro Ala Ala Trp Lys Gly Phe
1               5                   10                  15

```
Lys Gly Gly His Trp Gln Glu Glu Ile Asn Ile Arg Asp Phe Ile Gln
             20                  25                  30

Asn Asn Phe Thr Gln Tyr Asn Gly Asp Glu Ser Phe Leu Ala Gly Pro
             35                  40                  45

Thr Ala Ala Thr Lys Thr Leu Asn Asp Lys Val Leu Glu Leu Lys Lys
 50                  55                  60

Gln Glu Arg Ala Ala Gly Gly Val Leu Asp Ala Asp Thr Lys Val Val
 65                  70                  75                  80

Ala Thr Ile Thr Ser His Gly Pro Gly Tyr Ile Gln Lys Asp Leu Glu
                 85                  90                  95

Lys Ile Val Gly Leu Gln Thr Asp Lys Pro Leu Lys Arg Ala Phe Met
                100                 105                 110

Pro Phe Gly Gly Ile Arg Met Ala Asp Asp Ala Leu Lys Ser Tyr Gly
             115                 120                 125

Tyr Thr Pro Asp Glu Glu Asn Asp Lys Ile Phe Thr Glu Tyr Arg Lys
             130                 135                 140

Thr His Asn Gln Gly Val Phe Asp Val Tyr Thr Pro Asp Met Arg Lys
145                 150                 155                 160

Ala Arg His Tyr Lys Ile Ile Thr Gly Leu Pro Asp Ala Tyr Ala Arg
                165                 170                 175

Gly Arg Leu Ile Pro Asp Leu Pro Arg Val Ala Val Tyr Gly Ile Asp
             180                 185                 190

Arg Leu Met Glu Asp Lys Ala Asn Asp Phe Ala His Ile Gly Asp Gly
             195                 200                 205

Glu Leu Thr Asp Asp Val Ile Arg Leu Arg Glu Val Gln Asp Gln
210                 215                 220

Tyr Arg Ala Leu Ala Asp Met Lys Lys Met Ala Ala Ser Tyr Gly Tyr
225                 230                 235                 240

Asp Ile Ser Lys Pro Ala Thr Asn Ala Gln Glu Ala Ile Gln Trp Met
             245                 250                 255

Tyr Phe Ala Tyr Leu Ala Ala Ile Lys Thr Gln Asn Gly Ala Ala Met
             260                 265                 270

Ser Val Gly Arg Ile Asp Thr Thr Met Asp Ile Phe Ile Gln Arg Asp
             275                 280                 285

Leu Asp Asn Gly Val Leu Asp Glu Ser Gln Ala Gln Glu Leu Ile Asp
290                 295                 300

Gln Phe Val Met Lys Leu Arg Met Val Arg Phe Ile Arg Thr Glu Glu
305                 310                 315                 320

Tyr Asn Ser Leu Phe Ser Gly Asp Pro Ile Trp Ala Thr Leu Ser Met
             325                 330                 335

Cys Gly Leu Gly Val Asp Gly Gln His His Val Thr Lys Thr Ala Phe
             340                 345                 350

Arg Ile Leu Lys Thr Leu Asp Asn Met Gly Ala Ala Pro Glu Pro Asn
             355                 360                 365

Ile Thr Ile Leu Trp Ser Asp Arg Leu Pro Asp Phe Lys Arg Tyr
370                 375                 380

Ala Thr Glu Val Ser Ile Asp Ser Ser Thr Ile Gln Tyr Glu Asn Asp
385                 390                 395                 400

Asp Leu Met Arg Val Gln Trp Gly Thr Asp Tyr Tyr Gly Ile Ala Cys
                405                 410                 415

Cys Val Ser Ala Gln Pro Ile Ala Asp Gly Ile Gln Tyr Phe Gly Ala
             420                 425                 430

Arg Ala Asn Leu Ala Lys Ala Ile Leu Tyr Ala Ile Asn Gly Gly Arg
```

```
                435                 440                 445
Asp Glu Ile Ala Gly Asp Gln Val Gly Pro Ala Tyr Glu Pro Ile Thr
450                 455                 460
Ser Glu Tyr Ile Asp Tyr Asp Glu Phe Met Lys Lys Leu Asp Lys Gln
465                 470                 475                 480
Met Asp Trp Leu Ala Asp Thr Tyr Val Asn Ser Leu Asn Ala Ile His
                485                 490                 495
Tyr Met His Asp Lys Tyr Tyr Tyr Glu Ala Ala Gln Leu Ala Leu Lys
                500                 505                 510
Asn Thr Asp Leu Asp Arg Thr Phe Ala Thr Gly Ile Ser Gly Leu Ser
515                 520                 525
His Ala Ala Asp Ser Ile Ser Ala Ile Lys Tyr Gly His Val Lys Val
530                 535                 540
Ile Arg Asp Glu Arg Gly Ile Ala Val Asp Phe Lys Ala Asp Asn Asp
545                 550                 555                 560
Tyr Pro Arg Tyr Gly Asn Asn Asp Asp Arg Ala Asp Asp Ile Ala Lys
                565                 570                 575
Trp Leu Val Lys Glu Leu Tyr Ser Lys Met Asn Thr His His Leu Tyr
                580                 585                 590
Arg Asn Ala Lys Leu Ser Thr Ser Val Leu Thr Ile Thr Ser Asn Val
                595                 600                 605
Val Tyr Gly Lys Asn Thr Gly Thr Thr Pro Asn Gly Arg Gln Lys Gly
610                 615                 620
Glu Pro Phe Ser Pro Gly Ala Asn Pro Ala Tyr Gly Ala Glu Lys Ser
625                 630                 635                 640
Gly Ala Leu Ala Ser Leu Leu Ser Thr Ala Lys Leu Pro Tyr Arg Tyr
                645                 650                 655
Ala Thr Asp Gly Ile Ser Asn Thr Phe Gly Val Thr Pro Asn Thr Leu
                660                 665                 670
Gly His Asp Leu Glu Ser Arg Lys Asp Thr Leu Val Asn Met Leu Asp
                675                 680                 685
Gly Tyr Met Lys Asn Asp Gly Met His Leu Asn Ile Asn Val Phe Asn
690                 695                 700
Lys Asp Thr Leu Ile Asp Ala Gln Lys His Pro Glu Glu Tyr Pro Thr
705                 710                 715                 720
Leu Thr Val Arg Val Ser Gly Tyr Cys Val Tyr Phe Ala Asp Leu Thr
                725                 730                 735
Lys Glu Gln Gln Asp Asp Val Ile Ser Arg Thr Phe Phe Glu Ser Met
                740                 745                 750

<210> SEQ ID NO 53
<211> LENGTH: 2445
<212> TYPE: DNA
<213> ORGANISM: Lactobacillus plantarum
<220> FEATURE:
<221> NAME/KEY: misc_feature
<223> OTHER INFORMATION: JDM1

<400> SEQUENCE: 53
atgatcatgt ctgaaacttt aactaaaaca acgacaacta ttaaccactt cggtaaattg      60
acgccaatga tggatcgctt acgcgatagc atcattgatg caaaacctta tgtcgatcca     120
gaacgggcga ttctcacaac cgaaacttat cgacaacacc aagacgaaca agtcgatata     180
ttacgggcta aatgcttga acacgttctt gataaaatga gtatcttcat tgaagatgat     240
actttaattg ttggtaacca agcacgccaa atcgttggg caccagtatt ccctgagtat     300
```

```
tctatgaatt gggtcattga tgaattagat acatttgaga agcgtcctgg tgacgttttc      360
tatattacgg agaaatctaa ggaagaactt cgtgcgattg cgcctttctg gaaacataat      420
accttggaag accgcggcta cgctagtttt ccagaagcaa gtcgtatttt ttatgattta      480
ggtattattg gagccgatgg taatatcact tctggtgatg gtcacattgc ggtcgactat      540
aaaaacgttg ttaataaggg acttaaatgg tatgaagacc gcattaagac agcacttgct      600
aatcttgacc ttactgattt taaccagcaa aaacaatact atttctataa agcgggccta      660
attgtaatcg atgccattca caatttttgct aaacgttacg cccaattagc gtccaagcaa     720
gctcaaaaca cgacatccgc aactcgcaaa gcacaacttg aaaaaatcgc ccaaattcta      780
aacaaggttc cttacgaacc tgcaaattca ttttatgaag cgattcaagc tgtctggtta      840
gttcatctga ccttacaaat cgaatccaac ggtcattctg tctcatatgg tcgtctagat      900
cagtacctag atccattcta tgagcacgat ttaaaaactg gtgctattga cgccaacggt      960
gcaaccgaat tactcacaaa cttatgtctt aagacgttaa cgattaataa agtacgctca     1020
tggcaacata ctgaattttc tgcagggagt cccctctacc aaaacattac gattggtggt     1080
caaacaccag atggtaaaga tgccgttaat ccgacgtcct atctgatttt acgagcaatt     1140
gcgcaagcac atttaccaca acccaactta acggtccgtt atcaccatgg cttaagcgat     1200
aagtttatgc gtgaatgtgt cgaagttatt aaacaaggct taggtatgcc tgcgtttaat     1260
aacgacgaaa ttattattcc gtcgtttatt cgtcgtggcg tcaagaaaga agacgcctat     1320
aattacagtg ccatcggttg tgtcgaaaca gcgatccctg aaaatggggg ctatcgttgc     1380
accgggatga gcttcattaa cttcccacgc gttctcttac tcattatgaa tggtggcatt     1440
gatcctgaat ctggcaaacg gttattaccc gattatggta agttcactga tatgacttct     1500
tttgatcaac ttatgactgc ttgggacaaa gcgctccgtg aaatgacacg acaaagtgtg     1560
attatcgaaa atagttgtga tttggctttg gaacaaaaatt atcctgatat tctctgctcc     1620
gttttaaccg acgattgtat cggtcgtggt aagaccatta agaaggtgg cgcggtatac      1680 gactttatca gtggattaca agttggtatt gctaacctag cggactccct agctgcaatc     1740
aagaaacttg tctttgaaga aagaagttg acaacaaccc aactttggca cgcacttacc      1800
actgattttg cggatgaaga cggtgaaaag attcggcaga tgctcattaa tgatgcccca     1860
aagtatggta acgatgatga ttatgttgat gatttgattg ttgaagctta taaaccatat     1920
attgatgaaa ttgccaagta caaaaacacg cgctacggtc gcggccctat tggtggcttg     1980
cgttacgcag gaacctcttc tatttcggcc aacgttggtc aagggcacag cactttggct     2040
acaccagatg gtcggcacgc tcggacacca ttagccgaag gttgctcacc agaacatgca     2100
atggatacta atgcccaac tgctgtgttc aaatcagttt ccaagttatc cactaaggac      2160
atcactggtg gcgtattact gaaccaaaag atgtcaccac aaattctacg gagtgatgaa     2220
agctgcatga aattggttgc actactacga accttcttca accgacttca tggttaccat     2280
gtccaataca acattgtttc acgggatacc ttgattgatg cacagaacca tcctgacaag     2340
caccgtgact tgattgttcg ggttgctgga tattccgcct tcttcgtggg cctatccaaa     2400
gaaacccaag atgatattat cgaacggacg gagcagtctc tataa                     2445
```

<210> SEQ ID NO 54
<211> LENGTH: 814
<212> TYPE: PRT
<213> ORGANISM: Lactobacillus plantarum
<220> FEATURE:

```
<221> NAME/KEY: MISC_FEATURE
<223> OTHER INFORMATION: JDM1

<400> SEQUENCE: 54

Met Ile Met Ser Glu Thr Leu Thr Lys Thr Thr Thr Ile Asn His
1               5                   10                  15

Phe Gly Lys Leu Thr Pro Met Met Asp Arg Leu Arg Asp Ser Ile Ile
                20                  25                  30

Asp Ala Lys Pro Tyr Val Asp Pro Glu Arg Ala Ile Leu Thr Thr Glu
                35                  40                  45

Thr Tyr Arg Gln His Gln Asp Glu Gln Val Asp Ile Leu Arg Ala Lys
            50                  55                  60

Met Leu Glu His Val Leu Asp Lys Met Ser Ile Phe Ile Glu Asp Asp
65              70                  75                  80

Thr Leu Ile Val Gly Asn Gln Ala Arg Gln Asn Arg Trp Ala Pro Val
                85                  90                  95

Phe Pro Glu Tyr Ser Met Asn Trp Val Ile Asp Glu Leu Asp Thr Phe
                100                 105                 110

Glu Lys Arg Pro Gly Asp Val Phe Tyr Ile Thr Glu Lys Ser Lys Glu
            115                 120                 125

Glu Leu Arg Ala Ile Ala Pro Phe Trp Lys His Asn Thr Leu Glu Asp
            130                 135                 140

Arg Gly Tyr Ala Ser Phe Pro Glu Ala Ser Arg Ile Phe Tyr Asp Leu
145                 150                 155                 160

Gly Ile Ile Gly Ala Asp Gly Asn Ile Thr Ser Gly Asp Gly His Ile
                165                 170                 175

Ala Val Asp Tyr Lys Asn Val Val Asn Lys Gly Leu Lys Trp Tyr Glu
                180                 185                 190

Asp Arg Ile Lys Thr Ala Leu Ala Asn Leu Asp Leu Thr Asp Phe Asn
            195                 200                 205

Gln Gln Lys Gln Tyr Tyr Phe Tyr Lys Ala Gly Leu Ile Val Ile Asp
            210                 215                 220

Ala Ile His Asn Phe Ala Lys Arg Tyr Ala Gln Leu Ala Ser Lys Gln
225                 230                 235                 240

Ala Gln Asn Thr Thr Ser Ala Thr Arg Lys Ala Gln Leu Glu Lys Ile
                245                 250                 255

Ala Gln Ile Leu Asn Lys Val Pro Tyr Glu Pro Ala Asn Ser Phe Tyr
                260                 265                 270

Glu Ala Ile Gln Ala Val Trp Leu Val His Leu Thr Leu Gln Ile Glu
            275                 280                 285

Ser Asn Gly His Ser Val Ser Tyr Gly Arg Leu Asp Gln Tyr Leu Asp
            290                 295                 300

Pro Phe Tyr Glu His Asp Leu Lys Thr Gly Ala Ile Asp Ala Asn Gly
305                 310                 315                 320

Ala Thr Glu Leu Leu Thr Asn Leu Cys Leu Lys Thr Leu Thr Ile Asn
                325                 330                 335

Lys Val Arg Ser Trp Gln His Thr Glu Phe Ser Ala Gly Ser Pro Leu
                340                 345                 350

Tyr Gln Asn Ile Thr Ile Gly Gly Gln Thr Pro Asp Gly Lys Asp Ala
            355                 360                 365

Val Asn Pro Thr Ser Tyr Leu Ile Leu Arg Ala Ile Ala Gln Ala His
            370                 375                 380

Leu Pro Gln Pro Asn Leu Thr Val Arg Tyr His His Gly Leu Ser Asp
385                 390                 395                 400
```

```
Lys Phe Met Arg Glu Cys Val Glu Val Ile Lys Gln Gly Leu Gly Met
            405                 410                 415
Pro Ala Phe Asn Asn Asp Glu Ile Ile Ile Pro Ser Phe Ile Arg Arg
        420                 425                 430
Gly Val Lys Lys Glu Asp Ala Tyr Asn Tyr Ser Ala Ile Gly Cys Val
            435                 440                 445
Glu Thr Ala Ile Pro Gly Lys Trp Gly Tyr Arg Cys Thr Gly Met Ser
        450                 455                 460
Phe Ile Asn Phe Pro Arg Val Leu Leu Leu Ile Met Asn Gly Gly Ile
465                 470                 475                 480
Asp Pro Glu Ser Gly Lys Arg Leu Leu Pro Asp Tyr Gly Lys Phe Thr
            485                 490                 495
Asp Met Thr Ser Phe Asp Gln Leu Met Thr Ala Trp Asp Lys Ala Leu
        500                 505                 510
Arg Glu Met Thr Arg Gln Ser Val Ile Glu Asn Ser Cys Asp Leu
            515                 520                 525
Ala Leu Glu Gln Asn Tyr Pro Asp Ile Leu Cys Ser Val Leu Thr Asp
        530                 535                 540
Asp Cys Ile Gly Arg Gly Lys Thr Ile Lys Glu Gly Gly Ala Val Tyr
545                 550                 555                 560
Asp Phe Ile Ser Gly Leu Gln Val Gly Ile Ala Asn Leu Ala Asp Ser
            565                 570                 575
Leu Ala Ala Ile Lys Lys Leu Val Phe Glu Glu Lys Lys Leu Thr Thr
        580                 585                 590
Thr Gln Leu Trp His Ala Leu Thr Thr Asp Phe Ala Asp Glu Asp Gly
            595                 600                 605
Glu Lys Ile Arg Gln Met Leu Ile Asn Asp Ala Pro Lys Tyr Gly Asn
        610                 615                 620
Asp Asp Asp Tyr Val Asp Asp Leu Ile Val Glu Ala Tyr Lys Pro Tyr
625                 630                 635                 640
Ile Asp Glu Ile Ala Lys Tyr Lys Asn Thr Arg Tyr Gly Arg Gly Pro
            645                 650                 655
Ile Gly Gly Leu Arg Tyr Ala Gly Thr Ser Ser Ile Ser Ala Asn Val
        660                 665                 670
Gly Gln Gly His Ser Thr Leu Ala Thr Pro Asp Gly Arg His Ala Arg
            675                 680                 685
Thr Pro Leu Ala Glu Gly Cys Ser Pro Glu His Ala Met Asp Thr Asn
        690                 695                 700
Gly Pro Thr Ala Val Phe Lys Ser Val Ser Lys Leu Ser Thr Lys Asp
705                 710                 715                 720
Ile Thr Gly Gly Val Leu Leu Asn Gln Lys Met Ser Pro Gln Ile Leu
            725                 730                 735
Arg Ser Asp Glu Ser Cys Met Lys Leu Val Ala Leu Leu Arg Thr Phe
        740                 745                 750
Phe Asn Arg Leu His Gly Tyr His Val Gln Tyr Asn Ile Val Ser Arg
            755                 760                 765
Asp Thr Leu Ile Asp Ala Gln Asn His Pro Asp Lys His Arg Asp Leu
        770                 775                 780
Ile Val Arg Val Ala Gly Tyr Ser Ala Phe Phe Val Gly Leu Ser Lys
785                 790                 795                 800
Glu Thr Gln Asp Asp Ile Ile Glu Arg Thr Glu Gln Ser Leu
            805                 810
```

<210> SEQ ID NO 55
<211> LENGTH: 2262
<212> TYPE: DNA
<213> ORGANISM: Lactobacillus casei
<220> FEATURE:
<221> NAME/KEY: misc_feature
<223> OTHER INFORMATION: bl23

<400> SEQUENCE: 55

| | | | | | |
|---|---|---|---|---|---|
| atgaaacagc | ttgacgaaac | caaagttcct | aattattggg | aaggctttaa | cggcggcgac | 60 |
| tggcaagaag | aaattaatgt | gcgcgatttt | atcgagcata | acctgaacca | atatgacggg | 120 |
| gacgaaagtt | tccttgctgg | ccccactgaa | gcgacaacag | tcctgaacaa | tcaggttcta | 180 |
| aatttaaaga | agcaagaacg | tgcaaatggc | ggtgttttgg | atgctgacaa | caatattcca | 240 |
| tctacgatca | cctcacacgg | ccctggttat | ttgaacaaag | atcttgaaaa | gattgttggt | 300 |
| gttcagaccg | acaagccatt | caaacgagca | ttcatgccat | ttggcggtat | tcgaatggct | 360 |
| gaagatgcat | tggaatctta | tggcttcaag | acagatcctc | aagaacacaa | gattttcaat | 420 |
| gaatatcgta | agacccataa | ccaaggtgtc | tttgatgctt | ataccctga | tatgcgaaag | 480 |
| gctcgccatt | acaagatcgt | gactggcttg | ccagacgcat | acggccgtgg | ccggattgtt | 540 |
| tctgatttcc | cacggatcgc | tgtttacggg | atcgatcgtt | taatggctga | agttcaag | 600 |
| gattataact | tgaccggcga | cggcgaaatg | actgacgatg | taatcaaact | gcgtgaagaa | 660 |
| atcaatgaac | aatatcgtgc | cttaaacgac | atgaagaaga | tggccaagga | atatggctat | 720 |
| gacatctcgc | gtccggcagc | taatgcgcaa | gaagctgttc | agtggatcta | ctttggctat | 780 |
| ctggctgctg | ttaagactca | aaacggtgcc | gcaatgtccg | ttggccggat | cgatacggtt | 840 |
| attgatgctt | atatccaacg | cgatatgcgc | ttaggcaaat | tgaacgaaga | acaggcacag | 900 |
| gaactgattg | atcatttggt | tatgaaattg | cggatggttc | gtttcatccg | gactgaagaa | 960 |
| tataactcac | tgttctcagg | cgatccaatc | tgggcaaccct | tgtcattggc | aggaatgggc | 1020 |
| aatgatggcc | gtcaccacgt | taccaagacg | gctttccgtt | tcctgaagac | tttggacaac | 1080 |
| atgggcgcag | caccagaacc | aaacatcacc | ttgctttgga | gcgaacgctt | gccagaaggc | 1140 |
| ttcaaacgct | atgcaaccga | gtatccatc | caaagttcaa | ccattcaata | tgaaaatgat | 1200 |
| gacctgatgc | gcaacgaatg | gggtaccgat | tactacggta | ttgcttgctg | tgtctcggca | 1260 |
| caaccaattg | ctgatggcgt | tcaatacttt | ggtgcccgtg | ctaacttagc | taagacggtt | 1320 |
| ctgtatgcga | tcaacggtgg | gaaagatgaa | attcaggaag | cgcaagtagg | gcctgaatat | 1380 |
| gcaccgatca | ccagcgatta | cattgattac | aaagaattca | tgaataagtt | cgacaagatg | 1440 |
| atggactggc | tggccgacac | gtatgtcaat | gctttgaatg | tgattcacta | tatgcatgac | 1500 |
| aagtattatt | atgaagctgc | acagctggca | ttgaaggata | cccaactgaa | ccggaccttc | 1560 |
| gcaaccggga | tttccggcct | gtcacacgcg | gttgattcca | tcagtgcaat | caagtatggt | 1620 |
| catgtcaagg | caattcgcga | tgaaaacggt | gttgcagttg | acttcgttgc | tgacaatgat | 1680 |
| gactatccac | gctatggtaa | caacgatgat | cgcgctgatg | acatcgctaa | gtggttggtt | 1740 |
| aagaccttct | ataacaagat | gaacacgcat | catctgtatc | gcggcgcgaa | gttgagtacc | 1800 |
| agtgtcctga | ccattacctc | caacgtggtt | tatggtaaga | atacagggac | aacaccaaac | 1860 |
| ggtcgtcaaa | aaggcgaacc | attctcacca | ggtgccaacc | cggcatacgg | cgcagaaaag | 1920 |
| aacggcgcat | tggcatcctt | gatgtccacc | gccaagattc | cgtatcatta | cgcaactgac | 1980 |
| ggcattagta | atacgtttgg | ggttactccg | aacacactgg | gccacgatga | tgaaactcgt | 2040 |

```
aaggatacct tggttcacat ggttgacggc tatatggaaa acagcggcat gcatttgaac    2100
atcaacgtct tcaacaagga gaccctgatt gatgctcaga agcacccaga agaataccca    2160
acattgaccg ttcgggtttc tggctactgc gtctacttcg cagatttgac caaggaacaa    2220
caagacgatg tcattgctcg gaccttcttc gaagaaatgt aa                        2262
```

<210> SEQ ID NO 56
<211> LENGTH: 753
<212> TYPE: PRT
<213> ORGANISM: Lactobacillus casei
<220> FEATURE:
<221> NAME/KEY: MISC_FEATURE
<223> OTHER INFORMATION: bl23

<400> SEQUENCE: 56

| Met | Lys | Gln | Leu | Asp | Glu | Thr | Lys | Val | Pro | Asn | Tyr | Trp | Glu | Gly | Phe |
|---|---|---|---|---|---|---|---|---|---|---|---|---|---|---|---|
| 1 | | | | 5 | | | | | 10 | | | | | 15 | |

| Asn | Gly | Gly | Asp | Trp | Gln | Glu | Glu | Ile | Asn | Val | Arg | Asp | Phe | Ile | Glu |
| | | | 20 | | | | | 25 | | | | | 30 | | |

| His | Asn | Leu | Asn | Gln | Tyr | Asp | Gly | Asp | Glu | Ser | Phe | Leu | Ala | Gly | Pro |
| | | | 35 | | | | | 40 | | | | | 45 | | |

| Thr | Glu | Ala | Thr | Thr | Val | Leu | Asn | Asn | Gln | Val | Leu | Asn | Leu | Lys | Lys |
| | 50 | | | | | 55 | | | | | 60 | | | | |

| Gln | Glu | Arg | Ala | Asn | Gly | Gly | Val | Leu | Asp | Ala | Asp | Asn | Asn | Ile | Pro |
| 65 | | | | | 70 | | | | | 75 | | | | | 80 |

| Ser | Thr | Ile | Thr | Ser | His | Gly | Pro | Gly | Tyr | Leu | Asn | Lys | Asp | Leu | Glu |
| | | | | 85 | | | | | 90 | | | | | 95 | |

| Lys | Ile | Val | Gly | Val | Gln | Thr | Asp | Lys | Pro | Phe | Lys | Arg | Ala | Phe | Met |
| | | | | 100 | | | | | 105 | | | | | 110 | |

| Pro | Phe | Gly | Gly | Ile | Arg | Met | Ala | Glu | Asp | Ala | Leu | Glu | Ser | Tyr | Gly |
| | | | 115 | | | | | 120 | | | | | 125 | | |

| Phe | Lys | Thr | Asp | Pro | Gln | Glu | His | Lys | Ile | Phe | Asn | Glu | Tyr | Arg | Lys |
| | 130 | | | | | 135 | | | | | 140 | | | | |

| Thr | His | Asn | Gln | Gly | Val | Phe | Asp | Ala | Tyr | Thr | Pro | Asp | Met | Arg | Lys |
| 145 | | | | | 150 | | | | | 155 | | | | | 160 |

| Ala | Arg | His | Tyr | Lys | Ile | Val | Thr | Gly | Leu | Pro | Asp | Ala | Tyr | Gly | Arg |
| | | | | 165 | | | | | 170 | | | | | 175 | |

| Gly | Arg | Ile | Val | Ser | Asp | Phe | Pro | Arg | Ile | Ala | Val | Tyr | Gly | Ile | Asp |
| | | | | 180 | | | | | 185 | | | | | 190 | |

| Arg | Leu | Met | Ala | Glu | Lys | Phe | Lys | Asp | Tyr | Asn | Leu | Thr | Gly | Asp | Gly |
| | | | 195 | | | | | 200 | | | | | 205 | | |

| Glu | Met | Thr | Asp | Asp | Val | Ile | Lys | Leu | Arg | Glu | Glu | Ile | Asn | Glu | Gln |
| | 210 | | | | | 215 | | | | | 220 | | | | |

| Tyr | Arg | Ala | Leu | Asn | Asp | Met | Lys | Lys | Met | Ala | Lys | Glu | Tyr | Gly | Tyr |
| 225 | | | | | 230 | | | | | 235 | | | | | 240 |

| Asp | Ile | Ser | Arg | Pro | Ala | Ala | Asn | Ala | Gln | Glu | Ala | Val | Gln | Trp | Ile |
| | | | | 245 | | | | | 250 | | | | | 255 | |

| Tyr | Phe | Gly | Tyr | Leu | Ala | Ala | Val | Lys | Thr | Gln | Asn | Gly | Ala | Ala | Met |
| | | | | 260 | | | | | 265 | | | | | 270 | |

| Ser | Val | Gly | Arg | Ile | Asp | Thr | Val | Ile | Asp | Ala | Tyr | Ile | Gln | Arg | Asp |
| | | | 275 | | | | | 280 | | | | | 285 | | |

| Met | Arg | Leu | Gly | Lys | Leu | Asn | Glu | Glu | Gln | Ala | Gln | Glu | Leu | Ile | Asp |
| | 290 | | | | | 295 | | | | | 300 | | | | |

| His | Leu | Val | Met | Lys | Leu | Arg | Met | Val | Arg | Phe | Ile | Arg | Thr | Glu | Glu |
| 305 | | | | | 310 | | | | | 315 | | | | | 320 |

Tyr Asn Ser Leu Phe Ser Gly Asp Pro Ile Trp Ala Thr Leu Ser Leu
            325                 330                 335

Ala Gly Met Gly Asn Asp Gly Arg His His Val Thr Lys Thr Ala Phe
        340                 345                 350

Arg Phe Leu Lys Thr Leu Asp Asn Met Gly Ala Ala Pro Glu Pro Asn
            355                 360                 365

Ile Thr Leu Leu Trp Ser Glu Arg Leu Pro Glu Gly Phe Lys Arg Tyr
        370                 375                 380

Ala Thr Glu Val Ser Ile Gln Ser Ser Thr Ile Gln Tyr Glu Asn Asp
385                 390                 395                 400

Asp Leu Met Arg Asn Glu Trp Gly Thr Asp Tyr Tyr Gly Ile Ala Cys
            405                 410                 415

Cys Val Ser Ala Gln Pro Ile Ala Asp Gly Val Gln Tyr Phe Gly Ala
            420                 425                 430

Arg Ala Asn Leu Ala Lys Thr Val Leu Tyr Ala Ile Asn Gly Gly Lys
        435                 440                 445

Asp Glu Ile Gln Glu Ala Gln Val Gly Pro Tyr Ala Pro Ile Thr
        450                 455                 460

Ser Asp Tyr Ile Asp Tyr Lys Glu Phe Met Asn Lys Phe Asp Lys Met
465                 470                 475                 480

Met Asp Trp Leu Ala Asp Thr Tyr Val Asn Ala Leu Asn Val Ile His
            485                 490                 495

Tyr Met His Asp Lys Tyr Tyr Glu Ala Ala Gln Leu Ala Leu Lys
        500                 505                 510

Asp Thr Gln Leu Asn Arg Thr Phe Ala Thr Gly Ile Ser Gly Leu Ser
            515                 520                 525

His Ala Val Asp Ser Ile Ser Ala Ile Lys Tyr Gly His Val Lys Ala
530                 535                 540

Ile Arg Asp Glu Asn Gly Val Ala Val Asp Phe Val Ala Asp Asn Asp
545                 550                 555                 560

Asp Tyr Pro Arg Tyr Gly Asn Asn Asp Asp Arg Ala Asp Ile Ala
            565                 570                 575

Lys Trp Leu Val Lys Thr Phe Tyr Asn Lys Met Asn Thr His His Leu
        580                 585                 590

Tyr Arg Gly Ala Lys Leu Ser Thr Ser Val Leu Thr Ile Thr Ser Asn
        595                 600                 605

Val Val Tyr Gly Lys Asn Thr Gly Thr Thr Pro Asn Gly Arg Gln Lys
        610                 615                 620

Gly Glu Pro Phe Ser Pro Gly Ala Asn Pro Ala Tyr Gly Ala Glu Lys
625                 630                 635                 640

Asn Gly Ala Leu Ala Ser Leu Met Ser Thr Ala Lys Ile Pro Tyr His
            645                 650                 655

Tyr Ala Thr Asp Gly Ile Ser Asn Thr Phe Gly Val Thr Pro Asn Thr
            660                 665                 670

Leu Gly His Asp Asp Glu Thr Arg Lys Asp Thr Leu Val His Met Val
        675                 680                 685

Asp Gly Tyr Met Glu Asn Ser Gly Met His Leu Asn Ile Asn Val Phe
        690                 695                 700

Asn Lys Glu Thr Leu Ile Asp Ala Gln Lys His Pro Glu Glu Tyr Pro
705                 710                 715                 720

Thr Leu Thr Val Arg Val Ser Gly Tyr Cys Val Tyr Phe Ala Asp Leu
            725                 730                 735

Thr Lys Glu Gln Gln Asp Asp Val Ile Ala Arg Thr Phe Phe Glu Glu

```
              740            745            750
Met

<210> SEQ ID NO 57
<211> LENGTH: 2262
<212> TYPE: DNA
<213> ORGANISM: Lactobacillus casei
<220> FEATURE:
<221> NAME/KEY: misc_feature
<223> OTHER INFORMATION: ATCC 334

<400> SEQUENCE: 57
atgaaacagc ttgacgaaac caaagttcct aattattggg aaggctttaa cggcggcgac        60
tggcaagaag aaattaatgt gcgcgatttt atcgagcata acctgaacca atatgacggg       120
gacgaaagtt tccttgctgg tcccactgaa gcgacaacag tcctgaacaa tcaggttcta       180
aatttaaaga agcaagaacg tgcaaatggc ggtgttttgg atgctgacaa caatattcca       240
tctacgatca cctcacacgg ccctggttat ttgaacaaag atcttgaaaa gattgttggt       300
gttcagaccg acaagccatt caaacgagca ttcatgccat ttggcggtat tcgaatggct       360
gaagatgcat tggaatctta tggcttcaag acagatcctc aagaacacaa gattttcaat       420
gaatatcgta agacccataa ccaaggtgtc tttgatgctt ataccctga tatgcgaaag       480 gctcgccatt acaagatcgt gactggcttg ccagacgcat acggccgcgg ccggattgtt       540
tctgatttcc cacggatcgc tgtttacggg atcgatcgtt taatggctga agttcaag       600 gattataact tgaccggcga cggcgaaatg actgacgatg taatcaaatt gcgtgaagaa       660
atcaatgaac aatatcgtgc cttaaacgac atgaagaaga tggccaagga atatggctat       720
gacatctcgc gtccggcagc taatgcgcaa gaagctgttc agtggatcta ctttggctat       780
ctggctgctg ttaagactca aaacggtgcc gcaatgtccg ttggccggat cgatacggtt       840
attgatgctt atatccaacg cgatatgcgc ttaggcaaat gaacgaaga acaggcacag       900 gaactgattg atcatttggt tatgaaattg cggatggttc gtttcatccg gactgaagaa       960
tataactcac tgttctcagg cgatccaatc tgggcaacct tgtcattggc aggaatgggc      1020
aatgatggcc gtcaccacgt taccaagacg gctttccgtt tcctgaagac tttggacaac      1080
atgggcgcag caccagaacc aaacatcacc ttgctttgga gcgaacgctt gccagaaggc      1140
tttaaacgct atgcaaccga gtatccatc caaagttcaa ccattcaata tgaaaatgat      1200
gacctgatgc gcaatgaatg gggtaccgat tactacggta ttgcttgctg tgtctcggca      1260
caaccaattg ctgatggcgt tcaatacttt ggtgcccgtg ctaacttagc taagacggtt      1320
ctgtatgcga tcaacggtgg taaagatgaa attcaggaag cgcaagtagg gcctgaatat      1380
gcaccgatca ccagcgatta cattgattac aaagaattca tgaataagtt cgacaagatg      1440
atggactggc tggccgacac gtatgtcaat gctttgaatg tgattcacta tatgcatgac      1500
aagtattatt atgaagctgc acagctggca ttgaaggata cccaactgaa ccggaccttc      1560
gcaaccggga tttccggcct gtcacacgcg gttgattcca tcagtgcaat caagtatggt      1620
catgtcaagg caattcgcga tgaaaatggt gttgcagttg acttcgttgc tgacaatgat      1680
gactatccac gttatggtaa caacgatgat cgcgctgatg acatcgctaa gtggttggtt      1740
aagaccttct ataacaagat gaacacgcat catctgtatc gcggcgcgaa gttgagtacc      1800
agtgtcctga ccattacttc caacgtggtt tatggtaaga atacagggac aacaccaaac      1860
ggtcgtcaaa aaggcgaacc attctcacca ggtgccaacc cggcatacgg cgcagaaaag      1920
```

-continued

```
aacggcgcat tggcatcctt gatgtccacc gccaagattc cgtatcatta cgcaactgac    1980
ggcattagta atacgtttgg ggttactccg aacacactgg gccacgatga tgaaactcgt    2040
aaggatacct tggttcacat ggttgacggc tatatggaaa acagcggcat gcatttgaac    2100
atcaacgtct tcaacaagga gaccctgatt gatgctcaga agcacccaga agaatatcca    2160
acattgaccg ttcgggtttc tggctactgc gtctacttcg cagatttgac caaggaacaa    2220
caagacgatg tcattgctcg gaccttcttc gaagaaatgt aa                      2262
```

<210> SEQ ID NO 58
<211> LENGTH: 753
<212> TYPE: PRT
<213> ORGANISM: Lactobacillus casei
<220> FEATURE:
<221> NAME/KEY: MISC_FEATURE
<223> OTHER INFORMATION: ATCC 334

<400> SEQUENCE: 58

```
Met Lys Gln Leu Asp Glu Thr Lys Val Pro Asn Tyr Trp Glu Gly Phe
1               5                   10                  15

Asn Gly Gly Asp Trp Gln Glu Glu Ile Asn Val Arg Asp Phe Ile Glu
            20                  25                  30

His Asn Leu Asn Gln Tyr Asp Gly Asp Glu Ser Phe Leu Ala Gly Pro
        35                  40                  45

Thr Glu Ala Thr Thr Val Leu Asn Asn Gln Val Leu Asn Leu Lys Lys
    50                  55                  60

Gln Glu Arg Ala Asn Gly Gly Val Leu Asp Ala Asp Asn Asn Ile Pro
65                  70                  75                  80

Ser Thr Ile Thr Ser His Gly Pro Gly Tyr Leu Asn Lys Asp Leu Glu
                85                  90                  95

Lys Ile Val Gly Val Gln Thr Asp Lys Pro Phe Lys Arg Ala Phe Met
            100                 105                 110

Pro Phe Gly Gly Ile Arg Met Ala Glu Asp Ala Leu Glu Ser Tyr Gly
        115                 120                 125

Phe Lys Thr Asp Pro Gln Glu His Lys Ile Phe Asn Glu Tyr Arg Lys
    130                 135                 140

Thr His Asn Gln Gly Val Phe Asp Ala Tyr Thr Pro Asp Met Arg Lys
145                 150                 155                 160

Ala Arg His Tyr Lys Ile Val Thr Gly Leu Pro Asp Ala Tyr Gly Arg
                165                 170                 175

Gly Arg Ile Val Ser Asp Phe Pro Arg Ile Ala Val Tyr Gly Ile Asp
            180                 185                 190

Arg Leu Met Ala Glu Lys Phe Lys Asp Tyr Asn Leu Thr Gly Asp Gly
        195                 200                 205

Glu Met Thr Asp Asp Val Ile Lys Leu Arg Glu Ile Asn Glu Gln
    210                 215                 220

Tyr Arg Ala Leu Asn Asp Met Lys Lys Met Ala Lys Glu Tyr Gly Tyr
225                 230                 235                 240

Asp Ile Ser Arg Pro Ala Ala Asn Ala Gln Glu Ala Val Gln Trp Ile
                245                 250                 255

Tyr Phe Gly Tyr Leu Ala Ala Val Lys Thr Gln Asn Gly Ala Ala Met
            260                 265                 270

Ser Val Gly Arg Ile Asp Thr Val Ile Asp Ala Tyr Ile Gln Arg Asp
        275                 280                 285

Met Arg Leu Gly Lys Leu Asn Glu Glu Gln Ala Gln Glu Leu Ile Asp
    290                 295                 300
```

```
His Leu Val Met Lys Leu Arg Met Val Arg Phe Ile Arg Thr Glu Glu
305                 310                 315                 320

Tyr Asn Ser Leu Phe Ser Gly Asp Pro Ile Trp Ala Thr Leu Ser Leu
            325                 330                 335

Ala Gly Met Gly Asn Asp Gly Arg His His Val Thr Lys Thr Ala Phe
            340                 345                 350

Arg Phe Leu Lys Thr Leu Asp Asn Met Gly Ala Ala Pro Glu Pro Asn
            355                 360                 365

Ile Thr Leu Leu Trp Ser Glu Arg Leu Pro Glu Gly Phe Lys Arg Tyr
            370                 375                 380

Ala Thr Glu Val Ser Ile Gln Ser Ser Thr Ile Gln Tyr Glu Asn Asp
385                 390                 395                 400

Asp Leu Met Arg Asn Glu Trp Gly Thr Asp Tyr Tyr Gly Ile Ala Cys
            405                 410                 415

Cys Val Ser Ala Gln Pro Ile Ala Asp Gly Val Gln Tyr Phe Gly Ala
            420                 425                 430

Arg Ala Asn Leu Ala Lys Thr Val Leu Tyr Ala Ile Asn Gly Gly Lys
            435                 440                 445

Asp Glu Ile Gln Glu Ala Gln Val Gly Pro Tyr Ala Pro Ile Thr
450                 455                 460

Ser Asp Tyr Ile Asp Tyr Lys Glu Phe Met Asn Lys Phe Asp Lys Met
465                 470                 475                 480

Met Asp Trp Leu Ala Asp Thr Tyr Val Asn Ala Leu Asn Val Ile His
            485                 490                 495

Tyr Met His Asp Lys Tyr Tyr Glu Ala Ala Gln Leu Ala Leu Lys
            500                 505                 510

Asp Thr Gln Leu Asn Arg Thr Phe Ala Thr Gly Ile Ser Gly Leu Ser
            515                 520                 525

His Ala Val Asp Ser Ile Ser Ala Ile Lys Tyr Gly His Val Lys Ala
            530                 535                 540

Ile Arg Asp Glu Asn Gly Val Ala Val Asp Phe Val Ala Asp Asn Asp
545                 550                 555                 560

Asp Tyr Pro Arg Tyr Gly Asn Asn Asp Asp Arg Ala Asp Ile Ala
            565                 570                 575

Lys Trp Leu Val Lys Thr Phe Tyr Asn Lys Met Asn Thr His His Leu
            580                 585                 590

Tyr Arg Gly Ala Lys Leu Ser Thr Ser Val Leu Thr Ile Thr Ser Asn
            595                 600                 605

Val Val Tyr Gly Lys Asn Thr Gly Thr Thr Pro Asn Gly Arg Gln Lys
            610                 615                 620

Gly Glu Pro Phe Ser Pro Gly Ala Asn Pro Ala Tyr Gly Ala Glu Lys
625                 630                 635                 640

Asn Gly Ala Leu Ala Ser Leu Met Ser Thr Ala Lys Ile Pro Tyr His
            645                 650                 655

Tyr Ala Thr Asp Gly Ile Ser Asn Thr Phe Gly Val Thr Pro Asn Thr
            660                 665                 670

Leu Gly His Asp Asp Glu Thr Arg Lys Asp Thr Leu Val His Met Val
            675                 680                 685

Asp Gly Tyr Met Glu Asn Ser Gly Met His Leu Asn Ile Asn Val Phe
            690                 695                 700

Asn Lys Glu Thr Leu Ile Asp Ala Gln Lys His Pro Glu Glu Tyr Pro
705                 710                 715                 720
```

Thr Leu Thr Val Arg Val Ser Gly Tyr Cys Val Tyr Phe Ala Asp Leu
            725                 730                 735

Thr Lys Glu Gln Gln Asp Asp Val Ile Ala Arg Thr Phe Phe Glu Glu
        740                 745                 750

Met

<210> SEQ ID NO 59
<211> LENGTH: 2376
<212> TYPE: DNA
<213> ORGANISM: Bifidobacterium adolescentis

<400> SEQUENCE: 59

| | |
|---|---|
| atggcagcag ttgatgcaac ggcggtctcc caggaggaac ttgaggctaa ggcttgggaa | 60 |
| ggcttcaccg agggcaactg gcagaaggac attgatgtcc gcgacttcat ccagaagaac | 120 |
| tacacgccat atgagggcga cgagtccttc ctggctgacg ccaccgacaa gaccaagcac | 180 |
| ctgtggaagt atctgacga caactatctg tccgtggagc gcaagcagcg cgtctacgac | 240 |
| gtggacaccc acaccccggc gggcatcgac gccttcccgg ccggctacat cgattccccg | 300 |
| gaagtcgaca atgtgattgt cggtctgcag accgatgtgc cgtgcaagcg cgccatgatg | 360 |
| ccgaacggcg gctggcgtat ggtcgagcag gccatcaagg aagccggcaa ggagcccgat | 420 |
| ccggagatca agaagatctt caccaagtac cgcaagaccc acaacgacgg cgtcttcggc | 480 |
| gtctacacca agcagatcaa ggtagctcgc acaacaagaa tcctcaccgg cctgccggat | 540 |
| gcctacggcc gtggccgcat catcggcgat taccgtcgtg tggccctgta cggcgtgaac | 600 |
| gcgctgatca agttcaagca gcgcgacaag gactccatcc cgtaccgcaa cgacttcacc | 660 |
| gagccggaga tcgagcactg gatccgcttc cgtgaggagc atgacgagca gatcaaggcc | 720 |
| ctgaagcagc tgatcaacct cggcaacgag tacggcctcg acctgtcccg ccggcacag | 780 |
| accgcacagg aagccgtgca gtggacctac atgggctacc tcgcctccgt caagagccag | 840 |
| gacggcgccg ccatgtcctt cggccgtgtc tccaccttct tcgacgtcta cttcgagcgc | 900 |
| gacctgaagg ccggcaagat caccgagacc gacgcacagg agatcatcga taacctggtc | 960 |
| atgaagctgc gcatcgtgcg cttcctgcgc accaaggatt acgacgcgat cttctccggc | 1020 |
| gatccgtact gggcgacttg gtccgacgcc ggcttcggcg acgacggccg taccatggtc | 1080 |
| accaagacct cgttccgtct gctcaacacc ctgaccctcg agcacctcgg acctggcccg | 1140 |
| gagccgaaca tcaccatctt ctgggatccg aagctgccgg aagcctacaa gcgcttctgc | 1200 |
| gcccgaatct ccatcgacac ctcggccatc cagtacgagt ccgataagga aatccgctcc | 1260 |
| cactggggcg acgacgccgc catcgcatgc tgcgtctccc cgatgcgcgt gggcaagcag | 1320 |
| atgcagttct tcgccgcccg tgtgaactcc gccaaggccc tgctgtacgc catcaacggc | 1380 |
| ggacgcgacg agatgaccgg catgcaggtc atcgacaagg gcgtcatcga cccgatcaag | 1440 |
| ccggaagccg atggcacgct ggattacgag aaggtcaagg ccaactacga gaaggccctc | 1500 |
| gaatggctgt ccgagaccta tgtgatggct ctgaacatca tccattacat gcatgataag | 1560 |
| tacgcttacg agtccatcga gatggctctg cacgacaagg aagtgtaccg caccctcggc | 1620 |
| tgcggcatgt ccgccctgtc gatcgcggcc gactccctgt ccgcatgcaa gtacgccaag | 1680 |
| gtctacccga tctacaacaa ggacgccaag accacgccgg ccacgagaa cgagtacgtc | 1740 |
| gaaggcgccg atgacgatct gatcgtcggc taccgcaccg aaggcgactt cccgctgtac | 1800 |
| ggcaacgatg atgaccgtgc cgacgacatc gccaagtggg tcgtctccac cgtcatgggc | 1860 |
| caggtcaagc gtctgccggt gtaccgcgac gccgtcccga cccagtccat cctgaccatc | 1920 |

```
acctccaatg tggaatacgg caaggccacc ggcgccttcc cgtccggcca caagaagggc    1980
accccgtacg ctccgggcgc caacccggag aacggcatgg actcccacgg catgctgccg    2040
tccatgttct ccgtcggcaa gatcgactac aacgacgctc ttgacggcat ctcgctgacc    2100
aacaccatca cccctgatgg tctgggccgc gacgaggaag agcgtatcgg caacctcgtt    2160
ggcatcctgg acgccggcaa cggccacggc ctgtaccacg ccaacatcaa cgtgctgcgc    2220
aaggagcagc tcgaggatgc cgtcgagcat ccggagaagt acccgcacct gaccgtgcgc    2280
gtctccggct acgcggtgaa cttcgtcaag ctcaccaagg aacagcagct cgacgtgatc    2340
tcccgtacgt tccaccaggg cgctgtcgtc gactga                              2376
```

<210> SEQ ID NO 60
<211> LENGTH: 791
<212> TYPE: PRT
<213> ORGANISM: Bifidobacterium adolescentis

<400> SEQUENCE: 60

```
Met Ala Ala Val Asp Ala Thr Ala Val Ser Gln Glu Glu Leu Glu Ala
1               5                   10                  15

Lys Ala Trp Glu Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

Ser Phe Leu Ala Asp Ala Thr Asp Lys Thr Lys His Leu Trp Lys Tyr
    50                  55                  60

Leu Asp Asp Asn Tyr Leu Ser Val Glu Arg Lys Gln Arg Val Tyr Asp
65                  70                  75                  80

Val Asp Thr His Thr Pro Ala Gly Ile Asp Ala Phe Pro Ala Gly Tyr
                85                  90                  95

Ile Asp Ser Pro Glu Val Asp Asn Val Ile Val Gly Leu Gln Thr Asp
            100                 105                 110

Val Pro Cys Lys Arg Ala Met Met Pro Asn Gly Gly Trp Arg Met Val
        115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Ala Leu Ile Lys Phe Lys Gln Arg
        195                 200                 205

Asp Lys Asp Ser Ile Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Gln Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Val Lys Ser Gln Asp Gly Ala Ala Met Ser Phe Gly
        275                 280                 285
```

-continued

```
Arg Val Ser Thr Phe Phe Asp Val Tyr Phe Glu Arg Asp Leu Lys Ala
            290                 295                 300
Gly Lys Ile Thr Glu Thr Asp Ala Gln Glu Ile Ile Asp Asn Leu Val
305                 310                 315                 320
Met Lys Leu Arg Ile Val Arg Phe Leu Arg Thr Lys Asp Tyr Asp Ala
                325                 330                 335
Ile Phe Ser Gly Asp Pro Tyr Trp Ala Thr Trp Ser Asp Ala Gly Phe
            340                 345                 350
Gly Asp Asp Gly Arg Thr Met Val Thr Lys Thr Ser Phe Arg Leu Leu
        355                 360                 365
Asn Thr Leu Thr Leu Glu His Leu Gly Pro Gly Pro Glu Pro Asn Ile
370                 375                 380
Thr Ile Phe Trp Asp Pro Lys Leu Pro Glu Ala Tyr Lys Arg Phe Cys
385                 390                 395                 400
Ala Arg Ile Ser Ile Asp Thr Ser Ala Ile Gln Tyr Glu Ser Asp Lys
                405                 410                 415
Glu Ile Arg Ser His Trp Gly Asp Asp Ala Ala Ile Ala Cys Cys Val
            420                 425                 430
Ser Pro Met Arg Val Gly Lys Gln Met Gln Phe Phe Ala Ala Arg Val
        435                 440                 445
Asn Ser Ala Lys Ala Leu Leu Tyr Ala Ile Asn Gly Gly Arg Asp Glu
450                 455                 460
Met Thr Gly Met Gln Val Ile Asp Lys Gly Val Ile Asp Pro Ile Lys
465                 470                 475                 480
Pro Glu Ala Asp Gly Thr Leu Asp Tyr Glu Lys Val Lys Ala Asn Tyr
                485                 490                 495
Glu Lys Ala Leu Glu Trp Leu Ser Glu Thr Tyr Val Met Ala Leu Asn
            500                 505                 510
Ile Ile His Tyr Met His Asp Lys Tyr Ala Tyr Glu Ser Ile Glu Met
        515                 520                 525
Ala Leu His Asp Lys Glu Val Tyr Arg Thr Leu Gly Cys Gly Met Ser
530                 535                 540
Gly Leu Ser Ile Ala Ala Asp Ser Leu Ser Ala Cys Lys Tyr Ala Lys
545                 550                 555                 560
Val Tyr Pro Ile Tyr Asn Lys Asp Ala Lys Thr Thr Pro Gly His Glu
                565                 570                 575
Asn Glu Tyr Val Glu Gly Ala Asp Asp Leu Ile Val Gly Tyr Arg
            580                 585                 590
Thr Glu Gly Asp Phe Pro Leu Tyr Gly Asn Asp Asp Arg Ala Asp
        595                 600                 605
Asp Ile Ala Lys Trp Val Val Ser Thr Val Met Gly Gln Val Lys Arg
610                 615                 620
Leu Pro Val Tyr Arg Asp Ala Val Pro Thr Gln Ser Ile Leu Thr Ile
625                 630                 635                 640
Thr Ser Asn Val Glu Tyr Gly Lys Ala Thr Gly Ala Phe Pro Ser Gly
                645                 650                 655
His Lys Lys Gly Thr Pro Tyr Ala Pro Gly Ala Asn Pro Glu Asn Gly
            660                 665                 670
Met Asp Ser His Gly Met Leu Pro Ser Met Phe Ser Val Gly Lys Ile
        675                 680                 685
Asp Tyr Asn Asp Ala Leu Asp Gly Ile Ser Leu Thr Asn Thr Ile Thr
690                 695                 700
Pro Asp Gly Leu Gly Arg Asp Glu Glu Glu Arg Ile Gly Asn Leu Val
```

| | 705 | | | | 710 | | | | 715 | | | | 720 | |
|---|---|---|---|---|---|---|---|---|---|---|---|---|---|---|

Gly Ile Leu Asp Ala Gly Asn Gly His Gly Leu Tyr His Ala Asn Ile
                        725                            730                          735

Asn Val Leu Arg Lys Glu Gln Leu Glu Asp Ala Val Glu His Pro Glu
                        740                            745                          750

Lys Tyr Pro His Leu Thr Val Arg Val Ser Gly Tyr Ala Val Asn Phe
                        755                            760                          765

Val Lys Leu Thr Lys Glu Gln Gln Leu Asp Val Ile Ser Arg Thr Phe
                        770                            775                          780

His Gln Gly Ala Val Val Asp
785                  790

<210> SEQ ID NO 61
<211> LENGTH: 2415
<212> TYPE: DNA
<213> ORGANISM: Bifidobacterium longum
<220> FEATURE:
<221> NAME/KEY: misc_feature
<223> OTHER INFORMATION: NCC2705

<400> SEQUENCE: 61

```
gtgaagatgc gaaacctaca accccattta aggagtgaca tgaccgcagt ggaaaatgca      60
gctgtctccc aggaggagct cgacgccaag gcgtgggccg gcttcaccga gggcaactgg     120
cagaaggata ttgacgtccg cgacttcatc cagaagaact acaccccgta cgagggcgac     180
gagacattcc tggctcctgc caccgagaag accaagcacc tgtggaagta cctcgacgac     240
aactacctgg ccgtggagcg caagcagcgc gtctacgacg tggacaccca taccccggcc     300
gacgtcgacg ccttcccggc cggctacatc gactccccgg aagtcgataa cgtggtcgtt     360
ggcctccaga ccgacgttcc ctgcaagcgc gcgatgatgc cgaacggtgg ctggcgcatg     420
gtcgagcagg ccatcaagga agccggcaag gaaccggatc cggagatcaa gaagatcttc     480
accaagtacc gcaagaccca caacgacggc gtcttcggcg tgtacaccaa gcagatcaag     540
gtcgcccgcc acaacaagat cctcaccggt ctgccggacg cctacggccg tggccgcatc     600
atcggcgact accgccgcgt cgccctgtac ggcgtgaaca agctcatcgc cttcaagaag     660
cgcgacaagg actccgtgcc gtaccgcaac gacttcaccg agccggagat cgagcactgg     720
atccgcttcc gtgaggagca cgacgagcag atcaaggccc tgaagaagct catcaacctc     780
ggcaacgagt acggcctcga cctgtcccgc ccggcccaga ccgcgcagga agccgtgcag     840
tggacctaca tgggctacct ggcctccatc aagtcccagg acggcgccgc catgtccttc     900
ggccgcaact ccgccttcct cgactgctac atcgagcgcg acctccaggc cggcaagatc     960
accgagaccg acgcccagga gctcatcgac aacatcgtca tgaagctgcg catcgtcgcc    1020
ttcctgcgta ccaaggacta cgattcgatc ttctccggcg acccgtactg ggcgacctgg    1080
tccgacgccg gcttcggcga tgacggccgt cgatggtca ccaagacctc gttccgtctg    1140
ctcaacaccc tgaccctcga gcacctcgga cctggccccg agccgaacat caccatcttc    1200
tgggatccga agctgcctga ggcctacaag cgcttctgcg ccaagatctc catcgacacc    1260
tcggccatcc agtacgagtc cgacaaggag attcgtagcc actggggcga cgacgcgcgct    1320
atcgcatgct gcgtgtcccc gatgcgtgtc ggcaagcaga tgcagttctt cgccgcccgc    1380
gtgaactccg ccaaggccct gctgtacgcc atcaacggcg ccgcgacga tgaccggc      1440
atgcaggtca tcgacaaggg cgtgatcgag ccgattaccc cggaggccga cggcaccctg    1500
gactacgaga aggtcaagaa caactacgag aaggctctcg agtggctgtc cgagacctac    1560
```

-continued

```
gtcatggccc tgaacatcat ccactacatg cacgataagt acgcgtacga gtccatcgag    1620
atggccctgc acgacaagga agtgtaccgc accctcggct gcggcatgtc cggtctgtcc    1680
atcgccgccg actccctcgc cgccgtcaag tacgccaagg tctacccgat ctacaacaag    1740
gacgcgaaga ccctggaagg ccacgagtac gagtacgttg agggcgccga cgacgacctg    1800
atcgtcggct accgcaccga gggcgagttc ccggtctacg caacgacga cgaccgcgcc    1860 gacgacatcg ccaagtgggt cgtctccacg gtcatgggcc aggtcaagag gctcccggtc    1920
taccgcggcg ccgtcccgac ccagtccatc ctgacgatca cctccaacgt cgagtacggc    1980
aagaacaccg gttccttccc gtccggccac gccaagggca ccccgtacgc tccgggcgcc    2040
aacccggaga acggcatgga ctcccacggc atgctgccgt ccatgttctc cgtcggcaag    2100
atcgactaca cgacgctct tgacggcatc tcgctgacca acaccatcac ccctgatggc    2160
ctgggccgcg acgaggacga gcgcatcggc aacctggtcg gcatcctgga cgccggcaac    2220
ggccacggcc tctaccacgc gaacatcaac gttctgcgca aggagaccat ggaggacgcc    2280
gtcgagcacc ccgaaaagta cccgcacctg accgtgcgtg tctccggcta cgcggtgaac    2340
ttcgtcaagc tcaccaagga gcagcagctc gacgtcatct cccgtacctt ccaccagggt    2400
gccgtcgtcg actga                                                     2415
```

<210> SEQ ID NO 62
<211> LENGTH: 804
<212> TYPE: PRT
<213> ORGANISM: Bifidobacterium longum
<220> FEATURE:
<221> NAME/KEY: MISC_FEATURE
<223> OTHER INFORMATION: NCC2705

<400> SEQUENCE: 62

```
Met Lys Met Arg Asn Leu Gln Pro His Leu Arg Ser Asp Met Thr Ala
1               5                   10                  15

Val Glu Asn Ala Ala Val Ser Gln Glu Leu Asp Ala Lys Ala Trp
            20                  25                  30

Ala Gly Phe Thr Glu Gly Asn Trp Gln Lys Asp Ile Asp Val Arg Asp
        35                  40                  45

Phe Ile Gln Lys Asn Tyr Thr Pro Tyr Glu Gly Asp Glu Thr Phe Leu
    50                  55                  60

Ala Pro Ala Thr Glu Lys Thr Lys His Leu Trp Lys Tyr Leu Asp Asp
65                  70                  75                  80

Asn Tyr Leu Ala Val Glu Arg Lys Gln Arg Val Tyr Asp Val Asp Thr
                85                  90                  95

His Thr Pro Ala Asp Val Asp Ala Phe Pro Ala Gly Tyr Ile Asp Ser
            100                 105                 110

Pro Glu Val Asp Asn Val Val Val Gly Leu Gln Thr Asp Val Pro Cys
        115                 120                 125

Lys Arg Ala Met Met Pro Asn Gly Gly Trp Arg Met Val Glu Gln Ala
    130                 135                 140

Ile Lys Glu Ala Gly Lys Glu Pro Asp Pro Glu Ile Lys Lys Ile Phe
145                 150                 155                 160

Thr Lys Tyr Arg Lys Thr His Asn Asp Gly Val Phe Gly Val Tyr Thr
                165                 170                 175

Lys Gln Ile Lys Val Ala Arg His Asn Lys Ile Leu Thr Gly Leu Pro
            180                 185                 190

Asp Ala Tyr Gly Arg Gly Arg Ile Ile Gly Asp Tyr Arg Arg Val Ala
```

```
                195                 200                 205
Leu Tyr Gly Val Asn Lys Leu Ile Ala Phe Lys Lys Arg Asp Lys Asp
210                 215                 220
Ser Val Pro Tyr Arg Asn Asp Phe Thr Glu Pro Glu Ile Glu His Trp
225                 230                 235                 240
Ile Arg Phe Arg Glu Glu His Asp Glu Gln Ile Lys Ala Leu Lys Lys
        245                 250                 255
Leu Ile Asn Leu Gly Asn Glu Tyr Gly Leu Asp Leu Ser Arg Pro Ala
            260                 265                 270
Gln Thr Ala Gln Glu Ala Val Gln Trp Thr Tyr Met Gly Tyr Leu Ala
        275                 280                 285
Ser Ile Lys Ser Gln Asp Gly Ala Ala Met Ser Phe Gly Arg Asn Ser
290                 295                 300
Ala Phe Leu Asp Cys Tyr Ile Glu Arg Asp Leu Gln Ala Gly Lys Ile
305                 310                 315                 320
Thr Glu Thr Asp Ala Gln Glu Leu Ile Asp Asn Ile Val Met Lys Leu
            325                 330                 335
Arg Ile Val Arg Phe Leu Arg Thr Lys Asp Tyr Asp Ser Ile Phe Ser
        340                 345                 350
Gly Asp Pro Tyr Trp Ala Thr Trp Ser Asp Ala Gly Phe Gly Asp Asp
            355                 360                 365
Gly Arg Ser Met Val Thr Lys Thr Ser Phe Arg Leu Leu Asn Thr Leu
370                 375                 380
Thr Leu Glu His Leu Gly Pro Gly Pro Glu Pro Asn Ile Thr Ile Phe
385                 390                 395                 400
Trp Asp Pro Lys Leu Pro Glu Ala Tyr Lys Arg Phe Cys Ala Lys Ile
            405                 410                 415
Ser Ile Asp Thr Ser Ala Ile Gln Tyr Glu Ser Asp Lys Glu Ile Arg
            420                 425                 430
Ser His Trp Gly Asp Asp Ala Ala Ile Ala Cys Cys Val Ser Pro Met
        435                 440                 445
Arg Val Gly Lys Gln Met Gln Phe Phe Ala Ala Arg Val Asn Ser Ala
    450                 455                 460
Lys Ala Leu Leu Tyr Ala Ile Asn Gly Gly Arg Asp Glu Met Thr Gly
465                 470                 475                 480
Met Gln Val Ile Asp Lys Gly Val Ile Glu Pro Ile Thr Pro Glu Ala
            485                 490                 495
Asp Gly Thr Leu Asp Tyr Glu Lys Val Lys Asn Asn Tyr Glu Lys Ala
            500                 505                 510
Leu Glu Trp Leu Ser Glu Thr Tyr Val Met Ala Leu Asn Ile Ile His
        515                 520                 525
Tyr Met His Asp Lys Tyr Ala Tyr Glu Ser Ile Glu Met Ala Leu His
    530                 535                 540
Asp Lys Glu Val Tyr Arg Thr Leu Gly Cys Gly Met Ser Gly Leu Ser
545                 550                 555                 560
Ile Ala Ala Asp Ser Leu Ala Ala Val Lys Tyr Ala Lys Val Tyr Pro
            565                 570                 575
Ile Tyr Asn Lys Asp Ala Lys Thr Leu Glu Gly His Glu Tyr Glu Tyr
            580                 585                 590
Val Glu Gly Ala Asp Asp Leu Ile Val Gly Tyr Arg Thr Glu Gly
        595                 600                 605
Glu Phe Pro Val Tyr Gly Asn Asp Asp Arg Ala Asp Ile Ala
610                 615                 620
```

```
Lys Trp Val Val Ser Thr Val Met Gly Gln Val Lys Arg Leu Pro Val
625                 630                 635                 640

Tyr Arg Gly Ala Val Pro Thr Gln Ser Ile Leu Thr Ile Thr Ser Asn
                645                 650                 655

Val Glu Tyr Gly Lys Asn Thr Gly Ser Phe Pro Ser Gly His Ala Lys
            660                 665                 670

Gly Thr Pro Tyr Ala Pro Gly Ala Asn Pro Glu Asn Gly Met Asp Ser
        675                 680                 685

His Gly Met Leu Pro Ser Met Phe Ser Val Gly Lys Ile Asp Tyr Asn
    690                 695                 700

Asp Ala Leu Asp Gly Ile Ser Leu Thr Asn Thr Ile Thr Pro Asp Gly
705                 710                 715                 720

Leu Gly Arg Asp Glu Asp Glu Arg Ile Gly Asn Leu Val Gly Ile Leu
                725                 730                 735

Asp Ala Gly Asn Gly His Gly Leu Tyr His Ala Asn Ile Asn Val Leu
            740                 745                 750

Arg Lys Glu Thr Met Glu Asp Ala Val Glu His Pro Glu Lys Tyr Pro
        755                 760                 765

His Leu Thr Val Arg Val Ser Gly Tyr Ala Val Asn Phe Val Lys Leu
    770                 775                 780

Thr Lys Glu Gln Gln Leu Asp Val Ile Ser Arg Thr Phe His Gln Gly
785                 790                 795                 800

Ala Val Val Asp

<210> SEQ ID NO 63
<211> LENGTH: 2376
<212> TYPE: DNA
<213> ORGANISM: Bifidobacterium longum
<220> FEATURE:
<221> NAME/KEY: misc_feature
<223> OTHER INFORMATION: DJO10A

<400> SEQUENCE: 63
atgaccgcag tggaaaatgc agctgtctcc caggaggagc tcgacgccaa ggcgtgggcc      60
ggcttcaccg agggcaactg gcagaaggat attgacgtcc gcgacttcat ccagaagaac     120
tacaccccgt acgagggcga cgagacattc ctggctcctg ccaccgagaa gaccaagcac     180
ctgtggaagt acctcgacga caactacctg gccgtggagc gcaagcagcg cgtctacgac     240
gtggacaccc ataccccggc cgacgtcgac gccttcccgg ccggctacat cgactccccg     300
gaagtcgata acgtggtcgt tggcctccag accgacgttc cctgcaagcg cgcgatgatg     360
ccgaacggtg gctggcgcat ggtcgagcag gccatcaagg aagccggcaa ggaaccggat     420
ccggagatca agaagatctt caccaagtac cgcaagaccc acaacgacgg cgtcttcggc     480
gtgtacacca gcagatcaa ggtcgcccgc cacaacaaga tcctcaccgg tctgccggac     540
gcctacggcc gtggccgcat catcggcgac taccgccgcg tcgccctgta cggcgtgaac     600
aagctcatcg ccttcaagaa gcgcgacaag gactccgtgc cgtaccgcaa cgacttcacc     660
gagccggaga tcgagcactg gatccgcttc cgtgaggagc acgacgagca gatcaaggcc     720
ctgaagaagc tcatcaacct cggcaacgag tacggcctcg acctgtcccg ccggcccag      780 accgcgcagg aagccgtgca gtggacctac atgggctacc tggcctccat caagtcccag     840
gacggcgccg ccatgtcctt cggccgcaac tccgccttcc tcgactgcta catcgagcgc     900
gacctccagg ccggcaagat caccgagacc gacgcccagg agctcatcga caacatcgtc     960
```

```
atgaagctgc gcatcgtgcg cttcctgcgt accaaggact acgattcgat cttctccggc    1020
gacccgtact gggcgacctg gtccgacgcc ggcttcggcg atgacggccg ttcgatggtc    1080
accaagacct cgttccgtct gctcaacacc ctgaccctcg agcacctcgg acctggcccc    1140
gagccgaaca tcaccatctt ctgggatccg aagctgcctg aggcctacaa gcgcttctgc    1200
gccaagatct ccatcgacac ctcggccatc cagtacgagt ccgacaagga gattcgcagc    1260
cactggggcg acgacgctgc tatcgcctgc tgcgtgtccc cgatgcgtgt cggcaagcag    1320
atgcagttct tcgccgcccg cgtgaactcc gccaaggccc tgctgtacgc catcaacggc    1380
ggccgcgacg agatgaccgg catgcaggtc atcgacaagg cgtgatcga gccgattacc    1440
ccggaggccg acggcaccct ggactacgag aaggtcaaga acaactacga aaggctctc    1500
gagtggctgt ccgagaccta cgtcatggcc ctgaacatca tccactacat gcacgataag    1560
tacgcgtacg agtccatcga gatggccctg cacgacaagg aagtgtaccg caccctcggc    1620
tgcggcatgt ccggtctgtc catcgccgcc gactccctcg ccgccgtcaa gtacgccaag    1680
gtctacccga tctacaacaa ggacgcgaag accctggaag ccacgagta cgagtacgtt    1740
gagggcgccg acgacgacct gatcgtcggc taccgcaccg agggcgagtt cccggtctac    1800
ggcaacgacg acgaccgcgc cgacgacatc gccaagtggg tcgtctccac ggtcatgggc    1860
caggtcaaga ggctcccggt ctaccgcggc gccgtcccga cccagtccat cctgacgatc    1920
acctccaacg tcgagtacgg caagaacacc ggttccttcc cgtccggcca cgccaagggc    1980
accccgtacg ctccgggcgc caacccggag aacggcatgg actcccacgg catgctgccg    2040
tccatgttct ccgtcggcaa gatcgactac aacgacgctc ttgacggcat ctcgctgacc    2100
aacaccatca cccctgatgg cctgggccgc gacgaggacg agcgcatcgg caacctggtc    2160
ggcatcctgg acgccggcaa cggccacggc ctctaccacg cgaacatcaa cgttctgcgc    2220
aaggagacca tggaggacgc cgtcgagcac cccgaaaagt acccgcacct gaccgtgcgt    2280
gtctccggct acgcggtgaa cttcgtcaag ctcaccaagg agcagcagct cgacgtcatc    2340
tcccgtacct tccaccaggg tgccgtcgtc gactga                              2376

<210> SEQ ID NO 64
<211> LENGTH: 791
<212> TYPE: PRT
<213> ORGANISM: Bifidobacterium longum
<220> FEATURE:
<221> NAME/KEY: MISC_FEATURE
<223> OTHER INFORMATION: DJO10A

<400> SEQUENCE: 64

Met Thr Ala Val Glu Asn Ala Ala Val Ser Gln Glu Glu Leu Asp Ala
1               5                   10                  15

Lys Ala Trp Ala Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

Thr Phe Leu Ala Pro Ala Thr Glu Lys Thr Lys His Leu Trp Lys Tyr
    50                  55                  60

Leu Asp Asp Asn Tyr Leu Ala Val Glu Arg Lys Gln Arg Val Tyr Asp
65                  70                  75                  80

Val Asp Thr His Thr Pro Ala Asp Val Asp Ala Phe Pro Ala Gly Tyr
                85                  90                  95

Ile Asp Ser Pro Glu Val Asp Asn Val Val Gly Leu Gln Thr Asp
            100                 105                 110
```

```
Val Pro Cys Lys Arg Ala Met Met Pro Asn Gly Gly Trp Arg Met Val
        115                 120                 125
Glu Gln Ala Ile Lys Glu Ala Gly Lys Glu Pro Asp Pro Glu Ile Lys
    130                 135                 140
Lys Ile Phe Thr Lys Tyr Arg Lys Thr His Asn Asp Gly Val Phe Gly
145                 150                 155                 160
Val Tyr Thr Lys Gln Ile Lys Val Ala Arg His Asn Lys Ile Leu Thr
                165                 170                 175
Gly Leu Pro Asp Ala Tyr Gly Arg Gly Arg Ile Ile Gly Asp Tyr Arg
            180                 185                 190
Arg Val Ala Leu Tyr Gly Val Asn Lys Leu Ile Ala Phe Lys Lys Arg
            195                 200                 205
Asp Lys Asp Ser Val Pro Tyr Arg Asn Asp Phe Thr Glu Pro Glu Ile
        210                 215                 220
Glu His Trp Ile Arg Phe Arg Glu His Asp Glu Gln Ile Lys Ala
225                 230                 235                 240
Leu Lys Lys Leu Ile Asn Leu Gly Asn Glu Tyr Gly Leu Asp Leu Ser
                245                 250                 255
Arg Pro Ala Gln Thr Ala Gln Glu Ala Val Gln Trp Thr Tyr Met Gly
        260                 265                 270
Tyr Leu Ala Ser Ile Lys Ser Gln Asp Gly Ala Ala Met Ser Phe Gly
        275                 280                 285
Arg Asn Ser Ala Phe Leu Asp Cys Tyr Ile Glu Arg Asp Leu Gln Ala
        290                 295                 300
Gly Lys Ile Thr Glu Thr Asp Ala Gln Glu Leu Ile Asp Asn Ile Val
305                 310                 315                 320
Met Lys Leu Arg Ile Val Arg Phe Leu Arg Thr Lys Tyr Asp Ser
                325                 330                 335
Ile Phe Ser Gly Asp Pro Tyr Trp Ala Thr Trp Ser Asp Ala Gly Phe
                340                 345                 350
Gly Asp Asp Gly Arg Ser Met Val Thr Lys Thr Ser Phe Arg Leu Leu
        355                 360                 365
Asn Thr Leu Thr Leu Glu His Leu Gly Pro Gly Pro Glu Pro Asn Ile
    370                 375                 380
Thr Ile Phe Trp Asp Pro Lys Leu Pro Glu Ala Tyr Lys Arg Phe Cys
385                 390                 395                 400
Ala Lys Ile Ser Ile Asp Thr Ser Ala Ile Gln Tyr Glu Ser Asp Lys
            405                 410                 415
Glu Ile Arg Ser His Trp Gly Asp Ala Ala Ile Ala Cys Cys Val
            420                 425                 430
Ser Pro Met Arg Val Gly Lys Gln Met Gln Phe Phe Ala Ala Arg Val
        435                 440                 445
Asn Ser Ala Lys Ala Leu Leu Tyr Ala Ile Asn Gly Gly Arg Asp Glu
    450                 455                 460
Met Thr Gly Met Gln Val Ile Asp Lys Gly Val Ile Glu Pro Ile Thr
465                 470                 475                 480
Pro Glu Ala Asp Gly Thr Leu Asp Tyr Glu Lys Val Lys Asn Asn Tyr
                485                 490                 495
Glu Lys Ala Leu Glu Trp Leu Ser Glu Thr Tyr Val Met Ala Leu Asn
            500                 505                 510
Ile Ile His Tyr Met His Asp Lys Tyr Ala Tyr Glu Ser Ile Glu Met
        515                 520                 525
```

| | | | | | | | | | | | | |
|---|---|---|---|---|---|---|---|---|---|---|---|---|
|Ala|Leu|His|Asp|Lys|Glu|Val|Tyr|Arg|Thr|Leu|Gly|Cys|Gly|Met|Ser|
| |530| | | |535| | | |540| | | | | | |

Ala Leu His Asp Lys Glu Val Tyr Arg Thr Leu Gly Cys Gly Met Ser
    530            535            540

Gly Leu Ser Ile Ala Ala Asp Ser Leu Ala Ala Val Lys Tyr Ala Lys
545            550            555            560

Val Tyr Pro Ile Tyr Asn Lys Asp Ala Lys Thr Leu Glu Gly His Glu
         565             570            575

Tyr Glu Tyr Val Glu Gly Ala Asp Asp Leu Ile Val Gly Tyr Arg
        580            585            590

Thr Glu Gly Glu Phe Pro Val Tyr Gly Asn Asp Asp Arg Ala Asp
    595            600            605

Asp Ile Ala Lys Trp Val Val Ser Thr Val Met Gly Gln Val Lys Arg
610            615            620

Leu Pro Val Tyr Arg Gly Ala Val Pro Thr Gln Ser Ile Leu Thr Ile
625            630            635            640

Thr Ser Asn Val Glu Tyr Gly Lys Asn Thr Gly Ser Phe Pro Ser Gly
         645             650            655

His Ala Lys Gly Thr Pro Tyr Ala Pro Gly Ala Asn Pro Glu Asn Gly
        660            665            670

Met Asp Ser His Gly Met Leu Pro Ser Met Phe Ser Val Gly Lys Ile
        675            680            685

Asp Tyr Asn Asp Ala Leu Asp Gly Ile Ser Leu Thr Asn Thr Ile Thr
        690            695            700

Pro Asp Gly Leu Gly Arg Asp Glu Asp Glu Arg Ile Gly Asn Leu Val
705            710            715            720

Gly Ile Leu Asp Ala Gly Asn Gly His Gly Leu Tyr His Ala Asn Ile
            725            730            735

Asn Val Leu Arg Lys Glu Thr Met Glu Asp Ala Val Glu His Pro Glu
        740            745            750

Lys Tyr Pro His Leu Thr Val Arg Val Ser Gly Tyr Ala Val Asn Phe
        755            760            765

Val Lys Leu Thr Lys Glu Gln Gln Leu Asp Val Ile Ser Arg Thr Phe
770            775            780

His Gln Gly Ala Val Val Asp
785            790

<210> SEQ ID NO 65
<211> LENGTH: 2379
<212> TYPE: DNA
<213> ORGANISM: Bifidobacterium animalis
<220> FEATURE:
<221> NAME/KEY: misc_feature
<223> OTHER INFORMATION: DSM 10140

<400> SEQUENCE: 65

```
atgtcagcaa ttgaaaacgt ggccgaggtg tccccggaag ccatcaagga acaggcttgg      60
gaggggttcg ttcccggcaa ctgggagaag gacatcgacg ttcgtgactt cattcagaag     120
aactacacgc cttacgaggg tgatgaatcg ttcctcgcgg atgcgaccga caagacgaag     180
tacctgtgga agtacctcga cgacaactat ctggcggtgg agcgcaagca gcgtgtctat     240
gatgtggaca cccacacgcc ggcggatatc gacgccttcc cggctggcta tatcgattcc     300
ccggagatcg acaatgtgat cgtcggcctg cagaccgatg agccatgcaa gcgagccatg     360
atgccgaatg gcggttggcg catggtggag caggccatca aggaggccgg caaggagccg     420
gacccggcga tcaagaagat cttcaccaag taccgcaaga cgcataacga cggtgtgttc     480
ggcgtctata cgaagaacat caaagtggca cgccacaaca agattctcac cggcctgccg     540
```

```
gatgcctacg gccgcggccg catcatcggc gactaccgtc gtgtggccct gtatggcgtg      600
gatgcgctga ttaagttcaa gcagcgtgac aaggacgcca tcccgtaccg caacgacttc      660
tcggagaccg agatcgagca ctggatccgt taccgcgagg agcacgacga gcagattaag      720
gctctgaaga agctcatcaa cctaggcaag gaatacggac tcgatttggc gcgccccgcc      780
atgaacgcgc gtgaggccgt gcagtggacc tacatgggct acctcgcctc catcaagagc      840
caggacggcg ccgcgatgag cttcggccgc gtgtcagcgt tcttcgacat ctacttcgag      900
cgcgatctca aggaaggcaa gatcaccgag accgacgccc aggagatcat cgacaatctg      960
gtgatgaagc tgcgcatcgt gcgattcctg cgcaccaagg actacgattc gatcttctcg     1020 ggcgaccct actgggcgac atggtcggat gcaggcttcg gcgacgatgg ccgcaccatg      1080
gtcaccaaga cgtcgttccg tctgctcaac acgctcacgc tcgagcattt gggacccgga     1140
cccgaaccga acatcacgat tttctgggat ccgaagctgc cggaaggcta caagcgtttc     1200
tgcgcccaga tctccattga tacctcggcc atccagtatg aatccgacaa ggagatccgc     1260
aaccattggg gtgacgatgc ggccattgca tgctgcgtct ccccgatgcg tgtgggcaag     1320
caaatgcagt tcttcgcggc tcgcgtgaac tccgccaagg cgctgctcta cgcgatcaac     1380
ggcggccgtg acgagatgac cggcatgcag gtgatcgaca agggcatcat cgagccgatc     1440
cagcccgagg ctgacggcac gctcgattac gagaaggtga aggccaacta tgagaaggcc     1500
ctcgaatggc tttcggagac ctacgtcgaa gcgctgaaca tcattcatta catgcatgac     1560
aagtatgcgt atgagtccat cgagatgcg ctgcacgacc gcgaggtcta ccgcaccctg      1620
ggctgcggca tgtccggcct gtcgatcgcc gccgattcgc tttccgcatg caagtacgcc     1680
aaggtgtacc caatctacaa caaggacgcc aaggacatgc cgggtcacga gtacgaatat     1740
gtcgaaggcg cggacgacga tctggtggtc ggctaccgca ccgagggcga gttcccgctt     1800
tacggcaacg acgacgatcg tgccgatgac attgccaagt gggtcgtgtc caccgtcatg     1860
ggccaggtca agcgcctgcc ggtgtatcgt ggtgccgtcc ccacgcagtc gatcctcacg     1920
atcacctcga acgtcgagta tgcaagaac accggatcct tcccgtcggg ccacgccaag     1980
ggaacgccgt acgcccgggg cgcgaacccg gagaacggca tggactccca tggcatgctc     2040
ccctcgatgt tctcggtggg caagatcgat tacaacgacg cccttgacgg catctcgctg     2100
acgaacacga tcacacccga cggcctgggc cgcgatgagg acgaacgcat cagcaacctc     2160
gtcggcatcc tcgacgcagg caacggccat ggactgtacc atgcgaacat caacgtgctg     2220
cgcaaggaac agctcgaaga cgccgtggag caccccggaga agtacccgca cctgaccgtg     2280
cgcgtctccg gttacgccgt gaacttcgtc aagcttacga aggaacagca gcttgacgtc     2340
atttcccgca ccttccatca gggcgcggtc gaggactaa                            2379
```

<210> SEQ ID NO 66
<211> LENGTH: 792
<212> TYPE: PRT
<213> ORGANISM: Bifidobacterium animalis
<220> FEATURE:
<221> NAME/KEY: misc_feature
<223> OTHER INFORMATION: DSM 10140

<400> SEQUENCE: 66

Met Ser Ala Ile Glu Asn Val Ala Glu Val Ser Pro Glu Ala Ile Lys
1               5                   10                  15

Glu Gln Ala Trp Glu Gly Phe Val Pro Gly Asn Trp Glu Lys Asp Ile
            20                  25                  30

```
Asp Val Arg Asp Phe Ile Gln Lys Asn Tyr Thr Pro Tyr Glu Gly Asp
         35                  40                  45

Glu Ser Phe Leu Ala Asp Ala Thr Asp Lys Thr Lys Tyr Leu Trp Lys
 50                  55                  60

Tyr Leu Asp Asp Asn Tyr Leu Ala Val Glu Arg Lys Gln Arg Val Tyr
 65                  70                  75                  80

Asp Val Asp Thr His Thr Pro Ala Asp Ile Asp Ala Phe Pro Ala Gly
                 85                  90                  95

Tyr Ile Asp Ser Pro Glu Ile Asp Asn Val Ile Val Gly Leu Gln Thr
                100                 105                 110

Asp Glu Pro Cys Lys Arg Ala Met Met Pro Asn Gly Gly Trp Arg Met
        115                 120                 125

Val Glu Gln Ala Ile Lys Glu Ala Gly Lys Glu Pro Asp Pro Ala Ile
    130                 135                 140

Lys Lys Ile Phe Thr Lys Tyr Arg Lys Thr His Asn Asp Gly Val Phe
145                 150                 155                 160

Gly Val Tyr Thr Lys Asn Ile Lys Val Ala Arg His Asn Lys Ile Leu
                165                 170                 175

Thr Gly Leu Pro Asp Ala Tyr Gly Arg Gly Arg Ile Ile Gly Asp Tyr
                180                 185                 190

Arg Arg Val Ala Leu Tyr Gly Val Asp Ala Leu Ile Lys Phe Lys Gln
        195                 200                 205

Arg Asp Lys Asp Ala Ile Pro Tyr Arg Asn Asp Phe Ser Glu Thr Glu
    210                 215                 220

Ile Glu His Trp Ile Arg Tyr Arg Glu Glu His Asp Glu Gln Ile Lys
225                 230                 235                 240

Ala Leu Lys Lys Leu Ile Asn Leu Gly Lys Glu Tyr Gly Leu Asp Leu
                245                 250                 255

Ala Arg Pro Ala Met Asn Ala Arg Glu Ala Val Gln Trp Thr Tyr Met
        260                 265                 270

Gly Tyr Leu Ala Ser Ile Lys Ser Gln Asp Gly Ala Ala Met Ser Phe
    275                 280                 285

Gly Arg Val Ser Ala Phe Phe Asp Ile Tyr Phe Glu Arg Asp Leu Lys
    290                 295                 300

Glu Gly Lys Ile Thr Glu Thr Asp Ala Gln Glu Ile Ile Asp Asn Leu
305                 310                 315                 320

Val Met Lys Leu Arg Ile Val Arg Phe Leu Arg Thr Lys Asp Tyr Asp
                325                 330                 335

Ser Ile Phe Ser Gly Asp Pro Tyr Trp Ala Thr Trp Ser Asp Ala Gly
                340                 345                 350

Phe Gly Asp Asp Gly Arg Thr Met Val Thr Lys Thr Ser Phe Arg Leu
        355                 360                 365

Leu Asn Thr Leu Thr Leu Glu His Leu Gly Pro Gly Pro Glu Pro Asn
    370                 375                 380

Ile Thr Ile Phe Trp Asp Pro Lys Leu Pro Glu Gly Tyr Lys Arg Phe
385                 390                 395                 400

Cys Ala Gln Ile Ser Ile Asp Thr Ser Ala Ile Gln Tyr Glu Ser Asp
                405                 410                 415

Lys Glu Ile Arg Asn His Trp Gly Asp Asp Ala Ala Ile Ala Cys Cys
                420                 425                 430

Val Ser Pro Met Arg Val Gly Lys Gln Met Gln Phe Phe Ala Ala Arg
        435                 440                 445
```

```
Val Asn Ser Ala Lys Ala Leu Leu Tyr Ala Ile Asn Gly Gly Arg Asp
    450                 455                 460

Glu Met Thr Gly Met Gln Val Ile Asp Lys Gly Ile Ile Glu Pro Ile
465                 470                 475                 480

Gln Pro Glu Ala Asp Gly Thr Leu Asp Tyr Glu Lys Val Lys Ala Asn
                485                 490                 495

Tyr Glu Lys Ala Leu Glu Trp Leu Ser Glu Thr Tyr Val Glu Ala Leu
            500                 505                 510

Asn Ile Ile His Tyr Met His Asp Lys Tyr Ala Tyr Glu Ser Ile Glu
        515                 520                 525

Met Ala Leu His Asp Arg Glu Val Tyr Arg Thr Leu Gly Cys Gly Met
530                 535                 540

Ser Gly Leu Ser Ile Ala Ala Asp Ser Leu Ser Ala Cys Lys Tyr Ala
545                 550                 555                 560

Lys Val Tyr Pro Ile Tyr Asn Lys Asp Ala Lys Asp Met Pro Gly His
                565                 570                 575

Glu Tyr Glu Tyr Val Gly Ala Asp Asp Leu Val Val Gly Tyr
            580                 585                 590

Arg Thr Glu Gly Glu Phe Pro Leu Tyr Gly Asn Asp Asp Arg Ala
            595                 600                 605

Asp Asp Ile Ala Lys Trp Val Val Ser Thr Val Met Gly Gln Val Lys
610                 615                 620

Arg Leu Pro Val Tyr Arg Gly Ala Val Pro Thr Gln Ser Ile Leu Thr
625                 630                 635                 640

Ile Thr Ser Asn Val Glu Tyr Gly Lys Asn Thr Gly Ser Phe Pro Ser
                645                 650                 655

Gly His Ala Lys Gly Thr Pro Tyr Ala Pro Gly Ala Asn Pro Glu Asn
            660                 665                 670

Gly Met Asp Ser His Gly Met Leu Pro Ser Met Phe Ser Val Gly Lys
        675                 680                 685

Ile Asp Tyr Asn Asp Ala Leu Asp Gly Ile Ser Leu Thr Asn Thr Ile
690                 695                 700

Thr Pro Asp Gly Leu Gly Arg Asp Glu Asp Glu Arg Ile Ser Asn Leu
705                 710                 715                 720

Val Gly Ile Leu Asp Ala Gly Asn Gly His Gly Leu Tyr His Ala Asn
                725                 730                 735

Ile Asn Val Leu Arg Lys Glu Gln Leu Glu Asp Ala Val Glu His Pro
            740                 745                 750

Glu Lys Tyr Pro His Leu Thr Val Arg Val Ser Gly Tyr Ala Val Asn
        755                 760                 765

Phe Val Lys Leu Thr Lys Glu Gln Gln Leu Asp Val Ile Ser Arg Thr
770                 775                 780

Phe His Gln Gly Ala Val Glu Asp
785                 790
```

<210> SEQ ID NO 67
<211> LENGTH: 2226
<212> TYPE: DNA
<213> ORGANISM: Clostridium cellulolyticum

<400> SEQUENCE: 67

```
atggatccat ggagatattt caaaaacgga aattggtccg aggaaataga tgtaagggat      60
tttattatta ataattatat accatataaa ggagatgatt ccttttttaaa aggccctact    120
gaaaagactc aaaaactctg gaaaaagtc agtggtatcc ttgacgagga aagagagaac     180
```

| | |
|---|---|
| ggaggagttc tcgatgttga taccaaaata atatcaacta tcacttcgca tgaacccgga | 240 |
| tatattgata aggatttgga aaagattgta ggattgcaga cggataaacc tctaaaaagg | 300 |
| ggtataatgc ctttcggtgg tatcaggatg gtagtaaagg gcggagaggc ctacggcaaa | 360 |
| aagattgacg aaagtgttgt aaagctattt actgaatata ggaagactca caatgacggt | 420 |
| gtttacgatg tctatactcc cgaaatgatg agggcgaaaa aagcaggtat tataaccggg | 480 |
| cttcctgatg catacggtag aggaagaata atcggtgatt acagaagagt tgcactgtat | 540 |
| ggggttgaca ggcttatcgg agataagcaa aaacaactta caagcctaga aatggattac | 600 |
| atggacagtg aaaccataca ggaaagggaa gaaagaaaaa gtcagataaa agctcttgag | 660 |
| tacttaaagc aaatggctga atgtatggc tttgatattt caaggcctgc tgaaaccgca | 720 |
| caggaagcat ttcaatggtt gtatttcggt ttcctcggag cagtaaagga gcagaatggt | 780 |
| gcggctatga gtcttggaag agtttcaaca ttccttgata tttatataga aagggatatg | 840 |
| aaggagggga cacttaccga agaagaggca caggagcttg ttgaccattt tgttatgaag | 900 |
| cttagattag taagattcct gagaactcca gagtatgaga aactgttctc aggtgaccct | 960 |
| acatggataa ccgaaagcat tggaggtatg ggtcttgacg gacgtactct ggtaacgaag | 1020 |
| aattccttca gaatgctgca taccctattt aatctgggtc atgcacccga gcccaatatg | 1080 |
| acggtgcttt ggtcggtgca tctgcctgat ggctttaaga aatactgctc atatgtttct | 1140 |
| atcaatacaa gctctatcca atacgagagc gatgatataa tgaggtatta ttggggagac | 1200 |
| gactacggca tagcatgctg tgtttcagcc atgagaatag gaaagcagat gcagttcttc | 1260 |
| ggagcccgct gcaatatggc gaaagctttg ttgtatgcaa ttaacggggg gcgtgatgaa | 1320 |
| aaatcgggcg ttcaggtagg acctataatg caggctattg agactgaata tcttgattat | 1380 |
| gatgatgtaa taagaggtt cgacgcagta ctaacatggg ttgcaagact ttacatcaac | 1440 |
| actctgaata taatacacta tatgcatgac aagtacgctt atgaaagact acagatggct | 1500 |
| ttgcacgaca aggacatatt aagaacaatg gcctgcggaa tagcaggatt atctgtagtt | 1560 |
| gcggattctc tgagtgcaat taaatatgca aaggtaaagg taataagaaa tgaagagggg | 1620 |
| cttgccgttg actatgacat agaaggtgat tatccgaaat ttggaaataa cgacgaccgt | 1680 |
| gtagacaata tagccgtaat gctggtaaaa agctttatgg agaagctgga aaagcagaga | 1740 |
| acctacaggc actctgttcc tacccttca atactgacta ttcatcaaa tgttgtatac | 1800 |
| ggagctaaga caggtaatac acctgacgga agaaaagcgg gagaacccct tcggaccgggt | 1860 |
| gcaaacccaa tgcacggaag agacttgaac ggtgcacttg cagttcttaa atccatttca | 1920 |
| aagctgcctt accagtttgc acaggacggt atatcataca ctttttcaat agtaccaaag | 1980 |
| gcacttggaa aagaggaaga tacaaggatc aacaaccttg tgtcactgct tgactcttac | 2040 |
| tttaaagaag gcggacatca cattaatatc aatgtatttg agagagaaat gctgctggat | 2100 |
| gcaatggatc atcctgaaaa gtacccacag ctcacaatca gggtatccgg ctatgcggta | 2160 |
| aactttataa aattgacgag ggaacagcag ctagatgtaa ttaacagaac gatacatgaa | 2220 |
| aatata | 2226 |

<210> SEQ ID NO 68
<211> LENGTH: 742
<212> TYPE: PRT
<213> ORGANISM: Clostridium cellulolyticum

<400> SEQUENCE: 68

-continued

```
Met Asp Pro Trp Arg Tyr Phe Lys Asn Gly Asn Trp Ser Glu Glu Ile
 1               5                  10                  15

Asp Val Arg Asp Phe Ile Ile Asn Asn Tyr Ile Pro Tyr Lys Gly Asp
            20                  25                  30

Asp Ser Phe Leu Lys Gly Pro Thr Glu Lys Thr Gln Lys Leu Trp Lys
        35                  40                  45

Lys Val Ser Gly Ile Leu Asp Glu Glu Arg Glu Asn Gly Gly Val Leu
 50                  55                  60

Asp Val Asp Thr Lys Ile Ser Thr Ile Ser His Glu Pro Gly
 65                  70                  75                  80

Tyr Ile Asp Lys Asp Leu Glu Lys Ile Val Gly Leu Gln Thr Asp Lys
                85                  90                  95

Pro Leu Lys Arg Gly Ile Met Pro Phe Gly Gly Ile Arg Met Val Val
            100                 105                 110

Lys Gly Gly Glu Ala Tyr Gly Lys Lys Ile Asp Glu Ser Val Val Lys
        115                 120                 125

Leu Phe Thr Glu Tyr Arg Lys Thr His Asn Asp Gly Val Tyr Asp Val
    130                 135                 140

Tyr Thr Pro Glu Met Met Arg Ala Lys Lys Ala Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Arg Leu Ile Gly Asp Lys Gln Lys Gln
            180                 185                 190

Leu Thr Ser Leu Glu Met Asp Tyr Met Asp Ser Glu Thr Ile Gln Glu
    195                 200                 205

Arg Glu Glu Arg Lys Ser Gln Ile Lys Ala Leu Glu Tyr Leu Lys Gln
210                 215                 220

Met Ala Glu Met Tyr Gly Phe Asp Ile Ser Arg Pro Ala Glu Thr Ala
225                 230                 235                 240

Gln Glu Ala Phe Gln Trp Leu Tyr Phe Gly Phe Leu Gly Ala Val Lys
                245                 250                 255

Glu Gln Asn Gly Ala Ala Met Ser Leu Gly Arg Val Ser Thr Phe Leu
            260                 265                 270

Asp Ile Tyr Ile Glu Arg Asp Met Lys Glu Gly Thr Leu Thr Glu Glu
    275                 280                 285

Glu Ala Gln Glu Leu Val Asp His Phe Val Met Lys Leu Arg Leu Val
290                 295                 300

Arg Phe Leu Arg Thr Pro Glu Tyr Glu Lys Leu Phe Ser Gly Asp Pro
305                 310                 315                 320

Thr Trp Ile Thr Glu Ser Ile Gly Gly Met Gly Leu Asp Gly Arg Thr
                325                 330                 335

Leu Val Thr Lys Asn Ser Phe Arg Met Leu His Thr Leu Phe Asn Leu
            340                 345                 350

Gly His Ala Pro Glu Pro Asn Met Thr Val Leu Trp Ser Val His Leu
    355                 360                 365

Pro Asp Gly Phe Lys Lys Tyr Cys Ser Tyr Val Ser Ile Asn Thr Ser
370                 375                 380

Ser Ile Gln Tyr Glu Ser Asp Asp Ile Met Arg Tyr Tyr Trp Gly Asp
385                 390                 395                 400

Asp Tyr Gly Ile Ala Cys Cys Val Ser Ala Met Arg Ile Gly Lys Gln
                405                 410                 415

Met Gln Phe Phe Gly Ala Arg Cys Asn Met Ala Lys Ala Leu Leu Tyr
```

```
                420                425                430
Ala Ile Asn Gly Gly Arg Asp Glu Lys Ser Gly Val Gln Val Gly Pro
            435                440                445

Ile Met Gln Ala Ile Glu Thr Glu Tyr Leu Asp Tyr Asp Val Ile
450                455                460

Lys Arg Phe Asp Ala Val Leu Thr Trp Val Ala Arg Leu Tyr Ile Asn
465                470                475                480

Thr Leu Asn Ile Ile His Tyr Met His Asp Lys Tyr Ala Tyr Glu Arg
                485                490                495

Leu Gln Met Ala Leu His Asp Lys Asp Ile Leu Arg Thr Met Ala Cys
                500                505                510

Gly Ile Ala Gly Leu Ser Val Val Ala Asp Ser Leu Ser Ala Ile Lys
            515                520                525

Tyr Ala Lys Val Lys Val Ile Arg Asn Glu Glu Gly Leu Ala Val Asp
530                535                540

Tyr Asp Ile Glu Gly Asp Tyr Pro Lys Phe Gly Asn Asn Asp Asp Arg
545                550                555                560

Val Asp Asn Ile Ala Val Met Leu Val Lys Ser Phe Met Glu Lys Leu
                565                570                575

Glu Lys Gln Arg Thr Tyr Arg His Ser Val Pro Thr Leu Ser Ile Leu
                580                585                590

Thr Ile Thr Ser Asn Val Val Tyr Gly Ala Lys Thr Gly Asn Thr Pro
            595                600                605

Asp Gly Arg Lys Ala Gly Glu Pro Phe Gly Pro Gly Ala Asn Pro Met
610                615                620

His Gly Arg Asp Leu Asn Gly Ala Leu Ala Val Leu Lys Ser Ile Ser
625                630                635                640

Lys Leu Pro Tyr Gln Phe Ala Gln Asp Gly Ile Ser Tyr Thr Phe Ser
                645                650                655

Ile Val Pro Lys Ala Leu Gly Lys Glu Glu Asp Thr Arg Ile Asn Asn
                660                665                670

Leu Val Ser Leu Leu Asp Ser Tyr Phe Lys Glu Gly His His Ile
            675                680                685

Asn Ile Asn Val Phe Glu Arg Glu Met Leu Leu Asp Ala Met Asp His
690                695                700

Pro Glu Lys Tyr Pro Gln Leu Thr Ile Arg Val Ser Gly Tyr Ala Val
705                710                715                720

Asn Phe Ile Lys Leu Thr Arg Glu Gln Gln Leu Asp Val Ile Asn Arg
                725                730                735

Thr Ile His Glu Asn Ile
            740

<210> SEQ ID NO 69
<211> LENGTH: 2283
<212> TYPE: DNA
<213> ORGANISM: Escherichia coli

<400> SEQUENCE: 69
atgtccgagc ttaatgaaaa gttagccaca gcctgggaag ttttaccaa aggtgactgg      60 cagaatgaag taaacgtccg tgacttcatt cagaaaaact acactccgta cgagggtgac     120
gagtccttcc tggctggcgc tactgaagcg accaccaccc tgtgggacaa agtaatggaa     180
ggcgttaaac tggaaaaccg cactcacgcg ccagttgact ttgacaccgc tgttgcttcc     240
accatcacct ctcacgacgc tggctacatc aacaagcagc ttgagaaaat cgttggtctg     300
```

```
cagactgaag ctccgctgaa acgtgctctt atcccgttcg gtggtatcaa aatgatcgaa        360
ggttcctgca aagcgtacaa ccgcgaactg gatccgatga tcaaaaaaat cttcactgaa        420
taccgtaaaa ctcacaacca gggcgtgttc gacgtttaca ctccggacat cctgcgttgc        480
cgtaaatctg gtgttctgac cggtctgcca gatgcatatg gccgtggccg tatcatcggt        540
gactaccgtc gcgttgcgct gtacggtatc gactacctga tgaaagacaa actggcacag        600
ttcacttctc tgcaggctga tctggaaaac ggcgtaaacc tggaacagac tatccgtctg        660
cgcgaagaaa tcgctgaaca gcaccgcgct ctgggtcaga tgaaagaaat ggctgcgaaa        720
tacggctacg acatctctgg tccggctacc aacgctcagg aagctatcca gtggacttac        780
ttcggctacc tggctgctgt taagtctcag aacggtgctg caatgtcctt cggtcgtacc        840
tccacctccc tggatgtgta catcgaacgt gacctgaaag ctggcaagat caccgaacaa        900
gaagcgcagg aaatggttga ccacctggtc atgaaactgc gtatggttcg cttcctgcgt        960
actccggaat acgatgaact gttctctggc gacccgatct gggcaaccga atctatcggt       1020
ggtatgggcc tcgacggtcg taccctggtt accaaaaaca gcttccgttt cctgaacacc       1080
ctgtacacca tgggtccgtc tccggaaccg aacatgacca ttctgtggtc tgaaaaactg       1140
ccgctgaact tcaagaaatt cgccgctaaa gtgtccatcg acacctcttc tctgcagtat       1200
gagaacgatg acctgatgcg tccggacttc aacaacgatg actacgctat tgcttgctgc       1260
gtaagcccga tgatcgttgg taaacaaatg cagttcttcg gtgcgcgtgc aaacctggcg       1320
aaaaccatgc tgtacgcaat caacggcggc gttgacgaaa aactgaaaat gcaggttggt       1380
ccgaagtctg aaccgatcaa aggcgatgtc ctgaactatg atgaagtgat ggagcgcatg       1440
gatcacttca tggactggct ggctaaacag tacatcactg cactgaacat catccactac       1500
atgcacgaca gtacagctac gaagcctctc tgatggcgc tgcacgaccg tgacgttatc       1560
cgcaccatgg cgtgtggtat cgctggtctg tccgttgctg ctgactccct gtctgcaatc       1620
aaatatgcga agttaaaacc gattcgtgac gaagacggtc tggctatcga cttcgaaatc       1680
gaaggcgaat acccgcagtt tggtaacaat gatccgcgtg tagatgacct ggctgttgac       1740
ctggtagaac gtttcatgaa gaaaattcag aaactgcaca cctaccgtga cgctatcccg       1800
actcagtctg ttctgaccat cacttctaac gttgtgtatg gtaagaaaac gggtaacacc       1860
ccagacggtc gtcgtgctgg cgcgccgttc ggacgggtg ctaacccgat gcacggtcgt       1920
gaccagaaag gtgcagtagc ctctctgact tccgttgcta aactgccgtt tgcttacgct       1980
aaagatggta tctcctacac cttctctatc gttccgaacg cactgggtaa agacgacgaa       2040
gttcgtaaga ccaacctggc tggtctgatg gatggttact tccaccacga agcatccatc       2100
gaaggtggtc agcacctgaa cgttaacgtg atgaaccgtg aaatgctgct cgacgcgatg       2160
gaaaacccgg aaaaatatcc gcagctgacc atccgtgtat ctggctacgc agtacgtttc       2220
aactcgctga ctaaagaaca gcagcaggac gttattactc gtaccttcac tcaatctatg       2280
taa                                                                     2283
```

<210> SEQ ID NO 70
<211> LENGTH: 760
<212> TYPE: PRT
<213> ORGANISM: Escherichia coli

<400> SEQUENCE: 70

```
Met Ser Glu Leu Asn Glu Lys Leu Ala Thr Ala Trp Glu Gly Phe Thr
1               5                   10                  15
```

```
Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
 50                  55                  60

Glu Asn Arg Thr His Ala Pro Val Asp Phe Asp Thr Ala Val Ala Ser
65                   70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
            165                 170                 175

Arg Ile Ile Gly Asp Tyr Arg Arg Val Ala Leu Tyr Gly Ile Asp Tyr
        180                 185                 190

Leu Met Lys Asp Lys Leu Ala Gln Phe Thr Ser Leu Gln Ala Asp Leu
    195                 200                 205

Glu Asn Gly Val Asn Leu Glu Gln Thr Ile Arg Leu Arg Glu Glu Ile
210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
            245                 250                 255

Gln Trp Thr Tyr Phe Gly Tyr Leu Ala Ala Val Lys Ser Gln Asn Gly
        260                 265                 270

Ala Ala Met Ser Phe Gly Arg Thr Ser Thr Phe Leu Asp Val Tyr Ile
    275                 280                 285

Glu Arg Asp Leu Lys Ala Gly Lys Ile Thr Glu Gln Glu Ala Gln Glu
290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
            325                 330                 335

Glu Ser Ile Gly Gly Met Gly Leu Asp Gly Arg Thr Leu Val Thr Lys
        340                 345                 350

Asn Ser Phe Arg Phe Leu Asn Thr Leu Tyr Thr Met Gly Pro Ser Pro
    355                 360                 365

Glu Pro Asn Met Thr Ile Leu Trp Ser Glu Lys Leu Pro Leu Asn Phe
370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
            405                 410                 415

Ile Ala Cys Cys Val Ser Pro Met Ile Val Gly Lys Gln Met Gln Phe
        420                 425                 430
```

| | | | | | | | | | | | | |
|---|---|---|---|---|---|---|---|---|---|---|---|---|
|Phe|Gly|Ala|Arg|Ala|Asn|Leu|Ala|Lys|Thr|Met|Leu|Tyr|Ala|Ile|Asn|
| | |435| | | |440| | | |445| | |

Phe Gly Ala Arg Ala Asn Leu Ala Lys Thr Met Leu Tyr Ala Ile Asn
            435                 440                 445

Gly Gly Val Asp Glu Lys Leu Lys Met Gln Val Gly Pro Lys Ser Glu
    450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
    610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
            660                 665                 670

Asn Ala Leu Gly Lys Asp Glu Val Arg Lys Thr Asn Leu Ala Gly
        675                 680                 685

Leu Met Asp Gly Tyr Phe His His Glu Ala Ser Ile Glu Gly Gly Gln
    690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
        755                 760

<210> SEQ ID NO 71
<211> LENGTH: 594
<212> TYPE: DNA
<213> ORGANISM: Chlamydomonas reinhardtii
<220> FEATURE:
<221> NAME/KEY: misc_feature
<223> OTHER INFORMATION: PflA1

<400> SEQUENCE: 71
atgttgaagg ctgcgttgcc acgaattatg aacgctgcta gcatgtcttg tgcagctact      60
gggctgcagc gctccggtcc gctggcgatg aacgctgcga ctacatcgcg aacgggccc      120 gcttcagggc ttccgaaaca ttcctggggt gccagtgctc gacgagcatt tgttgcacct    180

```
gccactatct cggaacggct gcagccgaag ctctcgacga attactcggt ggttctgccg    240
caatacgagc ccacggatcc ctcgggcatc cctgaggttt tcggaaacgt gcattcaaca    300
gaaagcatga gcgcggtgga cggccctggc gtacggtggt ccgcaactac ctcaagccac    360
gcggcggcat caccatcagc ggcggcgagg ccatgctgca gccacacttt tgtgtccaccg   420 tgttccaggt tccagggcat tgagctgctg ccgtaccacg tgttgggccg caacaagtgg    480
gaggtcatgg ggctgccgta ccccctggac ggcacgaaca cgccgccgca cgagcaggta    540
cgggccgtga tcaaggtgtt caacgacaac gacgttcccg tcatctgcgc cgag         594
```

```
<210> SEQ ID NO 72
<211> LENGTH: 198
<212> TYPE: PRT
<213> ORGANISM: Chlamydomonas reinhardtii
<220> FEATURE:
<221> NAME/KEY: MISC_FEATURE
<223> OTHER INFORMATION: PflA1

<400> SEQUENCE: 72

Met Leu Lys Ala Ala Leu Pro Arg Ile Met Asn Ala Ala Ser Met Ser
1               5                   10                  15

Cys Ala Ala Thr Gly Leu Gln Arg Ser Gly Pro Leu Ala Met Asn Ala
            20                  25                  30

Ala Thr Thr Ser Arg Thr Gly Pro Ala Ser Gly Leu Pro Lys His Ser
        35                  40                  45

Trp Gly Ala Ser Ala Arg Arg Ala Phe Val Ala Pro Ala Thr Ile Ser
    50                  55                  60

Glu Arg Leu Gln Pro Lys Leu Ser Thr Asn Tyr Ser Val Val Leu Pro
65                  70                  75                  80

Gln Tyr Glu Pro Thr Asp Pro Ser Gly Ile Pro Glu Val Phe Gly Asn
                85                  90                  95

Val His Ser Thr Glu Ser Met Ser Ala Val Asp Gly Pro Gly Val Arg
            100                 105                 110

Trp Ser Ala Thr Thr Ser Ser His Ala Ala Ser Pro Ser Ala Ala
            115                 120                 125

Ala Arg Pro Cys Cys Ser His Thr Leu Cys Pro Pro Cys Ser Arg Phe
        130                 135                 140

Gln Gly Ile Glu Leu Leu Pro Tyr His Val Leu Gly Arg Asn Lys Trp
145                 150                 155                 160

Glu Val Met Gly Leu Pro Tyr Pro Leu Asp Gly Thr Asn Thr Pro Pro
                165                 170                 175

His Glu Gln Val Arg Ala Val Ile Lys Val Phe Asn Asp Asn Asp Val
            180                 185                 190

Pro Val Ile Cys Ala Glu
        195
```

```
<210> SEQ ID NO 73
<211> LENGTH: 801
<212> TYPE: DNA
<213> ORGANISM: Neocallimastix frontalis

<400> SEQUENCE: 73
atgccagcta tcgttgatcc aactactatg gattatatgg aagtcaaggg caatgtccat    60
tcaactgaaa gtttggcttg tcttgaaggt ccaggaaaca gattccttt attttttaaat   120 ggttgtgctg ctcgttgctt atactgtagt aatccagata cttgggatga aactgttggt    180
```

```
actccaatga ccgttggcca acttattaag aagattggaa atcttaaaaa ctactatatc    240
aattctgttg gtggtggtgg tgtcactgtt tctggtggtg aaccattaac tcaatttggt    300
ttcttatctt gtttcttata tgctgtcaag aagcacttaa atcttcatac ctgtgttgaa    360
accactggtc aaggttgtac taaggcttgg aattcagttt tacctcatac tgacttatgc    420
ttagtatgta ttaaacatgc tattccagaa aaatacgaac aaattactcg tactaagaaa    480
ttagatagat gtcttaagtt ccttaaggaa ttagaaaaga gaaacattcc atggtggtgt    540
cgttacgttg ttcttccagg ttacactgat tctaaggaag atattgaagc tttaattgaa    600
ttagttaaga acagtccaac ttgtgaaaga attgaattcc ttccataccc cgaattaggt    660
aaaaacaaat gggaagaatt aggtattgaa tatccattaa agaatattaa acaacttaag    720
aaaagtgaaa ttaaatggat ctgtgatatg gtccgtgaag ctttcaagga ccgtaatatt    780
ccagttactg gtgatactta a                                              801
```

<210> SEQ ID NO 74
<211> LENGTH: 266
<212> TYPE: PRT
<213> ORGANISM: Neocallimastix frontalis

<400> SEQUENCE: 74

```
Met Pro Ala Ile Val Asp Pro Thr Thr Met Asp Tyr Met Glu Val Lys
1               5                   10                  15

Gly Asn Val His Ser Thr Glu Ser Leu Ala Cys Leu Glu Gly Pro Gly
            20                  25                  30

Asn Arg Phe Leu Leu Phe Leu Asn Gly Cys Ala Ala Arg Cys Leu Tyr
        35                  40                  45

Cys Ser Asn Pro Asp Thr Trp Asp Glu Thr Val Gly Thr Pro Met Thr
    50                  55                  60

Val Gly Gln Leu Ile Lys Lys Ile Gly Asn Leu Lys Asn Tyr Tyr Ile
65                  70                  75                  80

Asn Ser Val Gly Gly Gly Val Thr Val Ser Gly Gly Glu Pro Leu
                85                  90                  95

Thr Gln Phe Gly Phe Leu Ser Cys Phe Leu Tyr Ala Val Lys Lys His
            100                 105                 110

Leu Asn Leu His Thr Cys Val Glu Thr Thr Gly Gln Gly Cys Thr Lys
        115                 120                 125

Ala Trp Asn Ser Val Leu Pro His Thr Asp Leu Cys Leu Val Cys Ile
    130                 135                 140

Lys His Ala Ile Pro Glu Lys Tyr Glu Gln Ile Thr Arg Thr Lys Lys
145                 150                 155                 160

Leu Asp Arg Cys Leu Lys Phe Leu Lys Glu Leu Glu Lys Arg Asn Ile
                165                 170                 175

Pro Trp Trp Cys Arg Tyr Val Val Leu Pro Gly Tyr Thr Asp Ser Lys
            180                 185                 190

Glu Asp Ile Glu Ala Leu Ile Glu Leu Val Lys Asn Ser Pro Thr Cys
        195                 200                 205

Glu Arg Ile Glu Phe Leu Pro Tyr Pro Glu Leu Gly Lys Asn Lys Trp
    210                 215                 220

Glu Glu Leu Gly Ile Glu Tyr Pro Leu Lys Asn Ile Lys Gln Leu Lys
225                 230                 235                 240

Lys Ser Glu Ile Lys Trp Ile Cys Asp Met Val Arg Glu Ala Phe Lys
                245                 250                 255

Asp Arg Asn Ile Pro Val Thr Gly Asp Thr
```

<210> SEQ ID NO 75
<211> LENGTH: 2496
<212> TYPE: DNA
<213> ORGANISM: Chlamydomonas reinhardtii
<220> FEATURE:
<221> NAME/KEY: misc_feature
<223> OTHER INFORMATION: PflA

<400> SEQUENCE: 75

```
atgttaacac ccttaagcta tcctatcatc aacaccgtct cgtcaagtct gccagcgctt      60
cacgccatga gccagatgct gctggagaag acaatgcgcc ggggcctcgc cacggtctcg     120
gccgcagcga gctccgctgt tggccggccc atcccatgg ctgttaggtc gccgatgcgc     180
tcgatggccg ctgccagcgc ggccgctgag gccctccgg tggcacccag ccacagctgc      240
gctgctgacc ccgacaagca cccgcacctg cccgacccccc gcccgaagcc ggccgtggac     300
gcgggcatca cgtccagaa gtatgtgcag acaactaca ccgcttacgc cggcaactcg       360
tccttcctgg ctggccccac tgacaacacc aagaagctgt ggagcgagct ggagaagatg     420
attgccaccg agatcgagaa gggcgtgatg acgtggatc cctccaagcc ctccaccatc      480
accgccttcc gcccggcta catcgacaag gacctggaga cggtggtggg gctgcagacc      540
gacgcgccgc tcaagcgcgc catcaagccc ctgggcggcg tcaacatggt caaggcggcg     600
ctggagtcgt acggctacac ccccgacccc gaggtggccc gcctgtacag cacggtgcgc     660
aagacgcaca cagcggcgt gtttgacgcc tacacgacg agatgcgcgc cgcgcgcaag       720
agcggcatcc tgtccggcct gcccgacggc tacgccgcg ccgcatcat cggcgactac       780
cgccgcgtgg cgctgtacgg cgtggacgcg ctgatcaagg ccaagaagac cgacctgaag     840
cacaacctgc tgggcgtgat ggacgaggag aagatccgcc tgcgcgagga ggtgaacgag     900
cagatccgcg cgctcagcga gctcaaggag atgggcgccg cctacggctt cgacctgagc     960
cgccccgccg ccaactcgcg cgaggcggtg cagtggctgt acttcggcta cctgggcgcc    1020
gtcaaggagc aggacggcgc cgccatgagc ctgggccgca tcgacgcctt cctggacacc    1080
tactttgagc gcgacctcaa ggccggcacc atcactgagg ccgaggtgca ggagctgatc    1140
gaccacttcg tcatgaagct gcgcatcgtg cgccagctgc gcacgcccga gtacaacgcg    1200
ctgtttgccg gcgaccccac ctgggtcacc tgcgtgctgg cggcactga cgccagcggc    1260
aaggccatgg tcaccaagac cagcttccgc ctgctcaaca ccctgtacaa cctgggcccc    1320
gcgcccgagc ccaacctgac ggtgctgtgg aacgacaacc tgcccgcgcc cttcaaggag    1380
ttctgcgcca aggtgtcgct ggacaccagc tccatccagt acgagtccga caacctcatg    1440
agcaagctgt ttggctccga ctactccatc gcctgctgcg tgtcggccat gcgcgtgggc    1500
aaggacatgc agtactttgg cgcccgcgcc aacctgccca gctgctgct gtacacgctc    1560
aacggcggcc gcgacgaggt gtcgggcgac caggtgggc caagttcgc gccggtgcgc     1620
agccccaccg cgccgttgga ctatgaggag gtcaaggcca gatcgagga cggcatggag    1680
tggctggcct ccatgtacgc gaacaccatg aacatcatcc actacatgca cgacaagtac    1740
gactacgagc ggctgcagat ggcgctgcac gacacgcacg tgcgccgcct gctggcgttc    1800
ggcatcagcg gcctgtccgt ggtgaccgac tcgctgtcgg ccatcaagta cgcccaggtg    1860
acgcccgtga ttgacgagcg cggcctcatg acggacttca aggtgagggg cagcttcccc    1920
aagtacggca acgacgatga ccgcgtggac gagatcgccg agtgggtggt gtccaccttc    1980
```

-continued

```
tccagcaagc tggccaagca gcacacctac cgcaactcgg tgcccacgct gtcggtgctg      2040
accatcacct ccaacgtggt gtacggcaag aagacgggct ccaccccga cggccgcaag       2100 aagggcgagc ccttcgcgcc cggcgccaac ccgctgcacg gccgcgacgc ccacggcgct      2160
ctggcctcgc tcaactcggt ggccaagctg ccctacacca tgtgcctgga cggcatctcc      2220
aacaccttct cgctcatccc ccaggtgctg ggcaggggcg gcgagcacga gcgcgccacc      2280
aacctggcct ccatcctgga cggctacttt gccaacggcg ccaccacat caacgtcaac       2340 gtgctcaacc gctccatgct catggacgcc gtggagcacc ccgagaagta ccccaacctc      2400
accatccgcg tgtccgggta cgctgtgcac ttcgcgcgcc tcacgcgcga gcagcagctg      2460
gaggtgatcg cgcgcacctt ccacgacacc atgtaa                                2496
```

<210> SEQ ID NO 76
<211> LENGTH: 831
<212> TYPE: PRT
<213> ORGANISM: Chlamydomonas reinhardtii
<220> FEATURE:
<221> NAME/KEY: MISC_FEATURE
<223> OTHER INFORMATION: PflA

<400> SEQUENCE: 76

```
Met Leu Thr Pro Leu Ser Tyr Pro Ile Ile Asn Thr Val Ser Ser
 1               5                  10                  15

Leu Pro Ala Leu His Ala Met Ser Gln Met Leu Leu Glu Lys Thr Met
                20                  25                  30

Arg Arg Gly Leu Ala Thr Val Ser Ala Ala Ser Ser Ala Val Gly
        35                  40                  45

Arg Pro Ile Pro Met Ala Val Arg Ser Pro Met Arg Ser Met Ala Ala
    50                  55                  60

Ala Ser Ala Ala Ala Glu Ala Leu Pro Val Ala Pro Ser His Ser Cys
65                  70                  75                  80

Ala Ala Asp Pro Asp Lys His Pro His Leu Pro Asp Pro Arg Pro Lys
                85                  90                  95

Pro Ala Val Asp Ala Gly Ile Asn Val Gln Lys Tyr Val Gln Asp Asn
            100                 105                 110

Tyr Thr Ala Tyr Ala Gly Asn Ser Ser Phe Leu Ala Gly Pro Thr Asp
        115                 120                 125

Asn Thr Lys Lys Leu Trp Ser Glu Leu Glu Lys Met Ile Ala Thr Glu
    130                 135                 140

Ile Glu Lys Gly Val Met Asp Val Asp Pro Ser Lys Pro Ser Thr Ile
145                 150                 155                 160

Thr Ala Phe Pro Pro Gly Tyr Ile Asp Lys Asp Leu Glu Thr Val Val
                165                 170                 175

Gly Leu Gln Thr Asp Ala Pro Leu Lys Arg Ala Ile Lys Pro Leu Gly
            180                 185                 190

Gly Val Asn Met Val Lys Ala Ala Leu Glu Ser Tyr Gly Tyr Thr Pro
        195                 200                 205

Asp Pro Glu Val Ala Arg Leu Tyr Ser Thr Val Arg Lys Thr His Asn
    210                 215                 220

Ser Gly Val Phe Asp Ala Tyr Thr Asp Glu Met Arg Ala Ala Arg Lys
225                 230                 235                 240

Ser Gly Ile Leu Ser Gly Leu Pro Asp Gly Tyr Gly Arg Gly Arg Ile
                245                 250                 255

Ile Gly Asp Tyr Arg Arg Val Ala Leu Tyr Gly Val Asp Ala Leu Ile
            260                 265                 270
```

```
Lys Ala Lys Lys Thr Asp Leu Lys His Asn Leu Leu Gly Val Met Asp
        275                 280                 285
Glu Glu Lys Ile Arg Leu Arg Glu Val Asn Glu Gln Ile Arg Ala
290                 295                 300
Leu Ser Glu Leu Lys Glu Met Gly Ala Ala Tyr Gly Phe Asp Leu Ser
305                 310                 315                 320
Arg Pro Ala Ala Asn Ser Arg Glu Ala Val Gln Trp Leu Tyr Phe Gly
                325                 330                 335
Tyr Leu Gly Ala Val Lys Glu Gln Asp Gly Ala Ala Met Ser Leu Gly
                340                 345                 350
Arg Ile Asp Ala Phe Leu Asp Thr Tyr Phe Glu Arg Asp Leu Lys Ala
                355                 360                 365
Gly Thr Ile Thr Glu Ala Glu Val Gln Glu Leu Ile Asp His Phe Val
                370                 375                 380
Met Lys Leu Arg Ile Val Arg Gln Leu Arg Thr Pro Glu Tyr Asn Ala
385                 390                 395                 400
Leu Phe Ala Gly Asp Pro Thr Trp Val Thr Cys Val Leu Gly Gly Thr
                405                 410                 415
Asp Ala Ser Gly Lys Ala Met Val Thr Lys Thr Ser Phe Arg Leu Leu
                420                 425                 430
Asn Thr Leu Tyr Asn Leu Gly Pro Ala Pro Glu Pro Asn Leu Thr Val
                435                 440                 445
Leu Trp Asn Asp Asn Leu Pro Ala Pro Phe Lys Glu Phe Cys Ala Lys
                450                 455                 460
Val Ser Leu Asp Thr Ser Ser Ile Gln Tyr Glu Ser Asp Asn Leu Met
465                 470                 475                 480
Ser Lys Leu Phe Gly Ser Asp Tyr Ser Ile Ala Cys Cys Val Ser Ala
                485                 490                 495
Met Arg Val Gly Lys Asp Met Gln Tyr Phe Gly Ala Arg Ala Asn Leu
                500                 505                 510
Pro Lys Leu Leu Leu Tyr Thr Leu Asn Gly Gly Arg Asp Glu Val Ser
                515                 520                 525
Gly Asp Gln Val Gly Pro Lys Phe Ala Pro Val Arg Ser Pro Thr Ala
                530                 535                 540
Pro Leu Asp Tyr Glu Glu Val Lys Ala Lys Ile Glu Asp Gly Met Glu
545                 550                 555                 560
Trp Leu Ala Ser Met Tyr Ala Asn Thr Met Asn Ile Ile His Tyr Met
                565                 570                 575
His Asp Lys Tyr Asp Tyr Glu Arg Leu Gln Met Ala Leu His Asp Thr
                580                 585                 590
His Val Arg Arg Leu Leu Ala Phe Gly Ile Ser Gly Leu Ser Val Val
                595                 600                 605
Thr Asp Ser Leu Ser Ala Ile Lys Tyr Ala Gln Val Thr Pro Val Ile
                610                 615                 620
Asp Glu Arg Gly Leu Met Thr Asp Phe Lys Val Glu Gly Ser Phe Pro
625                 630                 635                 640
Lys Tyr Gly Asn Asp Asp Arg Val Asp Glu Ile Ala Glu Trp Val
                645                 650                 655
Val Ser Thr Phe Ser Ser Lys Leu Ala Lys Gln His Thr Tyr Arg Asn
                660                 665                 670
Ser Val Pro Thr Leu Ser Val Leu Thr Ile Thr Ser Asn Val Val Tyr
                675                 680                 685
```

Gly Lys Lys Thr Gly Ser Thr Pro Asp Gly Arg Lys Gly Glu Pro
    690             695                 700
Phe Ala Pro Gly Ala Asn Pro Leu His Gly Arg Asp Ala His Gly Ala
705                 710                 715                 720
Leu Ala Ser Leu Asn Ser Val Ala Lys Leu Pro Tyr Thr Met Cys Leu
                725                 730                 735
Asp Gly Ile Ser Asn Thr Phe Ser Leu Ile Pro Gln Val Leu Gly Arg
            740                 745                 750
Gly Gly Glu His Glu Arg Ala Thr Asn Leu Ala Ser Ile Leu Asp Gly
        755                 760                 765
Tyr Phe Ala Asn Gly Gly His His Ile Asn Val Asn Val Leu Asn Arg
770                 775                 780
Ser Met Leu Met Asp Ala Val Glu His Pro Glu Lys Tyr Pro Asn Leu
785                 790                 795                 800
Thr Ile Arg Val Ser Gly Tyr Ala Val His Phe Ala Arg Leu Thr Arg
                805                 810                 815
Glu Gln Gln Leu Glu Val Ile Ala Arg Thr Phe His Asp Thr Met
            820                 825                 830

<210> SEQ ID NO 77
<211> LENGTH: 2418
<212> TYPE: DNA
<213> ORGANISM: Piromyces sp. E2

<400> SEQUENCE: 77

```
atggaaagct tagctttatc caatgtcagt gttcttgcta acactgtttc tgttaacgct      60
gttgctgcca ccaaggtcgc tggtgtcaga atggccaagc atcccgcgc tcttcacacc     120
ccagctatga agactactct taagacttct aagaaggtcc cagctatgca agctaagacc     180
tacgccactc aagctccatg catcaccaac gatgctgctg ccaagagtga atcgatgtt      240
gaaggttgga ttaagaagca ctacacccca tacgaaggtg atggttcttt ccttgctggt     300
ccaactgaaa agaccaagaa gcttttcgcc aaggctgaag atacttagc taaggaacgt      360
gccaacggtg gtttatacga tgttgaccca cacactccat ccaccatcac ttcccacaag     420
ccaggttacc ttgacaaaga taacgaagtt atctacggtt accaaactga tgttccactt     480
aagagagcca ttaagccatt cggtggtgtt aacatggtta agaacgctct taaggctgtt     540
aacgttccaa tggacaagga agtcgaacac atttcactg actaccgtaa gactcacaac      600
actgctgtct tcgatcttta ctccaaggaa atgagatctg gtcgttccaa cgctatcatg     660
accggtttac cagatggtta cggtcgtggt cgtattattg tgattaccg tcgtgttgcc      720
ctttacggta ctgaccgtct tatcgcccaa aagaacaagg ataaggccga actccaaaag     780
agacaaatgg acgaaccaac catgaagctc attggtgaag ttgctgatca agttaaggct     840
cttaagcaac ttactcaaat ggccaagtcc tacggtattg atatctctaa gccagctaag     900
aacgccagag aagctactca atttgtttac tttggttact aggttctat caaggaacaa      960
gatggtgctg ccatgtctct tggtcgtgtt gatgccttcc ttgattgttt ctttgaaaac    1020
gatttaaaga acggtgttat cactgaagct gaagctcaag aaatcattga taaccttatc    1080
cttaagttac gtttcgctcg tcacttacgt accccagaat acaacgactt attcgctggt    1140
gatccaacct gggttactat gtctcttggt ggtatggat ctgatggtcg taccttagtt    1200
actaagactt cctccgtgt ccttaacact ctctacaact taggtccagc tccagaacca    1260
aacattactg tcctctggaa caaggctctt ccaaagaact tcaaggactt cgccactaag    1320
```

-continued

```
gtttctattg ataccbcttc catccaatac gaatccgatg ctcttatgtc tgccagattc    1380
ggtgatgact acggtattgc ttgctgtgtc tctgccatga gaattggtaa ggatatgcaa    1440
ttcttcggtg ctcgttgtaa ccttgccaag cttatgcttt acgtccttaa ccacggtaag    1500
gatgaaagaa ctggtaagca agtcggtcca gactttggtc cagttccaga aggtccaatt    1560
ccattcgact ggatgtggga aacctatgac aaggctatgg actggattgc caagctctac    1620
gttaacacca tgaacgttat ccacttctgt cacgaccaat actgttacga atcccttcaa    1680
atggctcttc acgataccga tgtccgtcgt cttatggcct cggtgttgc tggtctttcc      1740
gttgttgctg attccttctc tgctattaag tacgctaagg ttaccccagt ccgtgatgcc    1800
aagactggtt taactgttga cttcaagatt gaaggtgaat cccaaaatt cggtaatgat      1860
gatgaccgtg ttgatttctt cgccagaact gttactgaca gcttatcaa caagctcaga      1920
aagaccccaa cctaccgtgg tgctactcac actctttcta ttcttaccat tacctctaac    1980
gtcgtttacg gtaagaagac tggttctact ccagatggtc gtaaggctgg tcaaccattc    2040
gctccaggtt gtaacccaat gcacggtcgt gaattctctg gtgccgttgc ttctctttct    2100
tctgtcgcta aggttaacta cgactcttgt atggatggta tctctaacac cttctctatt    2160
gttccaaaca ctattggtaa gtccttacaa gaacgtcaag gtaaccttc cggtttatta     2220
gatggttact tcaccaaggg tgcccaccac cttaacgtta acgttcttaa gcgtgaaacc    2280
ttagaagacg ccatggccca cccagaaaac tatccaaacc ttactattcg tgtctctggt    2340
tacgctgtca actttgttaa gttaactcca caacaacaaa aggaagttat tgcccgtacc    2400
ttccacgaaa agatgtaa                                                  2418
```

<210> SEQ ID NO 78
<211> LENGTH: 805
<212> TYPE: PRT
<213> ORGANISM: Piromyces sp. E2

<400> SEQUENCE: 78

```
Met Glu Ser Leu Ala Leu Ser Asn Val Ser Val Leu Ala Asn Thr Val
1               5                   10                  15

Ser Val Asn Ala Val Ala Ala Thr Lys Val Ala Gly Val Arg Met Ala
                20                  25                  30

Lys Pro Ser Arg Ala Leu His Thr Pro Ala Met Lys Thr Thr Leu Lys
            35                  40                  45

Thr Ser Lys Lys Val Pro Ala Met Gln Ala Lys Thr Tyr Ala Thr Gln
        50                  55                  60

Ala Pro Cys Ile Thr Asn Asp Ala Ala Lys Ser Glu Ile Asp Val
65                  70                  75                  80

Glu Gly Trp Ile Lys Lys His Tyr Thr Pro Tyr Glu Gly Asp Gly Ser
                85                  90                  95

Phe Leu Ala Gly Pro Thr Glu Lys Thr Lys Lys Leu Phe Ala Lys Ala
            100                 105                 110

Glu Glu Tyr Leu Ala Lys Glu Arg Ala Asn Gly Gly Leu Tyr Asp Val
        115                 120                 125

Asp Pro His Thr Pro Ser Thr Ile Thr Ser His Lys Pro Gly Tyr Leu
    130                 135                 140

Asp Lys Asp Asn Glu Val Ile Tyr Gly Tyr Gln Thr Asp Val Pro Leu
145                 150                 155                 160

Lys Arg Ala Ile Lys Pro Phe Gly Gly Val Asn Met Val Lys Asn Ala
                165                 170                 175
```

```
Leu Lys Ala Val Asn Val Pro Met Asp Lys Glu Val Glu His Ile Phe
            180                 185                 190

Thr Asp Tyr Arg Lys Thr His Asn Thr Ala Val Phe Asp Leu Tyr Ser
        195                 200                 205

Lys Glu Met Arg Ser Gly Arg Ser Asn Ala Ile Met Thr Gly Leu Pro
    210                 215                 220

Asp Gly Tyr Gly Arg Gly Arg Ile Ile Gly Asp Tyr Arg Arg Val Ala
225                 230                 235                 240

Leu Tyr Gly Thr Asp Arg Leu Ile Ala Gln Lys Asn Lys Asp Lys Ala
                245                 250                 255

Glu Leu Gln Lys Arg Gln Met Asp Glu Pro Thr Met Lys Leu Ile Gly
            260                 265                 270

Glu Val Ala Asp Gln Val Lys Ala Leu Lys Gln Leu Thr Gln Met Ala
        275                 280                 285

Lys Ser Tyr Gly Ile Asp Ile Ser Lys Pro Ala Lys Asn Ala Arg Glu
    290                 295                 300

Ala Thr Gln Phe Val Tyr Phe Gly Tyr Leu Gly Ser Ile Lys Glu Gln
305                 310                 315                 320

Asp Gly Ala Ala Met Ser Leu Gly Arg Val Asp Ala Phe Leu Asp Cys
                325                 330                 335

Phe Phe Glu Asn Asp Leu Lys Asn Gly Val Ile Thr Glu Ala Glu Ala
            340                 345                 350

Gln Glu Ile Ile Asp Asn Leu Ile Leu Lys Leu Arg Phe Ala Arg His
        355                 360                 365

Leu Arg Thr Pro Glu Tyr Asn Asp Leu Phe Ala Gly Asp Pro Thr Trp
    370                 375                 380

Val Thr Met Ser Leu Gly Gly Met Gly Ser Asp Gly Arg Thr Leu Val
385                 390                 395                 400

Thr Lys Thr Ser Phe Arg Val Leu Asn Thr Leu Tyr Asn Leu Gly Pro
                405                 410                 415

Ala Pro Glu Pro Asn Ile Thr Val Leu Trp Asn Lys Ala Leu Pro Lys
            420                 425                 430

Asn Phe Lys Asp Phe Ala Thr Lys Val Ser Ile Asp Thr Ser Ser Ile
        435                 440                 445

Gln Tyr Glu Ser Asp Ala Leu Met Ser Ala Arg Phe Gly Asp Asp Tyr
    450                 455                 460

Gly Ile Ala Cys Cys Val Ser Ala Met Arg Ile Gly Lys Asp Met Gln
465                 470                 475                 480

Phe Phe Gly Ala Arg Cys Asn Leu Ala Lys Leu Met Leu Tyr Val Leu
                485                 490                 495

Asn His Gly Lys Asp Glu Arg Thr Gly Lys Gln Val Gly Pro Asp Phe
            500                 505                 510

Gly Pro Val Pro Glu Gly Pro Ile Pro Phe Asp Trp Met Trp Glu Thr
        515                 520                 525

Tyr Asp Lys Ala Met Asp Trp Ile Ala Lys Leu Tyr Val Asn Thr Met
    530                 535                 540

Asn Val Ile His Phe Cys His Asp Gln Tyr Cys Tyr Glu Ser Leu Gln
545                 550                 555                 560

Met Ala Leu His Asp Thr Asp Val Arg Arg Leu Met Ala Phe Gly Val
                565                 570                 575

Ala Gly Leu Ser Val Val Ala Asp Ser Phe Ser Ala Ile Lys Tyr Ala
            580                 585                 590

Lys Val Thr Pro Val Arg Asp Ala Lys Thr Gly Leu Thr Val Asp Phe
```

```
                595             600             605
Lys Ile Glu Gly Glu Phe Pro Lys Phe Gly Asn Asp Asp Arg Val
        610             615             620
Asp Phe Phe Ala Arg Thr Val Thr Asp Lys Leu Ile Asn Lys Leu Arg
625             630             635             640
Lys Thr Pro Thr Tyr Arg Gly Ala Thr His Thr Leu Ser Ile Leu Thr
                645             650             655
Ile Thr Ser Asn Val Val Tyr Gly Lys Lys Thr Gly Ser Thr Pro Asp
            660             665             670
Gly Arg Lys Ala Gly Gln Pro Phe Ala Pro Gly Cys Asn Pro Met His
        675             680             685
Gly Arg Glu Phe Ser Gly Ala Val Ala Ser Leu Ser Ser Val Ala Lys
        690             695             700
Val Asn Tyr Asp Ser Cys Met Asp Gly Ile Ser Asn Thr Phe Ser Ile
705             710             715             720
Val Pro Asn Thr Ile Gly Lys Ser Leu Gln Glu Arg Gln Gly Asn Leu
                725             730             735
Ser Gly Leu Leu Asp Gly Tyr Phe Thr Lys Gly Ala His His Leu Asn
            740             745             750
Val Asn Val Leu Lys Arg Glu Thr Leu Glu Asp Ala Met Ala His Pro
        755             760             765
Glu Asn Tyr Pro Asn Leu Thr Ile Arg Val Ser Gly Tyr Ala Val Asn
        770             775             780
Phe Val Lys Leu Thr Pro Gln Gln Lys Glu Val Ile Ala Arg Thr
785             790             795             800
Phe His Glu Lys Met
                805

<210> SEQ ID NO 79
<211> LENGTH: 2414
<212> TYPE: DNA
<213> ORGANISM: Neocallimastix frontalis

<400> SEQUENCE: 79
gcttagcttt atccaacgtc agtgttcttg ctaacactgt ttctattaac gctgttgctg      60
ccaccaaggt cgctggtgtc agaatggcta aaccaactcg tgctcttcac actccagcta     120
tgaagactac tcttaaggct tccaagaagg ctgctgttcc agtcatgcaa gccaagacct     180
acgctactgc tccagttatc actaacgatg ctgctgccaa gagcgaaatc gatgtcgaag     240
gttggattaa gaagcactat actccatacg aaggtgatgg ttctttcctt gctggtccaa     300
ctgaaaagac taagaagctt ttcgccaagg ctgaagaata cttagccaag aacgtgcta     360 acggtggttt atacgatgtt gacccacaca ctccatctac tattacctcc acaagccag     420 gttaccttga caaagaaaac gaagttattt acggttacca aactgatgtt cctcttaaga     480
gagccatcaa gccattcggt ggtgttaaca tggttaagaa cgctcttaag gctgttaatg     540
ttccaatgga caaggaagtc gaacacattt tctctgacta ccgtaagact cacaacactg     600
ctgtcttcga tatctactct aaggaaatga gagctggtcg ttccaacgct atcatgactg     660
gtttaccaga tggttacggt cgtggtcgta ttattggtga ttaccgtcgt gttgcccttt     720
acggtactga ccgtcttatc gcccaaaagg aaaagataa ggctgaactc caaagaagc     780 aaatggacga accaaccatg aaattaattg gtgaagttgc tgaccaagtt aaggctctta     840
agcaacttac tcaaatggct aagtcctacg gtattgatat taccaagcca gccaagaacg     900
```

```
ccagagaagc tactcaattt gtttacttcg gttacttagg ttctatcaag gaacaagatg      960
gtgctgccat gtctcttggt cgtgttgatg ctttcttaga ttgtttcttt gaaaacgatt     1020
taaagaatgg tgttatcact gaatctgaag ctcaagaaat cattgataac cttatcttaa     1080
agttacgttt cgctcgtcac ttacgtactc cagaatacaa cgacttattc gctggtgatc     1140
caacctgggt tactatgtct cttggtggta tgggtagtga tggtcgtacc ttagttacta     1200
agacttcctt ccgtgttctt aacactcttt acaacttagg tccagctcca gaaccaaaca     1260
tcactgtcct ctggaacaag aaccttccaa agaacttcaa ggacttcgct actaaggttt     1320
ctattgatac ctcttccatt caatacgaat ctgatgccct tatgtccgct agattcggtg     1380
atgattacgg aattgcctgc tgtgtttctg ccatgagaat tggtaaggat atgcaattct     1440
tcggtgctcg ttgtaacctt gctaagctta tgctttacgt ccttaaccat ggtaaggatg     1500
aaagaactgg taagcaagtt ggtccagact tcggtccagt tccagaaggt ccaattccat     1560
tcgactggat gtgggaaact tatgacaagg ctatggattg gattgccaag ctttacgtta     1620
acaccatgaa cgttattcac ttctgtcacg accaatactg ttacgaatct cttcaaatgg     1680
ctcttcacga taccgatgtc cgtcgtctta tggccttcgg tgttgctggt ctttctgttg     1740
ttgctgattc cttctctgct attaagtacg ctaaggttac tccaatccgt gatccaaaga     1800
ccggtttaac tgttgacttc aaggttgaag gtgaattccc aaaattcggt aacgatgatg     1860
accgtgttga cttcttcgcc agaactgtta ctgacaagct tattaacaag ttaagaaaga     1920
ctccaaccta ccgtggtgct acccacactc tttctattct taccattacc tctaacgtcg     1980
tttacggtaa agaaccggt tctactccag atggtcgtaa ggctggtcaa ccattcgccc      2040
caggttgtaa cccaatgcac ggtcgtgaat ctctggtgc cgttgcttct ctttcttccg       2100
ttgctaaggt taactacgat tcttgtatgg atggtatctc taacaccttc tctattgttc     2160
caaacactat cggtaagact ttacaagaac gtcaaggtaa cctttctggt ttattagatg     2220
gttacttcag caagggtgct caccatctta acgttaacgt tcttaagcgt gaaactttag     2280
aagatgccat ggctcaccca gaaaactatc caaaccttac tatccgtgtt tctggttatg     2340
ctgtcaactt cgttaagtta actccagccc aacaaaagga agttattgcc cgtaccttcc     2400
acgaaaagat gtaa                                                       2414
```

<210> SEQ ID NO 80
<211> LENGTH: 803
<212> TYPE: PRT
<213> ORGANISM: Neocallimastix frontalis

<400> SEQUENCE: 80

Leu Ala Leu Ser Asn Val Ser Val Leu Ala Asn Thr Val Ser Ile Asn
1               5                   10                  15

Ala Val Ala Ala Thr Lys Val Ala Gly Val Arg Met Ala Lys Pro Thr
            20                  25                  30

Arg Ala Leu His Thr Pro Ala Met Lys Thr Thr Leu Lys Ala Ser Lys
        35                  40                  45

Lys Ala Ala Val Pro Val Met Gln Ala Lys Thr Tyr Ala Thr Ala Pro
    50                  55                  60

Val Ile Thr Asn Asp Ala Ala Lys Ser Glu Ile Asp Val Glu Gly
65                  70                  75                  80

Trp Ile Lys Lys His Tyr Thr Pro Tyr Glu Gly Asp Gly Ser Phe Leu
                85                  90                  95

Ala Gly Pro Thr Glu Lys Thr Lys Lys Leu Phe Ala Lys Ala Glu Glu

```
            100                 105                 110
Tyr Leu Ala Lys Glu Arg Ala Asn Gly Gly Leu Tyr Asp Val Asp Pro
            115                 120                 125

His Thr Pro Ser Thr Ile Thr Ser His Lys Pro Gly Tyr Leu Asp Lys
    130                 135                 140

Glu Asn Glu Val Ile Tyr Gly Tyr Gln Thr Asp Val Pro Leu Lys Arg
145                 150                 155                 160

Ala Ile Lys Pro Phe Gly Gly Val Asn Met Val Lys Asn Ala Leu Lys
                165                 170                 175

Ala Val Asn Val Pro Met Asp Lys Glu Val Glu His Ile Phe Ser Asp
            180                 185                 190

Tyr Arg Lys Thr His Asn Thr Ala Val Phe Asp Ile Tyr Ser Lys Glu
        195                 200                 205

Met Arg Ala Gly Arg Ser Asn Ala Ile Met Thr Gly Leu Pro Asp Gly
    210                 215                 220

Tyr Gly Arg Gly Arg Ile Ile Gly Asp Tyr Arg Arg Val Ala Leu Tyr
225                 230                 235                 240

Gly Thr Asp Arg Leu Ile Ala Gln Lys Glu Lys Asp Lys Ala Glu Leu
                245                 250                 255

Gln Lys Lys Gln Met Asp Glu Pro Thr Met Lys Leu Ile Gly Glu Val
            260                 265                 270

Ala Asp Gln Val Lys Ala Leu Lys Gln Leu Thr Gln Met Ala Lys Ser
        275                 280                 285

Tyr Gly Ile Asp Ile Thr Lys Pro Ala Lys Asn Ala Arg Glu Ala Thr
    290                 295                 300

Gln Phe Val Tyr Phe Gly Tyr Leu Gly Ser Ile Lys Glu Gln Asp Gly
305                 310                 315                 320

Ala Ala Met Ser Leu Gly Arg Val Asp Ala Phe Leu Asp Cys Phe Phe
                325                 330                 335

Glu Asn Asp Leu Lys Asn Gly Val Ile Thr Glu Ser Glu Ala Gln Glu
            340                 345                 350

Ile Ile Asp Asn Leu Ile Leu Lys Leu Arg Phe Ala Arg His Leu Arg
        355                 360                 365

Thr Pro Glu Tyr Asn Asp Leu Phe Ala Gly Asp Pro Thr Trp Val Thr
    370                 375                 380

Met Ser Leu Gly Gly Met Gly Ser Asp Gly Arg Thr Leu Val Thr Lys
385                 390                 395                 400

Thr Ser Phe Arg Val Leu Asn Thr Leu Tyr Asn Leu Gly Pro Ala Pro
                405                 410                 415

Glu Pro Asn Ile Thr Val Leu Trp Asn Lys Asn Leu Pro Lys Asn Phe
            420                 425                 430

Lys Asp Phe Ala Thr Lys Val Ser Ile Asp Thr Ser Ser Ile Gln Tyr
        435                 440                 445

Glu Ser Asp Ala Leu Met Ser Ala Arg Phe Gly Asp Asp Tyr Gly Ile
    450                 455                 460

Ala Cys Cys Val Ser Ala Met Arg Ile Gly Lys Asp Met Gln Phe Phe
465                 470                 475                 480

Gly Ala Arg Cys Asn Leu Ala Lys Leu Met Leu Tyr Val Leu Asn His
                485                 490                 495

Gly Lys Asp Glu Arg Thr Gly Lys Gln Val Gly Pro Asp Phe Gly Pro
            500                 505                 510

Val Pro Glu Gly Pro Ile Pro Phe Asp Trp Met Trp Glu Thr Tyr Asp
        515                 520                 525
```

| | | | | | | | | | | | |
|---|---|---|---|---|---|---|---|---|---|---|---|
|Lys|Ala|Met|Asp|Trp|Ile|Ala|Lys|Leu|Tyr|Val|Asn|Thr|Met|Asn|Val|
| |530| | | |535| | | |540| | |
|Ile|His|Phe|Cys|His|Asp|Gln|Tyr|Cys|Tyr|Glu|Ser|Leu|Gln|Met|Ala|
|545| | | |550| | | |555| | | |560|
|Leu|His|Asp|Thr|Asp|Val|Arg|Arg|Leu|Met|Ala|Phe|Gly|Val|Ala|Gly|
| | | |565| | | |570| | | |575|
|Leu|Ser|Val|Val|Ala|Asp|Ser|Phe|Ser|Ala|Ile|Lys|Tyr|Ala|Lys|Val|
| | | |580| | | |585| | | |590|
|Thr|Pro|Ile|Arg|Asp|Pro|Lys|Thr|Gly|Leu|Thr|Val|Asp|Phe|Lys|Val|
| | |595| | | |600| | | |605|
|Glu|Gly|Glu|Phe|Pro|Lys|Phe|Gly|Asn|Asp|Asp|Arg|Val|Asp|Phe|
| |610| | | |615| | | |620|
|Phe|Ala|Arg|Thr|Val|Thr|Asp|Lys|Leu|Ile|Asn|Lys|Leu|Arg|Lys|Thr|
|625| | | |630| | | |635| | | |640|
|Pro|Thr|Tyr|Arg|Gly|Ala|Thr|His|Thr|Leu|Ser|Ile|Leu|Thr|Ile|Thr|
| | | |645| | | |650| | | |655|
|Ser|Asn|Val|Val|Tyr|Gly|Lys|Lys|Thr|Gly|Ser|Thr|Pro|Asp|Gly|Arg|
| | | |660| | | |665| | | |670|
|Lys|Ala|Gly|Gln|Pro|Phe|Ala|Pro|Gly|Cys|Asn|Pro|Met|His|Gly|Arg|
| | |675| | | |680| | | |685|
|Glu|Phe|Ser|Gly|Ala|Val|Ala|Ser|Leu|Ser|Ser|Val|Ala|Lys|Val|Asn|
| |690| | | |695| | | |700|
|Tyr|Asp|Ser|Cys|Met|Asp|Gly|Ile|Ser|Asn|Thr|Phe|Ser|Ile|Val|Pro|
|705| | | |710| | | |715| | | |720|
|Asn|Thr|Ile|Gly|Lys|Thr|Leu|Gln|Glu|Arg|Gln|Gly|Asn|Leu|Ser|Gly|
| | | |725| | | |730| | | |735|
|Leu|Leu|Asp|Gly|Tyr|Phe|Ser|Lys|Gly|Ala|His|His|Leu|Asn|Val|Asn|
| | | |740| | | |745| | | |750|
|Val|Leu|Lys|Arg|Glu|Thr|Leu|Glu|Asp|Ala|Met|Ala|His|Pro|Glu|Asn|
| | |755| | | |760| | | |765|
|Tyr|Pro|Asn|Leu|Thr|Ile|Arg|Val|Ser|Gly|Tyr|Ala|Val|Asn|Phe|Val|
| |770| | | |775| | | |780|
|Lys|Leu|Thr|Pro|Ala|Gln|Gln|Lys|Glu|Val|Ile|Ala|Arg|Thr|Phe|His|
|785| | | |790| | | |795| | | |800|
|Glu|Lys|Met|

```
<210> SEQ ID NO 81
<211> LENGTH: 2619
<212> TYPE: DNA
<213> ORGANISM: Clostridium phytofermentans

<400> SEQUENCE: 81
atgacgaaaa aagtggaatt acagacaact ggattagtag actctctcga agcattaaca    60
gcaaaattta gagagttaaa agaagcacaa gagctctttg ctacctacac tcaagagcaa   120
gtagataaaa tcttctttgc tgctgccatg gctgccaatc agcaacgtat tccgttagca   180
aagatggctg tagaagaaac gggtatgggt attgtagaag ataaagtaat taagaatcat   240
tatgctgcag agtatattta caatgcatac aaagatacaa aaacatgtgg agtggttgaa   300
gaagatccta gcttcggtat caaaaaaatt gcagagccaa tcggcgtagt tgcagctgta   360
atcccaacta ccaatcctac ctccactgct atctttaaaa cattactttg tttaaagact   420
cgtaacgcaa tcatcatcag cccacatcct cgtgctaaga actgtaccat cgcagctgct   480
aaggtagttt tagatgctgc agttgctgca ggtgctcctg ctggtataat tggatggatt   540
```

-continued

```
gatgttccat cacttgaatt aaccaatgaa gttatgaaaa atgcagacat catccttgca      600
actggtggac ctggtatggt aaaggctgct tattcttctg gtaaaccagc acttggtgtt      660
ggcgcaggta ataccoctgt tattatggat gaaagctgcg atgttcgcct tgcagtaagc      720
tctattattc actctaagac atttgataac ggtatgattt gtgcttccga gcaatccgta      780
attattagtg ataagattta tgaagctgct aagaaagaat tcaaggatcg tggttgccac      840
atctgctccc cagaagagac tcagaagctt cgtgaaacaa tcctaattaa tggtgctctt      900
aacgctaaaa ttgttggaca aagcgctcat acgattgcaa agcttgcagg atttgatgta      960
gcagaagctg ctaagatttt aattggtgaa gtagaatccg ttgaactaga agaacaattt     1020
gcacacgaga aactttctcc agttcttgct atgtacaaat caaatccctt tgatgatgca     1080
gtaagcaaag ctgctcgtct tgttgcagat ggcggttatg ccatacttc ttccatctat      1140 attaatgtag gtaccggaca agaaaagatt gcaaagtttt ctgatgctat gaagacttgc     1200
cgtattcttg taaatacacc atcctcccat ggtggtatcg gtgacccttta taactttaaa     1260 ttagctccat ctcttactct tggttgtggc tcctggggcg gtaactctgt atcagaaaac     1320
gtaggagtaa agcacttaat caacattaag acagttgctg agaggagaga aaacatgctt     1380
tggtttagag cacctgagaa agtatacttt aagaagggtt gtttaccagt agccctcgca     1440
gaattaaaag atgtaatgaa taaaagaaa gtattcattg taaccgatgc tttcctttat      1500
aaaaatggct atacaaaatg tgttactgat cagttagatg ctatgggaat tcagcatact     1560
acttactatg atgttgctcc agatccatct ttagctagtg ctacagaagg tgcagaagcg     1620
atgagactct tcgagccaga ctgtattatc gcactcggtg gtggttctgc aatggatgcc     1680
ggaaagatta tgtgggttat gtatgaacac cctgaagtaa acttccttga ccttgcaatg     1740
cgtttcatgg atattagaaa gcgtgtttac tccttcccta agatgggcga aaaagcttac     1800
tttatcgcag ttccaacttc ctccggtact ggttctgaag ttacaccatt tgctgttatt     1860
accgatgaga gaactggcgt aaaatatcca cttgcagatt acgaattact tcctaagatg     1920
gctattattg atgccgatat gatgatgaat caacctaagg gattaacttc tgcttccggt     1980
attgatgccc ttacccatgc attagaggca tatgcttcta tcatggctac tgactatacg     2040
gatggtttag cattaaaagc tatgaagaat atcttcgctt accttccaag cgcatatgaa     2100
aatggtgccg ctgatccggt tgcaagagaa aagatggcag atgcttctac cttagctggt     2160
atggcattcg caaatgcatt cttaggaatt tgccactcca tggctcataa attaggtgca     2220
ttccaccact taccacacgg tgtagcaaac gcactcttaa tcaacgaagt aatgcgcttt     2280
aactccgtta gcattcctac aaagatgggt actttctctc aataccaata cccacatgcg     2340
ttagatcgtt atgtagaatg tgcgaacttc ttaggtattg ccggaaagaa cgacaatgag     2400
aaattcgaaa accttcttaa ggcaattgat gaattaaaag aaaagttgg tatcaagaaa     2460 tccatcaaag aatatggcgt agacgagaaa tatttcttag atactttaga tgctatggtt     2520
gaacaggctt tcgatgatca gtgtactggt gctaacccaa gatatccatt aatgaaggaa     2580
atcaaggaaa tctatcttaa agtgtactac ggtaaataa                            2619
```

<210> SEQ ID NO 82
<211> LENGTH: 872
<212> TYPE: PRT
<213> ORGANISM: Clostridium phytofermentans

<400> SEQUENCE: 82

```
Met Thr Lys Lys Val Glu Leu Gln Thr Thr Gly Leu Val Asp Ser Leu
1               5                   10                  15

Glu Ala Leu Thr Ala Lys Phe Arg Glu Leu Lys Glu Ala Gln Glu Leu
            20                  25                  30

Phe Ala Thr Tyr Thr Gln Glu Gln Val Asp Lys Ile Phe Phe Ala Ala
                35                  40                  45

Ala Met Ala Ala Asn Gln Gln Arg Ile Pro Leu Ala Lys Met Ala Val
        50                  55                  60

Glu Glu Thr Gly Met Gly Ile Val Glu Asp Lys Val Ile Lys Asn His
65                  70                  75                  80

Tyr Ala Ala Glu Tyr Ile Tyr Asn Ala Tyr Lys Asp Thr Lys Thr Cys
                85                  90                  95

Gly Val Val Glu Glu Asp Pro Ser Phe Gly Ile Lys Lys Ile Ala Glu
                100                 105                 110

Pro Ile Gly Val Val Ala Ala Val Ile Pro Thr Thr Asn Pro Thr Ser
            115                 120                 125

Thr Ala Ile Phe Lys Thr Leu Leu Cys Leu Lys Thr Arg Asn Ala Ile
        130                 135                 140

Ile Ile Ser Pro His Pro Arg Ala Lys Asn Cys Thr Ile Ala Ala Ala
145                 150                 155                 160

Lys Val Val Leu Asp Ala Ala Val Ala Ala Gly Ala Pro Ala Gly Ile
                165                 170                 175

Ile Gly Trp Ile Asp Val Pro Ser Leu Glu Leu Thr Asn Glu Val Met
            180                 185                 190

Lys Asn Ala Asp Ile Ile Leu Ala Thr Gly Gly Pro Gly Met Val Lys
        195                 200                 205

Ala Ala Tyr Ser Ser Gly Lys Pro Ala Leu Gly Val Gly Ala Gly Asn
        210                 215                 220

Thr Pro Val Ile Met Asp Glu Ser Cys Asp Val Arg Leu Ala Val Ser
225                 230                 235                 240

Ser Ile Ile His Ser Lys Thr Phe Asp Asn Gly Met Ile Cys Ala Ser
                245                 250                 255

Glu Gln Ser Val Ile Ile Ser Asp Lys Ile Tyr Glu Ala Ala Lys Lys
            260                 265                 270

Glu Phe Lys Asp Arg Gly Cys His Ile Cys Ser Pro Glu Glu Thr Gln
        275                 280                 285

Lys Leu Arg Glu Thr Ile Leu Ile Asn Gly Ala Leu Asn Ala Lys Ile
        290                 295                 300

Val Gly Gln Ser Ala His Thr Ile Ala Lys Leu Ala Gly Phe Asp Val
305                 310                 315                 320

Ala Glu Ala Ala Lys Ile Leu Ile Gly Glu Val Glu Ser Val Glu Leu
                325                 330                 335

Glu Glu Gln Phe Ala His Glu Lys Leu Ser Pro Val Leu Ala Met Tyr
            340                 345                 350

Lys Ser Lys Ser Phe Asp Asp Ala Val Ser Lys Ala Ala Arg Leu Val
        355                 360                 365

Ala Asp Gly Gly Tyr Gly His Thr Ser Ser Ile Tyr Ile Asn Val Gly
        370                 375                 380

Thr Gly Gln Glu Lys Ile Ala Lys Phe Ser Asp Ala Met Lys Thr Cys
385                 390                 395                 400

Arg Ile Leu Val Asn Thr Pro Ser Ser His Gly Gly Ile Gly Asp Leu
                405                 410                 415

Tyr Asn Phe Lys Leu Ala Pro Ser Leu Thr Leu Gly Cys Gly Ser Trp
```

```
                420             425             430
        Gly Gly Asn Ser Val Ser Glu Asn Val Gly Val Lys His Leu Ile Asn
                    435             440             445
        Ile Lys Thr Val Ala Glu Arg Arg Glu Asn Met Leu Trp Phe Arg Ala
                450             455             460
        Pro Glu Lys Val Tyr Phe Lys Lys Gly Cys Leu Pro Val Ala Leu Ala
        465             470             475             480
        Glu Leu Lys Asp Val Met Asn Lys Lys Val Phe Ile Val Thr Asp
                        485             490             495
        Ala Phe Leu Tyr Lys Asn Gly Tyr Thr Lys Cys Val Thr Asp Gln Leu
                    500             505             510
        Asp Ala Met Gly Ile Gln His Thr Thr Tyr Tyr Asp Val Ala Pro Asp
                515             520             525
        Pro Ser Leu Ala Ser Ala Thr Glu Gly Ala Glu Ala Met Arg Leu Phe
            530             535             540
        Glu Pro Asp Cys Ile Ile Ala Leu Gly Gly Gly Ser Ala Met Asp Ala
        545             550             555             560
        Gly Lys Ile Met Trp Val Met Tyr Glu His Pro Glu Val Asn Phe Leu
                        565             570             575
        Asp Leu Ala Met Arg Phe Met Asp Ile Arg Lys Arg Val Tyr Ser Phe
                    580             585             590
        Pro Lys Met Gly Glu Lys Ala Tyr Phe Ile Ala Val Pro Thr Ser Ser
                595             600             605
        Gly Thr Gly Ser Glu Val Thr Pro Phe Ala Val Ile Thr Asp Glu Arg
            610             615             620
        Thr Gly Val Lys Tyr Pro Leu Ala Asp Tyr Glu Leu Leu Pro Lys Met
        625             630             635             640
        Ala Ile Ile Asp Ala Asp Met Met Met Asn Gln Pro Lys Gly Leu Thr
                        645             650             655
        Ser Ala Ser Gly Ile Asp Ala Leu Thr His Ala Leu Glu Ala Tyr Ala
                    660             665             670
        Ser Ile Met Ala Thr Asp Tyr Thr Asp Gly Leu Ala Leu Lys Ala Met
                675             680             685
        Lys Asn Ile Phe Ala Tyr Leu Pro Ser Ala Tyr Glu Asn Gly Ala Ala
            690             695             700
        Asp Pro Val Ala Arg Glu Lys Met Ala Asp Ala Ser Thr Leu Ala Gly
        705             710             715             720
        Met Ala Phe Ala Asn Ala Phe Leu Gly Ile Cys His Ser Met Ala His
                        725             730             735
        Lys Leu Gly Ala Phe His His Leu Pro His Gly Val Ala Asn Ala Leu
                    740             745             750
        Leu Ile Asn Glu Val Met Arg Phe Asn Ser Val Ser Ile Pro Thr Lys
                755             760             765
        Met Gly Thr Phe Ser Gln Tyr Gln Tyr Pro His Ala Leu Asp Arg Tyr
            770             775             780
        Val Glu Cys Ala Asn Phe Leu Gly Ile Ala Gly Lys Asn Asp Asn Glu
        785             790             795             800
        Lys Phe Glu Asn Leu Leu Lys Ala Ile Asp Glu Leu Lys Glu Lys Val
                        805             810             815
        Gly Ile Lys Lys Ser Ile Lys Glu Tyr Gly Val Asp Glu Lys Tyr Phe
                    820             825             830
        Leu Asp Thr Leu Asp Ala Met Val Glu Gln Ala Phe Asp Asp Gln Cys
                835             840             845
```

Thr Gly Ala Asn Pro Arg Tyr Pro Leu Met Lys Glu Ile Lys Glu Ile
    850                 855                 860

Tyr Leu Lys Val Tyr Tyr Gly Lys
865                 870

<210> SEQ ID NO 83
<211> LENGTH: 2676
<212> TYPE: DNA
<213> ORGANISM: Escherichia coli

<400> SEQUENCE: 83

| | | | | | |
|---|---|---|---|---|---|
| atggctgtta | ctaatgtcgc | tgaacttaac | gcactcgtag | agcgtgtaaa | aaaagcccag | 60 |
| cgtgaatatg | ccagtttcac | tcaagagcaa | gtagacaaaa | tcttccgcgc | cgccgctctg | 120 |
| gctgctgcag | atgctcgaat | cccactcgcg | aaaatggccg | ttgccgaatc | cggcatgggt | 180 |
| atcgtcgaag | ataaagtgat | caaaaaccac | tttgcttctg | aatatatcta | caacgcctat | 240 |
| aaagatgaaa | aaacctgtgg | tgttctgtct | gaagacgaca | cttttggtac | catcactatc | 300 |
| gctgaaccaa | tcggtattat | ttgcggtatc | gttccgacca | ctaacccgac | ttcaactgct | 360 |
| atcttcaaat | cgctgatcag | tctgaagacc | cgtaacgcca | ttatcttctc | cccgcacccg | 420 |
| cgtgcaaaag | atgccaccaa | caaagcggct | gatatcgttc | tgcaggctgc | tatcgctgcc | 480 |
| ggtgctccga | agatctgatc | ggctggatc | gatcaacctt | ctgttgaact | gtctaacgca | 540 |
| ctgatgcacc | acccagacat | caacctgatc | ctcgcgactg | gtggtccggg | catggttaaa | 600 |
| gccgcataca | gctccggtaa | accagctatc | ggtgtaggcg | cgggcaacac | tccagttgtt | 660 |
| atcgatgaaa | ctgctgatat | caaacgtgca | gttgcatctg | tactgatgtc | caaaaccttc | 720 |
| gacaacggcg | taatctgtgc | ttctgaacag | tctgttgttg | ttgttgactc | tgtttatgac | 780 |
| gctgtacgtg | aacgttttgc | aacccacggc | ggctatctgt | gcagggtaa | agagctgaaa | 840 |
| gctgttcagg | atgttatcct | gaaaaacggt | gcgctgaacg | cggctatcgt | tggtcagcca | 900 |
| gcctataaaa | ttgctgaact | ggcaggcttc | tctgtaccag | aaaacaccaa | gattctgatc | 960 |
| ggtgaagtga | ccgttgttga | tgaaagcgaa | ccgttcgcac | atgaaaaact | gtcccccgact | 1020 |
| ctggcaatgt | accgcgctaa | agatttcgaa | gacgcggtag | aaaaagcaga | gaaactggtt | 1080 |
| gctatgggcg | gtatcggtca | tacctcttgc | ctgtacactg | accaggataa | ccaaccggct | 1140 |
| cgcgtttctt | acttcggtca | gaaaatgaaa | acggcgcgta | tcctgattaa | caccccagcg | 1200 |
| tctcagggtg | gtatcggtga | cctgtataac | ttcaaactcg | caccttccct | gactctgggt | 1260 |
| tgtggttctt | ggggtggtaa | ctccatctct | gaaaacgttg | gtccgaaaca | cctgatcaac | 1320 |
| aagaaaaccg | ttgctaagcg | agctgaaaac | atgttgtggc | acaaacttcc | gaaatctatc | 1380 |
| tacttccgcc | gtggctccct | gccaatccgc | ctggatgaag | tgattactga | tggccacaaa | 1440 |
| cgtgcgctca | tcgtgactga | ccgcttcctg | ttcaacaatg | ttatgctga | tcagatcact | 1500 |
| tccgtactga | aagcagcagg | cgttgaaact | gaagtcttct | cgaagtaga | agcggacccg | 1560 |
| accctgagca | tcgttcgtaa | aggtgcagaa | ctggcaaact | ccttcaaacc | agacgtgatt | 1620 |
| atcgcgctgg | gtggtggttc | cccgatggac | gccgcgaaga | tcatgtgggt | tatgtacgaa | 1680 |
| catccggaaa | ctcacttcga | agagctggcg | ctgcgcttta | tggatatccg | taaacgtatc | 1740 |
| tacaagttcc | cgaaaatggg | cgtgaaagcg | aaaatgatcg | ctgtcaccac | cacttctggt | 1800 |
| acaggttctg | aagtcactcc | gtttgcggtt | gtaactgacg | acgctactgg | tcagaaatat | 1860 |
| ccgctggcag | actatgcgct | gactccggat | atggcgattg | tcgacgccaa | cctggttatg | 1920 |

```
gacatgccga agtccctgtg tgctttcggt ggtctggacg cagtaactca cgccatggaa      1980
gcttatgttt ctgtactggc atctgagttc tctgatggtc aggctctgca ggcactgaaa      2040
ctgctgaaag aatatctgcc agcgtcctac cacgaagggt ctaaaaatcc ggtagcgcgt      2100
gaacgtgttc acagtgcagc gactatcgcg ggtatcgcgt ttgcgaacgc cttcctgggt      2160
gtatgtcact caatggcgca caaactgggt tcccagttcc atattccgca cggtctggca      2220
aacgccctgc tgatttgtaa cgttattcgc tacaatgcga acgacaaccc gaccaagcag      2280
actgcattca gccagtatga ccgtccgcag gctcgccgtc gttatgctga aattgccgac      2340
cacttgggtc tgagcgcacc gggcgaccgt actgctgcta agatcgagaa actgctggca      2400
tggctggaaa cgctgaaagc tgaactgggt attccgaaat ctatccgtga agctggcgtt      2460
caggaagcag acttcctggc gaacgtggat aaactgtctg aagatgcatt cgatgaccag      2520
tgcaccggcg ctaacccgcg ttacccgctg atctccgagc tgaaacagat tctgctggat      2580
acctactacg tcgtgatta tgtagaaggt gaaactgcag cgaagaaaga agctgctccg      2640
gctaaagctg agaaaaaagc gaaaaaatcc gcttaa                               2676
```

<210> SEQ ID NO 84
<211> LENGTH: 891
<212> TYPE: PRT
<213> ORGANISM: Escherichia coli

<400> SEQUENCE: 84

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240
```

```
Asp Asn Gly Val Ile Cys Ala Ser Glu Gln Ser Val Val Val Asp
            245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
            275                 280                 285

Asn Gly Ala Leu Asn Ala Ala Ile Val Gly Gln Pro Ala Tyr Lys Ile
            290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
            325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
            355                 360                 365

Ser Cys Leu Tyr Thr Asp Gln Asp Asn Gln Pro Ala Arg Val Ser Tyr
            370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
            405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
            435                 440                 445

Glu Asn Met Leu Trp His Lys Leu Pro Lys Ser Ile Tyr Phe Arg Arg
            450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
            485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
            565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
            645                 650                 655

His Ala Met Glu Ala Tyr Val Ser Val Leu Ala Ser Glu Phe Ser Asp
```

```
                660               665               670
Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
        690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 85
<211> LENGTH: 2865
<212> TYPE: DNA
<213> ORGANISM: Chlamydomonas reinhardtii
<220> FEATURE:
<221> NAME/KEY: misc_feature
<223> OTHER INFORMATION: AdhE

<400> SEQUENCE: 85
atgatgtcct ccagcctcgt ctctggcaag agggttgccg tgccctctgc tgccaagccc    60
tgtgctgctg tgccgctgcc ccgcgtggcc ggtcgccgga ctgctgcacg cgttgtctgc   120
gaggctgctc cctctggcgc cgcccctgcc agccccaagg ctgaggctgc tgcgcccgtt   180
gccgctgccc cggccacccc ccatgctgag gtgaagaagg agcgcgcccc agccaccgat   240
gaggcgctga cggagctgaa ggcgctgctg aagcgcgccc agaccgccca ggcgcagtac   300
tccacctaca cccaggagca ggtggacgag atcttccgcg ccgccgccga ggccgccaac   360 gccgccgta tccccctggc caagatggcc gtggaggaga cccgcatggg cgtggctgag   420
gacaaggtgg tgaagaacca cttcgcctcc gagttcatct acaacaagta caagcacact   480
aagacctgcg gcgtcatcga gcacgacccc gccggcggca tccagaaggt ggctgagccc   540
gtgggcgtca ttgccggtat cgtgcccacc accaacccca cctccaccgc catcttcaag   600
tcgctgctgt cgctcaagac ccgcaacgcg ctggtgctgt gccgcacccc cgccgccgcc   660
aagagcacca tcgccgccgc gcgcatcgtg cgtgacgccg ccgtggccgc cggcgcgccg   720
```

| | |
|---|---|
| cccaacatca tcagctgggt ggagacgccc tcgctgccgg tgtcccaggc gctgatgcag | 780 |
| gcgactgaga tcaacctcat cctggccacc ggtggcccgg ccatggtgcg cgccgcctac | 840 |
| tcgtccggca acccgtcgct gggtgtgggc gccggcaaca ccccggccct gattgacgag | 900 |
| actgccgacg tggccatggc cgtgtcctcc atcctgctgt ccaagacctt tgacaacggc | 960 |
| gtcatctgcg cctcggagca gtcggtggtg gtggtggcca aggcctacga cgccgtgcgc | 1020 |
| accgagttcg tgcgccgcgg ggcctacttc ctgaccgagg acgacaaggt caaggtccgc | 1080 |
| gccggtgtgg ttgtggacgg caagctgaac cccaacattg tgggccagtc catccccaag | 1140 |
| ctggcggccc tgttcggcat caaggtgccc cagggcacca aggtgctcat cggcgaggtg | 1200 |
| gagaagatcg cccccgagga ggcgctgtcg caggagaagc tgtgccccat cctggccatg | 1260 |
| taccgggcgc ccgactacga ccacggcgtc aagatggcct gcgagctcat catgtacggc | 1320 |
| ggcgccggcc acacctcggt gctgtacacc aacccgctca caacgccca catccagcag | 1380 |
| taccagagcg cggtcaagac cgtgcgcatc ctcatcaaca cccccgcctc gcagggcgcc | 1440 |
| attggtgacc tgtacaactt ccacctggac ccctccctca ccctgggctg cggcacctgg | 1500 |
| ggctccacct cggtgtccac caacgtgggc ccgcagcacc tgctgaacat caagaccgtc | 1560 |
| accgcgcgcc gcgagaacat gctgtggttc cgcgtgccgc ccaagatcta cttcaagggc | 1620 |
| ggctgcctgg aggtgcgct gaccgatctg cgtggcaaat cgcgcgcttt cattgtcacg | 1680 |
| gacaagccgc ttttgacat gggatacgcc gacaaggtca cccacatcct ggacagcatt | 1740 |
| aacgtgcacc accaggtgtt ctaccacgtg acccccgacc cgaccctggc ctgcattgag | 1800 |
| gcgggtctga aggagatcct ggagttcaag cccgatgtca tcatcgcgct gggtggtggc | 1860 |
| tcgcccatgg acgccgccaa gatcatgtgg ctgatgtacg agtgccccga cacccgcttc | 1920 |
| gacggcctgg ccatgcgctt catggacatc cgcaagcgcg tgtacgaggt gccggagctg | 1980 |
| ggcaagaagg ccaccatggt gtgcatcccc accaccagtg gcaccggctc ggaggtgacg | 2040 |
| cccttctcgg tggtcaccga cgagcgcctg ggcgccaagt accccctggc cgattacgcc | 2100 |
| ctgaccccca gcatggccat tgtggacccc cagctggtgc tcaacatgcc caagaagctg | 2160 |
| accgcctggg gcggcattga cgcgctcacg cacgcgctgg agagctacgt gtccatctgc | 2220 |
| gccaccgact acaccaaggg tctgtcgcgc gaggccatca gcctgctgtt caagtacctg | 2280 |
| ccccgcgcct acgccaacgg ctccaacgac tacctggcgc gtgagaaggt gcactacgcc | 2340 |
| gccacgattg ccggcatggc cttcgccaac gccttcctgg gcatctgcca ctccatggcg | 2400 |
| cacaagctgg gcgccgccta ccacgtgcct cacggcctgg ccaacgccgc gctgatcagc | 2460 |
| cacgtcatcc gctacaacgc caccgacatg cccgccaagc aggccgcctt cccgcagtac | 2520 |
| gagtacccca ccgccaagca ggactacgcc gacctggcca catgctgggg cctgggcggc | 2580 |
| aacacggtgg acgagaaggt gatcaagctg attgaggcgg tggaggagct caaggccaag | 2640 |
| gtggacatcc cgcccaccat caaggagatc ttcaacgacc ccaaggtgga cgccgacttc | 2700 |
| ctggcgaacg tggacgccct ggccgaggac gccttcgacg accagtgcac gggcgccaac | 2760 |
| ccgcgctacc cgctcatggc cgacctgaag cagctctacc tggacgccca cgccgcgccc | 2820 |
| atcctgcccg tcaagaccct ggagttcttc tccaagatca actaa | 2865 |

<210> SEQ ID NO 86
<211> LENGTH: 954
<212> TYPE: PRT
<213> ORGANISM: Chlamydomonas reinhardtii
<220> FEATURE:
<221> NAME/KEY: MISC_FEATURE
<223> OTHER INFORMATION: AdhE

<400> SEQUENCE: 86

| | | | | | | | | | | | | | | |
|---|---|---|---|---|---|---|---|---|---|---|---|---|---|---|
| Met | Met | Ser | Ser | Ser | Leu | Val | Ser | Gly | Lys | Arg | Val | Ala | Val | Pro | Ser |
| 1 | | | | 5 | | | | | 10 | | | | | 15 | |
| Ala | Ala | Lys | Pro | Cys | Ala | Ala | Val | Pro | Leu | Pro | Arg | Val | Ala | Gly | Arg |
| | | | 20 | | | | | 25 | | | | | 30 | | |
| Arg | Thr | Ala | Ala | Arg | Val | Val | Cys | Glu | Ala | Ala | Pro | Ser | Gly | Ala | Ala |
| | | 35 | | | | | 40 | | | | | 45 | | | |
| Pro | Ala | Ser | Pro | Lys | Ala | Glu | Ala | Ala | Pro | Val | Ala | Ala | Ala | Pro | |
| | 50 | | | | | 55 | | | | | 60 | | | | |
| Ala | Thr | Pro | His | Ala | Glu | Val | Lys | Lys | Glu | Arg | Ala | Pro | Ala | Thr | Asp |
| 65 | | | | | 70 | | | | | 75 | | | | | 80 |
| Glu | Ala | Leu | Thr | Glu | Leu | Lys | Ala | Leu | Leu | Lys | Arg | Ala | Gln | Thr | Ala |
| | | | | 85 | | | | | 90 | | | | | 95 | |
| Gln | Ala | Gln | Tyr | Ser | Thr | Tyr | Thr | Gln | Glu | Gln | Val | Asp | Glu | Ile | Phe |
| | | | | 100 | | | | | 105 | | | | | 110 | |
| Arg | Ala | Ala | Glu | Ala | Ala | Asn | Ala | Ala | Arg | Ile | Pro | Leu | Ala | Lys | |
| | | | 115 | | | | | 120 | | | | | 125 | | |
| Met | Ala | Val | Glu | Glu | Thr | Arg | Met | Gly | Val | Ala | Glu | Asp | Lys | Val | Val |
| 130 | | | | | 135 | | | | | 140 | | | | | |
| Lys | Asn | His | Phe | Ala | Ser | Glu | Phe | Ile | Tyr | Asn | Lys | Tyr | Lys | His | Thr |
| 145 | | | | | 150 | | | | | 155 | | | | | 160 |
| Lys | Thr | Cys | Gly | Val | Ile | Glu | His | Asp | Pro | Ala | Gly | Gly | Ile | Gln | Lys |
| | | | | 165 | | | | | 170 | | | | | 175 | |
| Val | Ala | Glu | Pro | Val | Gly | Val | Ile | Ala | Gly | Ile | Val | Pro | Thr | Thr | Asn |
| | | | 180 | | | | | 185 | | | | | 190 | | |
| Pro | Thr | Ser | Thr | Ala | Ile | Phe | Lys | Ser | Leu | Leu | Ser | Leu | Lys | Thr | Arg |
| | | | 195 | | | | | 200 | | | | | 205 | | |
| Asn | Ala | Leu | Val | Leu | Cys | Pro | His | Pro | Arg | Ala | Lys | Ser | Thr | Ile | |
| | 210 | | | | | 215 | | | | | 220 | | | | |
| Ala | Ala | Ala | Arg | Ile | Val | Arg | Asp | Ala | Ala | Val | Ala | Ala | Gly | Ala | Pro |
| 225 | | | | | 230 | | | | | 235 | | | | | 240 |
| Pro | Asn | Ile | Ile | Ser | Trp | Val | Glu | Thr | Pro | Ser | Leu | Pro | Val | Ser | Gln |
| | | | | 245 | | | | | 250 | | | | | 255 | |
| Ala | Leu | Met | Gln | Ala | Thr | Glu | Ile | Asn | Leu | Ile | Leu | Ala | Thr | Gly | Gly |
| | | | 260 | | | | | 265 | | | | | 270 | | |
| Pro | Ala | Met | Val | Arg | Ala | Ala | Tyr | Ser | Ser | Gly | Asn | Pro | Ser | Leu | Gly |
| | | 275 | | | | | 280 | | | | | 285 | | | |
| Val | Gly | Ala | Gly | Asn | Thr | Pro | Ala | Leu | Ile | Asp | Glu | Thr | Ala | Asp | Val |
| | 290 | | | | | 295 | | | | | 300 | | | | |
| Ala | Met | Ala | Val | Ser | Ser | Ile | Leu | Leu | Ser | Lys | Thr | Phe | Asp | Asn | Gly |
| 305 | | | | | 310 | | | | | 315 | | | | | 320 |
| Val | Ile | Cys | Ala | Ser | Glu | Gln | Ser | Val | Val | Val | Ala | Lys | Ala | Tyr | |
| | | | | 325 | | | | | 330 | | | | | 335 | |
| Asp | Ala | Val | Arg | Thr | Glu | Phe | Val | Arg | Arg | Gly | Ala | Tyr | Phe | Leu | Thr |
| | | | 340 | | | | | 345 | | | | | 350 | | |
| Glu | Asp | Asp | Lys | Val | Lys | Val | Arg | Ala | Gly | Val | Val | Asp | Gly | Lys | |
| | | | 355 | | | | | 360 | | | | | 365 | | |
| Leu | Asn | Pro | Asn | Ile | Val | Gly | Gln | Ser | Ile | Pro | Lys | Leu | Ala | Ala | Leu |
| | 370 | | | | | 375 | | | | | 380 | | | | |
| Phe | Gly | Ile | Lys | Val | Pro | Gln | Gly | Thr | Lys | Val | Leu | Ile | Gly | Glu | Val |
| 385 | | | | | 390 | | | | | 395 | | | | | 400 |

-continued

```
Glu Lys Ile Gly Pro Glu Ala Leu Ser Gln Glu Lys Leu Cys Pro
                405                 410                 415
Ile Leu Ala Met Tyr Arg Ala Pro Asp Tyr Asp His Gly Val Lys Met
        420                 425                 430
Ala Cys Glu Leu Ile Met Tyr Gly Gly Ala Gly His Thr Ser Val Leu
        435                 440                 445
Tyr Thr Asn Pro Leu Asn Asn Ala His Ile Gln Gln Tyr Gln Ser Ala
    450                 455                 460
Val Lys Thr Val Arg Ile Leu Ile Asn Thr Pro Ala Ser Gln Gly Ala
465                 470                 475                 480
Ile Gly Asp Leu Tyr Asn Phe His Leu Asp Pro Ser Leu Thr Leu Gly
                485                 490                 495
Cys Gly Thr Trp Gly Ser Thr Ser Val Ser Thr Asn Val Gly Pro Gln
                500                 505                 510
His Leu Leu Asn Ile Lys Thr Val Thr Ala Arg Arg Glu Asn Met Leu
            515                 520                 525
Trp Phe Arg Val Pro Pro Lys Ile Tyr Phe Lys Gly Gly Cys Leu Glu
        530                 535                 540
Val Ala Leu Thr Asp Leu Arg Gly Lys Ser Arg Ala Phe Ile Val Thr
545                 550                 555                 560
Asp Lys Pro Leu Phe Asp Met Gly Tyr Ala Asp Lys Val Thr His Ile
                565                 570                 575
Leu Asp Ser Ile Asn Val His His Gln Val Phe Tyr His Val Thr Pro
                580                 585                 590
Asp Pro Thr Leu Ala Cys Ile Glu Ala Gly Leu Lys Glu Ile Leu Glu
            595                 600                 605
Phe Lys Pro Asp Val Ile Ile Ala Leu Gly Gly Gly Ser Pro Met Asp
        610                 615                 620
Ala Ala Lys Ile Met Trp Leu Met Tyr Glu Cys Pro Asp Thr Arg Phe
625                 630                 635                 640
Asp Gly Leu Ala Met Arg Phe Met Asp Ile Arg Lys Arg Val Tyr Glu
                645                 650                 655
Val Pro Glu Leu Gly Lys Lys Ala Thr Met Val Cys Ile Pro Thr Thr
            660                 665                 670
Ser Gly Thr Gly Ser Glu Val Thr Pro Phe Ser Val Val Thr Asp Glu
        675                 680                 685
Arg Leu Gly Ala Lys Tyr Pro Leu Ala Asp Tyr Ala Leu Thr Pro Ser
690                 695                 700
Met Ala Ile Val Asp Pro Gln Leu Val Leu Asn Met Pro Lys Lys Leu
705                 710                 715                 720
Thr Ala Trp Gly Gly Ile Asp Ala Leu Thr His Ala Leu Glu Ser Tyr
                725                 730                 735
Val Ser Ile Cys Ala Thr Asp Tyr Thr Lys Gly Leu Ser Arg Glu Ala
            740                 745                 750
Ile Ser Leu Leu Phe Lys Tyr Leu Pro Arg Ala Tyr Ala Asn Gly Ser
        755                 760                 765
Asn Asp Tyr Leu Ala Arg Glu Lys Val His Tyr Ala Ala Thr Ile Ala
    770                 775                 780
Gly Met Ala Phe Ala Asn Ala Phe Leu Gly Ile Cys His Ser Met Ala
785                 790                 795                 800
His Lys Leu Gly Ala Ala Tyr His Val Pro His Gly Leu Ala Asn Ala
                805                 810                 815
Ala Leu Ile Ser His Val Ile Arg Tyr Asn Ala Thr Asp Met Pro Ala
```

```
                820             825             830
Lys Gln Ala Ala Phe Pro Gln Tyr Glu Tyr Pro Thr Ala Lys Gln Asp
            835                 840                 845
Tyr Ala Asp Leu Ala Asn Met Leu Gly Leu Gly Gly Asn Thr Val Asp
            850                 855                 860
Glu Lys Val Ile Lys Leu Ile Glu Ala Val Glu Leu Lys Ala Lys
865                 870                 875                 880
Val Asp Ile Pro Pro Thr Ile Lys Glu Ile Phe Asn Asp Pro Lys Val
                885                 890                 895
Asp Ala Asp Phe Leu Ala Asn Val Asp Ala Leu Ala Glu Asp Ala Phe
            900                 905                 910
Asp Asp Gln Cys Thr Gly Ala Asn Pro Arg Tyr Pro Leu Met Ala Asp
            915                 920                 925
Leu Lys Gln Leu Tyr Leu Asp Ala His Ala Ala Pro Ile Leu Pro Val
            930                 935                 940
Lys Thr Leu Glu Phe Phe Ser Lys Ile Asn
945                 950

<210> SEQ ID NO 87
<211> LENGTH: 2658
<212> TYPE: DNA
<213> ORGANISM: Piromyces sp. E2

<400> SEQUENCE: 87
atgtccggat tacaaatgtt ccaaaacctt tctctttacg gtagtctcgc cgaaatcgat      60
actagcgaaa agcttaacga agctatggac aaattaactg ctgcccaaga caattcaga     120
gaatacaacc aagaacaagt tgacaaaatc ttcaaggctg ttgctttagc tgcttctcaa     180
aaccgtgttg ctttcgctaa gtacgcacac gaagaaaccc aaaagggtgt tttcgaagat     240
aaggttatca agaacgaatt cgctgctgat tacatttacc acaagtactg caatgacaag     300
accgccggta tcattgaata tgatgaagcc aatggtctta tggaaattgc tgaaccagtt     360
ggtccagttg ttggtattgc tccagttact aacccaactt ctactatcat ctacaagtct     420
ttaattgcct taaagacccg taactgtatt atcttctcac acatccagg agctcacaag     480
gcctctgttt tcgttgttaa ggtcttacac aagctgctg ttaaggctgg tgccccagaa     540
aactgtattc aaatcatctt cccaaagatg gatttaacta ctgaattatt acaccaccaa     600
aagactcgtt tcatttgggc tactggtggt ccaggtttag ttcacgcctc ttacacttct     660
ggtaagccag ctcttggtgg tggtccaggt aatgctccag ctcttattga tgaaacttgt     720
gatatgaacg aagctgttgg ttctatcgtt gtttctaaga ctttcgattg tggtatgatc     780
tgtgccactg aaaacgctgt tgtcgttgtc aatctgtct acgaaaactt cgttgctacc     840
atgaagaagc gtggtgccta cttcatgact ccagaagaaa ccaagaaggc ttctaacctt     900
cttttcggag aaggtatgag attaaatgct aaggctgttg gtcaaactgc caagactta     960
gctgaaatgg ccggtttcga agtcccagaa acaccgttg ttctctgtgg tgaagcttct    1020
gaagttaaat tcgaagaacc aatggctcac gaaaagttaa ctactatcct cggtatctac    1080
aaggctaagg actttgacga tgtgtcaga ttatgtaagg aattagttac tttcggtggt    1140
aagggtcaca ctgctgttct ctacaccaac caaaacaaca aggaccgtat tgaaaagtac    1200
caaaacgaag ttccagcctt ccacatctta gttgacatgc catcttccct cggttgtatt    1260
ggtgatatgt acaacttccg tcttgctcca gctcttacca ttacttgtgg tactatgggt    1320
ggtggttcct cctctgataa cattggtcca aagcacttac ttaacatcaa gcgtgttggt    1380
```

```
atgagacgcg aaaacatgct ttggttcaag attccaaagt ctgtctactt caagcgtgct    1440
atcctttctg aagctttatc tgacttacgt gacacccaca agcgtgctat cattattacc    1500
gatagaacta tgactatgtt aggtcaaact gacaagatca ttaaggcttg tgaaggtcat    1560
ggtatggtct gcactgtcta cgataaggtt gtcccagatc caactatcaa gtgtattatg    1620
gaaggtgtta atgaaatgaa cgtcttcaag ccagatttag ctattgctct tggtggtggt    1680
tctgctatgg atgccgctaa gatgatgcgt ttattctacg aatacccaga ccaagactta    1740
caagatattg ctactcgttt cgtcgatatc cgtaagcgtg ttgttggttg tccaaagctt    1800
ggtagactta ttaagactct tgtctgtatc ccaactacct ctggtactgg tgccgaagtt    1860
actccattcg ctgtcgttac ctctgaagaa ggtcgtaagt acccattagt cgactacgaa    1920
cttactccag atatggctat tgttgatcca gaattcgctg ttggtatgcc aaagcgttta    1980
acttcttgga ctggtattga tgctcttacc cacgccattg aatcttacgt ttctattatg    2040
gctactgact tcactagacc atactctctc cgtgctgttg gtcttatctt cgaatccctt    2100
tcccttgctt acaacaacgg taaggatatt gaagctcgtg aaaagatgca caatgcttct    2160
gctattgctg gtatggcctt tgccaacgct ttccttggtt gttgtcactc tgttgctcac    2220
caacttggtt ccgtctacca cattccacac ggtcttgcca acgctttaat gctttctcac    2280
atcattaagt acaacgctac tgactctcca gttaagatgg gtaccttccc acaatacaag    2340
tacccacaag ctatgcgtca ctacgctgaa attgctgaac tcttattacc accaactcaa    2400
gttgttaaga tgactgatgt tgataaggtt caatacttaa ttgaccgtgt tgaacaatta    2460
aaggctgacg ttggtattcc aaagtctatt aaggaaactg gaatggttac tgaagaagac    2520
ttcttcaaca aggttgacca agttgctatc atggccttcg atgaccaatg tactggtgct    2580
aacccacgtt acccattagt ttctgaatta aaacaattaa tgattgatgc ctggaacggt    2640
gttgtcccaa agctctaa                                                  2658
```

<210> SEQ ID NO 88
<211> LENGTH: 885
<212> TYPE: PRT
<213> ORGANISM: Piromyces sp. E2

<400> SEQUENCE: 88

```
Met Ser Gly Leu Gln Met Phe Gln Asn Leu Ser Leu Tyr Gly Ser Leu
1               5                   10                  15

Ala Glu Ile Asp Thr Ser Glu Lys Leu Asn Glu Ala Met Asp Lys Leu
            20                  25                  30

Thr Ala Ala Gln Glu Gln Phe Arg Glu Tyr Asn Gln Glu Gln Val Asp
        35                  40                  45

Lys Ile Phe Lys Ala Val Ala Leu Ala Ala Ser Gln Asn Arg Val Ala
    50                  55                  60

Phe Ala Lys Tyr Ala His Glu Glu Thr Gln Lys Gly Val Phe Glu Asp
65                  70                  75                  80

Lys Val Ile Lys Asn Glu Phe Ala Ala Asp Tyr Ile Tyr His Lys Tyr
                85                  90                  95

Cys Asn Asp Lys Thr Ala Gly Ile Ile Glu Tyr Asp Glu Ala Asn Gly
            100                 105                 110

Leu Met Glu Ile Ala Glu Pro Val Gly Pro Val Val Gly Ile Ala Pro
        115                 120                 125

Val Thr Asn Pro Thr Ser Thr Ile Ile Tyr Lys Ser Leu Ile Ala Leu
    130                 135                 140
```

```
Lys Thr Arg Asn Cys Ile Ile Phe Ser Pro His Pro Gly Ala His Lys
145                 150                 155                 160

Ala Ser Val Phe Val Lys Val Leu His Gln Ala Ala Val Lys Ala
            165                 170                 175

Gly Ala Pro Glu Asn Cys Ile Gln Ile Ile Phe Pro Lys Met Asp Leu
            180                 185                 190

Thr Thr Glu Leu Leu His His Gln Lys Thr Arg Phe Ile Trp Ala Thr
            195                 200                 205

Gly Gly Pro Gly Leu Val His Ala Ser Tyr Thr Ser Gly Lys Pro Ala
            210                 215                 220

Leu Gly Gly Gly Pro Gly Asn Ala Pro Ala Leu Ile Asp Glu Thr Cys
225                 230                 235                 240

Asp Met Asn Glu Ala Val Gly Ser Ile Val Val Ser Lys Thr Phe Asp
                245                 250                 255

Cys Gly Met Ile Cys Ala Thr Glu Asn Ala Val Val Val Glu Ser
                260                 265                 270

Val Tyr Glu Asn Phe Val Ala Thr Met Lys Lys Arg Gly Ala Tyr Phe
            275                 280                 285

Met Thr Pro Glu Glu Thr Lys Lys Ala Ser Asn Leu Leu Phe Gly Glu
            290                 295                 300

Gly Met Arg Leu Asn Ala Lys Ala Val Gly Gln Thr Ala Lys Thr Leu
305                 310                 315                 320

Ala Glu Met Ala Gly Phe Glu Val Pro Glu Asn Thr Val Leu Cys
                325                 330                 335

Gly Glu Ala Ser Glu Val Lys Phe Glu Pro Met Ala His Glu Lys
                340                 345                 350

Leu Thr Thr Ile Leu Gly Ile Tyr Lys Ala Lys Asp Phe Asp Asp Gly
            355                 360                 365

Val Arg Leu Cys Lys Glu Leu Val Thr Phe Gly Gly Lys Gly His Thr
            370                 375                 380

Ala Val Leu Tyr Thr Asn Gln Asn Asn Lys Asp Arg Ile Glu Lys Tyr
385                 390                 395                 400

Gln Asn Glu Val Pro Ala Phe His Ile Leu Val Asp Met Pro Ser Ser
                405                 410                 415

Leu Gly Cys Ile Gly Asp Met Tyr Asn Phe Arg Leu Ala Pro Ala Leu
                420                 425                 430

Thr Ile Thr Cys Gly Thr Met Gly Gly Ser Ser Asp Asn Ile
            435                 440                 445

Gly Pro Lys His Leu Leu Asn Ile Lys Arg Val Gly Met Arg Arg Glu
            450                 455                 460

Asn Met Leu Trp Phe Lys Ile Pro Lys Ser Val Tyr Phe Lys Arg Ala
465                 470                 475                 480

Ile Leu Ser Glu Ala Leu Ser Asp Leu Arg Asp Thr His Lys Arg Ala
                485                 490                 495

Ile Ile Ile Thr Asp Arg Thr Met Thr Met Leu Gly Gln Thr Asp Lys
            500                 505                 510

Ile Ile Lys Ala Cys Glu Gly His Gly Met Val Cys Thr Val Tyr Asp
            515                 520                 525

Lys Val Val Pro Asp Pro Thr Ile Lys Cys Ile Met Glu Gly Val Asn
            530                 535                 540

Glu Met Asn Val Phe Lys Pro Asp Leu Ala Ile Ala Leu Gly Gly Gly
545                 550                 555                 560
```

| | | | | | | | | | | | |
|---|---|---|---|---|---|---|---|---|---|---|---|
|Ser|Ala|Met|Asp|Ala|Ala|Lys|Met|Met|Arg|Leu|Phe|Tyr|Glu|Tyr|Pro|
| | | |565| | | |570| | | |575|
|Asp|Gln|Asp|Leu|Gln|Asp|Ile|Ala|Thr|Arg|Phe|Val|Asp|Ile|Arg|Lys|
| | | |580| | | |585| | | |590|
|Arg|Val|Val|Gly|Cys|Pro|Lys|Leu|Gly|Arg|Leu|Ile|Lys|Thr|Leu|Val|
| | | |595| | | |600| | | |605|
|Cys|Ile|Pro|Thr|Thr|Ser|Gly|Thr|Gly|Ala|Glu|Val|Thr|Pro|Phe|Ala|
| | |610| | | |615| | | |620|
|Val|Val|Thr|Ser|Glu|Glu|Gly|Arg|Lys|Tyr|Pro|Leu|Val|Asp|Tyr|Glu|
|625| | | |630| | | |635| | | |640|
|Leu|Thr|Pro|Asp|Met|Ala|Ile|Val|Asp|Pro|Glu|Phe|Ala|Val|Gly|Met|
| | | |645| | | |650| | | |655|
|Pro|Lys|Arg|Leu|Thr|Ser|Trp|Thr|Gly|Ile|Asp|Ala|Leu|Thr|His|Ala|
| | | |660| | | |665| | | |670|
|Ile|Glu|Ser|Tyr|Val|Ser|Ile|Met|Ala|Thr|Asp|Phe|Thr|Arg|Pro|Tyr|
| | | |675| | | |680| | | |685|
|Ser|Leu|Arg|Ala|Val|Gly|Leu|Ile|Phe|Glu|Ser|Leu|Ser|Leu|Ala|Tyr|
| | |690| | | |695| | | |700|
|Asn|Asn|Gly|Lys|Asp|Ile|Glu|Ala|Arg|Glu|Lys|Met|His|Asn|Ala|Ser|
|705| | | |710| | | |715| | | |720|
|Ala|Ile|Ala|Gly|Met|Ala|Phe|Ala|Asn|Ala|Phe|Leu|Gly|Cys|Cys|His|
| | | |725| | | |730| | | |735|
|Ser|Val|Ala|His|Gln|Leu|Gly|Ser|Val|Tyr|His|Ile|Pro|His|Gly|Leu|
| | | |740| | | |745| | | |750|
|Ala|Asn|Ala|Leu|Met|Leu|Ser|His|Ile|Ile|Lys|Tyr|Asn|Ala|Thr|Asp|
| | | |755| | | |760| | | |765|
|Ser|Pro|Val|Lys|Met|Gly|Thr|Phe|Pro|Gln|Tyr|Lys|Tyr|Pro|Gln|Ala|
| | |770| | | |775| | | |780|
|Met|Arg|His|Tyr|Ala|Glu|Ile|Ala|Glu|Leu|Leu|Leu|Pro|Pro|Thr|Gln|
|785| | | |790| | | |795| | | |800|
|Val|Val|Lys|Met|Thr|Asp|Val|Asp|Lys|Val|Gln|Tyr|Leu|Ile|Asp|Arg|
| | | |805| | | |810| | | |815|
|Val|Glu|Gln|Leu|Lys|Ala|Asp|Val|Gly|Ile|Pro|Lys|Ser|Ile|Lys|Glu|
| | | |820| | | |825| | | |830|
|Thr|Gly|Met|Val|Thr|Glu|Glu|Asp|Phe|Phe|Asn|Lys|Val|Asp|Gln|Val|
| | | |835| | | |840| | | |845|
|Ala|Ile|Met|Ala|Phe|Asp|Asp|Gln|Cys|Thr|Gly|Ala|Asn|Pro|Arg|Tyr|
| | | |850| | | |855| | | |860|
|Pro|Leu|Val|Ser|Glu|Leu|Lys|Gln|Leu|Met|Ile|Asp|Ala|Trp|Asn|Gly|
|865| | | |870| | | |875| | | |880|
|Val|Val|Pro|Lys|Leu|
| | | |885|

<210> SEQ ID NO 89
<211> LENGTH: 2200
<212> TYPE: DNA
<213> ORGANISM: Saccharomyces cerevisiae
<220> FEATURE:
<221> NAME/KEY: misc_feature
<223> OTHER INFORMATION: GPDI locus
<220> FEATURE:
<221> NAME/KEY: misc_feature
<222> LOCATION: (522)..(1698)
<223> OTHER INFORMATION: coding sequence

<400> SEQUENCE: 89
tacaaacgca acacgaaaga acaaaaaaag aagaaaacag aaggccaaga cagggtcaat    60

```
gagactgttg tcctcctact gtccctatgt ctctggccga tcacgcgcca ttgtccctca      120
gaaacaaatc aaacacccac accccgggca cccaaagtcc ccaccacac caccaatacg       180 taaacggggc gccccctgca ggccctcctg cgcgcggcct cccgccttgc ttctctcccc      240 ttcctttct ttttccagtt ttccctattt tgtcccttt tccgcacaac aagtatcaga       300
atgggttcat caaatctatc caacctaatt cgcacgtaga ctggcttggt attggcagtt     360
tcgtagttat atatatacta ccatgagtga aactgttacg ttaccttaaa ttctttctcc     420
ctttaatttt cttttatctt actctcctac ataagacatc aagaaacaat tgtatattgt     480 acacccccc cctccacaaa cacaaatatt gataatataa agatgtctgc tgctgctgat      540
agattaaact taacttccgg ccacttgaat gctggtagaa agagaagttc ctcttctgtt     600
tctttgaagg ctgccgaaaa gcctttcaag gttactgtga ttggatctgg taactggggt     660
actactattg ccaaggtggt tgccgaaaat tgtaagggat acccagaagt tttcgctcca     720
atagtacaaa tgtgggtgtt cgaagaagag atcaatggtg aaaaattgac tgaaatcata     780
aatactagac atcaaaacgt gaaatacttg cctggcatca ctctacccga caatttggtt     840
gctaatccag acttgattga ttcagtcaag gatgtcgaca tcatcgtttt caacattcca     900
catcaatttt tgccccgtat ctgtagccaa ttgaaaggtc atgttgattc acacgtcaga     960
gctatctcct gtctaaaggg ttttgaagtt ggtgctaaag tgtccaatt gctatcctct     1020 tacatcactg aggaactagg tattcaatgt ggtgctctat ctggtgctaa cattgccacc    1080
gaagtcgctc aagaacactg gtctgaaaca acagttgctt accacattcc aaaggatttc     1140
agaggcgagg gcaaggacgt cgaccataag gttctaaagg ccttgttcca cagaccttac     1200
ttccacgtta gtgtcatcga agatgttgct ggtatctcca tctgtggtgc tttgaagaac    1260
gttgttgcct taggttgtgg tttcgtcgaa ggtctaggct ggggtaacaa cgcttctgct    1320
gccatccaaa gagtcggttt gggtgagatc atcagattcg gtcaaatgtt tttcccagaa    1380
tctagagaag aaacatacta ccaagagtct gctggtgttg ctgatttgat caccacctgc    1440
gctggtggta gaaacgtcaa ggttgctagg ctaatggcta cttctggtaa ggacgcctgg    1500
gaatgtgaaa aggagttgtt gaatggccaa tccgctcaag gtttaattac ctgcaaagaa    1560
gttcacgaat ggttggaaac atgtggctct gtcgaagact ccccattatt tgaagccgta    1620
taccaaatcg tttacaacaa ctacccaatg aagaacctgc cggacatgat tgaagaatta    1680
gatctacatg aagattagat ttattggaga aagataacat atcatacttt cccccacttt    1740
tttcgaggct cttctatatc atattcataa attagcatta tgtcatttct cataactact    1800
ttatcacgtt agaaattact tattattatt aaattaatac aaaatttagt aaccaaataa    1860
atataaataa atatgtatat ttaaatttta aaaaaaaaat cctatagagc aaaaggattt    1920
tccattataa tattagctgt acacctcttc cgcattttt gagggtggtt acaacaccac     1980
tcattcagag gctgtcggca cagttgcttc tagcatctgg cgtccgtatg tatgggtgta    2040
ttttaaataa taaacaaagt gccacacctt caccaattat gtctttaaga aatggacaag    2100
ttccaaagag cttgcccaag gctcgacaag gatgtacttt ggaatatcta tattcaagta    2160
cgtggcgcgc atatgtttga gtgtgcacac aataaaggtt                          2200

<210> SEQ ID NO 90
<211> LENGTH: 1060
<212> TYPE: DNA
<213> ORGANISM: Saccharomyces cerevisiae
<220> FEATURE:
```

```
<221> NAME/KEY: misc_feature
<223> OTHER INFORMATION: gpd1 delta mutation
<220> FEATURE:
<221> NAME/KEY: misc_feature
<222> LOCATION: (523)..(542)
<223> OTHER INFORMATION: coding sequence
<220> FEATURE:
<221> NAME/KEY: misc_feature
<222> LOCATION: (543)..(558)
<223> OTHER INFORMATION: coding sequence not deleted

<400> SEQUENCE: 90
tacaaacgca acacgaaaga acaaaaaaag aagaaaacag aaggccaaga cagggtcaat      60
gagactgttg tcctcctact gtccctatgt ctctggccga tcacgcgcca ttgtccctca     120
gaaacaaatc aaacacccac accccgggca cccaaagtcc ccacccacac caccaatacg     180
taaacggggc gccccctgca ggccctcctg cgcgcggcct cccgccttgc ttctctcccc     240
ttccttttct ttttccagtt ttccctattt tgtccctttt tccgcacaac aagtatcaga     300
atgggttcat caaatctatc caacctaatt cgcacgtaga ctggcttggt attggcagtt     360
tcgtagttat atatatacta ccatgagtga aactgttacg ttaccttaaa ttctttctcc     420
ctttaatttt cttttatctt actctcctac ataagacatc aagaaacaat tgtatattgt     480
acacccccc cctccacaaa cacaaatatt gataatataa agatgtctgc tgctgctgat     540
agtctacatg aagattagat ttattggaga aagataacat atcatacttt cccccacttt     600
tttcgaggct cttctatatc atattcataa attagcatta tgtcatttct cataactact     660
ttatcacgtt agaaattact tattattatt aaattaatac aaaatttagt aaccaaataa     720
atataaataa atatgtatat ttaaatttta aaaaaaaaat cctatagagc aaaaggattt     780
tccattataa tattagctgt acacctcttc cgcatttttt gagggtggtt acaacaccac     840
tcattcagag gctgtcggca cagttgcttc tagcatctgg cgtccgtatg tatgggtgta     900
ttttaaataa taaacaaagt gccacacctt caccaattat gtctttaaga aatggacaag     960
ttccaaagag cttgcccaag gctcgacaag gatgtacttt ggaatatcta tattcaagta    1020
cgtggcgcgc atatgtttga gtgtgcacac aataaaggtt                         1060

<210> SEQ ID NO 91
<211> LENGTH: 2369
<212> TYPE: DNA
<213> ORGANISM: Saccharomyces cerevisiae
<220> FEATURE:
<221> NAME/KEY: misc_feature
<223> OTHER INFORMATION: GPD2 locus
<220> FEATURE:
<221> NAME/KEY: misc_feature
<222> LOCATION: (487)..(1806)
<223> OTHER INFORMATION: coding sequence

<400> SEQUENCE: 91
atagccatca tgcaagcgtg tatcttctaa gattcagtca tcatcattac cgagtttgtt      60
ttccttcaca tgatgaagaa ggtttgagta tgctcgaaac aataagacga cgatggctct     120
gccattgtta tattacgctt tgcggcgag gtgccgatgg gttgctgagg ggaagagtgt     180
ttagcttacg gacctattgc cattgttatt ccgattaatc tattgttcag cagctcttct     240
ctaccctgtc attctagtat tttttttttt tttttttggt tttactttt ttcttcttg      300
ccttttttc ttgttacttt ttttctagtt tttttccctt ccactaagct ttttccttga     360
tttatccttg ggttcttctt tctactcctt tagatttttt ttttatatat taattttaa     420
gtttatgtat tttggtagat tcaattctct ttcccttttcc ttttccttcg ctccccttcc    480
```

```
ttatcaatgc ttgctgtcag aagattaaca agatacacat tccttaagcg aacgcatccg      540
gtgttatata ctcgtcgtgc atataaaatt ttgccttcaa gatctacttt cctaagaaga      600
tcattattac aaacacaact gcactcaaag atgactgctc atactaatat caaacagcac      660
aaacactgtc atgaggacca tcctatcaga agatcggact ctgccgtgtc aattgtacat      720
ttgaaacgtg cgcccttcaa ggttacagtg attggttctg gtaactgggg gaccaccatc      780
gccaaagtca ttgcggaaaa cacagaattg cattcccata tcttcgagcc agaggtgaga      840
atgtgggttt ttgatgaaaa gatcggcgac gaaaatctga cggatatcat aaatacaaga      900
caccagaacg ttaaatatct acccaatatt gacctgcccc ataatctagt ggccgatcct      960
gatcttttac actccatcaa gggtgctgac atccttgttt tcaacatccc tcatcaattt     1020
ttaccaaaca tagtcaaaca attgcaaggc acgtggccc ctcatgtaag ggccatctcg     1080
tgtctaaaag ggttcgagtt gggctccaag ggtgtgcaat tgctatcctc ctatgttact     1140
gatgagttag gaatccaatg tggcgcacta tctggtgcaa acttggcacc ggaagtggcc     1200
aaggagcatt ggtccgaaac caccgtggct taccaactac caaaggatta tcaaggtgat     1260
ggcaaggatg tagatcataa gattttgaaa ttgctgttcc acagaccta cttccacgtc      1320 aatgtcatcg atgatgttgc tggtatatcc attgccggtg ccttgaagaa cgtcgtggca     1380
cttgcatgtg gtttcgtaga aggtatggga tggggtaaca atgcctccgc agccattcaa     1440
aggctgggtt taggtgaaat tatcaagttc ggtagaatgt ttttcccaga atccaaagtc     1500
gagacctact atcaagaatc cgctggtgtt gcagatctga tcaccacctg ctcaggcggt     1560
agaaacgtca aggttgccac atacatggcc aagaccggta agtcagcctt ggaagcagaa     1620
aaggaattgc ttaacggtca atccgcccaa gggataatca catgcagaga agttcacgag     1680
tggctacaaa catgtgagtt gacccaagaa ttcccattat tcgaggcagt ctaccagata     1740
gtctacaaca acgtccgcat ggaagaccta ccggagatga ttgaagagct agacatcgat     1800
gacgaataga cactctcccc cccctcccc ctctgatctt tcctgttgcc tcttttccc      1860 ccaaccaatt tatcattata cacaagttct acaactacta ctagtaacat tactacagtt     1920
attataattt tctattctct ttttctttaa gaatctatca ttaacgttaa tttctatata     1980
tacataacta ccattataca cgctattatc gtttacatat cacatcaccg ttaatgaaag     2040
atacgacacc ctgtacacta acacaattaa ataatcgcca taaccttttc tgttatctat     2100
agcccttaaa gctgtttctt cgagcttttt cactgcagta attctccaca tgggcccagc     2160
cactgagata agagcgctat gttagtcact actgacggct ctccagtcat ttatgtgatt     2220
ttttagtgac tcatgtcgca tttggcccgt ttttttccgc tgtcgcaacc tatttccatt     2280
aacggtgccg tatggaagag tcatttaaag gcaggagaga gagattactc atcttcattg     2340
gatcagattg atgactgcgt acggcagat                                        2369
```

<210> SEQ ID NO 92
<211> LENGTH: 1024
<212> TYPE: DNA
<213> ORGANISM: Saccharomyces cerevisiae
<220> FEATURE:
<221> NAME/KEY: misc_feature
<223> OTHER INFORMATION: gpd2 delta mutation

<400> SEQUENCE: 92

```
atagccatca tgcaagcgtg tatcttctaa gattcagtca tcatcattac cgagtttgtt       60
ttccttcaca tgatgaagaa ggtttgagta tgctcgaaac aataagacga cgatggctct      120
```

```
gccattgtta tattacgctt ttgcggcgag gtgccgatgg gttgctgagg ggaagagtgt    180
ttagcttacg gacctattgc cattgttatt ccgattaatc tattgttcag cagctcttct    240
ctaccctgtc attctagtat tttttttttt tttttttggt tttactttt tttcttcttg     300 cctttttttc ttgttacttt ttttctagtt ttttttcctt ccactaagct ttttccttga    360
tttatccttg ggttcttctt tctactcctt tagatttttt ttttatatat taattttttaa   420 gtttatgtat tttggtagat tcaattctct ttcccttttcc ttttccttcg ctcccctttcc  480 ttatcctctg atctttcctg ttgcctcttt tcccccaac caatttatca ttatacacaa     540
gttctacaac tactactagt aacattacta cagttattat aatttctat tctctttttc     600 tttaagaatc tatcattaac gttaatttct atatatacat aactaccatt atacacgcta    660
ttatcgttta catatcacat caccgttaat gaaagatacg cacccctgta cactaacaca    720
attaaataat cgccataacc ttttctgtta tctatagccc ttaaagctgt ttcttcgagc    780
tttttcactg cagtaattct ccacatgggc ccagccactg agataagagc gctatgttag    840
tcactactga cggctctcca gtcatttatg tgattttta gtgactcatg tcgcatttgg     900
cccgtttttt tccgctgtcg caacctattt ccattaacgg tgccgtatgg aagagtcatt    960
taaaggcagg agagagagat tactcatctt cattggatca gattgatgac tgcgtacggc   1020
agat                                                                1024

<210> SEQ ID NO 93
<211> LENGTH: 3180
<212> TYPE: DNA
<213> ORGANISM: Saccharomyces cerevisiae
<220> FEATURE:
<221> NAME/KEY: misc_feature
<223> OTHER INFORMATION: FDH1 locus
<220> FEATURE:
<221> NAME/KEY: misc_feature
<222> LOCATION: (880)..(2007)
<223> OTHER INFORMATION: coding sequence

<400> SEQUENCE: 93
tatttttcta tagatattta cactccgcaa gtgcaaaaaa aaagcattat cgctaacgat     60
caagaggaac tgagacctta ttagttgtct ttgttggcgt aacataaatt tcttaggaaa    120
agagaaaatt atctcgaagg caaaaataaa ccaagcctcg agtttaatgg ttttctaaaa    180
aacactttaa aaacagatcg ccataaaagg agaagctccg taggagaccg ttttcgaaac    240
ctatgtagaa ataaagggaa agctccaacg gtttggataa atctttagaa gcatagagtt    300
tatacaacat tcagtacgaa atgtactctc gaaacgttct cttttcacgg tgcttagtag    360
cagaaaaaag tgtcggaaat tacctatttt gtcaccactc gaggataggc ttgaaagaga    420
gttttaaccc caacttttct attttgcact tgtttggcta tggtttaaaa cattctgttt    480
ggaccaacag cccaagcggc ttatcccttt tcttttttc ccttataatc gggaatttcc     540
ttactaggaa ggcaccgata ctagaactcc gaatgaaaaa gacatgccag taataaaact    600
attttgatgt tatgcggaat atactattct tggattattc actgttaact aaaagttgga    660
gaaatcactc tgcactgtca atcattgaaa aaagaacat ataaaagggc acaaaattga     720
gtctttttta atgagttctt gctgaggaaa gtttagttaa tatatcattt acgtaaaata    780
tgcatattct tgtattgtgc ttttttatt cattttaagc aggaacaatt tacaagtatt     840
gcaacgctaa tcaaatcaaa ataacagctg aaaattaata tgtcgaaggg aaaggttttg    900 ctggttctt acgaaggtgg taagcatgct gaagagcagg aaaagttatt ggggtgtatt    960
```

```
gaaaatgaac ttggtatcag aaatttcatt gaagaacagg gatacgagtt ggttactacc   1020
attgacaagg accctgagcc aacctcaacg gtagacaggg agttgaaaga cgctgaaatt   1080
gtcattacta cgcccttttt ccccgcctac atctcgagaa acaggattgc agaagctcct   1140
aacctgaagc tctgtgtaac cgctggcgtc ggttcagacc atgtcgattt agaagctgca   1200
aatgaacgga aaatcacggt caccgaagtt actggttcta acgtcgtttc tgtcgcagag   1260
cacgttatgg ccacaatttt ggttttgata agaaactata atggtggtca tcaacaagca   1320
attaatggtg agtgggatat tgccggcgtg gctaaaaatg agtatgatct ggaagacaaa   1380
ataatttcaa cggtaggtgc cggtagaatt ggatataggg ttctggaaag attggtcgca   1440
tttaatccga agaagttact gtactacgac taccaggaac tacctgcgga agcaatcaat   1500
agattgaacg aggccagcaa gcttttcaat ggcagaggtg atattgttca gagagtagag   1560
aaattggagg atatggttgc tcagtcagat gttgttacca tcaactgtcc attgcacaag   1620
gactcaaggg gtttattcaa taaaaagctt atttcccaca tgaaagatgg tgcatacttg   1680
gtgaataccg ctagaggtgc tatttgtgtc gcagaagatg ttgccgaggc agtcaagtct   1740 ggtaaaattgg ctggctatgg tggtgatgtc tgggataagc aaccagcacc aaaagaccat   1800
ccctggagga ctatggacaa taaggaccac gtgggaaacg caatgactgt tcatatcagt   1860
ggcacatctc tggatgctca aaagaggtac gctcagggag taaagaacat cctaaatagt   1920
tacttttcca aaaagtttga ttaccgtcca caggatatta ttgtgcagaa tggttcttat   1980
gccaccagag cttatggaca gaagaaataa gagtgattat gagtatttgt gagcagaagt   2040
tttccggtct cctttgttc ttgttttggc gtattctcca ctattcgtcc atagcacatt    2100
tataccttag ctaaatattt tgtaaagcaa aattttcgtt atctcttaaa aaatagaaga   2160
gcggtttatt aatatcaaat aattgaaact gctgatatgg tagctatata caaaatctgc   2220
tgtcaaaatt tggcagtaaa cgatcttcac ggtagcggtt caaataaaga ggaaaagtct   2280
ttctccctta ctgtttttct ggaatttggc tcgtcgttaa taacagaact aaagatacag   2340
taaaaggaga gatcgcaatc aacttcatta attgtaacag tagcataatc acaactgatc   2400
atctacacta taaacagttt ttatttctaa ttatgggcgc ctggccggct caaacattgt   2460
gcttttaaga ctccaaaagt atctgctgca gaaaagagcc atataatgtt aagtgttcag   2520
ggataggtta tcgcttacta cttcaaacgt ttcgaaggaa agccagggaa gcctatatct   2580
gattccctgt ttcataatcc aatgcagcca ctagcttata attatttgaa ctatttgtcg   2640
aacatcacag taataaaatc cccagaaagt tccacttgct gcatattggc acctgttgat   2700
tcactctcca tcactttttt gttagccgcc cagcctagaa agtctttaaa tacatctgaa   2760 atttttttt tttaacagt gcacccgtgc atcatacctc atgcaaggta ccttttttc     2820 tcaaaggtat tgtcttccat tgaagtggca ctatggcatg atgaaccctg agcatttctg   2880
aattcaacag aaccaaattg tccagaaata aatctgtccg acatgaatta tgaaactttt   2940
tttcaattaa gtgaagagaa ttttgcagcg tcttaccatt attttgaccc attggtcgca   3000
tgtttgcgct ttgacttcga gaaccatgtt aaagcttact tgtacgacaa ccaatgaagt   3060
atattacggc agttttttg gactgggtca aaaaagtgt tgcataatca aatcaggaac    3120
acattaaaat gttgtaaaat ttgtcttagt atcacctgag tggttattca ttacgtacta   3180

<210> SEQ ID NO 94
<211> LENGTH: 1630
<212> TYPE: DNA
```

<213> ORGANISM: Saccharomyces cerevisiae
<220> FEATURE:
<221> NAME/KEY: misc_feature
<223> OTHER INFORMATION: fdh1 delta mutation

<400> SEQUENCE: 94

```
tattttcta tagatattta cactccgcaa gtgcaaaaaa aaagcattat cgctaacgat    60
caagaggaac tgagacctta ttagttgtct ttgttggcgt aacataaatt tcttaggaaa   120
agagaaaatt atctcgaagg caaaaataaa ccaagcctcg agtttaatgg ttttctaaaa   180
aacactttaa aaacagatcg ccataaaagg agaagctccg taggagaccg ttttcgaaac   240
ctatgtagaa ataaagggaa agctccaacg gtttggataa atctttagaa gcatagagtt   300
tatacaacat tcagtacgaa atgtactctc gaaacgttct cttttcacgg tgcttagtag   360
cagaaaaaag tgtcggaaat taccattttt gtcaccactc gaggataggc ttgaaagaga   420
gttttaaccc caacttttct attttgcact tgtttggcta tggtttaaaa cattctgttt   480
ggaccaacag cccaagcggc ttatccctt tcttttttc ccttataatc gggaattcc     540
ttactaggaa ggcaccgata ctagaactcc gaatgaaaaa gacatgccag taataaaact   600
attttgatgt tatgcggaat atactattct tggattattc actgttaact aaaagttgga   660
gaaatcactc tgcactgtca tggcagtaaa cgatcttcac ggtagcggtt caaataaaga   720
ggaaaagtct ttctccctta ctgttttct ggaatttggc tcgtcgttaa taacagaact   780
aaagatacag taaaggaga gatcgcaatc aacttcatta attgtaacag tagcataatc    840
acaactgatc atctcactta taaacagttt ttatttctaa ttatgggcgc ctggccggct   900
caaacattgt gcttttaaga ctccaaaagt atctgctgca gaaaagagcc atataatgtt   960
aagtgttcag ggataggtta tcgcttacta cttcaaacgt ttcgaaggaa agccagggaa  1020
gcctatatct gattccctgt ttcataatcc aatgcagcca ctagcttata attatttgaa  1080
ctatttgtcg aacatcacag taataaaatc cccagaaagt tccacttgct gcatattggc  1140
acctgttgat tcactctcca tcacttttt gttagccgcc cagcctagaa agtctttaaa   1200
tacatctgaa atttttttt tttttaacagt gcacccgtgc atcatacctc atgcaaggta  1260
cctttttttc tcaaaggtat tgtcttccat tgaagtggca ctatggcatg atgaaccctg  1320
agcatttctg aattcaacag aaccaaattg tccagaaata aatctgtccg acatgaatta  1380
tgaaactttt tttcaattaa gtgaagagaa ttttgcagcg tcttaccatt attttgaccc  1440
attggtcgca tgtttgcgct ttgacttcga gaaccatgtt aaagcttact tgtacgacaa  1500
ccaatgaagt atattacggc agtttttttg gactgggtca aaaaagtgt tgcataatca   1560
aatcaggaac acattaaaat gttgtaaaat ttgtcttagt atcacctgag tggttattca  1620
ttacgtacta                                                         1630
```

<210> SEQ ID NO 95
<211> LENGTH: 2668
<212> TYPE: DNA
<213> ORGANISM: Saccharomyces cerevisiae
<220> FEATURE:
<221> NAME/KEY: misc_feature
<223> OTHER INFORMATION: FDH2 locus
<220> FEATURE:
<221> NAME/KEY: misc_feature
<222> LOCATION: (801)..(1929)
<223> OTHER INFORMATION: coding sequence

<400> SEQUENCE: 95

```
tgtcgagaca atgtcattgc aagttatata acattgtaa tacatcacct cgatgaaaga    60
```

```
gaaactggaa tgatagatct cttttttctca aaatttcgtt aatatgtaat aataaggttc    120
ctgatgtaat ttgttttttgt acaaattatt ttagattctg gaggttcaaa taaaatatat    180
attacagcca acgattaggg gggacaagac ttgattacac atttttcgtt ggtaacttga    240 ctctttttatg aaaagaaaac attaagttga aggtgcacgc ttgaggcgct ccttttttcat   300 ggtgcttagc agcagatgaa agtgtcagaa gttacctatt tgtcaccat ttgagaataa    360 gcttgaaaga aagttgtaac cccaactttt ctatcttgca cttgtttgga ccaacagcca    420
aacggcttat ccctttttctt ttcccttata atcgggaatt tccttactag gaaggcaccg   480
atactataac tccgaatgaa aaagacatgc cagtaataaa aataattgat gttatgcgga    540
atatactatt cttggattat tcactgttaa ctaaaagttg gagaaatcac tctgcactgt    600
caatcattga aaaaagaac atataaaagg gcacaaaatc gagtcttttt taatgagttc    660
ttgctgagga aaattttagtt aatatatcat ttacataaaa catgcatatt attgtgttgt  720 actttctttta ttcattttaa gcaggaataa ttacaagtat tgcaacgcta atcaaatcga  780
aataacagct gaaaattaat atgtcgaagg gaaaggtttt gctggttctt tatgaaggtg   840
gtaagcatgc tgaagagcag gaaaagttat tggggtgtat tgaaaatgaa cttggtatca  900
gaaatttcat tgaagaacag ggatacgagt tggttactac cattgacaag gaccctgagc  960
caacctcaac ggtagacagg gagttgaaag acgctgaaat tgtcattact acgcccttt   1020 tccccgccta catctcgaga aacaggattg cagaagctcc taacctgaag ctctgtgtaa  1080
ccgctggcgt cggttcagac catgtcgatt tagaagctgc aaatgaacgg aaaatcacgg  1140
tcaccgaagt tactggttct aacgtcgttt ctgtcgcaga gcacgttatg gccacaattt  1200
tggttttgat aagaaactat aatggtggtc atcaataagc aattaatggt gagtgggata  1260
ttgccggcgt ggctaaaaaa tgagtatgat ctggaagaca aaataatttc aacggtaggt  1320
gccggtagaa ttggatatag ggttctggaa agattggtcg catttaatcc gaagaagtta  1380
ctgtactacg actaccagga actacctgcg gaagcaatca atagattgaa cgaggccagc  1440
aagcttttca atggcagagg tgatattgtt cagagagtag agaaattgga ggatatggtt  1500
gctcagtcag atgttgttac catcaactgt ccattgcaca aggactcaag gggtttattc  1560
aataaaaagc ttatttccca catgaaagat ggtgcatact tggtgaatac cgctagaggt  1620
gctatttgtg tcgcagaaga tgttgccgag gcagtcaagt ctggtaaatt ggctggctat  1680
ggtggtgatg tctgggataa gcaaccagca ccaaaagacc atccctggag gactatggac  1740
aataaggacc acgtgggaaa cgcaatgact gttcatatca gtggcacatc tctgcatgct  1800
caaaagaggt acgctcaggg agtaaagaac atcctaaata gttactttct caaaaagttt  1860
gattaccgtc cacaggatat tattgtgcag aatggttctt atgccaccag agcttatgga  1920
cagaagaaat aagagtgatt atgagtattt gtgagcagaa gttttccggt ctcctttttgt  1980 tcttgttttg gcgtattctc cactattcgt ccatagcaca tttataccttt agctaaatat  2040 tttgtaaagc aaaattttcg ttatctctta aaaaatagaa gagcggttta ttaatatcaa  2100
ataattgaaa ctgctgatat ggtagctata tacaaaatct gctgtcaaaa tttggcagta  2160
aacgatcttc acggtagcgg ttcaaataaa gaggaaaagt ccttctcccct tactgttttt  2220 ctggaatttg gctcgtcgtt aataacagaa ctaaagatac agtaaaagga gagatcgcaa  2280
tcaacttcat taattgtaac agtagcataa tcacaactgg ttatctgcgt tatagacaat  2340
tcttactcac aatgatgggc gcttagttgg ctgtaaacgt cgcttttttaa aactccgaaa  2400
```

```
agttaccgct acagaaaaaa accataaatg tatgctagtt gcgcagagag gtttagggtc    2460
caaaatttac taccctgtcg ctcactacag cgactgtccc gaattaagcc cgaagagacg    2520
cagaactgtt gtatgaacct catgaaacca ctgatcttga agatttagac cttcagaatc    2580
gttttcaatt agaagtatac aagaagtctt tgtacaataa tgtcaagaca gagctctgaa    2640
ttatagttca gccttgttat ttttttt                                        2668
```

<210> SEQ ID NO 96
<211> LENGTH: 1539
<212> TYPE: DNA
<213> ORGANISM: Saccharomyces cerevisiae
<220> FEATURE:
<221> NAME/KEY: misc_feature
<222> LOCATION: (801)..(1539)
<223> OTHER INFORMATION: deleted coding sequence

<400> SEQUENCE: 96

```
tgtcgagaca atgtcattgc aagttatata aacattgtaa tacatcacct cgatgaaaga     60
gaaactggaa tgatagatct cttttttctca aaatttcgtt aatatgtaat aataaggttc    120
ctgatgtaat ttgttttttgt acaaattatt ttagattctg gaggttcaaa taaaatatat    180
attacagcca acgattaggg gggacaagac ttgattacac attttttcgtt ggtaacttga    240 ctctttatg aaaagaaaac attaagttga aggtgcacgc ttgaggcgct ccttttttcat    300 ggtgcttagc agcagatgaa agtgtcagaa gttacctatt tgtcaccat ttgagaataa    360 gcttgaaaga aagttgtaac cccaactttt ctatcttgca cttgtttgga ccaacagcca    420
aacggcttat cccttttctt ttccttata atcgggaatt tccttactag gaaggcaccg    480
atactataac tccgaatgaa aaagacatgc cagtaataaa ataattgat gttatgcgga    540 atatactatt cttggattat tcactgttaa ctaaaagttg gagaaatcac tctgcactgt    600
caatcattga aaaaagaac atataaagg gcacaaaatc gagtcttttt taatgagttc    660
ttgctgagga aaatttagtt aatatatcat ttacataaaa catgcatatt attgtgttgt    720 actttctttta ttcattttaa gcaggaataa ttacaagtat tgcaacgcta atcaaatcga    780
aataacagct gaaattaat taagagtgat tatgagtatt tgtgagcaga agttttccgg    840
tctccttttg ttcttgtttt ggcgtattct ccactattcg tccatagcac atttatacct    900
tagctaaata ttttgtaaag caaaatttc gttatctctt aaaaaataga agagcggttt    960
attaatatca aataattgaa actgctgata tggtagctat atacaaaatc tgctgtcaaa   1020
atttggcagt aaacgatctt cacggtagcg gttcaaataa agaggaaaag tccttctccc   1080
ttactgtttt tctggaattt ggctcgtcgt taataacaga actaaagata cagtaaaagg   1140
agagatcgca atcaacttca ttaattgtaa cagtagcata atcacaactg ttatctgcg   1200 ttatagacaa ttcttactca caatgatggg cgcttagttg gctgtaaacg tcgcttttta   1260
aaactccgaa aagttaccgc tacagaaaaa aaccataaat gtatgctagt tgcgcagaga   1320
ggtttagggt ccaaaattta ctaccctgtc gctcactaca gcgactgtcc cgaattaagc   1380
ccgaagagac gcagaactgt tgtatgaacc tcatgaaacc actgatcttg aagatttaga   1440
ccttcagaat cgttttcaat tagaagtata caagaagtct ttgtacaata atgtcaagac   1500
agagctctga attatagttc agccttgtta tttttttt                            1539
```

<210> SEQ ID NO 97
<211> LENGTH: 2863
<212> TYPE: DNA
<213> ORGANISM: Saccharomyces cerevisiae

```
<220> FEATURE:
<221> NAME/KEY: misc_feature
<223> OTHER INFORMATION: GPD1 at GPD2 locus
<220> FEATURE:
<221> NAME/KEY: misc_feature
<222> LOCATION: (941)..(2113)
<223> OTHER INFORMATION: inserted CDP1

<400> SEQUENCE: 97
```

| | | | | | |
|---|---|---|---|---|---|
| agtaactgtg | acgatatcaa | ctctttttt | attatgtaat | aagcaaacaa | gcacgaatgg | 60 |
| ggaaagccta | tgtgcaatca | ccaaggtcgt | ccctttttc | ccatttgcta | atttagaatt | 120 |
| taaagaaacc | aaaagaatga | agaaagaaaa | caaatactag | ccctaacccct | gacttcgttt | 180 |
| ctatgataat | accctgcttt | aatgaacggt | atgccctagg | gtatatctca | ctctgtacgt | 240 |
| tacaaactcc | ggttatttta | tcggaacatc | cgagcacccg | cgccttcctc | aacccaggca | 300 |
| ccgcccccag | gtaaccgtgc | gcgatgagct | aatcctgagc | catcacccac | cccacccgtt | 360 |
| gatgacagca | attcgggagg | gcgaaaaata | aaaactggag | caaggaatta | ccatcaccgt | 420 |
| caccatcacc | atcatatcgc | cttagcctct | agccatagcc | atcatgcaag | cgtgtatctt | 480 |
| ctaagattca | gtcatcatca | ttaccgagtt | tgttttcctt | cacatgatga | agaaggtttg | 540 |
| agtatgctcg | aaacaataag | acgacgatgg | ctctgccatt | gttatattac | gcttttgcgg | 600 |
| cgaggtgccg | atgggttgct | gaggggaaga | gtgtttagct | tacggaccta | ttgccattgt | 660 |
| tattccgatt | aatctattgt | tcagcagctc | ttctctaccc | tgtcattcta | gtattttttt | 720 |
| ttttttttt | tggttttact | ttttttct | cttgccttt | tttcttgtta | ctttttttct | 780 |
| agtttttttt | ccttccacta | agcttttcc | ttgatttatc | cttgggttct | tctttctact | 840 |
| cctttagatt | ttttttat | atattaattt | ttaagtttat | gtattttggt | agattcaatt | 900 |
| ctctttccct | ttccttttcc | ttcgctcccc | ttccttatca | atgtctgctg | ctgctgatag | 960 |
| attaaactta | acttccggcc | acttgaatgc | tggtagaaag | agaagttcct | cttctgtttc | 1020 |
| tttgaaggct | gccgaaaagc | ctttcaaggt | tactgtgatt | ggatctggta | actgggtac | 1080 |
| tactattgcc | aaggtggttg | ccgaaaattg | taagggatac | ccagaagttt | tcgctccaat | 1140 |
| agtacaaatg | tgggtgttcg | aagaagagat | caatggtgaa | aaattgactg | aaatcataaa | 1200 |
| tactagacat | caaaacgtga | atacttgcc | tggcatcact | ctacccgaca | atttggttgc | 1260 |
| taatccagac | ttgattgatt | cagtcaagga | tgtcgacatc | atcgttttca | acattccaca | 1320 |
| tcaattttg | ccccgtatct | gtagccaatt | gaaaggtcat | gttgattcac | acgtcagagc | 1380 |
| tatctcctgt | ctaaagggtt | ttgaagttgg | tgctaaaggt | gtccaattgc | tatcctctta | 1440 |
| catcactgag | gaactaggta | ttcaatgtgg | tgctctatct | ggtgctaaca | ttgccaccga | 1500 |
| agtcgctcaa | gaacactggt | ctgaaacaac | agttgcttac | cacattccaa | aggatttcag | 1560 |
| aggcgagggc | aaggacgtcg | accataaggt | tctaaaggcc | ttgttccaca | gaccttactt | 1620 |
| ccacgttagt | gtcatcgaag | atgttgctgg | tatctccatc | tgtggtgctt | tgaagaacgt | 1680 |
| tgttgccta | ggttgtggtt | tcgtcgaagg | tctaggctgg | ggtaacaacg | cttctgctgc | 1740 |
| catccaaaga | gtcggtttgg | gtgagatcat | cagattcggt | caaatgtttt | tcccagaatc | 1800 |
| tagagaagaa | acatactacc | aagagtctgc | tggtgttgct | gatttgatca | ccacctgcgc | 1860 |
| tggtggtaga | aacgtcaagg | ttgctaggct | aatggctact | tctggtaagg | acgcctggga | 1920 |
| atgtgaaaag | gagttgttga | atggccaatc | cgctcaaggt | ttaattacct | gcaaagaagt | 1980 |
| tcacgaatgg | ttgaaaacat | gtggctctgt | cgaagacttc | ccattatttg | aagccgtata | 2040 |
| ccaaatcgtt | tacaacaact | acccaatgaa | gaacctgccg | gacatgattg | aagaattaga | 2100 |

```
tctacatgaa gattagacac tctcccccc cctcccctc tgatctttcc tgttgcctct    2160
ttttccccca accaatttat cattatacac aagttctaca actactacta gtaacattac    2220
tacagttatt ataattttct attctctttt tctttaagaa tctatcatta acgttaattt    2280
ctatatatac ataactacca ttatacacgc tattatcgtt tacatatcac atcaccgtta    2340
atgaaagata cgacaccctg tacactaaca caattaaata atcgccataa ccttttctgt    2400
tatctatagc ccttaaagct gtttcttcga gcttttcac tgcagtaatt ctccacatgg    2460
gcccagccac tgagataaga gcgctatgtt agtcactact gacggctctc cagtcattta    2520
tgtgattttt tagtgactca tgtcgcattt ggcccgtttt tttccgctgt cgcaacctat    2580
ttccattaac ggtgccgtat ggaagagtca tttaaaggca ggagagagag attactcatc    2640
ttcattggat cagattgatg actgcgtacg gcagatagtg taatctgagc agttgcgaga    2700
cccagactgg cactgtctca atagtatatt aatgggcata cattcgtact cccttgttct    2760
tgcccacagt tctctctctc tttacttctt gtatcttgtc tccccattgt gcagcgataa    2820
ggaacattgt tctaatatac acggatacaa aagaaataca cat                      2863

<210> SEQ ID NO 98
<211> LENGTH: 12394
<212> TYPE: DNA
<213> ORGANISM: Saccharomyces cerevisiae
<220> FEATURE:
<221> NAME/KEY: misc_feature
<223> OTHER INFORMATION: M2158 AADH integrations at the GPD1 locus

<400> SEQUENCE: 98
tagattcttt tcgaatttgt ggtgaagata ggaaagttgg tacagttctc catcaatttt     60
ccatattttg ctaaaaactc ccttgcatgt ctctttgcat tcatttctcc tgtatacggg    120
ttcaacacat caatcgaatt ttgcaaagtt gtctccattt ctagaagact ttcatcggga    180
ataaaaaatt catatccatt attcaaaaac gataatgatc cctcgtactt acctgtgtaa    240
ttggatattt tataccatac ttcaaaaata tccttggcct cacttctggt aggataccdt    300
tcgccatgtc tgccaatcat ttgaacttgc gttaatctac aaccttcagg aatatcagtg    360
ggtataccgt agttagcggg aaaggagaaa tatggcgcag accctccaag aaagggaaac    420
agactcttct gagagccaat tagttcaata tccgcaaaac ttctgagtgg gatggagagt    480
gccttagata atagaacacc taaacaaatg gcaaaaataa cgggcttcac cattgttcct    540
gtatggtgta ttagaacata gctgaaaata cttctgcctc aaaaaagtgt taaaaaaaag    600
aggcattata tagaggtaaa gcctacaggc gcaagataac acatcaccgc tctcccccct    660
ctcatgaaaa gtcatcgcta agaggaaca ctgaaggttc ccgtaggttg tctttggcac    720
aaggtagtac atggtaaaaa ctcaggatgg aataattcaa attcaccaat ttcaacgtcc    780
cttgtttaaa aagaaaagaa tttttctctt taaggtagca ctaatgcatt atcgatgatg    840
taaccattca cacaggttat ttagcttttg atccttgaac cattaattaa cccagaaata    900
gaaattaccc aagtggggct ctccaacaca atgagaggaa aggtgacttt taagggggc    960 cagaccctgt taaaaacctt tgatggctat gtaataatag taaattaagt gcaaacatgt    1020
aagaaagatt ctcggtaacg accatacaaa tattgggcgt gtggcgtagt cggtagcgcg    1080
ctcccttagc atgggagagg tctccggttc gattccggac tcgtccaaat tattttttac    1140
tttccgcggt gccgagatgc agacgtggcc aactgtgtct gccgtcgcaa aatgatttga    1200
attttgcgtc gcgcacgttt ctcacgtaca taataagtat tttcatacag ttctagcaag    1260
```

```
acgaggtggt caaaatagaa gcgtcctatg ttttacagta caagacagtc catactgaaa   1320
tgacaacgta cttgactttt cagtattttc tttttctcac agtctggtta tttttgaaag   1380
cgcacgaaat atatgtaggc aagcattttc tgagtctgct gacctctaaa attaatgcta   1440
ttgtgcacct tagtaaccca aggcaggaca gttaccttgc gtggtgttac tatggccgga   1500
agcccgaaag agttatcgtt actccgatta ttttgtacag ctgatgggac cttgccgtct   1560 tcatttttt tttttttcac ctatagagcc gggcagagct gcccggctta actaagggcc   1620 ggaaaaaaa cggaaaaaag aaagccaagc gtgtagacgt agtataacag tatatctgac   1680
acgcacgtga tgaccacgta atcgcatcgc ccctcacctc tcacctctca ccgctgactc   1740
agcttcacta aaaggaaaa tatatactct ttcccaggca aggtgacagc ggtccccgtc   1800
tcctccacaa aggcctctcc tggggtttga gcaagtctaa gtttacgtag cataaaaatt   1860
ctcggattgc gtcaaataat aaaaaaagta accccacttc tacttctaca tcggaaaaac   1920
attccattca catatcgtct ttggcctatc ttgttttgtc ctcggtagat caggtcagta   1980
caaacgcaac acgaaagaac aaaaaagaa gaaaacagaa ggccaagaca gggtcaatga   2040
gactgttgtc ctcctactgt ccctatgtct ctggccgatc acgcgccatt gtccctcaga   2100
aacaaatcaa acacccacac cccgggcacc caaagtcccc acccacacca ccaatacgta   2160
aacggggcgc cccctgcagg ccctcctgcg cgcggcctcc cgccttgctt ctctcccctt   2220 cctttcttt ttccagtttt ccctatttg tccctttttc cgcacaacaa gtatcagaat   2280
gggttcatca aatctatcca acctaattcg cacgtagact ggcttggtat tggcagtttc   2340
gtagttatat atatactacc atgagtgaaa ctgttacgtt accttaaatt ctttctccct   2400
ttaattttct tttatcttac tctcctacat aagacatcaa gaaacaattg tatattgtac   2460
accccccccc tccacaaaca caaatattga taatataaag atggctgtta ctaatgtcgc   2520
tgaacttaac gcactcgtag agcgtgtaaa aaaagcccag cgtgaatatg ccagtttcac   2580
tcaagagcaa gtagacaaaa tcttccgcgc cgccgctctg gctgctgcag atgctcgaat   2640
cccactcgcg aaaatggccg ttgccgaatc cggcatgggt atcgtcgaag ataaagtgat   2700
caaaaaccac tttgcttctg aatatatcta caacgcctat aaagatgaaa aaacctgtgg   2760
tgttctgtct gaagacgaca ctttggtac catcactatc gctgaaccaa tcggtattat   2820
ttgcggtatc gttccgacca ctaacccgac ttcaactgct atcttcaaat cgctgatcag   2880
tctgaagacc cgtaacgcca ttatcttctc cccgcacccg cgtgcaaaag atgccaccaa   2940
caaagcggct gatatcgttc tgcaggctgc tatcgctgcc ggtgctccga agatctgat   3000 cggctggatc gatcaacctt ctgttgaact gtctaacgca ctgatgcacc cccagacat   3060 caacctgatc ctcgcgactg gtggtccggg catggttaaa gccgcataca gctccggtaa   3120
accagctatc ggtgtaggcg cgggcaacac tccagttgtt atcgatgaaa ctgctgatat   3180
caaacgtgca gttgcatctg tactgatgtc caaaccttc gacaacggcg taatctgtgc   3240
ttctgaacag tctgttgttg ttgttgactc tgtttatgac gctgtacgtg aacgttttgc   3300
aacccacggc ggctatctgt tgcagggtaa agagctgaaa gctgttcagg atgttatcct   3360
gaaaaacggt gcgctgaacg cggctatcgt tggtcagcca gcctataaaa ttgctgaact   3420
ggcaggcttc tctgtaccag aaaacaccaa gattctgatc ggtgaagtga ccgttgttga   3480
tgaaagcgaa ccgttcgcac atgaaaaact gtccccgact ctggcaatgt accgcgctaa   3540
agatttcgaa gacgcggtag aaaaagcaga gaaactggtt gctatgggcg gtatcggtca   3600
```

```
tacctcttgc ctgtacactg accaggataa ccaaccggct cgcgtttctt acttcggtca   3660
gaaaatgaaa acggcgcgta tcctgattaa cacccccagcg tctcagggtg gtatcggtga   3720
cctgtataac ttcaaactcg caccttccct gactctgggt tgtggttctt ggggtggtaa   3780
ctccatctct gaaaacgttg gtccgaaaca cctgatcaac aagaaaaccg ttgctaagcg   3840
agctgaaaac atgttgtggc acaaacttcc gaaatctatc tacttccgcc gtggctccct   3900
gccaatcgcg ctggatgaag tgattactga tggccacaaa cgtgcgctca tcgtgactga   3960
ccgcttcctg ttcaacaatg gttatgctga tcagatcact tccgtactga aagcagcagg   4020
cgttgaaact gaagtcttct tcgaagtaga agcggacccg accctgagca tcgttcgtaa   4080
aggtgcagaa ctggcaaact ccttcaaacc agacgtgatt atcgcgctgg tggtggttc   4140
cccgatggac gccgcgaaga tcatgtgggt tatgtacgaa catccggaaa ctcacttcga   4200
agagctggcg ctgcgcttta tggatatccg taaacgtatc tacaagttcc cgaaaatggg   4260
cgtgaaagcg aaaatgatcg ctgtcaccac cacttctggt acaggttctg aagtcactcc   4320
gtttgcggtt gtaactgacg acgctactgg tcagaaaatat ccgctggcag actatgcgct   4380
gactccggat atggcgattg tcgacgccaa cctggttatg acatgccga agtccctgtg   4440
tgctttcggt ggtctggacg cagtaactca cgccatggaa gcttatgttt ctgtactggc   4500
atctgagttc tctgatggtc aggctctgca ggcactgaaa ctgctgaaag aatatctgcc   4560
agcgtcctac cacgaagggt ctaaaaatcc ggtagcgcgt gaacgtgttc acagtgcagc   4620
gactatcgcg ggtatcgcgt ttgcgaacgc cttcctgggt gtatgtcact caatggcgca   4680
caaactgggt tcccagttcc atattccgca cggtctggca aacgccctgc tgatttgtaa   4740
cgttattcgc tacaatgcga acgacaaccc gaccaagcag actgcattca gccagtatga   4800
ccgtccgcag gctcgccgtc gttatgctga aattgccgac cacttgggtc tgagcgcacc   4860
gggcgaccgt actgctgcta agatcgagaa actgctggca tggctggaaa cgctgaaagc   4920
tgaactgggt attccgaaat ctatccgtga agctggcgtt caggaagcag acttcctggc   4980
gaacgtggat aaaactgtct gaagatgcatt cgatgaccag tgcaccggcg ctaacccgcg   5040
ttacccgctg atctccgagc tgaaacagat tctgctggat acctactacg tcgtgatta   5100
tgtagaaggt gaaactgcag cgaagaaaga agctgctccg gctaaagctg agaaaaaagc   5160
gaaaaatcc gcttaagtcg agagcttttg attaagcctt ctagtccaaa aaacacgttt   5220
ttttgtcatt tatttcattt tcttagaata gtttagttta ttcattttat agtcacgaat   5280
gttttatgat tctatatagg gttgcaaaca agcatttttc atttttatgtt aaaacaattt   5340
caggtttacc ttttattctg cttgtggtga cgcgtgtatc cgcccgctct tttggtcacc   5400
catgtatttta attgcataaa taattcttaa aagtggagct agtctatttc tatttacata   5460
cctctcattt ctcatttcct cctaatgtgt caatgatcat attcttaact ggaccgatct   5520
tattcgtcag attcaaacca aaagttctta gggctaccac aggaggaaaa ttagtgtgat   5580
ataatttaaa taatttatcc gccattccta atagaacgtt gttcgacgga tatctttctg   5640
cccaaaaggg ttctaagctc aatgaagagc caatgtctaa acctcgttac attgaaaata   5700
cagtaaatgg ttccaccatt attatgttgg tcttgtttag tatggccgat cggcgtgtgt   5760
tttgtttgca ccttttatat agtagaagaa tatttgtctt aattcttatt agtactgcaa   5820
cctaaccact aattatcaac aattattgga ttatataaag gaggtaaatt gccggattaa   5880
aatcaaatat cattcatcaa caagtattca tattgtcggc atattttac atgcggtgta   5940
agtatttgga tcgtattctt atagtgtcaa tacctcgaag cagcgtttca agtaccagac   6000
```

```
gtatgtagga acttttaac gtcgagtccg taagatttga tcagtattaa aaaaatctag    6060
ataaatgagt ggtacaaata aaacatcat taaaaatcgt taaataaaaa agtatgaaga    6120
tcatctatta aagtattagt agccattagc cttaaaaaaa tcagtgctag tttaagtata    6180
atctcgggcg cgccggccga ggcggttaag cggattttt cgcttttttc tcagctttag    6240
ccggagcagc ttctttcttc gctgcagttt caccttctac ataatcacga ccgtagtagg    6300
tatccagcag aatctgtttc agctcggaga tcagcgggta acgcgggtta gcgccggtgc    6360
actggtcatc gaatgcatct tcagacagtt tatccacgtt cgccaggaag tctgcttcct    6420
gaacgccagc ttcacggata gatttcggaa tacccagttc agctttcagc gtttccagcc    6480
atgccagcag tttctcgatc ttagcagcag tacggtcgcc cggtgcgctc agacccaagt    6540
ggtcggcaat ttcagcataa cgacggcgag cctgcgacg gtcatactgg ctgaatgcag    6600
tctgcttggt cgggttgtcg ttcgcattgt agcgaataac gttacaaatc agcagggcgt    6660
ttgccagacc gtgcggaata tggaactggg aacccagttt gtgcgccatt gagtgacata    6720
cacccaggaa ggcgttcgca aacgcgatac ccgcgatagt cgctgcactg tgaacacgtt    6780
cacgcgctac cggatttta gacccttcgt ggtaggacgc tggcagatat tctttcagca    6840
gtttcagtgc ctgcagagcc tgaccatcag agaactcaga tgccagtaca gaaacataag    6900
cttccatggc gtgagttact gcgtccagac caccgaaagc acacagggac ttcggcatgt    6960
ccataaccag gttggcgtcg acaatcgcca tatccggagt cagcgcatag tctgccagcg    7020
gatatttctg accagtagcg tcgtcagtta caaccgcaaa cggagtgact tcagaacctg    7080
taccagaagt ggtggtgaca gcgatcattt tcgctttcac gcccattttc gggaacttgt    7140
agatacgttt acggatatcc ataaagcgca gcgccagctc ttcgaagtga gtttccggat    7200
gttcgtacat aacccacatg atcttcgcgg cgtccatcgg gaaccacca cccagcgcga    7260 taatcacgtc tggtttgaag gagttttgcca gttctgcacc tttacgaacg atgctcaggg    7320
tcgggtccgc ttctacttcg aagaagactt cagtttcaac gcctgctgct ttcagtacgg    7380
aagtgatctg atcagcataa ccattgttga acaggaagcg gtcagtcacg atgagcgcac    7440
gtttgtggcc atcagtaatc acttcatcca gcgcgattgg cagggagcca cggcggaagt    7500
agatagattt cggaagttg tgccacaaca tgtttcagc tcgcttagca acggttttct    7560
tgttgatcag gtgtttcgga ccaacgtttt cagagatgga gttaccaccc caagaaccac    7620
aacccagagt cagggaaggt gcgagtttga agttatacag gtcaccgata ccaccctgag    7680
acgctggggt gttaatcagg atacgcgccg tttttcatttt ctgaccgaag taagaaacgc    7740
gagccggttg gttatcctgg tcagtgtaca ggcaagaggt atgaccgata ccgcccatag    7800
caaccagttt ctctgctttt tctaccgcgt cttcgaaatc tttagcgcgg tacattgcca    7860
gagtcgggga cagttttca tgtgcgaacg gttcgctttc atcaacaacg gtcacttcac    7920
cgatcagaat cttggtgttt tctggtacag agaagcctgc cagttcagca atttataggg    7980
ctggctgacc aacgatagcc gcgttcagcg caccgttttt caggataaca tcctgaacag    8040
ctttcagctc tttaccctgc aacagatagc cgccgtgggt tgcaaaacgt tcacgtacag    8100
cgtcataaac agagtcaaca acaacaacag actgttcaga agcacagatt acgccgttgt    8160
cgaaggtttt ggacatcagt acagatgcaa ctgcacgttt gatatcagca gtttcatcga    8220
taacaactgg agtgttgccc gcgcctacac cgatagctgg tttaccggag ctgtatgcgg    8280 cttttaaccat gcccggacca ccagtcgcga ggatcaggtt gatgtctggg tggtgcatca    8340
```

```
gtgcgttaga cagttcaaca gaaggttgat cgatccagcc gatcagatct ttcggagcac    8400
cggcagcgat agcagcctgc agaacgatat cagccgcttt gttggtggca tcttttgcac    8460
gcgggtgcgg ggagaagata atggcgttac gggtcttcag actgatcagc gatttgaaga    8520
tagcagttga agtcgggtta gtggtcggaa cgataccgca aataataccg attggttcag    8580
cgatagtgat ggtaccaaaa gtgtcgtctt cagacagaac accacaggtt ttttcatctt    8640
tataggcgtt gtagatatat tcagaagcaa agtggttttt gatcacttta tcttcgacga    8700
tacccatgcc ggattcggca acggccattt tcgcgagtgg gattcgagca tctgcagcag    8760
ccagagcggc ggcgcggaag attttgtcta cttgctcttg agtgaaactg gcatattcac    8820
gctgggcttt ttttacacgc tctacgagtg cgttaagttc agcgacatta gtaacagcca    8880
taattcttaa ttaactttga tatgattttg tttcagattt tttatataaa gctttcccca    8940
aatagtgcta aagtgaactt agattttttg gtacctgttt cgaaattaaa aatagaaaaa    9000
tttctctccc tatattgtta ttcttacttc aaatttgttt atcgtttatt tactaggcga    9060
gacttgagta gacgacaatc caaatagaat taacagattt tattggtaga aagcaataat    9120
attctttaga tggttgagaa taaagaagta aaaaaaccag taaagagaaa aagaaaagga    9180
agaaaattaa agaaaaagga tgattacaca agaagataat aaaaaaactc ctttattaag    9240
agcggaagaa tttaataatg aagatgggaa taagcaaaac aaaaacaaag aagggaaaaa    9300
aaataaaaaa tcgtatttat ttatttaaaa aatcatgttg atgacgacaa tggaaaaaaa    9360
aaaccgattt cactttctca tccttatatt tttcaaaggt tgatgcaagt cgatctcaaa    9420
tcggataacg ctgccaactg ggaaattccg caattccgca agaaaaaaaa aaatgtgaaa    9480
acgtgattgc attttttaca ggtcctaaag gatttagccc acatatcaag agggtggcag    9540
taattgcact gattaagcat tcgtcagcat taggcgaatg tgtgcatgaa tattgccagt    9600
gtgctcgata ttagagagta cattgaagaa tattgtaccg gattatgtac aataactttg    9660
ttaatgagat attaattttc ttttttacta gccgctatcc catgcacgat gctaaatttc    9720
aagaagaaac tgagatttaa aaaattagtg gaagctgata aaacggacta taatggtgta    9780
tggattgagg aatctcgaca tgttttttcca tcgttttcaa cgatgactgt aacccgtaga    9840
ttgaaccagg catgccaaag ttagttagat cagggtaaaa attatagatg aggtatttat    9900
tggagaaaga taacatatca tactttcccc cactttttttc gaggctcttc tatatcatat    9960
tcataaatta gcattatgtc atttctcata actactttat cacgttagaa attacttatt   10020
attattaaat taatacaaaa tttagtaacc aaataaatat aaataaatat gtatatttaa   10080
attttaaaaa aaaaatccta tagagcaaaa ggattttcca ttataatatt agctgtacac   10140
ctcttccgca ttttttgagg gtggttacaa caccactcat tcagaggctg tcggcacagt   10200
tgcttctagc atctggcgtc cgtatgtatg ggtgtatttt aaataataaa caaagtgcca   10260
caccttcacc aattatgtct ttaagaaatg gacaagttcc aaagagcttg cccaaggctc   10320
gacaaggatg tactttggaa tatctatatt caagtacgtg gcgcgcatat gtttgagtgt   10380
gcacacaata aaggttttta gatattttgc ggcgtcctaa gaaaataagg ggtttcttaa   10440
aaaataacaa tagcaaacaa agttccttac gatgatttca gatgtgaata gcatggtcat   10500
gatgagtata tacgtttttta taaataatta aaagttttcc tcttgtctgt ttttttgttg   10560
gctcgtggtt gttctcgaaa aaggagagtt tcatttttcg aaataggtga ttatcatcat   10620
gttgttatca ccccacgacg aagataatac ggagctcacc gttttctttt ttttcccctt   10680
tggctgaaat ttcccaccag aacaaacgtg acaaaattat ctttgaatcc aaagtagctt   10740
```

```
atatatatac gtagaagtgt ttcgagacac acatccaaat acgaggttgt tcaatttaaa    10800
cccaagaata cataaaaaaa atatagatat attaacttag taaacaatga ctgcaagcac    10860
accatccaat gtcatgacat tgttcttgtt aaggcatgga caaagtgaat tgaatcacga    10920
gaatatattc tgtggttgga ttgacgctaa gctaaccgaa aaaggtaaag aacaagctcg    10980
tcattctgcc gagctaatcg aacaatattg taaagctaat aatttgagat taccccagat    11040
tggttacacc tcacgtttaa ttaggaccca acagaccata gaaacgatgt gtgaagaatt    11100
taagttaaag ccacaactgc aggttgttta cgactttaat aaaatcaaac ttggagacga    11160
atttggcagt gatgacaagg ataatatgaa aatcccgatt cttcaaactt ggaggctaaa    11220
tgaacgtcat tacggttcct ggcagggcca gaggaaaccg aatgttttaa aagaatatgg    11280
taaggataaa tatatgttca ttaggagaga ttacgagggt aagccaccac ctgtagatct    11340
tgaccgtgag atgattcaac aagaaaatga gaagggctct tctactgggt acgaattcaa    11400
ggagccaaac agacaaataa aatatgaatt ggaatgcagc aatcatgaca ttgtattacc    11460
ggattccgaa tctcttcgtg aagtggttta tagattgaat ccttttctac aaaatgtcat    11520
attaaaatta gccaatcaat atgatgaatc ttcatgcctg attgtgggcc atggaagttc    11580
agtgagatcg ctactgaaaa ttctggaggg tatatcagat gatgacatca gaatgttga    11640 tattccaaat ggtatcccct tagtcgttga attagataag aataatggtc ttaagtttat    11700
cagaaaattc tacctagatc ctgaatctgc taagatcaat gctgagaaag tccgtaatga    11760
gggtttcata aaaaatcctt aagggggta agtatataat ataattgtgt attttccgaa    11820
gtataatgaa accaataga aaacttatta taagtccaat gaggtacttt aaaaatgtga    11880
tatttataag aacattcctg aatgcagata tatgatatat attgtaaata tatatagatg    11940
tgtatatgta tttccatttt gtgtgaggtt ttcttctttt atctcctata taatttgtaa    12000
ccttaattaa cccatgacat aaccaatatt agcctttgca aattttgtaa cttcttgacg    12060
ttgttctaac gacaaatctt catgcttcga ttttatatgc cttgttaaag catccagtct    12120
cgaaaacgtc ttctgatagc cctcagatcc aagaattttt atacactccg agcaacggaa    12180
gacaatcttc cttttagcgt gaatggtatt ttggtgtctc gttaaatcat aggaccttga    12240
aaattgggca ccacacggtt catttgtaat gagattcatt atctgacacg taaatatttc    12300
gttattaccg tcagaagatg acgtatgggc cgatggtgat gcagtcgaag gtttcgaatt    12360
cgaatttgta gatgaatgtg aagataagtg cttc                              12394
```

<210> SEQ ID NO 99
<211> LENGTH: 13300
<212> TYPE: DNA
<213> ORGANISM: Escherichia coli
<220> FEATURE:
<221> NAME/KEY: misc_feature
<223> OTHER INFORMATION: M2158 AADH integrations at the GPD1 locus

<400> SEQUENCE: 99

```
cagaattggt gatattcttc attatcccct cgacatcttt acttttgatc agctttgtgt     60
atagcgggat atccgattgg aacttggctt cagcaacaaa cttgccaaag tggattctcc    120
tactcaagct ttgcaaacat tctatatctc tagtggcaac agaaccgaag ttattcttat    180
catcaccatc tctttcgaa attaatggta taatctttc aatataaact tttttattt       240 tatcattgta attaacttct ggggcataag gcgccaaaat ttgtgggtag ttaatgctcg    300
gtaagaatga tttctgaatc ttgtcaggaa agaagggagt ttcatcaggt gattcgaatc    360
```

-continued

```
ttctgatgcg agaatgcgca atttcaagat ttgaaagagc ccaatccaag aaagatcctt      420
taaaattcgg aatttctaaa cctggatggt ttgcctcata aactgaagga catgtggcga      480
aatgcgacct ctcaataaat ttgaagatga tcgaatcctc cattctaact aattcatctc      540
taatattttg tagatttaaa acagtttctg gttttgtgaa atccatatct tataccaatt      600
ttatgcagga tgctgagtgc tatttgttag caaaacggaa tcgatgtttc aacttttcaa      660 tactttttt cttcttttct tcgaacttcg aagattatag agatccattg aaaatttacg       720
ataaaggaaa tgcaacacga agtttgaaaa aaagttgata ttgaaaaaaa aaaaaaaga       780 gaaccaaaaa aaaattaaaa aacgtgaaaa cgatggttta acacttttt tcgaatttgg       840 tatacgtgga aaaacgaatg tatagatgca tttttaaaga atatatataa aatttagtaa      900
ttgtattccg cgagcggcgc aataggtgat ttcatttagc tgctttcagt ttgcgtatca      960
tttcttcatt gatcttggct tctctatcta aatcctcttt cgacttgtaa agtccccaag     1020
ttctaaacca taagaaccgc ctcaatctgg aaaatttgtc agtatcaaga ccataattcg     1080
tgtatgactg aatcaaatgt aatccacttt cgtcatgagt aaattcggcc ttgctcagag     1140
actcctggat tttggctaac aacgcagtcc cttcgatgca tatagctagg ccacaaatta     1200
tgccaataac ggtccatggg ttgatgtttt cttgaattct ttcgttttc atgctatttg     1260 cgtcttccca gtcccagcg ttccagtatt catactgcgc gttagagtgg tagccataag     1320
agccggcata ttggtaattt tcagtattaa cgttagaacg tggtgaatac gatgtggtcc     1380
agccttgcct cgttgtgtca tatacgatct ttttctttgg gtcacaaaga atatcatatg     1440
cttgagagat gactttaaat ctatgtagtt tttcgcttga tgttagcagc agcggtgatt     1500
tactatcact gttggtaacc ttttctgagc taaatatttg aatgttatcg gaatggtcag     1560
ggtggtacaa ttttacataa cgatgatatt ttttttttaa cgacttcttg tccagtttag     1620
gatttccaga tccggccttt ggaatgccaa aaatatcata gggagttgga tctgccaact     1680
caggccattg ttcatccctt atcgtaagtt ttctattgcc attttatcg ttcgctgtag     1740 catacttagc tataaaagtg atttgtgggg gacactttc tacacatgat aagtgccact     1800
tgaataaaaa tgggtatacg aacttatggt gtagcataac aaatatattg caagtagtga     1860
cctatggtgt gtagatatac gtacagttag ttacgagcct aaagacacaa cgtgtttgtt     1920
aattatactg tcgctgtaat atcttctctt ccattatcac cggtcattcc ttgcaggggc     1980
ggtagtaccc ggagccctg aacttttctt ttttttttg cgaaattaaa aagttcattt      2040
tcaattcgac aatgagatct acaagccatt gttttatgtt gatgagagcc agcttaaaga     2100
gttaaaaatt tcatagctac tagtcttcta ggcgggttat ctactgatcc gagcttccac     2160
taggatagca cccaaacacc tgcatatttg gacgaccttt acttacacca ccaaaaacca     2220
ctttcgcctc tcccgcccct gataacgtcc actaattgag cgattacctg agcggtcctc     2280
ttttgtttgc agcatgagac ttgcatactg caaatcgtaa gtagcaacgt ctcaaggtca     2340
aaactgtatg gaaaccttgt cacctcactt aattctagct agcctaccct gcaagtcaag     2400
aggtctccgt gattcctagc cacctcaagg tatgcctctc cccggaaact gtggcctttt     2460
ctggcacaca tgatctccac gatttcaaca tataaatagc ttttgataat ggcaatatta     2520
atcaaattta ttttacttct ttcttgtaac atctctcttg taatccctta ttccttctag     2580 ctattttca taaaaaacca agcaactgct tatcaacaca caaacactaa atcaaaatgg     2640
ctgttactaa tgtcgctgaa cttaacgcac tcgtagagcg tgtaaaaaaa gcccagcgtg     2700
```

```
aatatgccag tttcactcaa gagcaagtag acaaaatctt ccgcgccgcc gctctggctg    2760
ctgcagatgc tcgaatccca ctcgcgaaaa tggccgttgc cgaatccggc atgggtatcg    2820
tcgaagataa agtgatcaaa aaccactttg cttctgaata tatctacaac gcctataaag    2880
atgaaaaaac ctgtggtgtt ctgtctgaag acgacacttt tggtaccatc actatcgctg    2940
aaccaatcgg tattatttgc ggtatcgttc cgaccactaa cccgacttca actgctatct    3000
tcaaatcgct gatcagtctg aagacccgta acgccattat cttctccccg cacccgcgtg    3060
caaaagatgc caccaacaaa gcggctgata tcgttctgca ggctgctatc gctgccggtg    3120
ctccgaaaga tctgatcggc tggatcgatc aaccttctgt tgaactgtct aacgcactga    3180
tgcaccaccc agacatcaac ctgatcctcg cgactggtgg tccgggcatg gttaaagccg    3240
catacagctc cggtaaacca gctatcggtg taggcgcggg caacactcca gttgttatcg    3300
atgaaactgc tgatatcaaa cgtgcagttg catctgtact gatgtccaaa accttcgaca    3360
acggcgtaat ctgtgcttct gaacagtctg ttgttgttgt tgactctgtt tatgacgctg    3420
tacgtgaacg ttttgcaacc cacggcggct atctgttgca gggtaaagag ctgaaagctg    3480
ttcaggatgt tatcctgaaa aacggtgcgc tgaacgcggc tatcgttggt cagccagcct    3540
ataaaattgc tgaactggca ggcttctctg taccagaaaa caccaagatt ctgatcggtg    3600
aagtgaccgt tgttgatgaa gcgaaccgt tcgcacatga aaaactgtcc ccgactctgg    3660
caatgtaccg cgctaaagat ttcgaagacg cggtagaaaa agcagagaaa ctggttgcta    3720
tgggcggtat cggtcatacc tcttgcctgt acactgacca ggataaccaa ccggctcgcg    3780
tttcttactt cggtcagaaa atgaaaacgg cgcgtatcct gattaacacc ccagcgtctc    3840
agggtggtat cggtgaccty tataacttca aactcgcacc ttccctgact ctgggttgtg    3900
gttcttgggg tggtaactcc atctctgaaa acgttggtcc gaaacacctg atcaacaaga    3960
aaaccgttgc taagcgagct gaaaacatgt tgtggcacaa acttccgaaa tctatctact    4020
tccgccgtgg ctccctgcca atcgcgctgg atgaagtgat tactgatggc cacaaacgtg    4080
cgctcatcgt gactgaccgc ttcctgttca acaatggtta tgctgatcag atcacttccg    4140
tactgaaagc agcaggcgtt gaaactgaag tcttcttcga agtagaagcg gacccgaccc    4200
tgagcatcgt tcgtaaaggt gcagaactgg caaactcctt caaaccagac gtgattatcg    4260
cgctgggtgg tggttccccg atggacgccg cgaagatcat gtgggttatg tacgaacatc    4320
cggaaactca cttcgaagag ctggcgctgc gctttatgga tatccgtaaa cgtatctaca    4380
agttcccgaa aatgggcgtg aaagcgaaaa tgatcgctgt caccaccact tctggtacag    4440
gttctgaagt cactccgttt gcggttgtaa ctgacgacgc tactggtcag aaatatccgc    4500
tggcagacta tgcgctgact ccggatatgg cgattgtcga cgccaacctg gttatggaca    4560
tgccgaagtc cctgtgtgct ttcggtggtc tggacgcagt aactcacgcc atggaagctt    4620
atgtttctgt actggcatct gagttctctg atggtcaggc tctgcaggca ctgaaactgc    4680
tgaaagaata tctgccagcg tcctaccacg aagggtctaa aaatccggta gcgcgtgaac    4740
gtgttcacag tgcagcgact atcgcgggta tcgcgtttgc gaacgccttc ctgggtgtat    4800
gtcactcaat ggcgcacaaa ctgggttccc agttccatat tccgcacggt ctggcaaacg    4860
ccctgctgat ttgtaacgtt attcgctaca atgcgaacga caacccgacc aagcagactg    4920
cattcagcca gtatgaccgt ccgcaggctc gccgtcgtta tgctgaaatt gccgaccact    4980
tgggtctgag cgcaccgggc gaccgtactg ctgctaagat cgagaaactg ctggcatggc    5040
tggaaacgct gaaagctgaa ctgggtattc cgaaatctat ccgtgaagct ggcgttcagg    5100
```

```
aagcagactt cctggcgaac gtggataaac tgtctgaaga tgcattcgat gaccagtgca   5160
ccggcgctaa cccgcgttac ccgctgatct ccgagctgaa acagattctg ctggatacct   5220
actacggtcg tgattatgta gaaggtgaaa ctgcagcgaa gaagaagct gctccggcta    5280 aagctgagaa aaaagcgaaa aaatccgctt aagtcgagag cttttgatta agccttctag   5340
tccaaaaaac acgttttttt gtcattatt tcattttctt agaatagttt agtttattca    5400
ttttatagtc acgaatgttt tatgattcta tatagggttg caaacaagca ttttcattt    5460 tatgttaaaa caatttcagg tttacctttt attctgcttg tggtgacgcg tgtatccgcc   5520
cgctcttttg gtcacccatg tatttaattg cataaataat tcttaaaagt ggagctagtc   5580
tatttctatt tacataccte tcatttctca tttcctccta atgtgtcaat gatcatattc   5640
ttaactggac cgatcttatt cgtcagattc aaaccaaaag ttcttagggc taccacagga   5700
ggaaaattag tgtgatataa tttaaataat ttatccgcca ttcctaatag aacgttgttc   5760
gacggatatc tttctgccca aaagggttct aagctcaatg aagagccaat gtctaaacct   5820
cgttacattg aaaatacagt aaatggttcc accattatta tgttggtctt gtttagtatg   5880
gccgatcggc gtgtgttttg tttgcacctt ttatatagta gaagaatatt tgtcttaatt   5940
cttattagta ctgcaaccta accactaatt atcaacaatt attggattat ataaaggagg   6000
taaattgccg gattaaaatc aaatatcatt catcaacaag tattcatatt gtcggcatat   6060
ttttacatgc ggtgtaagta tttggatcgt attcttatag tgtcaatacc tcgaagcagc   6120
gtttcaagta ccagacgtat gtaggaactt tttaacgtcg agtccgtaag atttgatcag   6180
tattaaaaaa atctagataa atgagtggta caaataaaaa catcattaaa aatcgttaaa   6240
taaaaaagta tgaagatcat ctattaaagt attagtagcc attagcctta aaaaaatcag   6300
tgctagttta agtataatct cgggcgcgcc ggccgaggcg gttaagcgga tttttcgct    6360 tttttctcag ctttagccgg agcagcttct ttcttcgctg cagtttcacc ttctacataa   6420
tcacgaccgt agtaggtatc cagcagaatc tgtttcagct cggagatcag cgggtaacgc   6480
gggttagcgc cggtgcactg gtcatcgaat gcatcttcag acagtttatc cacgttcgcc   6540
aggaagtctg cttcctgaac gccagcttca cggatagatt tcggaatacc cagttcagct   6600
ttcagcgttt ccagccatgc cagcagtttc tcgatcttag cagcagtacg gtcgcccggt   6660
gcgctcagac ccaagtggtc ggcaatttca gcataacgac ggcgagcctg cggacggtca   6720
tactggctga atgcagtctg cttggtcggg ttgtcgttcg cattgtagcg aataacgtta   6780
caaatcagca gggcgtttgc cagaccgtgc ggaatatgga actgggaacc cagtttgtgc   6840
gccattgagt gacatacacc caggaaggcg ttcgcaaacg cgatacccgc gatagtcgct   6900
gcactgtgaa cacgttcacg cgctaccgga ttttagacc cttcgtggta ggacgctggc    6960
agatattctt tcagcagttt cagtgcctgc agagcctgac catcagagaa ctcagatgcc   7020
agtacagaaa cataagcttc catggcgtga gttactgcgt ccagaccacc gaaagcacac   7080
agggacttcg gcatgtccat aaccaggttg gcgtcgacaa tcgccatatc cggagtcagc   7140
gcatagtctg ccagcggata tttctgacca gtagcgtcgt cagttacaac cgcaaacgga   7200
gtgacttcag aacctgtacc agaagtggtg gtgacagcga tcattttcgc tttcacgccc   7260
attttcggga acttgtagat acgtttacgg atatccataa agcgcagcgc cagctcttcg   7320
aagtgagttt ccgatgttc gtacataacc cacatgatct tcgcggcgtc catcggggaa    7380
ccaccaccca gcgcgataat cacgtctggt ttgaaggagt ttgccagttc tgcacctta    7440
```

```
cgaacgatgc tcagggtcgg gtccgcttct acttcgaaga agacttcagt ttcaacgcct      7500
gctgctttca gtacggaagt gatctgatca gcataaccat tgttgaacag gaagcggtca      7560
gtcacgatga gcgcacgttt gtggccatca gtaatcactt catccagcgc gattggcagg      7620
gagccacggc ggaagtagat agatttcgga agtttgtgcc acaacatgtt ttcagctcgc      7680
ttagcaacgg ttttcttgtt gatcaggtgt ttcggaccaa cgttttcaga gatggagtta      7740
ccaccccaag aaccacaacc cagagtcagg gaaggtgcga gtttgaagtt atacaggtca      7800
ccgataccac cctgagacgc tggggtgtta atcaggatac gcgccgtttt cattttctga      7860
ccgaagtaag aaacgcgagc cggttggtta tcctggtcag tgtacaggca agaggtatga      7920
ccgataccgc ccatagcaac cagtttctct gcttttcta ccgcgtcttc gaaatcttta       7980
gcgcggtaca ttgccagagt cggggacagt ttttcatgtg cgaacggttc gctttcatca     8040
acaacggtca cttcaccgat cagaatcttg gtgttttctg gtacagagaa gcctgccagt     8100
tcagcaattt tataggctgg ctgaccaacg atagccgcgt tcagcgcacc gttttcagg      8160 ataacatcct gaacagcttt cagctcttta ccctgcaaca gatagccgcc gtgggttgca     8220
aaacgttcac gtacagcgtc ataaacagag tcaacaacaa caacagactg ttcagaagca     8280
cagattacgc cgttgtcgaa ggttttggac atcagtacag atgcaactgc acgtttgata     8340
tcagcagttt catcgataac aactggagtg ttgcccgcgc ctacaccgat agctggttta     8400
ccggagctgt atgcggcttt aaccatgccc ggaccaccag tcgcgaggat caggttgatg     8460
tctgggtggt gcatcagtgc gttagacagt tcaacagaag gttgatcgat ccagccgatc     8520
agatctttcg gagcaccggc agcgatagca gcctgcagaa cgatatcagc cgctttgttg     8580
gtggcatctt ttgcacgcgg gtgcgggag aagataatgg cgttacgggt cttcagactg      8640
atcagcgatt tgaagatagc agttgaagtc gggttagtgg tcggaacgat accgcaaata     8700
ataccgattg gttcagcgat agtgatggta ccaaaagtgt cgtcttcaga cagaacacca     8760
caggtttttt catctttata ggcgttgtag atatattcag aagcaaagtg ttttttgatc     8820
actttatctt cgacgatacc catgccggat tcggcaacgg ccattttcgc gagtgggatt     8880
cgagcatctg cagcagccag agcggcggcg cggaagattt tgtctacttg ctcttgagtg     8940
aaactggcat attcacgctg gcttttttt acacgctcta cgagtgcgtt aagttcagcg      9000
acattagtaa cagccataat tcttaattaa ctttgatatg attttgtttc agatttttta     9060
tataaaagct ttcccaaata gtgctaaagt gaacttagat ttttttggtac ctgtttcgaa    9120 attaaaaata gaaaaatttc tctccctata ttgttattct tacttcaaat ttgtttatcg     9180
tttatttact aggcgagact tgagtagacg acaatccaaa tagaattaac agatttatt     9240 ggtagaaagc aataatattc tttagatggt tgagaataaa gaagtaaaaa aaccagtaaa     9300
gagaaaaaga aaaggaagaa aattaaagaa aaggatgat tacacaagaa gataataaaa     9360
aaactccttt attaagagcg gaagaattta ataatgaaga tgggaataag caaaacaaaa     9420
acaaagaagg gaaaaaaat aaaaaatcgt atttatttat ttaaaaaatc atgttgatga      9480
cgacaatgga aaaaaaaac cgatttcact ttctcatcct tatattttc aaaggttgat       9540 gcaagtcgat ctcaaatcgg ataacgctgc caactgggaa attccgcaat tccgcaagaa     9600 aaaaaaaat gtgaaaacgt gattgcattt tttacaggtc ctaaaggatt tagcccacat      9660
atcaagaggg tggcagtaat tgcactgatt aagcattcgt cagcattagg cgaatgtgtg    9720
catgaatatt gccagtgtgc tcgatattag agagtacatt gaagaatatt gtaccggatt     9780
atgtacaata actttgttaa tgagatatta attttctttt ttactagccg ctatcccatg     9840
```

```
cacgatgcta aatttcaaga agaaactgag atttaaaaaa ttagtggaag ctgataaaac    9900
ggactataat ggtgtatgga ttgaggaatc tcgacatgtt tttccatcgt tttcaacgat    9960
gactgtaacc cgtagattga accaggcatg ccaaagttag ttagatcagg gtaaaaatta   10020
tagatgaggt ttaattaaac aagcacgcag cacgctgtat ttacgtattt aattttatat   10080
atttgtgcat acactactag ggaagacttg aaaaaaacct aggaaatgaa aaaacgacac   10140
aggaagtccc gtatttacta ttttttcctt ccttttgatg gggcagggcg aaatagagg    10200
ataggataag cctactgctt agctgtttcc gtctctactt cggtagttgt ctcaattgtc   10260
gtttcagtat tacctttaga gccgctagac gatggttgag ctatttgttg agggaaaact   10320
aagttcatgt aacacacgca taacccgatt aaactcatga atagcttgat tgcaggaggc   10380
tggtccattg gagatggtgc cttatttttcc ttataggcaa cgatgatgtc ttcgtcggtg   10440
ttcaggtagt agtgtacact ctgaatcagg gagaaccagg caatgaactt gttcctcaag   10500
aaaatagcgg ccataggcat ggattggtta accacaccag atatgcttgg tgtggcagaa   10560
tatagtcctt ttggtggcgc aattttcttg tacctgtggt agaaagggag cggttgaact   10620
gttagtatat attggcaata tcagcaaatt tgaaagaaaa ttgtcggtga aaaacatacg   10680
aaacacaaag gtcgggcctt gcaacgttat tcaaagtcat tgtttagttg aggaggtagc   10740
agcggagtat atgtattcct ttttttttgcc tatggatgtt gtaccatgcc cattctgctc   10800
aagcttttgt taaaattatt tttcagtatt ttttcttcca tgttgcgcgt tacgagaaca   10860
gaagcgacag ataaccgcaa tcatacaact agcgctactg cggggtgtaa aaagcacaag   10920
aactaagcca agatcacaac agttatcgat aaaatagcag tgtttgcatg gccattgaga   10980
aggacaacat tggcgtgcgc gccaatgttg tctcaccatg tagctccaaa cgagttgtaa   11040
gagacggacc gctcacgctt ccgaagcggt cagaaaacgc ttcccagtat gcagttgacc   11100
tacattcaac ctgcaaatat tgctttgctt caagaaatga ttacacagac gtctatttttc  11160
ttctacataa tgcacgaaac ttgggcattt agtcatgtag ccgcctagcg agcctgggtg   11220
ccgtcctatc tcctttgttc gtgcaaagag acaggaacac acactgcgtt ctcttgcggc   11280
cggtctggcg gactcagggg tgcggcgttt gcttaaccgg agggaataat aaaatcgggg   11340
tgacgcaagt atgaagtcat gtgtgcttag caattacgta gagggattag aaataatagt   11400
gtgcggttat cggaaccggc tcttgttccc gtttagagca acccaggtgc aggcgtactt   11460
taaagtatttt tctttctttt ttttcctgct acttacgcta ggagctgccg cagctgcaaa   11520
gccgacgtcg gagaggcagg tgatcttcgg ctcggccgac aaatcccctg gatatcattg   11580
gcctgtcgag gtatcggccg cgtggaacta ccgggaatta ctatgcaaaa caattggaaa   11640
tctggtagga aaaccttgtt ctagaacttg gcgattgctg acaaagaaga aagggcctta   11700
ttgttgctgc ctcttttgtt gttcttcctc gtattgtctt gccggtgttc tttgtgtctt   11760
ttgtgtgtag gttcttacta ttatagtgct ctttgctatt atatttcttt cgttttcact   11820
ttgcgtaatg taacggtctt aaacaaagtt tttttttttt cgctcttgca ttttcctttt   11880
ctgctctatc ttatttgcta attgtagttt cagaagtttt acttaaatat agcactattt   11940
tccagtttta atgtttcttc tcattgcttt cttttataat tttcgcatat aattatacat   12000
ttacggtgtc ttaactctcc ctcttcaccc ctcattattc cagaaaatac taatacttct   12060
tcacacaaaa gaacgcagtt agacaatcaa caatgaatcc taaatcctct acacctaaga   12120
ttccaagacc caagaacgca tttattctgt tcagacagca ctaccacagg atcttaatag   12180
```

-continued

```
acgaatggac cgctcaaggt gtggaaatac cccataattc aaacatttct aaaattattg    12240
gtacgaagtg aagggcttaa caaccggaag ataaggcaca ctgggaaaat ctagcggaga    12300
aggagaaact agaacatgaa aggaagtatc ctgaatacaa atacaagccg gtaagaaagt    12360
ctaagaagaa gcaactactt ttgaaggaaa tcgagcaaca gcagcagcaa caacagaaag    12420
aacagcagca gcagaaacag tcacaaccgc aattacaaca gcccttaac aacaatatag     12480 ttcttatgaa aagagcacat tctctttcac catcttcctc ggtgtcaagc tcgaacagct    12540
atcagttcca attgaacaat gatcttaaga ggttgcctat tccttctgtt aatacttcta    12600
actatatggt ctccagatct ttaagtggac tacctttgac gcatgataag acggcaagag    12660
acctaccaca gctgtcatct caactaaatt ctattccata ttactcagct ccacacgacc    12720
cttcaacgag acatcattac ctcaacgtcg ctcaagctca accaagggct aactcgaccc    12780
ctcaattgcc ctttatttca tccattatca acaacagcag tcaaacaccg gtaactacaa    12840
ctaccacatc cacaacaact gcgacatctt ctcctgggaa attctcctct tctccgaact    12900
cctctgtact ggagaacaac agattaaaca gtatcaacaa ttcaaatcaa tatttacctc    12960 ccctctatt accttctctg caagattttc aactggatca gtaccagcag ctaaagcaga     13020
tgggaccaac ttatattgtc aaaccactgt ctcacaccag gaacaatcta ttgtccacaa    13080 ctaccctac gcatcatcac attcctcata taccaaacca aaacattcct ctacatcaaa     13140
ttataaactc aagcaacact gaggtcaccg ctaaaactag cctagtttct ccgaaatgat    13200 ttttttttc catttcttct ttccgttata ttatattata ctatattccc tttaactaaa     13260
aatttatgca tttggctcct gtttaataaa agtttaaatc                          13300
```

<210> SEQ ID NO 100
<211> LENGTH: 910
<212> TYPE: PRT
<213> ORGANISM: Bifidobacterium adolescentis

<400> SEQUENCE: 100

```
Met Ala Asp Ala Lys Lys Glu Glu Pro Thr Lys Pro Thr Pro Glu
1               5                   10                  15

Glu Lys Leu Ala Ala Ala Glu Ala Glu Val Asp Ala Leu Val Lys Lys
            20                  25                  30

Gly Leu Lys Ala Leu Asp Glu Phe Glu Lys Leu Asp Gln Lys Gln Val
        35                  40                  45

Asp His Ile Val Ala Lys Ala Ser Val Ala Ala Leu Asn Lys His Leu
    50                  55                  60

Val Leu Ala Lys Met Ala Val Glu Glu Thr His Arg Gly Leu Val Glu
65                  70                  75                  80

Asp Lys Ala Thr Lys Asn Ile Phe Ala Cys Glu His Val Thr Asn Tyr
                85                  90                  95

Leu Ala Gly Gln Lys Thr Val Gly Ile Ile Arg Glu Asp Asp Val Leu
            100                 105                 110

Gly Ile Asp Glu Ile Ala Glu Pro Val Gly Val Val Ala Gly Val Thr
        115                 120                 125

Pro Val Thr Asn Pro Thr Ser Thr Ala Ile Phe Lys Ser Leu Ile Ala
    130                 135                 140

Leu Lys Thr Arg Cys Pro Ile Ile Phe Gly Phe His Pro Gly Ala Gln
145                 150                 155                 160

Asn Cys Ser Val Ala Ala Ala Lys Ile Val Arg Asp Ala Ala Ile Ala
                165                 170                 175
```

```
Ala Gly Ala Pro Glu Asn Cys Ile Gln Trp Ile Glu His Pro Ser Ile
            180                 185                 190

Glu Ala Thr Gly Ala Leu Met Lys His Asp Gly Val Ala Thr Ile Leu
        195                 200                 205

Ala Thr Gly Gly Pro Gly Met Val Lys Ala Ala Tyr Ser Ser Gly Lys
    210                 215                 220

Pro Ala Leu Gly Val Gly Ala Gly Asn Ala Pro Ala Tyr Val Asp Lys
225                 230                 235                 240

Asn Val Asp Val Val Arg Ala Ala Asn Asp Leu Ile Leu Ser Lys His
                245                 250                 255

Phe Asp Tyr Gly Met Ile Cys Ala Thr Glu Gln Ala Ile Ile Ala Asp
            260                 265                 270

Lys Asp Ile Tyr Ala Pro Leu Val Lys Glu Leu Lys Arg Arg Lys Ala
        275                 280                 285

Tyr Phe Val Asn Ala Asp Glu Lys Ala Lys Leu Glu Gln Tyr Met Phe
    290                 295                 300

Gly Cys Thr Ala Tyr Ser Gly Gln Thr Pro Lys Leu Asn Ser Val Val
305                 310                 315                 320

Pro Gly Lys Ser Pro Gln Tyr Ile Ala Lys Ala Ala Gly Phe Glu Ile
                325                 330                 335

Pro Glu Asp Ala Thr Ile Leu Ala Ala Glu Cys Lys Glu Val Gly Glu
            340                 345                 350

Asn Glu Pro Leu Thr Met Glu Lys Leu Ala Pro Val Gln Ala Val Leu
        355                 360                 365

Lys Ser Asp Asn Lys Glu Gln Ala Phe Glu Met Cys Glu Ala Met Leu
370                 375                 380

Lys His Gly Ala Gly His Thr Ala Ala Ile His Thr Asn Asp Arg Asp
385                 390                 395                 400

Leu Val Arg Glu Tyr Gly Gln Arg Met His Ala Cys Arg Ile Ile Trp
            405                 410                 415

Asn Ser Pro Ser Ser Leu Gly Gly Val Gly Asp Ile Tyr Asn Ala Ile
        420                 425                 430

Ala Pro Ser Leu Thr Leu Gly Cys Gly Ser Tyr Gly Gly Asn Ser Val
    435                 440                 445

Ser Gly Asn Val Gln Ala Val Asn Leu Ile Asn Ile Lys Arg Ile Ala
450                 455                 460

Arg Arg Asn Asn Asn Met Gln Trp Phe Lys Ile Pro Ala Lys Thr Tyr
                470                 475                 480
465

Phe Glu Pro Asn Ala Ile Lys Tyr Leu Arg Asp Met Tyr Gly Ile Glu
            485                 490                 495

Lys Ala Val Ile Val Cys Asp Lys Val Met Glu Gln Leu Gly Ile Val
        500                 505                 510

Asp Lys Ile Ile Asp Gln Leu Arg Ala Arg Ser Asn Arg Val Thr Phe
    515                 520                 525

Arg Ile Ile Asp Tyr Val Glu Pro Glu Pro Ser Val Glu Thr Val Glu
530                 535                 540

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575

Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
```

```
                595                 600                 605
Ala Lys Leu Val Cys Ile Pro Thr Ser Ser Gly Thr Gly Ser Glu Val
    610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
        675                 680                 685

Phe Thr Asp Gly Met Ala Leu His Ala Ala Lys Leu Val Trp Asp Asn
690                 695                 700

Leu Ala Glu Ser Val Asn Gly Glu Pro Gly Glu Lys Thr Arg Ala
705                 710                 715                 720

Gln Glu Lys Met His Asn Ala Ala Thr Met Ala Gly Met Ala Phe Gly
                725                 730                 735

Ser Ala Phe Leu Gly Met Cys His Gly Met Ala His Thr Ile Gly Ala
            740                 745                 750

Leu Cys His Val Ala His Gly Arg Thr Asn Ser Ile Leu Leu Pro Tyr
        755                 760                 765

Val Ile Arg Tyr Asn Gly Ser Val Pro Glu Pro Thr Ser Trp Pro
770                 775                 780

Lys Tyr Asn Lys Tyr Ile Ala Pro Glu Arg Tyr Gln Glu Ile Ala Lys
785                 790                 795                 800

Asn Leu Gly Val Asn Pro Gly Lys Thr Pro Glu Glu Gly Val Glu Asn
                805                 810                 815

Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
        835                 840                 845

Ile Asp Gln Ile Gly Met Arg Ala Tyr Glu Asp Gln Cys Ala Pro Ala
850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910

<210> SEQ ID NO 101
<211> LENGTH: 870
<212> TYPE: PRT
<213> ORGANISM: Bacillus coagulans

<400> SEQUENCE: 101

Met Ala Ile Asp Glu Lys Val Val Gly Lys Ser Ala Gln Ile Thr Glu
1               5                   10                  15

Met Val Asp Ser Leu Val Ala Lys Gly Gln Lys Ala Leu Arg Glu Phe
            20                  25                  30

Met Glu Leu Asp Gln Ala Gln Val Asp Asn Ile Val Lys Gln Met Ala
        35                  40                  45

Leu Ala Gly Leu Glu Gln His Met Val Leu Ala Lys Met Ala Val Glu
    50                  55                  60
```

```
Glu Thr Gly Arg Gly Val Tyr Glu Asp Lys Met Thr Lys Asn Leu Phe
 65                  70                  75                  80

Ala Thr Glu Tyr Ile Tyr His Asn Ile Lys Tyr Asn Lys Thr Val Gly
                 85                  90                  95

Ile Ile Asp Glu Asn Asn Glu Gly Ile Val Lys Phe Ala Glu Pro
            100                 105                 110

Val Gly Val Ile Ala Gly Val Thr Pro Val Thr Asn Pro Thr Ser Thr
            115                 120                 125

Thr Met Phe Lys Ala Leu Ile Ala Lys Thr Arg Asn Pro Ile Ile
    130                 135                 140

Phe Ala Phe His Pro Ser Ala Gln Lys Cys Ser Ser His Ala Ala Lys
145                 150                 155                 160

Val Met Leu Asp Ala Val Lys Ala Gly Ala Pro Glu Asn Cys Ile
            165                 170                 175

Gln Trp Ile Glu Lys Pro Ala Ile Glu Ala Thr Gln Gln Leu Met Asn
            180                 185                 190

His Ser Gly Ile Ser Leu Ile Leu Ala Thr Gly Gly Ser Gly Met Val
        195                 200                 205

Lys Ser Ala Tyr Ser Ser Gly Lys Pro Ala Leu Gly Val Gly Pro Gly
210                 215                 220

Asn Val Pro Cys Tyr Ile Glu Lys Ser Ala Asp Ile Lys Arg Ala Val
225                 230                 235                 240

Asn Asp Leu Ile Leu Ser Lys Thr Phe Asp Asn Gly Met Ile Cys Ala
            245                 250                 255

Ser Glu Gln Ala Val Ile Ile Asp Lys Glu Ile Tyr Asp Asn Val Lys
            260                 265                 270

Asn Glu Leu Ile Ala Asn Gln Cys Tyr Phe Leu Asn Glu Ala Glu Lys
        275                 280                 285

Lys Lys Val Glu Lys Thr Val Ile Asn Glu Lys Thr Gln Ser Val Asn
290                 295                 300

Ser Ala Ile Val Gly Lys Pro Ala Tyr Glu Ile Ala Lys Met Ala Gly
305                 310                 315                 320

Val Asn Val Pro Glu Asp Thr Lys Ile Leu Ile Ala Glu Leu Thr Gly
            325                 330                 335

Val Gly Pro Asp Tyr Pro Leu Ser Arg Glu Lys Leu Ser Pro Val Leu
            340                 345                 350

Ala Cys Tyr Lys Ala Asn Ser Thr Lys Gln Gly Phe Glu Phe Ala Glu
            355                 360                 365

Ala Met Leu Glu Phe Gly Gly Leu Gly His Ser Ala Val Ile His Ser
    370                 375                 380

Thr Asn Asp Glu Val Ile Glu Gln Tyr Gly Leu Lys Met Lys Ala Gly
385                 390                 395                 400

Arg Ile Ile Val Asn Ser Pro Ser Ser Gln Gly Ala Ile Gly Asp Ile
            405                 410                 415

Tyr Asn Ala Tyr Met Pro Ser Leu Thr Leu Gly Cys Gly Thr Phe Gly
            420                 425                 430

Gly Asn Ser Val Ser Thr Asn Val Gly Val Ile Asn Leu Tyr Asn Val
        435                 440                 445

Lys Thr Met Ala Lys Arg Arg Val Asn Met Gln Trp Phe Lys Ile Pro
        450                 455                 460

Pro Arg Val Tyr Phe Glu Lys Asn Ser Val Gln Tyr Leu Glu Lys Met
465                 470                 475                 480

Pro Asp Ile Ser Ser Ala Phe Ile Val Thr Asp Pro Asp Met Val Arg
```

```
                485                 490                 495
Leu Gly Phe Val Glu Lys Val Leu Tyr Tyr Leu Arg Lys Arg Pro Asp
            500                 505                 510

Tyr Val His Cys Glu Ile Phe Ser Glu Val Glu Pro Asp Pro Ser Ile
            515                 520                 525

Glu Thr Val Arg Lys Gly Ala Ala Met Ala Ser Phe Gln Pro Asp
        530                 535                 540

Val Ile Ile Ala Leu Gly Gly Ser Ala Met Asp Ala Ala Lys Gly
545                 550                 555                 560

Met Trp Leu Phe Tyr Glu His Pro Glu Val Asp Phe Asn Glu Leu Lys
                565                 570                 575

Gln Lys Phe Met Asp Ile Arg Lys Arg Val Ala Lys Phe Pro Lys Leu
            580                 585                 590

Gly Glu Lys Ala Gln Leu Val Cys Ile Pro Thr Thr Ser Gly Thr Gly
        595                 600                 605

Ser Glu Val Thr Ser Phe Ala Val Ile Ser Asp Lys Lys Asn Asn Thr
    610                 615                 620

Lys Tyr Pro Leu Ala Asp Tyr Glu Leu Thr Pro Asp Val Ala Ile Ile
625                 630                 635                 640

Asp Pro Gln Phe Val Met Thr Val Pro Lys Ser Val Thr Ala Asp Thr
                645                 650                 655

Gly Met Asp Val Leu Thr His Ala Ile Glu Ala Tyr Val Ser Asn Met
            660                 665                 670

Ala Asn Asp Tyr Thr Asp Gly Leu Ala Ile Lys Ala Ile Gln Leu Val
        675                 680                 685

His Glu Tyr Leu Pro Lys Ala Tyr Ala Asn Gly Asn Asp Ala Leu Ala
    690                 695                 700

Arg Glu Lys Met His Asn Ala Ser Thr Leu Ala Gly Met Ala Phe Ser
705                 710                 715                 720

Asn Ala Phe Leu Gly Ile Asn His Ser Leu Ala His Lys Ile Gly Ala
                725                 730                 735

Glu Phe His Ile Pro His Gly Arg Ala Asn Ala Ile Leu Leu Pro His
            740                 745                 750

Val Ile Arg Tyr Asn Ala Gln Lys Pro Lys Lys Phe Ala Ala Phe Pro
        755                 760                 765

Lys Tyr Glu His Phe Ile Ala Asp Gln Arg Tyr Ala Glu Ile Ala Arg
    770                 775                 780

Val Leu Gly Leu Pro Ala Ser Thr Thr Glu Glu Gly Val Glu Ser Leu
785                 790                 795                 800

Cys Gln Glu Ile Ile Arg Met Cys Lys Leu Phe Asn Ile Pro Leu Ser
                805                 810                 815

Leu Lys Ala Ala Gly Val Asn Arg Ala Asp Phe Glu Lys Arg Val Ala
            820                 825                 830

Ile Ile Ala Asp Arg Ala Phe Glu Asp Gln Cys Thr Pro Ala Asn Pro
        835                 840                 845

Lys Leu Pro Leu Val Ser Glu Leu Glu Asp Ile Leu Arg Lys Ala Phe
    850                 855                 860

Glu Gly Val Glu Ala Lys
865                 870

<210> SEQ ID NO 102
<211> LENGTH: 867
<212> TYPE: PRT
<213> ORGANISM: Bacillus licheniformis
```

<400> SEQUENCE: 102

```
Met Ala Ile Glu Glu Lys Asn Met Lys Gln Lys Gln Asn Ala Ser Asn
1               5                   10                  15

Met Ile Asp Gln Leu Val Glu Lys Gly Leu Lys Ala Leu Glu Glu Phe
            20                  25                  30

Arg Ser Phe Asp Gln Glu Gln Ile Asp Glu Ile Val Lys Gln Met Ala
        35                  40                  45

Leu Ala Gly Leu Asp Gln His Met Pro Leu Ala Lys Leu Ala Val Glu
    50                  55                  60

Glu Thr Lys Arg Gly Val Tyr Glu Asp Lys Ile Ile Lys Asn Met Phe
65                  70                  75                  80

Ala Thr Glu Tyr Val Tyr His His Ile Lys Tyr Asp Lys Thr Val Gly
                85                  90                  95

Ile Ile Asn Glu Asn Glu His Asp Gly Val Ile Glu Ile Ala Glu Pro
            100                 105                 110

Val Gly Val Ile Ala Gly Val Thr Pro Val Thr Asn Pro Thr Ser Thr
        115                 120                 125

Thr Met Phe Lys Ser Leu Ile Ser Ile Lys Thr Arg Asn Pro Ile Val
130                 135                 140

Phe Ala Phe His Pro Ser Ala Gln Lys Cys Ser Arg Glu Ala Ala Arg
145                 150                 155                 160

Ile Leu Arg Asp Ala Ala Val Lys Ala Gly Ala Pro Asp Asn Cys Ile
                165                 170                 175

Gln Trp Ile Glu Thr Pro Ser Leu Asp Ala Thr Gln Ala Leu Met Thr
            180                 185                 190

His Pro Asn Val Ser Leu Ile Leu Ala Thr Gly Gly Ala Gly Met Val
        195                 200                 205

Lys Ser Ala Tyr Ser Ser Gly Lys Pro Ala Leu Gly Val Gly Pro Gly
    210                 215                 220

Asn Val Pro Cys Tyr Ile Glu Lys Ser Ala Asn Leu Lys Gln Ala Val
225                 230                 235                 240

Asn Asp Leu Ile Leu Ser Lys Thr Phe Asp Asn Gly Met Ile Cys Ala
                245                 250                 255

Ser Glu Gln Ala Val Ile Ile Asp Lys Gly Ile Tyr Ser Asp Val Lys
            260                 265                 270

Ala Glu Met Thr Arg Asn Asn Cys Tyr Phe Leu Asn Lys Thr Glu Lys
        275                 280                 285

Ser Lys Val Glu Lys Leu Val Ile Asn Glu Asn Thr Cys Ala Val Asn
    290                 295                 300

Ala Asp Ile Val Gly Met Pro Ala Phe Lys Ile Ala Glu Met Ala Gly
305                 310                 315                 320

Ile Lys Val Pro Gln Asp Thr Lys Ile Leu Ile Ala Glu Leu Glu Gly
                325                 330                 335

Val Gly Pro Asp Asp Pro Leu Ser Arg Glu Lys Leu Ser Pro Val Leu
            340                 345                 350

Ala Cys Tyr Lys Val Ser Gly Leu Glu Glu Gly Leu Lys Arg Ala Glu
        355                 360                 365

Glu Met Leu Ala Phe Gly Gly Thr Gly His Ser Ala Val Ile His Thr
    370                 375                 380

Asn Asp Gln Glu Ala Val Lys Glu Phe Gly Leu Arg Met Lys Ala Gly
385                 390                 395                 400

Arg Ile Ile Val Asn Ala Pro Ser Ser Gln Gly Ala Ile Gly Asp Ile
```

```
            405                 410                 415
Tyr Asn Ala Tyr Met Pro Ser Leu Thr Leu Gly Cys Gly Thr Tyr Gly
            420                 425                 430

Gly Asn Ser Val Ser Ser Asn Val Gly Ala Val His Leu Ile Asn Thr
            435                 440                 445

Lys Lys Val Ala Lys Arg Asn Val Asn Met Gln Trp Phe Lys Val Pro
    450                 455                 460

Pro Lys Ile Tyr Phe Glu Lys His Ala Thr Gln Tyr Leu Ala Lys Met
465                 470                 475                 480

Pro Asp Ile Ser Lys Ala Phe Ile Val Thr Asp Pro Gly Met Val Lys
            485                 490                 495

Leu Gly Tyr Val Asp Arg Ala Leu His Tyr Leu Arg Arg Arg Pro Asp
            500                 505                 510

Tyr Val His Cys Glu Ile Phe Ser Asp Val Glu Pro Asp Pro Ser Ile
            515                 520                 525

Glu Thr Val Met Asn Gly Val Asp Met Met Ala Lys Phe Gln Pro Asp
            530                 535                 540

Val Ile Ile Ala Leu Gly Gly Gly Ser Ala Met Asp Ala Ala Lys Gly
545                 550                 555                 560

Met Trp Met Phe Tyr Glu His Pro Asp Ala Glu Phe Phe Gly Leu Lys
                565                 570                 575

Gln Lys Phe Leu Asp Ile Arg Lys Arg Ile Val Lys Tyr Pro Lys Leu
            580                 585                 590

Gly Gly Lys Ala Lys Phe Val Ala Ile Pro Thr Thr Ser Gly Thr Gly
            595                 600                 605

Ser Glu Val Thr Ser Phe Ser Val Ile Thr Asp Lys Glu Thr Asn Thr
    610                 615                 620

Lys Tyr Pro Leu Ala Asp Tyr Glu Leu Thr Pro Asp Val Ala Ile Ile
625                 630                 635                 640

Asp Pro Gln Phe Val Met Thr Val Pro Lys His Ile Thr Ala Asp Thr
            645                 650                 655

Gly Met Asp Val Leu Thr His Ala Ile Glu Ser Tyr Val Ser Cys Met
            660                 665                 670

Ala Asn Asp Tyr Thr Asp Gly Leu Ala Met Lys Ala Ile Gln Leu Ile
            675                 680                 685

Phe Glu Tyr Leu Pro Arg Ala Tyr Lys Asn Gly Ser Asp Glu Leu Ala
            690                 695                 700

Arg Glu Lys Val His Asn Ala Ser Thr Ile Ala Gly Met Ala Phe Ser
705                 710                 715                 720

Asn Ala Phe Leu Gly Ile Asn His Ser Leu Ala His Lys Leu Gly Ala
                725                 730                 735

Glu Phe Gln Ile Ala His Gly Arg Ala Asn Ala Ile Leu Leu Pro His
            740                 745                 750

Val Ile Arg Tyr Asn Ala Ala Lys Pro Lys Lys Phe Thr Ala Phe Pro
            755                 760                 765

Lys Tyr Ser His Phe Ile Ala Asp Gln Arg Tyr Ala Glu Ile Ala Arg
            770                 775                 780

Thr Leu Gly Leu Pro Ala Lys Thr Thr Ala Glu Gly Val Glu Ser Leu
785                 790                 795                 800

Ile Gln Glu Ile Ile Ser Leu Ala Lys Glu Leu Lys Ile Pro Met Ser
            805                 810                 815

Ile Lys Gln Asn Gly Val Asp Ala Ala Ala Phe Glu Ser Lys Val Asp
            820                 825                 830
```

Leu Met Ala Glu Arg Ala Phe Glu Asp Gln Cys Thr Thr Ala Asn Pro
            835                 840                 845

Lys Leu Pro Leu Val Ser Glu Leu Ala Glu Ile Tyr Arg Ser Ala Tyr
        850                 855                 860

Lys Gly Val
865

<210> SEQ ID NO 103
<211> LENGTH: 866
<212> TYPE: PRT
<213> ORGANISM: Enterococcus faecium

<400> SEQUENCE: 103

Met Met Ala Lys Val Met Glu Lys Glu Lys Thr Lys Thr Ile Asp Val
1               5                   10                  15

Gln Ala Met Ile Asp Gly Leu Ala Glu Lys Ala Asn Val Ala Leu Lys
            20                  25                  30

Glu Met Glu Ser Phe Asp Gln Glu Lys Val Asp His Ile Val His Glu
        35                  40                  45

Met Ala Met Ala Ala Leu Asp Gln His Met Pro Leu Ala Lys Met Ala
    50                  55                  60

Val Glu Glu Thr Gly Arg Gly Val Tyr Glu Asp Lys Ala Ile Lys Asn
65                  70                  75                  80

Met Tyr Ala Ser Glu Tyr Ile Trp His Asn Ile Lys His Asp Lys Thr
                85                  90                  95

Val Gly Val Ile Asn Glu Asp Val Gln Lys Gly Leu Ile Glu Ile Ala
            100                 105                 110

Glu Pro Val Gly Val Val Cys Gly Val Thr Pro Thr Thr Asn Pro Thr
        115                 120                 125

Ser Thr Thr Ile Phe Lys Ser Met Ile Ala Leu Lys Thr Arg Asn Pro
    130                 135                 140

Ile Val Phe Ala Phe His Pro Ser Ala Gln Lys Ser Ser Ala Glu Ala
145                 150                 155                 160

Ala Arg Val Val Arg Asp Ala Ala Ile Ala Gly Ala Pro Glu Asn
                165                 170                 175

Cys Ile Gln Trp Ile Glu His Pro Ser Ile Glu Ala Thr Ser Met Leu
            180                 185                 190

Met Asn His Pro Gly Ile Ala Ile Val Leu Ala Thr Gly Gly Ala Gly
        195                 200                 205

Met Val Lys Ser Ala Tyr Ser Thr Gly Lys Pro Ala Leu Gly Val Gly
    210                 215                 220

Pro Gly Asn Val Pro Ala Tyr Ile Glu Lys Thr Ala Lys Ile Lys Arg
225                 230                 235                 240

Ala Val Asn Asp Leu Ile Val Ser Lys Thr Phe Asp Asn Gly Met Ile
                245                 250                 255

Cys Ala Ser Glu Gln Ala Val Ile Val Asp Lys Glu Ile Tyr Ala Ala
            260                 265                 270

Val Lys Ala Glu Phe Gln Ala His Gln Val Tyr Ile Val Lys Pro Asp
        275                 280                 285

Glu Leu Gln Lys Leu Glu Asp Ala Val Met Asn Glu Gly Lys Tyr Ala
    290                 295                 300

Val Asn Pro Ser Ile Val Gly His Ser Ala Met Glu Ile Ala Lys Leu
305                 310                 315                 320

Ala Gly Ile Ser Val Pro Lys Gly Thr Lys Met Leu Ile Ala Glu Leu

```
                    325                 330                 335
Glu Gly Val Gly Pro Asp Tyr Pro Leu Ser Arg Glu Lys Leu Ser Pro
                340                 345                 350

Val Leu Ala Met Ile Lys Ala Asn Asn Thr Asp His Ala Phe Asp Leu
                355                 360                 365

Cys Glu Gly Met Leu Asn Leu Gly Gly Leu Gly His Thr Ala Val Ile
                370                 375                 380

His Ser Glu Asn Glu Glu Leu His Val Lys Phe Gly Leu Arg Met Lys
385                 390                 395                 400

Ala Cys Arg Ile Leu Val Asn Thr Pro Ser Ala Glu Gly Gly Ile Gly
                405                 410                 415

Asp Ile Tyr Asn Glu Met Ile Pro Ser Leu Thr Leu Gly Cys Gly Ser
                420                 425                 430

Tyr Gly Lys Asn Ser Val Ser Arg Asn Val Ser Ala Val Asn Leu Ile
                435                 440                 445

Asn Val Lys Thr Val Ala Lys Arg Arg Asn Asn Met Gln Trp Phe Lys
            450                 455                 460

Leu Pro Pro Lys Ile Phe Phe Glu Lys Asn Ser Leu Leu Tyr Leu Glu
465                 470                 475                 480

Lys Met Glu Asn Val Glu Arg Val Met Ile Val Cys Asp Pro Gly Met
                485                 490                 495

Val Gln Phe Gly Tyr Cys Asp Thr Val Arg Glu Val Leu Ser Arg Arg
                500                 505                 510

Lys Asn Asp Val Lys Ile Glu Val Phe Ser Glu Val Glu Pro Asn Pro
            515                 520                 525

Ser Thr Asn Thr Val Tyr Ala Gly Thr Lys Leu Met Ala Asp Phe Lys
            530                 535                 540

Pro Asp Thr Val Ile Ala Leu Gly Gly Gly Ser Ala Met Asp Ala Ala
545                 550                 555                 560

Lys Gly Met Trp Met Phe Tyr Glu His Pro Asp Thr Ser Phe Phe Gly
                565                 570                 575

Ala Lys Gln Lys Phe Leu Asp Ile Arg Lys Arg Thr Tyr Lys Ile Asp
                580                 585                 590

Lys Pro Glu Lys Thr Gln Phe Val Cys Ile Pro Thr Thr Ser Gly Thr
            595                 600                 605

Gly Ser Glu Val Thr Pro Phe Ala Val Ile Thr Asp Ser Glu Thr His
            610                 615                 620

Val Lys Tyr Pro Leu Ala Asp Tyr Ala Leu Thr Pro Asp Val Ala Ile
625                 630                 635                 640

Val Asp Pro Gln Phe Val Met Ser Val Pro Ala Ser Val Thr Ala Asp
                645                 650                 655

Thr Gly Met Asp Val Leu Thr His Ala Ile Glu Ser Tyr Val Ser Val
                660                 665                 670

Met Ala Ser Asp Tyr Thr Arg Gly Leu Ser Leu Gln Ala Ile Lys Leu
            675                 680                 685

Val Phe Asp Tyr Leu Glu Lys Ser Val Lys Thr Pro Asp Met Glu Ser
            690                 695                 700

Arg Glu Lys Met His Asn Ala Ser Thr Met Ala Gly Met Ala Phe Ala
705                 710                 715                 720

Asn Ala Phe Leu Gly Ile Cys His Ser Val Ala His Lys Ile Gly Gly
                725                 730                 735

Glu Tyr Gly Ile Pro His Gly Arg Thr Asn Ala Ile Leu Leu Pro His
                740                 745                 750
```

```
Ile Ile Arg Tyr Asn Ala Lys Asp Pro Gln Lys His Ala Met Phe Pro
        755                 760                 765
Lys Tyr Asp Tyr Phe Arg Ala Asp Thr Asp Tyr Ala Asp Ile Ala Lys
    770                 775                 780
Phe Leu Gly Leu Lys Gly Glu Thr Thr Glu Glu Leu Val Glu Ala Leu
785                 790                 795                 800
Ala Thr Ala Val Tyr Glu Leu Gly Asn Ser Val Gly Ile Asn Met Ser
                805                 810                 815
Leu Lys Ala Gln Gly Val Thr Gln Glu Thr Leu Asp Thr Thr Val Asp
            820                 825                 830
Arg Met Ala Glu Leu Ala Tyr Glu Asp Gln Cys Thr Thr Ala Asn Pro
        835                 840                 845
Lys Glu Pro Leu Ile Ser Glu Leu Lys Gln Ile Ile Ile Asp Ala Tyr
    850                 855                 860
Asn Gly
865

<210> SEQ ID NO 104
<211> LENGTH: 3300
<212> TYPE: DNA
<213> ORGANISM: Saccharomyces cerevisiae
<220> FEATURE:
<221> NAME/KEY: misc_feature
<222> LOCATION: (601)..(2610)
<223> OTHER INFORMATION: coding sequence

<400> SEQUENCE: 104
aacgcggctg atgcttttat ttaggaagga atacttacat tatcatgaga acattgtcaa      60
gggcattctg atacgggcct tccatcgcaa gaaaaaggca gcaacggact gagggacgga     120
gagagttacg gcataagaag tagtaggaga gcagagtgtc ataaagttat attattctcg     180
tcctaaagtc aattagttct gttgcgcttg acaatatatg tcgtgtaata ccgtcccttta    240 gcagaagaaa gaaagacgga tccatatatg ttaaaatgct tcagagatgt ttctttaatg    300
tgccgtccaa caaaggtatc ttctgtagct tcctctattt tcgatcagat ctcatagtga    360
gaaggcgcaa ttcagtagtt aaaagcgggg aacagtgtga atccggagac ggcaagattg    420
cccggccctt tttgcggaaa agataaaaca agatatattg cacttttcc accaagaaaa    480 acaggaagtg gattaaaaaa tcaacaaagt ataacgccta ttgtcccaat aagcgtcggt    540
tgttcttctt tattatttta ccaagtacgc tcgagggtac attctaatgc attaaaagac    600
atgagtaatc ctcaaaaagc tctaaacgac tttctgtcca gtgaatctgt tcatacacat    660
gatagttcta ggaaacaatc taataagcag tcatccgacg aaggacgctc ttcatcacaa    720
ccttcacatc atcactctgg tggtactaac aacaataata acaataataa taataataat    780
aacagtaaca acaacaacaa cggcaacgat gggggaaatg atgacgacta tgattatgaa    840
atgcaagatt atagaccttc tccgcaaagt gcgcggccta ctcccacgta tgttccacaa    900
tattctgtag aaagtgggac tgctttcccg attcaagagg ttattcctag cgcatacatt    960
aacacacaag atataaacca taaagataac ggtccgccga gtgcaagcag taatagagca   1020
ttcaggccta gagggcagac cacagtgtcg gccaacgtgc ttaacattga agattttac    1080 aaaaatgcag acgatgcgca taccatcccg gagtcacatt tatcgagaag gagaagtagg   1140
tcgagggcta cgagtaatgc tgggcacagt gccaatacag gcgccacgaa tggcaggact   1200
actggtgccc aaactaatat ggaaagcaat gaatcaccac gtaacgtccc cattatggtg   1260
```

```
aagccaaaga cattatacca gaaccctcaa acacctacag tcttgccctc cacataccat    1320
ccaattaata aatggtcttc cgtcaaaaac acttatttga aggaattttt agccgagttt    1380
atgggaacaa tggttatgat tattttcggt agtgctgttg tttgtcaggt caatgttgct    1440
gggaaaatac agcaggacaa tttcaacgtg gctttggata accttaacgt taccgggtct    1500
tctgcagaaa cgatagacgc tatgaagagt ttaacatcct tggtttcatc cgttgcgggc    1560
ggtacctttg atgatgtggc attgggctgg gctgctgccg tggtgatggg ctatttctgc    1620
gctggtggta gtgccatctc aggtgctcat ttgaatccgt ctattacatt agccaatttg    1680
gtgtatagag gttttcccct gaagaaagtt ccttattact ttgctggaca attgatcggt    1740
gccttcacag gcgctttgat cttgtttatt tggtacaaaa gggtgttaca agaggcatat    1800
agcgattggt ggatgaatga agtgttgcg ggaatgtttt gcgttttcc aaagccttat     1860
ctaagttcag acggcaatt tttttccgaa tttttatgtg gagctatgtt acaagcagga    1920
acatttgcgc tgaccgatcc ttatacgtgt ttgtcctctg atgttttccc attgatgatg    1980
tttattttga ttttcattat caatgcttcc atggcttatc agacaggtac agcaatgaat    2040
ttggctcgtg atctgggccc acgtcttgca ctatatgcag ttggatttga tcataaaatg    2100
cttgggtgc atcatcatca tttcttttgg gttcccatgg taggcccatt tattggtgcg    2160
ttaatgggg ggttggttta cgatgtctgt atttatcagg gtcatgaatc tccagtcaac    2220
tggtctttac cagtttataa ggaaatgatt atgagagcct ggtttagaag gcctggttgg    2280
aagaagagaa atagagcaag aagaacatcg gacctgagtg acttctcata caataacgat    2340
gatgatgagg aatttggaga aagaatggct cttcaaaaga caaagaccaa gtcatctatt    2400
tcagacaacg aaaatgaagc aggagaaaag aaagtgcaat ttaaatctgt tcagcgcggc    2460
aaaagaacgt ttggtggtat accaacaatt cttgaagaag aagattccat tgaaactgct    2520
tcgctaggtg cgacgacgac tgattctatt gggttatccg acacatcatc agaagattcg    2580
cattatggta atgctaagaa ggtaacatga gaaaacagac aagaaaaaga aacaaataat    2640
atagactgat agaaaaaaat actgcttact accgccggta taatatatat atatatatat    2700
atttacatag atgattgcat agtgttttaa aaagctttcc taggttaagc tatgaatctt    2760
cataacctaa ccaactaaat atgaaaatac tgacccatcg tcttaagtaa gttgacatga    2820
actcagcctg gtcacctact atacatgatg tatcgcatgg atggaaagaa taccaaacgc    2880
taccttccag gttaatgata gtatccaaac ctagttggaa tttgccttga acatcaagca    2940
gcgattcgat atcagttggg agcatcaatt tggtcattgg aataccatct atgcttttct    3000
cctcccatat tcgcaaaagt agtaagggct cgttatatac ttttgaatat gtaagatata    3060
attctatatg atttagtaat ttattttcta tacgctcagt attttctgc agttgtcgag     3120
taggtattaa acgcaaaaga agtccatcct tttcatcatt caaatggaca tcttggcaaa    3180
gggcccagtt atgaaaatc tgggagtcat acaacgattg cagttggcta tgccactcct     3240
ggtaaggaat catcaagtct gataattctg ttttttagcc cttttttttt tttttcatg     3300
```

<210> SEQ ID NO 105
<211> LENGTH: 1326
<212> TYPE: DNA
<213> ORGANISM: Saccharomyces cerevisiae
<220> FEATURE:
<221> NAME/KEY: misc_feature
<223> OTHER INFORMATION: fps1 delta mutaion
<220> FEATURE:
<221> NAME/KEY: misc_feature
<222> LOCATION: (602)..(636)

<223> OTHER INFORMATION: coding sequence

<400> SEQUENCE: 105

```
aacgcggctg atgcttttat ttaggaagga atacttacat tatcatgaga acattgtcaa      60
gggcattctg atacgggcct tccatcgcaa gaaaaaggca gcaacggact gagggacgga     120
gagagttacg gcataagaag tagtaggaga gcagagtgtc ataaagttat attattctcg     180
tcctaaagtc aattagttct gttgcgcttg acaatatatg tcgtgtaata ccgtccctta     240
gcagaagaaa gaaagacgga tccatatatg ttaaaatgct tcagagatgt ttctttaatg     300
tgccgtccaa caaaggtatc ttctgtagct tcctctattt tcgatcagat ctcatagtga     360
gaaggcgcaa ttcagtagtt aaaagcgggg aacagtgtga atccggagac ggcaagattg     420
cccggccctt tttgcggaaa agataaaaca agatatattg cacttttccc accaagaaaa     480
acaggaagtg gattaaaaaa tcaacaaagt ataacgccta ttgtcccaat aagcgtcggt     540
tgttcttctt tattatttta ccaagtacgc tcgagggtac attctaatgc attaaaagac     600
gattcgcatt atggtaatgc taagaaggta acatgagaaa acagacaaga aaagaaaca     660
aataatatag actgatagaa aaaaatactg cttactaccg ccggtataat atatatatat     720
atatatattt acatagatga ttgcatagtg ttttaaaaag ctttcctagg ttaagctatg     780
aatcttcata acctaaccaa ctaaatatga aaatactgac ccatcgtctt aagtaagttg     840
acatgaactc agcctggtca cctactatac atgatgtatc gcatggatgg aaagaatacc     900
aaacgctacc ttccaggtta atgatagtat ccaaacctag ttggaatttg ccttgaacat     960
caagcagcga ttcgatatca gttgggagca tcaatttggt cattggaata ccatctatgc    1020
ttttctcctc ccatattcgc aaaagtagta agggctcgtt atatactttt gaatatgtaa    1080
gatataattc tatatgattt agtaatttat tttctatacg ctcagtattt ttctgcagtt    1140
gtcgagtagg tattaaacgc aaaagaagtc catccttttc atcattcaaa tggacatctt    1200
ggcaaagggc ccagttatgg aaaatctggg agtcatacaa cgattgcagt ggctatgcc    1260
actcctggta aggaatcatc aagtctgata attctgtttt ttagcccttt ttttttttt    1320
ttcatg                                                              1326
```

<210> SEQ ID NO 106
<211> LENGTH: 53
<212> TYPE: PRT
<213> ORGANISM: Saccharomyces fibuligera
<220> FEATURE:
<221> NAME/KEY: MISC_FEATURE
<223> OTHER INFORMATION: Sf GA (AE9)

<400> SEQUENCE: 106

```
Asp Asn Lys Asn Arg Tyr Lys Ile Asn Gly Asn Tyr Lys Ala Gly Cys
1               5                   10                  15
Asn Ser Lys Lys His Ile Val Glu Ser Pro Gln Leu Ser Ser Arg Gly
            20                  25                  30
Gly Cys Cys Asp His Ile Asp Asp Asn Gly Gln Leu Thr Glu Glu Ile
        35                  40                  45
Asn Arg Tyr Thr Gly
    50
```

<210> SEQ ID NO 107
<211> LENGTH: 34
<212> TYPE: PRT
<213> ORGANISM: Bifidobacterium adolescentis
<220> FEATURE:

<210> SEQ ID NO 107 (continued)
<221> NAME/KEY: MISC_FEATURE
<223> OTHER INFORMATION: Ba pflA

<400> SEQUENCE: 107

```
Cys Gln Asn Pro Asp Thr Trp Lys Met Arg Asp Gly Lys Pro Val Tyr
 1               5                  10                  15
Tyr Glu Gly Leu Thr Ser Ser Glu Glu Asn Val Glu Asn Asn Ala Lys
             20                  25                  30
Ile Cys
```

<210> SEQ ID NO 108
<211> LENGTH: 58
<212> TYPE: PRT
<213> ORGANISM: Bifidobacterium adolescentis
<220> FEATURE:
<221> NAME/KEY: MISC_FEATURE
<223> OTHER INFORMATION: Ba pflB

<400> SEQUENCE: 108

```
Trp Glu Gly Phe Thr Glu Gly Asn Trp Gln Lys Asp Ile Asp Val Arg
 1               5                  10                  15
Asp Cys Lys Gln Arg Asp Lys Asp Ser Ile Pro Tyr Arg Asn Asp Phe
             20                  25                  30
Thr Glu Cys Pro Glu Cys Cys Asn Thr Ile Thr Pro Asp Gly Leu Gly
         35                  40                  45
Arg Asp Glu Glu Glu Glu Arg Ile Gly Asn
             50                  55
```

<210> SEQ ID NO 109
<211> LENGTH: 53
<212> TYPE: PRT
<213> ORGANISM: Bifidobacterium adolescentis

<400> SEQUENCE: 109

```
Asp Ala Lys Lys Lys Glu Glu Pro Thr Lys Pro Thr Pro Glu Glu Lys
 1               5                  10                  15
Leu Cys Cys Lys Asn Leu Gly Val Asn Pro Gly Lys Thr Pro Glu Glu
             20                  25                  30
Gly Val Glu Asn Cys Gly Ser Tyr Gly Gly Asn Ser Val Ser Gly Val
         35                  40                  45
Asn Gln Ala Val Asn
     50
```

<210> SEQ ID NO 110
<211> LENGTH: 29
<212> TYPE: DNA
<213> ORGANISM: Artificial Sequence
<220> FEATURE:
<223> OTHER INFORMATION: Primer X11824

<400> SEQUENCE: 110
aagcctacag gcgcaagata acacatcac          29

<210> SEQ ID NO 111
<211> LENGTH: 59
<212> TYPE: DNA
<213> ORGANISM: Artificial Sequence
<220> FEATURE:
<223> OTHER INFORMATION: Primer X15546

<400> SEQUENCE: 111
ggacgaggca agctaaacag atctctagac ctactttata ttatcaatat ttgtgtttg          59

<210> SEQ ID NO 112
<211> LENGTH: 26
<212> TYPE: DNA
<213> ORGANISM: Artificial Sequence
<220> FEATURE:
<223> OTHER INFORMATION: Primer X15380

<400> SEQUENCE: 112
taggtctaga gatctgttta gcttgc                                          26

<210> SEQ ID NO 113
<211> LENGTH: 23
<212> TYPE: DNA
<213> ORGANISM: Artificial Sequence
<220> FEATURE:
<223> OTHER INFORMATION: Primer X15382

<400> SEQUENCE: 113
gagactacat gatagtccaa aga                                             23

<210> SEQ ID NO 114
<211> LENGTH: 59
<212> TYPE: DNA
<213> ORGANISM: Artificial Sequence
<220> FEATURE:
<223> OTHER INFORMATION: Primer X15547

<400> SEQUENCE: 114
ccgtttcttt tctttggact atcatgtagt ctcatttatt ggagaaagat aacatatca     59

<210> SEQ ID NO 115
<211> LENGTH: 35
<212> TYPE: DNA
<213> ORGANISM: Artificial Sequence
<220> FEATURE:
<223> OTHER INFORMATION: Primer X11829

<400> SEQUENCE: 115
ctcagcattg atcttagcag attcaggatc taggt                                35

<210> SEQ ID NO 116
<211> LENGTH: 29
<212> TYPE: DNA
<213> ORGANISM: Artificial Sequence
<220> FEATURE:
<223> OTHER INFORMATION: Primer X11816

<400> SEQUENCE: 116
gcagtcatca ggatcgtagg agataagca                                       29

<210> SEQ ID NO 117
<211> LENGTH: 59
<212> TYPE: DNA
<213> ORGANISM: Artificial Sequence
<220> FEATURE:
<223> OTHER INFORMATION: Primer X15548

<400> SEQUENCE: 117
ggacgaggca agctaaacag atctctagac ctatgataag gaagggagc gaaggaaaa      59

<210> SEQ ID NO 118
<211> LENGTH: 59
<212> TYPE: DNA
<213> ORGANISM: Artificial Sequence
<220> FEATURE:

```
<223> OTHER INFORMATION: Primer X15549

<400> SEQUENCE: 118
ccgtttcttt tctttggact atcatgtagt ctcctctgat ctttcctgtt gcctctttt        59

<210> SEQ ID NO 119
<211> LENGTH: 30
<212> TYPE: DNA
<213> ORGANISM: Artificial Sequence
<220> FEATURE:
<223> OTHER INFORMATION: Primer X11821

<400> SEQUENCE: 119
tcacaagagt gtgcagaaat aggaggtgga                                        30

<210> SEQ ID NO 120
<211> LENGTH: 30
<212> TYPE: DNA
<213> ORGANISM: Artificial Sequence
<220> FEATURE:
<223> OTHER INFORMATION: X16096

<400> SEQUENCE: 120
catggtgctt agcagcagat gaaagtgtca                                        30

<210> SEQ ID NO 121
<211> LENGTH: 59
<212> TYPE: DNA
<213> ORGANISM: Artificial Sequence
<220> FEATURE:
<223> OTHER INFORMATION: Primer X15554

<400> SEQUENCE: 121
ggacgaggca agctaaacag atctctagac ctaattaatt ttcagctgtt atttcgatt        59

<210> SEQ ID NO 122
<211> LENGTH: 59
<212> TYPE: DNA
<213> ORGANISM: Artificial Sequence
<220> FEATURE:
<223> OTHER INFORMATION: Primer X15555

<400> SEQUENCE: 122
ccgtttcttt tctttggact atcatgtagt ctcgagtgat tatgagtatt tgtgagcag        59

<210> SEQ ID NO 123
<211> LENGTH: 30
<212> TYPE: DNA
<213> ORGANISM: Artificial Sequence
<220> FEATURE:
<223> OTHER INFORMATION: Primer X11845

<400> SEQUENCE: 123
ttacttgtga aactgtctcc gctatgtcag                                        30

<210> SEQ ID NO 124
<211> LENGTH: 25
<212> TYPE: DNA
<213> ORGANISM: Artificial Sequence
<220> FEATURE:
<223> OTHER INFORMATION: Primer X15559

<400> SEQUENCE: 124
ggaaggcacc gatactagaa ctccg                                             25
```

```
<210> SEQ ID NO 125
<211> LENGTH: 59
<212> TYPE: DNA
<213> ORGANISM: Artificial Sequence
<220> FEATURE:
<223> OTHER INFORMATION: Primer X15550

<400> SEQUENCE: 125
gggacgaggc aagctaaaca gatctctaga cctaattaat tttcagctgt tattttgat      59

<210> SEQ ID NO 126
<211> LENGTH: 59
<212> TYPE: DNA
<213> ORGANISM: Artificial Sequence
<220> FEATURE:
<223> OTHER INFORMATION: Primer X15552

<400> SEQUENCE: 126
ccgtttcttt tctttggact atcatgtagt ctcgagtgat tatgagtatt tgtgagcag      59

<210> SEQ ID NO 127
<211> LENGTH: 31
<212> TYPE: DNA
<213> ORGANISM: Artificial Sequence
<220> FEATURE:
<223> OTHER INFORMATION: Primer X15553

<400> SEQUENCE: 127
accagcgtct ggtggacaaa cggccttcaa c                                    31

<210> SEQ ID NO 128
<211> LENGTH: 24
<212> TYPE: DNA
<213> ORGANISM: Artificial Sequence
<220> FEATURE:
<223> OTHER INFORMATION: Primer X15556

<400> SEQUENCE: 128
ccactcgagg ataggcttga aaga                                            24

<210> SEQ ID NO 129
<211> LENGTH: 59
<212> TYPE: DNA
<213> ORGANISM: Artificial Sequence
<220> FEATURE:
<223> OTHER INFORMATION: Primer X15870

<400> SEQUENCE: 129
ctaatcaaat caaaataaca gctgaaaatt aatgagtgat tatgagtatt tgtgagcag      59

<210> SEQ ID NO 130
<211> LENGTH: 59
<212> TYPE: DNA
<213> ORGANISM: Artificial Sequence
<220> FEATURE:
<223> OTHER INFORMATION: Primer X15871

<400> SEQUENCE: 130
aaaacttctg ctcacaaata ctcataatca ctcattaatt ttcagctgtt attttgatt      59

<210> SEQ ID NO 131
<211> LENGTH: 59
<212> TYPE: DNA
<213> ORGANISM: Artificial Sequence
<220> FEATURE:
<223> OTHER INFORMATION: Primer X17243
```

```
<400> SEQUENCE: 131
tagttagatc agggtaaaaa ttatagatga ggtattaatt ttcagctgtt atttcgatt      59

<210> SEQ ID NO 132
<211> LENGTH: 59
<212> TYPE: DNA
<213> ORGANISM: Artificial Sequence
<220> FEATURE:
<223> OTHER INFORMATION: Primer X16738

<400> SEQUENCE: 132
ctaatcaaat cgaaataaca gctgaaaatt aatacctcat ctataatttt taccctgat      59

<210> SEQ ID NO 133
<211> LENGTH: 59
<212> TYPE: DNA
<213> ORGANISM: Artificial Sequence
<220> FEATURE:
<223> OTHER INFORMATION: Primer X16620

<400> SEQUENCE: 133
tcggatcagt agataacccg cctagaagac taggttacat tgaaaataca gtaaatggt      59

<210> SEQ ID NO 134
<211> LENGTH: 59
<212> TYPE: DNA
<213> ORGANISM: Artificial Sequence
<220> FEATURE:
<223> OTHER INFORMATION: Primer X16621

<400> SEQUENCE: 134
tggtggaacc atttactgta ttttcaatgt aacctagtct tctaggcggg ttatctact      59

<210> SEQ ID NO 135
<211> LENGTH: 59
<212> TYPE: DNA
<213> ORGANISM: Artificial Sequence
<220> FEATURE:
<223> OTHER INFORMATION: Primer X13208

<400> SEQUENCE: 135
ccgaaatatt ccacggttta gaaaaaaatc ggaggtttag acattggctc ttcattgag      59

<210> SEQ ID NO 136
<211> LENGTH: 59
<212> TYPE: DNA
<213> ORGANISM: Artificial Sequence
<220> FEATURE:
<223> OTHER INFORMATION: Primer X13209

<400> SEQUENCE: 136
aagctcaatg aagagccaat gtctaaacct ccgattttt tctaaaccgt ggaatattt      59

<210> SEQ ID NO 137
<211> LENGTH: 59
<212> TYPE: DNA
<213> ORGANISM: Artificial Sequence
<220> FEATURE:
<223> OTHER INFORMATION: Primer X17242

<400> SEQUENCE: 137
acatcatctt taacttgaa tttattctct agctttcaat cattggagca atcatttta       59

<210> SEQ ID NO 138
<211> LENGTH: 59
```

```
<212> TYPE: DNA
<213> ORGANISM: Artificial Sequence
<220> FEATURE:
<223> OTHER INFORMATION: Primer X17241

<400> SEQUENCE: 138
gtccatgtaa aatgattgct ccaatgattg aaagctagag aataaattca agttaaaag       59

<210> SEQ ID NO 139
<211> LENGTH: 60
<212> TYPE: DNA
<213> ORGANISM: Artificial Sequence
<220> FEATURE:
<223> OTHER INFORMATION: Primer X16744

<400> SEQUENCE: 139
aaaaacttct gctcacaaat actcataatc actcctactt attcccttcg agattatatc      60

<210> SEQ ID NO 140
<211> LENGTH: 59
<212> TYPE: DNA
<213> ORGANISM: Artificial Sequence
<220> FEATURE:
<223> OTHER INFORMATION: Primer X17244

<400> SEQUENCE: 140
gttcctagat ataatctcga agggaataag taggagtgat tatgagtatt tgtgagcag       59

<210> SEQ ID NO 141
<211> LENGTH: 30
<212> TYPE: DNA
<213> ORGANISM: Artificial Sequence
<220> FEATURE:
<223> OTHER INFORMATION: Primer X11845

<400> SEQUENCE: 141
ttacttgtga aactgtctcc gctatgtcag                                       30

<210> SEQ ID NO 142
<211> LENGTH: 26
<212> TYPE: DNA
<213> ORGANISM: Artificial Sequence
<220> FEATURE:
<223> OTHER INFORMATION: Primer X15473

<400> SEQUENCE: 142
agtcatcagg atcgtaggag ataagc                                           26

<210> SEQ ID NO 143
<211> LENGTH: 59
<212> TYPE: DNA
<213> ORGANISM: Artificial Sequence
<220> FEATURE:
<223> OTHER INFORMATION: Primer X17460

<400> SEQUENCE: 143
agaagataat attttatat aattatatta atcctaatct tcatgtagat ctaattctt        59

<210> SEQ ID NO 144
<211> LENGTH: 59
<212> TYPE: DNA
<213> ORGANISM: Artificial Sequence
<220> FEATURE:
<223> OTHER INFORMATION: Primer X17459

<400> SEQUENCE: 144
```

```
cctttcctttt tccttcgctc ccttccctta tcaatggcag acgcaaagaa gaaggaaga    59
```

<210> SEQ ID NO 145
<211> LENGTH: 59
<212> TYPE: DNA
<213> ORGANISM: Artificial Sequence
<220> FEATURE:
<223> OTHER INFORMATION: Primer X17289

<400> SEQUENCE: 145

```
gtccatgtaa aatgattgct ccaatgattg aaagttacat tgaaaataca gtaaatggt    59
```

<210> SEQ ID NO 146
<211> LENGTH: 59
<212> TYPE: DNA
<213> ORGANISM: Artificial Sequence
<220> FEATURE:
<223> OTHER INFORMATION: Primer X17290

<400> SEQUENCE: 146

```
tggtggaacc atttactgta ttttcaatgt aactttcaat cattggagca atcattta     59
```

<210> SEQ ID NO 147
<211> LENGTH: 58
<212> TYPE: DNA
<213> ORGANISM: Artificial Sequence
<220> FEATURE:
<223> OTHER INFORMATION: Primer X15735

<400> SEQUENCE: 147

```
catcttttaa cttgaattta ttctctagcc tagtcttcta ggcgggttat ctactgat     58
```

<210> SEQ ID NO 148
<211> LENGTH: 59
<212> TYPE: DNA
<213> ORGANISM: Artificial Sequence
<220> FEATURE:
<223> OTHER INFORMATION: Primer X15736

<400> SEQUENCE: 148

```
agataacccg cctagaagac taggctagag aataaattca agttaaaaga tgatgttga    59
```

<210> SEQ ID NO 149
<211> LENGTH: 59
<212> TYPE: DNA
<213> ORGANISM: Artificial Sequence
<220> FEATURE:
<223> OTHER INFORMATION: Primer X17457

<400> SEQUENCE: 149

```
tgggggaaaa agaggcaaca ggaaagatca gagctactta ttcccttcga gattatatc    59
```

<210> SEQ ID NO 150
<211> LENGTH: 60
<212> TYPE: DNA
<213> ORGANISM: Artificial Sequence
<220> FEATURE:
<223> OTHER INFORMATION: Primer X17458

<400> SEQUENCE: 150

```
gttcctagat ataatctcga agggaataag tagctctgat ctttcctgtt gcctcttttt    60
```

<210> SEQ ID NO 151
<211> LENGTH: 26
<212> TYPE: DNA
<213> ORGANISM: Artificial Sequence

```
<220> FEATURE:
<223> OTHER INFORMATION: Primer X15476

<400> SEQUENCE: 151
gtagatctgc ccagaatgat gacgtt                                    26

<210> SEQ ID NO 152
<211> LENGTH: 23
<212> TYPE: DNA
<213> ORGANISM: Artificial Sequence
<220> FEATURE:
<223> OTHER INFORMATION: Primer X17826

<400> SEQUENCE: 152
tcgctaacga tcaagaggaa ctg                                       23

<210> SEQ ID NO 153
<211> LENGTH: 22
<212> TYPE: DNA
<213> ORGANISM: Artificial Sequence
<220> FEATURE:
<223> OTHER INFORMATION: Primer X16944

<400> SEQUENCE: 153
tacacgtgca tttggaccta tc                                        22

<210> SEQ ID NO 154
<211> LENGTH: 20
<212> TYPE: DNA
<213> ORGANISM: Artificial Sequence
<220> FEATURE:
<223> OTHER INFORMATION: Primer 17413

<400> SEQUENCE: 154
ggattcttcg agagctaaga                                           20

<210> SEQ ID NO 155
<211> LENGTH: 27
<212> TYPE: DNA
<213> ORGANISM: Artificial Sequence
<220> FEATURE:
<223> OTHER INFORMATION: Primer 15810

<400> SEQUENCE: 155
gacttgcagg gtaggctagc tagaatt                                   27

<210> SEQ ID NO 156
<211> LENGTH: 20
<212> TYPE: DNA
<213> ORGANISM: Artificial Sequence
<220> FEATURE:
<223> OTHER INFORMATION: Primer 17834

<400> SEQUENCE: 156
gctgcttcga ggtattgaca                                           20

<210> SEQ ID NO 157
<211> LENGTH: 24
<212> TYPE: DNA
<213> ORGANISM: Artificial Sequence
<220> FEATURE:
<223> OTHER INFORMATION: Primer 14554

<400> SEQUENCE: 157
ggctcttcat tgagcttaga accc                                      24
```

```
<210> SEQ ID NO 158
<211> LENGTH: 21
<212> TYPE: DNA
<213> ORGANISM: Artificial Sequence
<220> FEATURE:
<223> OTHER INFORMATION: Primer 16291

<400> SEQUENCE: 158
aactggaccg atcttattcg t                                                 21

<210> SEQ ID NO 159
<211> LENGTH: 25
<212> TYPE: DNA
<213> ORGANISM: Artificial Sequence
<220> FEATURE:
<223> OTHER INFORMATION: Primer 15229

<400> SEQUENCE: 159
agtccactgc ggagtcattt caaag                                             25

<210> SEQ ID NO 160
<211> LENGTH: 25
<212> TYPE: DNA
<213> ORGANISM: Artificial Sequence
<220> FEATURE:
<223> OTHER INFORMATION: Primer 16503

<400> SEQUENCE: 160
ctgccagcga attcgactct gcaat                                             25

<210> SEQ ID NO 161
<211> LENGTH: 30
<212> TYPE: DNA
<213> ORGANISM: Artificial Sequence
<220> FEATURE:
<223> OTHER INFORMATION: Primer 11317

<400> SEQUENCE: 161
cagtcgctgt agtgagcgac agggtagtaa                                        30

<210> SEQ ID NO 162
<211> LENGTH: 19
<212> TYPE: DNA
<213> ORGANISM: Artificial Sequence
<220> FEATURE:
<223> OTHER INFORMATION: Primer 16241

<400> SEQUENCE: 162
ctttgcatta gcatgcgta                                                    19

<210> SEQ ID NO 163
<211> LENGTH: 23
<212> TYPE: DNA
<213> ORGANISM: Artificial Sequence
<220> FEATURE:
<223> OTHER INFORMATION: Primer 16946

<400> SEQUENCE: 163
taggtcgaga ccagaatgca tgt                                               23

<210> SEQ ID NO 164
<211> LENGTH: 22
<212> TYPE: DNA
<213> ORGANISM: Artificial Sequence
<220> FEATURE:
<223> OTHER INFORMATION: Primer 16939
```

```
<400> SEQUENCE: 164
atgctgatgc atgtccacaa ag                                              22

<210> SEQ ID NO 165
<211> LENGTH: 23
<212> TYPE: DNA
<213> ORGANISM: Artificial Sequence
<220> FEATURE:
<223> OTHER INFORMATION: Primer 16940

<400> SEQUENCE: 165
ccttatcagt caattgagga aag                                             23

<210> SEQ ID NO 166
<211> LENGTH: 23
<212> TYPE: DNA
<213> ORGANISM: Artificial Sequence
<220> FEATURE:
<223> OTHER INFORMATION: Primer 16807

<400> SEQUENCE: 166
gcgatgagct aatcctgagc cat                                             23

<210> SEQ ID NO 167
<211> LENGTH: 24
<212> TYPE: DNA
<213> ORGANISM: Artificial Sequence
<220> FEATURE:
<223> OTHER INFORMATION: Primer 14567

<400> SEQUENCE: 167
tggttccacc attattatgt tggt                                            24

<210> SEQ ID NO 168
<211> LENGTH: 20
<212> TYPE: DNA
<213> ORGANISM: Artificial Sequence
<220> FEATURE:
<223> OTHER INFORMATION: Primer 17834

<400> SEQUENCE: 168
gctgcttcga ggtattgaca                                                 20

<210> SEQ ID NO 169
<211> LENGTH: 25
<212> TYPE: DNA
<213> ORGANISM: Artificial Sequence
<220> FEATURE:
<223> OTHER INFORMATION: Primer 14557

<400> SEQUENCE: 169
ctaaaccgtg gaatatttcg gatat                                           25

<210> SEQ ID NO 170
<211> LENGTH: 23
<212> TYPE: DNA
<213> ORGANISM: Artificial Sequence
<220> FEATURE:
<223> OTHER INFORMATION: Primer 16640

<400> SEQUENCE: 170
cctcatcagc tctggaacaa cga                                             23

<210> SEQ ID NO 171
```

```
<211> LENGTH: 24
<212> TYPE: DNA
<213> ORGANISM: Artificial Sequence
<220> FEATURE:
<223> OTHER INFORMATION: Primer 14552

<400> SEQUENCE: 171
gatccgagct tccactagga tagc                                          24

<210> SEQ ID NO 172
<211> LENGTH: 22
<212> TYPE: DNA
<213> ORGANISM: Artificial Sequence
<220> FEATURE:
<223> OTHER INFORMATION: Primer 17586

<400> SEQUENCE: 172
gcagtatgca agtctcatgc tg                                            22

<210> SEQ ID NO 173
<211> LENGTH: 23
<212> TYPE: DNA
<213> ORGANISM: Artificial Sequence
<220> FEATURE:
<223> OTHER INFORMATION: Primer 16806

<400> SEQUENCE: 173
gaacttgcag gcaccgatct tca                                           23

<210> SEQ ID NO 174
<211> LENGTH: 27
<212> TYPE: DNA
<213> ORGANISM: Artificial Sequence
<220> FEATURE:
<223> OTHER INFORMATION: Primer 13092

<400> SEQUENCE: 174
ccacaccata gacttcagcc ttcttag                                       27

<210> SEQ ID NO 175
<211> LENGTH: 22
<212> TYPE: DNA
<213> ORGANISM: Artificial Sequence
<220> FEATURE:
<223> OTHER INFORMATION: Primer 17586

<400> SEQUENCE: 175
gcagtatgca agtctcatgc tg                                            22

<210> SEQ ID NO 176
<211> LENGTH: 25
<212> TYPE: DNA
<213> ORGANISM: Artificial Sequence
<220> FEATURE:
<223> OTHER INFORMATION: Primer 10871

<400> SEQUENCE: 176
cgttcgctgt agcatactta gctat                                         25

<210> SEQ ID NO 177
<211> LENGTH: 24
<212> TYPE: DNA
<213> ORGANISM: Artificial Sequence
<220> FEATURE:
<223> OTHER INFORMATION: Primer 14554

<400> SEQUENCE: 177
```

```
ggctcttcat tgagcttaga accc                                          24
```

<210> SEQ ID NO 178
<211> LENGTH: 21
<212> TYPE: DNA
<213> ORGANISM: Artificial Sequence
<220> FEATURE:
<223> OTHER INFORMATION: Primer 16291

<400> SEQUENCE: 178

```
aactggaccg atcttattcg t                                             21
```

<210> SEQ ID NO 179
<211> LENGTH: 21
<212> TYPE: DNA
<213> ORGANISM: Artificial Sequence
<220> FEATURE:
<223> OTHER INFORMATION: Primer 17887

<400> SEQUENCE: 179

```
actgcctcat tgatggtggt a                                             21
```

<210> SEQ ID NO 180
<211> LENGTH: 23
<212> TYPE: DNA
<213> ORGANISM: Artificial Sequence
<220> FEATURE:
<223> OTHER INFORMATION: Primer 16640

<400> SEQUENCE: 180

```
cctcatcagc tctggaacaa cga                                           23
```

<210> SEQ ID NO 181
<211> LENGTH: 23
<212> TYPE: DNA
<213> ORGANISM: Artificial Sequence
<220> FEATURE:
<223> OTHER INFORMATION: Primer 16509

<400> SEQUENCE: 181

```
gtatgattgc ggttatctgt cgc                                           23
```

<210> SEQ ID NO 182
<211> LENGTH: 22
<212> TYPE: DNA
<213> ORGANISM: Artificial Sequence
<220> FEATURE:
<223> OTHER INFORMATION: Primer 13246

<400> SEQUENCE: 182

```
cctatggatg ttgtaccatg cc                                            22
```

<210> SEQ ID NO 183
<211> LENGTH: 28
<212> TYPE: DNA
<213> ORGANISM: Artificial Sequence
<220> FEATURE:
<223> OTHER INFORMATION: Primer 13095

<400> SEQUENCE: 183

```
ccaatatctt gcagtccatc ctcgtcgc                                      28
```

<210> SEQ ID NO 184
<211> LENGTH: 31
<212> TYPE: DNA

```
<213> ORGANISM: Artificial Sequence
<220> FEATURE:
<223> OTHER INFORMATION: Primer X18868

<400> SEQUENCE: 184
gccaaagtgg attctcctac tcaagctttg c                              31

<210> SEQ ID NO 185
<211> LENGTH: 59
<212> TYPE: DNA
<213> ORGANISM: Artificial Sequence
<220> FEATURE:
<223> OTHER INFORMATION: Primer X18844

<400> SEQUENCE: 185
tcggatcagt agataacccg cctagaagac tagtagctat gaaattttta actctttaa   59

<210> SEQ ID NO 186
<211> LENGTH: 59
<212> TYPE: DNA
<213> ORGANISM: Artificial Sequence
<220> FEATURE:
<223> OTHER INFORMATION: Primer X18845

<400> SEQUENCE: 186
agccagctta aagagttaaa aatttcatag ctactagtct tctaggcggg ttatctact   59

<210> SEQ ID NO 187
<211> LENGTH: 59
<212> TYPE: DNA
<213> ORGANISM: Artificial Sequence
<220> FEATURE:
<223> OTHER INFORMATION: Primer X15464

<400> SEQUENCE: 187
gtccatgtaa aatgattgct ccaatgattg aaagaggttt agacattggc tcttcattg   59

<210> SEQ ID NO 188
<211> LENGTH: 59
<212> TYPE: DNA
<213> ORGANISM: Artificial Sequence
<220> FEATURE:
<223> OTHER INFORMATION: Primer X15465

<400> SEQUENCE: 188
ctaagctcaa tgaagagcca atgtctaaac ctctttcaat cattggagca atcatttta   59

<210> SEQ ID NO 189
<211> LENGTH: 59
<212> TYPE: DNA
<213> ORGANISM: Artificial Sequence
<220> FEATURE:
<223> OTHER INFORMATION: Primer X11750

<400> SEQUENCE: 189
ataaaattaa atacgtaaat acagcgtgct gcgtgctcga ttttttttcta aaccgtgga   59

<210> SEQ ID NO 190
<211> LENGTH: 26
<212> TYPE: DNA
<213> ORGANISM: Artificial Sequence
<220> FEATURE:
<223> OTHER INFORMATION: Primer X15479

<400> SEQUENCE: 190
agcacgcagc acgctgtatt tacgta                                    26
```

```
<210> SEQ ID NO 191
<211> LENGTH: 30
<212> TYPE: DNA
<213> ORGANISM: Artificial Sequence
<220> FEATURE:
<223> OTHER INFORMATION: Primer X18869

<400> SEQUENCE: 191
agatcctgtg gtagtgctgt ctgaacagaa                                    30
```